(12) United States Patent
Bestvater et al.

(10) Patent No.: US 11,912,686 B2
(45) Date of Patent: *Feb. 27, 2024

(54) LPA RECEPTOR ANTAGONISTS AND USES THEREOF

(71) Applicant: Gilead Sciences, Inc., Foster City, CA (US)

(72) Inventors: Brian P. Bestvater, Vancouver (CA); Julie Farand, San Mateo, CA (US); Doris T. Tang, Burlingame, CA (US); Kin S. Yang, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/062,469

(22) Filed: Dec. 6, 2022

(65) Prior Publication Data

US 2023/0212151 A1 Jul. 6, 2023

Related U.S. Application Data

(63) Continuation of application No. 17/319,507, filed on May 13, 2021, now Pat. No. 11,584,738.

(60) Provisional application No. 63/130,242, filed on Dec. 23, 2020, provisional application No. 63/034,220, filed on Jun. 3, 2020.

(51) Int. Cl.
| | |
|---|---|
| *C07D 401/14* | (2006.01) |
| *C07D 405/14* | (2006.01) |
| *C07D 409/14* | (2006.01) |
| *C07D 413/14* | (2006.01) |

(52) U.S. Cl.
CPC ......... *C07D 401/14* (2013.01); *C07D 405/14* (2013.01); *C07D 409/14* (2013.01); *C07D 413/14* (2013.01)

(58) Field of Classification Search
CPC .................................................. C07D 401/14
See application file for complete search history.

(56) References Cited

U.S. PATENT DOCUMENTS

| | | |
|---|---|---|
| 10,662,172 B2 | 5/2020 | Shi et al. |
| 2003/0092749 A1 | 5/2003 | Dombroski et al. |
| 2017/0360759 A1 | 12/2017 | Cheng et al. |

FOREIGN PATENT DOCUMENTS

| WO | WO-2009135590 A1 | 11/2009 |
|---|---|---|
| WO | WO-2010068775 A2 | 6/2010 |
| WO | WO-2010077882 A2 | 7/2010 |
| WO | WO-2010077883 A2 | 7/2010 |
| WO | WO-2010141761 A2 | 12/2010 |
| WO | WO-2010141768 A2 | 12/2010 |
| WO | WO-2011017350 A2 | 2/2011 |
| WO | WO-2011037192 A1 | 3/2011 |
| WO | WO-2011041461 A2 | 4/2011 |
| WO | WO-2011041462 A2 | 4/2011 |
| WO | WO-2011041694 A2 | 4/2011 |
| WO | WO-2011041729 A2 | 4/2011 |
| WO | WO-2011053948 A1 | 5/2011 |
| WO | WO-2011159550 A2 | 12/2011 |
| WO | WO-2011159632 A1 | 12/2011 |
| WO | WO-2012039460 A1 | 3/2012 |
| WO | WO-2012078593 A2 | 6/2012 |
| WO | WO-2012078805 A1 | 6/2012 |
| WO | WO-2012100436 A1 | 8/2012 |
| WO | WO-2012138648 A1 | 10/2012 |
| WO | WO-2012138797 A1 | 10/2012 |
| WO | WO-2013/025733 A1 | 2/2013 |
| WO | WO-2013085824 A1 | 6/2013 |
| WO | WO-2013189862 A1 | 12/2013 |
| WO | WO-2013189864 A1 | 12/2013 |
| WO | WO-2013189865 A1 | 12/2013 |
| WO | WO-2014037303 A1 | 3/2014 |
| WO | WO-2014072486 A1 | 5/2014 |
| WO | WO-2014104372 A1 | 7/2014 |
| WO | WO-2014113485 A1 | 7/2014 |
| WO | WO-2014145873 A2 | 9/2014 |
| WO | WO-2015025164 A1 | 2/2015 |
| WO | WO-2015066456 A1 | 5/2015 |
| WO | WO-2015199234 A1 | 12/2015 |
| WO | WO-2017086430 A1 | 5/2017 |
| WO | WO-2017177004 A1 | 10/2017 |
| WO | WO-2017223016 A1 | 12/2017 |
| WO | WO-2019046239 A1 | 3/2019 |
| WO | WO-2019126084 A1 | 6/2019 |
| WO | WO-2019126085 A1 | 6/2019 |
| WO | WO-2019126086 A1 | 6/2019 |
| WO | WO-2019126087 A1 | 6/2019 |
| WO | WO-2019126089 A1 | 6/2019 |
| WO | WO-2019126090 A1 | 6/2019 |

(Continued)

OTHER PUBLICATIONS

Cheng, P. et al. (2021) "Discovery of an Oxycyclohexyl Acid Lysophosphatidic Acid Receptor 1 (LPA1) Antagonist BMS-986278 for the Treatment of Pulmonary Fibrotic Diseases" J. Med. Chem., 64, 21, 15549-15581.

Gallezot, J. et al. (2018) "Evaluation of the Lysophosphatidic Acid Receptor Type 1 Radioligand 11C-BMT-136088 for Lung Imaging in Rhesus Monkeys" The Journal of Nuclear Medicine, 59(2):327-333.

International Search Report and Written Opinion dated Jul. 26, 2021 for Intl. Appl. No. PCT/US2021/032293.

Office Action dated Mar. 16, 2022 on Taiwan Application No. 110117052.

Qian, et al. (2012) "Discovery of Highly Selective and Orally Active Lysophosphatidic Acid Receptor-1 Antagonists with Potent Activity on Human Lung Fibroblasts" J. Med. Chem., 55, 7920-7939.

(Continued)

*Primary Examiner* — Shawquia Jackson

(57) ABSTRACT

The present disclosure relates generally to compounds that bind to Lysophosphatidic Acid Receptor 1 (LPAR1) and act as antagonists of LPAR1. The disclosure further relates to the use of the compounds for the preparation of a medicament for the treatment of diseases and/or conditions through binding of LPAR1, including fibrosis and liver diseases such as non-alcoholic steatohepatitis (NASH), interstitial lung disease (ILD), or chronic kidney disease (CKD).

5 Claims, No Drawings

(56) References Cited

FOREIGN PATENT DOCUMENTS

| | | |
|---|---|---|
| WO | WO-2019126093 A1 | 6/2019 |
| WO | WO-2019126094 A1 | 6/2019 |
| WO | WO-2019126098 A1 | 6/2019 |
| WO | WO-2019126099 A1 | 6/2019 |
| WO | WO-2019126103 A1 | 6/2019 |
| WO | WO-2020060914 A1 | 3/2020 |
| WO | WO-2020060915 A1 | 3/2020 |
| WO | WO-2020060916 A1 | 3/2020 |
| WO | WO-2020081410 A2 | 4/2020 |
| WO | WO-2020257135 A1 | 12/2020 |
| WO | WO-2020257138 A1 | 12/2020 |
| WO | WO-2020257139 A1 | 12/2020 |
| WO | WO-2021020429 A1 | 2/2021 |
| WO | WO-2021097039 A1 | 5/2021 |
| WO | WO-2021110805 A1 | 6/2021 |
| WO | WO-2021247215 A1 | 12/2021 |
| WO | WO-2022013378 A1 | 1/2022 |
| WO | WO-2022034568 A1 | 2/2022 |
| WO | WO-2022100623 A1 | 5/2022 |
| WO | WO-2022100624 A1 | 5/2022 |
| WO | WO-2022100625 A1 | 5/2022 |
| WO | WO-2022174882 A1 | 8/2022 |
| WO | WO-2022174883 A1 | 8/2022 |
| WO | WO-2022240879 A1 | 11/2022 |
| WO | WO-2022241023 A1 | 11/2022 |

OTHER PUBLICATIONS

U.S. Appl. No. 17/096,150 (U.S. Pat. No. 11,548,871), filed Nov. 12, 2020, Brian P. Bestvater, et al.

U.S. Appl. No. 17/319,507 (U.S. Pat. No. 11,584,738), filed May 13, 2021, Brian P. Bestvater, et al.

U.S. Appl. No. 18/061,822, filed Dec. 5, 2022, Brian P. Bestvater, et al.

U.S. Appl. No. 17/319,471, filed May 13, 2021, Barton W. Phillips, et al.

U.S. Appl. No. 17/741,991, filed May 11, 2022, Brian P. Bestvater, et al.

U.S. Appl. No. 17/741,222, filed May 10, 2022, Brian P. Bestvater, et al.

U.S. Appl. No. 18/062,363, filed Dec. 6, 2022, Brian P. Bestvater, et al.

LPA RECEPTOR ANTAGONISTS AND USES THEREOF

CROSS-REFERENCES TO RELATED APPLICATIONS

This application is a continuation of U.S. patent application Ser. No. 17/319,507, filed on May 13, 2021, which claims the benefit under 35 U.S.C. § 119(e) of U.S. provisional application No. 63/130,242, filed on Dec. 23, 2020, and of U.S. provisional application No. 63/034,220, filed on Jun. 3, 2020, which are hereby incorporated herein by reference in their entireties for all purposes.

FIELD

The present disclosure relates to compounds that bind to and act as antagonists of a lysophosphatidic acid (LPA) receptor, such as LPAR1. The disclosure further relates to the use of the compounds for the treatment and/or prophylaxis of diseases and/or conditions associated with one or more LPA receptors, e.g., an LPAR1 associated disease or condition.

BACKGROUND

Lysophosphatidic acids (mono-acyl-glycerol-3-phosphate, LPA) are a class of biologically active phospholipids that can be produced from lysophosphatidyl choline (LPC), e.g., by the enzyme autotaxin. A typical LPA has a glycerol, an ester-linked fatty acid at the sn-1 position, and a phosphate head group at the sn-3 position. LPA with various fatty acids have been identified, including palmitoyl LPA (16:0), stearoyl LPA (18:0), oleoyl LPA (18:1), linoleoyl LPA (18:2) and arachidonyl LPA (20:4). LPA exerts a wide range of cellular responses, such as proliferation, differentiation, survival, migration, adhesion, invasion, and morphogenesis through a family of rhodopsin-like G protein-coupled receptors (GPCRs). Six LPA receptors have been been characterized and were found to differ in their tissue distribution and downstream signaling pathways. These six LPA receptors are often referred to interchangeably as LPAR1-6 (gene) or LPA1-6 (protein). LPA receptor mediated signaling has been shown to influence many biological processes such as wound healing, immunity, carcinogenesis, angiogenesis and neurogenesis.

In vivo studies involving LPA receptor-deficient mice or certain tool compounds have suggested a potential of LPA receptors as possible drug targets in a variety of diseases including cancer, fibrosis, inflammation, pain, and cardiovascular diseases. More recently, LPAR1 antagonists have been studied clinically in connection with fibrotic disease states such as idiopathic pulmonary fibrosis (IPF) and systemic sclerosis.

A need remains for LPA antagonists with desirable selectivity, potency, metabolic stability, or reduced detrimental effects.

SUMMARY

The present disclosure provides compounds useful as inhibitors of Lysophosphatidic Acid Receptor 1 (LPAR1). The disclosure further relates to the use of the compounds for the treatment and/or prophylaxis of diseases and/or conditions through binding of LPAR1 by said compounds.

In one embodiment, provided herein is a compound of Formula (I),

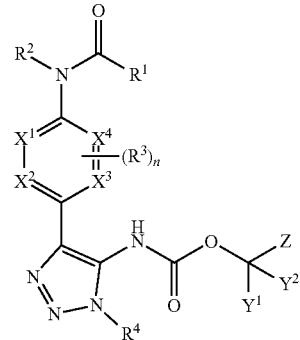

(I)

or a pharmaceutically acceptable salt thereof,
wherein:
$R^1$ is hydrogen, $C_{1-6}$ alkyl, $C_{2-6}$ alkenyl, $C_{2-6}$ alkynyl, $C_{3-10}$ cycloalkyl, 3 to 10 membered heterocyclyl having 1 to 4 heteroatoms independently selected from nitrogen, oxygen, and sulfur, 6 to 10 membered aryl, or 5 to 10 membered heteroaryl having 1 to 4 heteroatoms independently selected from nitrogen, oxygen, and sulfur, wherein each alkyl, alkenyl, alkynyl, cycloalkyl, heterocyclyl, aryl, or heteroaryl is optionally substituted with 1 to 4 $R^{1A}$, which can be the same or different, wherein each $R^{1A}$ is independently selected from halogen, cyano, nitro, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —$N(R^{1B1})(R^{1B2})$, —O—$R^{1B1}$, —S—$R^{1B1}$, —C(O)N$(R^{1B1})(R^{1B2})$, —$NR^{1B1}C(O)R^{1B2}$, —$NR^{1B1}C(O)N(R^{1B2})(R^{1B3})$, —$S(O)_{0-2}R^{1B1}$, —$S(O)_2N(R^{1B1})(R^{1B2})$, and —$NR^{1B1}S(O)_2R^{1B2}$, wherein each $R^{1B1}$, $R^{1B2}$ and $R^{1B3}$ is independently hydrogen, $C_{1-6}$ alkyl or $C_{3-6}$ cycloalkyl,
wherein each $R^{1A}$ alkyl, cycloalkyl, heterocyclyl, aryl, and heteroaryl is optionally substituted with 1 to 4 $R^{1C}$, which can be the same or different, and wherein each $R^{1C}$ is independently $C_{1-4}$ alkyl, halogen, cyano, —O—$R^{1D1}$, or —$N(R^{1D1})(R^{1D2})$, wherein each $R^{1D1}$ and $R^{1D2}$ is independently hydrogen or $C_{1-6}$ alkyl, and
wherein each $R^{1B1}$, $R^{1B2}$, and $R^{1B3}$ alkyl and each $R^{1B1}$, $R^{1B2}$, and $R^{1B3}$ cycloalkyl is optionally substituted with 1 to 3 halogens; or
$R^1$ is —O—$R^{1D1}$ or —$N(R^{1D1})(R^{1D2})$, wherein each $R^{1D1}$ and $R^{1D2}$ is independently hydrogen, $C_{1-6}$ alkyl, or $C_{3-6}$ cycloalkyl, wherein each $C_{1-6}$ alkyl, or $C_{3-6}$ cycloalkyl is optionally substituted with 1 to 4 $R^{1E}$, which can be the same or different, wherein each $R^{1E}$ is independently selected from halogen, cyano, hydroxy, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —O—$R^{1F1}$, —$N(R^{1F1})(R^{1F2})$, —C(O)N$(R^{1F1})(R^{1F2})$, —$NR^{1F1}C(O)R^{1F2}$, —$S(O)_{0-2}R^{1F1}$, —$S(O)_2N(R^{1F1})(R^{1F2})$, and —$NR^{1F1}S(O)_2R^{1F2}$, wherein each $R^{1F1}$ and $R^{1F2}$ is independently hydrogen or $C_{1-6}$ alkyl, wherein each $R^{1E}$ alkyl, cycloalkyl, aryl, and heteroaryl is optionally substituted with 1 to 3 $R^{1G}$, which can be the same or different, and wherein each $R^{1G}$ is independently $C_{1-4}$ alkyl, $C_{1-4}$ alkoxy, hydroxy, halogen, or cyano;

$R^2$ is hydrogen or $C_{1-6}$ alkyl optionally substituted with 1 to 3 substituents, which can be the same or different, independently selected from halogen, cyano, $C_{1-4}$ alkoxy, and $C_{3-10}$ cycloalkyl; or $R^2$ is $C_{3-6}$ cycloalkyl optionally substituted with 1 to 3 substituents, which can be the same or different, independently selected from halogen, cyano, $C_{1-4}$ alkoxy, and $C_{1-6}$ alkyl;

each $R^3$ is independently selected from deuterium, halogen, $C_{1-6}$ alkyl, $C_{3-6}$ cycloalkyl, —O—$R^{2A1}$, and —N($R^{2A1}$)($R^{2A2}$), wherein the $C_{1-6}$ alkyl is optionally substituted with 1 to 3 substituents, which can be the same or different, independently selected from $C_{1-4}$ alkoxy and halogen, and wherein each $R^{2A1}$ and $R^{2A2}$ is independently hydrogen or $C_{1-3}$ alkyl optionally substituted with 1 to 3 halogens, which can be the same or different;

n is 0, 1, 2, 3, or 4;

$R^4$ is $C_{1-6}$ alkyl optionally substituted with 1 to 3 substituents, which can be the same or different, independently selected from halogen, cyano, $C_{1-4}$ alkoxy, —C(O)N($R^{4A1}$), and —N($R^{4A1}$)($R^{4A2}$), wherein each $R^{4A1}$ and $R^{4A2}$ is independently hydrogen, $C_{1-6}$ alkyl, or $C_{3-10}$ cycloalkyl; or $R^4$ is $C_{3-6}$ cycloalkyl or 3 to 6 membered heterocyclyl having 1 or 2 heteroatoms independently selected from nitrogen, oxygen, and sulfur, wherein the cycloalkyl or heterocyclyl are optionally substituted with 1 to 3 substituents, which can be the same or different, independently selected from halogen, cyano, $C_{1-4}$ alkyl, and $C_{1-4}$ alkoxy;

each of $X^1$, $X^2$, $X^3$, and $X^4$ is independently selected from CH and N;

each $Y^1$ and $Y^2$ is independently hydrogen, deuterium, or $C_{1-6}$ alkyl optionally substituted with 1 to 3 substituents, which can be the same or different, independently selected from deuterium, halogen, cyano, $C_{2-3}$ alkynyl, $C_{1-4}$ alkoxy, and —C(O)NH—($C_{1-4}H_{3-9}$); and Z is $C_{1-8}$ alkyl, $C_{1-6}$ alkoxy, $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the alkyl, alkoxy, cycloalkyl, aryl, heterocyclyl, or heteroaryl are each optionally substituted with 1 to 3 substituents, which can be the same or different, independently selected from halogen, cyano, $C_{1-4}$ alkyl, $C_{1-4}$ alkoxy, and $C_{3-6}$ cycloalkyl, wherein the $C_{1-4}$ alkyl is optionally substituted with 1 to 3 substituents, which can be the same or different, selected from $C_{1-4}$ alkoxy and halogen; or $Y^1$ and Z together with the carbon to which they are attached form $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the cycloalkyl, aryl, heterocyclyl, or heteroaryl are each optionally substituted with 1 to 3 substituents, which can be the same or different, independently selected from cyano, $C_{1-4}$ alkyl, $C_{1-4}$ alkoxy, $C_{6-10}$ aryl, and halogen, wherein the $C_{1-4}$ alkyl is optionally substituted with 1 to 3 substituents, which can be the same or different, independently selected from $C_{1-4}$ alkoxy and halogen, and wherein the $C_{6-10}$ aryl is optionally substituted with 1 to 3 substituents, which can be the same or different, independently selected from $C_{1-4}$ alkyl, $C_{1-4}$ alkoxy, and halogen, and $Y^2$ is hydrogen or deuterium.

In some embodiments of the compound of Formula I or pharmaceutically acceptable salt thereof $R^1$ is hydrogen, $C_{1-6}$ alkyl, $C_{2-6}$ alkenyl, $C_{2-6}$ alkynyl, $C_{3-10}$ cycloalkyl, 3 to 10 membered heterocyclyl having 1 to 4 heteroatoms independently selected from nitrogen, oxygen, and sulfur, 6 to 10 membered aryl, or 5 to 10 membered heteroaryl having 1 to 4 heteroatoms independently selected from nitrogen, oxygen, and sulfur, wherein each alkyl, alkenyl, alkynyl, cycloalkyl, heterocyclyl, aryl, or heteroaryl is optionally substituted with 1 to 4 $R^{1A}$, which can be the same or different, wherein each $R^{1A}$ is independently selected from halogen, cyano, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —N($R^{1B1}$)($R^{1B2}$), —O—$R^{1B1}$, —S—$R^{1B1}$, —C(O)N($R^{1B1}$)($R^{1B2}$), —N$R^{1B1}$C(O)$R^{1B2}$, —N$R^{1B1}$C(O)N($R^{1B2}$)($R^{1B3}$), —S(O)$_{0-2}R^{1B1}$, —S(O)$_2$N($R^{1B1}$)($R^{1B2}$), and —N$R^{1B1}$S(O)$_2R^{1B2}$, wherein each $R^{1B1}$, $R^{1B2}$, and $R^{1B3}$ is independently hydrogen, or $C_{1-6}$ alkyl, wherein each $R^{1A}$ alkyl, cycloalkyl, heterocyclyl, aryl, and heteroaryl is optionally substituted with 1 to 4 $R^{1C}$, which can be the same or different, and wherein each $R^{1C}$ is independently $C_{1-4}$ alkyl, halogen, cyano, —O—$R^{1D1}$, —N($R^{1D1}$)($R^{1D2}$), and wherein each $R^{1D1}$ and $R^{1D2}$ is independently hydrogen or $C_{1-6}$ alkyl; or $R^1$ is —O—$R^{1D1}$ or —N($R^{1D1}$)($R^{1D2}$), wherein each $R^{1D1}$ and $R^{1D2}$ is independently hydrogen, $C_{1-6}$ alkyl, or $C_{3-6}$ cycloalkyl, wherein each $C_{1-6}$ alkyl, or $C_{3-6}$ cycloalkyl is optionally substituted with 1 to 4 $R^{1E}$, which can be the same or different, wherein each $R^{1E}$ is independently selected from halogen, cyano, hydroxy, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —O—$R^{1F1}$, —N($R^{1F1}$)($R^{1F2}$), —C(O)N($R^{1F1}$)($R^{1F2}$), —N$R^{1F1}$C(O)$R^{1F2}$, —S(O)$_{0-2}R^{1F1}$, —S(O)$_2$N($R^{1F1}$)($R^{1F2}$), and —N$R^{1F1}$S(O)$_2R^{1F2}$, wherein each $R^{1F1}$ and $R^{1F2}$ is independently hydrogen or $C_{1-6}$ alkyl, wherein each $R^{1E}$ alkyl, cycloalkyl, aryl, and heteroaryl is optionally substituted with 1 to 3 $R^{1G}$, which can be the same or different, and wherein each $R^{1G}$ is independently $C_{1-4}$ alkyl, $C_{1-4}$ alkoxy, hydroxy, halogen, or cyano;

$R^2$ is hydrogen or $C_{1-6}$ alkyl optionally substituted with 1 to 3 substituents, which can be the same or different, independently selected from halogen, cyano, $C_{1-4}$ alkoxy, and $C_{3-10}$ cycloalkyl; or $R^2$ is $C_{3-6}$ cycloalkyl optionally substituted with 1 to 3 substituents, which can be the same or different, independently selected from halogen, cyano, $C_{1-4}$ alkoxy, and $C_{1-6}$ alkyl;

each $R^3$ is independently selected from deuterium, halogen, $C_{1-6}$ alkyl, $C_{3-6}$ cycloalkyl, —O—$R^{2A1}$, and —N($R^{2A1}$)($R^{2A2}$), wherein the $C_{1-6}$ alkyl is optionally substituted with 1 to 3 substituents, which can be the same or different, independently selected from $C_{1-4}$ alkoxy and halogen, and wherein each $R^{241}$ and $R^{242}$ is independently hydrogen or $C_{1-3}$ alkyl optionally substituted with 1 to 3 halogens, which can be the same or different;

n is 0, 1, 2, 3, or 4;

$R^4$ is $C_{1-6}$ alkyl optionally substituted with 1 to 3 substituents, which can be the same or different, independently selected from halogen, cyano, $C_{1-4}$ alkoxy, —C(O)N($R^{441}$), and —N($R^{441}$)($R^{442}$), wherein each $R^{441}$ and $R^{442}$ is independently hydrogen, $C_{1-6}$ alkyl, or $C_{3-10}$ cycloalkyl; or $R^4$ is $C_{3-6}$ cycloalkyl or 3 to 6 membered heterocyclyl having 1 or 2 heteroatoms independently selected from nitrogen, oxygen, and sulfur, wherein the cycloalkyl or heterocyclyl are optionally substituted with 1 to 3 substituents, which can be the same or different, independently selected from halogen, cyano, $C_{1-4}$ alkyl and $C_{1-4}$ alkoxy;

each of $X^1$, $X^2$, $X^3$, and $X^4$ is independently selected from CH and N;

each $Y^1$ and $Y^2$ is independently hydrogen, deuterium, or $C_{1-6}$ alkyl optionally substituted with 1 to 3 substituents, which can be the same or different, independently selected from deuterium, halogen, cyano, $C_{2-3}$ alkynyl, $C_{1-4}$ alkoxy, and —C(O)NH—($C_{1-4}H_{3-9}$); and Z is $C_{1-8}$ alkyl, $C_{1-6}$ alkoxy, $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the alkyl, alkoxy, cycloalkyl, aryl, heterocyclyl, or heteroaryl are each optionally substituted with 1 to 3 substituents, which can be the same or different, independently selected from halogen, cyano, $C_{1-4}$ alkyl, $C_{1-4}$ alkoxy, and $C_{3-6}$ cycloalkyl, wherein the $C_{1-4}$ alkyl is optionally substituted with 1 to 3 substituents, which can be the same or different, selected from $C_{1-4}$ alkoxy and halogen; or $Y^1$ and Z together with the carbon to which they are attached form $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the cycloalkyl, aryl, heterocyclyl, or heteroaryl are each optionally substituted with 1 to 3 substituents, which can be the same or different, independently selected from cyano, $C_{1-4}$ alkyl, $C_{1-4}$ alkoxy, $C_{6-10}$ aryl, and halogen, wherein the $C_{1-4}$ alkyl is optionally substituted with 1 to 3 substituents, which can be the same or different, independently selected from $C_{1-4}$ alkoxy and halogen, and wherein the $C_{6-10}$ aryl is optionally substituted with 1 to 3 substituents, which can be the same or different, independently selected from $C_{1-4}$ alkyl, $C_{1-4}$ alkoxy, and halogen, and $Y^2$ is hydrogen or deuterium.

In some embodiments, provided herein are pharmaceutical compositions comprising a compound provided herein, or pharmaceutically acceptable salt thereof, and a pharmaceutically acceptable excipient or carrier. In some embodiments, the pharmaceutical compositions comprise a therapeutically effective amount of a compound provided herein, or pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or pharmaceutically acceptable salts thereof. In some embodiments, the pharmaceutical compositions further comprise a therapeutically effective amount of the one or more (e.g., one, two, three, four, one or two, one to three, or one to four) additional therapeutic agents, or pharmaceutically acceptable salts thereof.

In some embodiments, the present disclosure provides methods of inhibiting LPAR1 activity in a subject in need thereof, comprising administering to the subject a therapeutically effective amount of a compound provided herein (e.g., a compound of Formula (I), (Ia), (IIa), (IIb), (IIc), (IId), (IIe), (IIf), (IIg), (IIh), or (IIi)), or pharmaceutically acceptable salt thereof, or a pharmaceutical composition provided herein.

In some embodiments, the present disclosure provides methods of treating a patient having an LPAR1 mediated condition, comprising administering to the patient a therapeutically effective amount of a compound provided herein (e.g., a compound of Formula (I), (Ia), (IIa), (IIa), (IIc), (IId), (IIe), (IIf), (IIg), (IIh), or (IIi)), or pharmaceutically acceptable salt thereof, or a pharmaceutical composition provided herein.

DETAILED DESCRIPTION

The present disclosure relates to LPA receptor antagonists, such as antagonists of LPAR1. The disclosure also relates to compositions and methods relating to LPAR1 antagonists and the use of such compounds for treatment and/or prophylaxis of LPAR1-mediated diseases and conditions. The disclosure also relates to compositions and methods of treating and/or preventing liver disease including an LPAR1 antagonist in combination with one or more additional therapeutic agents.

It is commonly believed that patients with certain LPAR1-mediated diseases, such as cancer, fibrosis, inflammation, pain, and cardiovascular diseases, or liver diseases including non-alcoholic fatty liver disease (NAFLD) and non-alcoholic steatohepatitis (NASH) can benefit from the treatment with an LPAR1 antagonist and optionally one or more additional therapeutic agents.

Definitions and General Parameters

The description below is made with the understanding that the present disclosure is to be considered as an exemplification of the claimed subject matter and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

As used in the present specification, the following terms and phrases are generally intended to have the meanings as set forth below, except to the extent that the context in which they are used indicates otherwise.

A dash ("—") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named. A solid line coming out of the center of a ring indicates that the point of attachment for a substituent on the ring can be at any ring atom. For example, R$^a$ in the below structure can be attached to any of the five carbon ring atoms or R$^a$ can replace the hydrogen attached to the nitrogen ring atom:

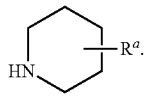

The prefix "C$_{u-v}$" indicates that the following group has from u to v carbon atoms. For example, "C$_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (e.g., 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" or "a compound provided herein" or "a compound described herein" refers to the compounds of Formula (I), (Ia), (IIa), (IIb), (IIc), (IId), (IIe), (IIf), (IIg), (IIh), or (IIi). Also included are the specific Compounds 1 to 338 provided herein (e.g., Examples 1-92).

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 8 carbon atoms (i.e., C$_{1-8}$ alkyl), 1 to 6 carbon atoms (i.e., C$_{1-6}$ alkyl), 1 to 4 carbon atoms (i.e., C$_{1-4}$ alkyl), or 1 to 3 carbon atoms (i.e., C$_{1-3}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

"Alkenyl" refers to an aliphatic group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., C$_{2-20}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethylcarbonyl, and benzoyl.

"Amino" refers to the group —NR$^y$R$^z$ wherein R$^y$ and R$^z$ are independently selected from the group consisting of hydrogen, alkyl, haloalkyl, aryl, heteroaryl, cycloalkyl, or heterocyclyl; each of which may be optionally substituted.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e., the cyclic group having at least one double bond). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl.

"Fused" refers to a ring which is bound to an adjacent ring. In some embodiments the fused ring system is a heterocyclyl. In some embodiments the fused ring system is a oxabicyclohexanyl. In some embodiments the fused ring system is

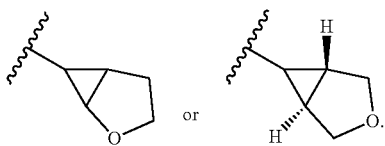 [SMILES: *C1C2CCOC12 ; *C1[C@@H]2COC[C@@H]12]

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems. In some embodiments the bridged ring is a bicyclopentanyl (bicycle [1.1.1]pentanyl) or bicyclooctanyl (bicycle[2.2.2]octanyl). In some embodiments, the bridge ring is

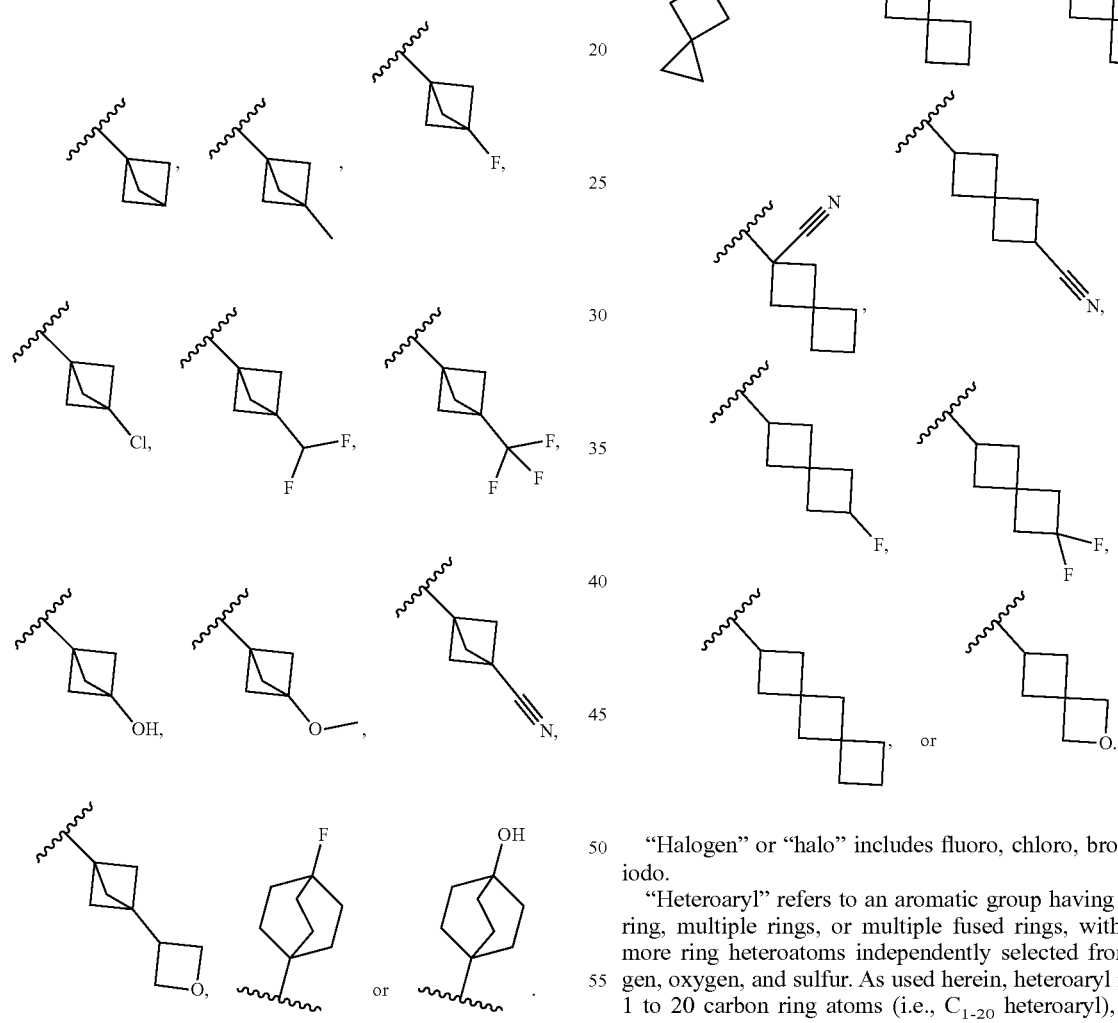

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents. In some embodiments the spiro substituent is a spiropentanyl (spiro [a.b]pentanyl), spirohexanyl, spiroheptanyl, or spirodecanyl. In some embodiments the spiro substituent is "Halogen" or "halo" includes fluoro, chloro, bromo, and iodo.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 carbon ring atoms (i.e., $C_{1-20}$ heteroaryl), 3 to 12 carbon ring atoms (i.e., $C_{3-12}$ heteroaryl), or 3 to 8 carbon ring atoms (i.e., $C_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" or "heterocycle" refers to a non-aromatic cyclic alkyl group, with one or more ring heteroatoms independently selected from nitrogen, oxygen and sulfur. As used herein, "heterocyclyl" or "heterocyclic ring" or "heterocycle" refer to rings that are saturated or partially saturated unless otherwise indicated, e.g., in some embodiments "heterocyclyl" or "heterocyclic ring" or "heterocycle" refers to rings that are partially saturated where specified. The term "heterocyclyl" or "heterocyclic ring" or "heterocycle" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 carbon ring atoms (i.e., $C_{2-20}$ heterocyclyl), 2 to 12 carbon ring atoms (i.e., $C_{2-12}$ heterocyclyl), 2 to 10 carbon ring atoms (i.e., $C_{2-10}$ heterocyclyl), 2 to 8 carbon ring atoms (i.e., $C_{2-8}$ heterocyclyl), 3 to 12 carbon ring atoms (i.e., $C_{3-12}$ heterocyclyl), 3 to 8 carbon ring atoms (i.e., $C_{3-8}$ heterocyclyl), or 3 to 6 carbon ring atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the terms "heterocycle", "heterocyclyl", and "heterocyclic ring" are used interchangeably.

"Hydroxy" or "hydroxyl" refers to the group —OH.

"Oxo" refers to the group (=O) or (O).

"Sulfonyl" refers to the group —$S(O)_2R^c$, where $R^c$ is alkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —$NH_2$ group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, amino, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, amino, alkoxy, halo, oxo, and hydroxyl; "substituted heterocyclyl" refers to a heterocyclyl group having one or more substituents including alkyl, amino, haloalkyl, heterocyclyl, cycloalkyl, aryl, heteroaryl, alkoxy, halo, oxo, and hydroxyl; "substituted aryl" refers to an aryl group having one or more substituents including halo, alkyl, amino, haloalkyl, cycloalkyl, heterocyclyl, heteroaryl, alkoxy, and cyano; "substituted heteroaryl" refers to an heteroaryl group having one or more substituents including halo, amino, alkyl, haloalkyl, cycloalkyl, aryl, heterocyclyl, heteroaryl, alkoxy, and cyano and "substituted sulfonyl" refers to a group —$S(O)_2R$, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

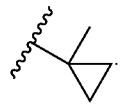 [SMILES: *C1(C)CC1]

The disclosures illustratively described herein may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. In case the compounds of the present disclosure contain one or more acidic or basic groups, the disclosure also comprises their corresponding pharmaceutically or toxicologically acceptable salts, in particular their pharmaceutically utilizable salts. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine, amino acids, or other bases known to persons skilled in the art. The compounds of the present disclosure which contain one or more basic groups, i.e., groups which can be protonated, can be present and can be used according to the disclosure in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to persons skilled in the art.

If the compounds of the present disclosure simultaneously contain acidic and basic groups in the molecule, the disclosure also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts.

The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources.

Furthermore, compounds disclosed herein may be subject to tautomerism. Where tautomerism, e.g., keto-enol tautomerism, of compounds or their prodrugs may occur, the individual forms, like, e.g., the keto and enol form, are each within the scope of the disclosure as well as their mixtures in any ratio. The same applies for stereoisomers, like, e.g., enantiomers, cis/trans isomers, diastereomers, conformers, and the like.

The term "protecting group" refers to a moiety of a compound that masks or alters the properties of a functional group or the properties of the compound as a whole. Chemical protecting groups and strategies for protection/deprotection are well known in the art. See e.g., Protective Groups in Organic Chemistry, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. The term "deprotecting" refers to removing the protecting group.

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

Further the compounds of the present disclosure may be present in the form of solvates, such as those which include as solvate water, or pharmaceutically acceptable solvates, such as alcohols, in particular ethanol. A "solvate" is formed by the interaction of a solvent and a compound.

In certain embodiments, provided are optical isomers, racemates, or other mixtures thereof of the compounds described herein or a pharmaceutically acceptable salt or a mixture thereof. If desired, isomers can be separated by methods well known in the art, e.g., by liquid chromatography. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high-pressure liquid chromatography (HPLC) column.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another. "Diastereomers" are stereoisomers that have at least two asymmetric atoms, but which are not mirror-images of each other.

Compounds disclosed herein and their pharmaceutically acceptable salts may, in some embodiments, include an asymmetric center and may thus give rise to enantiomers, diastereomers, and other stereoisomeric forms that may be defined, in terms of absolute stereochemistry, as (R)- or (S)- or, as (D)- or (L)- for amino acids. Some embodiments include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres of geometric asymmetry, and unless specified otherwise, it is intended that the compounds include both E and Z geometric isomers.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphoros, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The disclosure also includes "deuterated analogs" of compounds disclosed herein, in which from 1 to n hydrogens attached to a carbon atom is/are replaced by deuterium, in which n is the number of hydrogens in the molecule. Such compounds may exhibit increased resistance to metabolism and thus be useful for increasing the half-life of any compound of Formula (I) when administered to a mammal, e.g., a human. See, e.g., Foster, "Deuterium Isotope Effects in Studies of Drug Metabolism," Trends Pharmacol. Sci. 5(12): 524-527 (1984). Such compounds are synthesized by means well known in the art, for example by employing starting materials in which one or more hydrogens have been replaced by deuterium.

Deuterium labelled or substituted therapeutic compounds of the disclosure may have beneficial DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Furthermore, the present disclosure provides pharmaceutical compositions comprising a compound of the present disclosure, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure can encompass any composition made by admixing at least one compound of the present disclosure and a pharmaceutically acceptable carrier.

As used herein, "pharmaceutically acceptable carrier" includes excipients or agents such as solvents, diluents, dispersion media, coatings, antibacterial and antifungal agents, isotonic and absorption delaying agents and the like that are not deleterious to the disclosed compound or use thereof. The use of such carriers and agents to prepare compositions of pharmaceutically active substances is well known in the art (see, e.g., Remington's Pharmaceutical Sciences, Mace Publishing Co., Philadelphia, PA 17th Ed. (1985); and Modern Pharmaceutics, Marcel Dekker, Inc. 3rd Ed. (G.S. Banker & C.T. Rhodes, Eds.).

"IC$_{50}$" or "EC$_{50}$" refers to the inhibitory concentration required to achieve 50% of the maximum desired effect. In many cases here the maximum desired effect is the inhibition of LPA induced LPAR1 activation. This term is obtained using an in vitro assay, such as a calcium mobilization assay, evaluating the concentration-dependent inhibition of LPA induced LPAR1 activity.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival. In some embodiments, the term "treatment" or "treating" means administering a compound or pharmaceutically acceptable salt of Formula (I), (Ia), (IIa), (IIb), (IIc), (IId), (IIe), (IIf), (IIg), (IIh), or (IIi) for the purpose of: (i) delaying the onset of a disease, that is, causing the clinical symptoms of the disease not to develop or delaying the development thereof; (ii) inhibiting the disease, that is, arresting the development of clinical symptoms; and/or (iii) relieving the disease, that is, causing the regression of clinical symptoms or the severity thereof.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In some embodiments, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to LPAR1 antagonists. The therapeutically effective amount may vary depending on the subject, and disease or condition being treated, the weight and age of the subject, the severity of the disease or condition, and the manner of administering, which can readily be determined by one or ordinary skill in the art.

List of Abbreviations and Acronyms

| Abbreviation | Meaning |
|---|---|
| ACN or MeCN | Acetonitrile |
| aq. | Aqueous |
| Bn | Benzyl |
| COPD | Chronic Obstructive Pulmonary Disease |
| DCM | Dichloromethane |
| DIEA | N,N-Diisopropylethylamine |
| DMF | N,N-Dimethylformamide |
| DMSO | Dimethylsulfoxide |
| DPPA | Diphenylphosphoryl azide |
| EA | Ethyl acetate |
| EDTA | Ethylenediaminetetraacetic acid |
| ESI | Electronspray Ionization |
| Et | Ethyl |
| Et$_2$O | Diethyl ether |
| EtOAc | Ethyl acetate |
| h or hr(s) | Hour(s) |
| HBSS | Hanks' Balanced Salt solution |
| HCC | Hepatocellular carcinoma |
| HPLC | High performance liquid chromatography |
| LCMS or LC/MS | Liquid Chromatography Mass Spectrometry |
| LPA | Lysophosphatidic acid |
| LPC | Lysophosphatidylcholine |
| Me | Methyl |
| MeOH | Methanol |
| MS | Mass Spectrometry |
| m/z | Mass-to-charge ratio |
| NADPH | Dihydronicotinamide-adenine dinucleotide phosphate |
| NAFLD | Non-alcoholic fattyl liver disease |
| NASH | Non-alcoholic steatohepatitis |
| NMR | Nuclear Magnetic Resonance spectroscopy |
| PBC | Primary Biliary Cirrhosis |
| PE | Petroleum ether |
| PSC | Primary Sclerosing Choleangitis |
| rpm | Revolutions per minute |
| RT or rt | Room temperature |
| sat. | Saturated |
| TEMPO | 2,2,6,6-Tetramethylpiperidine 1-oxyl |
| TFA | Trifluoroacetic acid |
| THF | Tetrahydrofuran |
| T3P | Propanephosphonic acid anhydride |

As used herein, an "LPAR1 antagonist" refers to any agent that is capable of binding and inhibiting LPAR1. LPAR1, also known as LPA$_1$, is a GPCR that binds the lipid signaling molecule lysophosphatidic acid (LPA). Exemplary reference sequences for LPAR1 include the NCBI Reference Sequences NP_001392 (human protein), NP_001277415 (mouse protein), NM_001401 (human mRNA), and NM_001290486 (mouse mRNA). LPAR1 antagonists can act as competitive inhibitors of full or partial LPAR1 agonists, or as inverse agonists. The activity of an LPAR antagonist may be measured by methods known in the art, such as those described and cited in Castelino et al., 2010 Arthritis Rheum. 2011 May; 63(5): 1405-1415 or Swaney et al., J Pharmacol Exp Ther. 2011 March; 336(3):693-700.

As used herein, an "ACC inhibitor" refers to any agent that is capable of binding and inhibiting Acetyl-CoA carboxylase (ACC). ACC inhibitors can act as inhibitors or partial inhibitors of ACC. The agent can be a chemical compound or biological molecule (e.g., a protein or antibody). The activity of an ACC inhibitor can be measured by methods known in the art, such as those described and cited in U.S. Pat. No. 8,969,557 and/or in U.S. Pat. No. 10,208,063, both of which are incorporated herein by reference in their entirety.

As referred to herein, an "ASK1 inhibitor" can be any agent that is capable of inactivating an apoptosis signal regulating kinase 1 (ASK1) protein. The agent can be a chemical compound or biological molecule (e.g., a protein or antibody). The ASK1 protein activity can be measured by several different methods. For example, the activity of an ASK1 protein can be determined based on the ability of the ASK1 protein to phosphorylate a substrate protein. Methods for identifying an ASK1 inhibitor are known (see, e.g., U.S. 2007/0276050). Exemplary ASK1 substrate proteins include MAPKK3, MAPKK4, MAPKK6, MAPKK7, or fragments thereof. The ASK1 protein activity can also be measured by the phosphorylation level of the ASK1 protein, for example, the phosphorylation level of a threonine residue in the ASK1 protein corresponding to threonine 838 (T838) of a human full-length ASK1 protein or threonine 845 (T845) of a mouse full-length ASK1 protein. For example, where the ASK1 protein comprises a full-length human ASK1 protein sequence, an ASK1 inhibitor may attenuate phosphorylation of T838 in the full-length human ASK1 protein sequence. A site-specific antibody against human ASK1 T838 or mouse ASK1 T845 may be used to detect the phosphohorylation level.

As used herein, a "FXR agonist" refers to any agent that is capable of binding and activating farnesoid X receptor (FXR) which can be referred to as bile acid receptor (BAR) or NR1H4 (nuclear receptor subfamily 1, group H, member 4) receptor. FXR agonists can act as agonists or partial agonists of FXR. The agent can be a chemical compound or biological molecule (e.g., a protein or antibody). The activity of an FXR agonist can be measured by several different methods, e.g., in an in vitro assay using the fluorescence resonance energy transfer (FRET) cell free assay as described in Pellicciari, et al. Journal of Medicinal Chemistry, 2002 vol. 15, No. 45:3569-72.

Compounds

In one embodiment, provided herein is a compound of Formula (I),

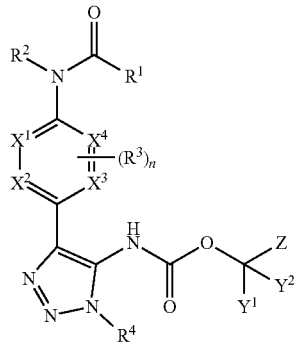

(I)

or a pharmaceutically acceptable salt thereof,
wherein:
$R^1$ is hydrogen, $C_{1-6}$ alkyl, $C_{2-6}$ alkenyl, $C_{2-6}$ alkynyl, $C_{3-10}$ cycloalkyl, 3 to 10 membered heterocyclyl having 1 to 4 heteroatoms independently selected from nitrogen, oxygen, and sulfur, 6 to 10 membered aryl, or 5 to 10 membered heteroaryl having 1 to 4 heteroatoms independently selected from nitrogen, oxygen, and sulfur, wherein each alkyl, alkenyl, alkynyl, cycloalkyl, heterocyclyl, aryl, or heteroaryl is optionally substituted with 1 to 4 $R^{1A}$, which can be the same or different, wherein each $R^{1A}$ is independently selected from halogen, cyano, nitro, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, $-N(R^{1B1})(R^{1B2})$, $-O-R^{1B1}$, $-S-R^{1B1}$, $-C(O)N(R^{1B1})(R^{1B2})$, $-NR^{1B1}C(O)R^{1B2}$, $-NR^{1B1}C(O)N(R^{1B2})(R^{1B3})$, $-S(O)_{0-2}R^{1B1}$, $-S(O)_2N(R^{1B1})(R^{1B2})$, and $-NR^{1B1}S(O)_2R^{1B2}$, wherein each $R^{1B1}$, $R^{1B2}$, and $R^{1B3}$ is independently hydrogen, $C_{1-6}$ alkyl, or $C_{3-6}$ cycloalkyl,
wherein each $R^{1A}$ alkyl, cycloalkyl, heterocyclyl, aryl, and heteroaryl is optionally substituted with 1 to 4 $R^{1C}$, which can be the same or different, and wherein each $R^{1C}$ is independently $C_{1-4}$ alkyl, halogen, cyano, $-O-R^{1D1}$, or $-N(R^{1D1})(R^{1D2})$, wherein each $R^{1D1}$ and $R^{1D2}$ is independently hydrogen or $C_{1-6}$ alkyl, and
wherein each $R^{1B1}$, $R^{1B2}$, and $R^{1B3}$ alkyl and each $R^{1B1}$, $R^{1B2}$, and $R^{1B3}$ cycloalkyl is optionally substituted with 1 to 3 halogens or
$R^1$ is $-O-R^{1D1}$ or $-N(R^{1D1})(R^{1D2})$, wherein each $R^{1D1}$ and $R^{1D2}$ is independently hydrogen, $C_{1-6}$ alkyl, or $C_{3-6}$ cycloalkyl, wherein each $C_{1-6}$ alkyl, or $C_{3-6}$ cycloalkyl is optionally substituted with 1 to 4 $R^{1E}$, which can be the same or different, wherein each $R^{1E}$ is independently selected from halogen, cyano, hydroxy, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, $-O-R^{1F1}$, $-N(R^{1F1})(R^{1F2})$, $-C(O)N(R^{1F1})(R^{1F2})$, $-NR^{1F1}C(O)R^{1F2}$, $-S(O)_{0-2}R^{1F1}$, $-S(O)_2N(R^{1F1})(R^{1F2})$, and $-NR^{1F1}S(O)_2R^{1F2}$, wherein each $R^{1F1}$ and $R^{1F2}$ is independently hydrogen or $C_{1-6}$ alkyl, wherein each $R^{1E}$ alkyl, cycloalkyl, aryl, and heteroaryl is optionally substituted with 1 to 3 $R^{1G}$, which can be the same or different, and wherein each $R^{1G}$ is independently $C_{1-4}$ alkyl, $C_{1-4}$ alkoxy, hydroxy, halogen, or cyano;
$R^2$ is hydrogen or $C_{1-6}$ alkyl optionally substituted with 1 to 3 substituents, which can be the same or different, independently selected from halogen, cyano, $C_{1-4}$ alkoxy, and $C_{3-10}$ cycloalkyl; or
$R^2$ is $C_{3-6}$ cycloalkyl optionally substituted with 1 to 3 substituents, which can be the same or different, independently selected from halogen, cyano, $C_{1-4}$ alkoxy, and $C_{1-6}$ alkyl;
each $R^3$ is independently selected from deuterium, halogen, $C_{1-6}$ alkyl, $C_{3-6}$ cycloalkyl, $-O-R^{2A1}$, and $-N(R^{2A1})(R^{2A2})$, wherein the $C_{1-6}$ alkyl is optionally substituted with 1 to 3 substituents, which can be the same or different, independently selected from $C_{1-4}$ alkoxy and halogen, and wherein each $R^{2A1}$ and $R^{2A2}$ is independently hydrogen or $C_{1-3}$ alkyl optionally substituted with 1 to 3 halogens, which can be the same or different;
n is 0, 1, 2, 3, or 4;
$R^4$ is $C_{1-6}$ alkyl optionally substituted with 1 to 3 substituents, which can be the same or different, independently selected from halogen, cyano, $C_{1-4}$ alkoxy, $-C(O)N(R^{4A1})(R^{4A2})$, and $-N(R^{4A1})(R^{4A2})$, wherein each $R^{4A1}$ and $R^{4A2}$ is independently hydrogen, $C_{1-6}$ alkyl, or $C_{3-10}$ cycloalkyl; or
$R^4$ is $C_{3-6}$ cycloalkyl or 3 to 6 membered heterocyclyl having 1 or 2 heteroatoms independently selected from nitrogen, oxygen, and sulfur, wherein the cycloalkyl or heterocyclyl are optionally substituted with 1 to 3 substituents, which can be the same or different, independently selected from halogen, cyano, $C_{1-4}$ alkyl and $C_{1-4}$ alkoxy;
each of $X^1$, $X^2$, $X^3$, and $X^4$ is independently selected from CH and N;
each $Y^1$ and $Y^2$ is independently hydrogen, deuterium, or $C_{1-6}$ alkyl optionally substituted with 1 to 3 substituents, which can be the same or different, independently selected from deuterium, halogen, cyano, $C_{2-3}$ alkynyl, $C_{1-4}$ alkoxy, and $-C(O)NH-(C_{1-4}H_{3-9})$; and
Z is $C_{1-8}$ alkyl, $C_{1-6}$ alkoxy, $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the alkyl, alkoxy, cycloalkyl, aryl, heterocyclyl, or heteroaryl are each optionally substituted with 1 to 3 substituents, which can be the same or different, independently selected from halogen, cyano, $C_{1-4}$ alkyl, $C_{1-4}$ alkoxy, and $C_{3-6}$ cycloalkyl, wherein the $C_{1-4}$ alkyl is optionally substituted with 1 to 3 substituents, which can be the same or different, selected from $C_{1-4}$ alkoxy and halogen; or
$Y^1$ and Z together with the carbon to which they are attached form $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the cycloalkyl, aryl, heterocyclyl, or heteroaryl are each optionally substituted with 1 to 3 substituents, which can be the same or different, independently selected from cyano, $C_{1-4}$ alkyl, $C_{1-4}$ alkoxy, $C_{6-10}$ aryl, and halogen, wherein the $C_{1-4}$ alkyl is optionally substituted with 1 to 3 substituents, which can be the same or different, independently selected from $C_{1-4}$ alkoxy and halogen, and wherein the $C_{6-10}$ aryl is optionally substituted with 1 to 3 substituents, which can be the same or different, independently selected from $C_{1-4}$ alkyl, $C_{1-4}$ alkoxy, and halogen, and $Y^2$ is hydrogen or deuterium.

In some embodiments of the compound of Formula I or pharmaceutically acceptable salt thereof $R^1$ is hydrogen, $C_{1-6}$ alkyl, $C_{2-6}$ alkenyl, $C_{2-6}$ alkynyl, $C_{3-10}$ cycloalkyl, 3 to 10 membered heterocyclyl having 1 to 4 heteroatoms independently selected from nitrogen, oxygen, and sulfur, 6 to 10 membered aryl, or 5 to 10 membered heteroaryl having 1 to 4 heteroatoms independently selected from nitrogen, oxygen, and sulfur, wherein each alkyl, alkenyl, alkynyl, cycloalkyl, heterocyclyl, aryl, or heteroaryl is optionally substituted with 1 to 4 $R^{1A}$, which can be the same or different, wherein each $R^{1A}$ is independently selected from halogen, cyano, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, $—N(R^{1B1})(R^{1B2})$, $—O—R^{1B1}$, $—S—R^{1B1}$, $—C(O)N(R^{1B1})(R^{1B2})$, $—NR^{1B1}C(O)R^{1B2}$, $—NR^{1B1}C(O)N(R^{1B2})(R^{1B3})$, $—S(O)_{0-2}R^{1B1}$, $—S(O)_2N(R^{1B1})(R^{1B2})$, and $—NR^{1B1}S(O)_2R^{1B2}$, wherein each $R^{1B1}$, $R^{1B2}$, and $R^{1B3}$ is independently hydrogen, or $C_{1-6}$ alkyl,
wherein each $R^{1A}$ alkyl, cycloalkyl, heterocyclyl, aryl, and heteroaryl is optionally substituted with 1 to 4 $R^{1C}$, which can be the same or different, and wherein each $R^{1C}$ is independently $C_{1-4}$ alkyl, halogen, cyano, $—O—R^{1D1}$, or $—N(R^{1D1})(R^{1D2})$, and wherein each $R^{1D1}$ and $R^{1D2}$ is independently hydrogen or $C_{1-6}$ alkyl; or $R^1$ is $—O—R^{1D1}$ or $—N(R^{1D1})(R^{1D2})$, wherein each $R^{1D1}$ and $R^{1D2}$ is independently hydrogen, $C_{1-6}$ alkyl, or $C_{3-6}$ cycloalkyl, wherein each $C_{1-6}$ alkyl, or $C_{3-6}$ cycloalkyl is optionally substituted with 1 to 4 $R^{1E}$, which can be the same or different, wherein each $R^{1E}$ is independently selected from halogen, cyano, hydroxy, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, $—O—R^{1F1}$, $—N(R^{1F1})(R^{1F2})$, $—C(O)N(R^{1F1})(R^{1F2})$, $—NR^{1F1}C(O)R^{1F2}$, $—S(O)_{0-2}R^{1F1}$, $—S(O)_2N(R^{1F1})(R^{1F2})$, and $—NR^{1F1}S(O)_2R^{1F2}$, wherein each $R^{1F1}$ and $R^{1F2}$ is independently hydrogen or $C_{1-6}$ alkyl, wherein each $R^{1E}$ alkyl, cycloalkyl, aryl, and heteroaryl is optionally substituted with 1 to 3 $R^{1G}$, which can be the same or different, and wherein each $R^{1G}$ is independently $C_{1-4}$ alkyl, $C_{1-4}$ alkoxy, hydroxy, halogen, or cyano;

$R^2$ is hydrogen or $C_{1-6}$ alkyl optionally substituted with 1 to 3 substituents, which can be the same or different, independently selected from halogen, cyano, $C_{1-4}$ alkoxy, and $C_{3-10}$ cycloalkyl; or $R^2$ is $C_{3-6}$ cycloalkyl optionally substituted with 1 to 3 substituents, which can be the same or different, independently selected from halogen, cyano, $C_{1-4}$ alkoxy, and $C_{1-6}$ alkyl;

each $R^3$ is independently selected from deuterium, halogen, $C_{1-6}$ alkyl, $C_{3-6}$ cycloalkyl, $—O—R^{241}$, and $—N(R^{241})(R^{242})$, wherein the $C_{1-6}$ alkyl is optionally substituted with 1 to 3 substituents, which can be the same or different, independently selected from $C_{1-4}$ alkoxy and halogen, and wherein each $R^{241}$ and $R^{242}$ is independently hydrogen or $C_{1-3}$ alkyl optionally substituted with 1 to 3 halogens, which can be the same or different;

n is 0, 1, 2, 3, or 4;

$R^4$ is $C_{1-6}$ alkyl optionally substituted with 1 to 3 substituents, which can be the same or different, independently selected from halogen, cyano, $C_{1-4}$ alkoxy, $—C(O)N(R^{4A1})$, and $—N(R^{4A1})(R^{4A2})$, wherein each $R^{4A1}$ and $R^{4A2}$ is independently hydrogen, $C_{1-6}$ alkyl, or $C_{3-10}$ cycloalkyl; or $R^4$ is $C_{3-6}$ cycloalkyl or 3 to 6 membered heterocyclyl having 1 or 2 heteroatoms independently selected from nitrogen, oxygen, and sulfur, wherein the cycloalkyl or heterocyclyl are optionally substituted with 1 to 3 substituents, which can be the same or different, independently selected from halogen, cyano, $C_{1-4}$ alkyl and $C_{1-4}$ alkoxy;

each of $X^1$, $X^2$, $X^3$ and $X^4$ is independently selected from CH and N;

each $Y^1$ and $Y^2$ is independently hydrogen, deuterium, or $C_{1-6}$ alkyl optionally substituted with 1 to 3 substituents, which can be the same or different, independently selected from deuterium, halogen, cyano, $C_{2-3}$ alkynyl, $C_{1-4}$ alkoxy, and $—C(O)NH—(C_{1-4}H_{3-9})$; and Z is $C_{1-8}$ alkyl, $C_{1-6}$ alkoxy, $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the alkyl, alkoxy, cycloalkyl, aryl, heterocyclyl, or heteroaryl are each optionally substituted with 1 to 3 substituents, which can be the same or different, independently selected from halogen, cyano, $C_{1-4}$ alkyl, $C_{1-4}$ alkoxy, and $C_{3-6}$ cycloalkyl, wherein the $C_{1-4}$ alkyl is optionally substituted with 1 to 3 substituents, which can be the same or different, selected from $C_{1-4}$ alkoxy and halogen; or $Y^1$ and Z together with the carbon to which they are attached form $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the cycloalkyl, aryl, heterocyclyl, or heteroaryl are each optionally substituted with 1 to 3 substituents, which can be the same or different, independently selected from cyano, $C_{1-4}$ alkyl, $C_{1-4}$ alkoxy, $C_{6-10}$ aryl, and halogen, wherein the $C_{1-4}$ alkyl is optionally substituted with 1 to 3 substituents, which can be the same or different, independently selected from $C_{1-4}$ alkoxy and halogen, and wherein the $C_{6-10}$ aryl is optionally substituted with 1 to 3 substituents, which can be the same or different, independently selected from $C_{1-4}$ alkyl, $C_{1-4}$ alkoxy, and halogen, and $Y^2$ is hydrogen or deuterium.

In some embodiments, the compound of Formula (I), or pharmaceutically acceptable salt thereof, is a compound of Formula (Ia):

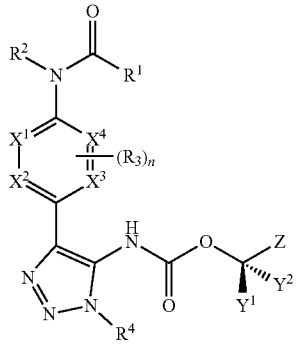

(Ia)

or pharmaceutically acceptable salt thereof.

In some embodiments of the compound of Formula (I) or (Ia), or pharmaceutically acceptable salt thereof, $R^2$ is hydrogen.

In some embodiments of the compound of Formula (I) or (Ia), or pharmaceutically acceptable salt thereof, $R^4$ is $C_{1-3}$ alkyl optionally substituted with 1 to 3 substituents, which can be the same or different, independently selected from cyano and F. In some embodiments of the compound of Formula (I) or (Ia), or pharmaceutically acceptable salt thereof, $R^4$ is —$CH_3$.

In some embodiments of the compound of Formula (I) or (Ia), or pharmaceutically acceptable salt thereof, $X^1$ is CH, $X^2$ is CH, $X^3$ is CH, and $X^4$ is CH.

In some embodiments of the compound of Formula (I) or (Ia), or pharmaceutically acceptable salt thereof, $X^1$ is $C(R^3)$, $X^2$ is CH, $X^3$ is CH, and $X^4$ is CH.

In some embodiments of the compound of Formula (I) or (Ia), or pharmaceutically acceptable salt thereof, $X^1$ is $C(R^3)$, $X^2$ is CH, $X^3$ is $C(R^3)$, and $X^4$ is CH.

In some embodiments of the compound of Formula (I) or (Ia), or pharmaceutically acceptable salt thereof, $X^1$ is N, $X^2$ is CH, $X^3$ is CH, and $X^4$ is $C(R^3)$.

In some embodiments of the compound of Formula (I) or (Ia), or pharmaceutically acceptable salt thereof, $X^1$ is CH, $X^2$ is N, $X^3$ is CH, and $X^4$ is $C(R^3)$.

In some embodiments of the compound of Formula (I) or (Ia), or pharmaceutically acceptable salt thereof, $X^1$ is $C(R^3)$, $X^2$ is N, $X^3$ is CH, and $X^4$ is CH.

In some embodiments of the compound of Formula (I) or (Ia), or pharmaceutically acceptable salt thereof, $X^1$ is $C(R^3)$, $X^2$ is N, $X^3$ is CH, and $X^4$ is $C(R^3)$.

In some embodiments of the compound of Formula (I) or (Ia), or pharmaceutically acceptable salt thereof, $X^1$ is $C(R^3)$, $X^2$ is CH, $X^3$ is $C(R^3)$, and $X^4$ is CH.

In some embodiments of the compound of Formula (I) or (Ia), or pharmaceutically acceptable salt thereof, $X^1$ is N, $X^2$ is CH, $X^3$ is N, and $X^4$ is $C(R^3)$.

In some embodiments of the compound of Formula (I) or (Ia), or pharmaceutically acceptable salt thereof, $X^1$ is $C(R^3)$, $X^2$ is N, $X^3$ is N, and $X^4$ is CH.

In some embodiments of the compound of Formula (I) or (Ia), or pharmaceutically acceptable salt thereof, $X^1$ is CH, $X^2$ is N, $X^3$ is N, and $X^4$ is CH.

In some embodiments of the compound of Formula (I) or (Ia), or pharmaceutically acceptable salt thereof, $X^1$ is N, $X^2$ is CH, $X^3$ is CH, and $X^4$ is CH.

In some embodiments of the compound of Formula (I) or (Ia), or pharmaceutically acceptable salt thereof, $X^1$ is N, $X^2$ is CH, $X^3$ is N, and $X^4$ is CH.

In some embodiments of the compound of Formula (I) or (Ia), or pharmaceutically acceptable salt thereof, $X^1$ is CH, $X^2$ is N, $X^3$ is $C(R^3)$, and $X^4$ is CH.

In some embodiments of the compound of Formula (I) or (Ia), or pharmaceutically acceptable salt thereof, $X^1$ is CH, $X^2$ is N, $X^3$ is CH, and $X^4$ is CH.

In some embodiments of the compound of Formula (I) or (Ia), or pharmaceutically acceptable salt thereof, $Y^2$ is hydrogen.

In some embodiments, the compound of Formula (I) or (Ia), or pharmaceutically acceptable salt thereof, is a compound of Formula (IIa):

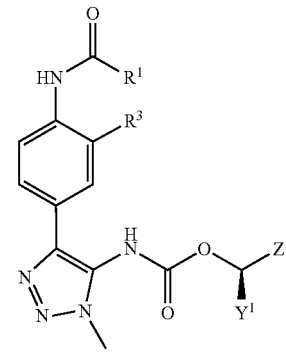

(IIa)

or a pharmaceutically acceptable salt thereof.

In some embodiments, the compound of Formula (I) or (Ia), or pharmaceutically acceptable salt thereof, is a compound of Formula (IIb):

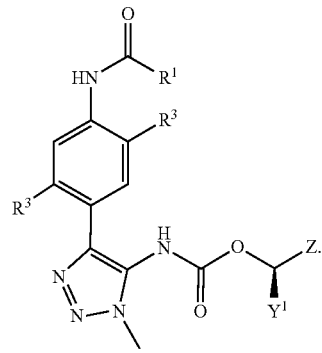

(IIb)

or a pharmaceutically acceptable salt thereof, wherein each $R^3$ can be the same or different.

In some embodiments, the compound of Formula (I) or (Ia), or pharmaceutically acceptable salt thereof, is a compound of Formula (IIc):

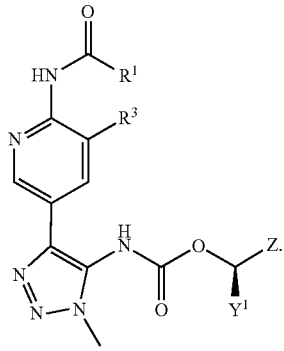

(IIc)

or a pharmaceutically acceptable salt thereof.

In some embodiments, the compound of Formula (I) or (Ia), or pharmaceutically acceptable salt thereof, is a compound of Formula (IId):

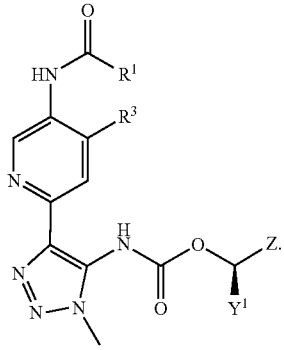

(IId)

or a pharmaceutically acceptable salt thereof.

In some embodiments, the compound of Formula (I) or (Ia), or pharmaceutically acceptable salt thereof, is a compound of Formula (IIe):

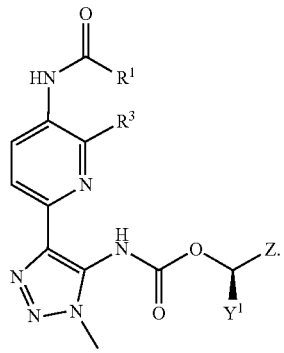

(IIe)

or a pharmaceutically acceptable salt thereof.

In some embodiments, the compound of Formula (I) or (Ia), or pharmaceutically acceptable salt thereof, is a compound of Formula (IIf):

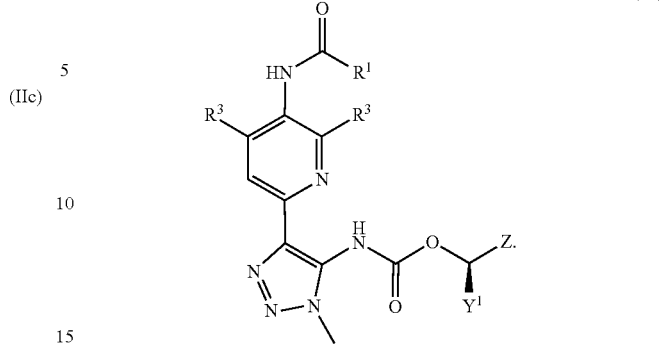

(IIf)

or a pharmaceutically acceptable salt thereof, wherein each $R^3$ can be the same or different.

In some embodiments, the compound of Formula (I) or (Ia), or pharmaceutically acceptable salt thereof, is a compound of Formula (IIg):

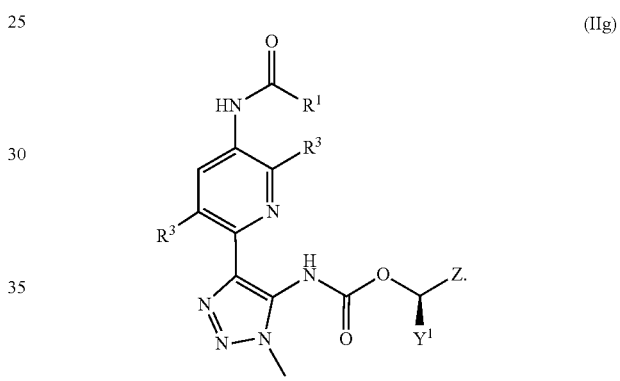

(IIg)

or a pharmaceutically acceptable salt thereof, wherein each $R^3$ can be the same or different.

In some embodiments, the compound of Formula (I) or (Ia), or pharmaceutically acceptable salt thereof, is a compound of Formula (IIh):

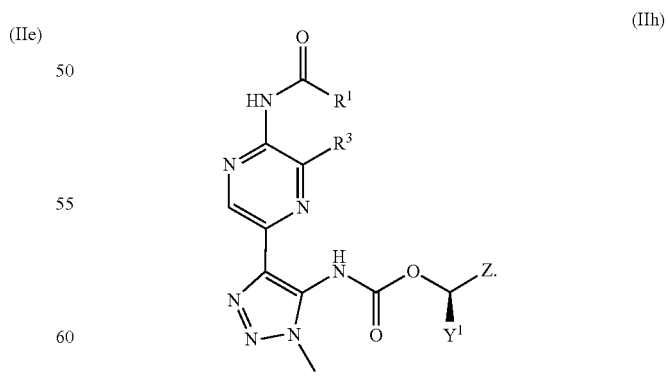

(IIh)

or a pharmaceutically acceptable salt thereof.

In some embodiments, the compound of Formula (I) or (Ia), or pharmaceutically acceptable salt thereof, is a compound of Formula (IIi):

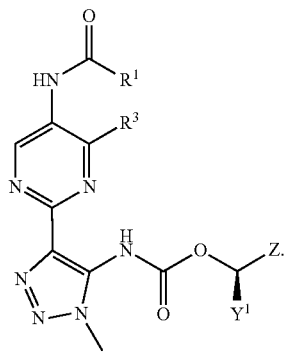

(IIi)

or a pharmaceutically acceptable salt thereof.

In some embodiments, the compound of Formula (I) or (Ia), or pharmaceutically acceptable salt thereof, is a compound of Formula (IIj):

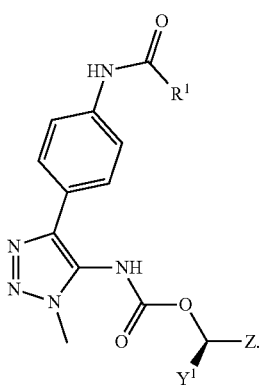

(IIj)

or a pharmaceutically acceptable salt thereof.

In some embodiments, the compound of Formula (I) or (Ia), or pharmaceutically acceptable salt thereof, is a compound of Formula (IIk):

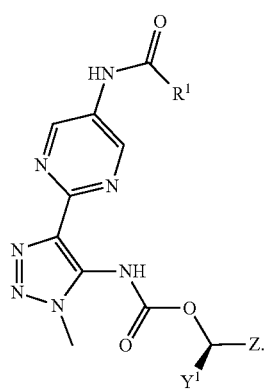

(IIk)

or a pharmaceutically acceptable salt thereof.

In some embodiments, the compound of Formula (I) or (Ia), or pharmaceutically acceptable salt thereof, is a compound of Formula (III):

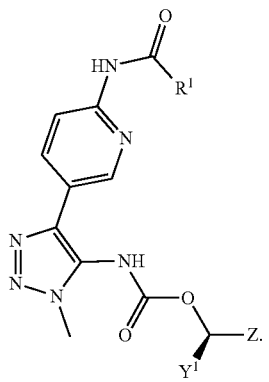

(III)

or a pharmaceutically acceptable salt thereof.

In some embodiments, the compound of Formula (I) or (Ia), or pharmaceutically acceptable salt thereof, is a compound of Formula (IIm):

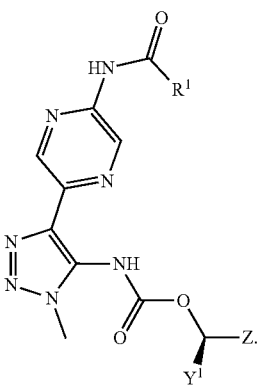

(IIm)

or a pharmaceutically acceptable salt thereof.

In some embodiments, the compound of Formula (I) or (Ia), or pharmaceutically acceptable salt thereof, is a compound of Formula (IIn):

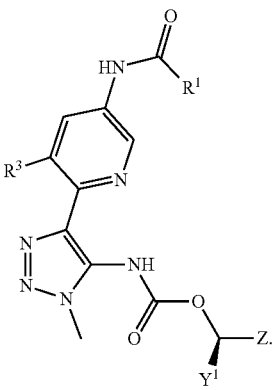

(IIn)

or a pharmaceutically acceptable salt thereof.

In some embodiments, the compound of Formula (I) or (Ia), or pharmaceutically acceptable salt thereof, is a compound of Formula (IIo):

(IIo)

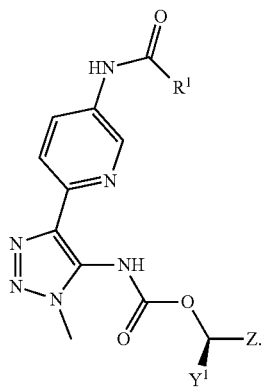

or a pharmaceutically acceptable salt thereof.

In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is hydrogen.

In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is $R^1$ is $C_{1-6}$ alkyl, $C_{2-6}$ alkenyl, or $C_{2-6}$ alkynyl, each optionally substituted with 1 to 4 $R^{1A}$, which can be the same or different, wherein each $R^{1A}$ is independently selected from halogen, cyano, nitro, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen or sulfur —$N(R^{1B1})(R^{1B2})$, —$O—R^{1B1}$, —$S—R^{1B1}$, —$C(O)N(R^{1B1})(R^{1B2})$, —$NR^{1B1}C(O)R^{1B2}$, —$NR^{1B1}C(O)N(R^{1B2})(R^{1B3})$, —$S(O)_{0-2}R^{1B1}$, —$S(O)_2N(R^{1B1})(R^{1B2})$, and —$NR^{1B1}S(O)_2R^{1B2}$, wherein each $R^{1B1}$, $R^{1B2}$, and $R^{1B3}$ is independently hydrogen, $C_{1-6}$ alkyl, or $C_{3-6}$ cycloalkyl, wherein each $R^{1A}$ alkyl, cycloalkyl, heterocyclyl, aryl, and heteroaryl is optionally substituted with 1 to 4 $R^{1C}$, which can be the same or different, wherein each $R^{1C}$ is independently $C_{1-4}$ alkyl, halogen, cyano, —$O—R^{1D1}$, or —$N(R^{1D1})(R^{1D2})$, wherein each $R^{1D1}$ and $R^{1D2}$ is independently hydrogen or $C_{1-6}$ alkyl, and wherein each $R^{1B1}$, $R^{1B2}$, and $R^{1B3}$ alkyl and each $R^{1B1}$, $R^{1B2}$, and $R^{1B3}$ cycloalkyl is optionally substituted with 1 to 3 halogens. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is $R^1$ is $C_{1-6}$ alkyl, $C_{2-6}$ alkenyl, or $C_{2-6}$ alkynyl, each optionally substituted with 1 to 4 $R^{1A}$, which can be the same or different, wherein each $R^{1A}$ is independently selected from halogen, cyano, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —$N(R^{1B1})(R^{1B2})$, —$O—R^{1B1}$, —$S—R^{1B1}$, —$C(O)N(R^{1B1})(R^{1B2})$, —$NR^{1B1}C(O)R^{1B2}$, —$NR^{1B1}C(O)N(R^{1B2})(R^{1B3})$, —$S(O)_{0-2}R^{1B1}$, —$S(O)_2N(R^{1B1})(R^{1B2})$, and —$NR^{1B1}S(O)_2R^{1B2}$, wherein each $R^{1B1}$, $R^{1B2}$, and $R^{1B3}$ is independently hydrogen or $C_{1-6}$ alkyl, wherein each $R^{1A}$ alkyl, cycloalkyl, heterocyclyl, aryl, and heteroaryl is optionally substituted with 1 to 4 $R^{1C}$, which can be the same or different, wherein each $R^{1C}$ is independently $C_{1-4}$ alkyl, halogen, cyano, —$O—R^{1D1}$, or —$N(R^{1D1})(R^{1D2})$, and wherein each $R^{1D1}$ and $R^{1D2}$ is independently hydrogen or $C_{1-6}$ alkyl. In some embodiments of the compound of Formula (I), (Ia), (IIa), (IIb), (IIc), (IId), (IIe), (IIf), (IIg), (IIh), or (IIi), or pharmaceutically acceptable salt thereof, $R^1$ is $C_{1-6}$ alkyl or $C_{2-6}$ alkynyl, each optionally substituted with 1 to 4 $R^{1A}$, which can be the same or different, wherein each $R^{1A}$ is independently selected from halogen, cyano, hydroxy, $C_{1-4}$ alkoxy, and $C_{3-6}$ cycloalkyl. In some embodiments, each halogen in $R^{1A}$ or $R^{1C}$ is —F. In some embodiments, each $R^{1A}$ is independently selected from —F, —CN, —OH, —$OCH_3$, or cyclopropyl. In some embodiments, each halogen in $R^{1A}$ or $R^{1C}$ is —F. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is $C_{1-6}$ alkyl or $C_{2-6}$ alkynyl, each optionally substituted with 1 to 4 $R^{1A}$, which can be the same or different, wherein each $R^{1A}$ is independently selected from —F, —CN, —OH, —$OCH_3$, or cyclopropyl. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is —$CH_3$, —$CHF_2$, —$CF_3$,

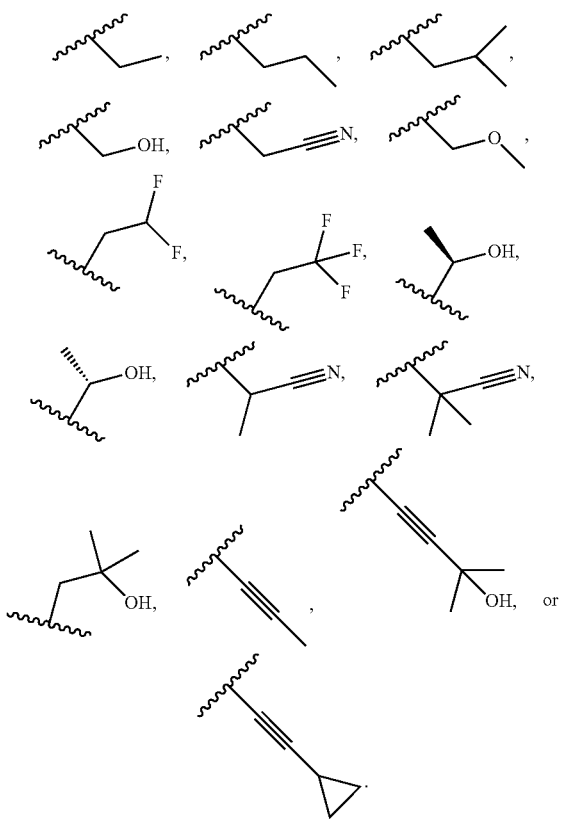

In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is —$O—R^{1D1}$ or —$N(R^{1D1})(R^{1D2})$, wherein each $R^{1D1}$ and $R^{1D2}$ is independently hydrogen, $C_{1-6}$ alkyl, or $C_{3-6}$ cycloalkyl, wherein each $C_{1-6}$ alkyl, or $C_{3-6}$ cycloalkyl is optionally substituted with 1 to 4 $R^{1E}$, which can be the same or different, wherein each $R^{1E}$ is independently selected from halogen, cyano, hydroxy, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —O—$R^{1F1}$, —N($R^{1F1}$)($R^{1F2}$), —C(O)N($R^{1F1}$)($R^{1F2}$), —$NR^{1F1}$C(O)$R^{1F2}$, —S(O)$_{0-2}R^{1F1}$, —S(O)$_2$N($R^{1F1}$)($R^{1F2}$), and —$NR^{1F1}$S(O)$_2R^{1F2}$, wherein each $R^{1F1}$ and $R^{1F2}$ is independently hydrogen or $C_{1-6}$ alkyl, wherein each $R^{1E}$ alkyl, cycloalkyl, aryl, and heteroaryl is optionally substituted with 1 to 3 $R^{1G}$, which can be the same or different, and wherein each $R^{1G}$ is independently $C_{1-4}$ alkyl, $C_{1-4}$ alkoxy, hydroxy, halogen, or cyano. In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, $R^1$ is —O—$R^{1D1}$ or —N($R^{1D1}$)($R^{1D2}$), wherein each $R^{1D1}$ and $R^{1D2}$ is independently hydrogen, $C_{1-6}$ alkyl, or $C_{3-6}$ cycloalkyl, wherein each $C_{1-6}$ alkyl, or $C_{3-6}$ cycloalkyl is optionally substituted with 1 to 3 $R^{1E}$, which can be the same or different, wherein each $R^{1E}$ is independently selected from halogen and —C(O)N($R^{1F1}$)($R^{1F1}$), wherein each —$R^{1F1}$ and —$R^{1F1}$ is independently hydrogen or $C_{1-4}$ alkyl. In some embodiments, each —$R^{1E}$ halogen is —F. In some embodiments, each —$R^{1G}$ halogen is —F. In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, $R^1$ is —O—$R^{1D1}$ or —N($R^{1D1}$)($R^{1D2}$), wherein each $R^{1D1}$ and $R^{1D2}$ is independently —H, —$CH_3$, —$C_2H_5$, or —C($CH_3$)$_3$. In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, $R^1$ is

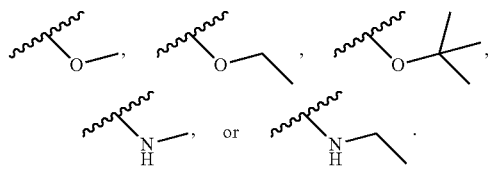

In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, $R^1$ is $C_{3-10}$ cycloalkyl optionally substituted with 1 to 4 $R^{1A}$, which can be the same or different, wherein each $R^{1A}$ is independently selected from halogen, cyano, nitro, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —N($R^{1B1}$)($R^{1B2}$), —O—$R^{1B1}$, —S—$R^{1B1}$, —C(O)N($R^{1B1}$)($R^{1B2}$), —$NR^{1B1}$C(O)$R^{1B2}$, —$NR^{1B1}$C(O)N($R^{1B2}$)($R^{1B3}$), —S(O)$_{0-2}R^{1B1}$, —S(O)$_2$N($R^{1B1}$)($R^{1B2}$), and —$NR^{1B1}$S(O)$_2R^{1B2}$, wherein each $R^{1B1}$, $R^{1B2}$, and $R^{1B3}$ is independently hydrogen, $C_{1-6}$ alkyl, or —$C_{3-6}$ cycloalkyl, wherein each $R^{1A}$ alkyl, cycloalkyl, heterocyclyl, aryl, and heteroaryl is optionally substituted with 1 to 4 $R^{1C}$, which can be the same or different, and wherein each $R^{1C}$ is independently $C_{1-4}$ alkyl, halogen, cyano, —O—$R^{1D1}$, or —N($R^{1D1}$)($R^{1D2}$), wherein each $R^{1D1}$ and $R^{1D2}$ is independently hydrogen or $C_{1-6}$ alkyl, and wherein each $R^{1B1}$ and $R^{1B2}$ alkyl and each $R^{1B1}$ and $R^{1B2}$ cycloalkyl is optionally substituted with 1 to 3 halogens. In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, $R^1$ is $C_{3-10}$ cycloalkyl optionally substituted with 1 to 4 $R^{1A}$, which can be the same or different, wherein each $R^{1A}$ is independently selected from halogen, cyano, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —N($R^{1B1}$)($R^{1B2}$), —O—$R^{1B1}$, —S—$R^{1B1}$, —C(O)N($R^{1B1}$)($R^{1B2}$), —$NR^{1B1}$C(O)$R^{1B2}$, —$NR^{1B1}$C(O)N($R^{1B2}$)($R^{1B3}$), —S(O)$_{0-2}R^{1B1}$, —S(O)$_2$N($R^{1B1}$)($R^{1B2}$), and —$NR^{1B1}$S(O)$_2R^{1B2}$, wherein each $R^{1B1}$, $R^{1B2}$, and $R^{1B3}$ is independently hydrogen or $C_{1-6}$ alkyl, wherein each $R^{1A}$ alkyl, cycloalkyl, heterocyclyl, aryl, and heteroaryl is optionally substituted with 1 to 4 $R^{1C}$, which can be the same or different, and wherein each $R^{1C}$ is independently $C_{1-4}$ alkyl, halogen, cyano, —O—$R^{1D1}$, or —N($R^{1D1}$)($R^{1D2}$), and wherein each $R^{1D1}$ and $R^{1D2}$ is independently hydrogen or $C_{1-6}$ alkyl. In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, $R^1$ is $C_{3-10}$ cycloalkyl optionally substituted with 1 to 4 $R^{1A}$, which can be the same or different, wherein each $R^{1A}$ is independently selected from halogen, cyano, nitro, oxo, $C_{1-4}$ alkyl, 3 to 6 membered heterocyclyl having 1 to 2 heteroatoms independently selected from nitrogen, oxygen, and sulfur, 5 or 6 membered heteroaryl having 1 or 2 heteroatoms independently selected from nitrogen or oxygen, —$OR^{1B1}$, and —C(O)N($R^{1B1}$)($R^{1B2}$), wherein each $R^{1B1}$ and $R^{1B2}$ is independently hydrogen, $C_{1-4}$ alkyl, or $C_{3-6}$ cycloalkyl, and wherein each $R^{1A}$ $C_{1-4}$ alkyl is optionally substituted with 1 to 3 halogens, and each heteroaryl in $R^{1A}$ is optionally substituted with 1 to 3 $C_{1-4}$ alkyl, and wherein each $R^{1B1}$ and $R^{1B2}$ alkyl and each $R^{1B1}$ and $R^{1B2}$ cycloalkyl is optionally substituted with 1 to 3 halogens. In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, $R^1$ is $C_{3-10}$ cycloalkyl optionally substituted with 1 to 4 $R^{1A}$, which can be the same or different, wherein each $R^{1A}$ is independently selected from halogen, cyano, oxo, $C_{1-4}$ alkyl, 3 to 6 membered heterocyclyl having 1 to 2 heteroatoms independently selected from nitrogen, oxygen, and sulfur, 5 or 6 membered heteroaryl having 1 or 2 heteroatoms independently selected from nitrogen or oxygen, —$OR^{1B1}$, and —C(O)N($R^{1B1}$)($R^{1B2}$), wherein each $R^{1B1}$ and $R^{1B2}$ is independently hydrogen or $C_{1-4}$ alkyl, and wherein each $R^{1A}$ $C_{1-4}$ alkyl is optionally substituted with 1 to 3 halogens, and each heteroaryl in $R^{1A}$ is optionally substituted with 1 to 3 $C_{1-4}$ alkyl. In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, $R^1$ is cyclopropyl or cyclobutyl, each optionally substituted with 1 to 4 $R^{1A}$, which can be the same or different, each independently selected from —F, —Cl, —CN, =O, —OH, —$CH_3$, —$CH_2F$, —$CHF_2$, —$CF_3$, —$CH_2$—OH, —$CH_2$—$NH_2$, —$OCH_3$, —$NH_2$, —NH—$CH_2$—$CF_3$,

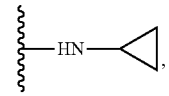

—NO₂, cyclopropyl, isoxazyl, phenyl, pyridyl, and —C(O)NH₂, wherein each isoxazyl or pyridyl is optionally substituted with 1 to 2 —F or —CH₃. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, R¹ is cyclopropyl or cyclobutyl, each optionally substituted with 1 to 4 R^{1A}, which can be the same or different, each independently selected from —F, —Cl, —CN, =O, —OH, —CH₃, —CH₂F, —CHF₂, —CF₃, —CH₂—OH, —CH₂—NH₂, —OCH₃, —NH₂, cyclopropyl, isoxazyl, phenyl, pyridyl, and —C(O)NH₂, wherein each isoxazyl or pyridyl is optionally substituted with 1 to 2 —F or —CH₃. In some embodiments of the compound of Formula (I), (Ia), (IIa), (IIb), (IIc), (IId), (IIe), (IIf), (IIg), (IIh), or (IIi), or pharmaceutically acceptable salt thereof, R¹ is cyclopropyl or cyclobutyl, each optionally substituted with 1 to 4 R^{1A}, which can be the same or different, each independently selected from —F, —Cl, —CN, =O, —OH, —CH₃, —CH₂F, —CHF₂, —CF₃, —OCH₃, isoxazyl, pyridyl, and —C(O)NH₂, wherein each isoxazyl or pyridyl is optionally substituted with 1 to 2 —CH₃. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, R¹ is

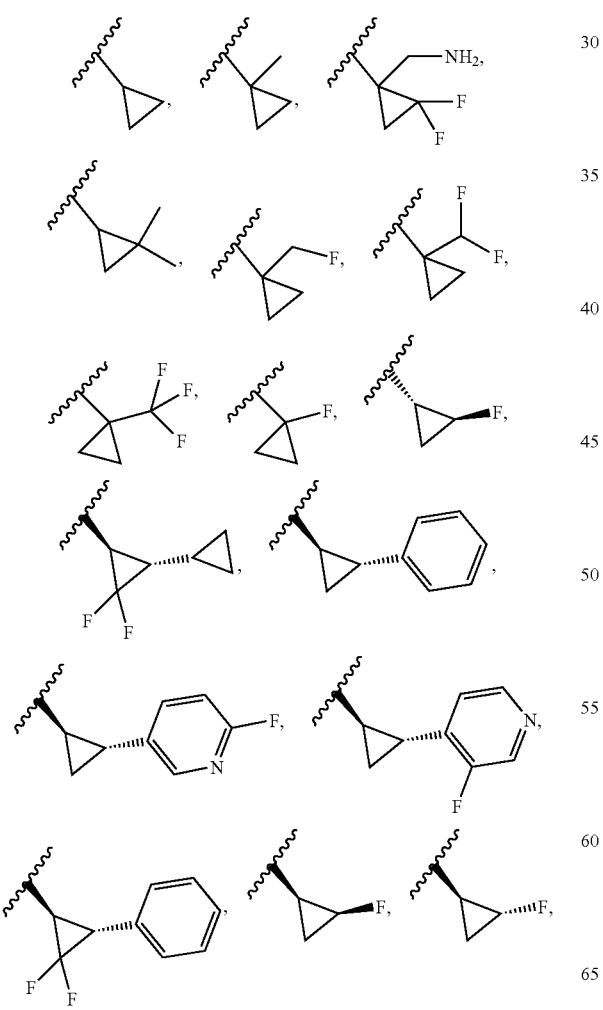

-continued

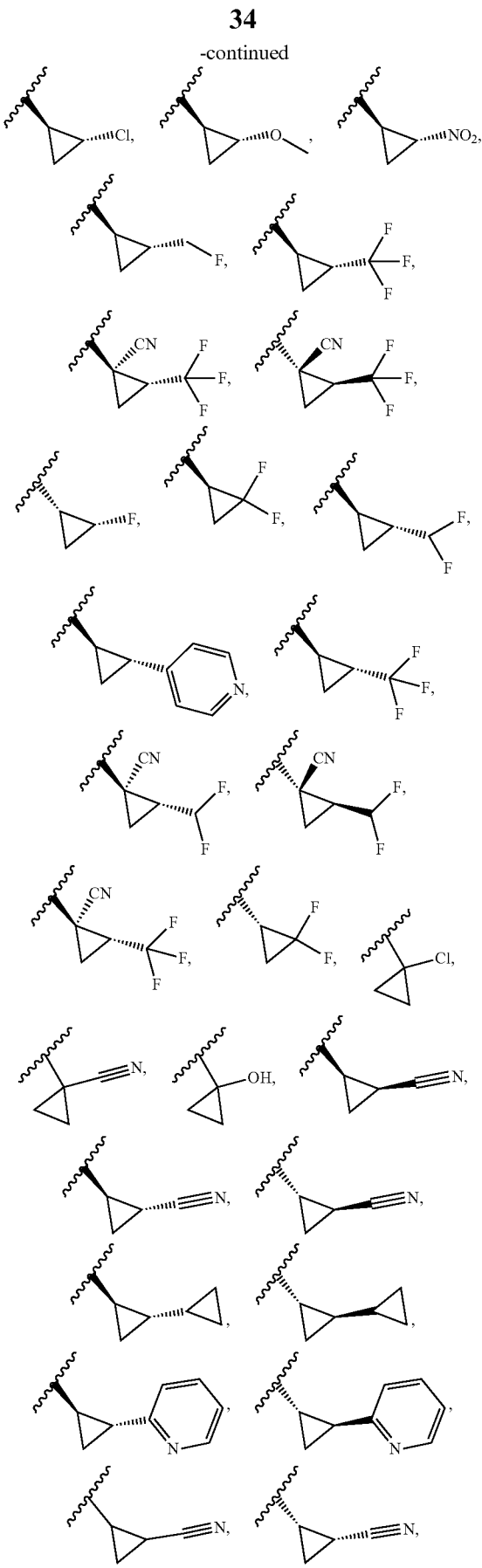

-continued
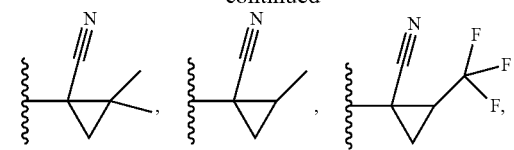
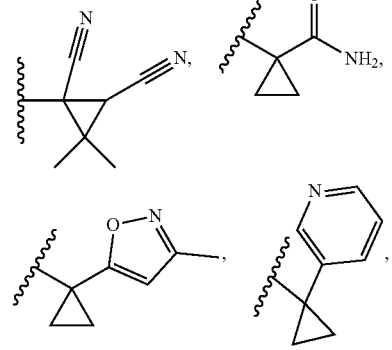
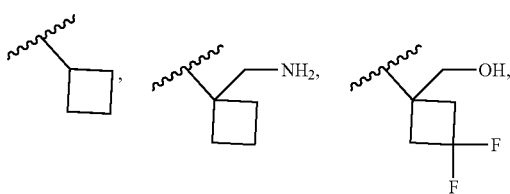
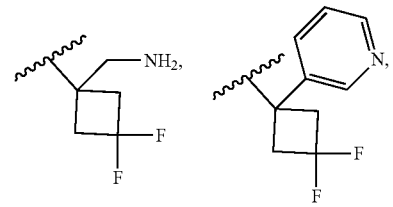
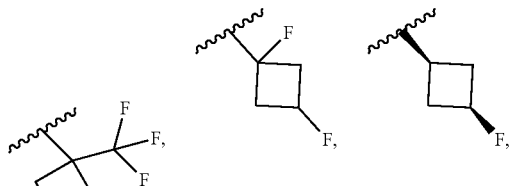
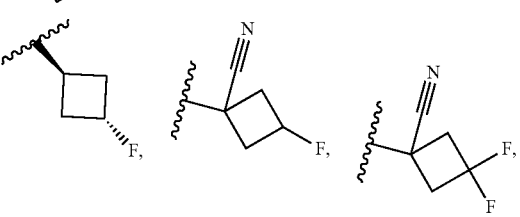
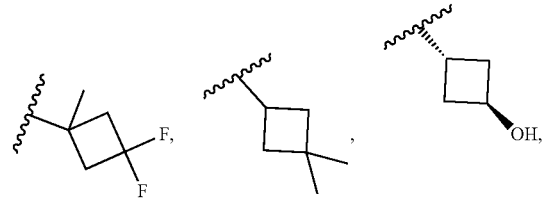
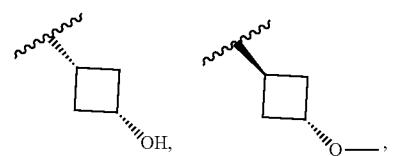
-continued
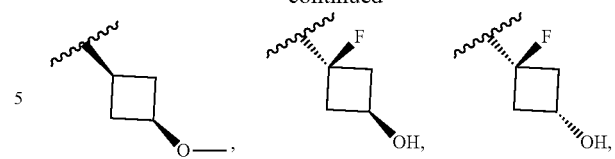
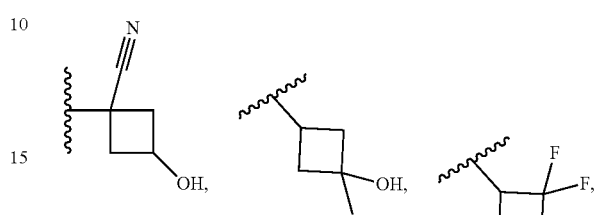
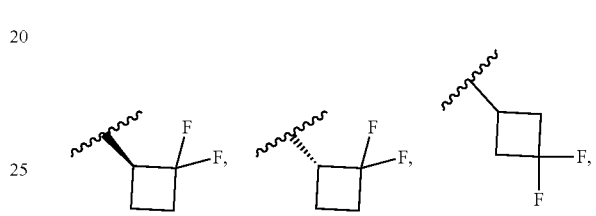
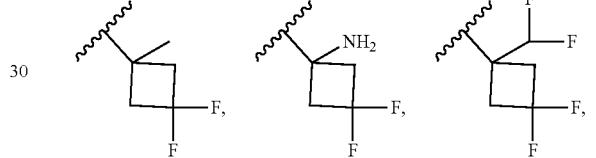
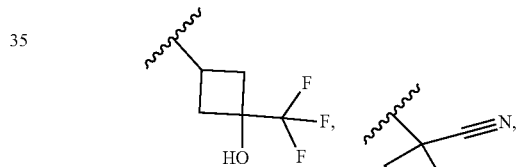
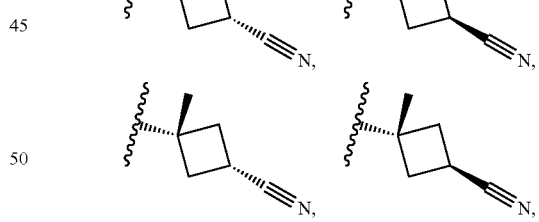
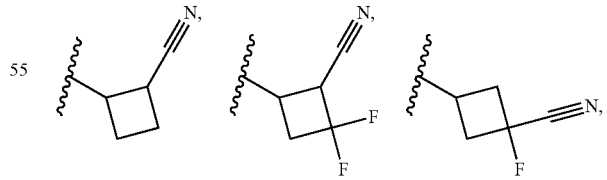
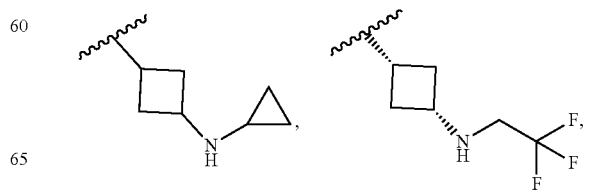

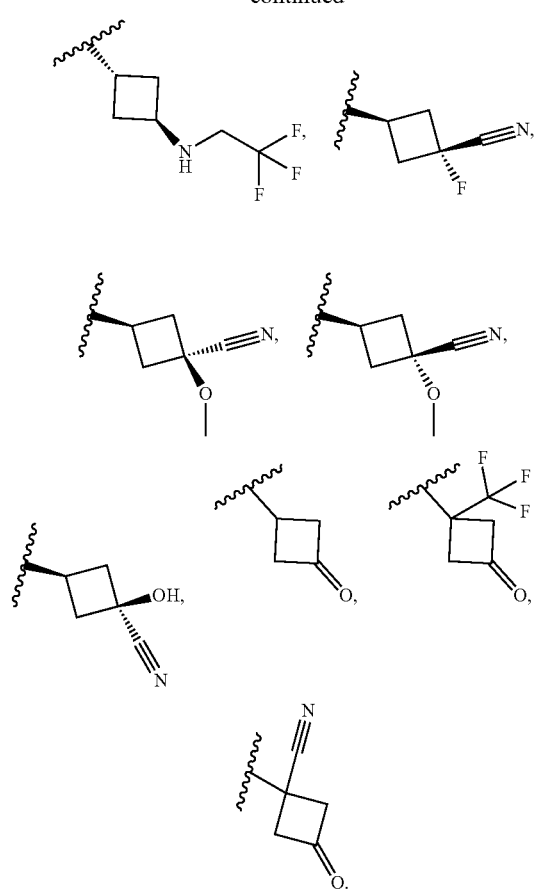
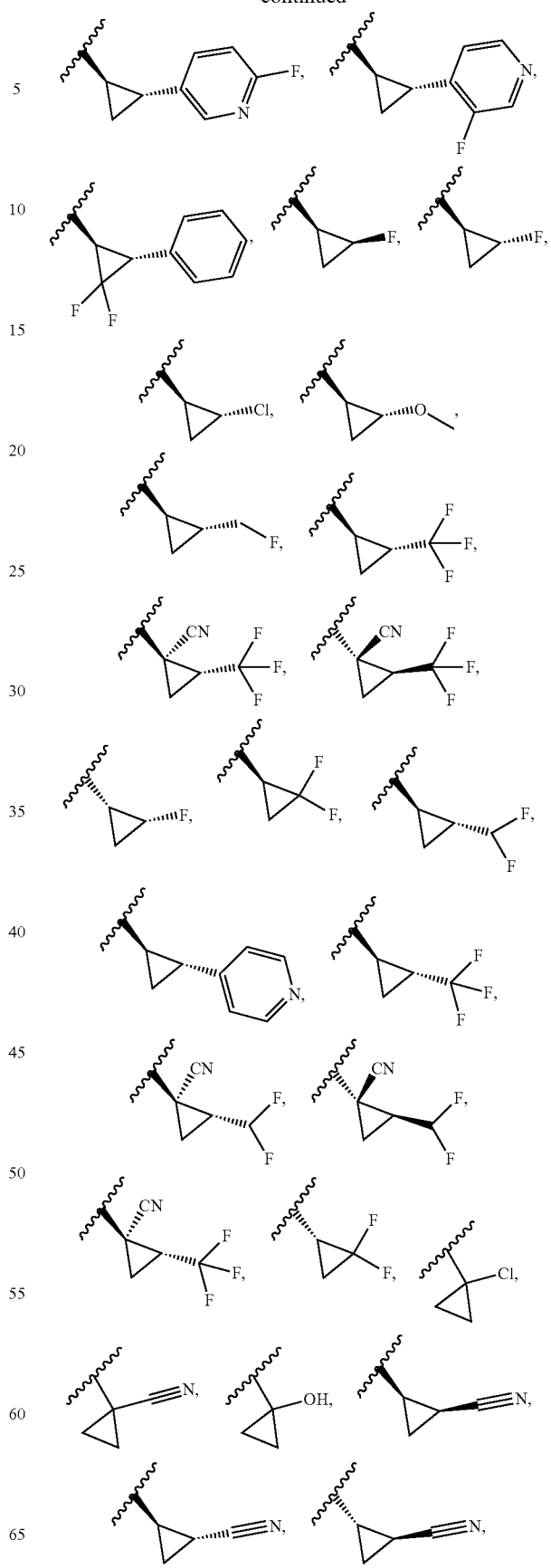
In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, $R^1$ is
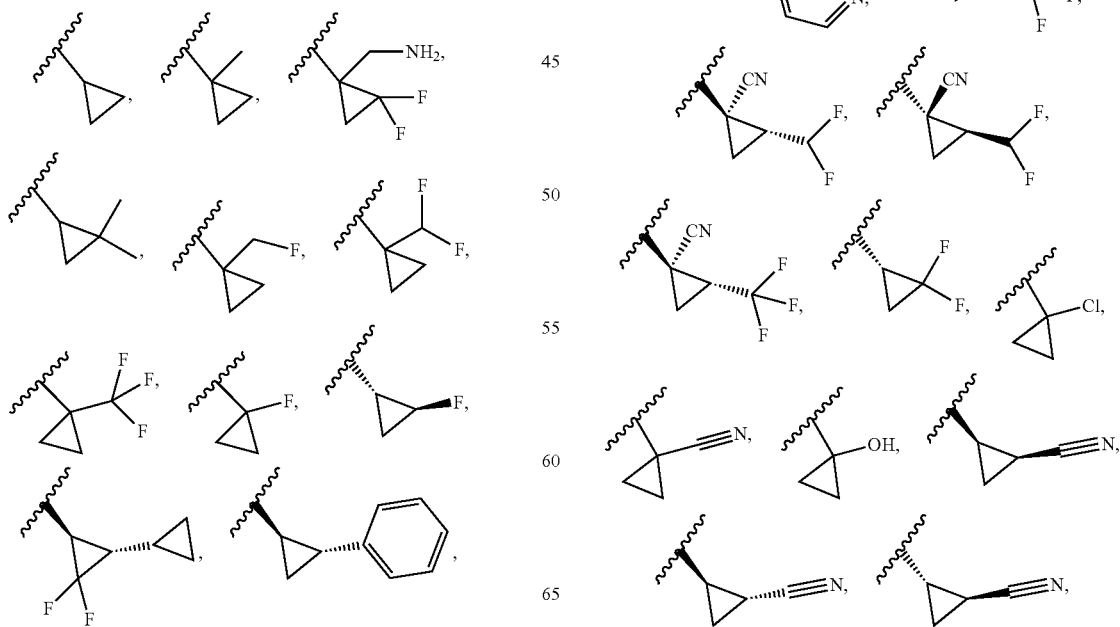

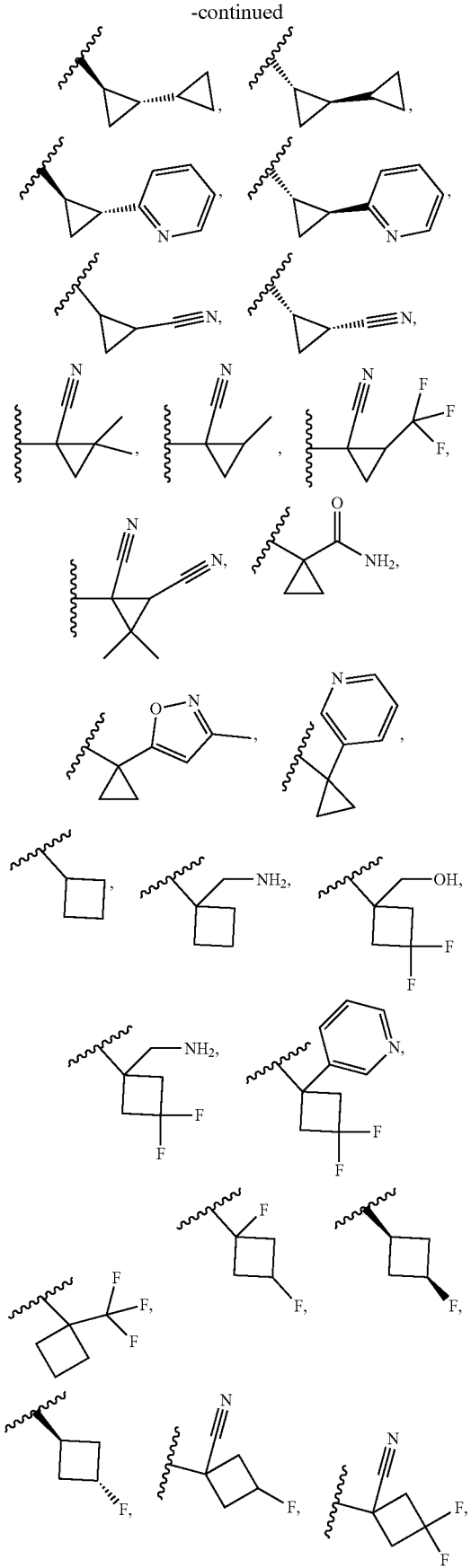
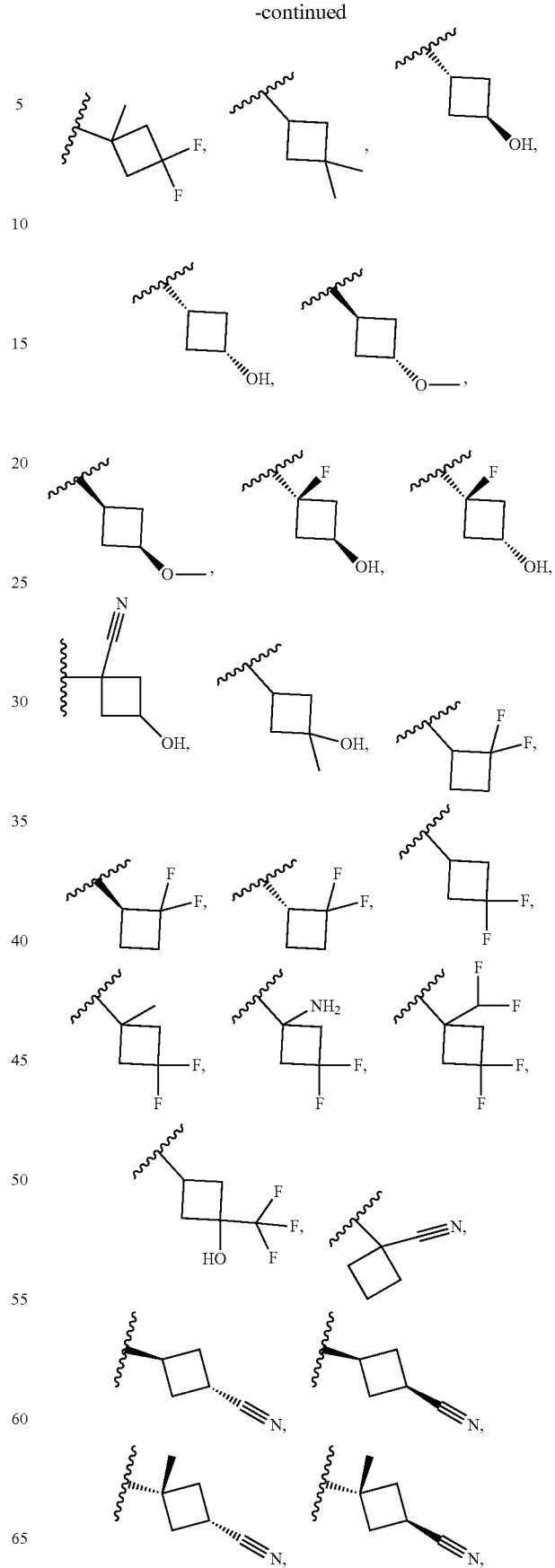

-continued
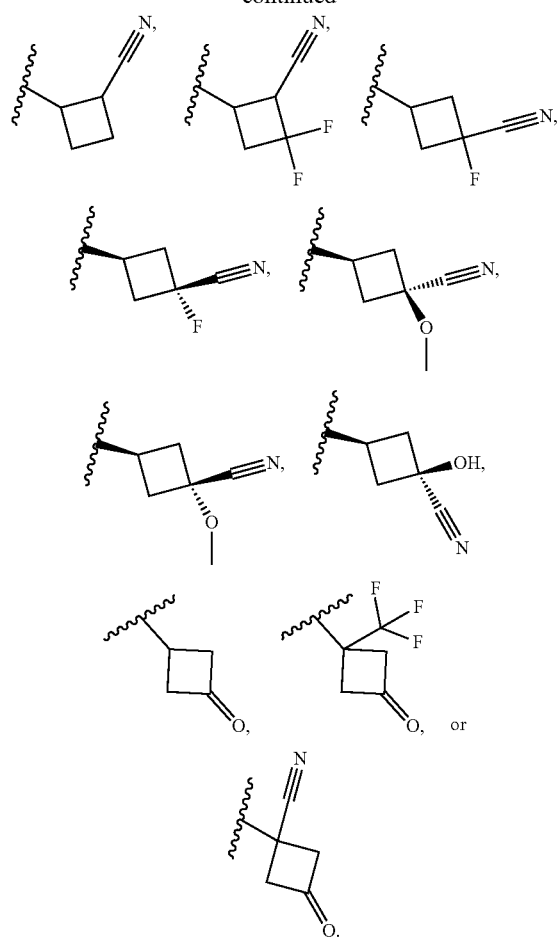
In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is
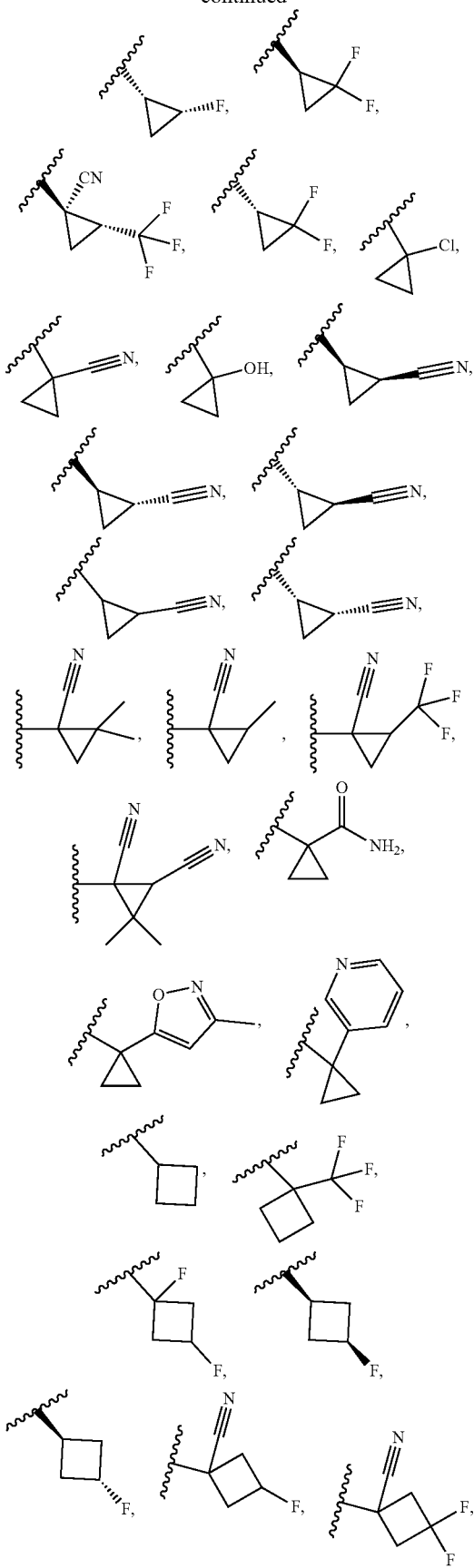

-continued

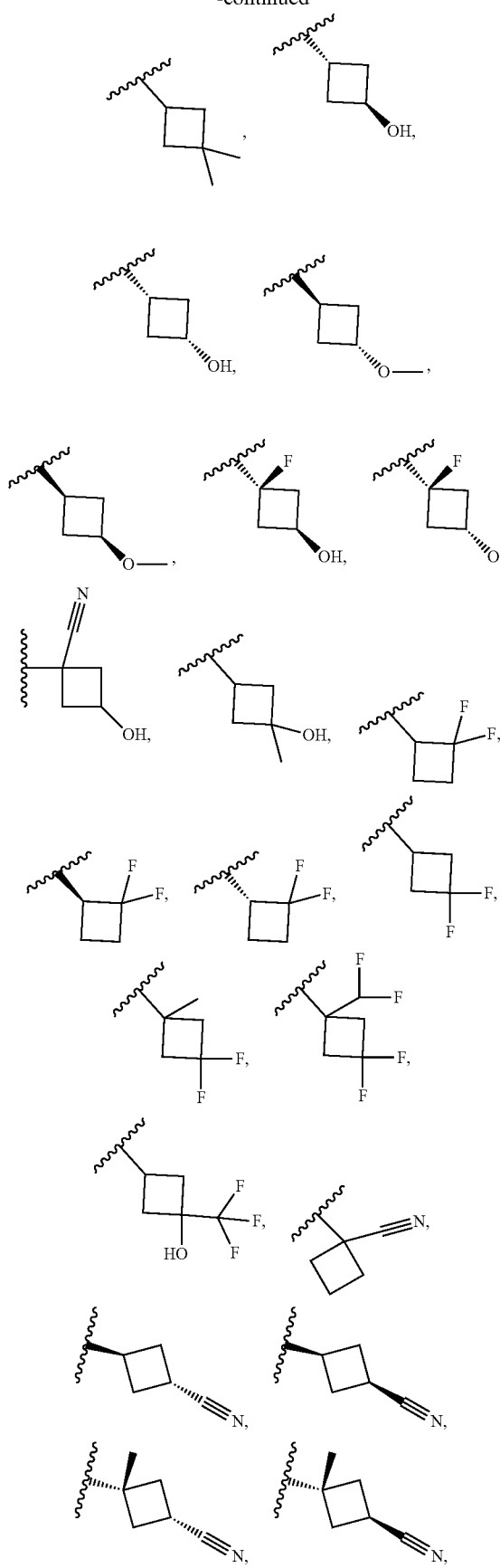

-continued

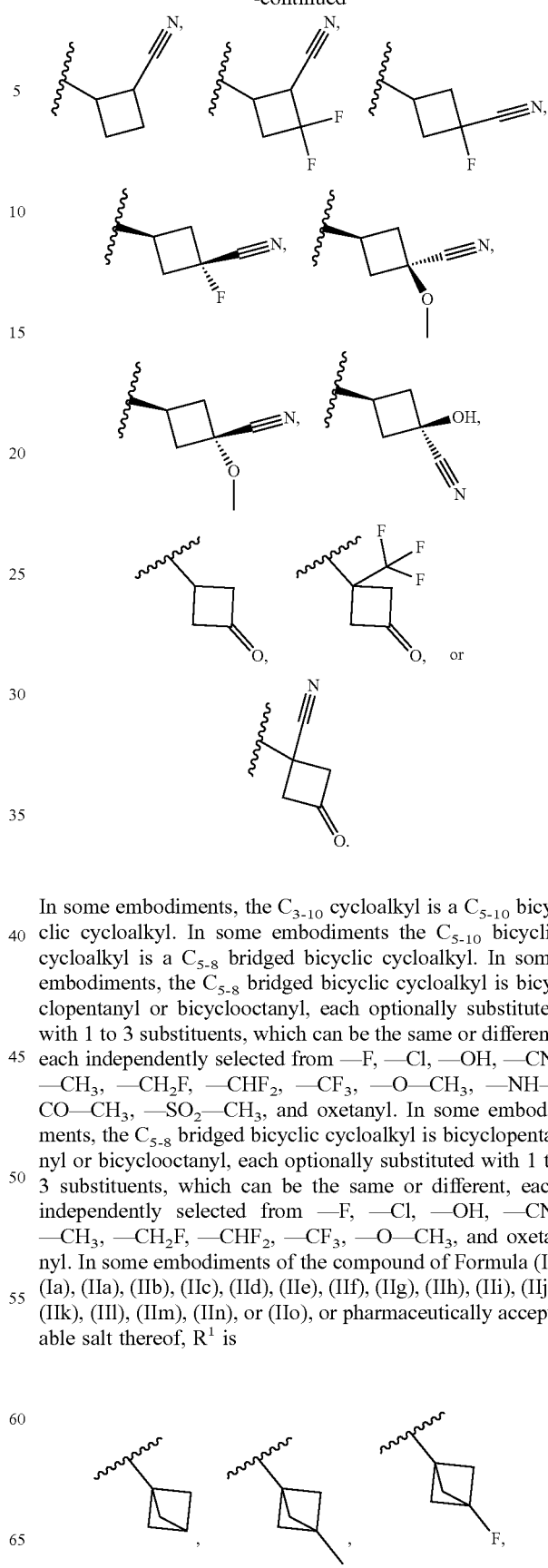

In some embodiments, the $C_{3-10}$ cycloalkyl is a $C_{5-10}$ bicyclic cycloalkyl. In some embodiments the $C_{5-10}$ bicyclic cycloalkyl is a $C_{5-8}$ bridged bicyclic cycloalkyl. In some embodiments, the $C_{5-8}$ bridged bicyclic cycloalkyl is bicyclopentanyl or bicyclooctanyl, each optionally substituted with 1 to 3 substituents, which can be the same or different, each independently selected from —F, —Cl, —OH, —CN, —CH$_3$, —CH$_2$F, —CHF$_2$, —CF$_3$, —O—CH$_3$, —NH—CO—CH$_3$, —SO$_2$—CH$_3$, and oxetanyl. In some embodiments, the $C_{5-8}$ bridged bicyclic cycloalkyl is bicyclopentanyl or bicyclooctanyl, each optionally substituted with 1 to 3 substituents, which can be the same or different, each independently selected from —F, —Cl, —OH, —CN, —CH$_3$, —CH$_2$F, —CHF$_2$, —CF$_3$, —O—CH$_3$, and oxetanyl. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is

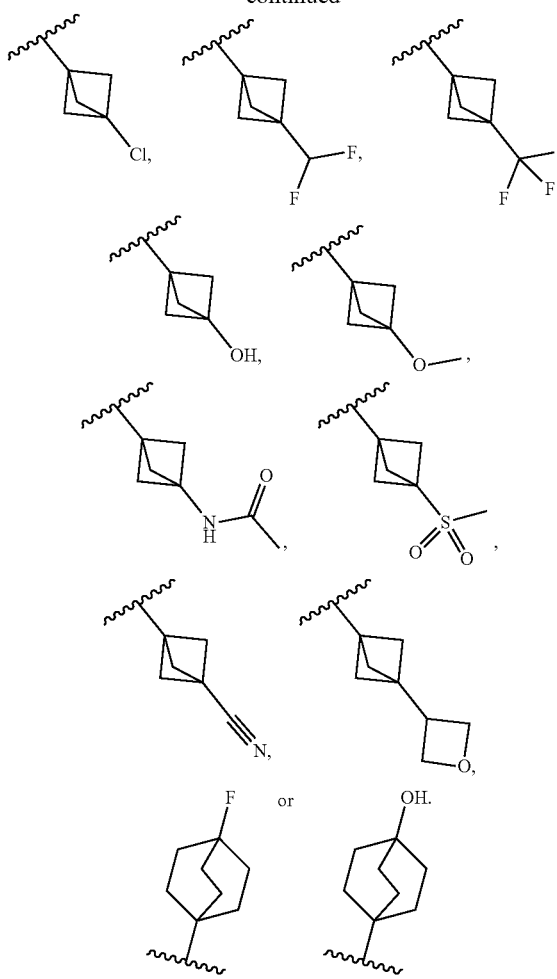

In some embodiments of the compound of Formula (I), (Ia), (IIa), (IIb), (IIc), (IId), (IIe), (IIf), (IIg), (IIh), or (IIi), (IIj), (IIk), (III), (IIm), (IIn), (IIo), or pharmaceutically acceptable salt thereof, $R^1$ is

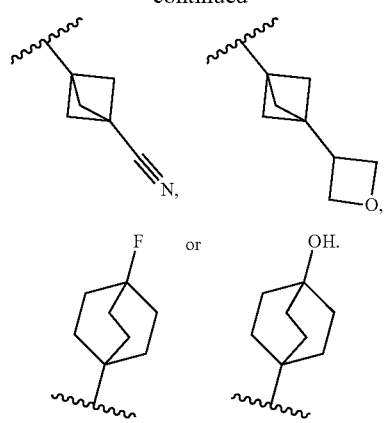

In some embodiments the $C_{5-10}$ bicyclic cycloalkyl is a $C_{5-10}$ spiro bicyclic cycloalkyl. In some embodiments, the $C_{5-10}$ spiro bicyclic cycloalkyl is spiropentanyl, spirohexanyl, spiroheptanyl, or spirodecanyl, each optionally substituted with 1 to 4 $R^{1A}$, which can be the same or different, wherein each $R^{1A}$ is each independently selected from —F, —Cl, —OH, —CH$_3$, —CH$_2$F, —CHF$_2$, —CF$_3$, —CN, and —O—CH$_3$. In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, $R^1$ is

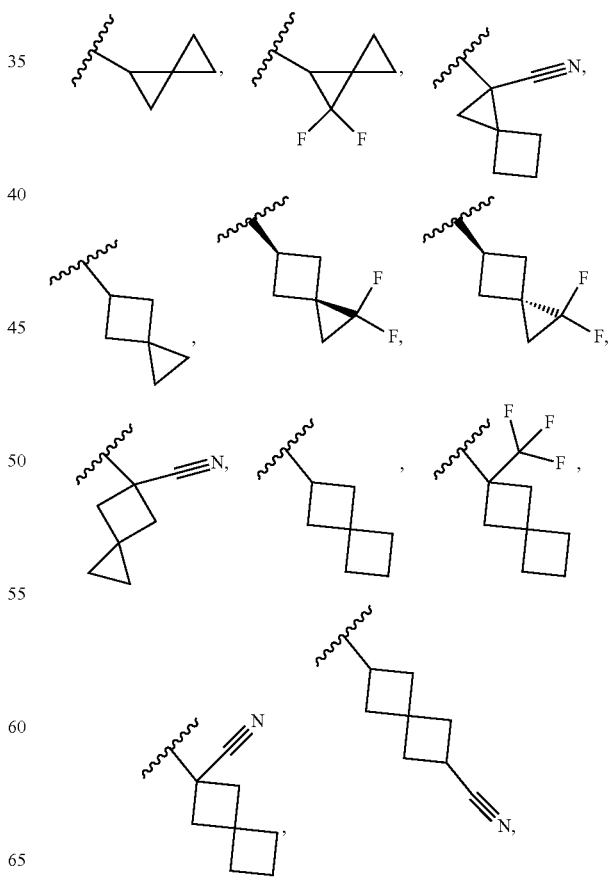

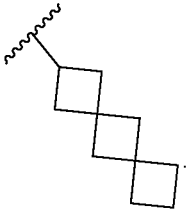

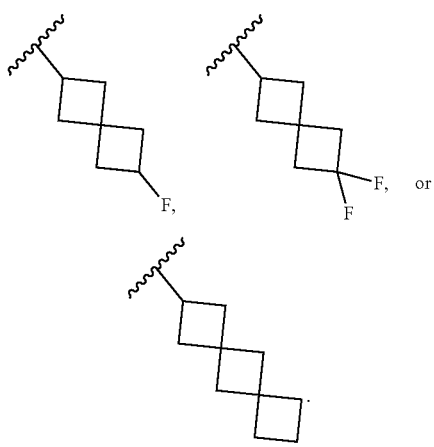

In some embodiments of the compound of Formula (I), (Ia), (IIa), (IIb), (IIc), (IId), (IIe), (IIf), (IIg), (IIh), (IIi), (IIj), (IIk), (Ill), (IIm), (IIn), or (IIo), or pharmaceutically acceptable salt thereof, $R^1$ is

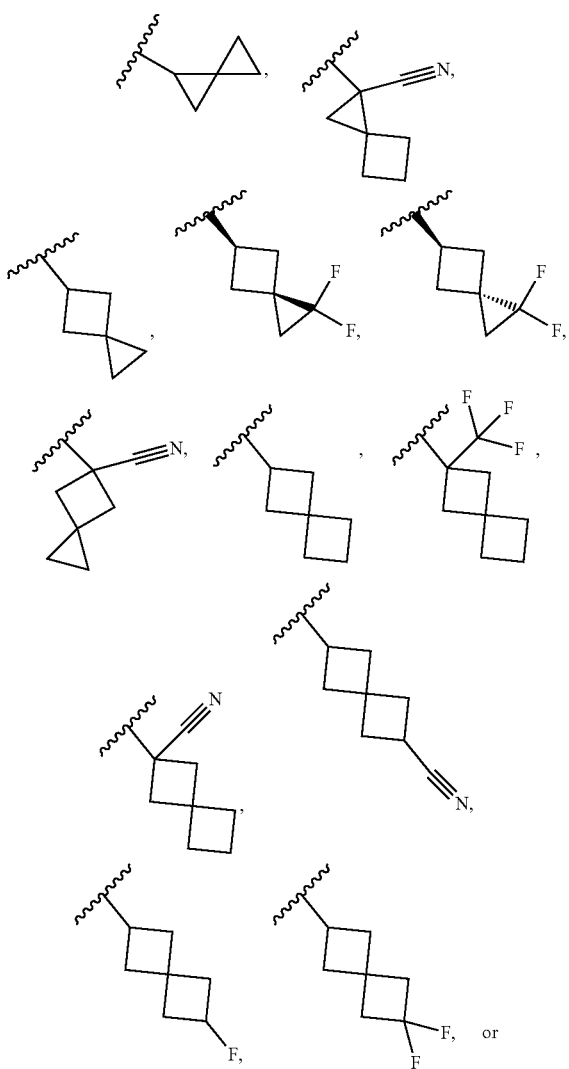

In some embodiments of the compound of Formula (I), (Ia), (IIa), (IIa), (IIc), (IId), (IIe), (IIf), (IIg), (IIh), (IIi), (IIj), (IIk), (Ill), (IIm), (IIn), or (IIo), or pharmaceutically acceptable salt thereof, $R^1$ is 3 to 10 membered heterocyclyl having 1 to 4 heteroatoms independently selected from nitrogen, oxygen, and sulfur, optionally substituted with 1 to 4 $R^{1A}$, which can be the same or different, wherein each $R^{1A}$ is independently selected from halogen, cyano, nitro, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, $-N(R^{1B1})(R^{1B2})$, $-O-R^{1B1}$, $-S-R^{1B1}$, $-C(O)N(R^{1B1})(R^{1B2})$, $-NR^{1B1}C(O)R^{1B2}$, $-NR^{1B1}C(O)N(R^{1B2})(R^{1B3})$, $-S(O)_{0-2}R^{1B1}$, $-S(O)_2N(R^{1B1})(R^{1B2})$, and $-NR^{1B1}S(O)_2R^{1B2}$, wherein each $R^{1B1}$, $R^{1B2}$, and $R^{1B3}$ is independently hydrogen, $C_{1-6}$ alkyl, or $C_{3-6}$ cycloalkyl, wherein each $R^{1A}$ alkyl, cycloalkyl, heterocyclyl, aryl, and heteroaryl is optionally substituted with 1 to 4 $R^{1C}$, which can be the same or different, and wherein each $R^{1C}$ is independently $C_{1-4}$ alkyl, halogen, cyano, $-O-R^{1D1}$, or $-N(R^{1D1})(R^{1D2})$, wherein each $R^{1D1}$ and $R^{1D2}$ is independently hydrogen or $C_{1-6}$ alkyl, and wherein each $R^{1B1}$ and $R^{1B2}$ alkyl and each $R^{1B1}$ and $R^{1B2}$ cycloalkyl is optionally substituted with 1 to 3 halogens. In some embodiments of the compound of Formula (I), (Ia), (IIa), (IIb), (IIc), (IId), (IIe), (IIf), (IIg), (IIh), (IIi), (IIj), (IIk), (Ill), (IIm), (IIn), or (IIo), or pharmaceutically acceptable salt thereof, $R^1$ is 3 to 10 membered heterocyclyl having 1 to 4 heteroatoms independently selected from nitrogen, oxygen, and sulfur, optionally substituted with 1 to 4 $R^{1A}$, which can be the same or different, wherein each $R^{1A}$ is independently selected from halogen, cyano, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen or sulfur, $-N(R^{1B1})(R^{1B2})$, $-O-R^{1B1}$, $-S-R^{1B1}$, $-C(O)N(R^{1B1})(R^{1B2})$, $-NR^{1B1}C(O)R^{1B2}$, $-NR^{1B1}C(O)N(R^{1B2})(R^{1B3})$, $-S(O)_{0-2}R^{1B1}$, $-S(O)_2N(R^{1B1})(R^{1B2})$, and $-NR^{1B1}S(O)_2R^{1B2}$, wherein each $R^{1B1}$, $R^{1B2}$, and $R^{1B3}$ is independently hydrogen or $C_{1-6}$ alkyl, wherein each $R^{1A}$ alkyl, cycloalkyl, heterocyclyl, aryl, and heteroaryl is optionally substituted with 1 to 4 $R^{1C}$, which can be the same or different, and wherein each $R^{1C}$ is independently $C_{1-4}$ alkyl, halogen, cyano, $-O-R^{1D1}$, or $-N(R^{1D1})(R^{1D2})$, wherein each $R^{1D1}$ and $R^{1D2}$ is independently hydrogen or $C_{1-6}$ alkyl. In some embodiments of the compound of Formula (I), (Ia), (IIa), (IIb), (IIc), (IId), (IIe), (IIf), (IIg), (IIh), (IIi), (IIj), (IIk), (Ill), (IIm), (IIn), or (IIo), or pharmaceutically acceptable salt thereof, $R^1$ is 3 to 8 membered heterocyclyl having 1 to 2 heteroatoms independently selected from nitrogen, oxygen, and sulfur, optionally substituted with 1 to 4 $R^{1A}$, which can be the same or different, each independently selected from halogen, cyano, oxo, or $C_{1-4}$ alkyl, wherein each $R^{1A}$ $C_{1-4}$ alkyl is optionally substituted with 1 to 3 $R^{1C}$, which can be the same or different, and wherein each $R^{1C}$ is independently $C_{1-4}$ alkoxy, halogen, or cyano. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is azetidinyl, oxetyl, thietanyl, pyrrolidinyl, dioxolanyl, tetrahydropyranyl, piperidinyl, or morpholinyl, each optionally substituted with 1 to 4 $R^{1A}$, which can be the same or different, each independently selected from —F, —Cl, —OH, —CN, —CH$_3$, —CH$_2$F, —CHF$_2$, —CF$_3$, —C$_2$H$_5$, —CH$_2$—CF$_3$, and —O—CH$_3$. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is azetidinyl, oxetyl, thietanyl, pyrrolidinyl, dioxolanyl, tetrahydropyranyl, or morpholinyl, each optionally substituted with 1 to 4 $R^{1A}$, which can be the same or different, each independently selected from —F, —Cl, —OH, —CN, —CH$_3$, —CH$_2$F, —CHF$_2$, —CF$_3$, and —O—CH$_3$. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is

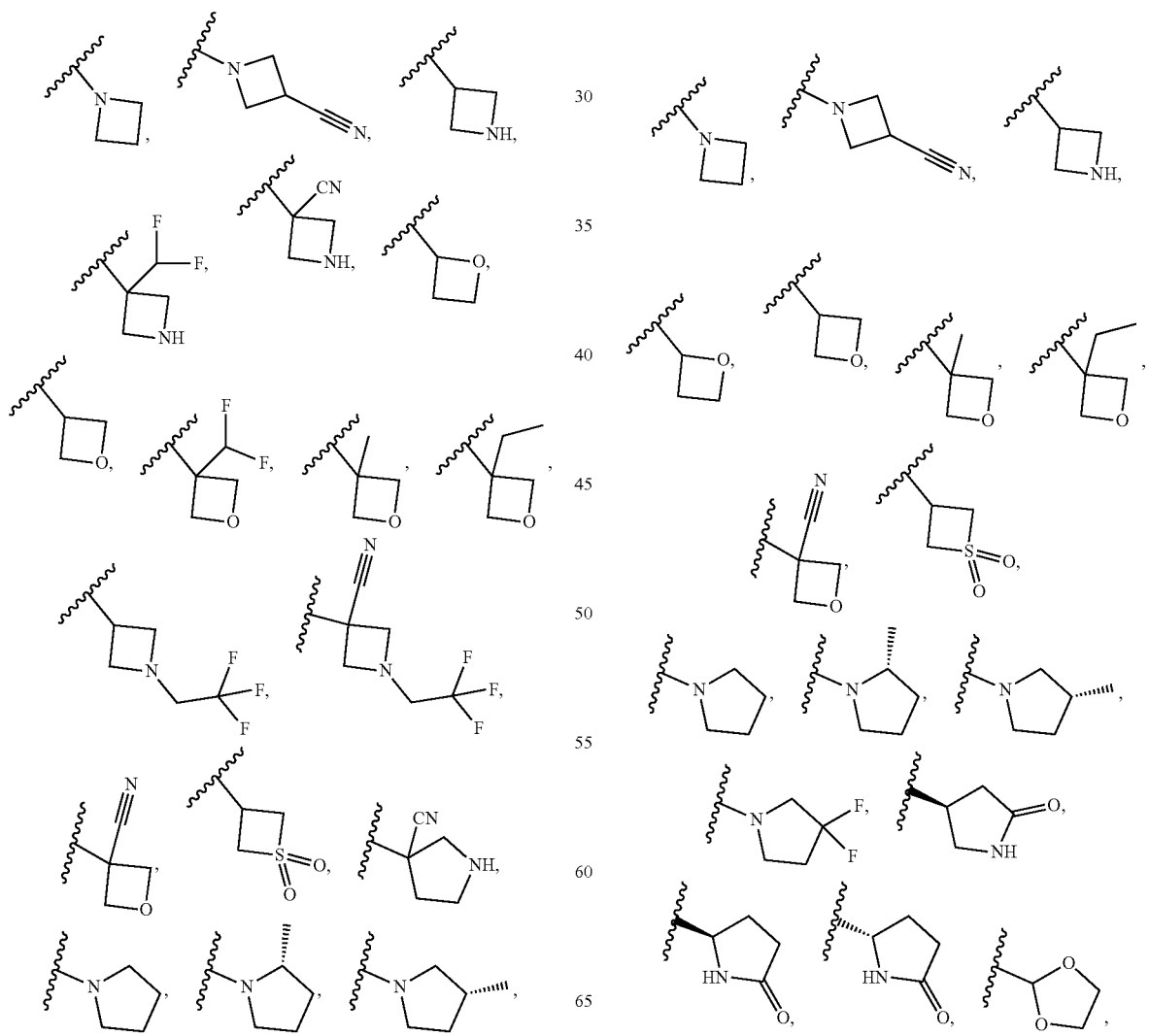

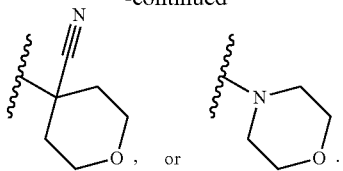

In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, the $R^1$ 3 to 10 membered heterocyclyl forms a bicyclic heterocyclyl. In some embodiments, the bicyclic heterocyclyl is a bridged bicyclic heterocyclyl. In some embodiments, the bridged bicyclic heterocyclyl is an oxabicyclohexanyl optionally substituted with 1 to 4 $R^{1A}$, which can be the same or different, wherein each $R^{1A}$ is independently selected from —F, —Cl, —OH, —CN, —CH$_3$, —CH$_2$F, —CHF$_2$, —CF$_3$, and —O—CH$_3$. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is

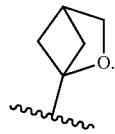

In some embodiments the bicyclic heterocyclyl is a fused bicyclic heterocyclyl. In some embodiments the fused bicyclic heterocyclyl is an oxabicyclohexanyl optionally substituted with 1 to 4 $R^{1A}$, which can be the same or different, wherein each $R^{1A}$ is independently selected from —F, —Cl, —OH, —CN, —CH$_3$, —CH$_2$F, —CHF$_2$, —CF$_3$, and —O—CH$_3$. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is

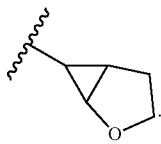 [SMILES: *C1C2CCOC12]

In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is

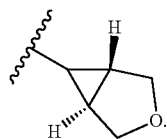 [SMILES: *C1[C@@H]2COC[C@@H]12]

In some embodiments, the bicyclic heterocyclyl is a spiro bicyclic heterocyclyl. In some embodiments, the spiro bicyclic heterocyclyl is an oxaspiroheptane optionally substituted with 1 to 4 substituents, which can be the same or different, each independently selected from —F, —Cl, —OH, —CN, —CH$_3$, —CH$_2$F, —CHF$_2$, —CF$_3$, and —O—CH$_3$. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is

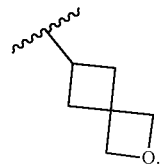 [SMILES: *C1CC2(COC2)C1]

In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is 6 to 10 membered aryl optionally substituted with 1 to 4 $R^{1A}$, which can be the same or different, wherein each $R^{1A}$ is independently selected from halogen, cyano, nitro, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —N(R$^{1B1}$)(R$^{1B2}$), —O—R$^{1B1}$, —S—R$^{1B1}$, —C(O)N(R$^{1B1}$)(R$^{1B2}$), —NR$^{1B1}$C(O)R$^{1B2}$, —NR$^{1B1}$C(O)N(R$^{1B2}$)(R$^{1B3}$), —S(O)$_{0-2}$R$^{1B1}$, —S(O)$_2$N(R$^{1B1}$)(R$^{1B2}$), and —NR$^{1B1}$S(O)$_2$R$^{1B2}$, wherein each R$^{1B1}$, R$^{1B2}$, and R$^{1B3}$ is independently hydrogen, $C_{1-6}$ alkyl, or $C_{3-6}$ cycloalkyl, wherein each R$^{1A}$ alkyl, cycloalkyl, heterocyclyl, aryl, and heteroaryl is optionally substituted with 1 to 4 $R^{1C}$, which can be the same or different, and wherein each R$^{1C}$ is independently $C_{1-4}$ alkyl, halogen, cyano, —O—R$^{1D1}$, or —N(R$^{1D1}$)(R$^{1D2}$), wherein each R$^{1D1}$ and R$^{1D2}$ is independently hydrogen or $C_{1-6}$ alkyl, and wherein each R$^{1B1}$ and R$^{1B2}$ alkyl and each R$^{1B1}$ and R$^{1B2}$ cycloalkyl is optionally substituted with 1 to 3 halogens. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is 6 to 10 membered aryl optionally substituted with 1 to 4 $R^{1A}$, which can be the same or different, wherein each $R^{1A}$ is independently selected from halogen, cyano, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —N(R$^{1B1}$)(R$^{1B2}$), —O—R$^{1B1}$, —S—R$^{1B1}$, —C(O)N(R$^{1B1}$)(R$^{1B2}$), —NR$^{1B1}$C(O)R$^{1B2}$, —NR$^{1B1}$C(O)N(R$^{1B2}$)(R$^{1B3}$), —S(O)$_{0-2}$R$^{1B1}$, —S(O)$_2$N(R$^{1B1}$)(R$^{1B2}$), and —NR$^{1B1}$S(O)$_2$R$^{1B2}$, wherein each R$^{1B1}$, R$^{1B2}$, and R$^{1B3}$ is independently hydrogen or $C_{1-6}$ alkyl, wherein each R$^{1A}$ alkyl, cycloalkyl, heterocyclyl, aryl, and heteroaryl is optionally substituted with 1 to 4 R$^{1C}$, which can be the same or different, and wherein each R$^{1C}$ is independently $C_{1-4}$ alkyl, halogen, cyano, —O—R$^{1D1}$, or —N(R$^{1D1}$)(R$^{1D2}$), wherein each R$^{1D1}$ and R$^{1D2}$ is independently hydrogen or $C_{1-6}$ alkyl. In some embodiments, $R^1$ is phenyl optionally substituted with 1 to 4 $R^{1A}$, which can be the same or different, wherein each $R^{1A}$ is independently selected from halogen, cyano, $C_{1-3}$ alkyl, or $C_{1-4}$ alkoxy. In some embodiments, $R^1$ is phenyl optionally substituted with 1 to 3 $R^{1A}$, which can be the same or different, wherein each $R^{1A}$ is independently selected from —F, —Cl, —CN, or —CH$_3$.

In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is 5 to 10 membered heteroaryl having 1 to 4 heteroatoms independently selected from nitrogen, oxygen, and sulfur, optionally substituted with 1 to 4 $R^{1A}$, which can be the same or different, wherein each $R^{1A}$ is independently selected from halogen, cyano, nitro, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —N($R^{1B1}$)($R^{1B2}$), —O—$R^{1B1}$, —S—$R^{1B1}$, —C(O)N($R^{1B1}$)($R^{1B2}$), —N$R^{1B1}$C(O)$R^{1B2}$, —N$R^{1B1}$C(O)N($R^{1B2}$)($R^{1B3}$), —S(O)$_{0-2}$$R^{1B1}$, —S(O)$_2$N($R^{1B1}$)($R^{1B2}$), and —N$R^{1B1}$S(O)$_2$$R^{1B2}$, wherein each $R^{1B1}$, $R^{1B2}$, and $R^{1B3}$ is independently hydrogen, $C_{1-6}$ alkyl, or $C_{3-6}$ cycloalkyl, wherein each $R^{1A}$ alkyl, cycloalkyl, heterocyclyl, aryl, and heteroaryl is optionally substituted with 1 to 4 $R^{1C}$, which can be the same or different, and wherein each $R^{1C}$ is independently $C_{1-4}$ alkyl, halogen, cyano, —O—$R^{1D1}$, or —N($R^{1D1}$)($R^{1D2}$), wherein each $R^{1D1}$ and $R^{1D2}$ is independently hydrogen or $C_{1-6}$ alkyl, and wherein each $R^{1B1}$ and $R^{1B2}$ alkyl and each $R^{1B1}$ and $R^{1B2}$ cycloalkyl is optionally substituted with 1 to 3 halogens. In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $R^1$ is 5 to 10 membered heteroaryl having 1 to 4 heteroatoms independently selected from nitrogen, oxygen, and sulfur, optionally substituted with 1 to 4 $R^{1A}$, which can be the same or different, wherein each $R^{1A}$ is independently selected from halogen, cyano, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —N($R^{1B1}$)($R^{1B2}$), —O—$R^{1B1}$, —S—$R^{1B1}$, —C(O)N($R^{1B1}$)($R^{1B2}$), —N$R^{1B1}$C(O)$R^{1B2}$, —N$R^{1B1}$C(O)N($R^{1B2}$)($R^{1B3}$), —S(O)$_{0-2}$$R^{1B1}$, —S(O)$_2$N($R^{1B1}$)($R^{1B2}$), and —N$R^{1B1}$S(O)$_2$$R^{1B2}$, wherein each $R^{1B1}$, $R^{1B2}$, and $R^{1B3}$ is independently hydrogen or $C_{1-6}$ alkyl, wherein each $R^{1A}$ alkyl, cycloalkyl, heterocyclyl, aryl, and heteroaryl is optionally substituted with 1 to 4 $R^{1C}$, which can be the same or different, and wherein each $R^{1C}$ is independently $C_{1-4}$ alkyl, halogen, cyano, —O—$R^{1D1}$, or —N($R^{1D1}$)($R^{1D2}$), wherein each $R^{1D1}$ and $R^{1D2}$ is independently hydrogen or $C_{1-6}$ alkyl. In some embodiments, $R^1$ is imidazolyl, pyrazolyl, pyridinyl, oxazolyl, isoxazolyl, oxadiazolyl, pyridinonyl, pyrimidinyl, pyridazinyl, benzoisoxazolyl, pyrazolopyridinyl, imidazopyridinyl, or benzoimidazolyl, each optionally substituted with 1 to 4 $R^{1A}$, which can be the same or different, wherein each $R^{1A}$ is independently selected from halogen, cyano, oxo, $C_{1-4}$ alkyl, $C_{3-10}$ cycloalkyl, 3 to 10 membered heterocyclyl having 1 to 4 heteroatoms independently selected from nitrogen and oxygen, —N($R^{1B1}$)($R^{1B2}$), —O—$R^{1B1}$, and —S(O)$_{0-2}$$R^{1B1}$, wherein each $R^{1B1}$ and $R^{1B2}$ is independently hydrogen or $C_{1-6}$ alkyl, wherein each $R^{1A}$ alkyl, cycloalkyl, and heterocyclyl, is optionally substituted with 1 to 4 $R^{1C}$, which can be the same or different, and wherein each $R^{1C}$ is independently $C_{1-4}$ alkyl, halogen, or cyano. In some embodiments, $R^1$ is imidazolyl, pyrazolyl, pyridinyl, oxazolyl, isoxazolyl, oxadiazolyl, pyridinonyl, pyrimidinyl, pyridazinyl, benzoisoxazolyl, pyrazolopyridinyl, imidazopyridinyl, or benzoimidazolyl, each optionally substituted with 1 to 4 $R^{1A}$, which can be the same or different, wherein each $R^{1A}$ is independently selected from halogen, cyano, oxo, methyl, cyclopropyl, morpholinyl, —N($R^{1B1}$)($R^{1B2}$), —O—$R^{1B1}$, and —S(O)$_{0-2}$$R^{1B1}$, wherein each $R^{1B1}$ and $R^{1B2}$ is independently hydrogen or methyl, wherein each $R^{1A}$ methyl, cyclopropyl, and morpholinyl is optionally substituted with 1 to 4 $R^{1C}$, which can be the same or different, and wherein each $R^{1C}$ is independently methyl, halogen, or cyano. In some embodiments, $R^1$ is imidazolyl, pyrazolyl, pyridinyl, oxazolyl, isoxazolyl, oxadiazolyl, pyridinonyl, pyrimidinyl, pyridazinyl, benzoisoxazolyl, pyrazolopyridinyl, imidazopyridinyl, or benzoimidazolyl, each optionally substituted with 1 to 4 substituents, which can be the same or different, each independently selected from halogen, cyano, $C_{1-4}$ alkyl, or $C_{1-4}$ alkoxy. In some embodiments, $R^1$ is imidazolyl, pyrazolyl, or pyridinyl, each optionally substituted with 1 to 4 substituents, which can be the same or different, each independently selected from halogen, cyano, $C_{1-4}$ alkyl, or $C_{1-4}$ alkoxy. In some embodiments, $R^1$ is imidazolyl, pyrazolyl, pyridinyl, oxazolyl, isoxazolyl, oxadiazolyl, pyridinonyl, pyrimidinyl, pyridazinyl, benzoisoxazolyl, pyrazolopyridinyl, imidazopyridinyl, or benzoimidazolyl, each optionally substituted with 1 to 3 substituents, which can be the same or different, each independently selected from —F, —Cl, —CN, —CH$_3$, —CHF$_2$, —CF$_3$, —OCH$_3$, —NH$_2$, —N(CH$_3$)$_2$, —SO$_2$—CH$_3$,

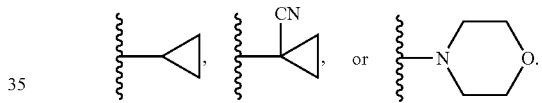

In some embodiments, $R^1$ is imidazolyl, pyrazolyl, or pyridinyl, each optionally substituted with 1 to 3 substituents, which can be the same or different, each independently selected from —F, —Cl, —CN, or —CH$_3$. In some embodiments, $R^1$ is

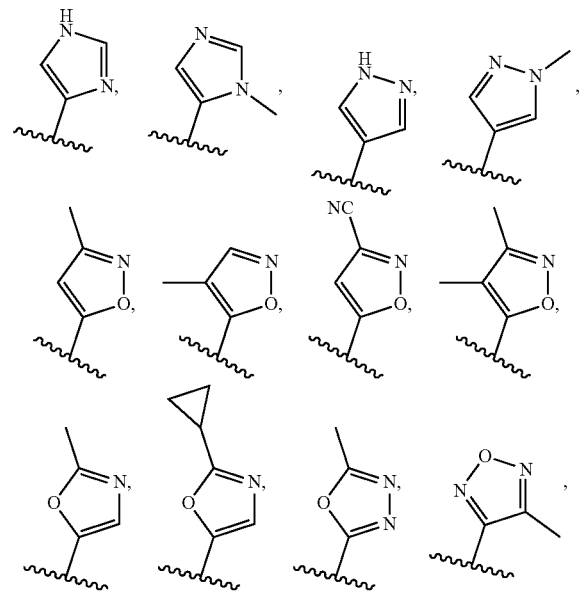

-continued
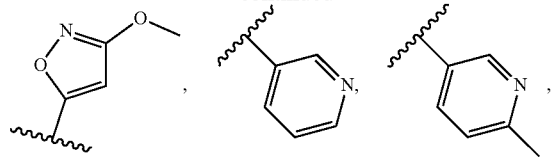
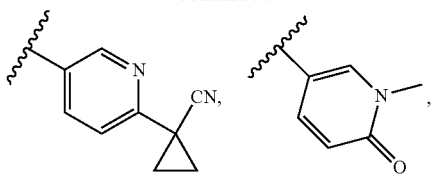
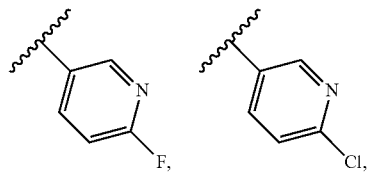
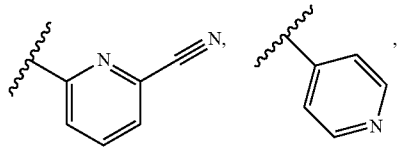
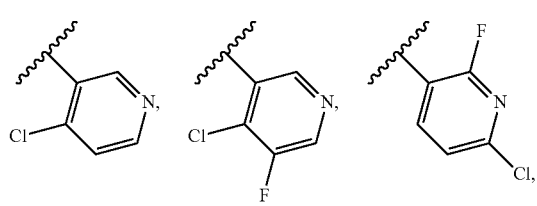
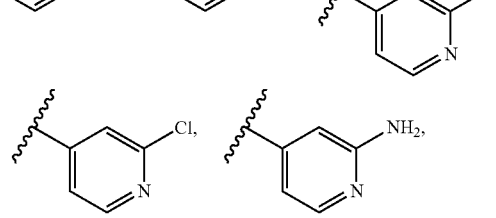
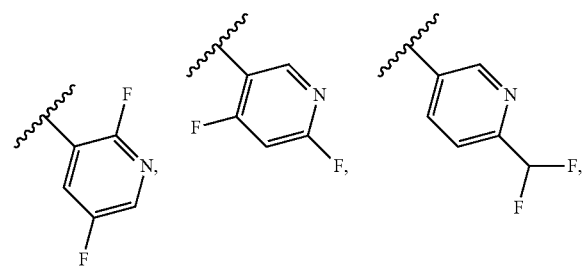
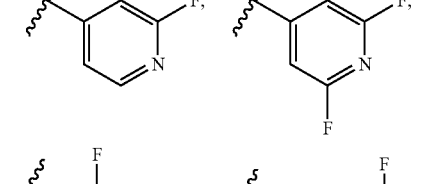
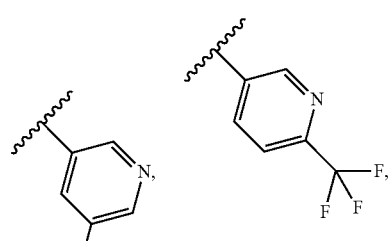
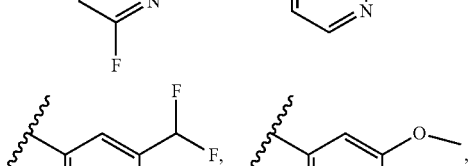
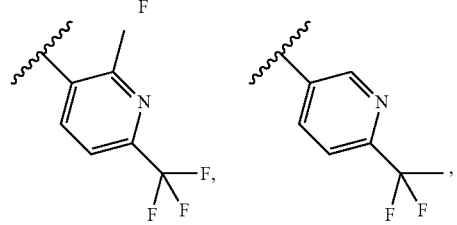
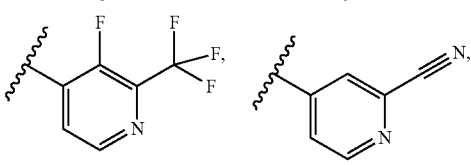
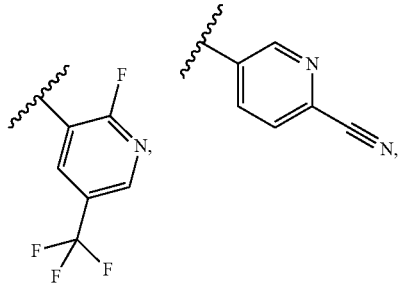
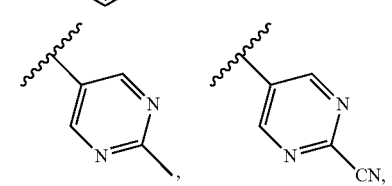

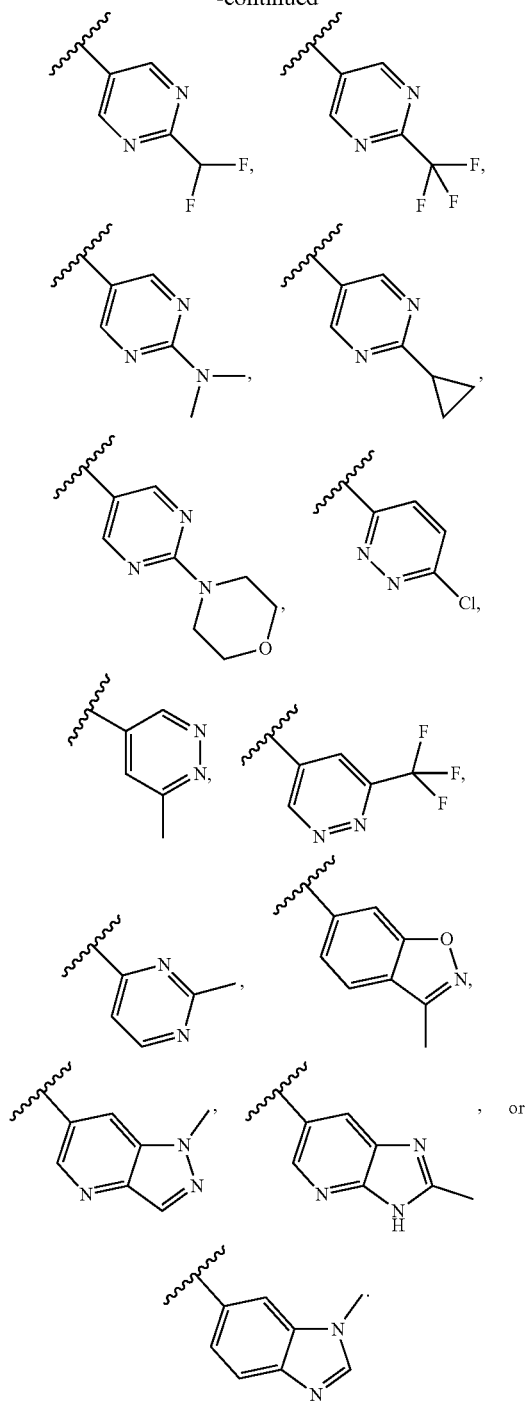

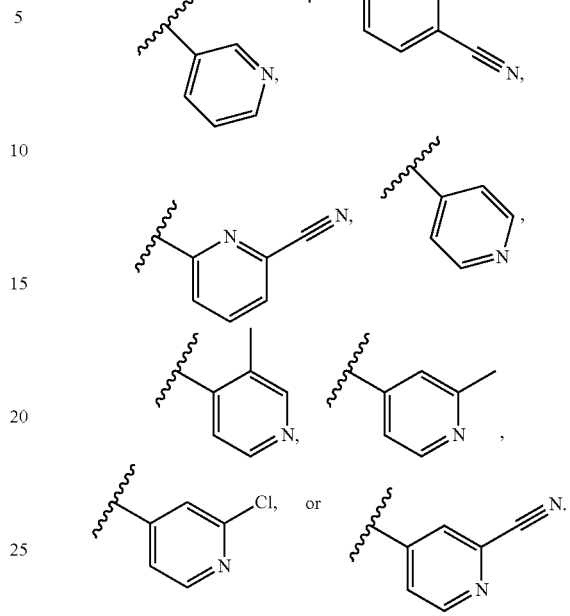

In some embodiments of the compound of Formula (I), (Ia), (IIa), (IIb), (IIc), (IId), (IIe), (IIf), (IIg), (IIh), (IIi), or (IIn), or pharmaceutically acceptable salt thereof, each $R^3$ is independently selected from deuterium, halogen, $C_{1-6}$ alkyl, $C_{3-6}$ cycloalkyl, —O—$R^{241}$, and —N($R^{241}$)($R^{242}$), wherein the $C_{1-6}$ alkyl is optionally substituted with 1 to 3 substituents, which can be the same or different, independently selected from $C_{1-4}$ alkoxy and halogen, and wherein each $R^{241}$ and $R^{242}$ is independently hydrogen or $C_{1-4}$ alkyl optionally substituted with 1 to 3 halogens, which can be the same or different. In some embodiments, each $R^3$ is independently selected from $C_{1-6}$ alkyl optionally substituted with 1 to 3 substituents, which can be the same or different, independently selected from halogen, cyano, $C_{1-4}$ alkoxy, and $C_{3-10}$ cycloalkyl. In some embodiments of the compound of Formula (I), (Ia), (IIa), (IIb), (IIc), (IId), (IIe), (IIf), (IIg), (IIh), (IIi), or (IIn), or pharmaceutically acceptable salt thereof, $R^3$ is —$CH_3$. In some embodiments of the compound of Formula (I), (Ia), (IIa), (IIb), (IIc), (IId), (IIe), (IIf), (IIg), (IIh), (IIi), or (IIn), or pharmaceutically acceptable salt thereof, $R^3$ is halogen. In some embodiments of the compound of Formula (I), (Ia), (IIa), (IIb), (IIc), (IId), (IIe), (IIf), (IIg), (IIh), (IIi), or (IIn), or pharmaceutically acceptable salt thereof, $R^3$ is —F. In some embodiments of the compound of Formula (I), (Ia), (IIa), (IIb), (IIc), (IId), (IIe), (IIf), (IIg), (IIh), (IIi), or (IIn), or pharmaceutically acceptable salt thereof, n is 0, 1, or 2. In some embodiments, n is 0. In some embodiments, n is 1. In some embodiments, n is 2.

In some embodiments of the compound of Formula (I) or (Ia), or pharmaceutically acceptable salt thereof, each $Y^1$ and $Y^2$ is independently hydrogen, deuterium, or $C_{1-6}$ alkyl optionally substituted with 1 to 3 substituents, which can be the same or different, independently selected from halogen, cyano, $C_{2-3}$ alkynyl, $C_{1-4}$ alkoxy, and —C(O)NH—($C_{1-4}$ $H_{3-9}$). In some embodiments of the compound of Formula (I), (Ia), (IIa), (IIb), (IIc), (IId), (IIe), (IIf), (IIg), (IIh), (IIi), (IIj), (IIk), (IIl), (IIm), (IIn), or (IIo), or pharmaceutically acceptable salt thereof, $Y^1$ is hydrogen, deuterium, or $C_{1-6}$ In some embodiments, $R^1$ is

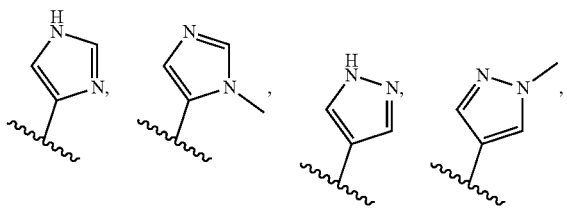

alkyl optionally substituted with 1 to 3 substituents, which can be the same or different, independently selected from halogen, cyano, $C_{2-3}$ alkynyl, $C_{1-4}$ alkoxy, and —C(O)NH—($C_{1-4}H_{3-9}$). In some embodiments, $Y_1$ is $C_{1-4}$ alkyl optionally substituted with 1 to 3 substituents, which can be the same or different, each independently selected from halogen, cyano, and $C_{1-4}$ alkoxy, and $Y_2$ is hydrogen. In some embodiments, $Y_1$ is methyl optionally substituted with 1 to 3 substituents, which can be the same or different, each independently selected from —F, —Cl, —CN, and —O—$CH_3$. In some embodiments, $Y_1$ is —$CH_3$ or —$CH_2F$.

In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, Z is $C_{6-12}$ aryl, optionally substituted with 1 to 3 substituents, which can be the same or different, each independently selected from halogen, cyano, $C_{1-4}$ alkyl, $C_{1-4}$ alkoxy, and $C_{3-6}$ cycloalkyl, wherein the $C_{1-4}$ alkyl is optionally substituted with 1 to 3 substituents, which can be the same or different, each independently selected from $C_{1-4}$ alkoxy and halogen. In some embodiments, Z is phenyl, optionally substituted with 1 to 3 substituents, which can be the same or different, each independently selected from halogen and $C_{1-4}$ alkyl. In some embodiments, Z is phenyl, optionally substituted with 1 to 3 substituents, which can be the same or different, each independently selected from —F and —Cl. In some embodiments, Z is

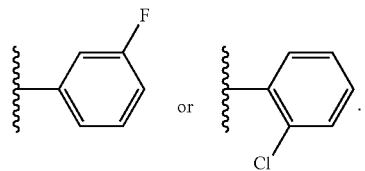 [SMILES: *c1cccc(F)c1 ; *c1ccccc1Cl]

In some embodiments, Z is 5 or 6 membered heteroaryl having 1-3 heteroatoms independently selected from nitrogen, oxygen, and sulfur, wherein the heteroaryl is optionally substituted with 1 to 3 substituents, which can be the same or different, each independently selected from halogen and $C_{1-4}$ alkyl. In some embodiments, Z is pyridyl, optionally substituted with 1 to 3 substituents, which can be the same or different, each independently selected from —F, —Cl, —Br, and —$CH_3$. In some embodiments, Z is

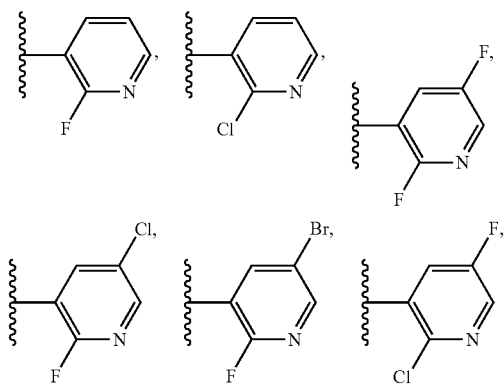

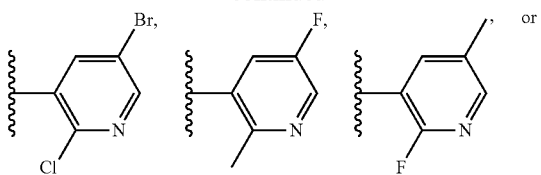

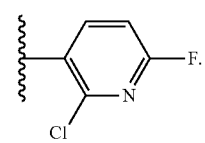

In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, $Y_1$ is —$CH_3$ and Z is

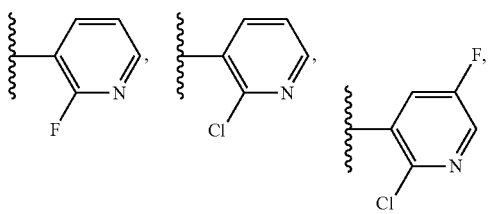

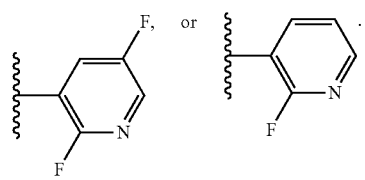

In some embodiments of the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, $Y_1$ is —$CH_3$ and Z is

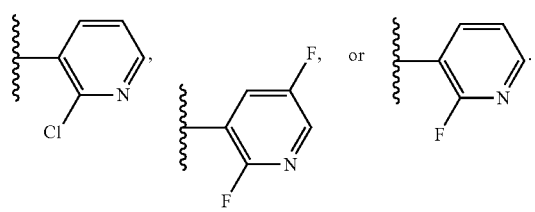 [SMILES: *c1cccnc1Cl ; *c1cc(F)cnc1F ; *c1cccnc1F]

In some embodiments the compound of Formula (I), (Ia), (IIa), (IIb), (IIc), (IId), (IIe), (IIf), (IIg), (IIh), (IIi), (IIj), (IIk), (III), (IIm), (IIn), or (IIo), or pharmaceutically acceptable salt thereof, is selected from the group consisting of:

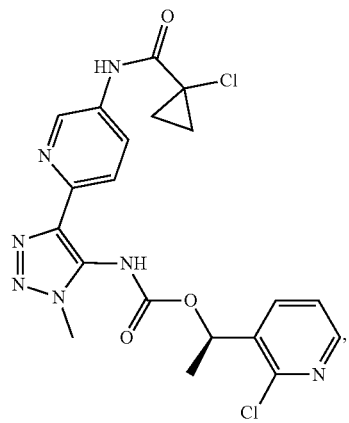
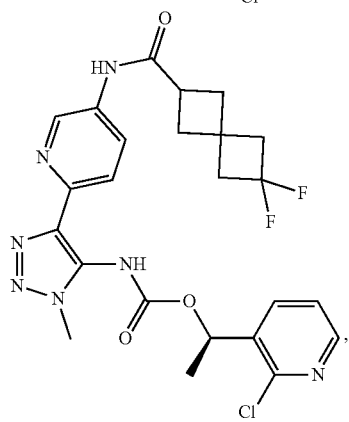
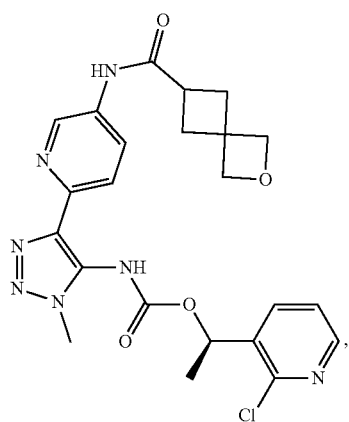
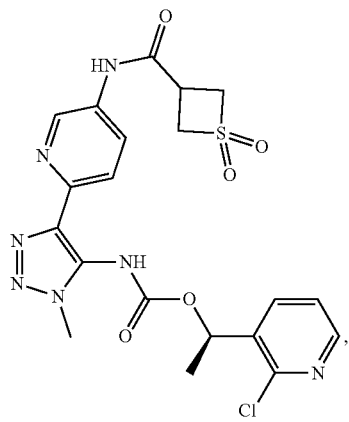
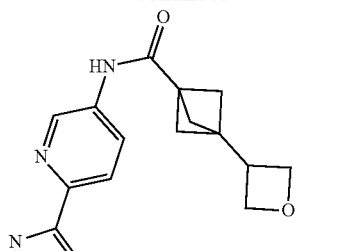
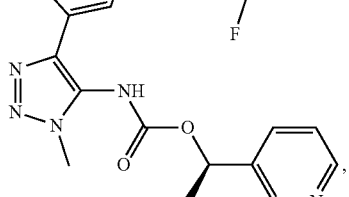
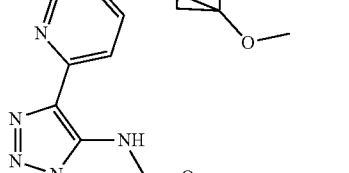
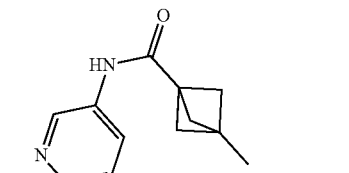

65
-continued
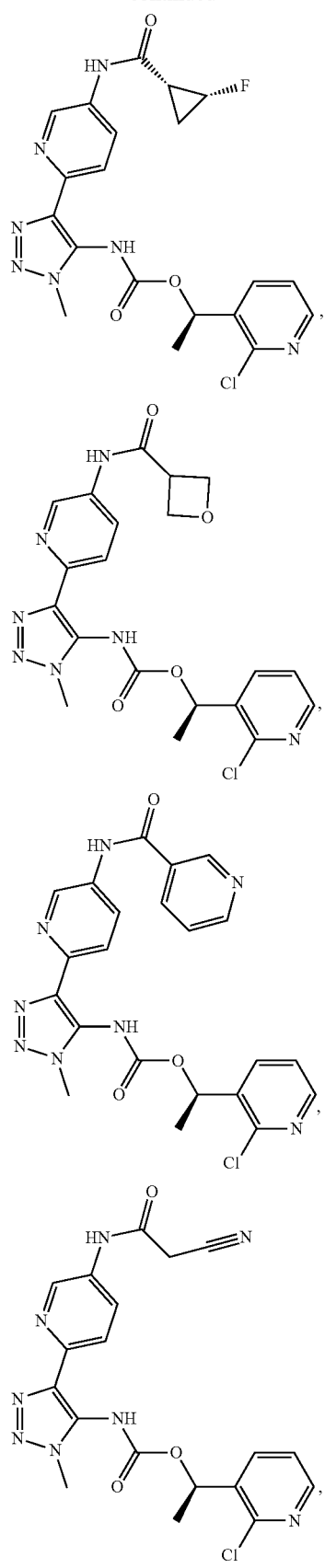
66
-continued
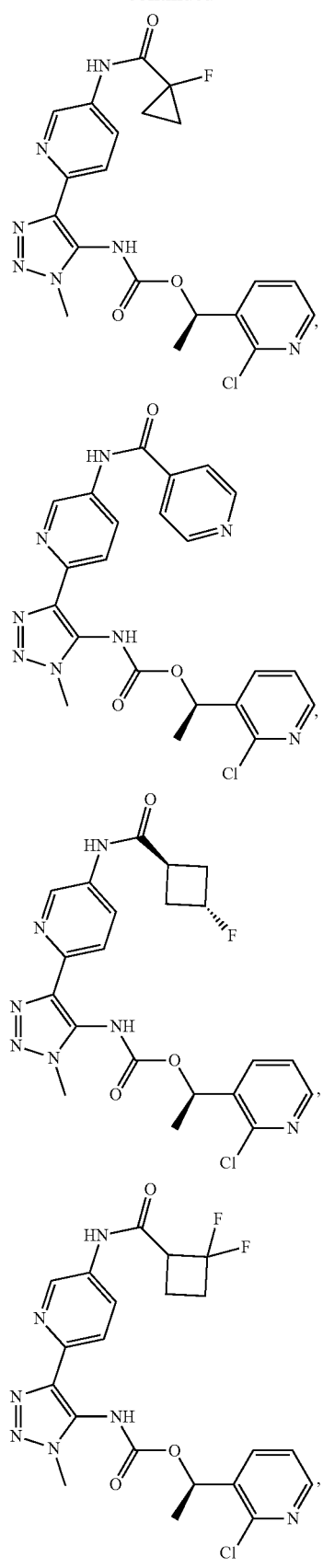

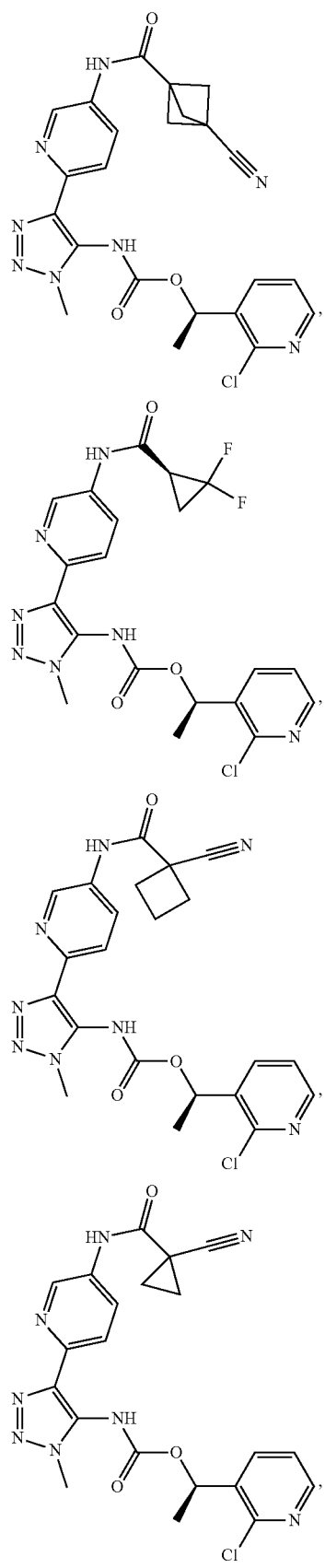
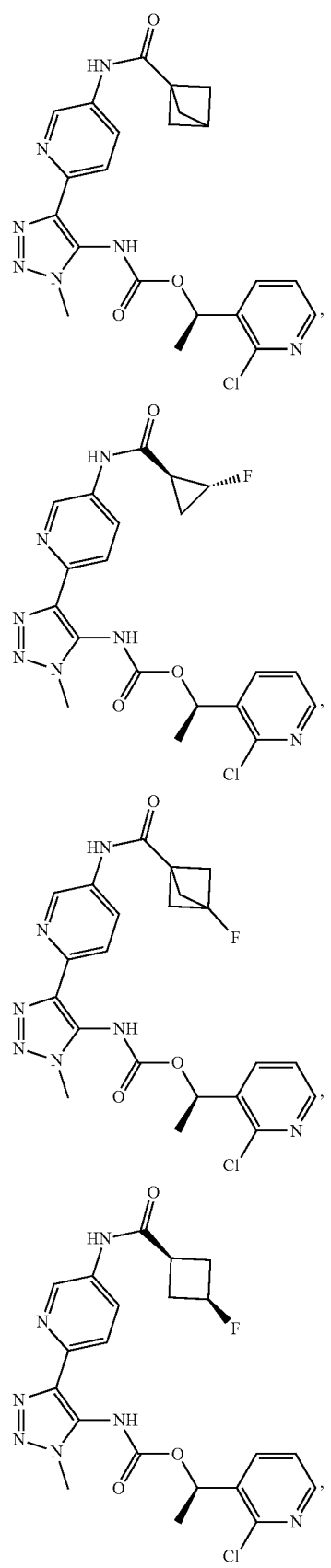

69
-continued
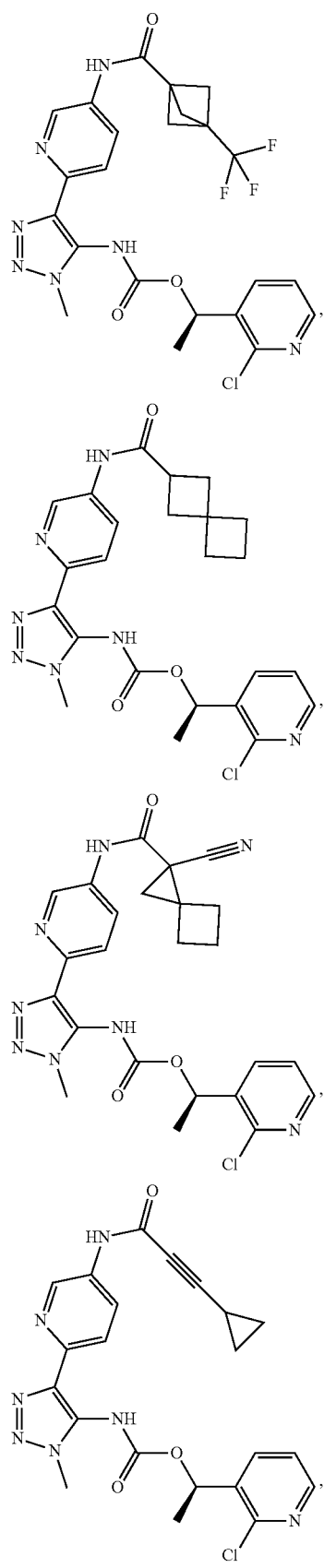
70
-continued
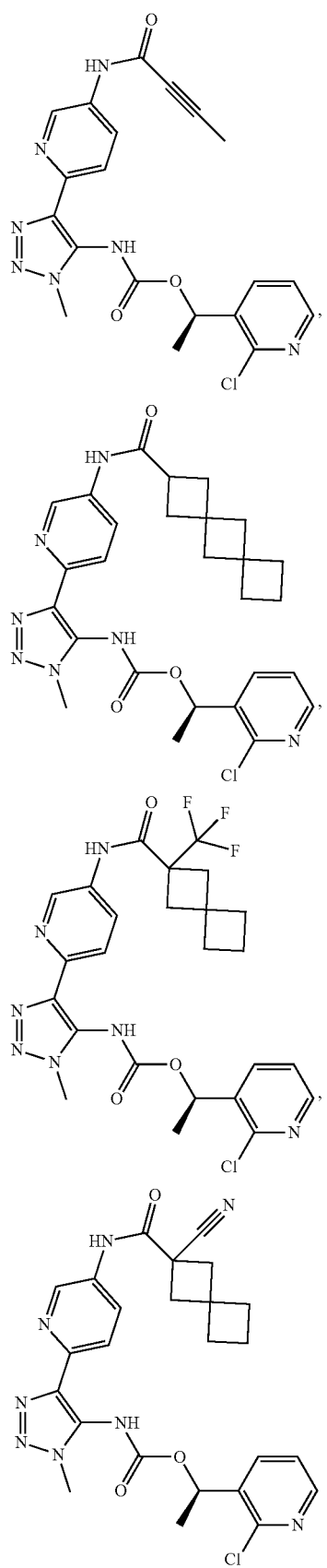

71
-continued
72
-continued
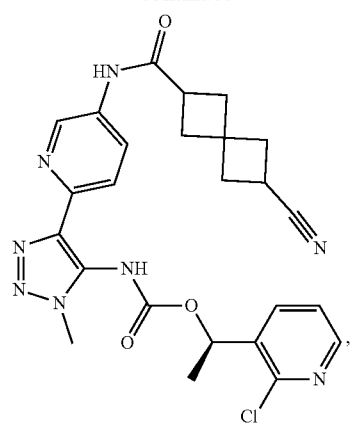
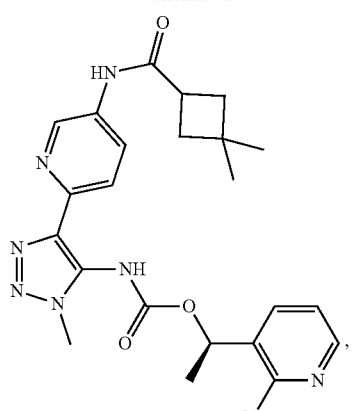

-continued
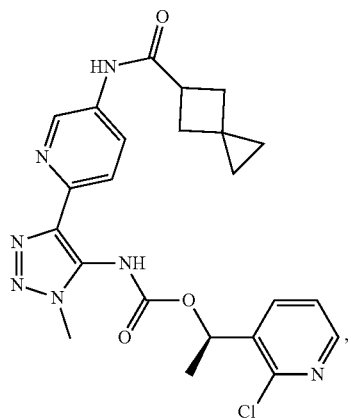
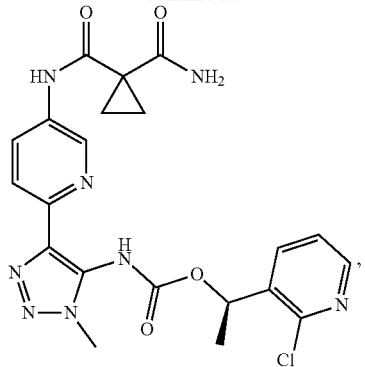
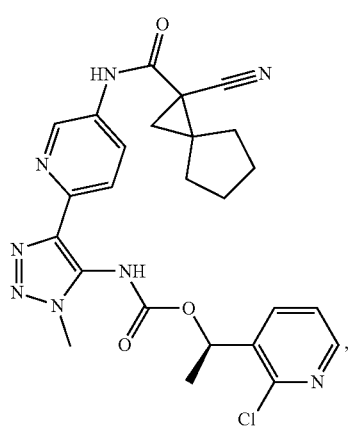
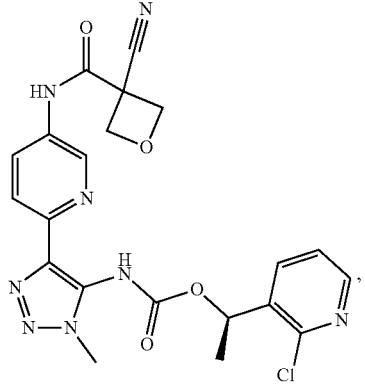
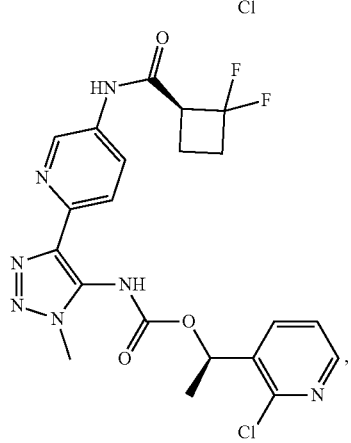
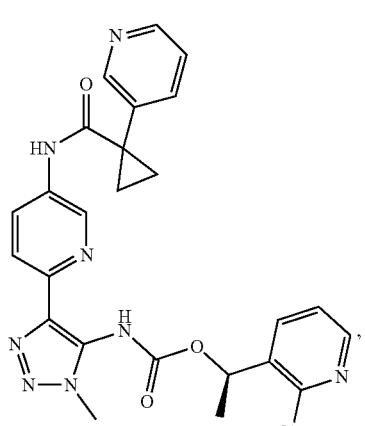
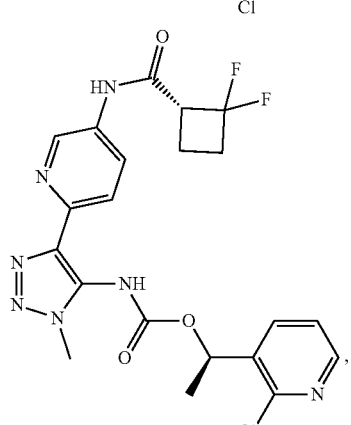
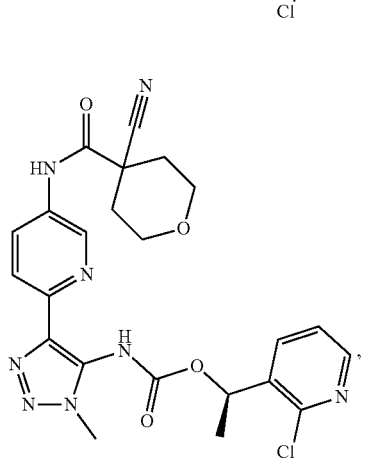

75
-continued
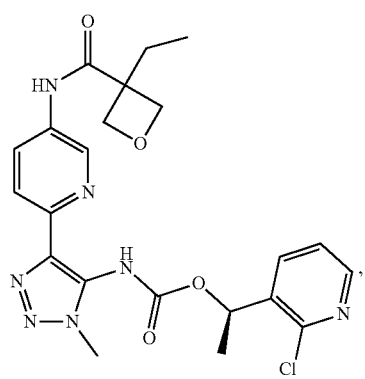
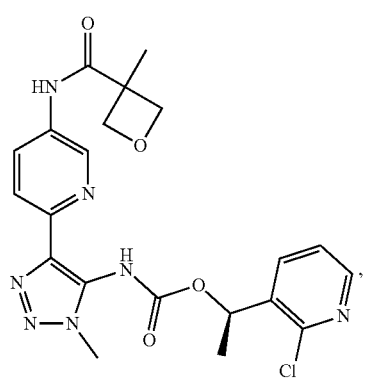
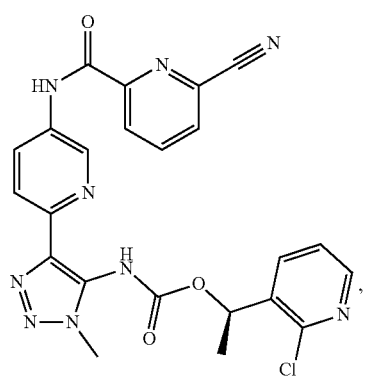
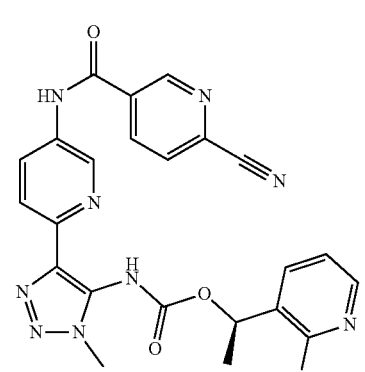
76
-continued
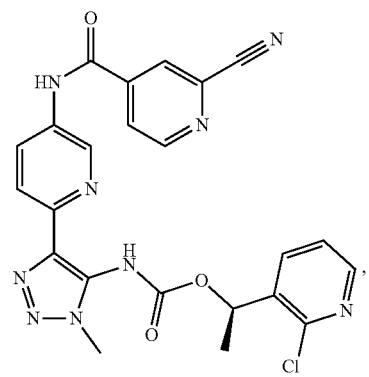
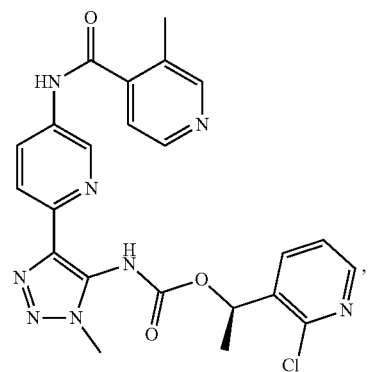
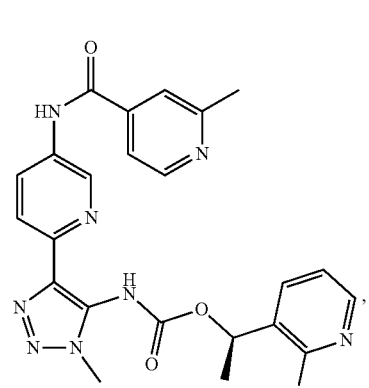
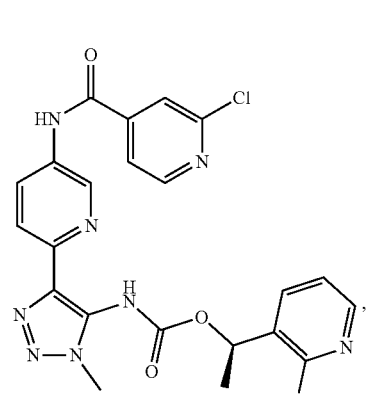

77
-continued
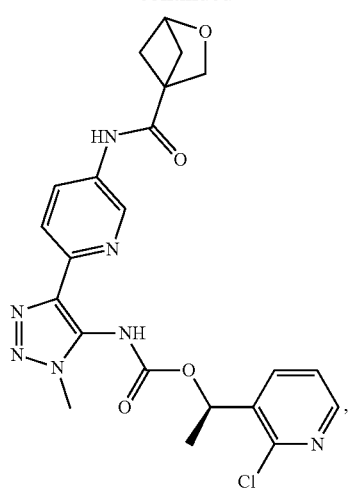
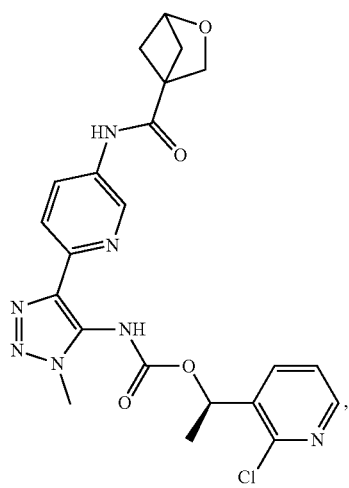
78
-continued
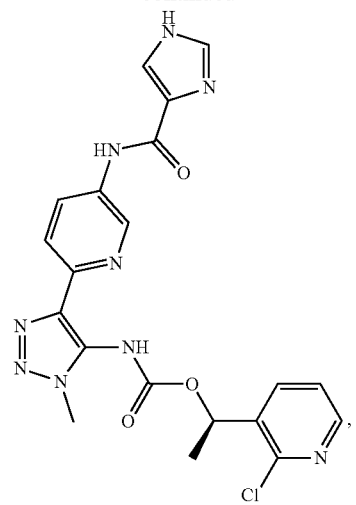
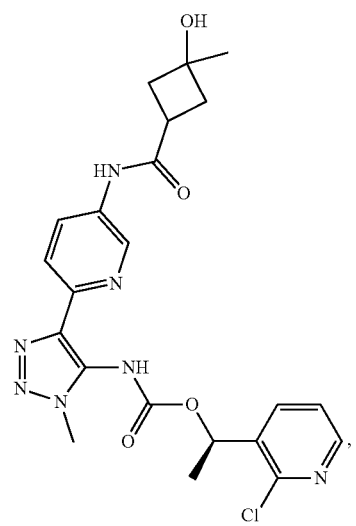

79
-continued
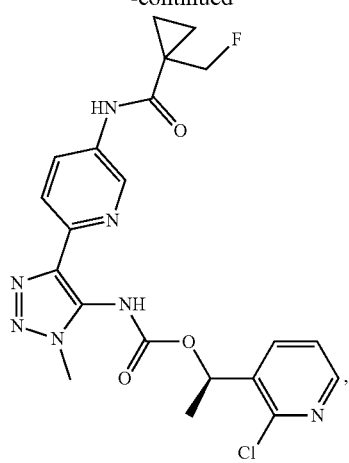
80
-continued
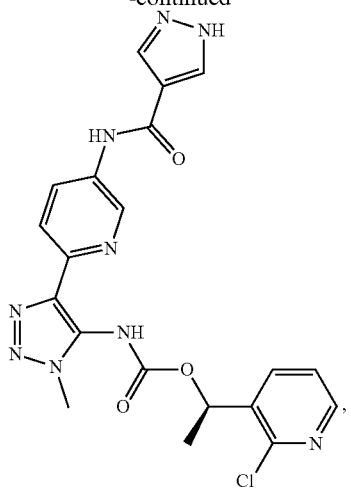
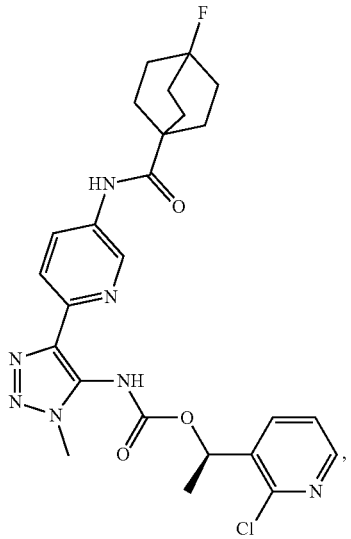

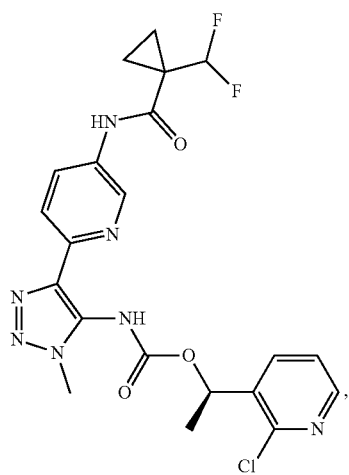
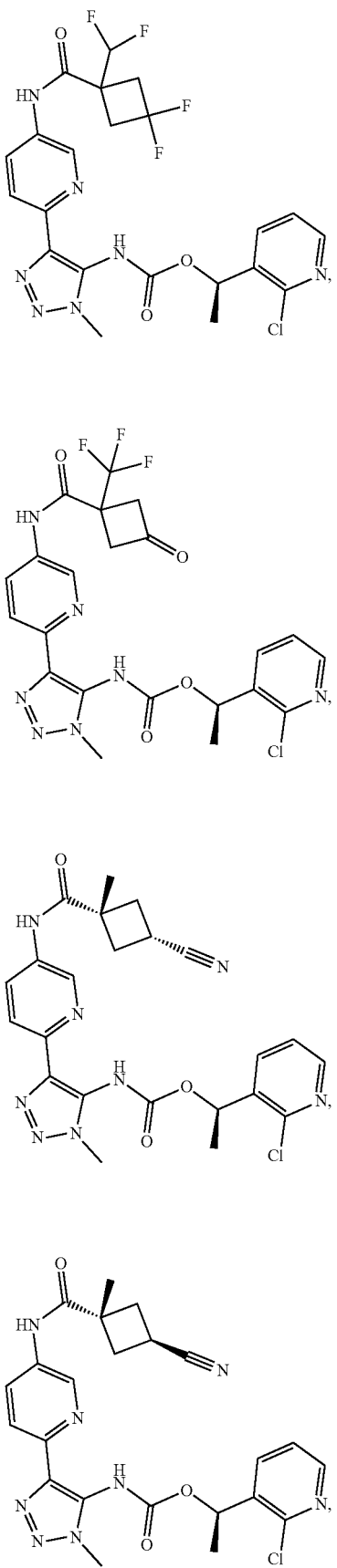

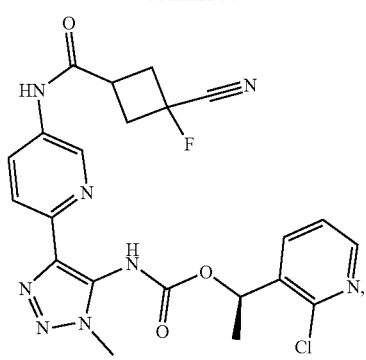
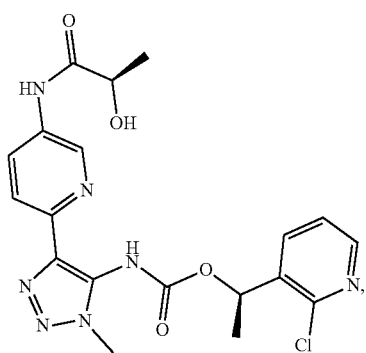
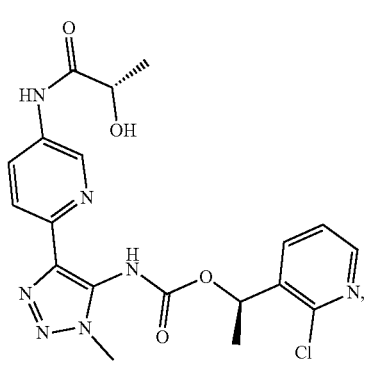
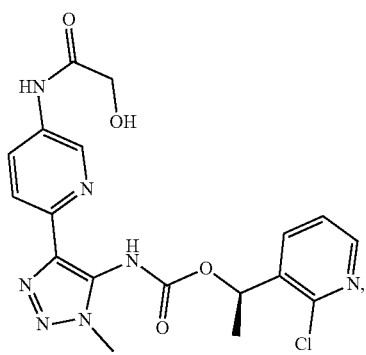
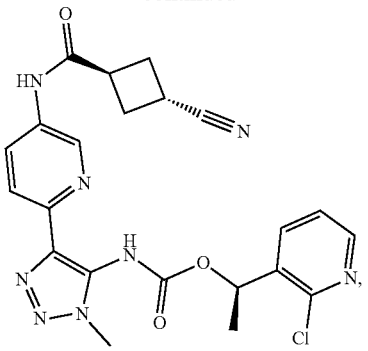
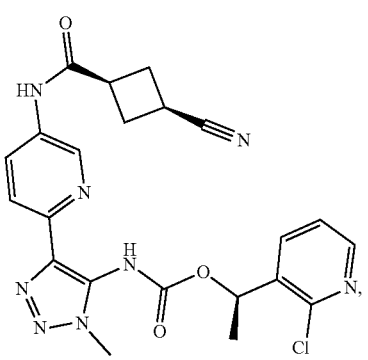
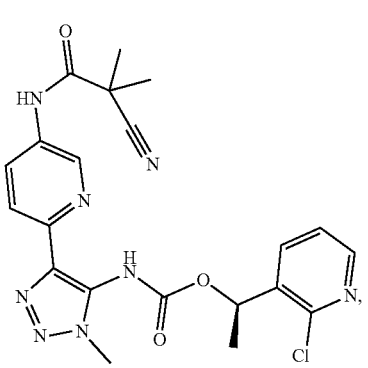
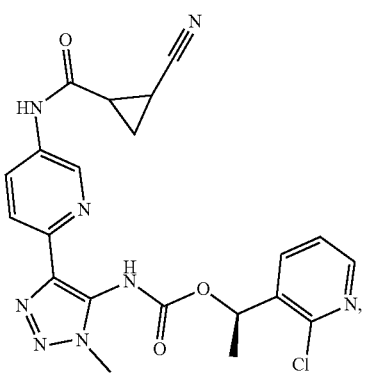

85
-continued
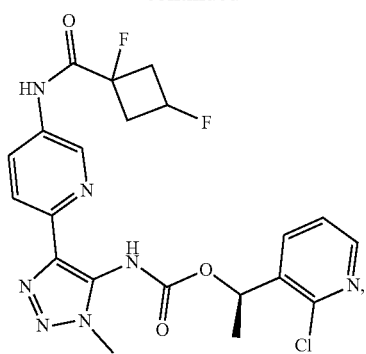
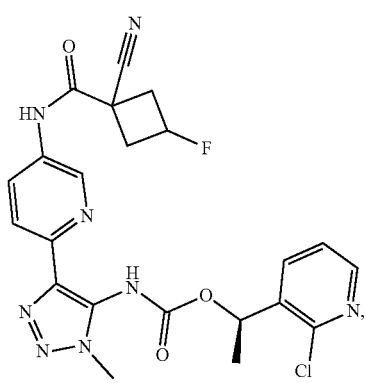
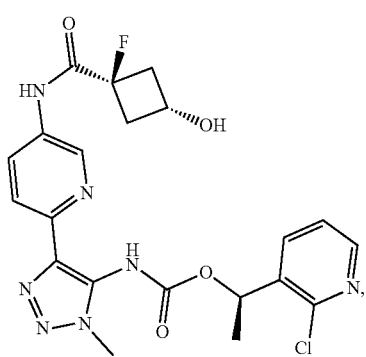
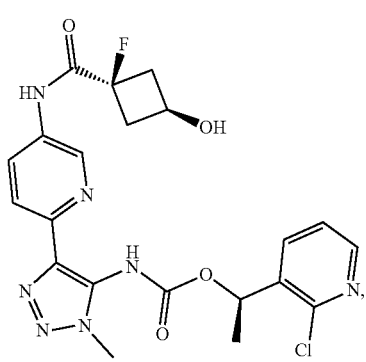
86
-continued
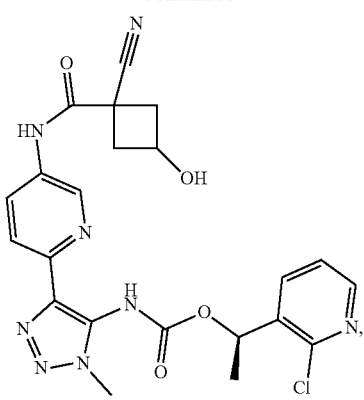
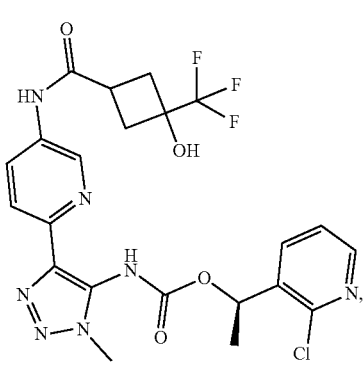
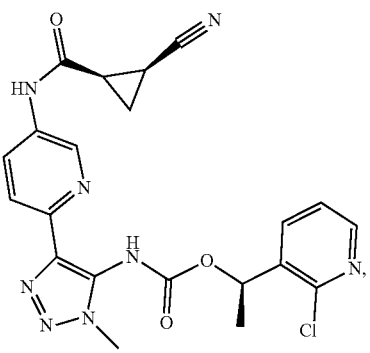
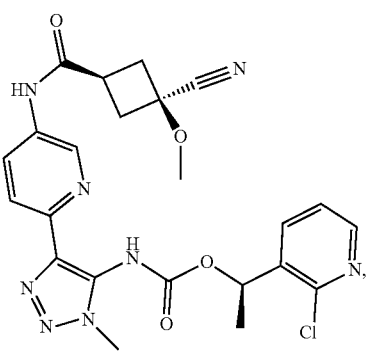

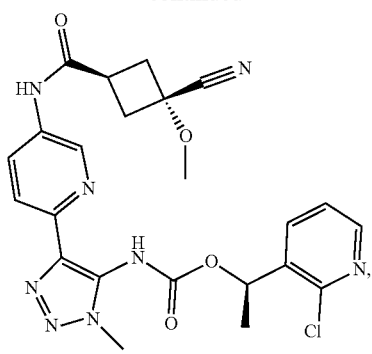
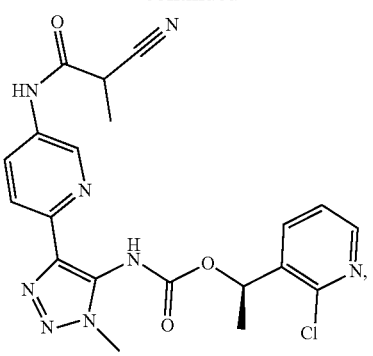
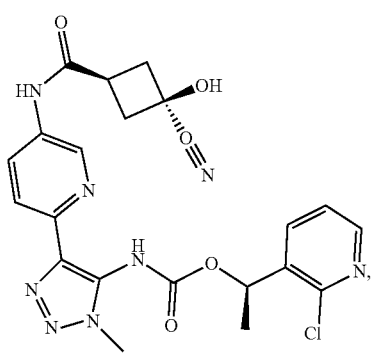
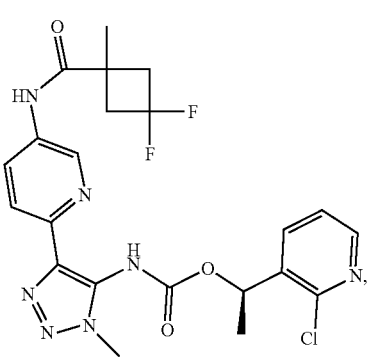
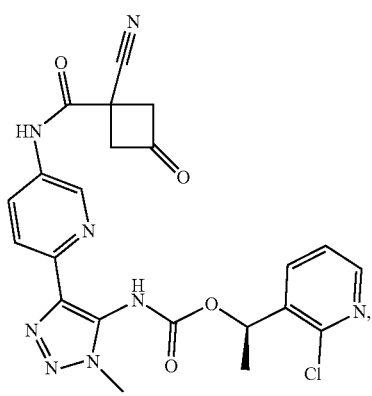
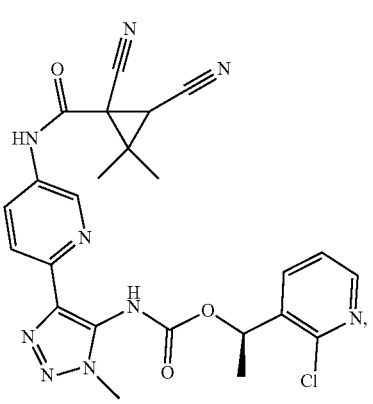
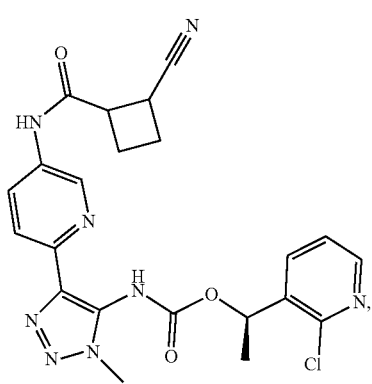
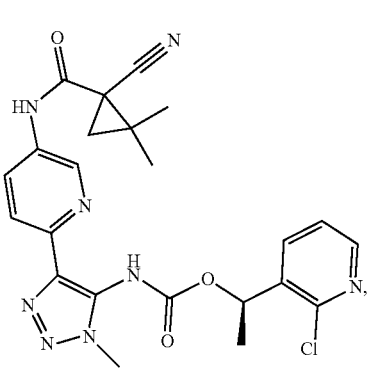

89
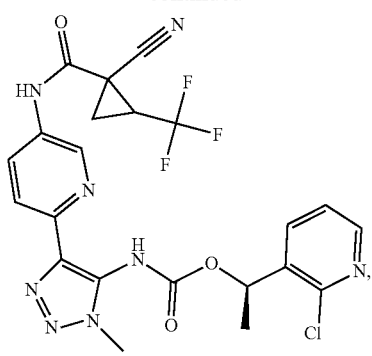
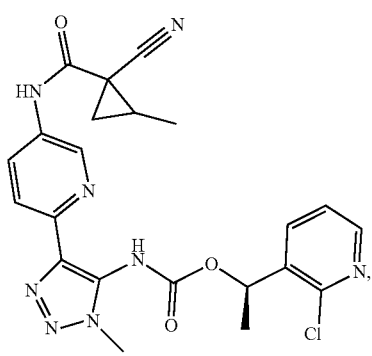
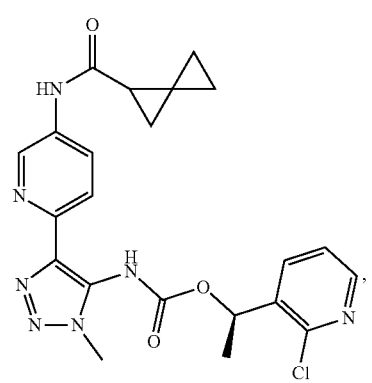
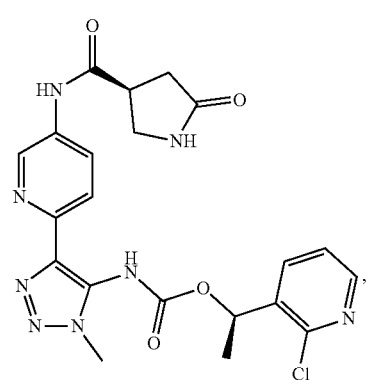
90
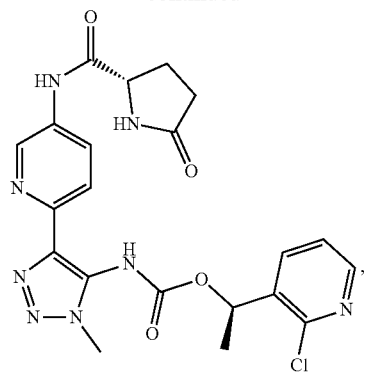
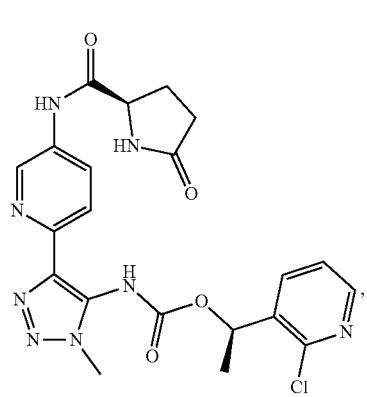
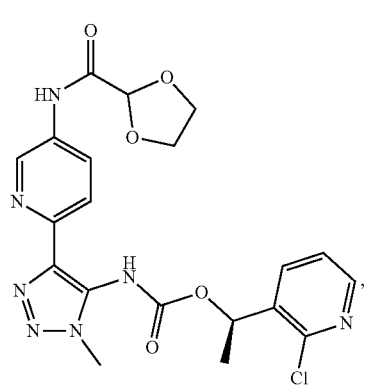
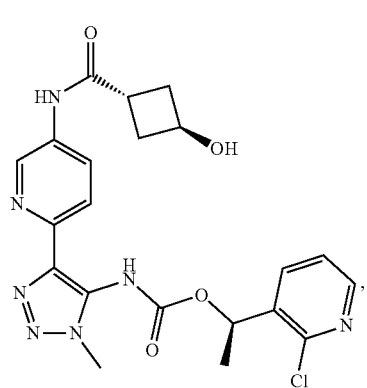

91
-continued
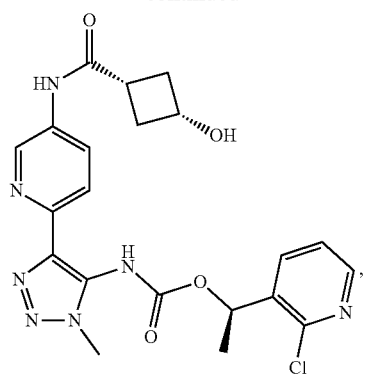
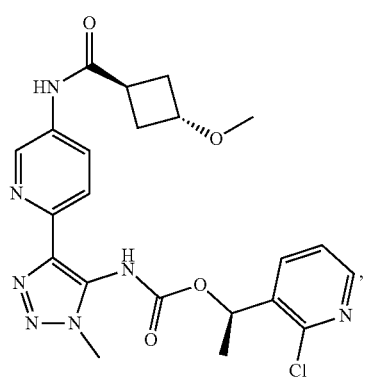
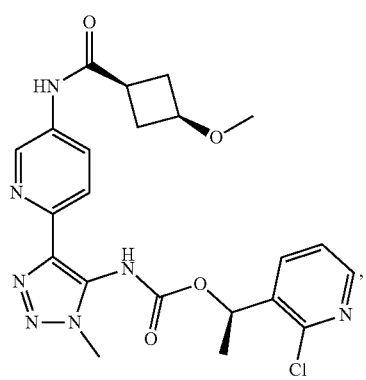
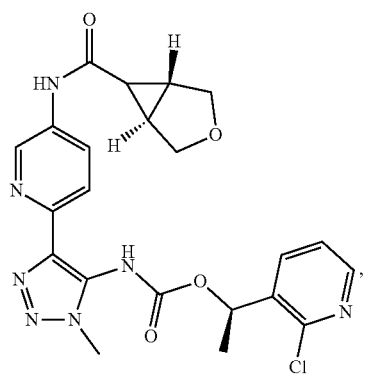
92
-continued
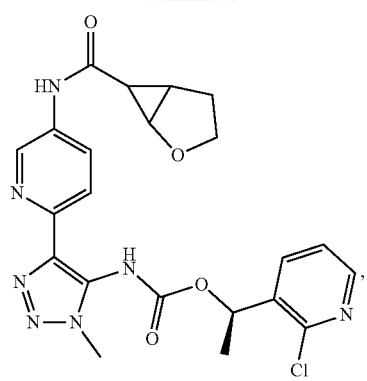
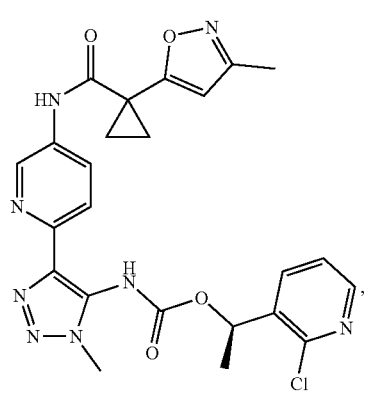
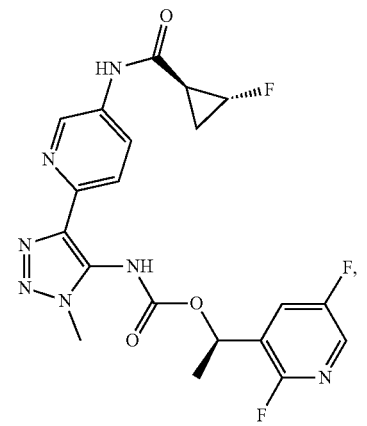
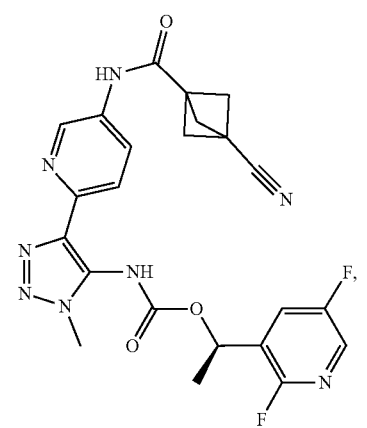

-continued

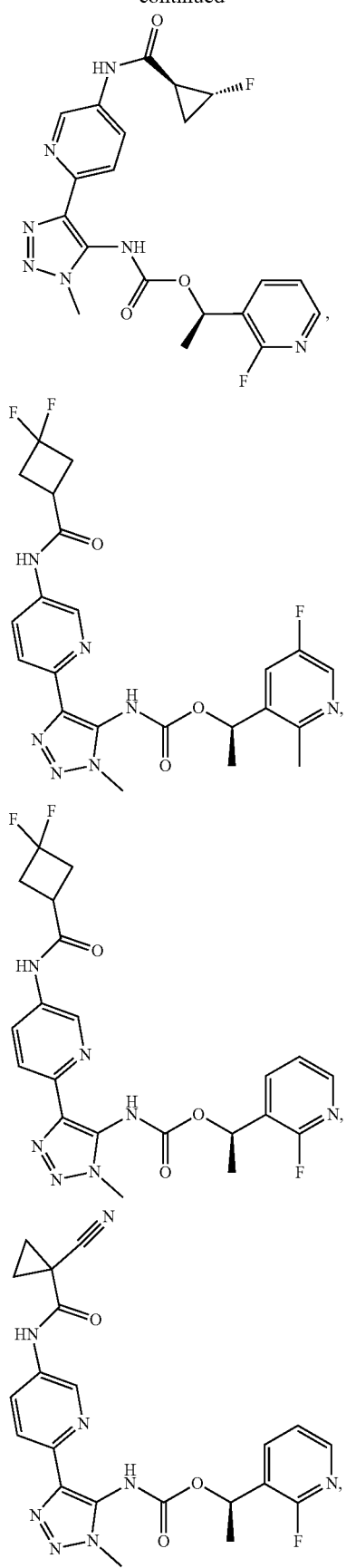
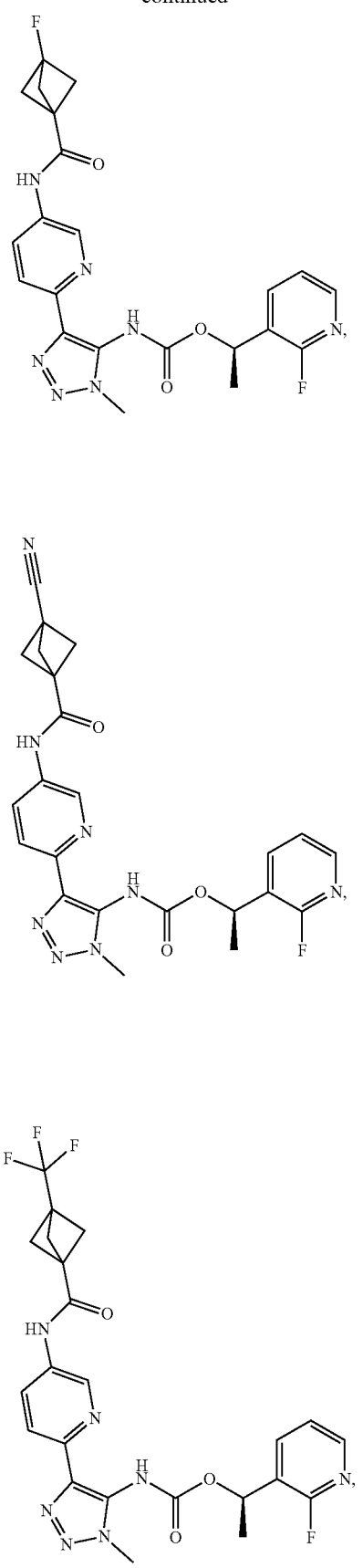

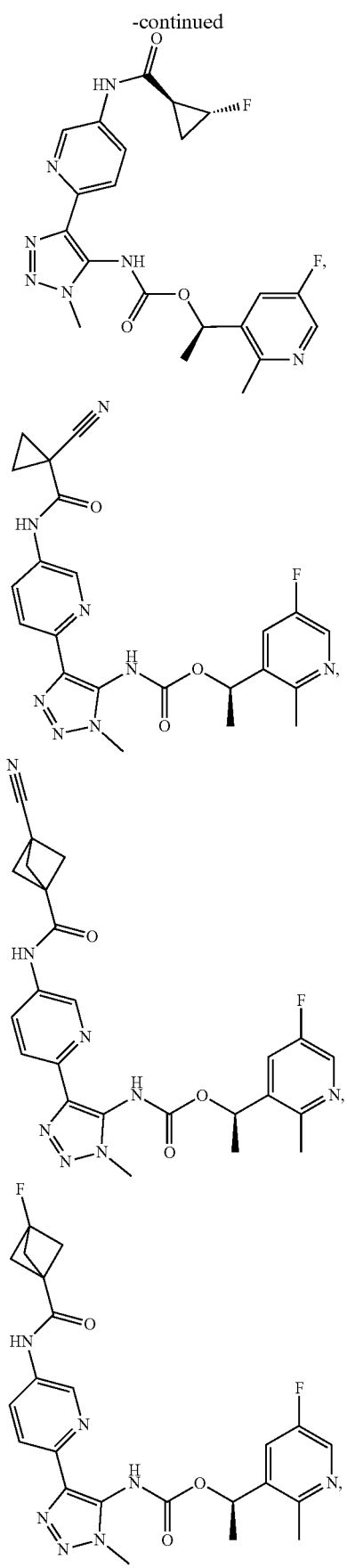
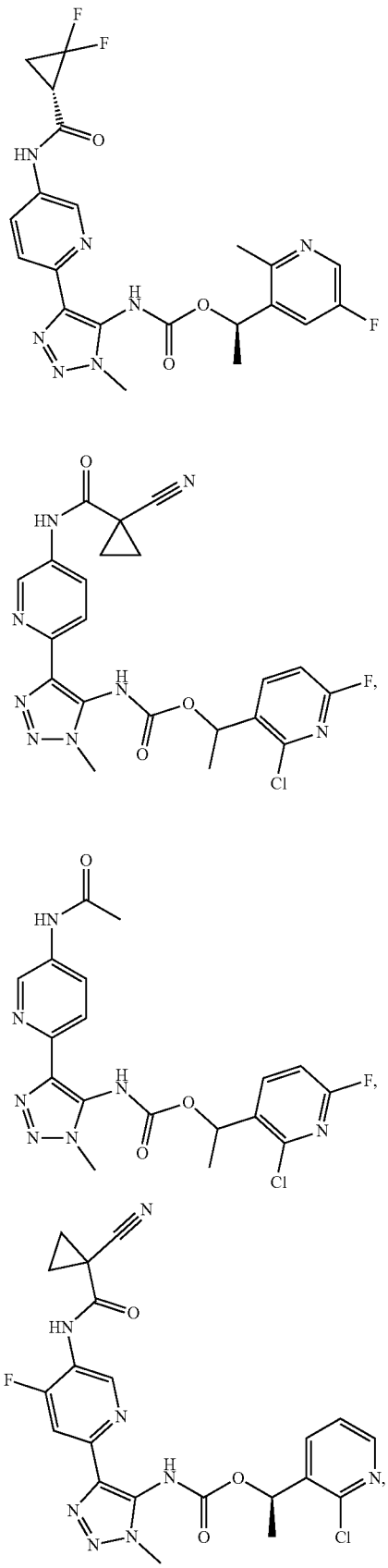

99
-continued
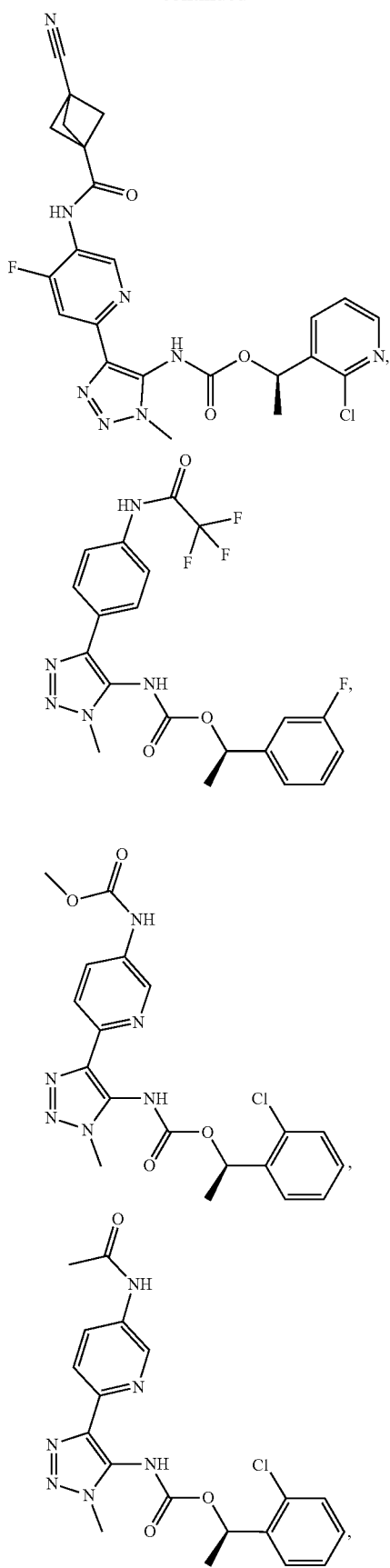
100
-continued
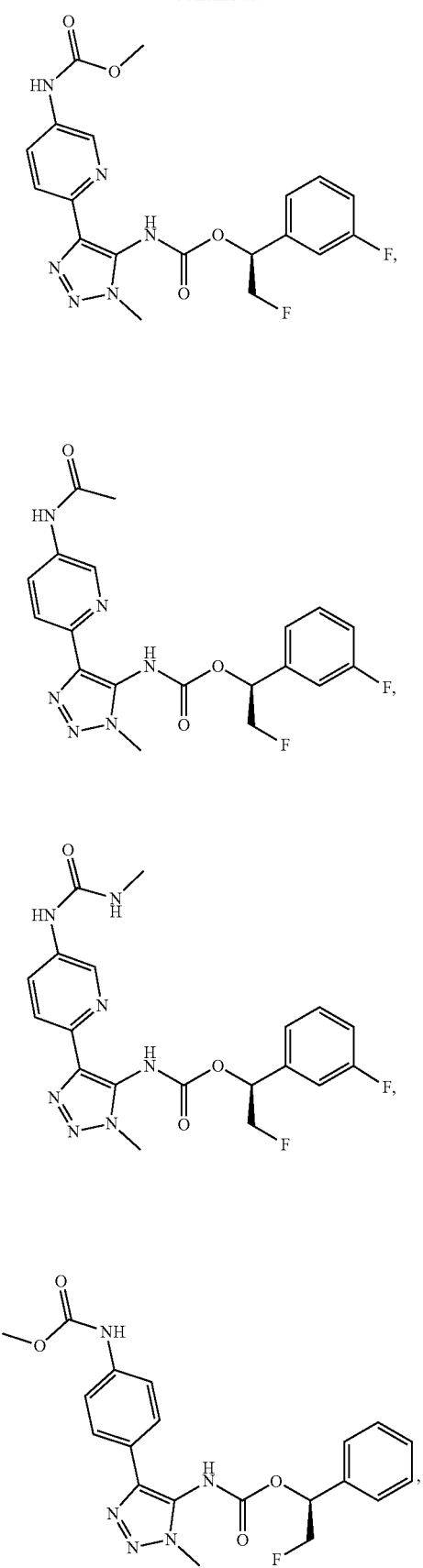

101 -continued

102 -continued

103
-continued
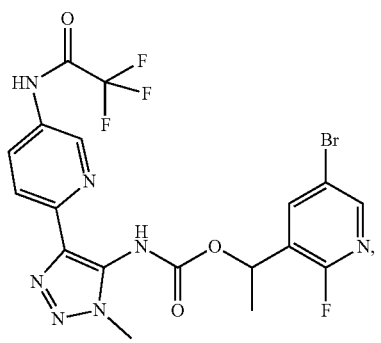
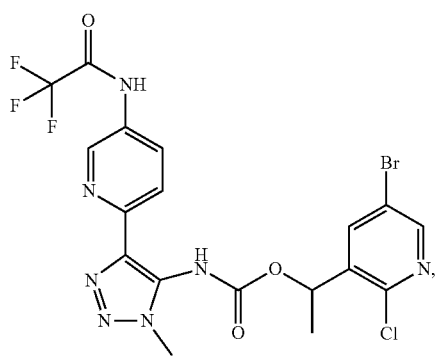
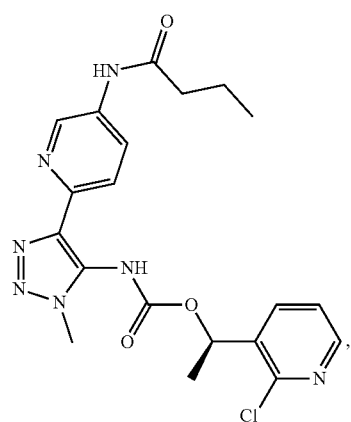
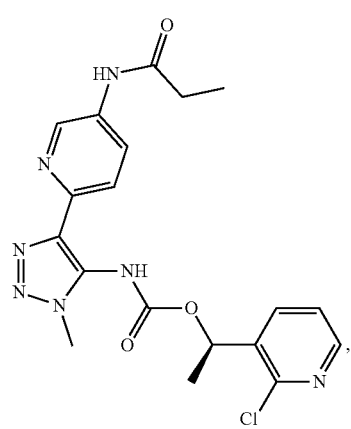
104
-continued
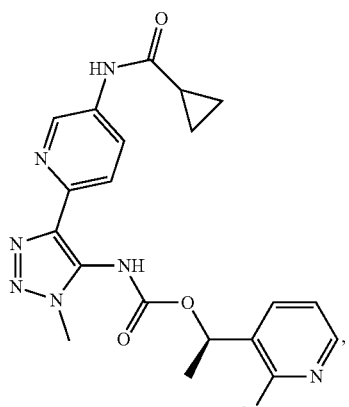
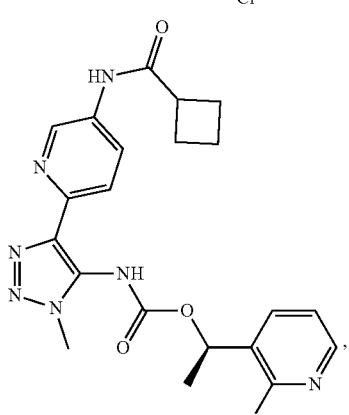
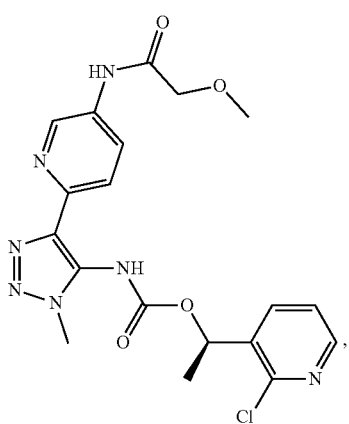
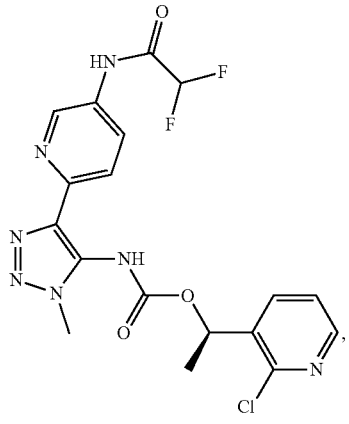

105
-continued
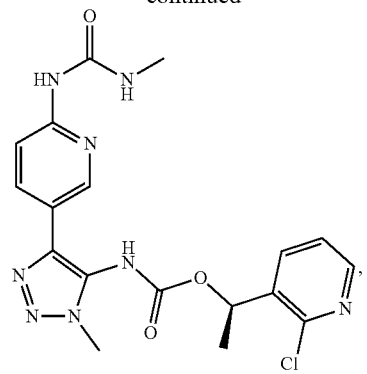
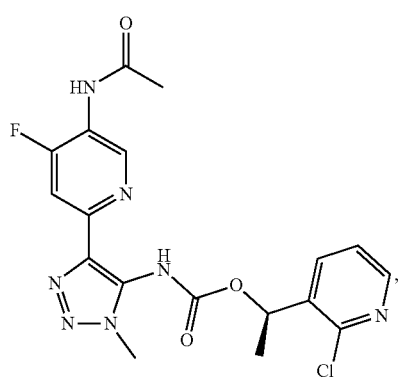
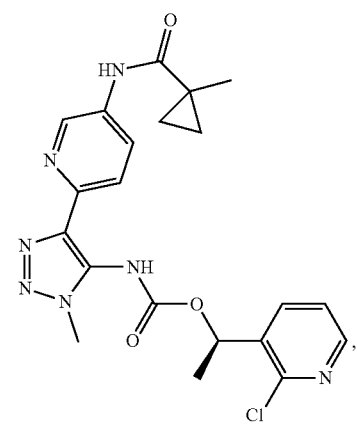
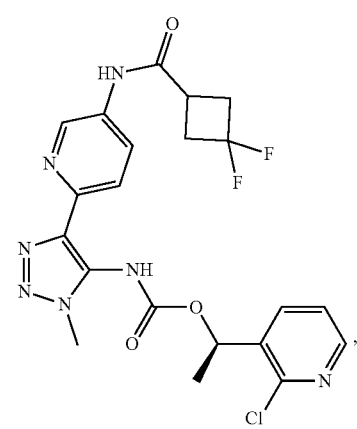
106
-continued
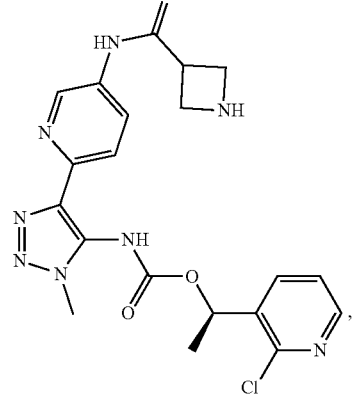
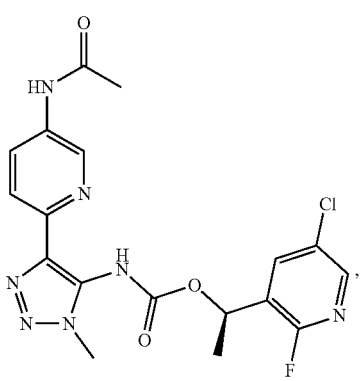
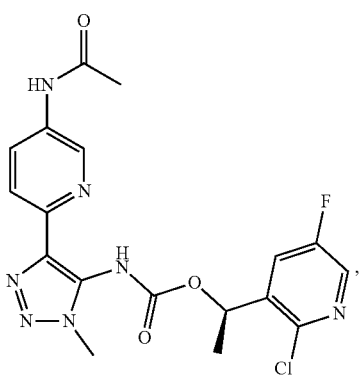
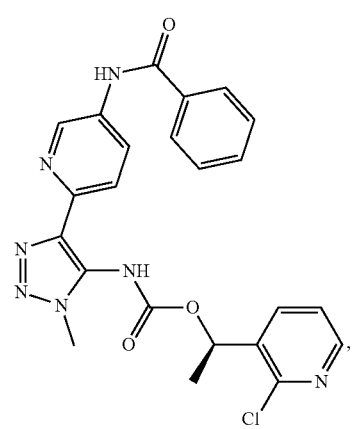

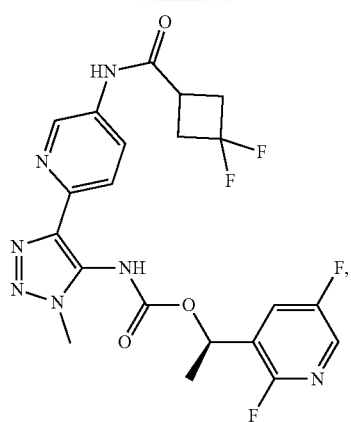
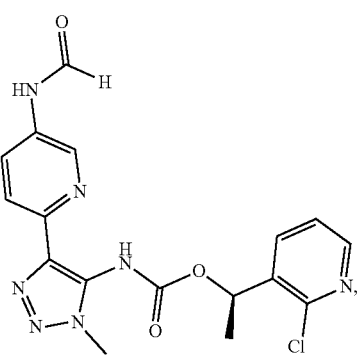
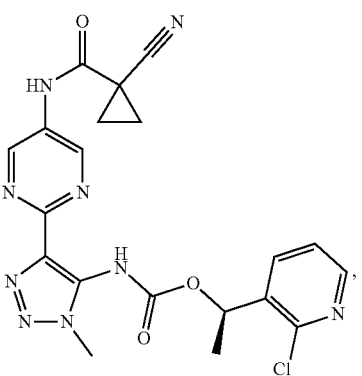
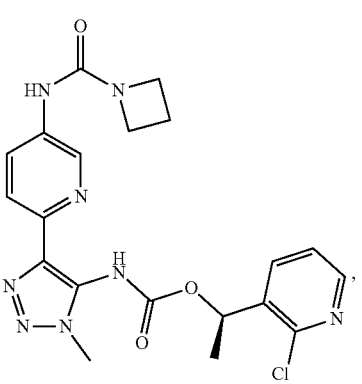
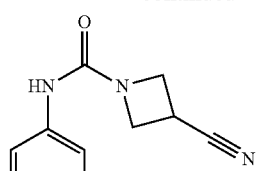
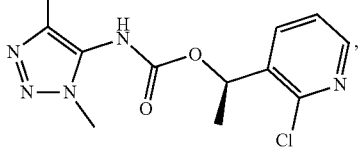
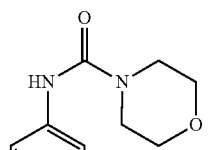
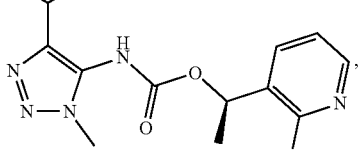
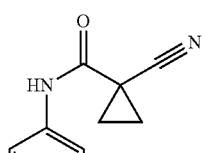
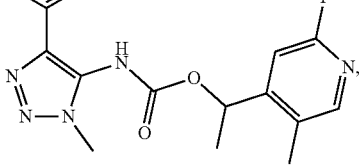
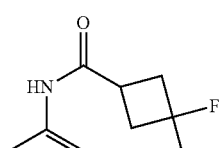
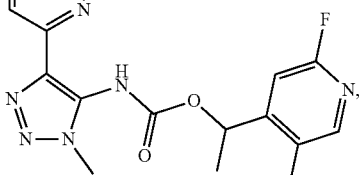

109
-continued
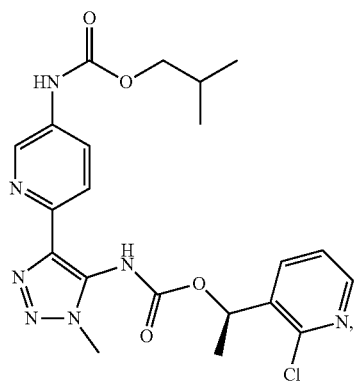
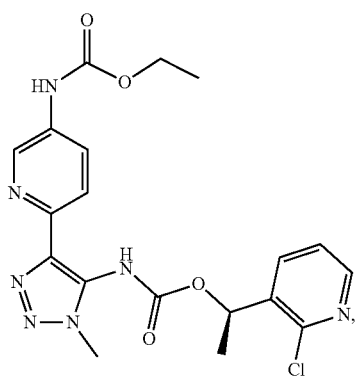
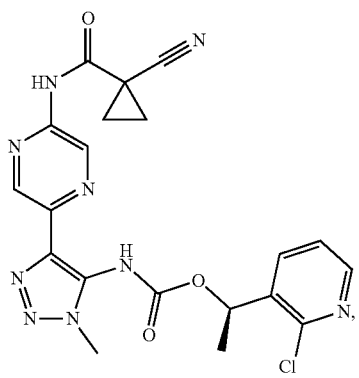
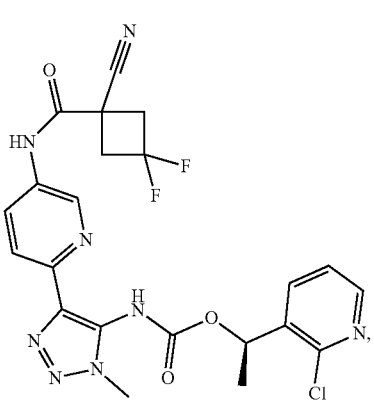
110
-continued
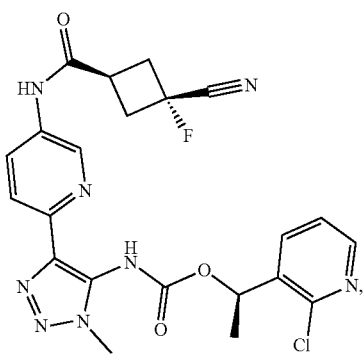
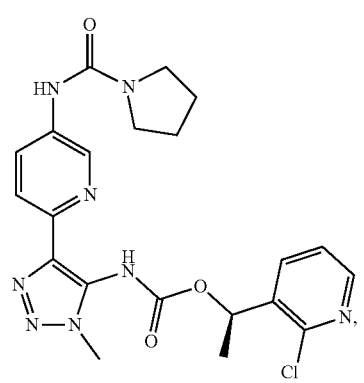
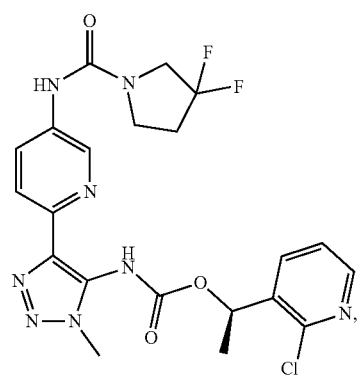
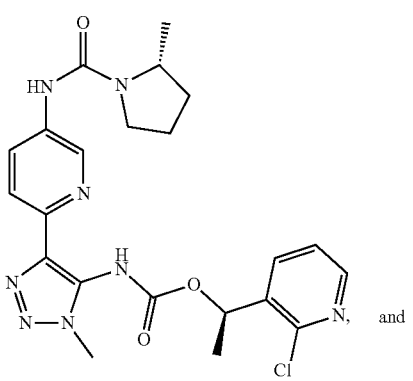
and or a pharmaceutically acceptable salt thereof.

In some embodiments the compound of Formula (I), (Ia), (IIa), (IIb), (IIc), (IId), (IIe), (IIf), (IIg), (IIh), (IIi), (IIj), (IIk), (IIl), (IIm), (IIn), (IIo), or pharmaceutically acceptable salt thereof, is selected from the group consisting of:

113
-continued
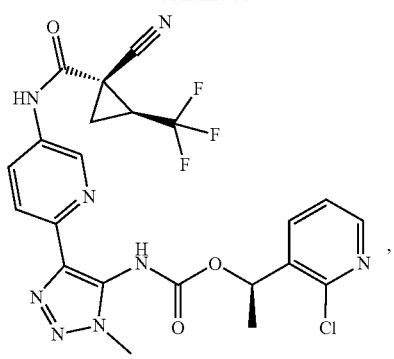
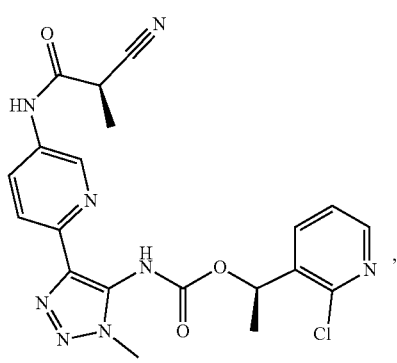
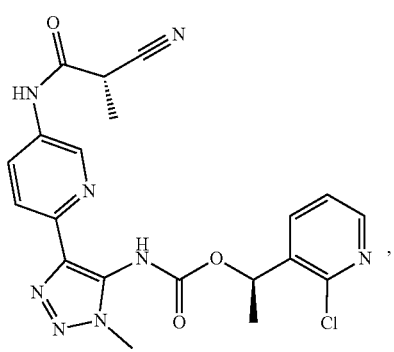
114
-continued
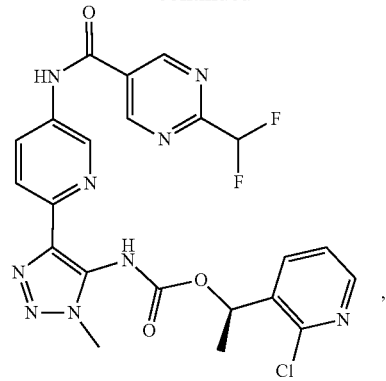
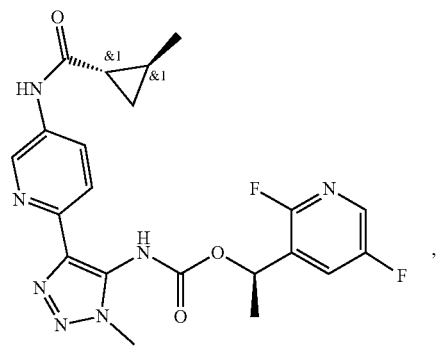

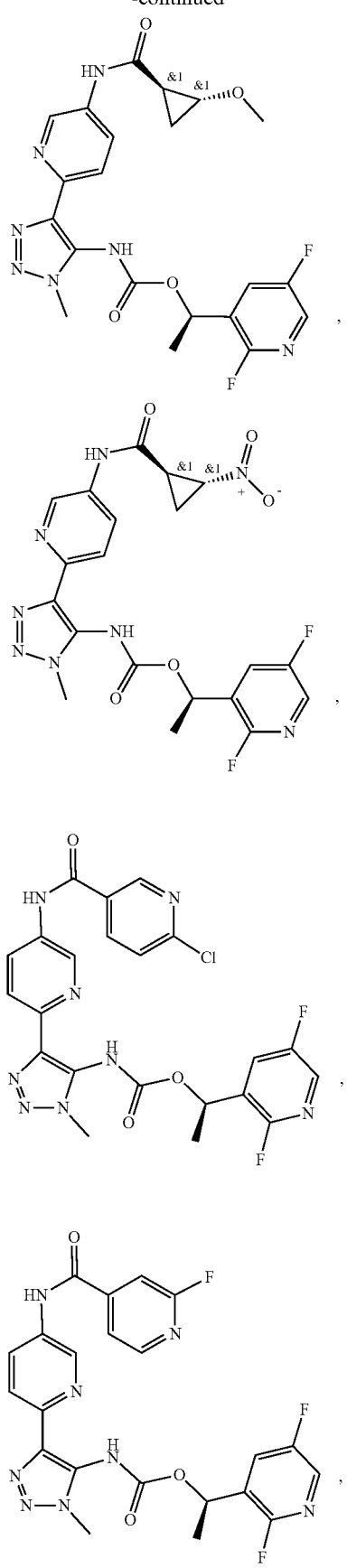
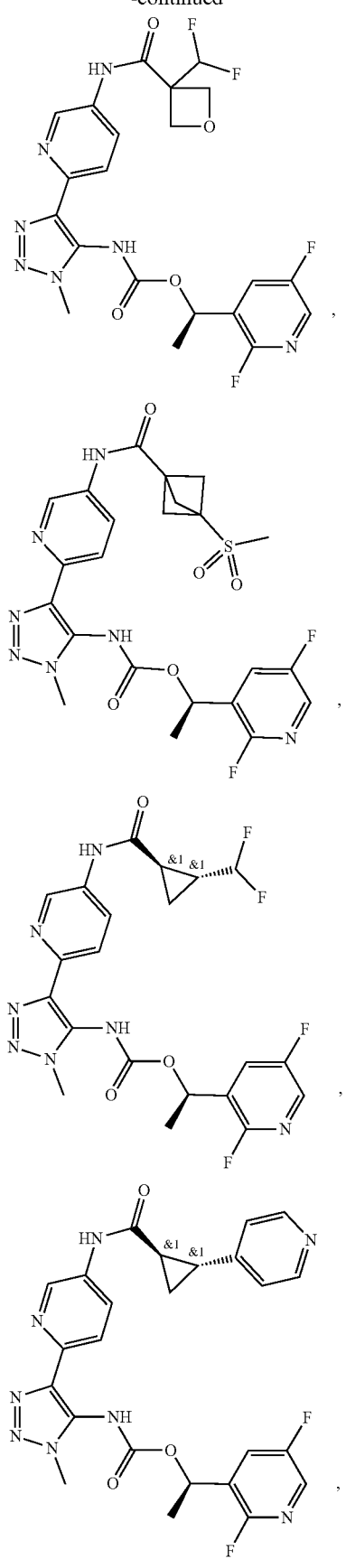

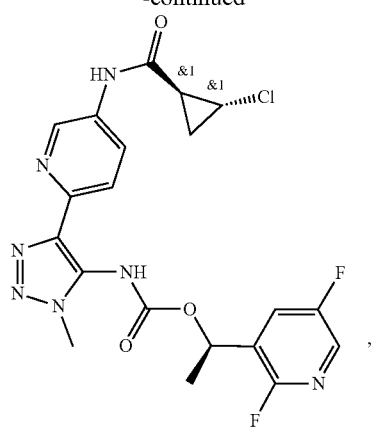
,
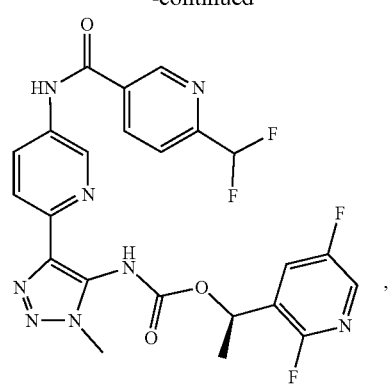
,
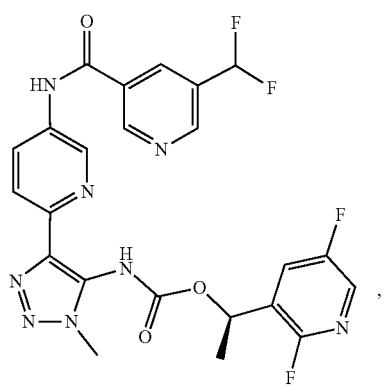
,
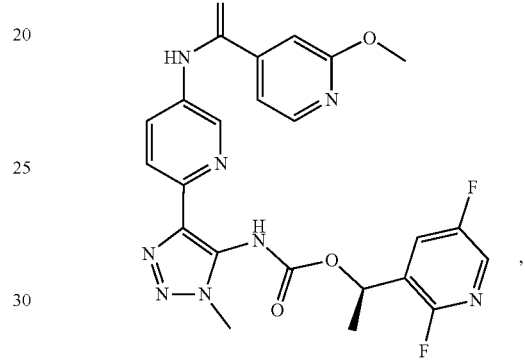
,
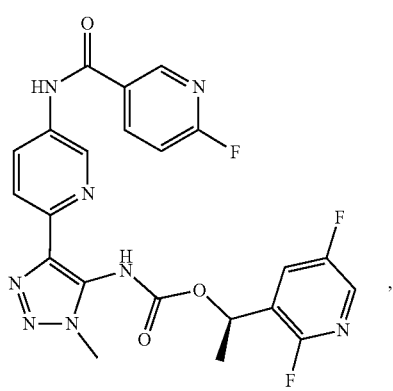
,
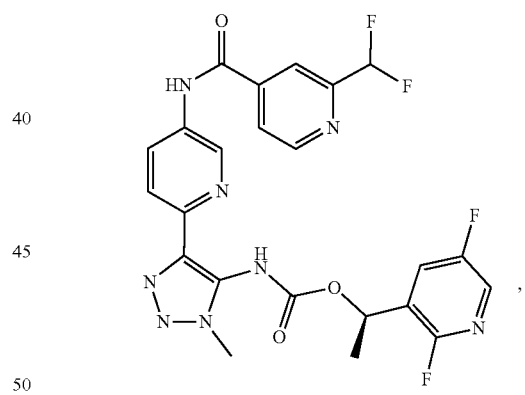
,
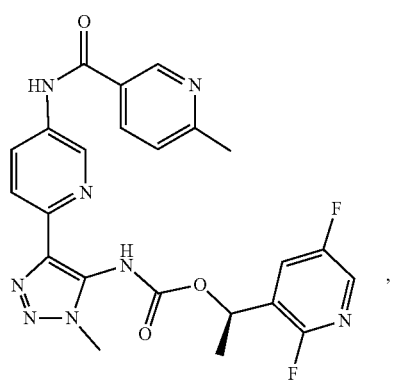
,
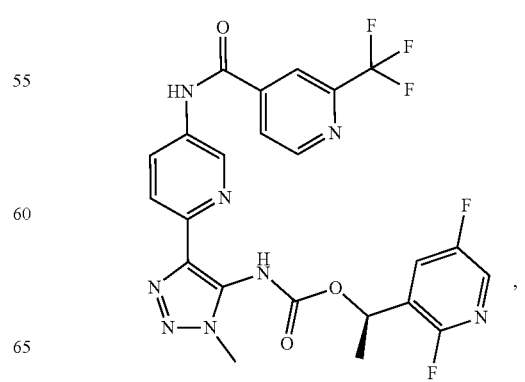
, 119
-continued
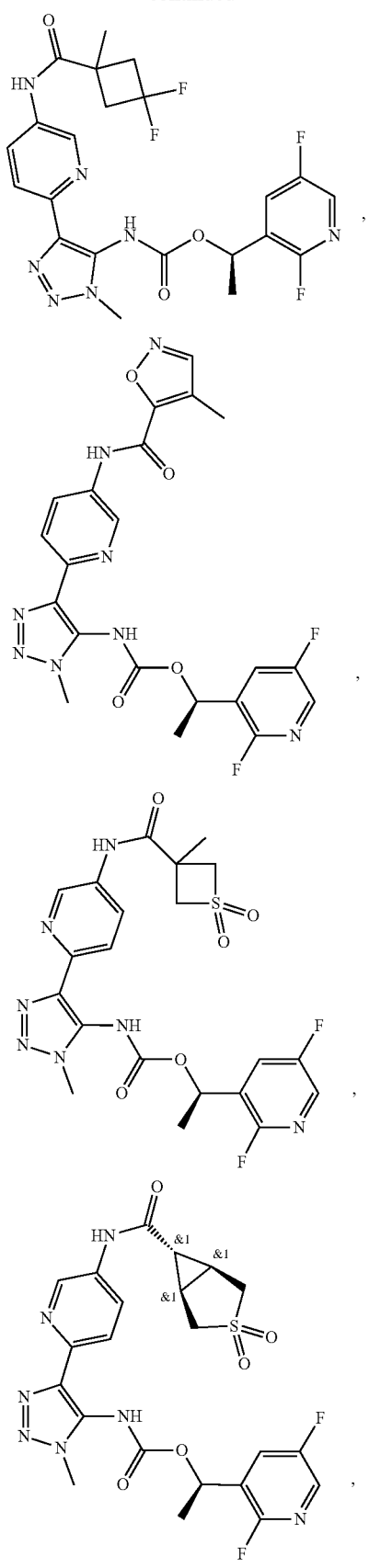
120
-continued
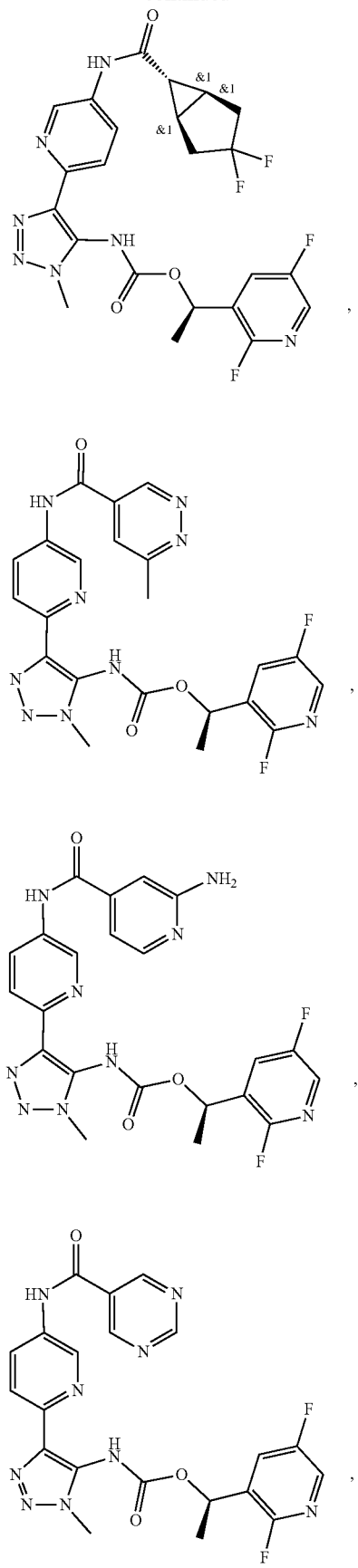

121
-continued
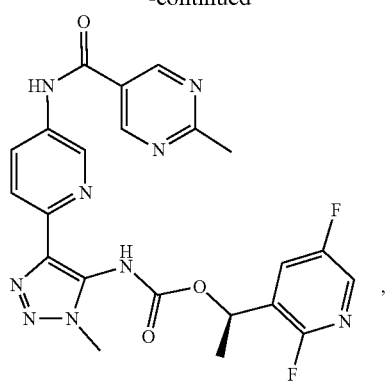
,
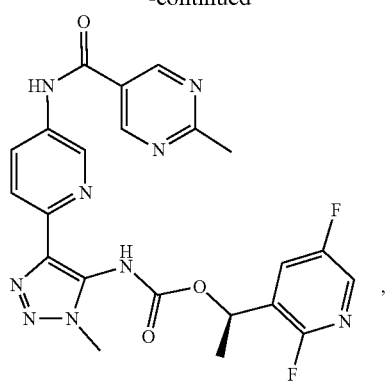
,
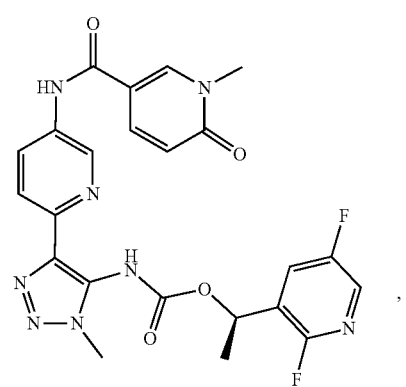
,
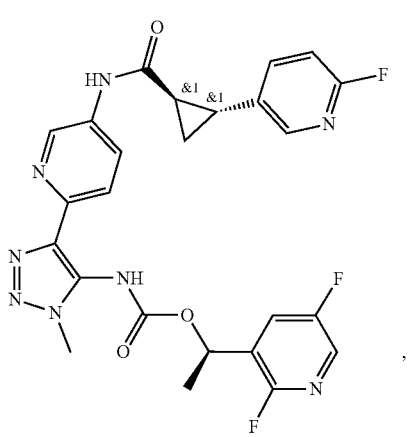
,
122
-continued
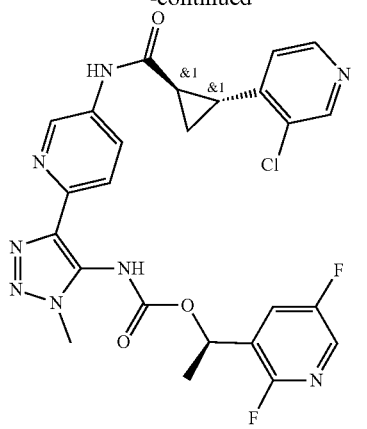
,
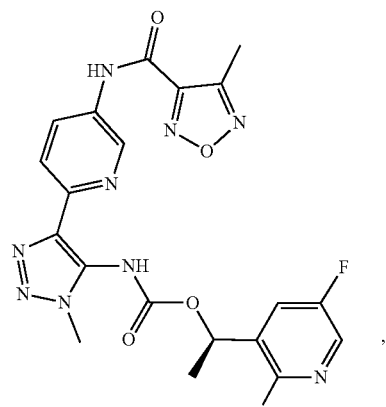
,
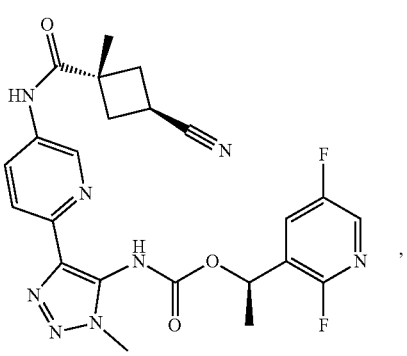
,
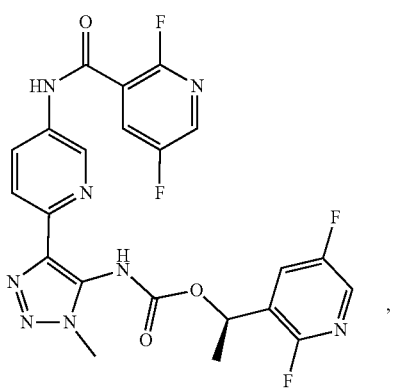
, 123
-continued
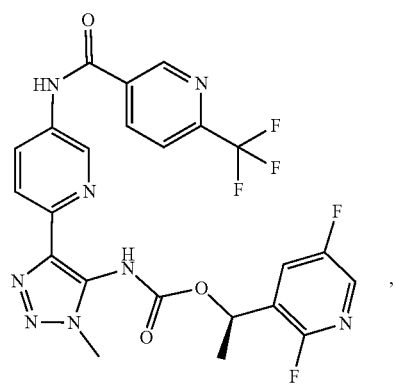
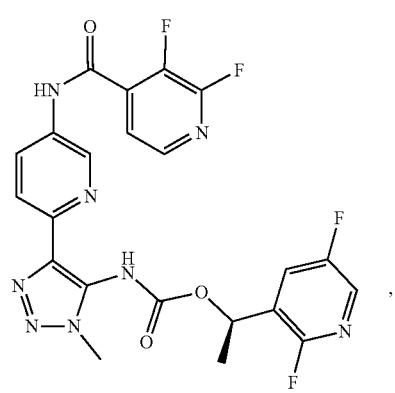
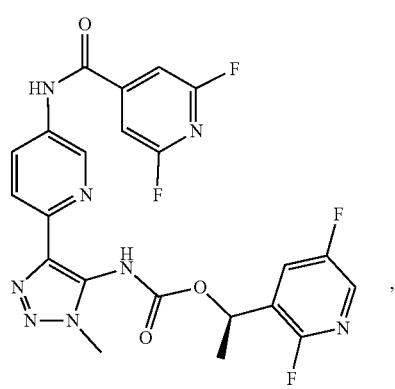
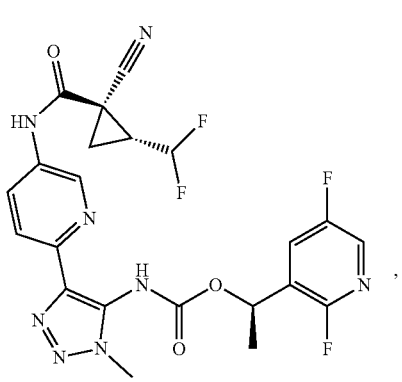
124
-continued
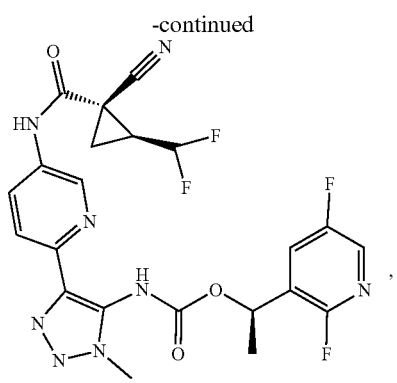
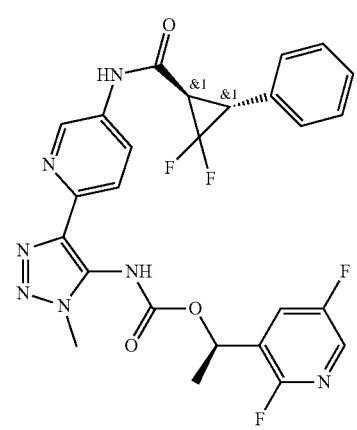
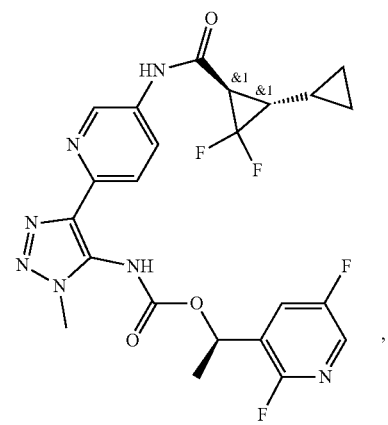
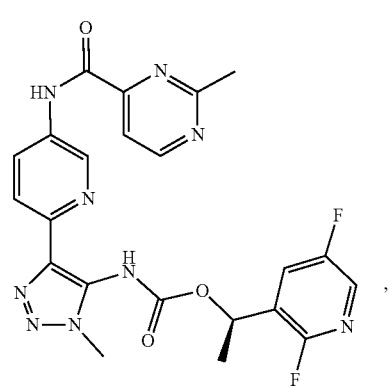

125
-continued
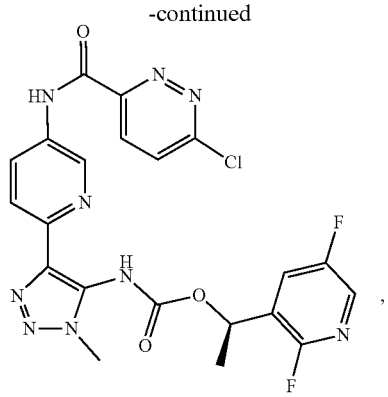
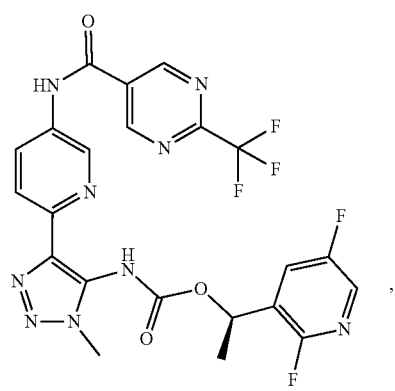
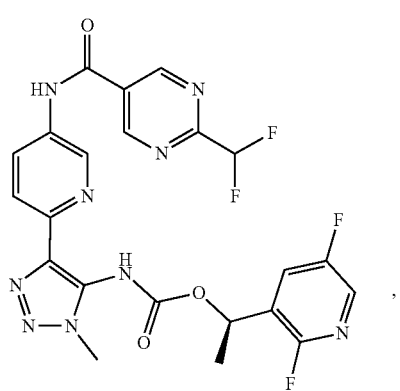
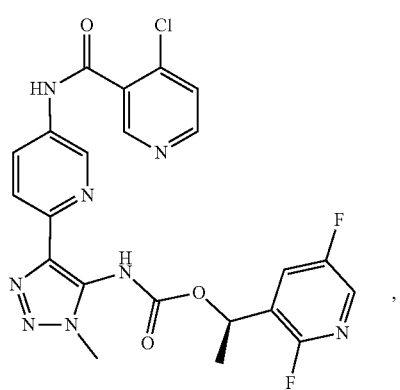
126
-continued
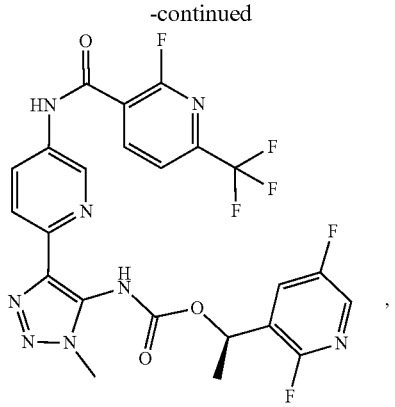
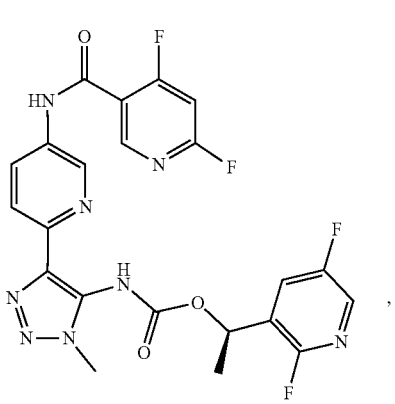
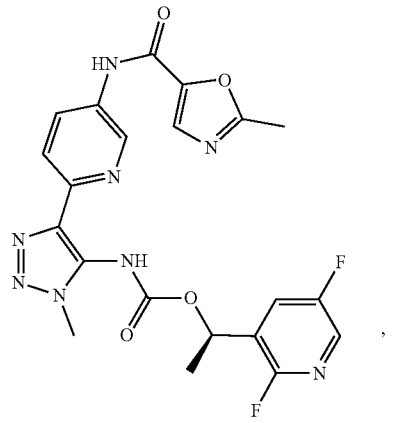
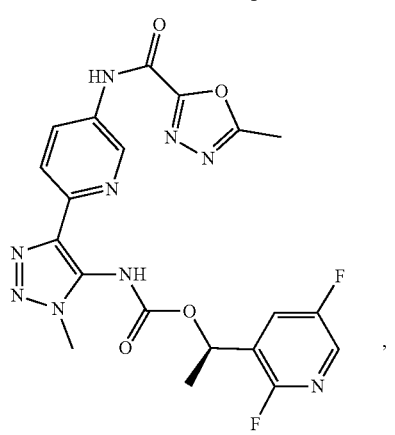

127
-continued
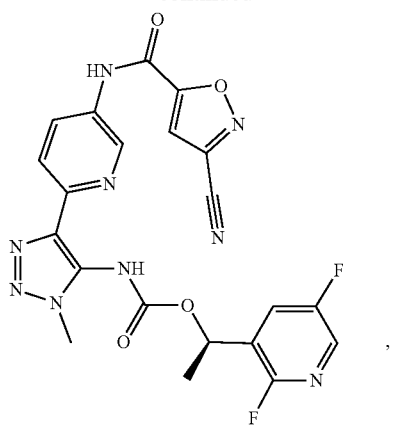
,
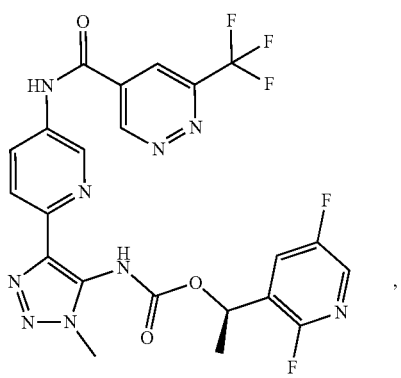
,
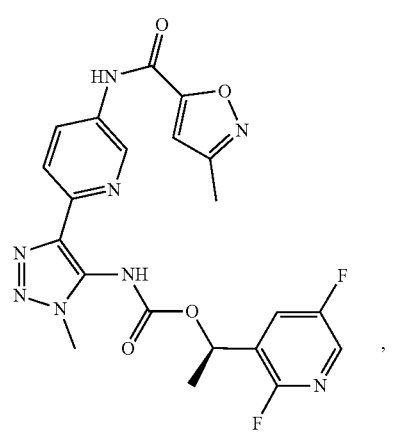
,
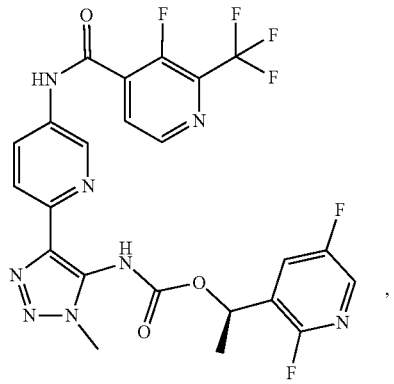
,
128
-continued
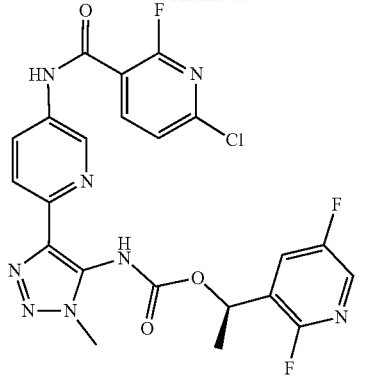
,
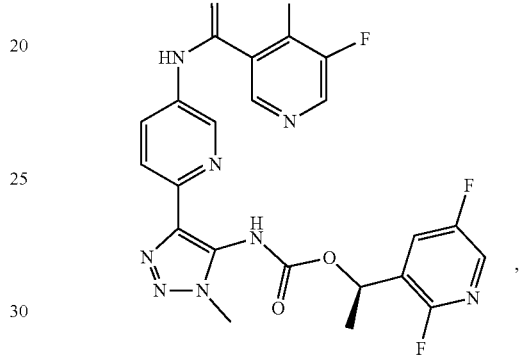
,
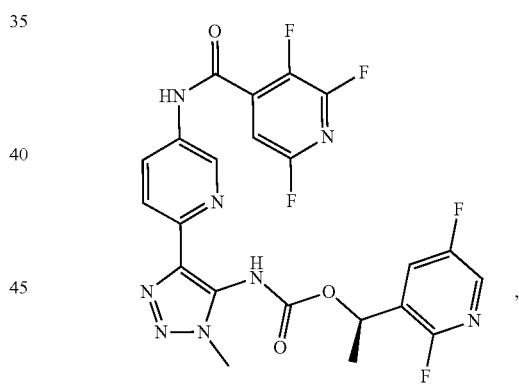
,
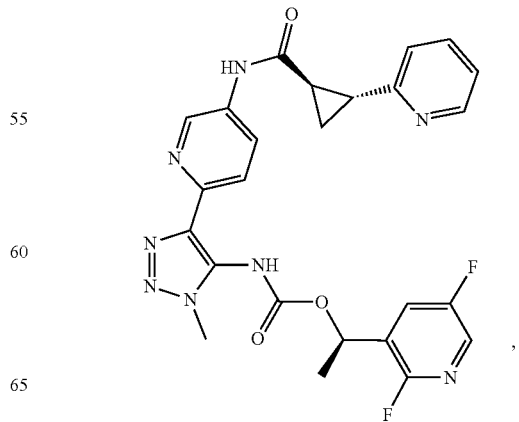
, 129
-continued
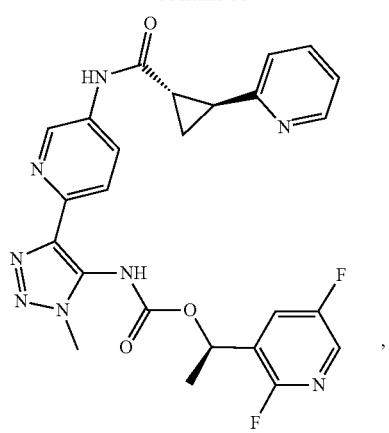
,
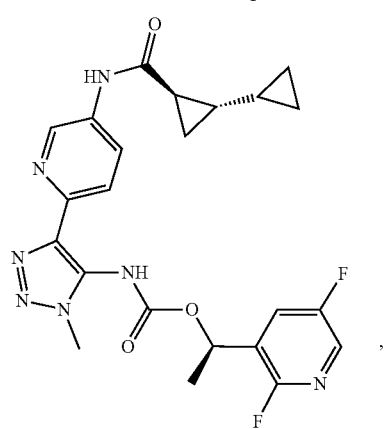
,
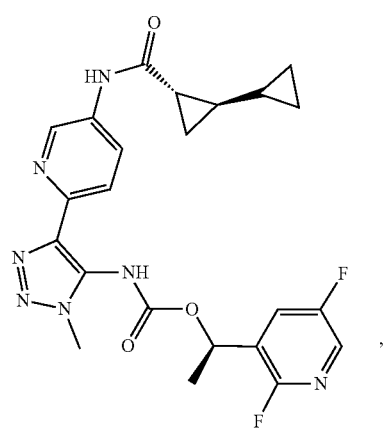
,
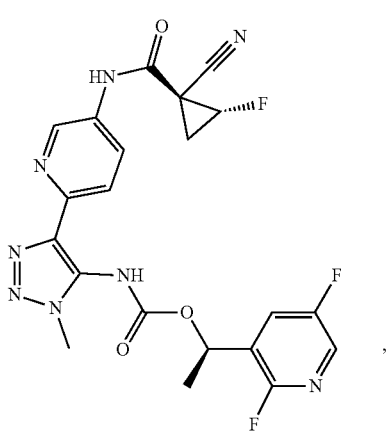
,
130
-continued
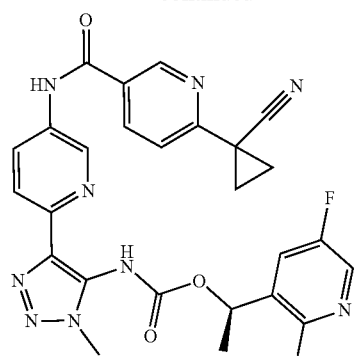
,
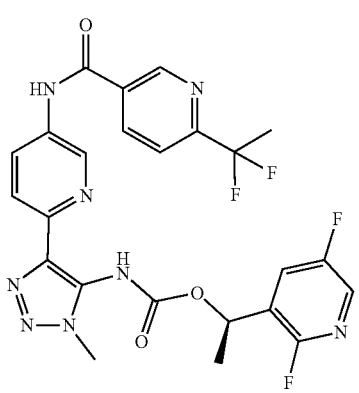
,
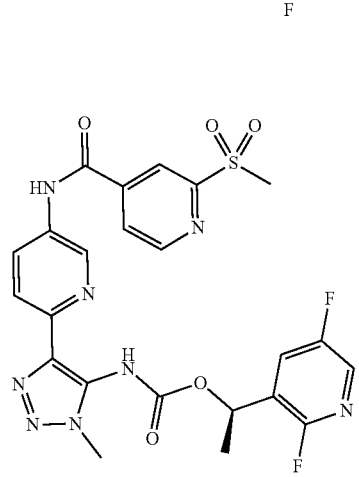
,
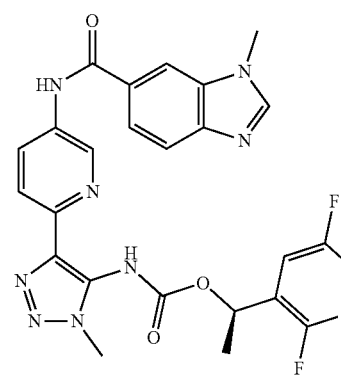
, 131
-continued
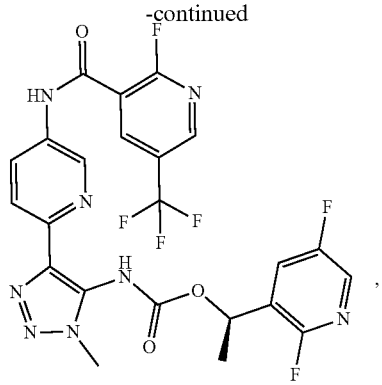
,
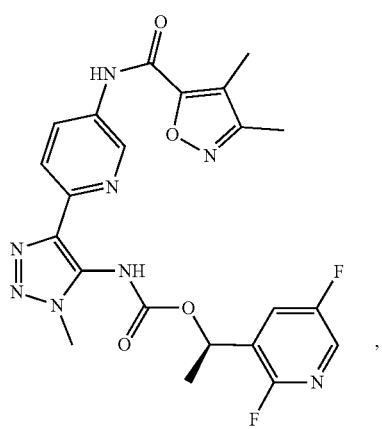
,
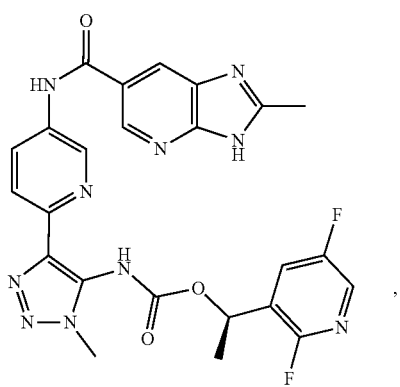
,
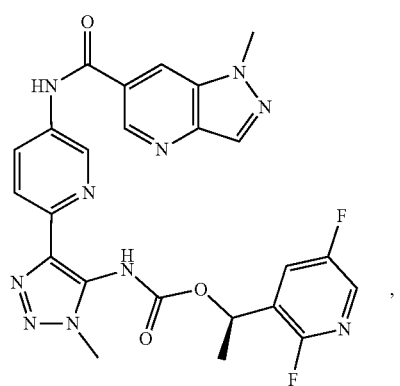
,
132
-continued
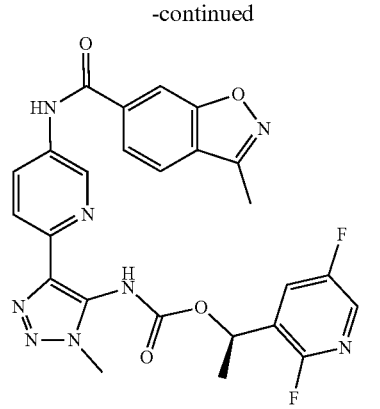
,
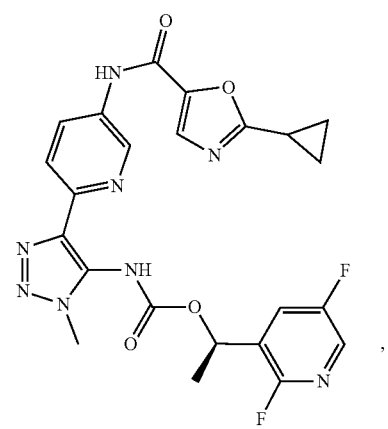
,
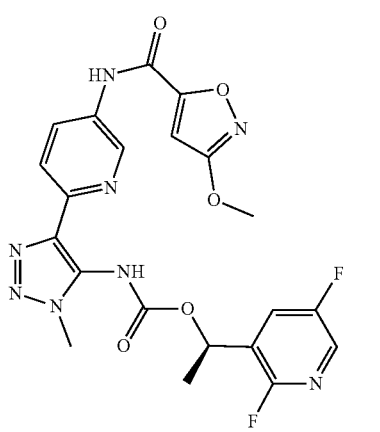
,
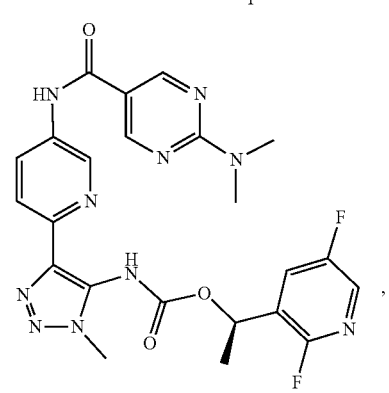
, 133
-continued
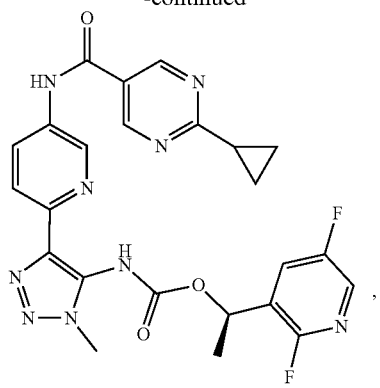
,
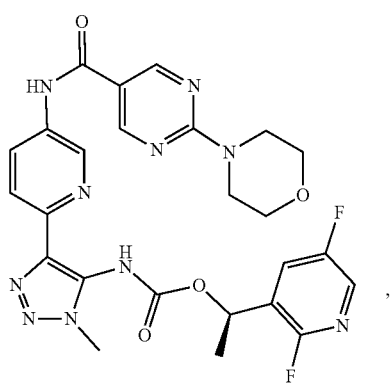
,
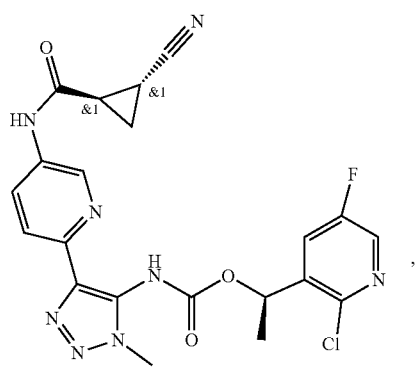
,
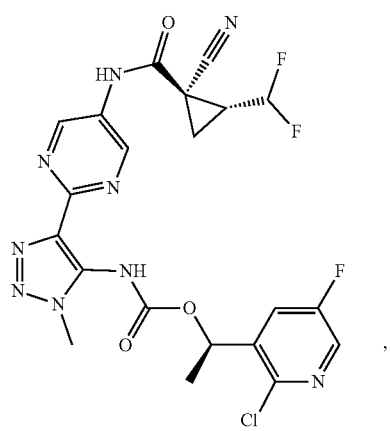
,
134
-continued
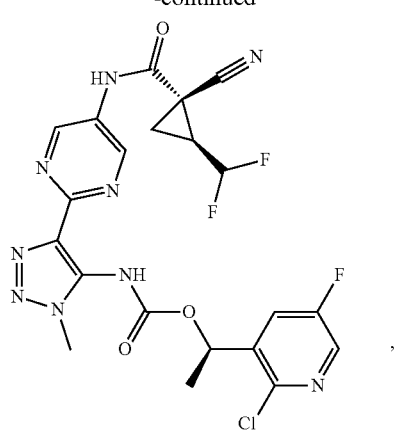
,
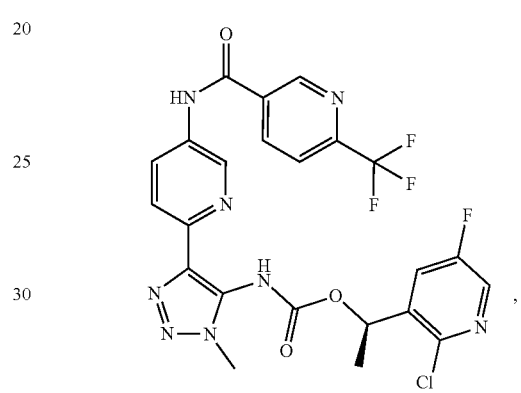
,
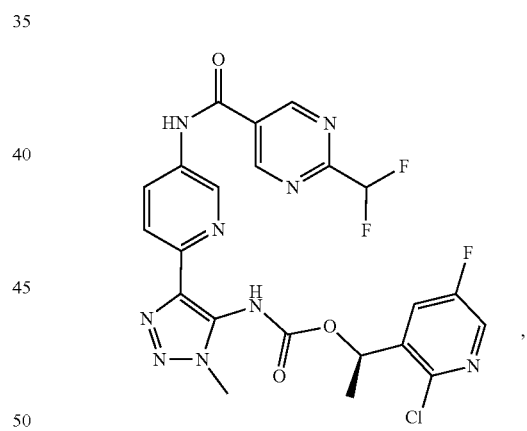
,
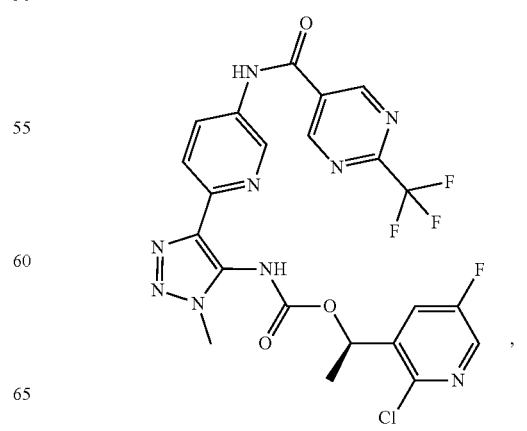
, 135
-continued
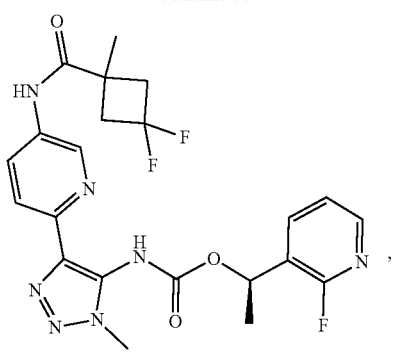,
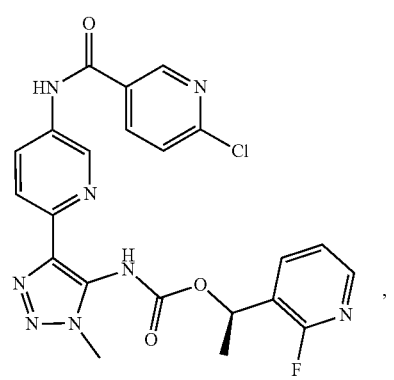,
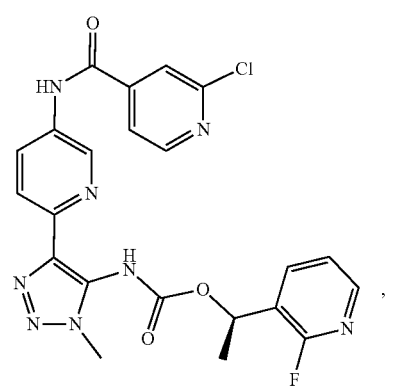,
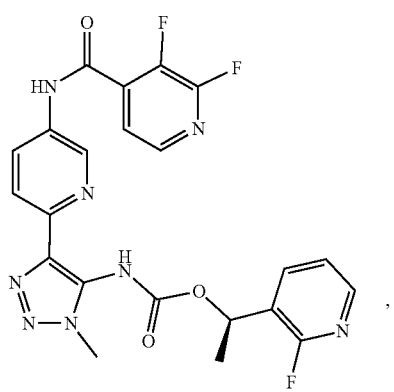,
136
-continued
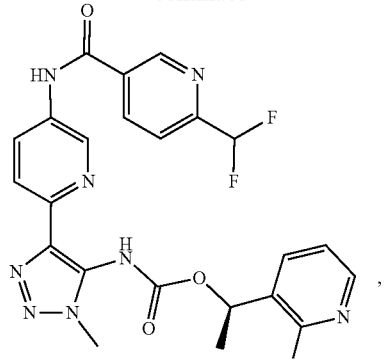,
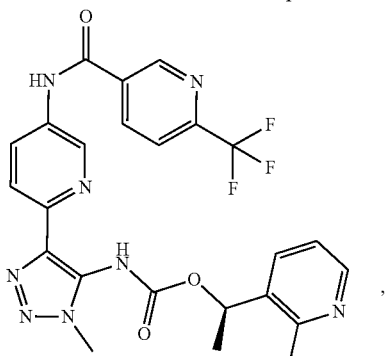,
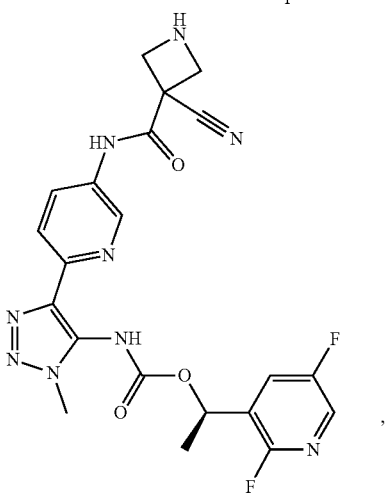,
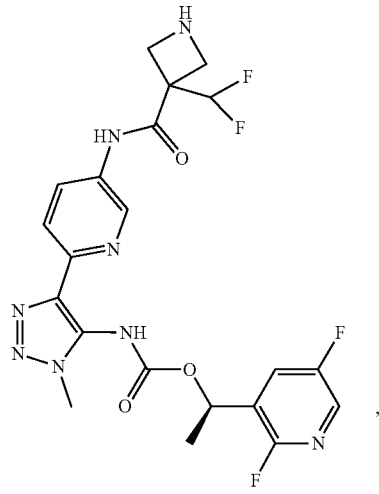, 137
-continued
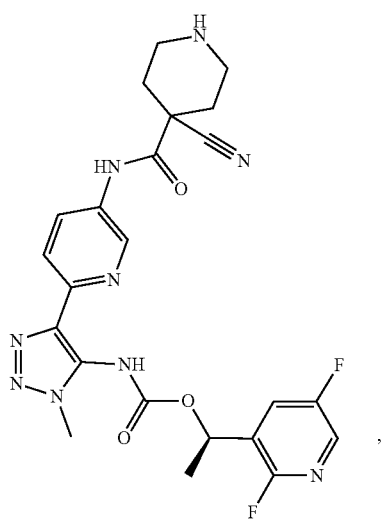
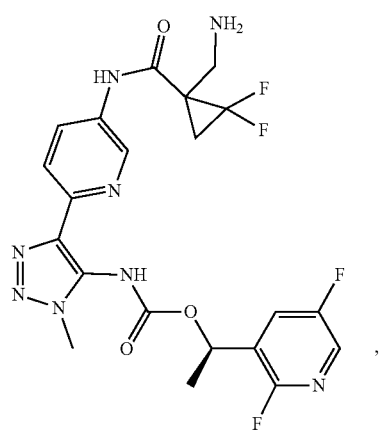
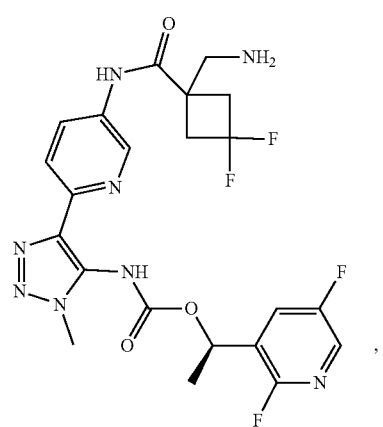
138
-continued
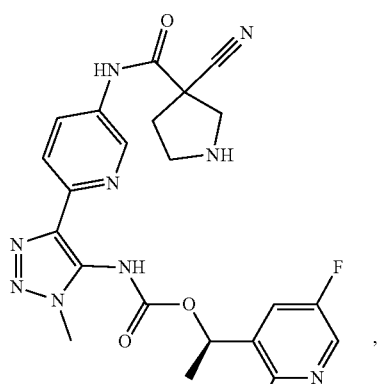
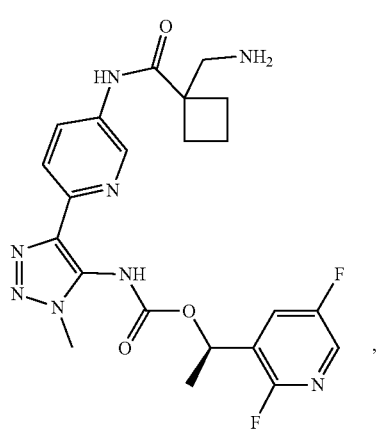
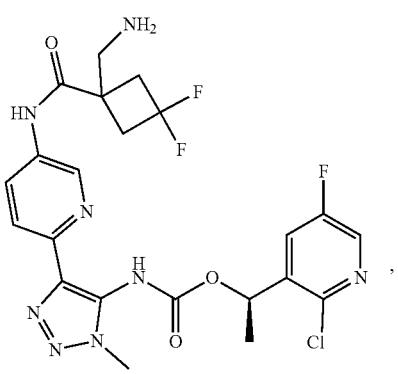
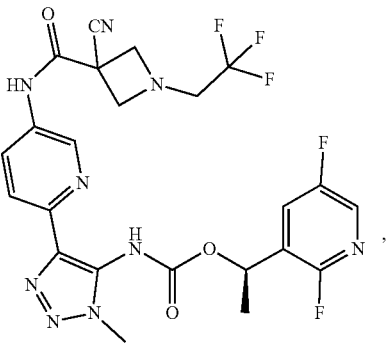

139
-continued
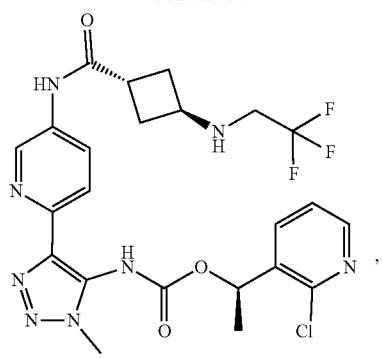
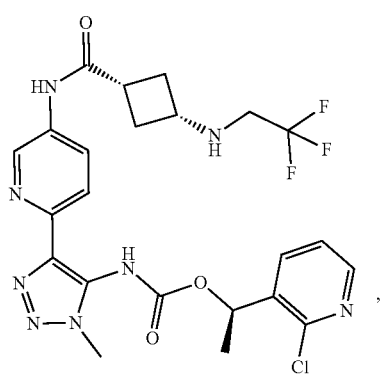
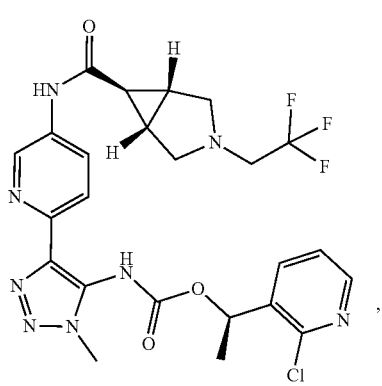
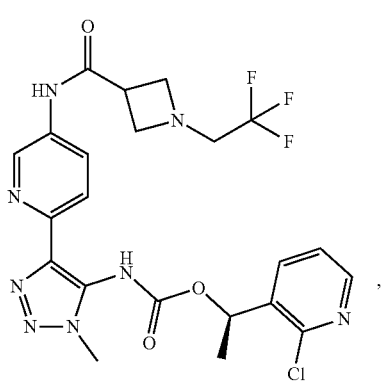
140
-continued
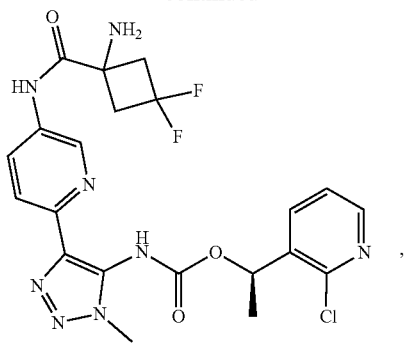
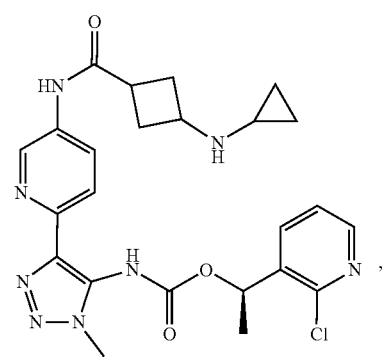
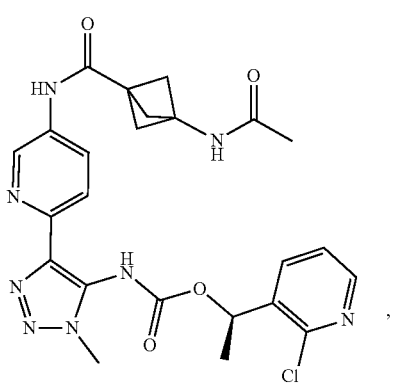
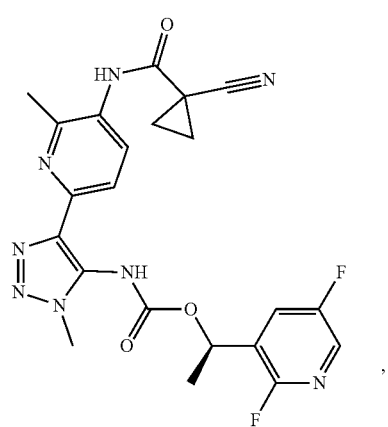

141
-continued
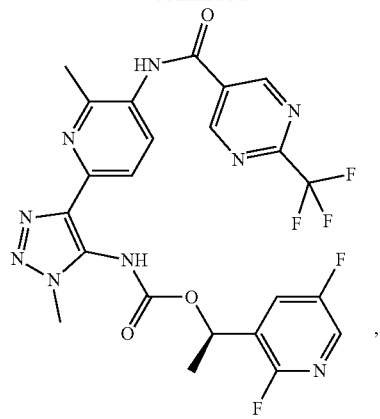
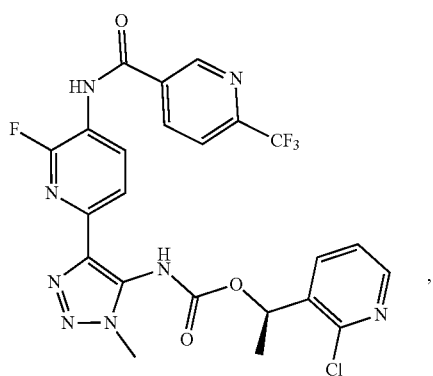
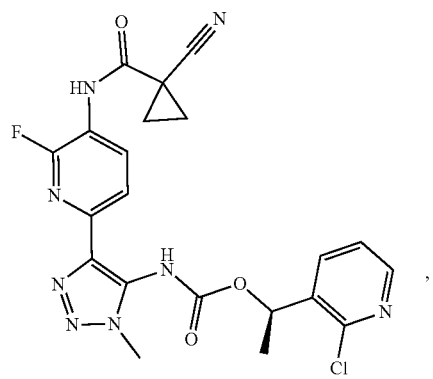
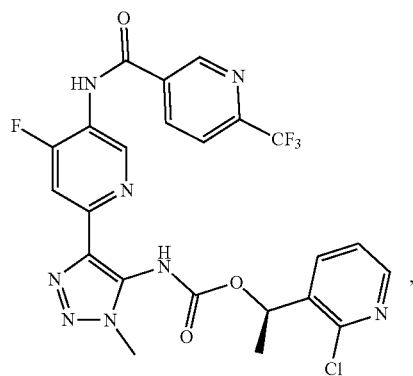
142
-continued
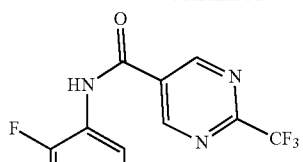
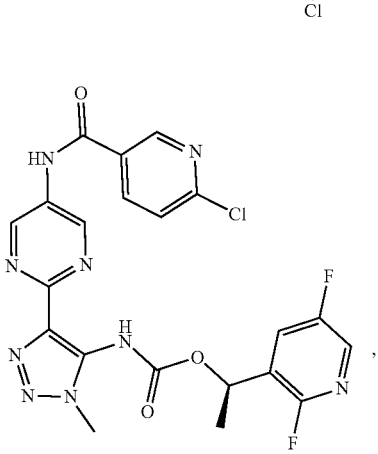
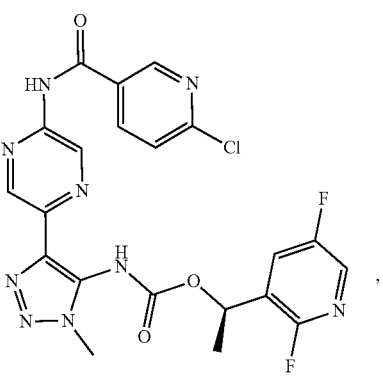
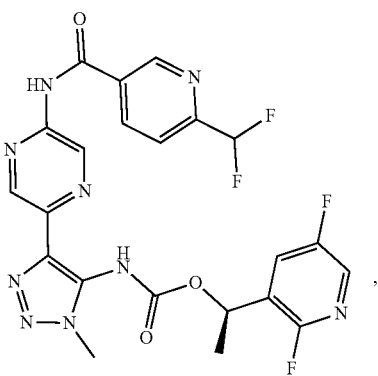

143
-continued
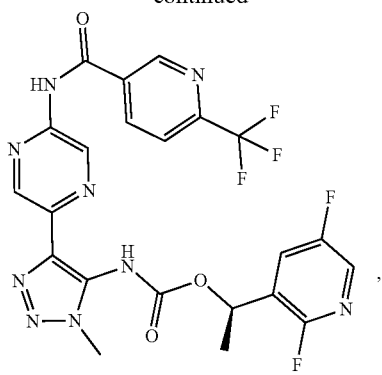
,

,
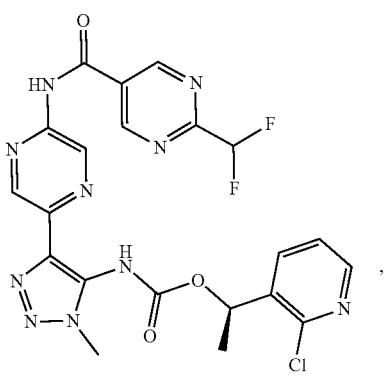
,
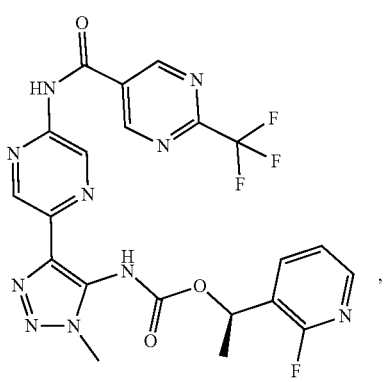
,
144
-continued
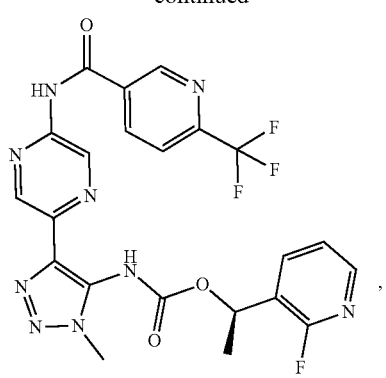
,
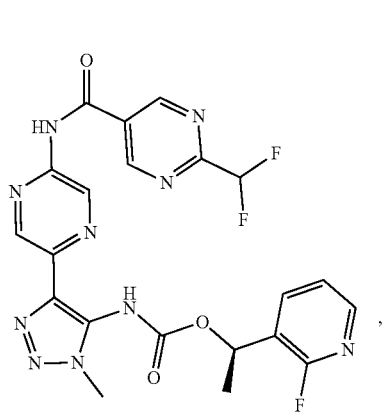
,
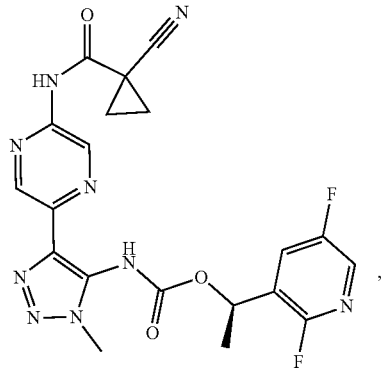
,
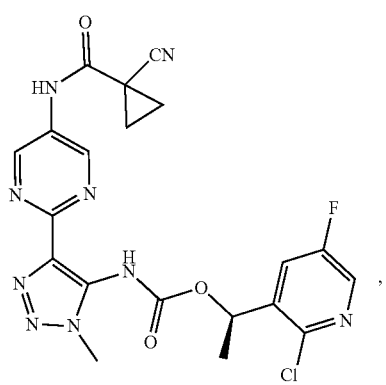
, 145
-continued
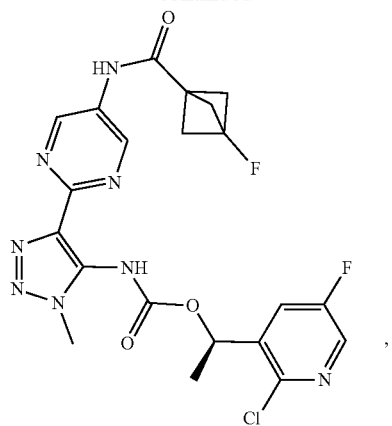
,
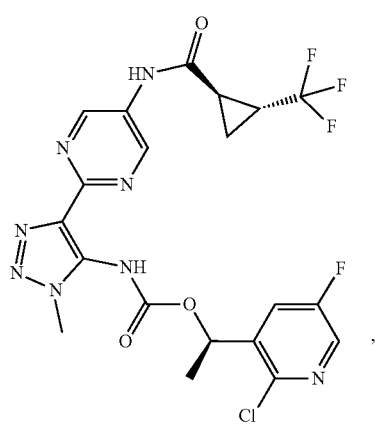
,
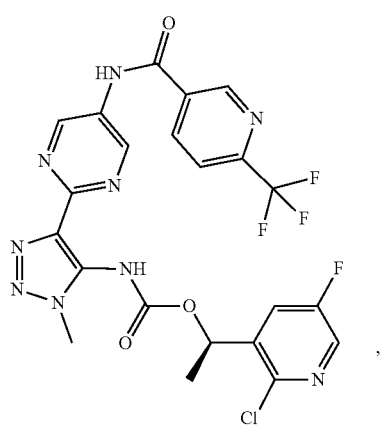
,
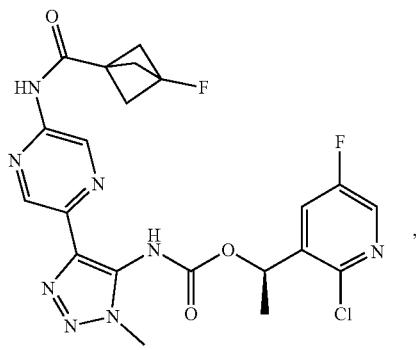
,
146
-continued
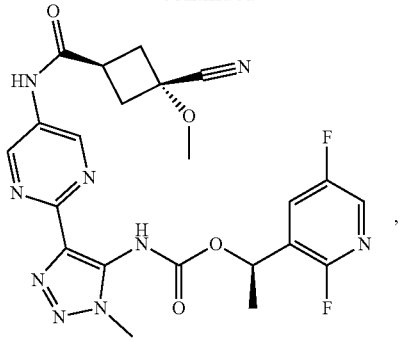
,
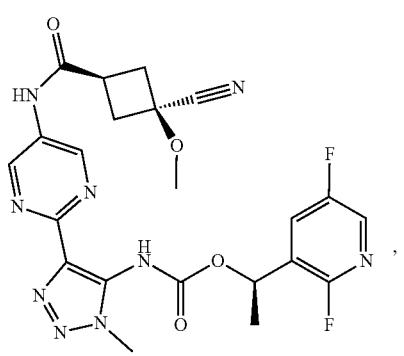
,
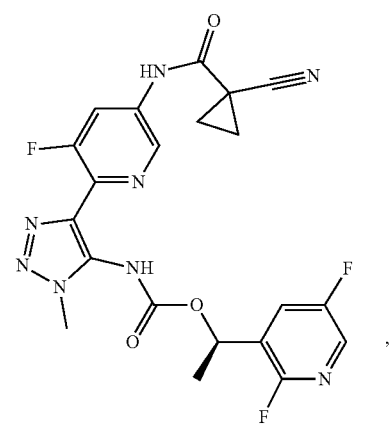
,
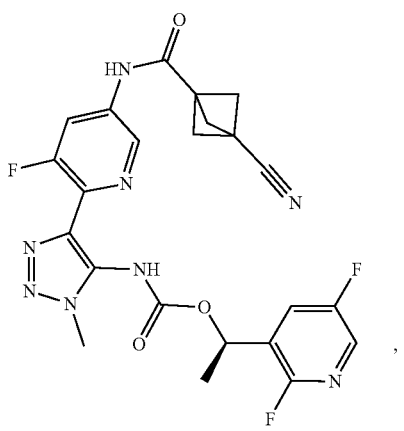
,

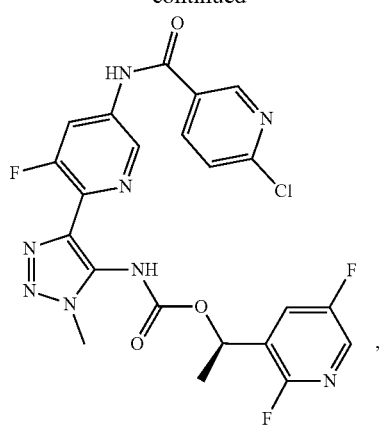

or a pharmaceutically acceptable salt thereof.

In some embodiments, the compound of Formula (I), (Ia), or (IIo), or pharmaceutically acceptable salt thereof, is:

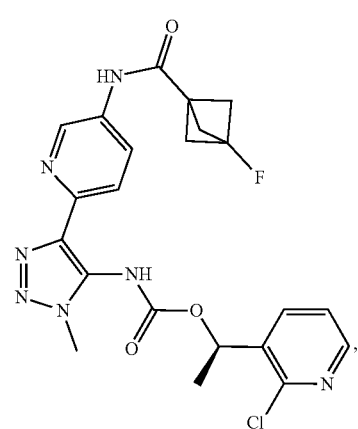 [SMILES: C[C@@H](OC(=O)Nc1c(-c2ccc(NC(=O)C34CC(F)(C3)C4)cn2)nnn1C)c1cccnc1Cl]

or pharmaceutically acceptable salt thereof.

In some embodiments, the compound of Formula (I), (Ia), or (IIo), or pharmaceutically acceptable salt thereof, is:

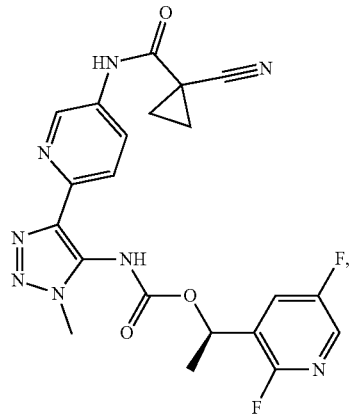 [SMILES: C[C@@H](OC(=O)Nc1c(-c2ccc(NC(=O)C3(C#N)CC3)cn2)nnn1C)c1cc(F)cnc1F]

or pharmaceutically acceptable salt thereof.

In some embodiments, the compound of Formula (I), (Ia), or (IIo), or pharmaceutically acceptable salt thereof, is:

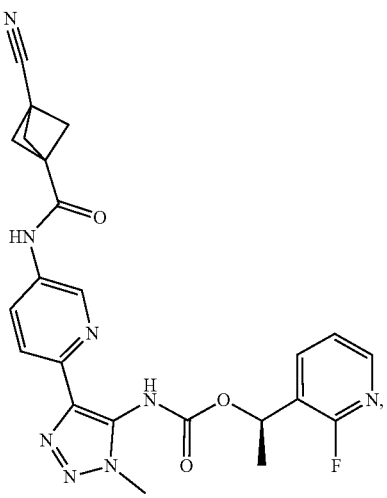 [SMILES: C[C@@H](OC(=O)Nc1c(-c2ccc(NC(=O)C34CC(C#N)(C3)C4)cn2)nnn1C)c1cccnc1F]

or pharmaceutically acceptable salt thereof.

In some embodiments, the compound of Formula (I), (Ia), or (IIo), or pharmaceutically acceptable salt thereof, is:

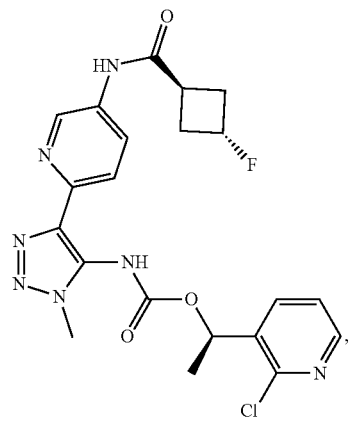 [SMILES: C[C@@H](OC(=O)Nc1c(-c2ccc(NC(=O)[C@H]3C[C@H](F)C3)cn2)nnn1C)c1cccnc1Cl]

or pharmaceutically acceptable salt thereof.

In some embodiments, the compound of Formula (I), (Ia), or (IIo), or pharmaceutically acceptable salt thereof, is:

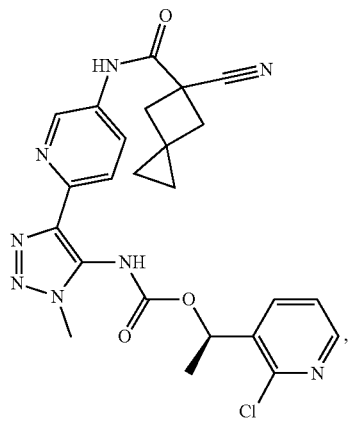 [SMILES: C[C@@H](OC(=O)Nc1c(-c2ccc(NC(=O)C3(C#N)CC4(CC4)C3)cn2)nnn1C)c1cccnc1Cl]

or pharmaceutically acceptable salt thereof.

In some embodiments, the compound of Formula (I), (Ia), or (IIo), or pharmaceutically acceptable salt thereof, is:

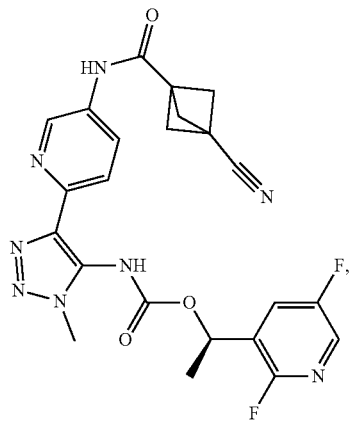 [SMILES: C[C@@H](OC(=O)Nc1c(-c2ccc(NC(=O)C34CC(C#N)(C3)C4)cn2)nnn1C)c1cc(F)cnc1F]

or pharmaceutically acceptable salt thereof.

In some embodiments, the compound of Formula (I), (Ia), or (IIo), or pharmaceutically acceptable salt thereof, is:

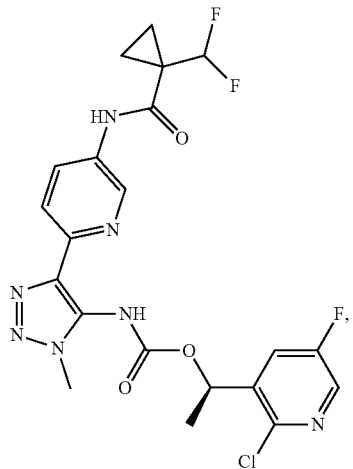 [SMILES: C[C@@H](OC(=O)Nc1c(-c2ccc(NC(=O)C3(C(F)F)CC3)cn2)nnn1C)c1cc(F)cnc1Cl]

or pharmaceutically acceptable salt thereof.

In some embodiments, the compound of Formula (I), (Ia), or (IIo), or pharmaceutically acceptable salt thereof, is:

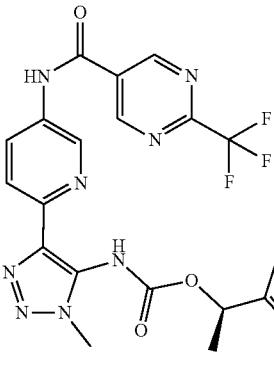

or pharmaceutically acceptable salt thereof.

In some embodiments, the compound of Formula (I), (Ia), or (IIo), or pharmaceutically acceptable salt thereof, is:

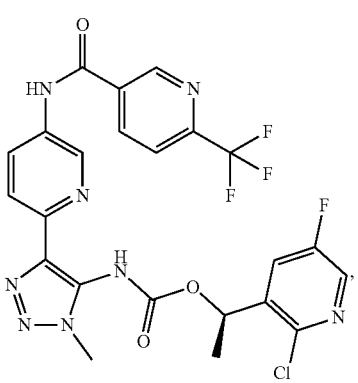 [SMILES: C[C@@H](OC(=O)Nc1c(-c2ccc(NC(=O)c3ccc(C(F)(F)F)nc3)cn2)nnn1C)c1cc(F)cnc1Cl]

or pharmaceutically acceptable salt thereof.

In some embodiments, the compound of Formula (I), (Ia), or (IIo), or pharmaceutically acceptable salt thereof, is:

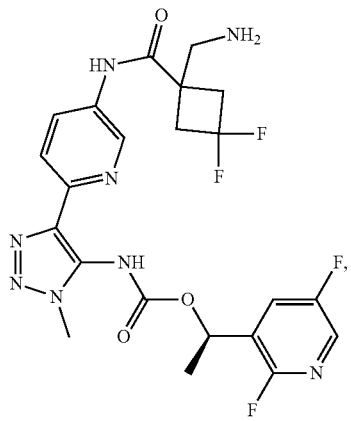 [SMILES: C[C@@H](OC(=O)Nc1c(-c2ccc(NC(=O)C3(CN)CC(F)(F)C3)cn2)nnn1C)c1cc(F)cnc1F]

or pharmaceutically acceptable salt thereof.

In some embodiments, the compound of Formula (I), (Ia), or (IIe), or pharmaceutically acceptable salt thereof, is:

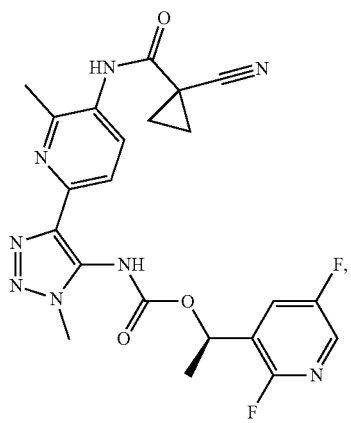 [SMILES: Cc1nc(-c2nnn(C)c2NC(=O)O[C@H](C)c2cc(F)cnc2F)ccc1NC(=O)C1(C#N)CC1]

or pharmaceutically acceptable salt thereof.

In some embodiments, the compound of Formula (I), (Ia), or (IIe), or pharmaceutically acceptable salt thereof, is:

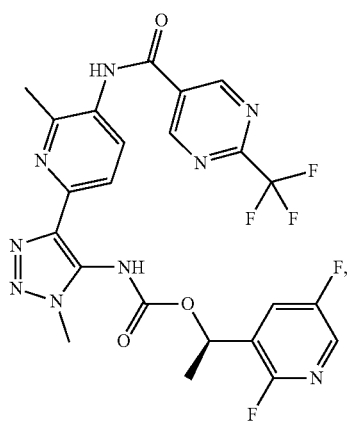 [SMILES: Cc1nc(-c2nnn(C)c2NC(=O)O[C@H](C)c2cc(F)cnc2F)ccc1NC(=O)c1cnc(C(F)(F)F)nc1]

or pharmaceutically acceptable salt thereof.

In some embodiments, the compound of Formula (I), (Ia), or (IIe), or pharmaceutically acceptable salt thereof, is:

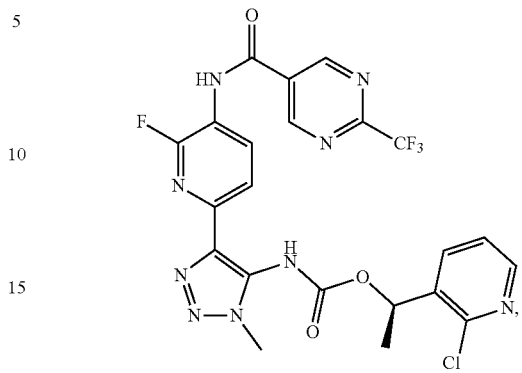

or pharmaceutically acceptable salt thereof.

Pharmaceutical Compositions and Modes of Administration

Furthermore, the present disclosure provides pharmaceutical compositions comprising at least one compound of the present disclosure, or a prodrug compound thereof, or a pharmaceutically acceptable salt or solvate thereof as active ingredient together with a pharmaceutically acceptable carrier.

The pharmaceutical composition of the present disclosure may additionally comprise one or more other compounds as active ingredients like a prodrug compound or other enzyme inhibitors.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of the present disclosure can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

In some embodiments, the compounds of the present disclosure may also be used as salts with various countercations to yield an orally available formulation.

The compounds of the present disclosure may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In some embodiments, compounds of the present disclosure are administered orally.

Kits

Provided herein are also kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, pre-loaded syringe, and intravenous bag.

Treatment Methods and Uses

The disclosure further relates to the use of compounds disclosed herein for the treatment and/or prophylaxis of diseases and/or conditions through binding of LPAR1 by said compounds. Further, the present disclosure relates to the use of said compounds for the preparation of a medicament for the treatment and/or prophylaxis of diseases and/or conditions through binding of LPAR1 by said compounds.

Medicaments as referred to herein may be prepared by conventional processes, including the combination of a compound according to the present disclosure and a pharmaceutically acceptable carrier.

In some embodiments, provided herein is a method of treating and/or preventing an LPAR1-mediated disease or condition in a patient in need thereof, comprising administering to the patient a therapeutically effective amount of a compound of Formula (I), (Ia), (IIa), (IIb), (IIc), (IId), (IIe), (IIf), (IIg), (IIh), (IIi), (IIj), (IIk), (III), (IIm), (IIn), or (IIo), or a pharmaceutically acceptable salt thereof, or a composition comprising a compound of Formula (I), (Ia), (IIa), (IIb), (IIc), (IId), (IIe), (IIf), (IIg), (IIh), (IIi), (IIj), (IIk), (III), (IIm), (IIn), or (IIo), or a pharmaceutically acceptable salt thereof.

In some embodiments, the LPAR1-mediated disease or condition includes those wherein an absolute or relative excess of LPA is present and/or observed.

In some embodiments, the LPAR1-mediated disease or condition includes fibrosis, wound healing, cancer, pain, respiratory disorders, allergic disorders, nervous system disorders, cardiovascular disorders, or inflammatory disorders.

In some embodiments, the LPAR1-mediated disease or condition is an interstitial lung disease (ILD). In some embodiments, the interstitial lung disease (ILD) is nonspecific interstitial pneumonitis (NSIP), sarcoidosis, asbestosis, an ILD related to an occupational exposure, progressive fibrosing ILD, idiopathic interstitial pneumonia (IIP), connective tissue disease-associated interstitial lung disease (CTD-ILD), rheumatoid arthritis-associated ILD, scleroderma-associated ILD, or extrinsic alveolar alveolitis.

In some embodiments, the LPAR1-mediated disease or condition is a chronic kidney disease (CKD). In some embodiments, the chronic kidney disease is complement glomerulopathy, membranous glomerulopathy, polycystic kidney disease, IgA nephropathy, focal segmental glomerulosclerosis (FSGS), or Alport Syndrome.

In some embodiments, the LPAR1-mediated disease or condition includes fibrosis. In some embodiments, fibrosis includes pulmonary fibrosis, renal fibrosis, hepatic fibrosis, ocular fibrosis, or cardiac fibrosis.

In some embodiments, the LPAR1-mediated disease or condition includes pulmonary fibrosis. In some embodiments, pulmonary fibrosis includes idiopathic pulmonary fibrosis (IPF). In some embodiments pulmonary fibrosis includes Progressive Fibrotic interstitial lung disease (PF-ILD). In some embodiments, pulmonary fibrosis includes pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced).

In some embodiments, the LPAR1-mediated disease or condition includes renal fibrosis. In some embodiments, renal fibrosis includes chronic nephropathies associated with injury/ibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; gut fibrosis, e.g., scleroderma, and radiation induced gut fibrosis.

In some embodiments, the LPAR1-mediated disease or condition includes liver fibrosis. In some embodiments, liver fibrosis includes liver cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis.

In some embodiments, the LPAR1-mediated disease or condition includes head and neck fibrosis, e.g., radiation induced.

In some embodiments, the LPAR1-mediated disease or condition includes corneal scarring, e.g., due to LASIK (laser-assisted in situ keratomileusis), corneal transplantation, or trabeculectomy. In some embodiments, a compound of Formula (I), (Ia), (IIa), (IIb), (IIc), (IId), (IIe), (IIf), (IIg), (IIh), (IIi), (IIj), (IIk), (III), (IIm), (IIn), or (IIo), or a pharmaceutically acceptable salt thereof, is used to improve the corneal sensitivity decrease caused by corneal operations such as LASIK or cataract operation, corneal sensitivity decrease caused by corneal degeneration, and dry eye symptom caused thereby. In some embodiments, a compound of Formula (I), (Ia), (IIa), (IIb), (IIc), (IId), (IIe), (IIf), (IIg), (IIh), (IIi), (IIj), (IIk), (III), (IIm), (IIn), or (IIo), or a pharmaceutically acceptable salt thereof, is used in the treatment or prevention of ocular inflammation and allergic conjunctivitis, vernal keratoconjunctivitis, and papillary conjunctivitis. In some embodiments, a compound of Formula (I), (Ia), (IIa), (IIb), (IIc), (IId), (IIe), (IIf), (IIg), (IIh), (IIi), (IIj), (IIk), (III), (IIm), (IIn), or (IIo), or a pharmaceutically acceptable salt thereof, is used in the treatment or prevention of Sjogren disease or inflammatory disease with dry eyes.

In some embodiments, the LPAR1-mediated disease or condition includes another fibrotic condition, such as hypertrophic scarring and keloids, e.g., burn induced or surgical, sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

In some embodiments, the LPAR1-mediated disease or condition includes pain. In some embodiments, pain includes neuropathic pain. In some embodiments, pain includes acute pain. In some embodiments, pain includes chronic pain.

In some embodiments, the LPAR1-mediated disease or condition includes cancer. In some embodiments, cancer includes ovarian cancer, colon cancer, prostate cancer, breast cancer, melanoma, head and neck cancer, bowel cancer (colorectal cancer), and thyroid cancer. In some embodiments, cancer includes solid tumors, such as (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases. In some embodiments, cancer includes, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hair) cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastema, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive, neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

In some embodiments, the LPAR1-mediated disease or condition includes a respiratory or allergic disorder. In some embodiments, the respiratory or allergic disorder includes asthma, peribronchiolar fibrosis, obliterative bronchiolitis, and chronic obstructive pulmonary disease (COPD). In some embodiments, the COPD includes chronic bronchitis or emphysema, pulmonary hypertension, interstitial lung fibrosis and/or airway inflammation, and cystic fibrosis. In some embodiments, the respiratory disease includes adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, and hypoxia.

In some embodiments, the LPAR1-mediated disease or condition includes a nervous system disorder. In some embodiments, the nervous system disorder includes Alzheimer's Disease, cerebral edema, cerebral ischemia, stroke, multiple sclerosis, neuropathies, Parkinson's Disease, a nervous condition found after blunt or surgical trauma (including post-surgical cognitive dysfunction and spinal cord or brim stem injury), as well as the neurological aspects of disorders such as degenerative disk disease and sciatica.

In some embodiments, the LPAR1-mediated disease or condition includes a cardiovascular disorder. In some embodiments, the cardiovascular disorder includes arrhythmia. (atrial or ventricular or both); atherosclerosis and its sequelae; angina; cardiac rhythm disturbances; myocardial ischemia; myocardial infarction; cardiac or vascular aneurysm; vasculitis; stroke; peripheral obstructive arteriopathy of a limb, an organ, or a tissue; reperfusion injury following ischemia of the brain, heart or other organ or tissue; endotoxic, surgical, or traumatic shock; hypertension; valvular heart disease; heart failure; abnormal blood pressure; shock; vasoconstriction (including that associated with migraines); vascular abnormality, and a cardiovascular insufficiency limited to a single organ or tissue.

In some embodiments, the LPAR1-mediated disease or condition includes lung fibrosis, kidney fibrosis, liver fibrosis, scarring, asthma, rhinitis, chronic obstructive pulmonary disease (COPD), pulmonary hypertension, interstitial lung fibrosis, arthritis, allergy, psoriasis, inflammatory bowel disease, adult respiratory distress syndrome, myocardial infarction, aneurysm, stroke, cancer, pain, proliferative disorders and inflammatory conditions.

In some embodiments, the LPAR1-mediated disease or condition is a liver disease. In some embodiments, the liver disease is hepatitis C, liver cancer, familial combined hyperlipidemia, non-alcoholic fatty liver disease (NAFLD), progressive familial intrahepatic cholestasis, primary biliary cirrhosis (PBC), or (PSC). In some embodiments, the liver disease is PSC. In some embodiments the liver disease comprises portal hypertension. In some embodiments, liver cancer comprises hepatocellular carcinoma (HCC), cholangiocarcinoma, angiosarcoma, or hemangiosarcoma. In some embodiments, liver cancer comprises HCC. In some embodiments, NAFLD comprises steatosis. In some embodiments, NAFLD comprises NASH. In some embodiments, NAFLD or NASH comprises liver fibrosis. In some embodiments, NAFLD or NASH comprises liver cirrhosis. In some embodiments, the NAFLD or NASH comprises compensated liver cirrhosis. In some embodiments, the NAFLD or NASH comprises decompensated liver fibrosis. In some embodiments, the NAFLD comprises HCC. In some embodiments, the liver disease is NASH.

In some embodiments, provided herein is a method of treating and/or preventing NAFLD or NASH in a patient in need thereof, comprising administering to the patient a therapeutically effective amount of a compound of Formula (I), (Ia), (IIa), (IIb), (IIc), (IId), (IIe), (IIf), (IIg), (IIh), (IIi), (IIj), (IIk), (Ill), (IIm), (IIn), or (IIo), or pharmaceutically acceptable salt thereof, or a composition comprising a compound of Formula (I), (Ia), (IIa), (IIb), (IIc), (IId), (IIe), (IIf), (IIg), (IIh), (IIi), (IIj), (IIk), (Ill), (IIm), (IIn), or (IIo), or pharmaceutically acceptable salt thereof. In some embodiments, NAFLD or NASH comprise liver fibrosis. In some embodiments, NAFLD or NASH comprise liver cirrhosis. In some embodiments, liver cirrhosis is compensated liver cirrhosis. In some embodiments, liver cirrhosis is decompensated liver cirrhosis. In some embodiments NAFLD or NASH comprise HCC.

In some embodiments, provided herein is a method of preventing a liver disease or condition in a patient in need thereof, comprising administering to the patient a therapeutically effective amount of a compound of Formula (I), (Ia), (IIa), (IIb), (IIc), (IId), (IIe), (IIf), (IIg), (IIh), (IIi), (IIj), (IIk), (Ill), (IIm), (IIn), or (IIo), or pharmaceutically acceptable salt thereof, or a composition comprising a compound of Formula (I), (Ia), (IIa), (IIb), (IIc), (IId), (IIe), (IIf), (IIg), (IIh), (IIi), (IIj), (IIk), (Ill), (IIm), (IIn), or (IIo), or pharmaceutically acceptable salt thereof. In some embodiments, the liver disease or condition is liver fibrosis. In some embodiments, the liver disease or condition is liver cirrhosis. In some embodiments, liver cirrhosis is compensated liver cirrhosis. In some embodiments, liver cirrhosis is decompensated liver cirrhosis. In some embodiments, the liver disease or condition is HCC.

In some embodiments, the present disclosure relates to the use of compounds according to Formula (I), (Ia), (IIa), (IIb), (IIc), (IId), (IIe), (IIf), (IIg), (IIh), (IIi), (IIj), (IIk), (Ill), (IIm), (IIn), or (IIo), or pharmaceutically acceptable salts thereof, in the preparation of a medicament for the prophylaxis and/or treatment of an LPAR1-mediated disease or condition disclosed herein.

Dosage

The effective dosage of active ingredient employed may vary depending on the particular compound employed, the mode of administration, the condition being treated and the severity of the condition being treated. Such dosage may be ascertained readily by a person skilled in the art.

When treating or preventing an LPAR1 mediated disease or condition for which compounds of the present disclosure are indicated, generally satisfactory results are obtained when the compounds of the present disclosure are administered at a daily dosage of from about 0.1 milligram to about 300 milligram per kilogram of animal body weight. In some embodiments, the compounds of the present disclosure are given as a single daily dose or in divided doses two to six times a day, or in sustained release form. For most large mammals, the total daily dosage is from about 1 milligram to about 1000 milligrams, or from about 1 milligram to about 50 milligrams. In the case of a 70 kg adult human, the total daily dose will generally be from about 0.1 milligrams to about 200 milligrams. This dosage regimen may be adjusted to provide the optimal therapeutic response. In some embodiments, the total daily dosage is from about 1 milligram to about 900 milligrams, about 1 milligram to about 800 milligrams, about 1 milligram to about 700 milligrams, about 1 milligram to about 600 milligrams, about 1 milligram to about 400 milligrams, about 1 milligram to about 300 milligrams, about 1 milligram to about 200 milligrams, about 1 milligram to about 100 milligrams, about 1 milligram to about 50 milligrams, about 1 milligram to about 20 milligram, or about 1 milligram to about 10 milligrams.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are frequently alternated with resting periods of about 1 to 28 days, commonly about 7 days or about 14 days, between cycles. The treatment cycles, in other embodiments, may also be continuous.

In some embodiments, the methods provided herein comprise administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Combinations

In some embodiments, a compound of Formula (I), (Ia), (IIa), (IIb), (IIc), (IId), (IIe), (IIf), (IIg), (IIh), (IIi), (IIj), (IIk), (III), (IIm), (IIn), or (IIo), provided herein, or pharmaceutically acceptable salt thereof, is administered in combination with one or more additional therapeutic agents to treat or prevent a disease or condition disclosed herein. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the pharmaceutical compositions provided herein have a compound of Formula (I), (Ia), (IIa), (IIb), (IIc), (IId), (IIe), (IIf), (IIg), (IIh), (IIi), (IIj), (IIk), (III), (IIm), (IIn), or (IIo), provided herein, or pharmaceutically acceptable salt thereof, and one or more additional therapeutic agents. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the one or more additional therapeutic agents are selected from a(n) angiotensin converting enzyme (ACE) inhibitor, Adenosine A3 receptor agonist, Adiponectin receptor agonist, AKT protein kinase inhibitor, AMP kinase activator, AMP-activated protein kinase (AMPK) activator, Amylin receptor agonist, Angiotensin II AT-1 receptor antagonist, Androgen receptor agonist, Apoptosis signal-regulating kinase 1 (ASK1) inhibitor, ATP citrate lyase inhibitor, Apolipoprotein C3 (APOC3) antagonist, Autophagy protein modulator, Autotaxin inhibitors, Axl tyrosine kinase receptor inhibitor, Bax protein stimulator, Bioactive lipid, Calcitonin agonist, Cannabinoid receptor modulator, Caspase inhibitor, Caspase-3 stimulator, Cathepsin inhibitor (e.g., cathepsin B inhibitor), Caveolin 1 inhibitor, CCR2 chemokine antagonist, CCR3 chemokine antagonist, CCR5 chemokine antagonist, CD3 antagonist, Chloride channel stimulator, cholesterol solubilizer, CNR1 inhibitor, Cyclin D1 inhibitor, Cytochrome P450 7A1 inhibitor, Cytochrome P450 2E1 (CYP2E1) inhibitor, Diacylglycerol O acyltransferase 1 inhibitor (DGAT1) inhibitor, Diacylglycerol O acyltransferase 1 inhibitor (DGAT2) inhibitor, CXCR4 chemokine antagonist, Dipeptidyl peptidase IV inhibitor, Endosialin modulator, Endothelial nitric oxide synthase stimulator, Eotaxin ligand inhibitor, Extracellular matrix protein modulator, Farnesoid X receptor agonist, Fatty acid synthase inhibitors, FGF1 receptor agonist, Fibroblast activation protein (FAP) inhibitor, Fibroblast growth factor receptor ligands (e.g., FGF-15, FGF-19, FGF-21), Fish oil, Galectin-3 inhibitor, Glucagon receptor agonist, Glucagon-like peptide 1 receptor agonist, Glucocorticoid receptor antagonist, Glucose 6-phosphate 1-dehydrogenase inhibitor, Glutaminase inhibitor, Glutathione precursor, G-protein coupled bile acid receptor 1 agonist, G-protein coupled receptor 84 antagonist, Hedgehog (Hh) modulator, Hepatitis C virus NS3 protease inhibitor, Hepatocyte nuclear factor 4 alpha modulator (HNF4A), Hepatocyte growth factor modulator, Histone deacetylase inhibitor, HMG CoA reductase inhibitor, 11β-Hydroxysteroid dehydrogenase (11β-HSD1) inhibitor, Hypoxia inducible factor-2 alpha inhibitor, IL-1β antagonist, IL-6 receptor agonist, IL-10 agonist, IL-11 antagonist, IL-17 antagonist, Ileal sodium bile acid cotransporter inhibitor, Insulin sensitizer, Insulin ligand agonist, Insulin receptor agonist, integrin modulator, Integrin antagonist interleukin-1 receptor-associated kinase 4 (IRAK4) inhibitor, Jak2 tyrosine kinase inhibitor, Ketohexokinase (KHK) inhibitors, Klotho beta stimulator, leptin, leptin analog, 5-Lipoxygenase inhibitor, Lipoprotein lipase inhibitor, Liver X receptor, LPL gene stimulator, Lysophosphatidate-1 receptor (LPAR-1) antagonist, Lysyl oxidase homolog 2 (LOXL2) inhibitor, LXR inverse agonist, Macrophage mannose receptor 1 modulator, Matrix metalloproteinase (MMPs) inhibitor, MCH receptor-1 antagonist, MEKK-5 protein kinase inhibitor, Membrane copper amine oxidase (VAP-1) inhibitor, Methionine aminopeptidase-2 inhibitor, Methyl CpG binding protein 2 modulator, MicroRNA-132 (miR-132) antagonist, MicroRNA-21(miR-21) inhibitor, Mitochondrial uncoupler, Mixed lineage kinase-3 inhibitor, Myelin basic protein stimulator, NACHT LRR PYD domain protein 3 (NLRP3) inhibitor, NAD-dependent deacetylase sirtuin-1 stimulator, NADPH oxidase inhibitor (NOX), Nicotinic acid receptor 1 agonist, P2X7 purinoceptor modulator, P2Y13 purinoceptor stimulator, PDE 3 inhibitor, PDE 4 inhibitor, PDE 5 inhibitor, PDGF receptor beta modulator, Peptidyl-prolyl cis-trans isomerase A inhibitor, Phenylalanine hydroxylase stimulator, Phospholipase C inhibitor, PPAR alpha agonist, PPAR gamma agonist, PPAR delta agonist, PPAR gamma modulator, PPAR alpha/delta agonist, PPAR alpha/gamma/delta agonist, Protease-activated receptor-2 antagonist, Protein kinase modulator, Rho associated protein kinase 2 (ROCK2) inhibitor, Snitrosoglutathione reductase (GSNOR) enzyme inhibitor, Sodium glucose transporter-2 (SGLT2) inhibitor, SREBP transcription factor inhibitor, STAT-1 inhibitor, STAT-3 modulator, Stearoyl CoA desaturase-1 inhibitor, Snitrosoglutathione reductase (GSNOR) enzyme inhibitor, Suppressor of cytokine signalling-1 stimulator, Suppressor of cytokine signalling-3 stimulator, Spleen tyorosine kinase (SYK) inhibitor, Transforming growth factor β (TGF-β), TGF-β antagonist (e.g., TGF-β1 antagonist, TGF-β2 antagonist, TGF-β3 antagonist, latent TGF β complex modulator), TGF-β receptor antagonist, Transforming growth factor β activated Kinase 1 (TAK1), Thyroid hormone receptor beta agonist, Toll-like receptor (TLR)-4 antagonist, Transglutaminase inhibitor, Tumor necrosis factor alpha (TNFα) ligand inhibitor, Tumor Progression Locus 2 (Tpl2) kinase inhibitor, Tyrosine kinase receptor modulator, GPCR modulator, nuclear hormone receptor modulator, WNT modulators, YAP/TAZ modulator, and Zonulin inhibitor.

Non-limiting examples of the one or more additional therapeutic agents include:

ACE inhibitors, such as enalapril;

Acetyl CoA carboxylase (ACC) inhibitors, such as NDI-010976 (firsocostat), DRM-01, gemcabene, PF-05175157, QLT-091382 or PF-05221304;

Acetyl CoA carboxylase/Diacylglycerol O acyltransferase 2 inhibitors, such as PF-07055341;

Acetaldehyde dehydrogenase inhibitors, such as ADX-629;

Adenosine receptor agonists, such as CF-102 (namodenoson), CF-101, CF-502, or CGS21680;

Adiponectin receptor agonists, such as ADP-355 or ADP-399;

Amylin/calcitonin receptor agonists, such as KBP-042 or KBP-089;

AMP activated protein kinase stimulators, such as PXL-770 or O-304;

AMP kinase activators/ATP citrate lyase inhibitors, such as as bempedoic acid (ETC-1002, ESP-55016);

AMP activated protein kinase/Endothelial nitric oxide synthase/NAD-dependent deacetylase sirtuin-1 stimulators, such as NS-0200 (leucine+metformin+sildenafil);

Androgen receptor agonists, such as LPCN-1144;

Angiotensin II AT-1 receptor antagonists, such as irbesartan;

Angiopoietin-related protein-3 inhibitors, such as IONIS-ANGPTL3-LRx;

Autotaxin inhibitors, such as PAT-505, PAT-048, GLPG-1690, X-165, PF-8380, AM-063, or BBT-877;

Axl tyrosine kinase receptor inhibitors, such as bemcentinib (BGB-324, R-428);

Bax protein stimulators, such as CBL-514;

Bioactive lipids, such as DS-102;

Cannabinoid receptor type 1 (CNR1) inhibitors, such as namacizumab, GWP-42004, REV-200, or CRB-4001;

Caspase inhibitors, such as emricasan;

Pan cathepsin B inhibitors, such as VBY-376;

Pan cathepsin inhibitors, such as VBY-825;

CCR2/CCR5 chemokine antagonists, such as cenicriviroc, maraviroc, CCX-872, or WXSH-0213;

CCR2 chemokine antagonists, such as propagermanium;

CCR2 chemokine/Angiotensin II AT-1 receptor antagonists, such as DMX-200, or DMX-250;

CCR2/CCR5 chemokine antagonists and FXR agonists, such as LJC-242 (tropifexor+cenivriviroc); CCR3 chemokine antagonists, such as bertilimumab;

Chloride channel stimulators, such as cobiprostone, or lubiprostone;

CD3 antagonists, such as NI-0401 (foralumab);

CXCR4 chemokine antagonists, such as AD-214;

Diglyceride acyltransferase 1 (DGAT1) inhibitors, such as GSK-3008356;

Diacylglycerol O acyltransferase 1 (DGAT1)/Cytochrome P450 2E1 inhibitors (CYP2E1), such as SNP-610;

Diglyceride acyltransferase 2 (DGAT2) inhibitors, such as IONIS-DGAT2Rx, or PF-06865571;

Dipeptidyl peptidase IV inhibitors, such as linagliptin or evogliptin;

Eotaxin ligand inhibitors, such as bertilimumab or CM-101;

Extracellular matrix protein modulators, such as CNX-024;

Farnesoid X receptor (FXR) agonists, such as AGN-242266, AGN-242256, EP-024297, RDX-023, BWL-200, AKN-083, EDP-305, GNF-5120, GS-9674, LMB-763, obeticholic acid, Px-102, Px-103, M790, M780, M450, M-480, MET-409, PX20606, EYP-001, TERN-101, TC-100, INT-2228;

Farnesoid X receptor (FXR)/G-protein coupled bile acid receptor 1 (TGR5) agonists, such as INT-767;

Fatty acid synthase inhibitors, such as TVB-2640;

FGF receptor agonists/Klotho beta stimulators, such as BFKB-8488A (RG-7992);

Fibroblast growth factor 19 (rhFGF19)/cytochrome P450 (CYP)7A1 inhibitors, such as NGM-282;

Fibroblast growth factor 21 (FGF-21) ligand, such as BMS-986171, BIO89-100, B-1344, or BMS-986036;

Fibroblast growth factor 21 (FGF-21)/glucagon like peptide 1 (GLP-1) agonists, such as YH-25723 (YH-25724; YH-22241) or AKR-001;

Fish oil compositions, such as icosapent ethyl (Vascepa®);

Galectin-3 inhibitors, such as GR-MD-02, GB-1107 (Gal-300), or GB1211 (Gal-400);

Glucagon-like peptide 1 receptor (GLP1R) agonists, such as AC-3174, liraglutide, cotadutide (MEDI-0382), exenatide, SAR-425899, LY-3305677, HM-15211, YH-25723, YH-GLP1, RPC-8844, PB-718, or semaglutide;

Glucocorticoid receptor antagonists, such as CORT-118335 (miricorilant);

Glucose 6-phosphate 1-dehydrogenase inhibitors, such as ST001;

G-protein coupled bile acid receptor 1 (TGR5) agonists, such as RDX-009 or INT-777;

Heat shock protein 47 (HSP47) inhibitors, such as ND-L02-s0201;

HMG CoA reductase inhibitors, such as atorvastatin, fluvastatin, pitavastatin, pravastatin, rosuvastatin, or simvastatin;

Hypoxia inducible factor-2 alpha inhibitors, such as PT-2567;

IL-10 agonists, such as peg-ilodecakin;

Ileal sodium bile acid cotransporter inhibitors, such as odevixibat (A-4250), volixibat potassium ethanolate hydrate (SHP-262), GSK2330672, CJ-14199, or elobixibat (A-3309);

Insulin sensitizers, such as, KBP-042, MSDC-0602K, MSDC-5514, Px-102, RG-125 (AZD4076), VVP-100X, CB-4211, or ETI-101;

Insulin ligand/dsInsulin receptor agonists, such as ORMD-0801;

Integrin antagonists, such as IDL-2965;

IL-6 receptor agonists, such as KM-2702;

Ketohexokinase (KHK) inhibitors, such as PF-06835919;

beta Klotho (KLB)-FGF1c agonist, such as MK-3655 (NGM-313);

5-Lipoxygenase inhibitors, such as tipelukast (MN-001), DS-102 (AF-102);

Lipoprotein lipase inhibitors, such as CAT-2003;

LPL gene stimulators, such as alipogene tiparvovec;

Liver X receptor (LXR) modulators, such as PX-L603, PX-L493, BMS-852927, T-0901317, GW-3965, or SR-9238;

Lysophosphatidate-1 receptor antagonists, such as BMT-053011, UD-009 (CP-2090), AR-479, ITMN-10534, BMS-986020, or KI-16198;

Lysyl oxidase homolog 2 inhibitors, such as simtuzumab or PXS-5382A (PXS-5338);

Macrophage mannose receptor 1 modulators, such as tilmanocept-Cy3 (technetium Tc 99m tilmanocept);

Membrane copper amine oxidase (VAP-1) inhibitors, such as TERN-201;
MEKK-5 protein kinase (ASK-1) inhibitors, such as GS-4997, SRT-015, or GS-444217, GST-HG-151;
MCH receptor-1 antagonists, such as CSTI-100 (ALB-127158);
Methionine aminopeptidase-2 inhibitors, such as ZGN-839, ZGN-839, or ZN-1345;
Methyl CpG binding protein 2 modulators, such as mercaptamine;
Mitochondrial uncouplers, such as 2,4-dinitrophenol or HU6;
Mixed lineage kinase-3 inhibitors, such as URMC-099-C;
Myelin basic protein stimulators, such as olesoxime;
NADPH oxidase 1/4 inhibitors, such as GKT-831 or APX-311;
Nicotinic acid receptor 1 agonists, such as ARI-3037MO;
Nitazoxinide;
NACHT LRR PYD domain protein 3 (NLRP3) inhibitors, such as KDDF-201406-03, NBC-6, IFM-514, or JT-194 (JT-349);
Nuclear receptor modulators, such as DUR-928 (DV-928);
P2X7 purinoceptor modulators, such as SGM-1019;
P2Y13 purinoceptor stimulators, such as CER-209;
PDE 3/4 inhibitors, such as tipelukast (MN-001);
PDE 5 inhibitors, such as sildenafil or MSTM-102;
PDGF receptor beta modulators, such as BOT-191 or BOT-509;
Peptidyl-prolyl cis-trans isomerase inhibitors, such as CRV-431 (CPI-432-32), NVP-018, or NV-556 (NVP-025);
Phenylalanine hydroxylase stimulators, such as HepaStem;
PPAR agonists (including PPAR alpha agonists, PPAR alpha/delta agonists, PPAR alpha/delta/gamma agonists, PPAR delta agonists), such as elafibranor (GFT-505), MBX-8025, deuterated pioglitazone R-enantiomer, pioglitazone, DRX-065, saroglitazar, or IVA-337; PPAR alpha agonists, such as aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (fish oil, e.g., icosapent ethyl (Vascepa®), or docosahexaenoic acid), pirinixic acid, GW409544, AZ 242, LY518674, NS-220, AVE8134, BMS-711939, aleglitazar, muraglitzar, or saroglitazar;
PPAR alpha/delta agonists such as elafibranor;
PPAR alpha/delta/gamma agonists such as lanifibranor;
PPAR delta agonists such as seladelpar;
Protease-activated receptor-2 antagonists, such as PZ-235;
Protein kinase modulators, such as CNX-014;
Rho associated protein kinase (ROCK) inhibitors, such as REDX-10178 (REDX-10325) or KD-025;
Semicarbazide-Sensitive Amine Oxidase/Vascular Adhesion Protein-1 (SSAO/VAP-1) Inhibitors, such as PXS-4728A;
S-nitrosoglutathione reductase (GSNOR) enzyme inhibitors, such as SL-891;
Sodium glucose transporter-2 (SGLT2) inhibitors, such as ipragliflozin, remogliflozin etabonate, ertugliflozin, dapagliflozin, tofogliflozin, or sotagliflozin;
SREBP transcription factor inhibitors, such as CAT-2003 or MDV-4463;
Stearoyl CoA desaturase-1 inhibitors, such as aramchol;
Thyroid hormone receptor (THR) beta agonists, such as resmetriom (MGL-3196), MGL-3745, or VK-2809;
TLR-2/TLR-4 antagonists, such as VB-201 (CI-201);
TLR-4 antagonists, such as JKB-121;
Tyrosine kinase receptor modulators, such as CNX-025 or GFE-2137 (repurposed nitazoxanide);
GPCR modulators, such as CNX-023;
Nuclear hormone receptor modulators, such as Px-102;
Xanthine oxidase/Urate anion exchanger 1 (URAT1) inhibitors, such as RLBN-1001, RLBN-1127; and
Zonulin Inhibitors, such as lorazotide acetate (INN-202).

Additional non-limiting examples of the one or more additional therapeutic agents include:
ACE inhibitors, such as, benazepril, imidapril;
Adenosine A3 receptor antagonists, such as FM-101;
Adropin stimulators, such as RBT-2;
Albumin modulators, such as SYNT-002;
Aldosterone/Mineralocorticoid receptor antagonists, such as MT-3995;
Allogeneic bone marrow-derived mesenchymal stromal cell therapy, such as ORBCEL-M;
Allogenic expanded adipose-derived stem cell therapy, such as Elixcyte™;
AMP activated protein kinase stimulator/Proprotein convertase PC9 inhibitors, such as O-304;
AMP activated protein kinase stimulators, such as DZCY-01, MK-8722, PXL-770;
Angiotensin II AT-1 receptor/CCR2 chemokine antagonists, such as DMX-200;
Angiotensin II AT-2 receptor agonists, such as MOR-107, irbesartan;
Angiotensin II receptor antagonists, such as losartan;
Angiotensinogen ligand inhibitors, such as ALN-AGT;
anti-C1 antibodies, such as BIVV-009 (sutimlimab);
anti-CB1 antibodies, such as GFB-024;
anti-CX3CR1 nanobodies, such as BI-655088;
anti-IL-6 antibodies, such as COR-001;
anti-VEGF-B antibodies, such as CSL-346;
APOA1 gene stimulators/Bromodomain containing protein 2/Bromodomain containing protein 4 inhibitors, such as apabetalone;
Bone morphogenetic protein-7 ligand modulators, such as BMP-7;
Calcium channel inhibitors, such as TBN (xiaotongqin);
Cannabinoid CB1 receptor antagonists, such as JNJ-2463;
CB1 inverse agonists, such as CRB-4001;
Chymase inhibitors, such as fulacimstat (BAY-1142524);
Cyclooxygenase 1 inhibitors, such as GLY-230;
Cyclooxygenase 2/Epoxide hydrolase inhibitors, such as COX-2/soluble epoxide hydrolase;
Cytochrome P450 11B2 inhibitors, such as aldosterone synthase inhibitors;
Ectonucleotide pyrophosphatase-PDE-2 inhibitors, such as BLD-0409;
Endothelin ET-A/Endothelin ET-B receptor antagonists, such as aprocitentan;
Enteropeptidase inhibitors, such as SCO-792;
Erythropoietin receptor antagonists, such as EPO-018B;
Farnesoid X receptor agonists, such as LMB-763;
FGF/PDGF/beta receptor antagonist/p38 MAP kinase inhibitors, such as pirfenidone;
GHR/IGF1 gene inhibitors, such as atesidorsen sodium;
GPR40 agonist/GPR84 antagonists, such as PBI-4050;
G-protein beta subunit inhibitors, such as galleon;
G-protein coupled receptor 84 modulators, such as PBI-4425;

Growth hormone ligand/Growth hormone receptor agonist, such as Jintropin AQ™;
Growth hormone receptor agonists, such as LAT-8881;
Guanylate cyclase receptor agonist/Guanylate cyclase stimulators, such as praliciguat;
Guanylate cyclase stimulators, such as MRL-001, runcaciguat;
Heme oxygenase 1 modulators, such as RBT-1;
HIF prolyl hydroxylase inhibitors, such as TRGX-154;
Insulin sensitizer/Kallikrein 1 modulators, such as DM-199;
Integrin alpha-V/beta-3 antagonists, such as VPI-2690B;
Interleukin 33 ligand inhibitors, such as MEDI-3506;
Kelch like ECH associated protein 1 modulator/Nuclear erythroid 2-related factor 2 stimulators, such as SFX-01;
LDHA gene inhibitors, such as nedosiran;
5-Lipoxygenase activating protein inhibitors, such as AZD-5718;
Lysophosphatidate-1 receptor antagonists, such as BMS-002, EPGN-696;
Matrix extracell phosphoglycoprotein modulator/Phosphatonin receptor agonist, such as TPX-200;
MEKK-5 protein kinase inhibitors, such as selonsertib;
Membrane copper amine oxidase inhibitors, such as UD-014;
Midkine ligand inhibitors, such as CAB-101;
Mineralocorticoid receptor antagonists, such as AZD-9977, esaxerenone, finerenone, KBP-5074;
Myosin 2 inhibitor, such as DeciMab™;
NADPH oxidase 1 inhibitors/NADPH oxidase 4 inhibitors, such as setanaxib;
NADPH oxidase inhibitors, such as APX-115;
NK1 receptor antagonist/Opioid receptor kappa agonist/Opioid receptor mu antagonist, such as AV-104;
Nuclear erythroid 2-related factor 2 stimulator/TGF beta ligand inhibitors, such as CU01-1001;
Nuclear factor kappa B inhibitors, such as mefunidone, bardoxolone methyl (NSC-713200);
PDE 4 inhibitors, such as ART-648, PCS-499;
PDGF receptor beta modulators, such as BOT-191;
PDGF/VEGF receptor antagonists, such as ANG-3070;
PR84 antagonist/GPR40 (FFAR1)/GPR120 (FFAR4) agonist/and a partial activator of peroxisome proliferator-activated receptors (PPAR), such as PBI-4547;
PRKAA2 gene stimulators/AMPK activators, such as PF-06679142, PF-06685249;
Prostacyclin (PGI2) agonists, such as YS-1402;
Protein C activator/Glycoprotein Ib (GPIb) antagonist, such as AB-002;
Protein NOV homolog modulators, such as BLR-200;
Protein tyrosine phosphatase-1B inhibitors, such as MSI-1436;
Reactive oxygen species modulator inhibitors, such as SUL-121;
Renin inhibitors, such as imarikiren hydrochloride;
Rho associated protein kinase 2 inhibitors, such as ANG-4201, RXC-007;
Sodium glucose transporter-2 inhibitors, such as canagliflozin, dapagliflozin propanediol, empagliflozin;
Thromboxane A2 receptor antagonist/Thromboxane synthesis inhibitors, such as SER-150;
Tissue transglutaminase inhibitors, such as ZED-1227;
TRP cation channel C5 inhibitors, such as GFB-887;
TRP cation channel C6 inhibitors, such as ALGX-2224;
Cell adhesion molecule inhibitors, such as glycoside bacterial adhesin antagonists;
Urate anion exchanger 1 (URAT1)/SLC22A12 inhibitors, such as verinurad (RDEA3170);
VIP 1/VIP 2 receptor agonists, such as LBT-3627; and
Xanthine oxidase inhibitors, such as TMX-049, TMX-049DN.

In some embodiments, the one or more additional therapeutic agents are selected from A-4250, AC-3174, acetylsalicylic acid, AK-20, alipogene tiparvovec, AMX-342, AN-3015, aramchol, ARI-3037MO, ASP-8232, AZD-2693, bertilimumab, Betaine anhydrous, BI-1467335, BMS-986036, BMS-986171, BMT-053011, BOT-191, BTT-1023, CAT-2003, cenicriviroc, CBW-511, CER-209, CF-102, CGS21680, CNX-014, CNX-023, CNX-024, CNX-025, cobiprostone, colesevelam, dapagliflozin, DCR-LIV1, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, fluasterone (ST-002), FT-4101, GKT-831, GNF-5120, GRI-0621, GR-MD-02, GS-300, GS-4997, GS-9674, HTD-1801, HST-202, HST-201, hydrochlorothiazide, icosabutate (PRC-4016), icosapent ethyl ester, IMM-124-E, INT-767, INV-240, IONIS-DGAT2Rx, ipragliflozin, Irbesarta, propagermanium, IVA-337, JKB-121, KB-GE-001, KBP-042, KD-025, M790, M780, M450, metformin, sildenafil, LC-280126, linagliptin, liraglutide, LJN-452 (tropifexor), LM-011, LM-002 (CVI-LM-002), LMB-763, LYN-100, MBX-8025, MDV-4463, mercaptamine, MGL-3196, MGL-3745, MP-301, MSDC-0602K, namacizumab, NC-101, NDI-010976, ND-L02-s0201 (BMS-986263), NGM-282, NGM-313, NGM-386, NGM-395, NP-160, norursodeoxycholic acid, NVP-022, O-304, obeticholic acid (OCA), 25HC3S, olesoxime, PAT-505, PAT-048, PBI-4547, pegilodecakin, pioglitazone, pirfenidone, PRI-724, PX20606, Px-102, PX-L603, PX-L493, PXS-4728A, PZ-235, RDX-009, remogliflozin etabonate, RG-125 (AZD4076), RPI-500, saroglitazar, semaglutide, simtuzumab, solithromycin, sotagliflozin, statins (atorvastatin, fluvastatin, pitavastatin, pravastatin, rosuvastatin, simvastatin), symbiotic, TCM-606F, TEV-45478, TQA-3526, tipelukast (MN-001), TLY-012, TRX-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, MU-117, ZGN-839, ZG-5216, ZSYM-008, and ZYSM-007.

In some embodiments, the methods and pharmaceutical compositions provided herein include a therapeutically effective amount of an Apoptosis Signal-Regulating Kinase 1 (ASK1) inhibitor and a therapeutically effective amount of an LPAR1 antagonist, wherein the LPAR1 antagonist is a compound of Formula (I), (Ia), (IIa), (IIb), (IIc), (IId), (IIe), (IIf), (IIg), (IIh), or (IIi) provided herein or pharmaceutically acceptable salt thereof.

In some embodiments of the methods and pharmaceutical compositions disclosed herein, the ASK1 inhibitor is GS-4997 (selonsertib, SEL).

ASK1 inhibitors can be synthesized and characterized using methods known to those of skill in the art, such as those described in U.S. 2007/0276050, U.S. 2011/0009410, and U.S. 2013/0197037.

In some embodiments, the methods and pharmaceutical compositions provided herein include a therapeutically effective amount of an Acetyl-CoA Carboxylase (ACC) inhibitor and a therapeutically effective amount of an LPAR1 antagonist, wherein the LPAR1 antagonist is a compound of Formula (I), (Ia), (IIa), (IIa), (IIc), (IId), (IIe), (IIf), (IIg), (IIh), or (IIi) provided herein or pharmaceutically acceptable salt thereof.

In some embodiments of the methods and pharmaceutical compositions disclosed herein, the ACC inhibitor is GS-0976 (firsocostat, FIR).

ACC inhibitors can be synthesized and characterized using methods known to those of skill in the art, such as those described in U.S. Pat. Nos. 9,453,026 and 10,183,951.

In some embodiments, the methods and compositions provided herein include a therapeutically effective amount of a PPAR agonist (e.g., PPAR alpha agonist, PPAR alpha/delta agonist, PPARalpha/delta/gamma agonist, PPAR delta agonist) or fish oil, a therapeutically effective amount of an Acetyl CoA Carboxylase (ACC) inhibitor, such as GS-0976 (firsocostat, FIR), and a therapeutically effective amount of an LPAR1 antagonist, wherein the LPAR1 antagonist is a compound of Formula (I), (Ia), (IIa), (IIb), (IIc), (IId), (IIe), (IIf), (IIg), (IIh), (IIi), (IIj), (IIk), (IIl), (IIm), (IIn), or (IIo), provided herein or pharmaceutically acceptable salt thereof. In some embodiments, the PPAR agonist is a PPAR alpha agonist. In some embodiments, the PPAR alpha agonist is selected from aluminum clofibrate, bezafibrate, ciprofibrate, choline fenofibrate, clinofibrate, clofibrate, clofibride, fenofibrate, gemfibrozil, pemafibrate, ronifibrate, simfibrate, pirinixic acid, GW409544, AZ 242, LY518674, NS-220, AVE8134, BMS-711939, aleglitazar, muraglitazar, and saroglitazar. In some embodiments, the PPAR agonist (e.g., PPAR alpha agonist) is a fibrate. In some embodiments, the PPAR agonist (e.g., PPAR alpha agonist) is fenofibrate. In some embodiments, the PPAR agonist is a PPAR alpha/delta agonist (e.g., elafibranor). In some embodiments, the PPAR agonist is a PPAR alpha/delta/gamma agonist (e.g., lanifibranor). In some embodiments, the PPAR agonist is a PPAR delta agonist (e.g., seladelpar). In some embodiments the fish oil is an omega-3 fatty acid or docosahexaenoic acid. In some embodiments, the fish oil is icosapent ethyl (e.g., Vascepa®).

In some embodiments, the methods and compositions provided herein include a therapeutically effective amount of a Farnesoid X Receptor (FXR) agonist and a therapeutically effective amount of an LPAR1 antagonist, wherein the LPAR1 antagonist is a compound of Formula (I), (Ia), (IIa), (IIb), (IIc), (IId), (IIe), (IIf), (IIg), (IIh), (IIi), (IIj), (IIk), (IIl), (IIm), (IIn), or (IIo), provided herein or pharmaceutically acceptable salt thereof.

In some embodiments of the methods and pharmaceutical compositions disclosed herein, the FXR agonist is GS-9674 (cilofexor, CILO).

In some embodiments of the methods and pharmaceutical compositions disclosed herein, the FXR agonist is a compound having the structure:

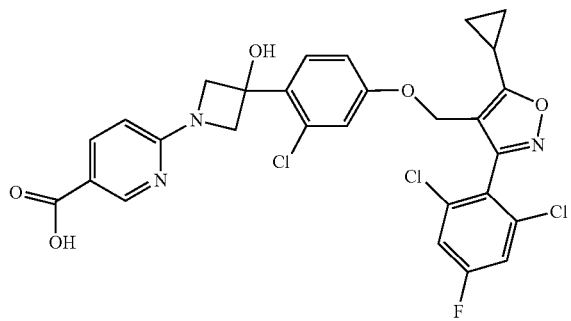 [SMILES: O=C(O)c1ccc(N2CC(O)(c3ccc(OCc4c(-c5c(Cl)cc(F)cc5Cl)noc4C4CC4)cc3Cl)C2)nc1]

or a pharmaceutically acceptable salt thereof.

In some embodiments, the methods and compositions provided herein include a therapeutically effective amount of a GLP-1 receptor agonist and a therapeutically effective amount of an LPAR1 antagonist, wherein the LPAR1 antagonist is a compound of Formula (I), (Ia), (II), (IIa), (IIb), (IIc), (IId), (IIe), (IIf), (IIg), (IIh), (IIi), (IIj), (IIk), (IIl), (IIm), (IIn), or (IIo) provided herein or a pharmaceutically acceptable salt thereof. In some embodiments, the GLP-1 receptor agonist is liraglutide or semaglutide. In some embodiments, the GLP-1 receptor agonist is semaglutide.

In some embodiments, the methods and compositions provided herein include a therapeutically effective amount of a TGFβ antagonist and a therapeutically effective amount of an LPAR1 antagonist, wherein the LPAR1 antagonist is a compound of Formula (I), (Ia), (IIa), (IIb), (IIc), (IId), (IIe), (IIf), (IIg), (IIh), (IIi), (IIj), (IIk), (IIl), (IIm), (IIn), or (IIo), provided herein or pharmaceutically acceptable salt thereof. In some embodiments, the TGFβ antagonist is a TGFβ-specific antibody. TGFβ-specific antibodies can be prepared and characterized using methods known to those of skill in the art, such as those described in PCT International Application Publication No. WO 2018/129329 and in U.S. Pat. No. 9,518,112. In some embodiments, the TGFβ antagonist binds to a TGFβ latency-associated peptide (LAP), e.g., TGFβ 1-LAP. TGFβ 1-LAP-specific antibodies can be prepared and characterized using methods known to those of skill in the art, such as those described in U.S. Pat. No. 8,198,412 or U.S. Pat. No. 10,017,567. In some embodiments, the TGFβ antagonist binds to TGFβ (e.g., TGFβ 1) in a context independent manner (e.g., independent of the presentation of TGFβ in a specific tissue or organ). In some embodiments, the TGFβ antagonist binds to TGFβ (e.g., TGFβ 1) in a context-dependent manner. In some embodiments, the TGFβ antagonist blocks activation of latent TGFβ (e.g., latent TGFβ 1) that is localized in extracellular matrix, e.g., in connective tissue of the liver. In some embodiments, the TGFβ antagonist blocks activation of latent TGFβ (e.g., latent TGFβ 1) that is localized in the thymus, a lymph node, or in a tumor microenvironment (e.g., in a patient having liver cancer). In some embodiments, the TGFβ antagonist blocks activation of latent TGFβ (e.g., latent TGFβ 1) by Latent TGFβ Binding Protein (LTBP). In some embodiments, the TGFβ antagonist blocks activation of latent TGFβ (e.g., latent TGFβ 1) by Glycoprotein-A Repetitions Predominant protein (GARP), as described, e.g., in U.S. Pat. No. 10,000,572. In some embodiments, the TGFβ antagonist is ARGX-115. In some embodiments, the TGFβ antagonist is an anti-latency-associated peptide (LAP) antibody that specifically binds to a LAP-TGFβ complex. In some embodiments, the anti-LAP antibody specifically binds to LAP-TGFβ complexes in extracellular matrix (ECM), e.g., of connective tissue in the liver. In some embodiments, the anti-LAP antibody specifically binds to LAP-TGFβ complexes on the surfaces of certain immunosuppressive cell types, such as regulatory T cells (Tregs), tumor-associated macrophages, or myeloid-derived suppressor cells, e.g., in a tumor microenvironment. In some embodiments, the anti-LAP antibody is a TLS-01 antibody. In some embodiments, the anti-LAP antibody specifically binds to LAP-TGFβ complexes in any context. In some embodiments, the anti-LAP antibody is a TLS-02 antibody. In some embodiments, the TGFβ antagonist comprises a TGFβ receptor. In some embodiments, the TGFβ antagonist is a TGFβ receptor-Fc fusion protein. In some embodiments, the TGFβ antagonist is an antibody comprising a TGFβ receptor. TGFβ antagonists comprising a TGFβ receptor that can be useful in connection with the compositions and methods provided herein have been described, e.g., in PCT International Publication Nos. WO 2019/113123 A1 and WO 2019/113464 A1.

In some embodiments the methods and compositions provided herein include a therapeutically effective amount of an LPAR1 antagonist and of an additional therapeutic agent selected from an ACE inhibitor, adenosine A3 receptor antagonist, adropin stimulator, albumin modulator, aldosterone antagonist, AMP activated protein kinase stimulator, angiotensin II AT-2 receptor agonist, angiotensin II receptor antagonist, angiotensinogen ligand inhibitor, APOA1 gene stimulator, apolipoprotein L1 modulator, bone morphogenetic protein-7 ligand modulator, bromodomain containing protein 2 inhibitor, bromodomain containing protein 4 inhibitor, calcium channel inhibitors, cannabinoid CB1 receptor antagonists, CB1 inverse agonists, CCR2 chemokine antagonist, chymase inhibitor, complement C1s subcomponent inhibitor, CX3CR1 chemokine antagonist, cyclooxygenase 1 inhibitor, cyclooxygenase 2 inhibitor, cytochrome P450 11B2 inhibitor, ectonucleotide pyrophosphatase-PDE-2 inhibitor, endothelin ET-A receptor antagonist, endothelin ET-B receptor antagonist, enteropeptidase inhibitor, epoxide hydrolase inhibitor, erythropoietin receptor antagonist, farnesoid X receptor agonist, FGF receptor antagonists, free fatty acid receptor 1 agonist, GHR gene inhibitor, glycoprotein Ib (GPIb) antagonist, GPR40 agonist, GPR84 antagonist, G-protein beta subunit inhibitor, G-protein coupled receptor 120 agonist, G-protein coupled receptor 84 modulator, growth hormone ligand, growth hormone receptor agonist, guanylate cyclase receptor agonists, guanylate cyclase stimulator, heme oxygenase 1 modulator, HIF prolyl hydroxylase inhibitor, IGF1 gene inhibitors, IgG receptor FcRn large subunit p51 modulator, IL-6 receptor antagonist, integrin alpha-V/beta-3 antagonist, interleukin 33 ligand inhibitor, Kelch-like ECH associated protein 1 modulator, LDHA gene inhibitor, 5-lipoxygenase activating protein inhibitor, lysophosphatidate-1 receptor antagonist, matrix extracellular phosphoglycoprotein modulator, membrane copper amine oxidase inhibitor, midkine ligand inhibitor, mineralocorticoid receptor antagonist, myosin 2 inhibitors, NADPH oxidase 1 inhibitor, NADPH oxidase 4 inhibitor, NADPH oxidase inhibitor, NK1 receptor antagonist, nuclear erythroid 2-related factor 2 stimulator, nuclear factor kappa B inhibitor, opioid receptor kappa agonist, opioid receptor mu antagonists p38 MAP kinase inhibitor, PDE4 inhibitor, PDGF receptor antagonist, PDGF receptor beta modulator, phosphatonin receptor agonist, PRKAA2 gene stimulator, proprotein convertase PC9 inhibitor, prostacyclin (PGI2) agonist, protein C activator, protein NOV homolog modulator, protein tyrosine phosphatase-1B inhibitor, reactive oxygen species modulator inhibitor, renin inhibitor, Rho associated protein kinase 2 inhibitor, SLC22A12 inhibitor, sodium glucose transporter-2 inhibitor, solute carrier family inhibitor, TGF beta ligand inhibitor, TGF beta receptor antagonist, thromboxane A2 receptor antagonist, thromboxane synthesis inhibitor, tissue transglutaminase inhibitor, TRP cation channel C5 inhibitor, TRP cation channel C6 inhibitor, tryptophanase inhibitor, unspecified cell adhesion molecule inhibitor, urate anion exchanger 1 inhibitor, vasopressin V1a receptor antagonist, VEGF receptor antagonist, VIP 1 receptor agonist, VIP 2 receptor agonist, and Xanthine oxidase inhibitor.

In some embodiments the methods and compositions provided herein include a therapeutically effective amount of an LPAR1 antagonist and of an additional therapeutic agent selected from a VEGFR inhibitor, a FGFR inhibitor, a PDGFR inhibitor, an autaxin inhibitor, a GPR84 agonist, a PASK inhibitor, a CFTR agonist, a JAK1 inhibitor, an ADAMTS5 inhibitor, a TOL2/3 inhibitor, a CTGF inhibitor, a soluble PTX2, an anti-galectin-3 antibody, an integrin-$\alpha_v$-$\beta_6$/$\alpha_v$-$\beta_1$ antagonist, a JNK1 inhibitor, a mineralocorticoid receptor antagonist, a Nrf2 activator, a chymase inhibitor, a PDE inhibitor, a NOX1/4 inhibitor, a leukotriene/thromboxane receptor antagonist, SLC22A12 inhibitor, an sGC inhibitor, and a xanthine oxidase inhibitor.

In some embodiments the methods and compositions provided herein include a therapeutically effective amount of an LPAR1 antagonist and of an additional therapeutic agent selected from nintedanib, pirfenidone, pamrevlumab, PRM-151, GB-0139, PLN-74809, CC-90001, finerenone, BAY1142524, PCS-499, setanaxib, SER150, RDEA3170, praliciguat, TMX-049, GLPG1690, GLPG1205, GLPG1972, GLPG4059, GLPG2737, GLPG3970, and filgotinib.

In some embodiments the methods and compositions provided herein include a therapeutically effective amount of an LPAR1 antagonist and of an additional therapeutic agent selected from A-717, ACF-TEI, alanyl-glutamine, ALLN-346, anti-SCF248 antibody, anti-TAGE monoclonal antibodies, anti-TGF beta antibodies, AST-120, BAY-2327949, BI-685509, DP-001, DZ-4001, GDT-01, LNP-1892, MEDI-8367, microRNA-targeting antisense oligonucleotide therapy, MK-2060, MPC-300-IV, NAV-003, Neo-Kidney Augment™ (NKA), NP-135, NP-160, NP-251, NRF-803, PBI-4610, PHN-033, R-HSC-010, salvianolic acid, SGF-3, SPD-01, Sugaheal variant, SZ-005, TCF-12, ITMC119-06, VAR-400, veverimer, VS-105, and XRx-221.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that these examples are exemplary and not exhaustive. Many changes can be made in the specific embodiments which are disclosed and still obtain a like or similar result without departing from the spirit and scope of the disclosure.

Compounds disclosed herein can be prepared according to the procedures of the following Schemes and Examples, using appropriate materials and are further exemplified by the following specific examples. Moreover, by utilizing the procedures described herein, in conjunction with ordinary skills in the art, additional compounds of the present disclosure claimed herein can be readily prepared. The examples further illustrate details for the preparation of the compounds of the present disclosure. Those skilled in the art will readily understand that known variations of the conditions and processes of the following preparative procedures can be used to prepare these compounds. For synthesizing compounds which are embodiments described in the present disclosure, inspection of the structure of the compound to be synthesized will provide the identity of each substituent group. In some cases, the identity of the final product can render apparent the identity of the necessary starting materials by a process of inspection, given the examples herein. Compounds can be isolated in the form of their pharmaceutically acceptable salts, such as those described above. Compounds described herein are typically stable and isolatable at room temperature and pressure.

An illustration of the preparation of compounds disclosed herein is shown below. Unless otherwise indicated, variables have the same meaning as described above. The examples presented below are intended to illustrate particular embodiments of the disclosure. Suitable starting materials, building blocks and reagents employed in the synthesis as described below are commercially available from AbovChem, Acros Organics, Astatech, Combi Blocks, Oakwood Chemical, or Sigma-Aldrich, for example, or can be routinely prepared by procedures described in the literature, for example in "March's Advanced Organic Chemistry: Reactions, Mechanisms, and Structure", $5^{th}$ Edition; John Wiley & Sons or T. Eicher, S. Hauptmann "The Chemistry of Heterocycles; Structures, Reactions, Synthesis and Application", $2^{nd}$ edition, Wiley-VCH 2003; Fieser et al. "Fiesers' Reagents for organic Synthesis" John Wiley & Sons 2000.

General Schemes

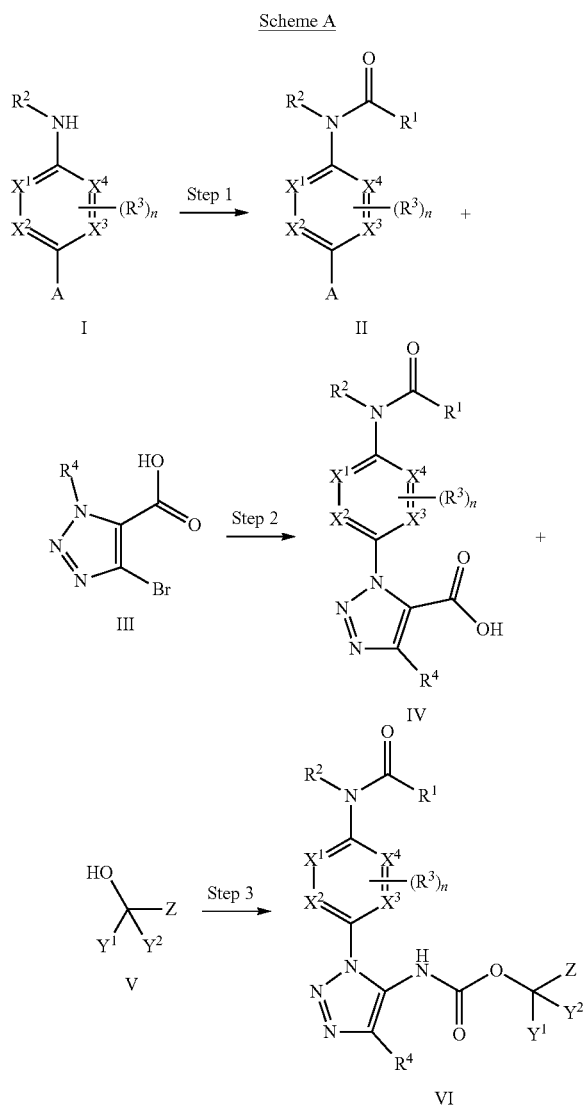

Scheme A provides a general synthesis of triazole carbamate aryl- and heteroaryl-carboxamides (VI). In the Schemes disclosed herein "A" can be a halogen such as Cl, Br, or I. Aryl or heteroaryl halide (I) can be readily prepared by electrophilic aromatic halogenation of the corresponding aryl or heteroaryl amine. Step one describes the acylation of aryl and heteroaryl amines (I). Amine (I) can be treated with an acid chloride, or a carboxylic acid with standard peptide coupling conditions such as the use of 1-Ethyl-3-(3-dimethylaminopropyl)carbodiimide (EDC) to provide the corresponding amides (II). Alternatively, the amine (I) can also be treated with a chloroformate, to provide the corresponding carbamate (II). Additionally, the amine (I) can be treated first with phosgene, to generate the intermediate isocyanate, which can then be trapped by an amine to provide the corresponding urea (II).

Step two describes a general synthesis of aryl or heteroaryl triazole carboxylic acids (IV) via cross coupling reaction. Aryl or heteroaryl halide (II) can first be converted to the corresponding boronic ester such as pinacol boronate via Miyaura borylation, and then subjected to Suzuki reaction conditions with bromo triazole carboxylic acid (III) to furnish the desired aryl or heteroaryl triazole carboxylic acid (IV). Alternatively, bromo triazole carboxylic acid (III) can first be converted to an organo-zinc species via lithium-halogen exchange and trapping with zinc chloride. Next, Negishi cross coupling with aryl or heteroaryl halide (II) provides the desired aryl or heteroaryl triazole carboxylic acid (IV).

Step three describes a general synthesis of triazole carbamate aryl- and heteroaryl-carboxamides (VI). An aryl or heteroaryl triazole carboxylic acid (IV) undergoes a Curtius rearrangement when treated with diphenylphosphoryl azide (DPPA), or alternatively with 1-propanephosphonic anhydride (T3P) solution and azidotrimethylsilane. The intermediate isocyanate is then trapped with an alcohol (V) to provide the desired aryl or heteroaryl triazole carbamate (VI).

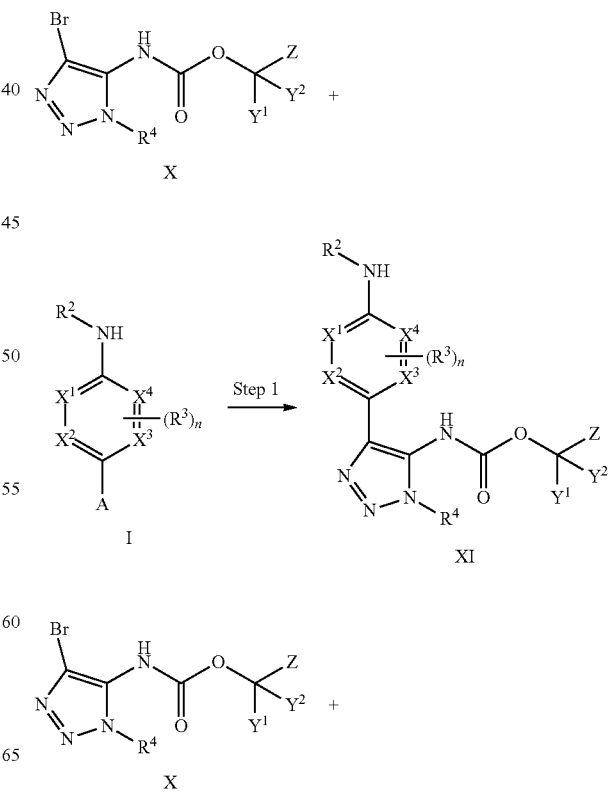

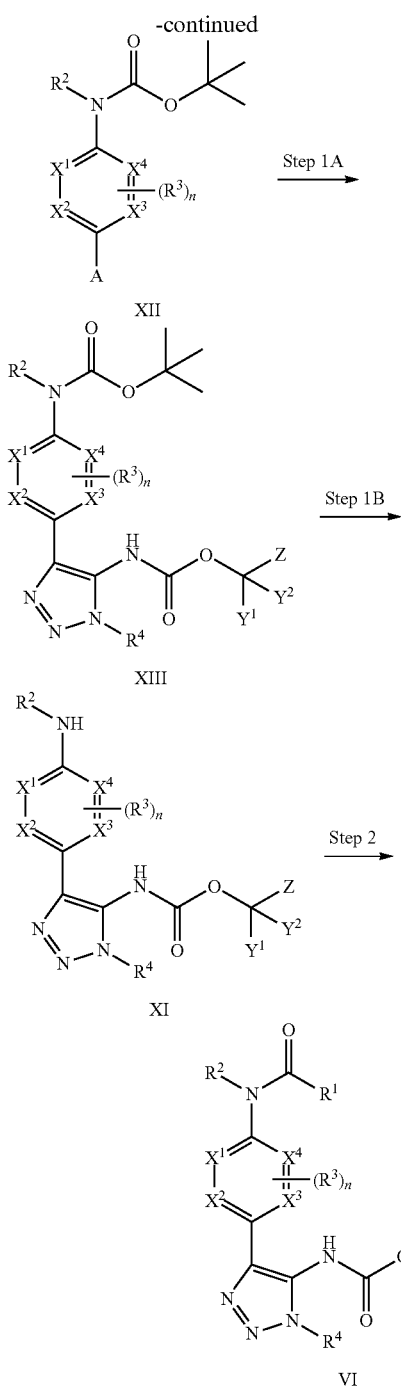

XII

XIII

XI

VI

Scheme B provides an alternative synthesis of triazole carbamate aryl- and heteroaryl-carboxamides (VI). Step one describes a general synthesis of amino-aryl or -heteroaryl triazole carbamates (XI) via cross coupling reaction. Bromo triazole carbamate (X) can first be converted to an organo-zinc species via lithium-halogen exchange and trapping with zinc chloride. Next, Negishi cross coupling with aryl or heteroaryl halide (I), provides the desired amino-aryl or -heteroaryl triazole carbamate (XI). Alternatively, aryl or heteroaryl halide (I) can first be converted to the corresponding boronic ester such as pinacol boronate via Miyaura borylation, and then subjected to Suzuki reaction conditions with bromo triazole carbamate (X) to furnish the desired amino-aryl or -heteroaryl triazole carbamate (XI).

Step 1A-B describes an alternative synthesis to amino-aryl or -heteroaryl triazole carbamate (XI). Tert-butyl carbamate (XII) can be readily prepared by treatment of the corresponding aryl or heteroaryl amines with di-tert-butyl dicarbonate. Aryl or heteroaryl halide (XII) can first be converted to the corresponding boronic ester such as pinacol boronate via Miyaura borylation, and then subjected to Suzuki reaction conditions with bromo triazole carbamate (X) to furnish the desired aryl or heteroaryl triazole carbamate (XIII). Alternatively, bromo triazole carbamate (X) can first be converted to an organo-zinc species via lithium-halogen exchange and trapping with zinc chloride. Next, Negishi cross coupling with aryl or heteroaryl halide (XII) provides the desired aryl or heteroaryl triazole carbamate (XIII). Next, the tert-butyl aryl or heteroaryl triazole carbamate (XIII) can be treated with acids such as hydrogen chloride (HCl) to furnish the amino-aryl or -heteroaryl triazole carbamate (XI) as the hydrochloride salt.

Step two describes the general synthesis of triazole carbamate aryl- and heteroaryl-carboxamides (VI). The amino-aryl or -heteroaryl triazole carbamate (XI) can be treated with an acid chloride, or a carboxylic acid with standard peptide coupling conditions such as the use of 1-Ethyl-3-(3-dimethylaminopropyl)carbodiimide (EDC) to provide the corresponding amides (VI). Alternatively, the amine (XI) can also be treated with a chloroformate, to provide the corresponding carbamate (VI). Additionally, the amine (XI) can be treated first with phosgene, to generate the intermediate isocyanate, which can then be trapped by an amine to provide the corresponding urea (VI).

Scheme C

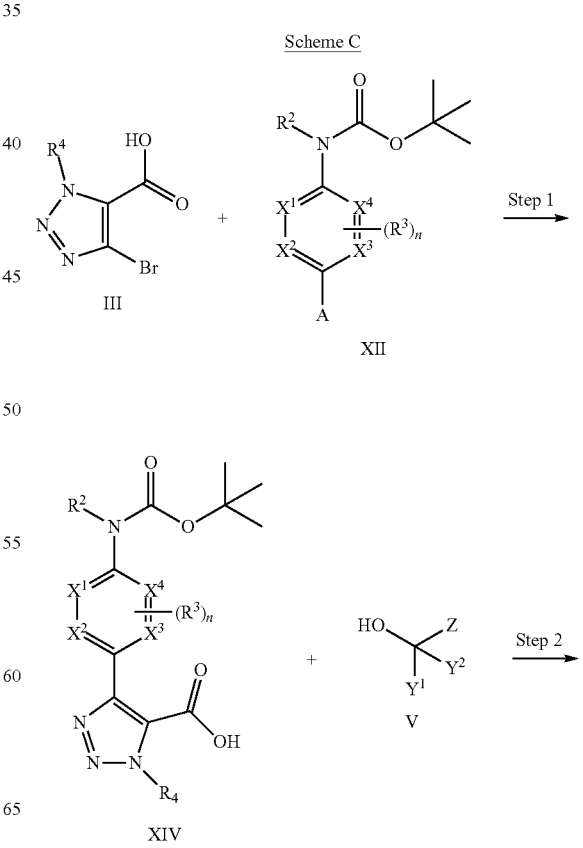

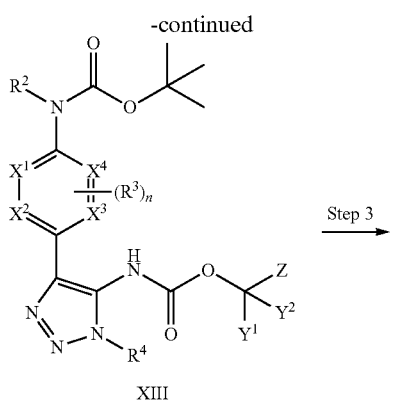

XIII

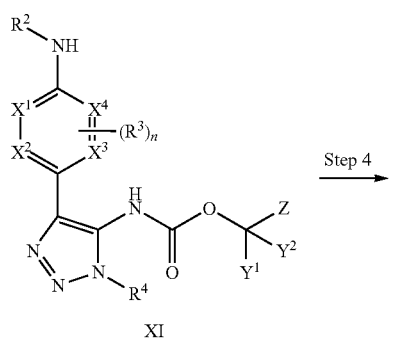

XI

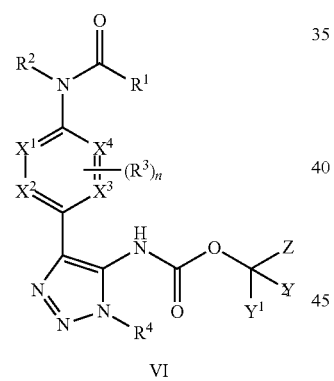

VI

Scheme C provides a general alternative synthesis of aryl or heteroaryl triazole carbamates (VI). Step one describes a general synthesis of aryl or heteroaryl triazole carboxylic acids (XIV) via cross coupling reaction. Aryl or heteroaryl halide (XII) can first be converted to the corresponding boronic ester such as pinacol boronate via Miyaura borylation, and then subjected to Suzuki reaction conditions with bromo triazole carboxylic acid (III) to furnish the desired aryl or heteroaryl triazole carboxylic acid (XIV). Alternatively, bromo triazole carboxylic acid (III) can first be converted to an organo-zinc species via lithium-halogen exchange and trapping with zinc chloride. Next, Negishi cross coupling with aryl or heteroaryl halide (XII) provides the desired aryl or heteroaryl triazole carboxylic acid (XIV).

Step two describes a general synthesis of carbamate containing aryl or heteroaryl triazoles (XIII) An aryl or heteroaryl triazole carboxylic acid (XIV) undergoes a Curtius rearrangement when treated with diphenylphosphoryl azide (DPPA), or alternatively with 1-propanephosphonic anhydride (T3P) solution and azidotrimethylsilane. The intermediate isocyanate is then trapped with an alcohol (V) to provide the desired aryl or heteroaryl triazole carbamate (XIII) Step three describes a general synthesis of amino-aryl or -heteroaryl triazole carbamate (XI). Tert-butyl aryl or heteroaryl carbamate (XIII) can be treated with acids such as hydrogen chloride (HCl) to furnish the amino-aryl or -heteroaryl triazole carbamate (XI) as the hydrochloride salt.

Step four describes the general synthesis of triazole carbamate aryl- and heteroaryl-carboxamides (VI). The amino-aryl or -heteroaryl triazole carbamate (XI) can be treated with an acid chloride, or a carboxylic acid with standard peptide coupling conditions such as the use of 1-Ethyl-3-(3-dimethylaminopropyl)carbodiimide (EDC) to provide the corresponding amides (VI). Alternatively, the amine (XI) can also be treated with a chloroformate, to provide the corresponding carbamate (VI). In the case where phenyl chloroformate is used, the resulting phenyl carbamate (VI) can be treated with an amine to generate the corresponding urea (VI). Additionally, the amine (XI) can be treated first with phosgene, to generate the intermediate isocyanate, which can then be trapped by an amine to provide the corresponding urea (VI).

Scheme D

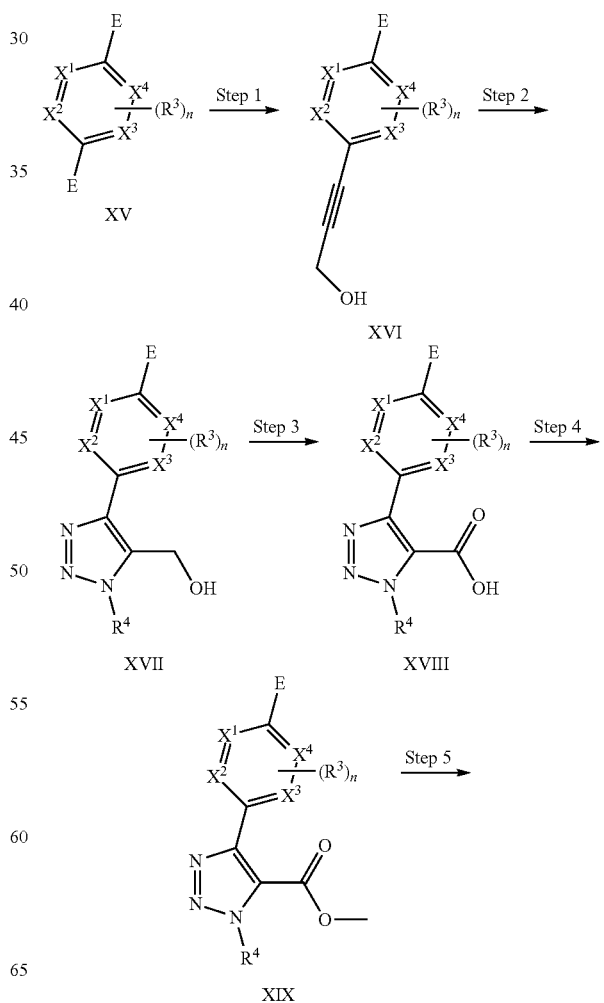

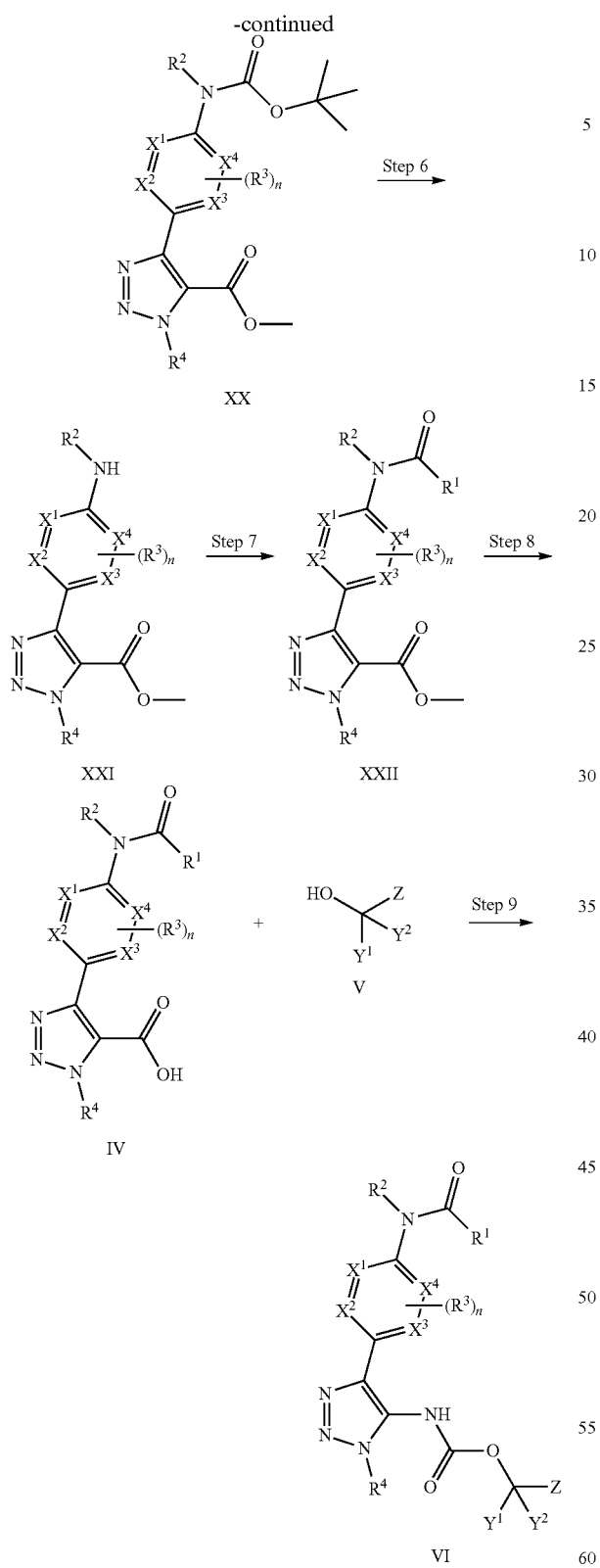

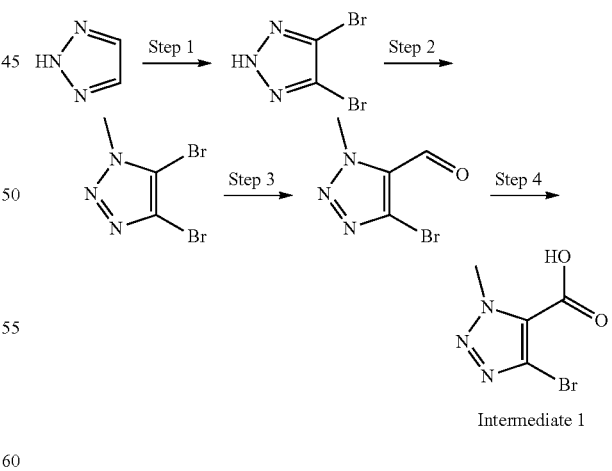

or heteroaryl-alkyne (XVI). The alkyne then ungoes a thermal or catalytic cycloaddition with an azide to generate the corresponding hydroxymethyl triazoles (XVII) in step two. Finally, oxidation of the primary alcohol using tetramethylpiperidinyloxy (TEMPO), and sodium chlorite provides the triazole carboxylic acid (XVIII) in step three.

In step four, the triazole carboxylic acid (XVIII) is protected as a methyl ester (XIX) such as by treatment with thionyl chloride. In step five, the aryl- or heteroaryl-halide (XIX) then undergoes a Buchwald-type amination with tert-butyl carbamate to generate the Boc-protected amine (XX).

In step six, exposure of Boc-protected amine (XX) to hydrochloric acid reveals the hydrochloride salt (XXI), which can be reacted in step seven with an acid chloride, or a carboxylic acid with standard peptide coupling conditions such as the use of 1-Ethyl-3-(3-dimethylaminopropyl)carbodiimide (EDC) to provide the corresponding amides (XXII). Alternatively, the amine (XXI) can also be treated with a chloroformate, to provide the corresponding carbamate (XXII). Additionally, the amine (XXI) can be treated first with phosgene, to generate the intermediate isocyanate, which can then be trapped by an amine to provide the corresponding urea (XXII). In step eight, the triazole ester (XXII) can be hydrolyzed upon treatment with base such as sodium hydroxide, to reveal the triazole carboxylic acid (IV). Lastly, step nine describes a Curtius rearrangement of triazole carboxylic acids (IV) via treatment with diphenylphosphoryl azide (DPPA), or alternatively with 1-propanephosphonic anhydride (T3P) solution and azidotrimethylsilane. The intermediate isocyanate is then trapped with an alcohol (V) to provide the desired aryl- or heteroaryl-triazole carbamate (VI).

Example 1

Preparation of 4-bromo-1-methyl-1H-1,2,3-triazole-5-carboxylic acid (Intermediate 1)

Step 1: 4,5-dibromo-2H-1,2,3-triazole

Bromine (2.8 mol) was added to a solution of 2H-1,2,3-triazole (1.4 mol) in water (600 mL) at 40° C. The resulting mixture was stirred for 2 hours at 40° C. After cooling to room temperature, the precipitate was collected by filtration.

Scheme D describes an alternative synthesis of synthesis of triazole carbamate aryl- and heteroaryl-carboxamides (VI). E can be a halogen, such as —Br or —I. In step one, an aryl- or heteroaryl-dihalide (XV) undergoes a Sonagashira coupling with propargyl alcohol to generate the aryl- The solid was washed with water (2×300 mL) and dried under vacuum to give 4,5-dibromo-2H-1,2,3-triazole.

Step 2: 4,5-dibromo-1-methyl-1H-1,2,3-triazole

To a mixture of 4,5-dibromo-2H-1,2,3-triazole (704 mmol) and K$_2$CO$_3$ (1.4 mol) in THF (1000 mL), iodomethane (1.0 mol) was added. The mixture was stirred for 12 hours at room temperature. The mixture was filtered, and the filter cake was washed with ethyl acetate (2×500 mL), the filtrate was concentrated under 40° C. to afford a crude product, which was purified by column chromatography to give 4,5-dibromo-1-methyl-1H-1,2,3-triazole.

Step 3: 4-bromo-1-methyl-1H-1,2,3-triazole-5-carbaldehyde

To a solution of 4,5-dibromo-1-methyl-1H-1,2,3-triazole (168.0 mmol) in THF (600 mL) was added isopropylmagnesium chloride (252.0 mmol) at −10° C. The mixture was stirred for 15 min, DMF (840 mmol) was added. After 1 hour, the mixture was treated with 250 mL of saturated ammonium chloride and extracted with DCM (2×350 mL). The combined organics were washed with 250 mL of brine, dried over Na$_2$SO$_4$, filtered and concentrated to give 4-bromo-1-methyl-1H-1,2,3-triazole-5-carbaldehyde.

Step 4: 4-bromo-1-methyl-1H-1,2,3-triazole-5-carboxylic acid

Oxone (651 mmol) was added to a solution of 4-bromo-1-methyl-1H-1,2,3-triazole-5-carbaldehyde (536 mmol) in DMF (800 mL) and the resulting suspension was stirred at room temperature overnight. The mixture reaction was diluted with H$_2$O (1000 mL), was adjusted to pH 3 with 1N HCl, and the aqueous phase was extracted with ethyl acetate (3×800 mL). The combined organics were washed with saturated Na$_2$CO$_3$ (2×500 mL), the aqueous phase was adjusted to pH 3 with 1N HCl. The precipitate was isolated by filtration and dried under reduced pressure to provide 4-bromo-1-methyl-1H-1,2,3-triazole-5-carboxylic acid (Intermediate 1).

Example 2

Preparation of (R)-1-(2-chlorophenyl)ethyl (4-bromo-1-methyl-1H-1,2,3-triazol-5-yl)carbamate (Intermediate 2A)

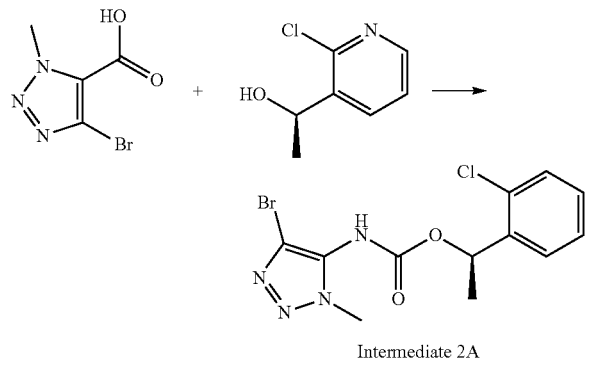

Intermediate 2A

To a suspension of 4-bromo-1-methyl-1H-1,2,3-triazole-5-carboxylic acid (24.3 mmol) in toluene (80 mL) was added DPPA (24.5 mmol), triethylamine (24.5 mmol), and (R)-1-(2-chlorophenyl)ethan-1-ol (36.5 mmol). The mixture was heated at 80° C. for 3 hours. The reaction mixture was filtered, and the filtrate was concentrated in vacuo. The residue was purified by silica chromatography to afford (R)-1-(2-chlorophenyl)ethyl (4-bromo-1-methyl-1H-1,2,3-triazol-5-yl)carbamate (Intermediate 2A).

Example 3

Preparation of (R)-1-(2-chloropyridin-3-yl)ethyl (4-bromo-1-methyl-1H-1,2,3-triazol-5-yl)carbamate (Intermediate 2B)

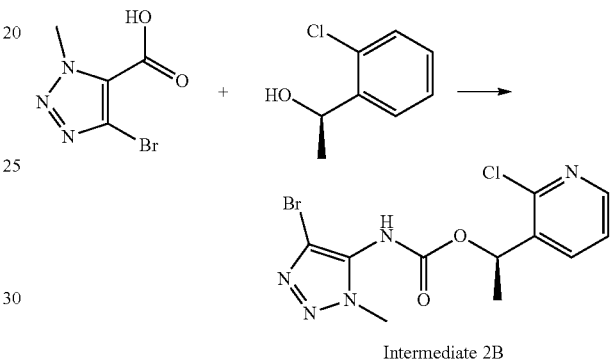

Intermediate 2B

4-Bromo-1-methyl-1H-1,2,3-triazole-5-carboxylic acid (95 mmol), 50% 1-propanephosphonic anhydride solution (143 mmol) in DMF, and azidotrimethylsilane (143 mmol), were suspended in THF (350 mL) under an atmosphere of argon. Triethylamine (143 mmol) was added and the resulting solution was allowed to stir for 30 minutes. (R)-1-(2-chloropyridin-3-yl)ethan-1-ol (143 mmol) was added and the mixture was heated at reflux, with a secondary bubbler attached to allow for venting, for 12 hours. The reaction mixture was cooled to room temperature, and the THF was removed in vacuo. The resulting crude material was dissolved in 500 mL ethyl acetate and extracted three times with 300 mL water. The crude mixture was then dried over sodium sulfate, filtered and the filtrate was concentrated. The crude was purified by silica gel column chromatography to provide (R)-1-(2-chloropyridin-3-yl)ethyl (4-bromo-1-methyl-1H-1,2,3-triazol-5-yl)carbamate (Intermediate 2B).

Example 4

Preparation of (R)-1-(2-fluoropyridin-3-yl)ethyl (4-bromo-1-methyl-1H-1,2,3-triazol-5-yl)carbamate (Intermediate 2C)

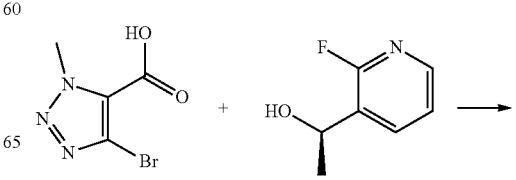

181

-continued

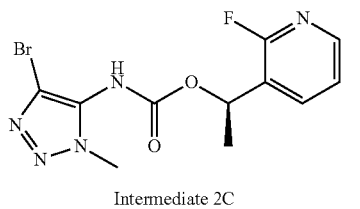

Intermediate 2C

Following the procedure described in Example 3 for the synthesis of (R)-1-(2-chloropyridin-3-yl)ethyl (4-bromo-1-methyl-1H-1,2,3-triazol-5-yl)carbamate (Intermediate 2B), using (R)-1-(2-fluoropyridin-3-yl)ethan-1-ol (143 mmol) in place of (R)-1-(2-chloropyridin-3-yl)ethan-1-ol, (R)-1-(2-fluoropyridin-3-yl)ethyl (4-bromo-1-methyl-1H-1,2,3-triazol-5-yl)carbamate was obtained (Intermediate 2C).

Example 5

Preparation of (R)-1-(3-fluorophenyl)ethyl (4-bromo-1-methyl-1H-1,2,3-triazol-5-yl)carbamate (Intermediate 2D)

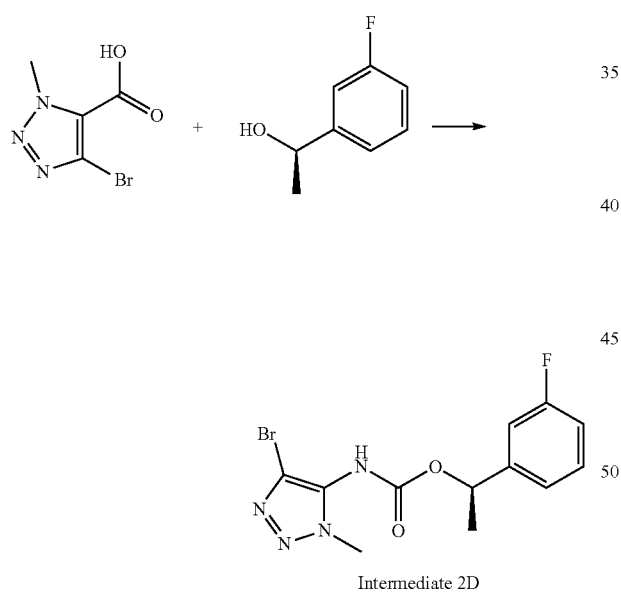

Intermediate 2D

Following the procedure described in Example 3 for the synthesis of (R)-1-(2-chloropyridin-3-yl)ethyl (4-bromo-1-methyl-1H-1,2,3-triazol-5-yl)carbamate (Intermediate 2B), using (R)-1-(3-fluorophenyl) ethan-1-ol (230 mmol) in place of (R)-1-(2-chloropyridin-3-yl)ethan-1-ol, (R)-1-(3-fluorophenyl)ethyl (4-bromo-1-methyl-1H-1,2,3-triazol-5-yl)carbamate was obtained (Intermediate 2D).

182

Example 6

Preparation of methyl 4-(5-aminopyridin-2-yl)-1-methyl-1H-1,2,3-triazole-5-carboxylate (Intermediate 3A)

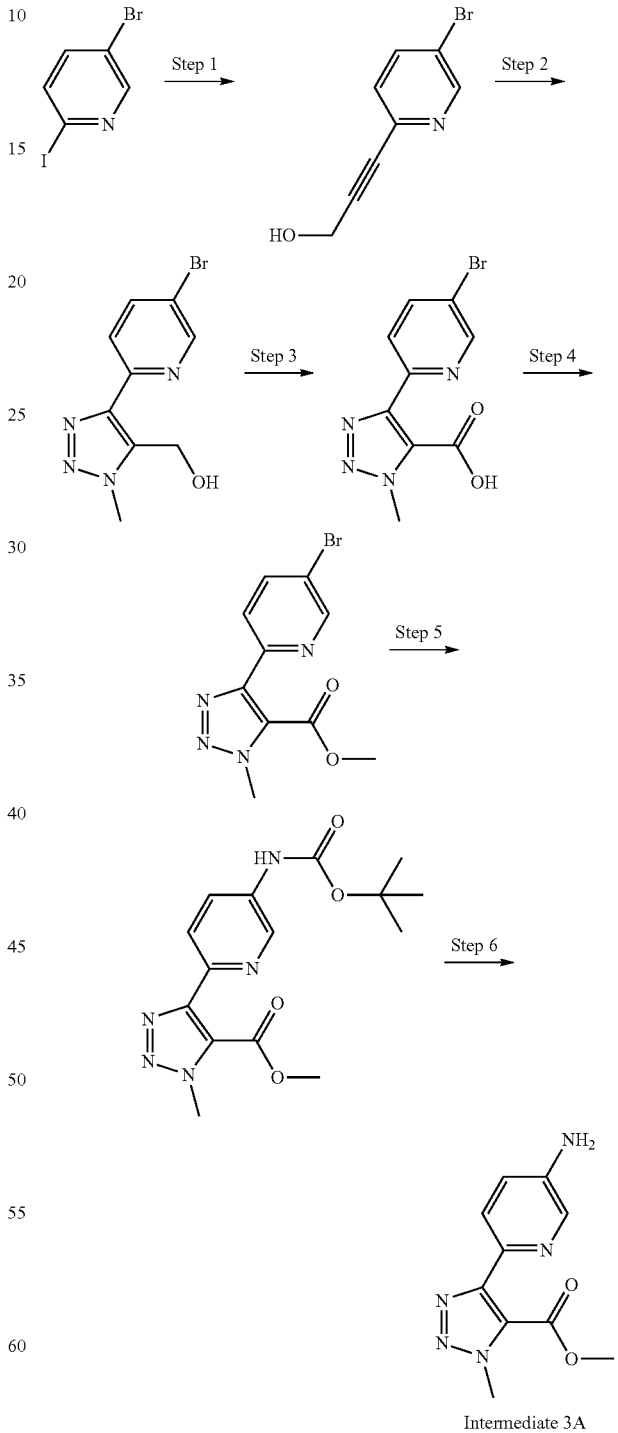

Intermediate 3A

Intermediate 3A was generally prepared according to Scheme D.

Step 1: 3-(5-bromopyridin-2-yl)prop-2-yn-1-ol

To a mixture of 5-bromo-2-iodopyridine (352.2 mmol) in THF (400 mL) was added Compound prop-2-yn-1-ol (370 mmol), triethylamine (1.06 mol), cuprous iodide (17.6 mmol) and bis(triphenylphosphine) palladium(II) chloride (10.6 mmol) under nitrogen atmosphere. The reaction mixture was stirred at room temperature for 16 hours. After completion of the reaction, the mixture was diluted with water (500 ml) and the solid was filtered. The filtrate was extracted with ethyl acetate (3×500 ml). The organic layer was dried over anhydrous sodium sulfate and concentrated under reduced pressure. The residue was triturated with ethyl acetate and ether and stirred for 2 hours and filtered. The filter cake was washed with ether to give 3-(5-bromopyridin-2-yl)prop-2-yn-1-ol.

Step 2: (4-(5-bromopyridin-2-yl)-1-methyl-1H-1,2,3-triazol-5-yl)methanol

Cuprous iodide (0.94 mmol) and tetrabutylammonium iodide (0.94 mmol) were mixed together and dissolved in THF (30 mL), stirred for 20 minutes to yield a solution. Then, 3-(5-bromo-2-pyridyl)prop-2-yn-1-ol (9.43 mmol) was added and the reaction was sparged with argon for 2 minutes. Pentamethylcyclopentadienylbis(triphenylphosphine)ruthenium(II) chloride (0.47 mmol) and azidomethyltrimethylsilane (24 mmol) were added and the reaction was sealed and heated to 80° C. for 16 hours. The reaction mixture was concentrated in vacuo, and then re-dissolved in THF (50 mL). Tetrabutylammonium fluoride (10 mL of a 1 M solution in THF) was added dropwise at room temperature and stirred for 1 hour. The mixture was quenched with saturated solution of sodium bicarbonate (100 mL) and extracted with DCM (3×100 mL). The organic layer was dried over anhydrous sodium sulfate and concentrated under reduced pressure. The residue was purified by silica gel chromatography to provide (4-(5-bromopyridin-2-yl)-1-methyl-1H-1,2,3-triazol-5-yl)methanol.

Step 3: 4-(5-bromopyridin-2-yl)-1-methyl-1H-1,2,3-triazole-5-carboxylic acid

[5-(5-bromo-2-pyridyl)-3-methyl-triazol-4-yl]methanol (4.83 mmol), 2,2,6,6-tetramethylpiperidinyloxy (TEMPO) (0.48 mmol), and sodium phosphate monobasic (12.08 mmol) were suspended in acetonitrile (50 ml) and water (40 ml). The solution was heated to 45° C. Then, 10 ml of a 1 M aqueous solution of sodium chlorite and a separate solution of sodium hypochlorite (10 ml of 0.01 M solution in water), were added simultaneously over 1 hour. The reaction was stirred at 45° C. for 16 hours. The mixture was cooled to room temperature and concentrated to remove acetonitrile. The product was filtered and the filter cake was washed with water (2×50 mL), and diethyl ether (50 mL) to provide 4-(5-bromopyridin-2-yl)-1-methyl-1H-1,2,3-triazole-5-carboxylic acid. LCMS M/Z (M+1)=283.1.

Step 4: methyl 4-(5-bromopyridin-2-yl)-1-methyl-1H-1,2,3-triazole-5-carboxylate 4-(5-bromopyridin-2-yl)-1-methyl-1H-1,2,3-triazole-5-carboxylic acid (14.1 mmol) was dissolved in 40 ml of methanol. The solution was cooled to 0° C. with an ice bath. Trimethylsilyldiazomethane (18.4 mmol) was added dropwise over 15 min. The ice bath was removed and the reaction was stirred for 5 hours. The reaction was quenched by the addition of saturated aqueous sodium bicarbonate and extracted with ethyl acetate. The organic layer was dried over anhydrous sodium sulfate and concentrated under reduced pressure. The residue was purified by silica gel chromatography to provide methyl 4-(5-bromopyridin-2-yl)-1-methyl-1H-1,2,3-triazole-5-carboxylate.

Step 5: Methyl 4-(5-((tert-butoxycarbonyl)amino)pyridin-2-yl)-1-methyl-1H-1,2,3-triazole-5-carboxylate Methyl 4-(5-bromopyridin-2-yl)-1-methyl-1H-1,2,3-triazole-5-carboxylate (11.1 mmol), tert-butyl carbamate (33 mmol), cesium carbonate (33 mmol), and Xantphos Pd G3 pre-catalyst (1.1 mmol) were suspended in dioxane (50 ml). The suspension was sparged with argon for 10 minutes and then heated to 95° C. for 4 hours. After completion of the reaction, the mixture was cooled and diluted with water (100 ml) and extracted with ethyl acetate (2×100 ml). The organic layer was dried over anhydrous sodium sulfate and concentrated under reduced pressure. The residue was purified by silica gel chromatography to provide methyl 4-(5-((tert-butoxycarbonyl)amino)pyridin-2-yl)-1-methyl-1H-1,2,3-triazole-5-carboxylate.

Step 6: Methyl 4-(5-aminopyridin-2-yl)-1-methyl-1H-1,2,3-triazole-5-carboxylate hydrochloride salt (Intermediate 3A)

To methyl 4-(5-((tert-butoxycarbonyl)amino)pyridin-2-yl)-1-methyl-1H-1,2,3-triazole-5-carboxylate (6 mmol), was added 4M HCl in dioxanes (14 mL) and the reaction was stirred vigorously at room temperature for 3 hours. After completion of the reaction, the solution was concentrated in vacuo to provide methyl 4-(5-aminopyridin-2-yl)-1-methyl-1H-1,2,3-triazole-5-carboxylate hydrochloride salt (Intermediate 3A).

Example 7

Preparation of 4-(5-((tert-butoxycarbonyl)amino)pyridin-2-yl)-1-methyl-1H-1,2,3-triazole-5-carboxylic acid (Intermediate 3B)

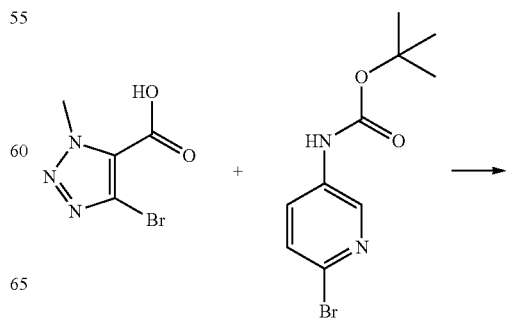

Example 8

Preparation of (R)-1-(3-fluorophenyl)ethyl (1-methyl-4-(4-(2,2,2-trifluoroacetamido)phenyl)-1H-1,2,3-triazol-5-yl)carbamate (Compound 1)

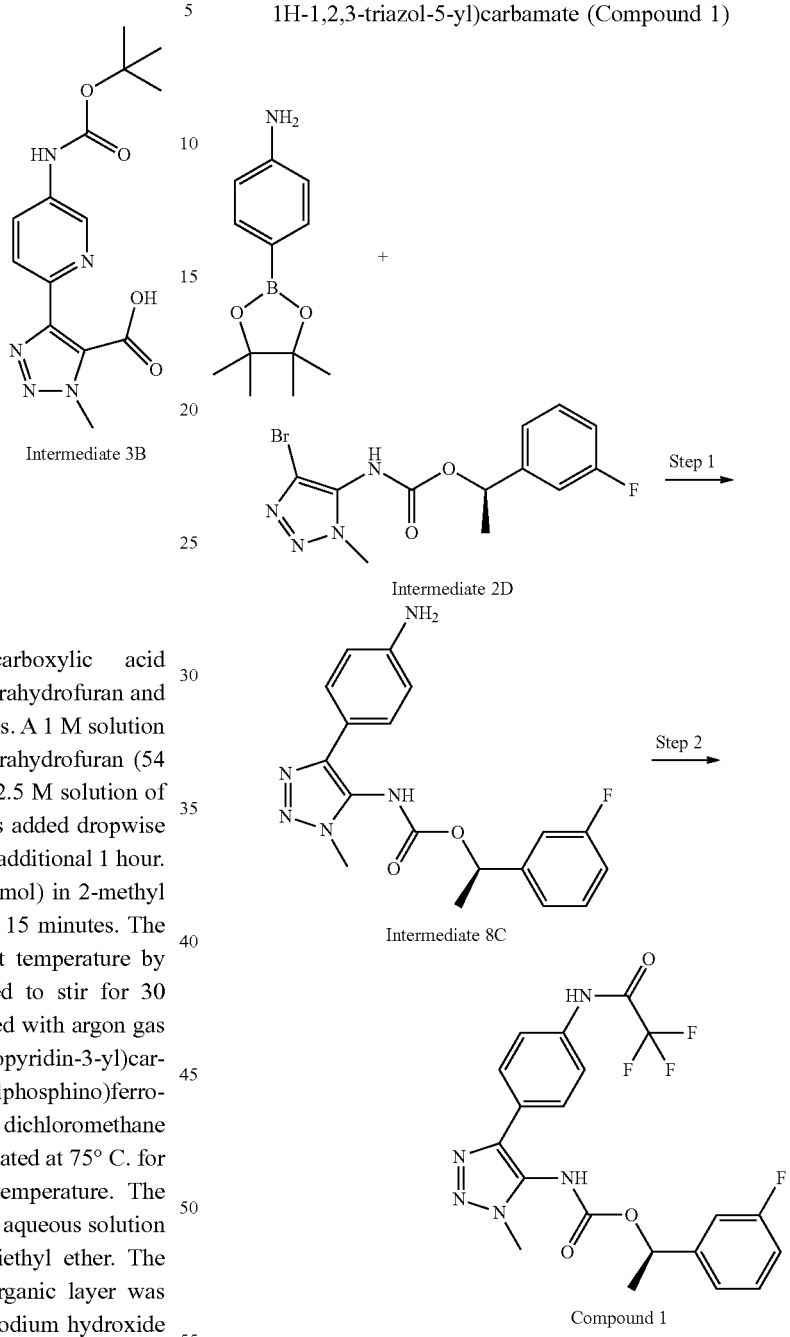

Intermediate 3B 4-bromo-1-methyl-1H-1,2,3-triazole-5-carboxylic acid (50 mmol) was dissolved in 500 mL of tetrahydrofuran and submerged in a −78° C. bath for 15 minutes. A 1 M solution of Lithium bis(trimethylsilyl)amide in tetrahydrofuran (54 mmol) was dropwise over 15 minutes. A 2.5 M solution of n-butyllithium (105 mmol) in hexanes was added dropwise over 20 minutes and allowed to stir for an additional 1 hour. A 1.9 M solution of zinc chloride (105 mmol) in 2-methyl tetrahydrofuran was added dropwise over 15 minutes. The reaction mixture was warmed to ambient temperature by submerging in a water bath and allowed to stir for 30 minutes. The resulting mixture was sparged with argon gas for 10 min, and then tert-butyl (6-bromopyridin-3-yl)carbamate (50 mmol) and [1,1'-Bis(diphenylphosphino)ferrocene]dichloropalladium(II), complex with dichloromethane (5 mmol) were added. The reaction was heated at 75° C. for 3 hours, and then cooled to ambient temperature. The reaction was diluted with 350 mL of a 2 M aqueous solution of sodium hydroxide and 300 mL of diethyl ether. The aqueous layer was separated, and the organic layer was extract with a 1 M aqueous solution of sodium hydroxide (100 mL). The combined aqueous layer was washed with a 1:1 mixture of ethyl acetate and diethyl ether (150 mL×2). 80 mL of concentrated hydrochloric acid was dropwise over 10 min under vigorous stirring to adjust pH to 4. The mixture was filtered, and the filter cake was washed with water (100 mL) and a 1:1 mixture of ethyl acetate and diethyl ether (100 mL×2). The precipitate was dried under reduced pressure to provide 4-(5-((tert-butoxycarbonyl)amino)pyridin-2-yl)-1-methyl-1H-1,2,3-triazole-5-carboxylic acid (Intermediate 3B).

Step 1: (R)-1-(3-fluorophenyl)ethyl (4-(4-aminophenyl)-1-methyl-1H-1,2,3-triazol-5-yl)carbamate A mixture of (R)-1-(3-fluorophenyl)ethyl (4-bromo-1-methyl-1H-1,2,3-triazol-5-yl)carbamate (Intermediate 2D) (0.370 mmol), 4-(4,4,5,5-tetramethyl-1,3,2-dioxaborolan-2-yl)aniline (0.407 mmol), tetrakis(triphenylphosphine)palladium(0) (0.037 mmol) and sodium carbonate (1.11 mmol) in 1,4-dioxane/water (3:1, 3.0 mL) was degassed with argon for 10 minutes. The vessel was sealed and heated at 100° C.

for 18 hours. The reaction was cooled to room temperature, diluted with saturated aqueous NH₄Cl and extracted with dichloromethane. The combined organic layers were washed with brine, dried over MgSO₄, filtered and concentrated under reduced pressure. The crude material was purified by silica gel chromatography to provide (R)-1-(3-fluorophenyl)ethyl (4-(4-aminophenyl)-1-methyl-1H-1,2,3-triazol-5-yl)carbamate (Intermediate 8C).

Step 2: (R)-1-(3-fluorophenyl)ethyl (1-methyl-4-(4-(2,2,2-trifluoroacetamido)phenyl)-1H-1,2,3-triazol-5-yl)carbamate (Compound 1)

To a solution of (R)-1-(3-fluorophenyl)ethyl (4-(4-aminophenyl)-1-methyl-1H-1,2,3-triazol-5-yl)carbamate (Intermediate 8C) (0.082 mmol) in dichloromethane (2.0 mL) was added trifluoroacetic anhydride (0.122 mmol). The solution was stirred at room temperature for 3 hours. The reaction was concentrated under reduced pressure and purified by reverse phase chromatography to provide (R)-1-(3-fluorophenyl)ethyl (1-methyl-4-(4-(2,2,2-trifluoroacetamido)phenyl)-1H-1,2,3-triazol-5-yl)carbamate (Compound 6). (MS (m/z) 452.0 [M+H]⁺). 1H NMR (400 MHz, DMSO-d6, mixture of rotamers) δ 11.36 (s, 1H), 9.97 (major) and 9.55 (minor) (s, 1H), 7.73 (s, 4H), 7.53-6.66 (m, 4H), 5.89-5.60 (m, 1H), 3.85 (s, 3H), 1.56 (major) and 1.24 (minor) (s, 3H).

Example 9

Preparation of [(1R)-1-(2-chloro-3-pyridyl)ethyl] N-[5-[5-[(1-cyanocyclopropanecarbonyl)amino]pyrimidin-2-yl]-3-methyl-triazol-4-yl]carbamate (Compound 2)

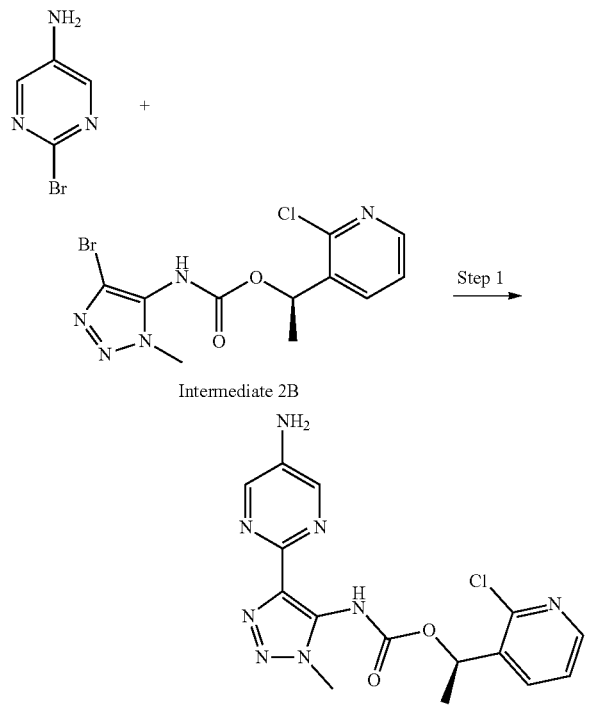

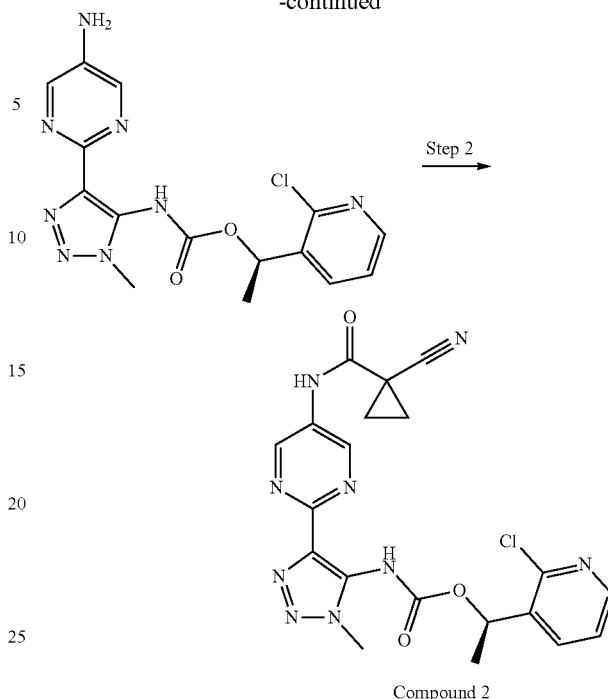

Compound 2

Step 1: [(1R)-1-(2-chloro-3-pyridyl)ethyl] N-[5-(5-aminopyrimidin-2-yl)-3-methyl-triazol-4-yl]carbamate To a mixture of (R)-1-(2-chloropyridin-3-yl)ethyl (4-bromo-1-methyl-1H-1,2,3-triazol-5-yl)carbamate (Intermediate 2B) (1.39 mmol) in tetrahydrofuran (14 mL) at −78° C. was added a 1 M solution of lithium bis(trimethylsilyl)amide (1.53 mmol) in THF. After 10 minutes, a 2.5 M solution of n-butyllithium (2.77 mmol) in hexanes was added. After 45 minutes, a 1.9 M solution of zinc chloride (4.30 mmol) in 2-MeTHF was added, and the reaction was stirred at room temperature for 45 minutes. At this point 2-bromopyrimidin-5-amine (1.94 mmol) and [1,1'-bis(diphenylphosphino)ferrocene]dichloropalladium(II), complex with dichloromethane (0.139 mmol) were added to the reaction and the reaction mixture was heated to 70° C. for 1 hour. After completion of the reaction, the mixture was cooled and quenched with saturated aqueous ammonium chloride. The mixture was diluted with ethyl acetate and organics were separated. The aqueous layer was extracted with ethyl acetate (3×10 mL). The combined organic layers were dried over anhydrous sodium sulfate and concentrated under reduced pressure. The residue was purified by column chromatography to provide [(1R)-1-(2-chloro-3-pyridyl)ethyl] N-[5-(5-aminopyrimidin-2-yl)-3-methyl-triazol-4-yl]carbamate.

Step 2: [(1R)-1-(2-chloro-3-pyridyl)ethyl]N-[5-[5-[(1-cyanocyclopropanecarbonyl)amino]pyrimidin-2-yl]-3-methyl-triazol-4-yl]carbamate (Compound 2)

A mixture of [(1R)-1-(2-chloro-3-pyridyl)ethyl] N-[5-(5-aminopyrimidin-2-yl)-3-methyl-triazol-4-yl]carbamate (0.08 mmol), 1-cyanocyclopropanecarboxylic acid (0.096 mmol), and 1-(3-dimethylaminopropyl)-3-ethylcarbodiimide hydrochloride (0.096 mmol) in pyridine (1.0 mL) was stirred at room temperature for 30 minutes. After completion of the reaction, the mixture was concentrated under reduced pressure. The residue was purified by reverse-phase HPLC to provide [(1R)-1-(2-chloro-3-pyridyl)ethyl] N-[5-[5-[(1-cyanocyclopropanecarbonyl)amino]pyrimidin-2-yl]-3-methyl-triazol-4-yl]carbamate. (MS (m/z) 468.1 [M+H]⁺). $^1$H NMR (400 MHz, Methanol-$d_4$) δ 9.04 (s, 2H), 8.30 (s, 1H), 8.00 (s, 1H), 7.45 (s, 1H), 6.08 (q, J=6.7 Hz, 1H), 3.99 (s, 3H), 1.82-1.75 (m, 2H), 1.73-1.67 (m, 2H), 1.59 (s, 3H).

Example 10

Preparation of Compounds 3 and 4

Compounds 3 and 4 were generally synthesized according Scheme B, Step 1. For example, (R)-1-(2-chloropyridin-3-yl)ethyl (1-methyl-4-(6-(3-methylureido)pyridin-3-yl)-1H-1,2,3-triazol-5-yl)carbamate (Compound 3) was prepared as follows.

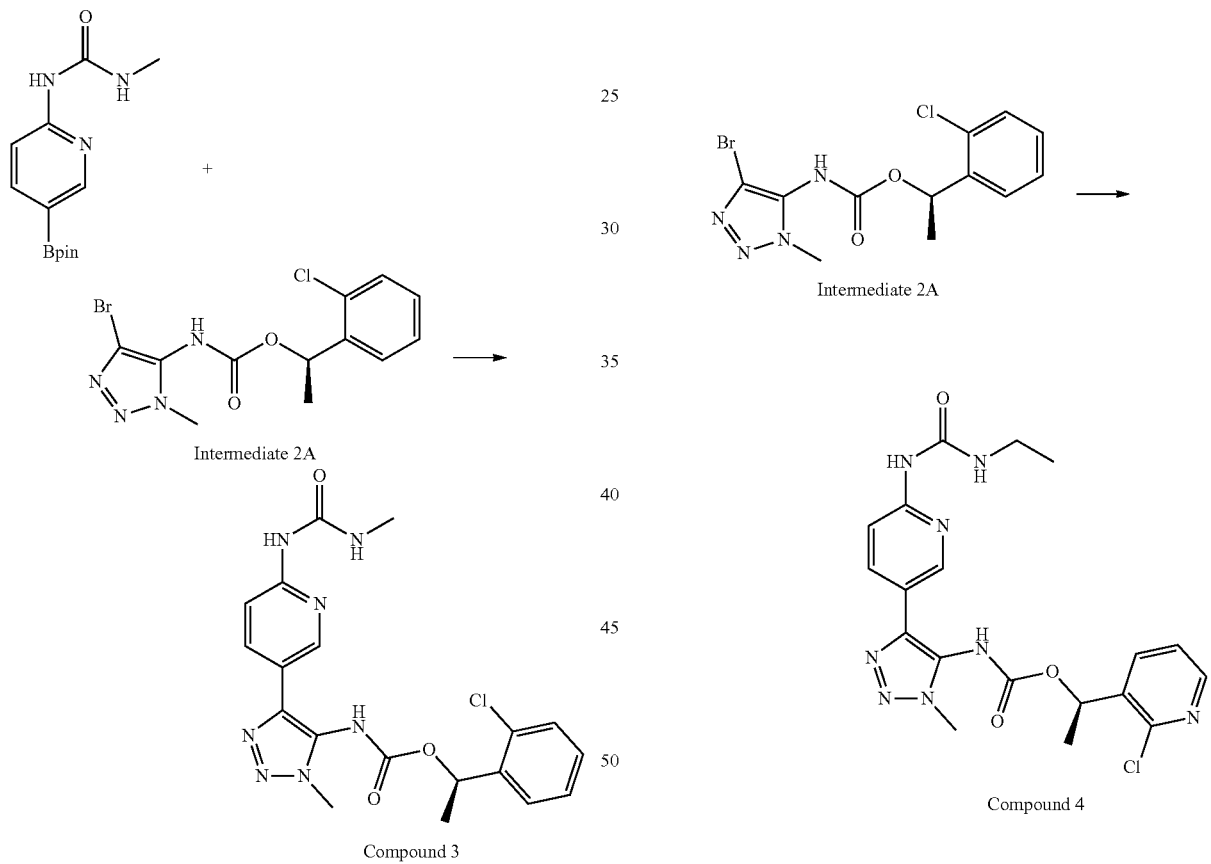

A mixture of 1-methyl-3-(5-(4,4,5,5-tetramethyl-1,3,2-dioxaborolan-2-yl)pyridin-2-yl)urea (1.67 mmol), (R)-1-(2-chlorophenyl)ethyl (4-bromo-1-methyl-1H-1,2,3-triazol-5-yl)carbamate (Intermediate 2A) (0.556 mmol), and sodium carbonate (1.67 mmol) in 3:1 1,4-dioxane/water (7 mL) was heated to 100° C. for 1 hour. The mixture was cooled and diluted with water. The mixture was extracted with ethyl acetate (3×10 mL). The combined organic layers were dried over anhydrous sodium sulfate and concentrated under reduced pressure. The residue was purified by reverse-phase HPLC to provide (R)-1-(2-chloropyridin-3-yl)ethyl (1-methyl-4-(6-(3-methylureido)pyridin-3-yl)-1H-1,2,3-triazol-5-yl)carbamate (Compound 3). (MS (m/z) 432.1 [M+H]⁺). 1H NMR (400 MHz, DMSO-d6) δ 10.05 (bs, 1H), 9.41 (bs, 1H), 8.47 (d, J=2.4 Hz, 1H), 8.40 (bs, 1H), 8.03-7.85 (m, 3H), 7.54 (bs, 1H), 7.42 (d, J=8.7 Hz, 1H), 5.93 (m, 1H), 3.85 (s, 3H), 2.75 (d, J=4.2 Hz, 3H), 1.60 (bs, 3H).

Compound 4 was similarly prepared according to Scheme C, Step 2 by reacting (R)-1-(2-chloropyridin-3-yl)ethyl (4-bromo-1-methyl-1H-1,2,3-triazol-5-yl)carbamate (Intermediate 2B) (Example 3) with 1-ethyl-3-(5-(4,4,5,5-tetramethyl-1,3,2-dioxaborolan-2-yl)pyridin-2-yl)urea following the general process described for Compound 3 to provide (R)-1-(2-chloropyridin-3-yl)ethyl (4-(6-(3-ethylureido)pyridin-3-yl)-1-methyl-1H-1,2,3-triazol-5-yl)carbamate (Compound 4). (MS (m/z) 444.2 [M+H]⁺). 1H NMR (400 MHz, DMSO-d6) δ 10.01 (s, 1H), 9.35 (s, 1H), 8.49 (d, J=2.3 Hz, 1H), 8.09-7.81 (m, 2H), 7.69-7.17 (m, 5H), 6.01 (m, 1H), 3.85 (s, 3H), 3.31-3.09 (m, 2H), 1.57 (bs, 3H), 1.11 (t, J=7.2 Hz, 3H).

Example 11

Preparation of [(1R)-1-(2-chloro-3-pyridyl)ethyl] N-[5-(5-acetamido-6-fluoro-2-pyridyl)-3-methyl-triazol-4-yl]carbamate (Compound 5)

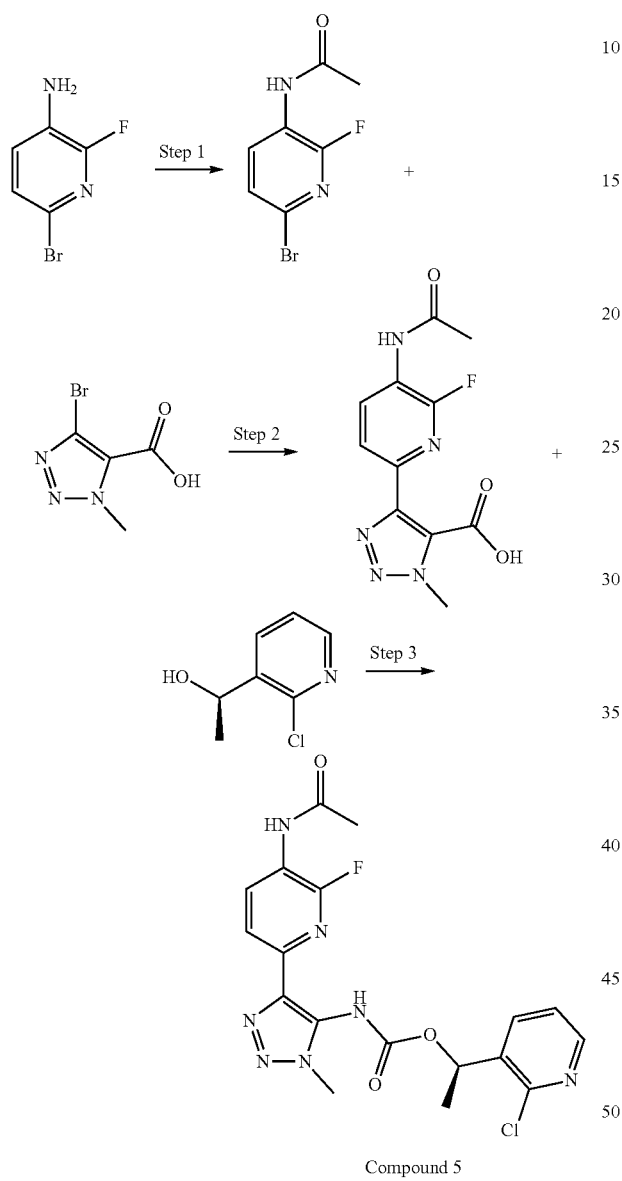

Compound 5

Step 1: N-(6-bromo-2-fluoro-3-pyridyl)acetamide

To a solution 6-bromo-2-fluoro-pyridin-3-amine (5.24 mmol) in dichloromethane (17 mL) was added pyridine (26.2 mmol) followed by acetyl chloride (22.9 mmol). The reaction was stirred overnight. After completion of the reaction, the mixture was diluted with water. The mixture was extracted with ethyl acetate (3×10 mL). The combined organic layers were dried over anhydrous sodium sulfate and concentrated under reduced pressure. The residue was purified by column chromatography to provide N-(6-bromo-2-fluoro-3-pyridyl)acetamide.

Step 2: 5-(5-acetamido-6-fluoro-2-pyridyl)-3-methyl-triazole-4-carboxylic acid A mixture of N-(6-bromo-2-fluoro-3-pyridyl)acetamide (0.485 mmol), 1,1'-Bis(diphenylphosphino)ferrocene-palladium(II)dichloride dichloromethane complex (0.0485 mmol), Bis(pinacolato)diboron (0.728 mmol), and potassium acetate (0.728 mmol) in 1,4-dioxane (5 mL) was heated to 100° C. for 1 hour. At this point, the reaction was cooled to room temperature, and 4-bromo-1-methyl-1H-1, 2,3-triazole-5-carboxylic acid (Intermediate 1) (0.485 mmol), potassium carbonate (0.971 mmol), and water (1.5 mL) were added to the reaction. The reaction was purged with nitrogen and heated to 100° C. for 1 hour. After completion of the reaction, the mixture was cooled and diluted with water. The mixture was extracted with ethyl acetate (3×10 mL). The combined organic layers were dried over anhydrous sodium sulfate and concentrated under reduced pressure. The residue was purified by reverse-phase HPLC to provide 5-(5-acetamido-6-fluoro-2-pyridyl)-3-methyl-triazole-4-carboxylic acid.

Step 3: [(1R)-1-(2-chloro-3-pyridyl)ethyl] N-[5-(5-acetamido-6-fluoro-2-pyridyl)-3-methyl-triazol-4-yl] carbamate (Compound 5)

To a mixture of 5-(5-acetamido-6-fluoro-2-pyridyl)-3-methyl-triazole-4-carboxylic acid (0.372 mmol), 1-propanephosphonic acid cyclic anhydride (50% in DMF, 0.559 mmol), and azidotrimethysilane (0.559 mmol) acid in THF (1.9 mL) was added triethylamine (0.745 mmol) dropwise. (1R)-1-(2-chloro-3-pyridyl)ethanol (0.559 mmol) was added and the flask was heated at 70° C. for 1 hour. After completion of the reaction, the mixture was cooled and diluted with water. The mixture was extracted with ethyl acetate (3×10 mL). The combined organic layers were dried over anhydrous sodium sulfate and concentrated under reduced pressure. The residue was purified by reverse-phase HPLC to provide [(1R)-1-(2-chloro-3-pyridyl)ethyl] N-[5-(5-acetamido-6-fluoro-2-pyridyl)-3-methyl-triazol-4-yl]carbamate (Compound 5). (MS (m/z) 434.1 [M+H]$^+$). $^1$H NMR (400 MHz, Methanol-$d_4$) δ 8.54 (dd, J=9.8, 8.3 Hz, 1H), 8.30 (s, 1H), 8.14 (s, 1H), 7.85 (d, J=8.2 Hz, 1H), 7.45 (s, 1H), 6.09 (q, J=6.4 Hz, 1H), 3.96 (s, 3H), 2.21 (s, 3H), 1.57 (d, J=48.3 Hz, 3H).

Example 12

Preparation of (R)-1-(2-chloropyridin-3-yl)ethyl (4-(4-aminophenyl)-1-methyl-1H-1,2,3-triazol-5-yl) carbamate (Intermediate 8B)

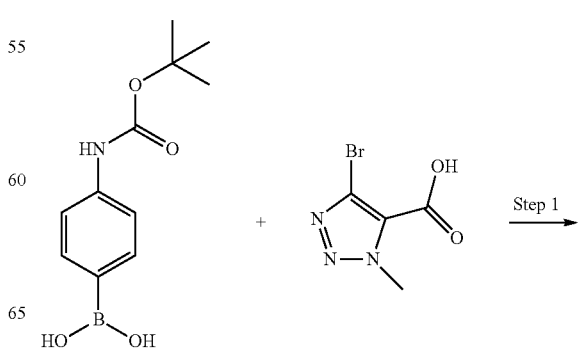

-continued

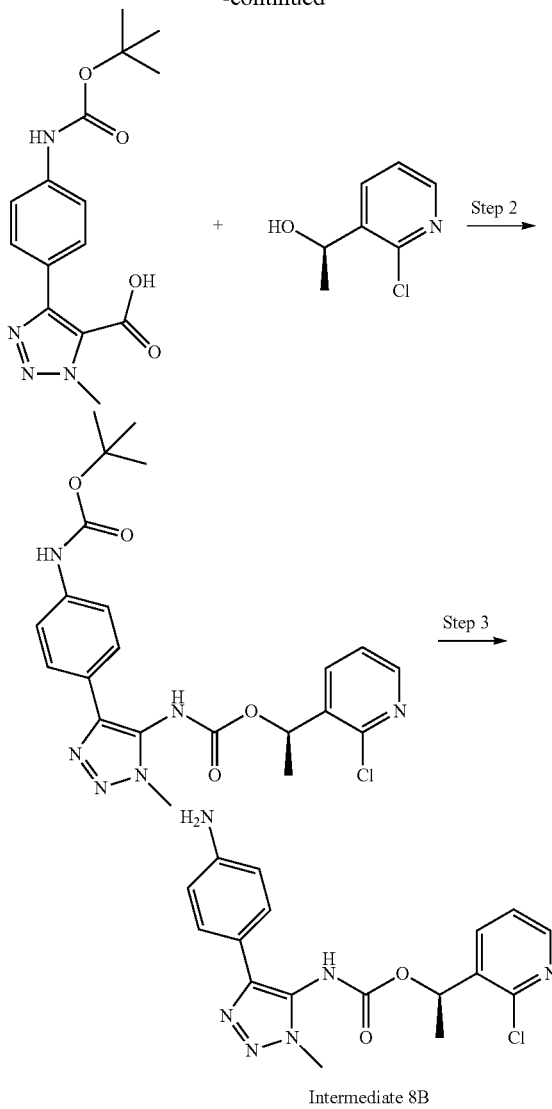

Intermediate 8B

Step 1: 4-(4-(((tert-butoxycarbonyl)amino)phenyl)-1-methyl-1H-1,2,3-triazole-5-carboxylic acid To a mixture of (4-((tert-butoxycarbonyl)amino)phenyl) boronic acid (2.7 mmol) and 4-bromo-1-methyl-1H-1,2,3-triazole-5-carboxylic acid (Intermediate 1) (2.4 mmol) was added potassium carbonate (7.3 mmol), and Pd(PPh$_3$)$_4$ (0.24 mmol). The mixture was suspended in 20 mL of a 10:1 mixture of Dioxane/water and sparged with argon gas for 5 min. The reaction was sealed and heated to 100° C. for 16 hours. The reaction was diluted with aqueous 1 M HCl, and brine, and extracted with ethyl acetate (25 mL×2). The combined organics were dried over sodium sulfate and concentrated. The residue was purified by silica gel column chromatography to provide 4-(4-(((tert-butoxycarbonyl)amino)phenyl)-1-methyl-1H-1,2,3-triazole-5-carboxylic acid.

Step 2: (R)-1-(2-chloropyridin-3-yl)ethyl (4-(4-((tert-butoxycarbonyl)amino)phenyl)-1-methyl-1H-1,2,3-triazol-5-yl)carbamate 4-(4-(((tert-butoxycarbonyl)amino)phenyl)-1-methyl-1H-1,2,3-triazole-5-carboxylic acid (1 mmol), 50% 1-propanephosphonic anhydride solution (1.4 mmol) in DMF, and azidotrimethylsilane (1.4 mmol), were suspended in THF (3 mL). Triethylamine (1.4 mmol) was added and the resulting solution was allowed to stir for 30 min at room temperature. (1R)-1-(2-chloro-3-pyridyl)ethanol (1.4 mmol) was added and the mixture was heated at reflux for 12 hours. The reaction mixture was cooled to room temperature, and the THF was removed in vacuo. The resulting crude material was purified by silica gel column chromatography to provide (R)-1-(2-chloropyridin-3-yl)ethyl (4-(4-(((tert-butoxycarbonyl)amino)phenyl)-1-methyl-1H-1,2,3-triazol-5-yl)carbamate.

Step 3: (R)-1-(2-chloropyridin-3-yl)ethyl (4-(4-aminophenyl)-1-methyl-1H-1,2,3-triazol-5-yl)carbamate (Intermediate 8B)

4M HCl in 1,4-dioxane (1 mL) was added to (R)-1-(2-chloropyridin-3-yl)ethyl (4-(4-(((tert-butoxycarbonyl)amino)phenyl)-1-methyl-1H-1,2,3-triazol-5-yl)carbamate (0.5 mmol). The resulting suspension was stirred for 18 h at room temperature. The reaction was concentrated to afford (R)-1-(2-chloropyridin-3-yl)ethyl (4-(4-aminophenyl)-1-methyl-1H-1,2,3-triazol-5-yl)carbamate (Intermediate 8B) as the hydrochloride salt.

Example 13

Preparation of (R)-1-(2-chloropyridin-3-yl)ethyl (4-(4-acetamidophenyl)-1-methyl-1H-1,2,3-triazol-5-yl)carbamate (Compound 6)

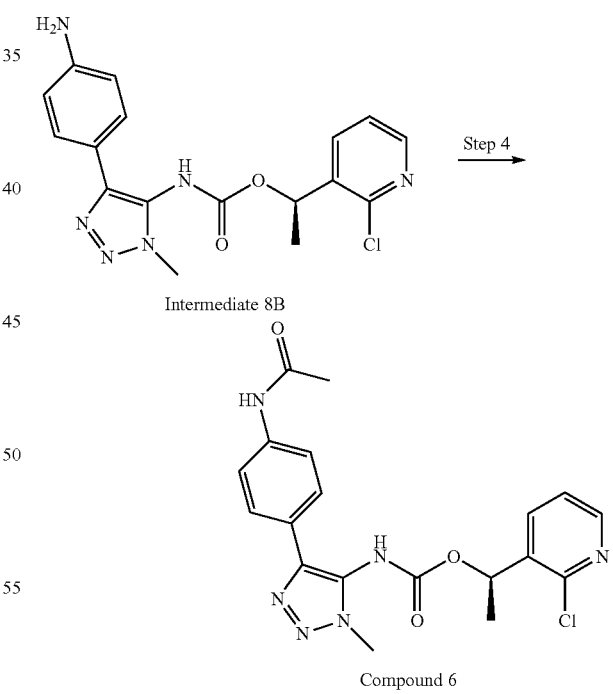

Step 4: (R)-1-(2-chloropyridin-3-yl)ethyl (4-(4-acetamidophenyl)-1-methyl-1H-1,2,3-triazol-5-yl)carbamate (Compound 6)

(R)-1-(2-chloropyridin-3-yl)ethyl (4-(4-aminophenyl)-1-methyl-1H-1,2,3-triazol-5-yl)carbamate (intermediate 8B)

hydrochloride salt (0.08 mmol) was dissolved in dichloromethane (1 mL), pyridine (0.2 mL). Acetyl chloride (0.16 mmol) was added dropwise at room temperature. After 30 min, the reaction was concentrated and dissolved in tetrahydrofuran (2 mL), and 0.5 M aqueous sodium hydroxide solution (2 mL) and stirred vigorously for 10 minutes. The reaction was quenched with sat. ammonium chloride and extracted with ethyl acetate (2×10 mL). The combined organics were dried over sodium sulfate, concentrated, and purified by reverse-phase HPLC to provide (R)-1-(2-chloropyridin-3-yl)ethyl (4-(4-acetamidophenyl)-1-methyl-1H-1,2,3-triazol-5-yl)carbamate (Compound 6). (MS (m/z) 415.08 [M+H]$^+$). $^1$H NMR (400 MHz, Methanol-d4) δ 8.36 (s, 1H), 8.06 (s, 1H), 7.65 (s, 4H), 7.56-6.99 (m, 1H), 6.11 (s, 1H), 3.95 (s, 3H), 2.17 (s, 3H), 1.82-1.19 (m, 3H).

Example 14

Preparation of (R)-1-(2-chloropyridin-3-yl)ethyl (4-(4-((methoxycarbonyl)amino)phenyl)-1-methyl-1H-1,2,3-triazol-5-yl)carbamate (Compound 7)

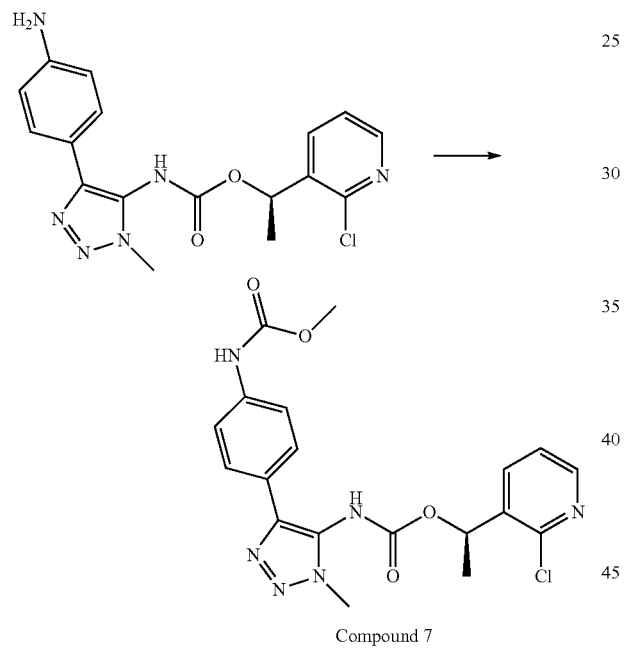

Compound 7

(R)-1-(2-chloropyridin-3-yl)ethyl (4-(4-aminophenyl)-1-methyl-1H-1,2,3-triazol-5-yl)carbamate (Intermediate 8B) hydrochloride salt (0.08 mmol) was dissolved in dichloromethane (1 mL), pyridine (0.2 mL). Methyl chloroformate chloride (0.16 mmol) was added dropwise at room temperature. After 30 minutes, the reaction was concentrated and dissolved in tetrahydrofuran (2 mL), and 0.5 M aqueous sodium hydroxide solution (2 mL) and stirred vigorously for 10 minutes. The reaction was quenched with sat. ammonium chloride, and extracted with ethyl acetate (2×10 mL). The combined organics were dried over sodium sulfate, concentrated, and purified by reverse-phase HPLC to provide (R)-1-(2-chloropyridin-3-yl)ethyl (4-(4-((methoxycarbonyl)amino)phenyl)-1-methyl-1H-1,2,3-triazol-5-yl)carbamate (Compound 7). (MS (m/z) 431.1 [M+H]$^+$). $^1$H NMR (400 MHz, Methanol-d4) δ 8.60-8.13 (m, 1H), 8.06 (s, 1H), 7.77-7.10 (m, 5H), 6.23-5.90 (m, 1H), 3.96 (s, 3H), 3.78 (s, 3H), 1.80-1.38 (m, 3H).

Example 15

Preparation of (S)-2-fluoro-1-phenylethyl (4-(5-aminopyridin-2-yl)-1-methyl-1H-1,2,3-triazol-5-yl) carbamate (Intermediate 8D)

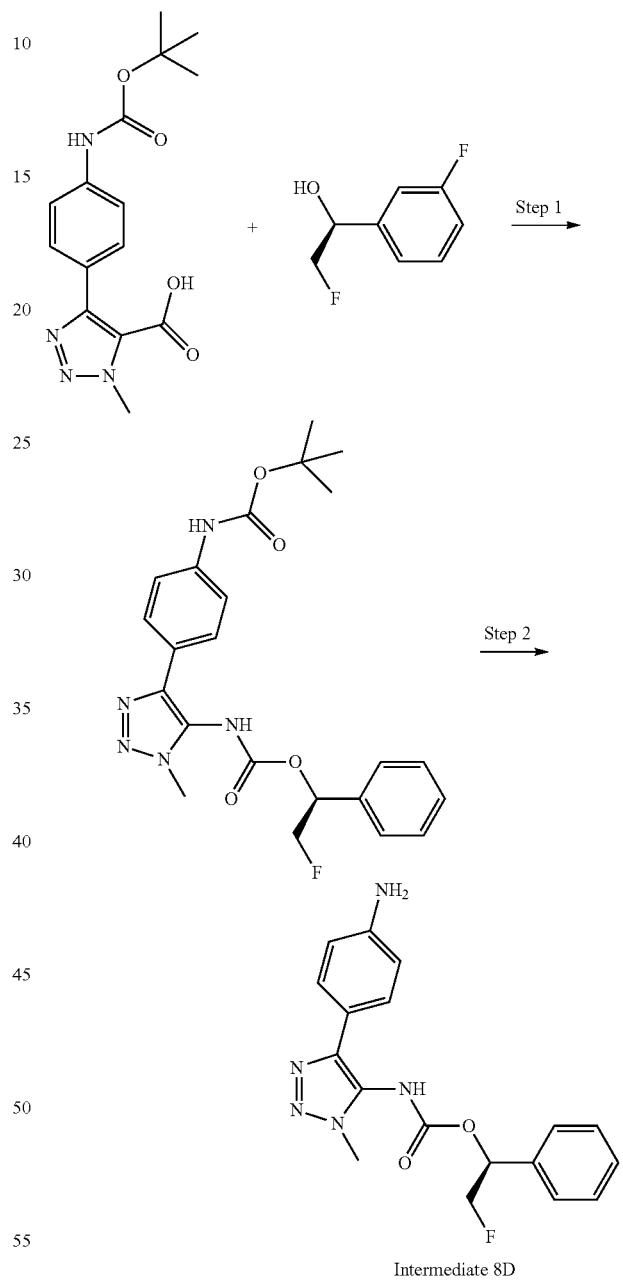

Intermediate 8D

Step 1: tert-butyl (S)-(6-(5-(((2-fluoro-1-phenylethoxy)carbonyl)amino)-1-methyl-1H-1,2,3-triazol-4-yl)pyridin-3-yl)carbamate Following the procedure described in Example 12 for the preparation of (R)-1-(2-chloropyridin-3-yl)ethyl (4-(4-((tert-butoxycarbonyl)amino)phenyl)-1-methyl-1H-1,2,3-triazol-5-yl)carbamate, using (S)-2-fluoro-1-(3-fluorophenyl)ethan-1-ol (0.73 mmol), in place of (R)-1-(2-chloropyridin-3-yl)ethan-1-ol, tert-butyl (S)-(6-(5-(((2-fluoro-1-phenylethoxy)carbonyl)amino)-1-methyl-1H-1,2,3-triazol-4-yl)pyridin-3-yl)carbamate was obtained.

Step 2: (S)-2-fluoro-1-phenylethyl (4-(5-aminopyridin-2-yl)-1-methyl-1H-1,2,3-triazol-5-yl)carbamate (Intermediate 8D)

4M HCl in 1,4-dioxane (1 mL) was added to tert-butyl (S)-(6-(5-(((2-fluoro-1-phenylethoxy)carbonyl)amino)-1-methyl-1H-1,2,3-triazol-4-yl)pyridin-3-yl)carbamate (0.34 mmol). The resulting suspension was stirred for 3 h at room temperature. The reaction was concentrated to afford (S)-2-fluoro-1-phenylethyl (4-(4-aminophenyl)-1-methyl-1H-1,2,3-triazol-5-yl)carbamate (Intermediate 8D) as the hydrochloride salt.

Example 16

Preparation of (R)-1-(2-chloropyridin-3-yl)ethyl (4-(5-(1-cyanocyclopropane-1-carboxamido)pyrazin-2-yl)-1-methyl-1H-1,2,3-triazol-5-yl)carbamate (Compound 8)

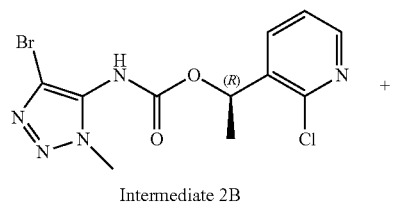

Intermediate 2B

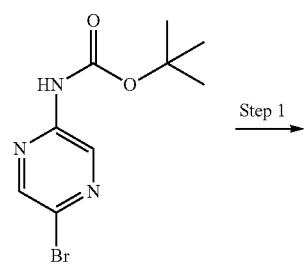

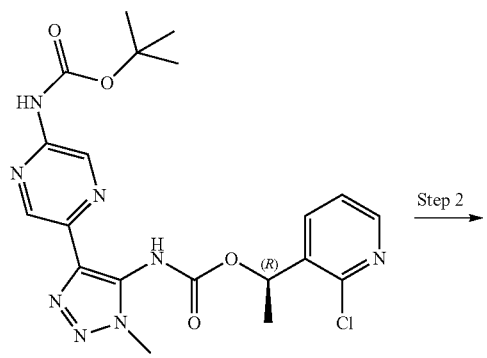

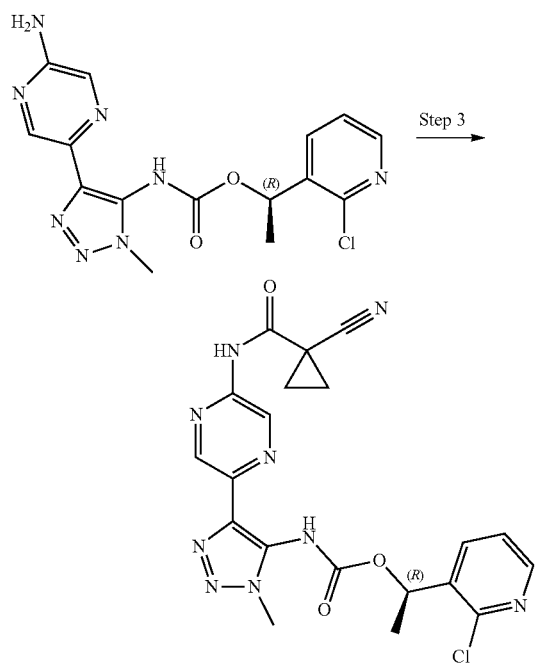

Compound 8

Step 1: (R)-1-(2-chloropyridin-3-yl)ethyl (4-(5-((tert-butoxycarbonyl)amino)pyrazin-2-yl)-1-methyl-1H-1,2,3-triazol-5-yl)carbamate To a solution of (R)-1-(2-chloropyridin-3-yl)ethyl (4-bromo-1-methyl-1H-1,2,3-triazol-5-yl)carbamate (Intermediate 2B) (0.42 mmol) in 3 mL THF at −78° C. was added a 1 N solution of lithium bis(trimethylsilyl)amide in THF (0.50 mmol, 1 M) dropwise. After 15 minutes a 1.6 M solution of n-butyllithium (nBuLi) in hexanes (0.83 mmol) was added dropwise. After 15 minutes a 1.9M solution of zinc chloride (ZnCl$_2$) in THF (1.0 mmol) was added dropwise, and the reaction warmed to room temperature over 20 minutes. A solution of tert-butyl (5-bromopyrazin-2-yl)carbamate (Br-pyrazine) (0.50 mmol) and (2-Dicyclohexylphosphino-2',4',6'-triisopropyl-1,1'-biphenyl)[2-(2'-amino-1,1'-biphenyl)]palladium(II) methanesulfonate (XPhos Pd G3) (0.042 mmol) in THF was added, and the reaction heated to 70° C. for 2 hours. The reaction was then cooled to room temperature and quenched with saturated aqueous NH$_4$Cl and extracted with EtOAc. The combined organic layers were dried over Na$_2$SO$_4$ and concentrated. Purified by silica gel chromatography (0-20% DCM/MeOH) to provide (R)-1-(2-chloropyridin-3-yl)ethyl (4-(5-((tert-butoxycarbonyl)amino)pyrazin-2-yl)-1-methyl-1H-1,2,3-triazol-5-yl)carbamate.

Step 2: (R)-1-(2-chloropyridin-3-yl)ethyl (4-(5-aminopyrazin-2-yl)-1-methyl-1H-1,2,3-triazol-5-yl)carbamate A solution of (R)-1-(2-chloropyridin-3-yl)ethyl (4-(5-((tert-butoxycarbonyl)amino)pyrazin-2-yl)-1-methyl-1H-1,2,3-triazol-5-yl)carbamate (0.126 mmol) in 4N HCl in dioxane was stirred at room temperature for 1 hour. Reaction was concentrated and placed under vacuum overnight, providing (R)-1-(2-chloropyridin-3-yl)ethyl (4-(5-aminopyrazin-2-yl)-1-methyl-1H-1,2,3-triazol-5-yl)carbamate.

Step 3: (R)-1-(2-chloropyridin-3-yl)ethyl (4-(5-(1-cyanocyclopropane-1-carboxamido)pyrazin-2-yl)-1-methyl-1H-1,2,3-triazol-5-yl)carbamate (Compound 8)

A solution of (R)-1-(2-chloropyridin-3-yl)ethyl (4-(5-aminopyrazin-2-yl)-1-methyl-1H-1,2,3-triazol-5-yl)carbamate (0.0729 mmol) in 0.2 mL DMF was treated with pyridine (0.729 mmol), 1-cyanocyclopropane-1-carboxylic acid (0.114 mmol) and EDC (0.0875 mmol) and stirred at room temperature for 3 hours. Diluted with aq. MeCN and purified by RP HPLC to provide (R)-1-(2-chloropyridin-3-yl)ethyl (4-(5-(1-cyanocyclopropane-1-carboxamido)pyrazin-2-yl)-1-methyl-1H-1,2,3-triazol-5-yl)carbamate (Compound 27). (MS (m/z) 467.9[M+H]+). 1H NMR (400 MHz, Methanol-d4) d 9.01 (s, 1H), 8.84 (s, 1H), 8.51-7.91 (m, 2H), 7.46 (s, 1H), 6.30-5.74 (m, 1H), 3.97 (s, 3H), 1.84-1.38 (m, 7H).

Example 17

Preparation of (R)-1-(2-chloropyridin-3-yl)ethyl (4-(5-acetamido-3-fluoropyridin-2-yl)-1-methyl-1H-1,2,3-triazol-5-yl)carbamate (Compound 9)

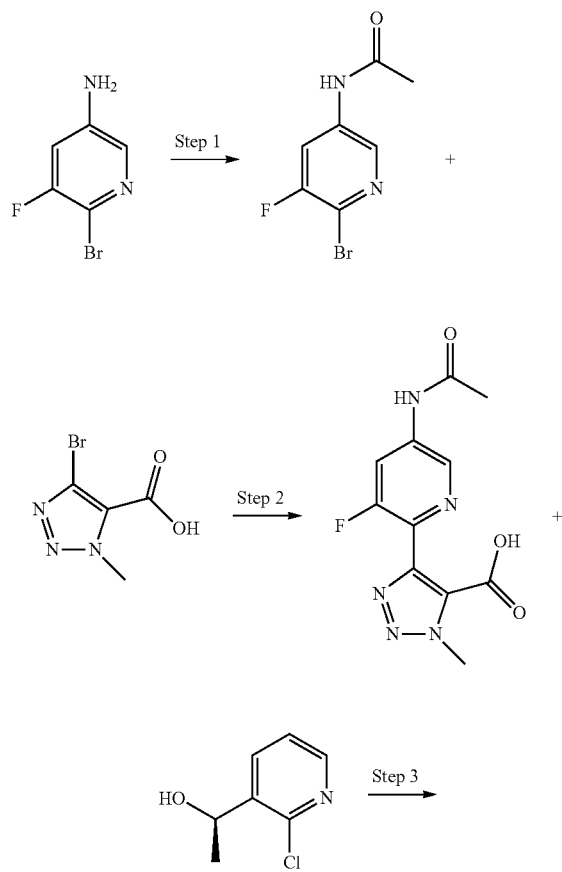

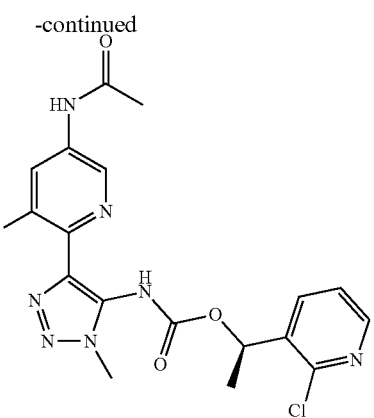

Compound 9

Step 1: N-(6-bromo-5-fluoro-3-pyridyl)acetamide

To a solution 6-bromo-5-fluoro-pyridin-3-amine (5.24 mmol) in dichloromethane (17 mL) was added pyridine (26.2 mmol) followed by acetyl chloride (22.9 mmol). The reaction was stirred overnight. After completion of the reaction, the mixture was diluted with water. The mixture was extracted with ethyl acetate (3×10 mL). The combined organic layers were dried over anhydrous sodium sulfate and concentrated under reduced pressure. The residue was purified by column chromatography to provide 6-bromo-5-fluoro-pyridin-3-amine.

Step 2: 4-(5-acetamido-3-fluoropyridin-2-yl)-1-methyl-1H-1,2,3-triazole-5-carboxylic acid To a mixture of 4-bromo-1-methyl-1H-1,2,3-triazole-5-carboxylic acid (Intermediate 1) (1.3 mmol) in tetrahydrofuran (20 mL) at −78° C. was added a 1 M solution of lithium bis(trimethylsilyl)amide (1.3 mmol) in THF. After 10 minutes, a 2.5 M solution of n-butyllithium (2.5 mmol) in Hexanes was added. After 45 minutes, a 1.9 M solution of zinc chloride (2.5 mmol) in 2-MeTHF was added, and the reaction was warmed to room temperature and stirred for 30 minutes. The reaction mixture was sparged with argon gas for 5 minutes, and then N-(6-bromo-5-fluoro-3-pyridyl)acetamide (0.84 mmol) and [1,1′-bis(diphenylphosphino)ferrocene]dichloropalladium(II), dichloromethane complex (0.08 mmol) were added. The reaction was heated at 70° C. for 2 hours, after which the reaction was cooled and diluted with 1 M aqueous hydrogen chloride solution (20 mL). The reaction mixture was extracted with ethyl acetate (30 mL×3). The combined organic layer was dried over sodium sulfate and concentrated to provide 4-(5-acetamido-3-fluoropyridin-2-yl)-1-methyl-1H-1,2,3-triazole-5-carboxylic acid which was used in the next step without further purification.

Step 3: (R)-1-(2-chloropyridin-3-yl)ethyl (4-(5-acetamido-3-fluoropyridin-2-yl)-1-methyl-1H-1,2,3-triazol-5-yl)carbamate (Compound 9)

(R)-1-(2-chloropyridin-3-yl)ethyl (4-(5-acetamido-3-fluoropyridin-2-yl)-1-methyl-1H-1,2,3-triazol-5-yl)carbamate (0.14 mmol), 50% 1-propanephosphonic anhydride solution (0.29 mmol) in DMF, and azidotrimethylsilane (0.29 mmol), were suspended in THF (2 mL). Triethylamine (0.43 mmol) was added and the resulting solution was allowed to stir for 30 minutes at room temperature. (1R)-1-(2-chloro-3-pyridyl)ethanol (0.29 mmol) was added and the mixture was heated at reflux for 4 hours. The reaction mixture was cooled to room temperature, and the THF was removed in vacuo. The resulting crude material was purified by reverse phase HPLC to provide (R)-1-(2-chloropyridin-3-yl)ethyl (4-(5-acetamido-3-fluoropyridin-2-yl)-1-methyl-1H-1,2,3-triazol-5-yl)carbamate (Compound 29). (MS (m/z) 434.0 [M+H]$^+$). $^1$H NMR (400 MHz, Methanol-d$_4$) δ 8.52 (s, 1H), 8.33 (s, 1H), 8.19-7.76 (m, 2H), 7.48 (s, 1H), 6.20-5.90 (m, 1H), 4.01 (s, 3H), 2.21 (s, 3H), 1.60 (s, 3H).

Example 18

Preparation of (R)-1-(2-chloropyridin-3-yl)ethyl (4-(5-amino-4-fluoropyridin-2-yl)-1-methyl-1H-1,2,3-triazol-5-yl)carbamate (Intermediate 7B)

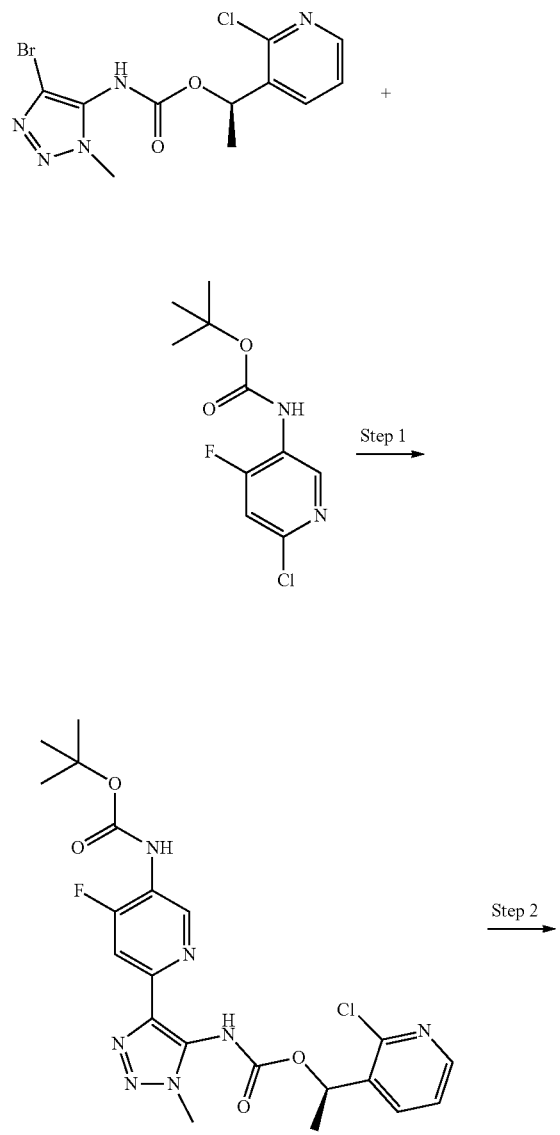

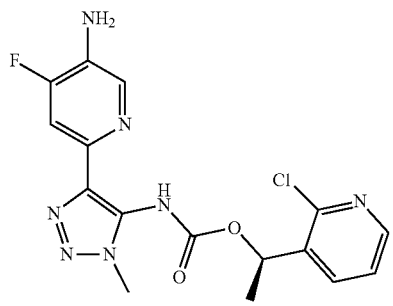

Intermedaite 7B

Step 1: (R)-1-(2-chloropyridin-3-yl)ethyl (4-(5-((tert-butoxycarbonyl)amino)-4-fluoropyridin-2-yl)-1-methyl-1H-1,2,3-triazol-5-yl)carbamate To a mixture of (R)-1-(2-chloropyridin-3-yl)ethyl (4-bromo-1-methyl-1H-1,2,3-triazol-5-yl)carbamate, (R)-1-(2-chlorophenyl)ethyl (4-bromo-1-methyl-1H-1,2,3-triazol-5-yl)carbamate (Intermediate 2A) (1 mmol) in tetrahydrofuran (15 mL) at −78° C. was added a 1 M solution of lithium bis(trimethylsilyl)amide (1.2 mmol) in tetrahydrofuran. After 10 minutes, a 2.5 M solution of n-butyllithium (2.5 mmol) in hexanes was added. After 45 minutes, a 1.9 M solution of zinc chloride (2.5 mmol) in 2-methyl tetrahydrofuran was added, and the reaction was warmed to and stirred at room temperature for 30 minutes. The reaction mixture was sparged with argon gas for 5 minutes, and then added tert-butyl (6-chloro-4-fluoropyridin-3-yl)carbamate (1.2 mmol) and [1,1'-bis(diphenylphosphino)ferrocene]dichloropalladium(II), dichloromethane complex (0.1 mmol). The reaction mixture was heated to 70° C. for 1 hour. After completion of the reaction, the mixture was cooled and quenched with 1 N aqueous hydrochloric acid (20 mL). The aqueous layer was extracted with ethyl acetate (3×10 mL). The combined organic layers were dried over anhydrous sodium sulfate and concentrated under reduced pressure to provide (R)-1-(2-chloropyridin-3-yl)ethyl (4-(5-((tert-butoxycarbonyl)amino)-4-fluoropyridin-2-yl)-1-methyl-1H-1,2,3-triazol-5-yl)carbamate which was used in the next step without further purification.

Step 2: (R)-1-(2-chloropyridin-3-yl)ethyl (4-(5-amino-4-fluoropyridin-2-yl)-1-methyl-1H-1,2,3-triazol-5-yl)carbamate (Intermediate 7B)

4 M HCl in 1,4-dioxane (1 mL) was added to (R)-1-(2-chloropyridin-3-yl)ethyl (4-(5-((tert-butoxycarbonyl)amino)-4-fluoropyridin-2-yl)-1-methyl-1H-1,2,3-triazol-5-yl)carbamate (0.49 mmol). The resulting suspension was stirred for 4 hours at room temperature. The reaction was concentrated to afford (R)-1-(2-chloropyridin-3-yl)ethyl (4-(5-amino-4-fluoropyridin-2-yl)-1-methyl-1H-1,2,3-triazol-5-yl)carbamate (Intermediate 7B) as the hydrochloride salt.

Example 19

Preparation of (R)-1-(2-chloropyridin-3-yl)ethyl (4-(5-acetamido-4-fluoropyridin-2-yl)-1-methyl-1H-1,2,3-triazol-5-yl)carbamate (Compound 10)

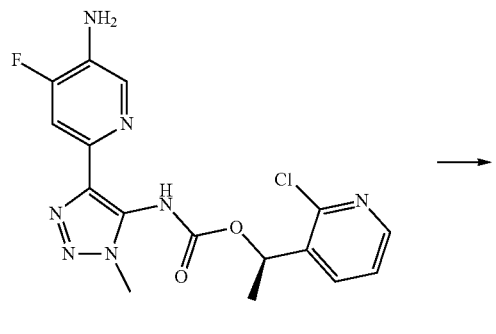

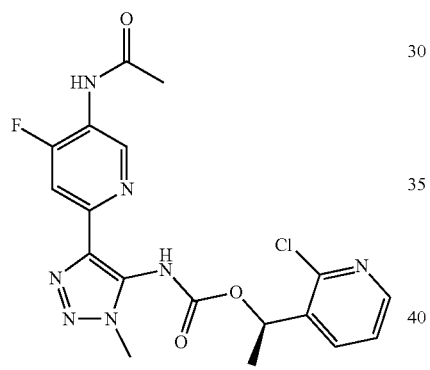

Compound 10

The hydrochloride salt of (R)-1-(2-chloropyridin-3-yl)ethyl (4-(5-amino-4-fluoropyridin-2-yl)-1-methyl-1H-1,2,3-triazol-5-yl)carbamate (Intermediate 7B) (0.05 mmol) was dissolved in dichloromethane (1 mL) and pyridine (0.2 mL). Acetyl chloride (0.1 mmol) was added dropwise at room temperature. After 30 minutes, the reaction was concentrated and dissolved in tetrahydrofuran (2 mL), and 1 M aqueous sodium hydroxide solution (2 mL) and stirred vigorously for 10 minutes. The reaction was quenched with sat. ammonium chloride and extracted with ethyl acetate (2×10 mL). The combined organics were dried over sodium sulfate, concentrated, and purified by reverse-phase HPLC to provide (R)-1-(2-chloropyridin-3-yl)ethyl (4-(5-acetamido-4-fluoropyridin-2-yl)-1-methyl-1H-1,2,3-triazol-5-yl)carbamate. (Compound 30) (MS (m/z) 434.0 [M+H]$^+$). $^1$H NMR (400 MHz, Methanol-d$_4$) δ 9.17 (d, J=9.8 Hz, 1H), 8.32 (d, J=4.4 Hz, 1H), 8.09 (s, 1H), 7.79 (d, J=11.5 Hz, 1H), 7.48 (s, 1H), 6.18-6.00 (m, 1H), 3.99 (s, 3H), 2.24 (s, 3H), 1.62 (s, 3H).

Example 20

Preparation of (R)-1-(2-chloropyridin-3-yl)ethyl(4-(5-((tert-butoxycarbonyl)amino)pyridin-2-yl)-1-methyl-1H-1,2,3-triazol-5-yl)carbamate (Compound 11)

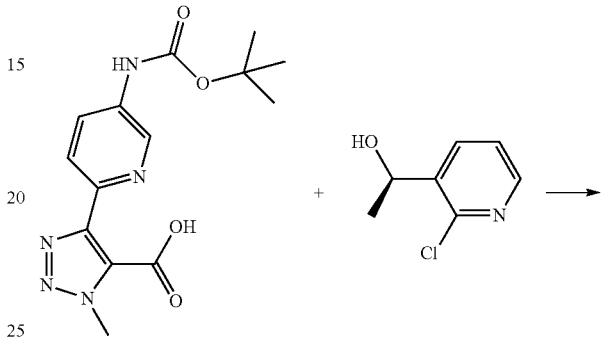

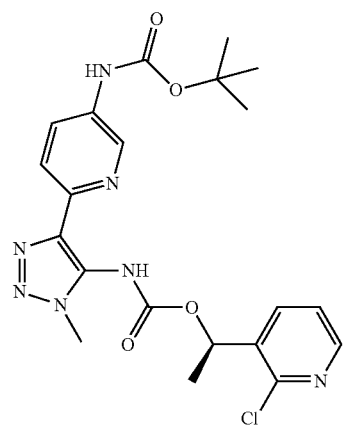

Compound 11

To a mixture of 4-(5-((tert-butoxycarbonyl)amino)pyridin-2-yl)-1-methyl-1H-1,2,3-triazole-5-carboxylic acid (9.4 mmol), 1-propanephosphonic acid cyclic anhydride (50% in THF, 14.1 mmol), and azidotrimethysilane (14.1 mmol) acid in THF (100 mL) was added triethylamine (23.5 mmol) dropwise. The reaction mixture was heated at 70° C. for 1 hour followed by addition of (R)-1-(2-chloropyridin-3-yl) ethan-1-ol (18.8 mmol) at the same temperature. After heating for 24 hours, the reaction was cooled to room temperature, concentrated and purified by silica gel chromatography to provide (R)-1-(2-chloropyridin-3-yl)ethyl (4-(5-((tert-butoxycarbonyl)amino)pyridin-2-yl)-1-methyl-1H-1,2,3-triazol-5-yl)carbamate. (Compound 11) (MS (m/z) 474.12 [M+H]$^+$). $^1$H NMR (400 MHz, Methanol-d4) δ 8.67 (s, 1H), 8.31 (s, 1H), 8.08 (s, 1H), 7.94 (dd, J=8.7, 2.6 Hz, 1H), 7.84 (dd, J=8.6, 0.8 Hz, 1H), 7.47 (s, 1H), 6.07 (d, J=6.7 Hz, 1H), 3.98 (s, 3H), 1.75-1.46 (m, 12H).

Example 21

Preparation of (R)-1-(2-chloropyridin-3-yl)ethyl (4-(5-aminopyridin-2-yl)-1-methyl-1H-1,2,3-triazol-5-yl)carbamate (Intermediate 5A)

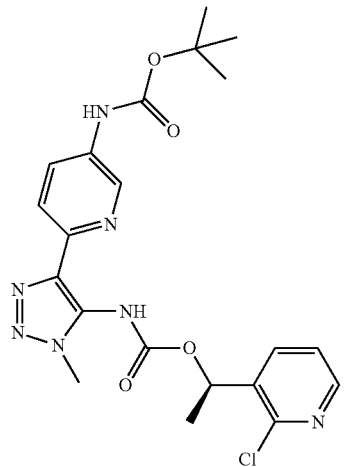

Intermediate 5A

Example 22

Preparation of (R)-1-(2,5-difluoropyridin-3-yl)ethyl (4-(5-aminopyridin-2-yl)-1-methyl-1H-1,2,3-triazol-5-yl)carbamate (Intermediate 5B)

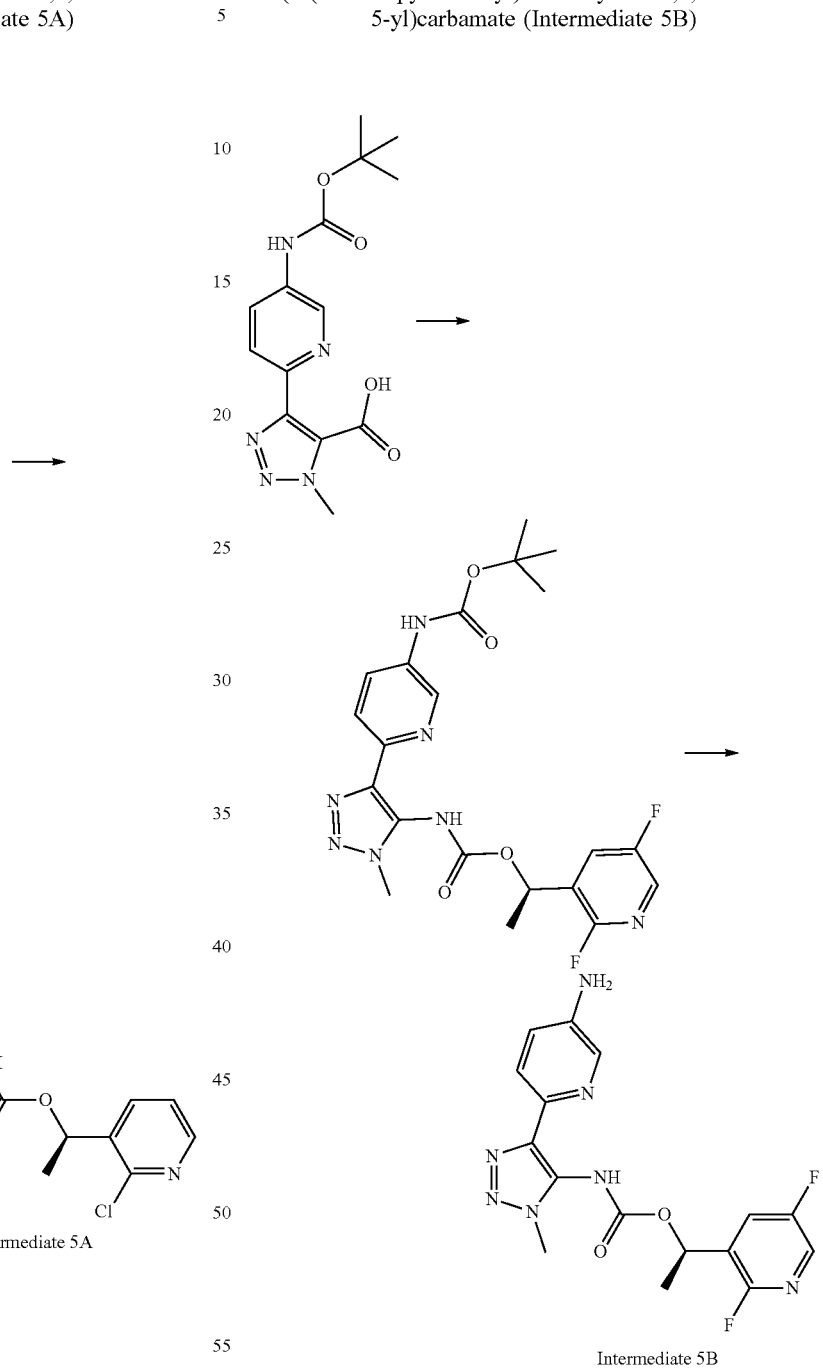

Intermediate 5B

4 M HCl in 1,4-dioxane (20 mL) was added to (R)-1-(2-chloropyridin-3-yl)ethyl (4-(5-((tert-butoxycarbonyl)amino)pyridin-2-yl)-1-methyl-1H-1,2,3-triazol-5-yl)carbamate (6.9 mmol). The resulting suspension was stirred for 18 hours at room temperature. The reaction was concentrated to afford (R)-1-(2-chloropyridin-3-yl)ethyl (4-(5-aminopyridin-2-yl)-1-methyl-1H-1,2,3-triazol-5-yl)carbamate (Intermediate 5A) as the hydrochloride salt.

Step 1: tert-butyl (R)-(6-(5-(((1-(2,5-difluoropyridin-3-yl)ethoxy)carbonyl)amino)-1-methyl-1H-1,2,3-triazol-4-yl)pyridin-3-yl)carbamate To a mixture of 4-(5-((tert-butoxycarbonyl)amino)pyridin-2-yl)-1-methyl-1H-1,2,3-triazole-5-carboxylic acid (10.6 mmol), 1-propanephosphonic acid cyclic anhydride (50% in THF, 16 mmol), and azidotrimethysilane (16 mmol) acid in THF (15 mL) was added triethylamine (27 mmol)

dropwise. The reaction mixture was heated at 70° C. for 0.5 hour followed by addition of (R)-1-(2,5-difluoropyridin-3-yl)ethan-1-ol (21 mmol) at the same temperature. After heating for 24 hours, the reaction was cooled to room temperature, concentrated and purified by silica gel chromatography to provide tert-butyl (R)-(6-(5-(((1-(2,5-difluoropyridin-3-yl)ethoxy)carbonyl)amino)-1-methyl-1H-1,2,3-triazol-4-yl)pyridin-3-yl)carbamate.

Step 2: (R)-1-(2,5-difluoropyridin-3-yl)ethyl (4-(5-aminopyridin-2-yl)-1-methyl-1H-1,2,3-triazol-5-yl)carbamate (Intermediate 5B)

4 M HCl in 1,4-dioxane (15 mL) was added to tert-butyl (R)-(6-(5-(((1-(2,5-difluoropyridin-3-yl)ethoxy)carbonyl)amino)-1-methyl-1H-1,2,3-triazol-4-yl)pyridin-3-yl)carbamate (4.2 mmol). The resulting suspension was stirred for 18 hours at room temperature. The reaction was concentrated to afford (R)-1-(2,5-difluoropyridin-3-yl)ethyl (4-(5-aminopyridin-2-yl)-1-methyl-1H-1,2,3-triazol-5-yl)carbamate (Intermediate 5B) as the hydrochloride salt.

Example 23

Preparation of (R)-1-(2-chloro-5-fluoropyridin-3-yl)ethyl (4-(5-aminopyridin-2-yl)-1-methyl-1H-1,2,3-triazol-5-yl)carbamate (Intermediate 5C)

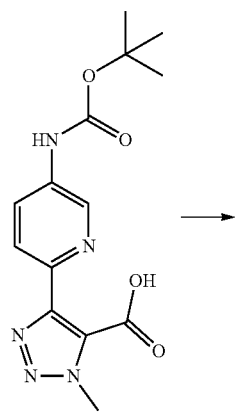

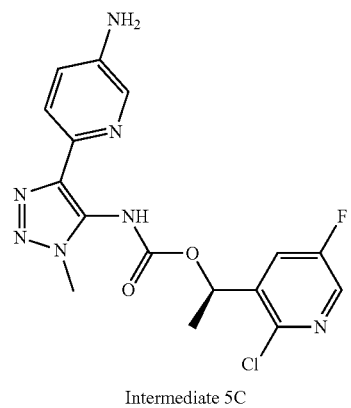

Intermediate 5C

Following the procedure described in Example 22 for the preparation of (R)-1-(2,5-difluoropyridin-3-yl)ethyl (4-(5-aminopyridin-2-yl)-1-methyl-1H-1,2,3-triazol-5-yl)carbamate (Intermediate 5B), using (R)-1-(2-chloro-5-fluoropyridin-3-yl)ethan-1-ol (1.7 mmol), in place of (R)-1-(2,5-difluoropyridin-3-yl)ethan-1-ol, (R)-1-(2-chloro-5-fluoropyridin-3-yl)ethyl (4-(5-aminopyridin-2-yl)-1-methyl-1H-1,2,3-triazol-5-yl)carbamate (Intermediate 5C) was obtained.

Example 24

Preparation of (R)-1-(2-fluoropyridin-3-yl)ethyl (4-(5-aminopyridin-2-yl)-1-methyl-1H-1,2,3-triazol-5-yl)carbamate (Intermediate 5D)

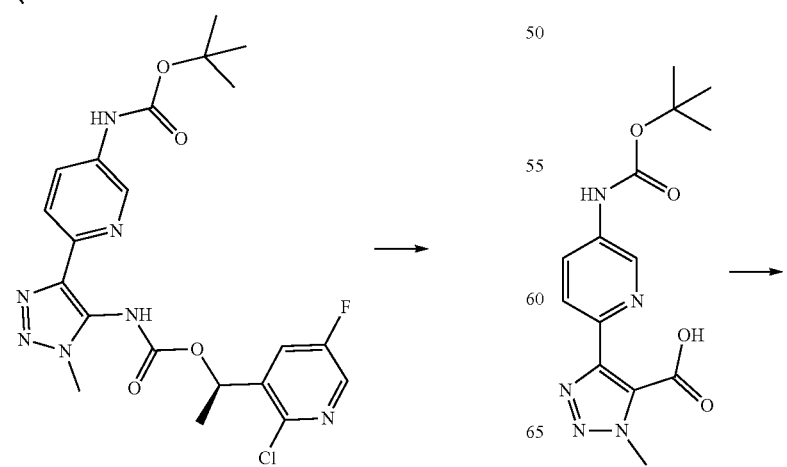

-continued

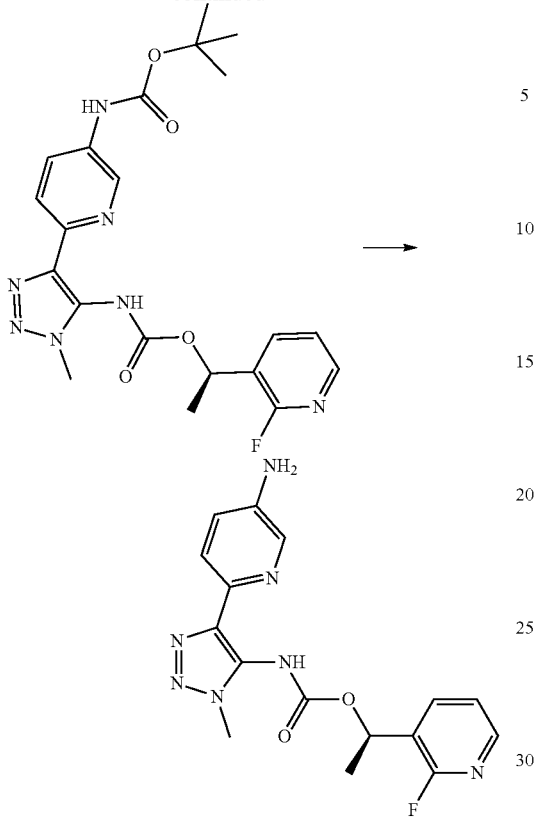

Intermediate 5D

Following the procedure described in Example 22 for the preparation of (R)-1-(2,5-difluoropyridin-3-yl)ethyl (4-(5-aminopyridin-2-yl)-1-methyl-1H-1,2,3-triazol-5-yl)carbamate (Intermediate 5B), using (R)-1-(2-fluoropyridin-3-yl)ethan-1-ol (7.0 mmol), in place of (R)-1-(2,5-difluoropyridin-3-yl)ethan-1-ol, (R)-1-(2-fluoropyridin-3-yl)ethyl (4-(5-aminopyridin-2-yl)-1-methyl-1H-1,2,3-triazol-5-yl)carbamate (Intermediate 5D) was obtained.

Example 25

Preparation of (R)-1-(5-fluoro-2-methylpyridin-3-yl)ethyl (4-(5-aminopyridin-2-yl)-1-methyl-1H-1,2,3-triazol-5-yl)carbamate (Intermediate 5E)

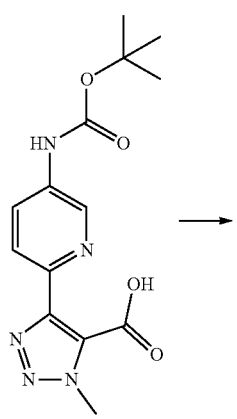

-continued

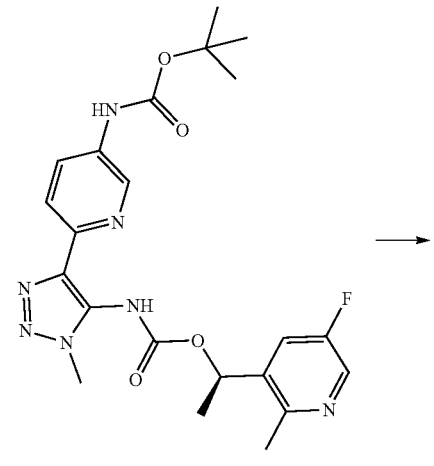

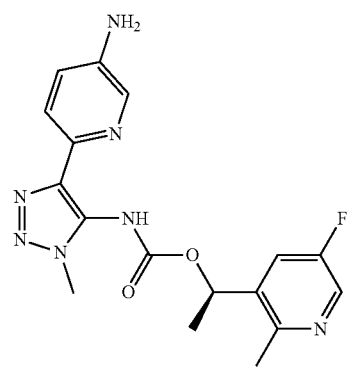

Intermediate 5E

Following the procedure described in Example 22 for the preparation of (R)-1-(2,5-difluoropyridin-3-yl)ethyl (4-(5-aminopyridin-2-yl)-1-methyl-1H-1,2,3-triazol-5-yl)carbamate (Intermediate 5B), using (R)-1-(5-fluoro-2-methylpyridin-3-yl)ethan-1-ol (6.4 mmol), in place of (R)-1-(2,5-difluoropyridin-3-yl)ethan-1-ol, (R)-1-(5-fluoro-2-methylpyridin-3-yl)ethyl (4-(5-aminopyridin-2-yl)-1-methyl-1H-1,2,3-triazol-5-yl)carbamate (Intermediate 5E) was obtained.

Example 26

Preparation of (R)-1-(2-chlorophenyl)ethyl (4-(5-aminopyridin-2-yl)-1-methyl-1H-1,2,3-triazol-5-yl)carbamate (Intermediate 6A)

Example 27

Preparation of (S)-2-fluoro-1-(3-fluorophenyl)ethyl (4-(5-aminopyridin-2-yl)-1-methyl-1H-1,2,3-triazol-5-yl)carbamate (Intermediate 6B)

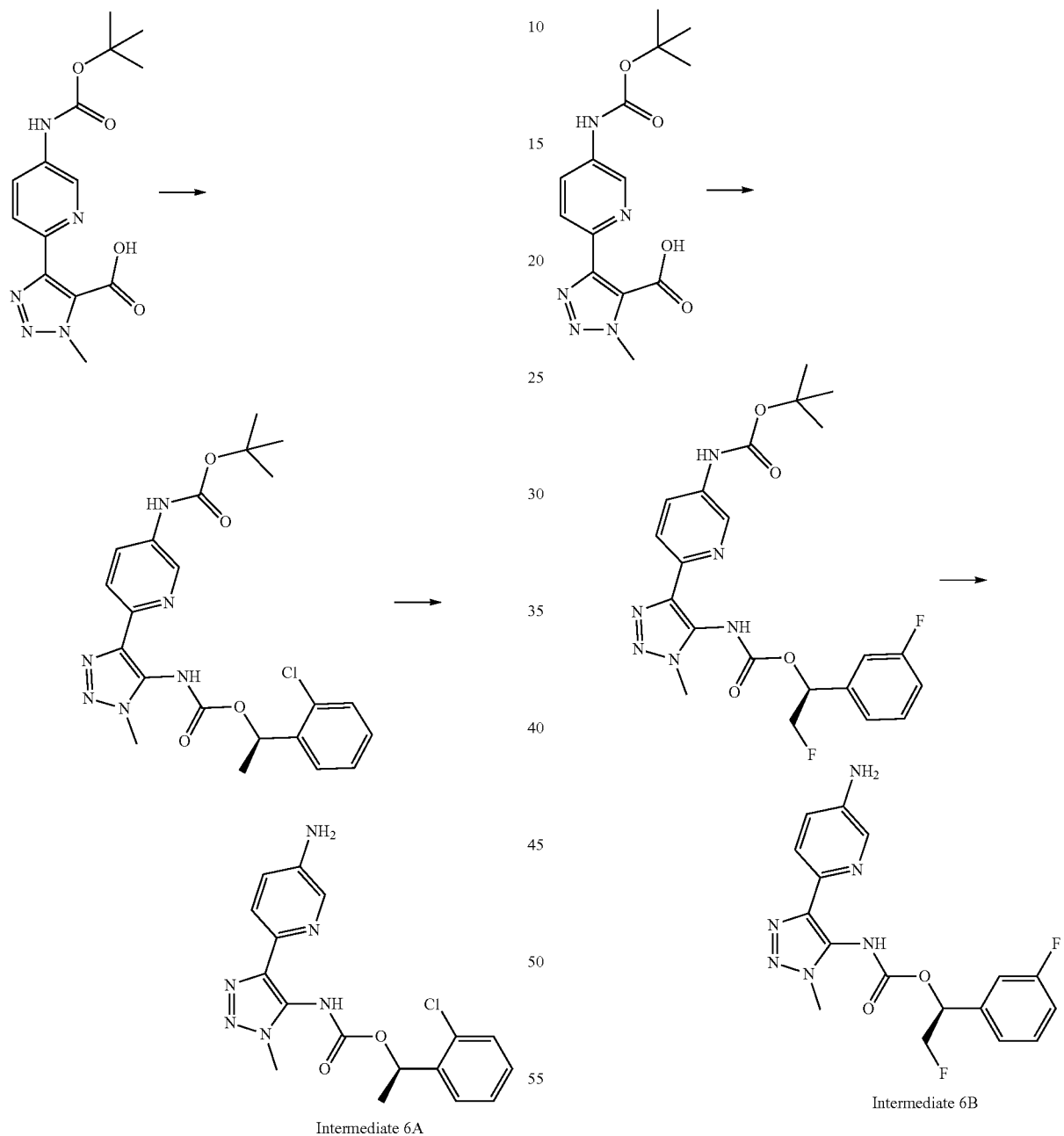

Intermediate 6A

Intermediate 6B

Following the procedure described in Example 22 for the preparation of (R)-1-(2,5-difluoropyridin-3-yl)ethyl (4-(5-aminopyridin-2-yl)-1-methyl-1H-1,2,3-triazol-5-yl)carbamate (Intermediate 5B), using (R)-1-(2-chlorophenyl)ethan-1-ol (3.2 mmol), in place of (R)-1-(2,5-difluoropyridin-3-yl)ethan-1-ol, (R)-1-(2-chlorophenyl)ethyl (4-(5-aminopyridin-2-yl)-1-methyl-1H-1,2,3-triazol-5-yl)carbamate (Intermediate 6A) was obtained.

Following the procedure described in Example 22 for the preparation of (R)-1-(2,5-difluoropyridin-3-yl)ethyl (4-(5-aminopyridin-2-yl)-1-methyl-1H-1,2,3-triazol-5-yl)carbamate (Intermediate 5B), using (S)-2-fluoro-1-(3-fluorophenyl)ethan-1-ol (2.3 mmol), in place of (R)-1-(2,5-difluoropyridin-3-yl)ethan-1-ol, (S)-2-fluoro-1-(3-fluorophenyl)ethyl (4-(5-aminopyridin-2-yl)-1-methyl-1H-1,2,3-triazol-5-yl)carbamate (Intermediate 6B) was obtained.

Example 28

Preparation of 1-(2-chloro-6-fluoropyridin-3-yl)ethan-1-ol

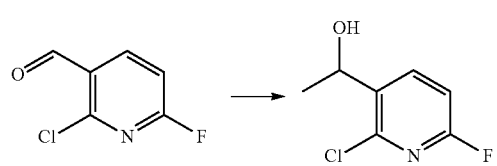

2-Chloro-6-fluoronicotinaldehyde (2.51 mmol) dissolved in methyl tetrahydrofuran (20 mL) was cooled in an ice/acetonitrile bath and then methylmagnesium bromide solution (3.0 M, 7.20 mmol) was added dropwise. The reaction mixture was quenched with addition of ethanol, and then diluted with ethyl acetate and washed with 10% citric acid. The organic layer was concentrated. The residue was purified by column chromatography to give 1-(2-chloro-6-fluoropyridin-3-yl)ethan-1-ol.

Example 29

Preparation of 1-(2-fluoro-5-methylpyridin-4-yl)ethan-1-ol

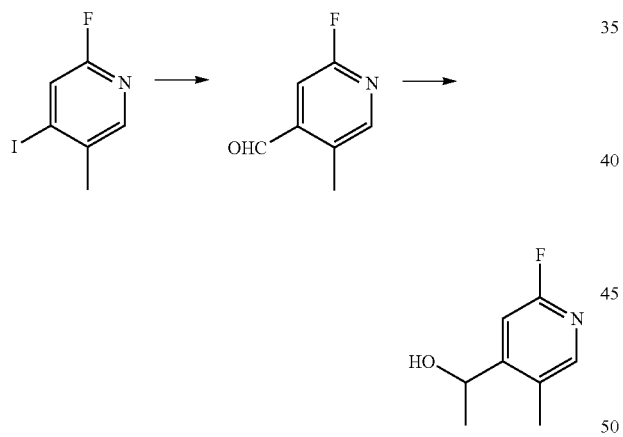

A solution of 2-fluoro-4-iodo-5-methylpyridine (4.22 mmol) in 20 mL THF was cooled to 0° C. and treated with 1.6 M nBuLi in hexanes (5.06 mmol). After 15 min DMF (12.7 mmol) was added dropwise. The reaction was stirred for 30 min, then warmed to room temperature and quenched with sat NH$_4$Cl. The mixture was extracted with EtOAc, dried with MgSO$_4$ and concentrated to provide 2-fluoro-5-methylisonicotinaldehyde. 2-fluoro-5-methylisonicotinaldehyde (5.5 mmol) was taken up in 25 mL THF and cooled to −15° C. in an ice-acetone bath. Treated with 3 M MeMgBr in THF (11.2 mmol) and stirred for 20 minutes. Quenched with sat NH$_4$Cl and extracted with EtOAc, dried with MgSO$_4$, filtered and concentrated to provide 1-(2-fluoro-5-methylpyridin-4-yl)ethan-1-ol (MS (m/z) 155.9 [M+H]+).

Example 30

Preparation of 1-(2,5-difluoropyridin-4-yl)ethan-1-ol

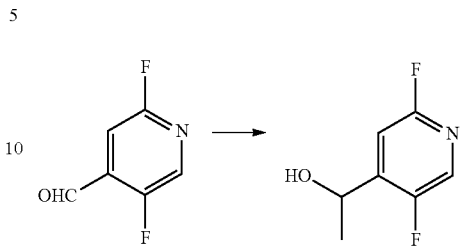

Following the procedure described in Example 29 for the synthesis of 1-(2-fluoro-5-methylpyridin-4-yl)ethan-1-ol, using 2,5-difluoroisonicotinaldehyde (11.9 mmol) in place of 2-fluoro-5-methylisonicotinaldehyde, 1-(2,5-difluoropyridin-4-yl)ethan-1-ol was obtained. (MS (m/z) 160.11[M+H]+).

Example 31

Preparation of 1-(5-bromo-2-fluoropyridin-3-yl)ethan-1-ol

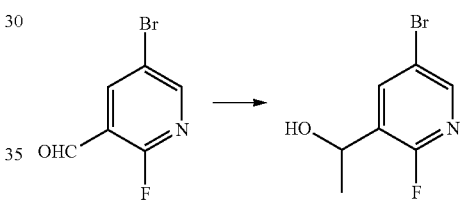

Following the procedure described in Example 29 for the synthesis of 1-(2-fluoro-5-methylpyridin-4-yl)ethan-1-ol, using 5-bromo-2-fluoronicotinaldehyde (7.35 mmol) in place of 2-fluoro-5-methylisonicotinaldehyde, 1-(5-bromo-2-fluoropyridin-3-yl)ethan-1-ol was obtained. (MS (m/z) 220.01[M+H]+).

Example 32

Preparation of 1-(5-bromo-2-chloropyridin-3-yl)ethan-1-ol

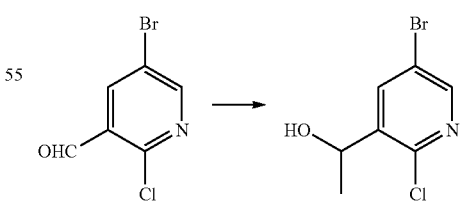

Following the procedure described in Example 29 for the synthesis of 1-(2-fluoro-5-methylpyridin-4-yl)ethan-1-ol, using 5-bromo-2-chloronicotinaldehyde (10.6 mmol) in place of 2-fluoro-5-methylisonicotinaldehyde, 1-(5-bromo-2-chloropyridin-3-yl)ethan-1-ol was obtained. (MS (m/z) 235.99[M+H]+).

Example 33

Preparation of 1-(2,5-difluoropyridin-4-yl)ethan-1-ol

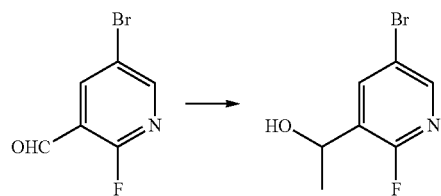

Following the procedure described in Example 29 for the synthesis of 1-(2-fluoro-5-methylpyridin-4-yl)ethan-1-ol, using 5-bromo-2-fluoronicotinaldehyde (7.4 mmol) in place of 2-fluoro-5-methylisonicotinaldehyde, 1-(5-bromo-2-fluoropyridin-3-yl)ethan-1-ol. (MS (m/z) 220.01 [M+H]+).

Example 34

Preparation of 1-(2-chloro-6-fluoropyridin-3-yl) ethyl (4-(5-aminopyridin-2-yl)-1-methyl-1H-1,2,3-triazol-5-yl)carbamate (Intermediate 5F)

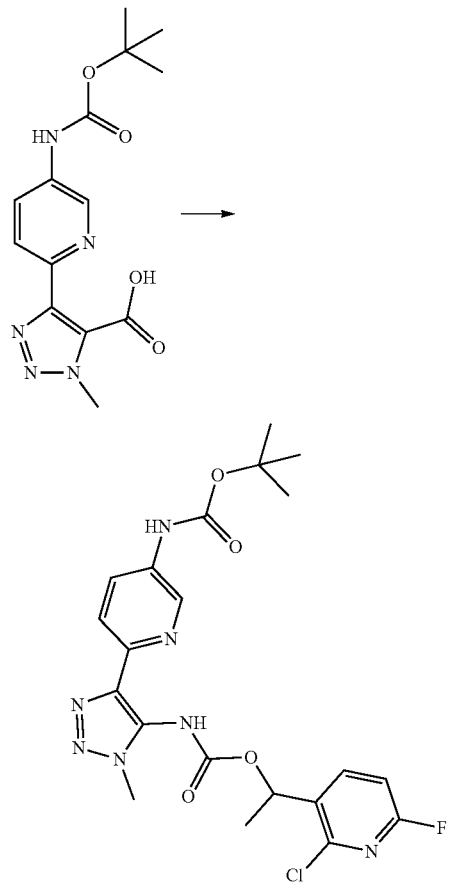

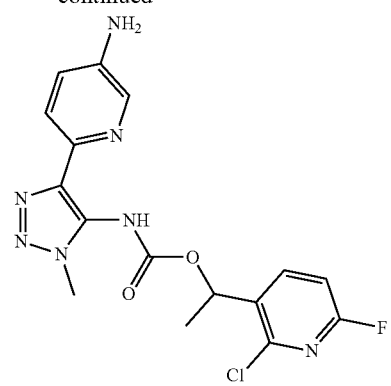

Intermediate 5F

Following the procedure described in Example 22 for the preparation of (R)-1-(2,5-difluoropyridin-3-yl)ethyl (4-(5-aminopyridin-2-yl)-1-methyl-1H-1,2,3-triazol-5-yl)carbamate (Intermediate 5B), using 1-(2-chloro-6-fluoropyridin-3-yl)ethan-1-ol (0.34 mmol), in place of (R)-1-(2,5-difluoropyridin-3-yl)ethan-1-ol, 1-(2-chloro-6-fluoropyridin-3-yl)ethyl (4-(5-aminopyridin-2-yl)-1-methyl-1H-1,2,3-triazol-5-yl)carbamate (Intermediate 5F) was obtained.

Example 35

Preparation of 1-(5-bromo-2-fluoropyridin-3-yl) ethyl (1-methyl-4-(5-(2,2,2-trifluoroacetamido)pyridin-2-yl)-1H-1,2,3-triazol-5-yl)carbamate (Compound 12)

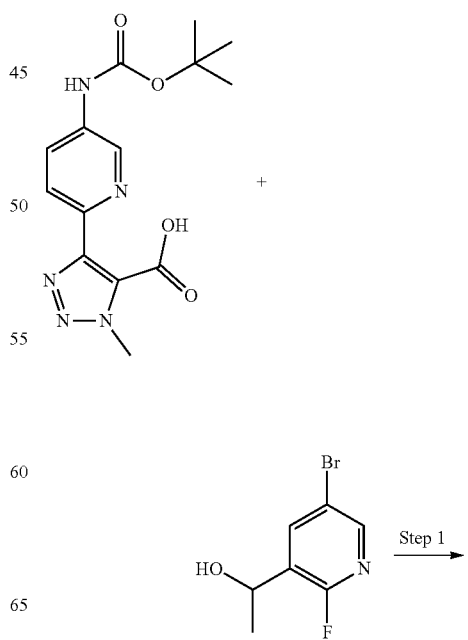

217

-continued

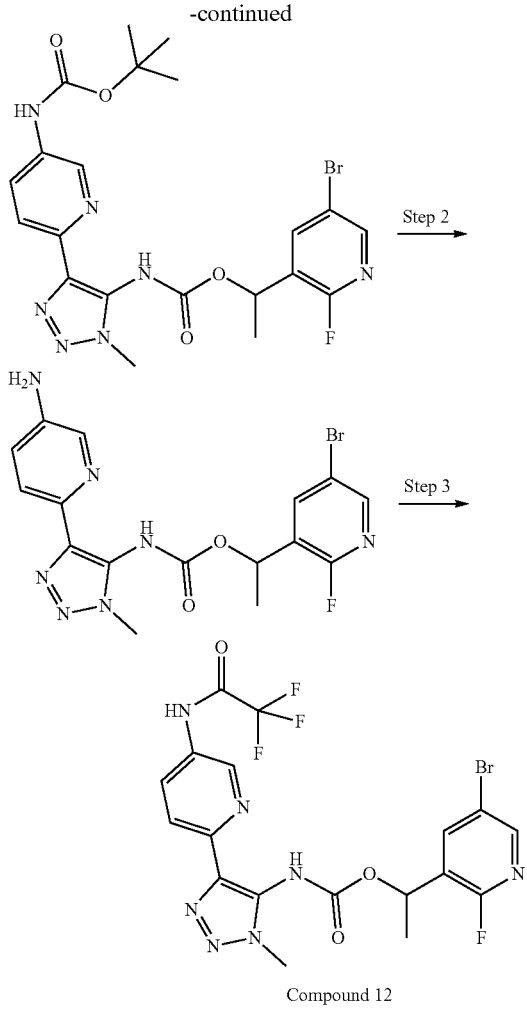

Compound 12

Step 1: tert-butyl (6-(5-(((1-(5-bromo-2-fluoropyridin-3-yl)ethoxy)carbonyl)amino)-1-methyl-1H-1,2,3-triazol-4-yl)pyridin-3-yl)carbamate A solution of tert-butyl (6-(5-(((1-(5-bromo-2-fluoropyridin-3-yl)ethoxy)carbonyl)amino)-1-methyl-1H-1,2,3-triazol-4-yl)pyridin-3-yl)carbamate (0.125 mmol) in 0.2 mL THF was treated with T3P (0.25 mmol), trimethylsilyl-azide (TMS-N3) (0.25 mmol) and triethylamine (TEA) (0.25 mmol) and stirred at room temperature for 20 minutes. A solution of 1-(5-bromo-2-fluoropyridin-3-yl)ethan-1-ol in 200 µL THF was added and the mixture heated at 65° C. for 90 minutes. The mixture was then diluted with DCM and washed with aq. NaHCO3. Purified by silica gel chromatography to provide tert-butyl (6-(5-(((1-(5-bromo-2-fluoropyridin-3-yl)ethoxy)carbonyl)amino)-1-methyl-1H-1,2,3-triazol-4-yl)pyridin-3-yl)carbamate.

Step 2: 2,2,2-trifluoroacetic acid, 6-(5-(((1-(5-bromo-2-fluoropyridin-3-yl)ethoxy)carbonyl)amino)-1-methyl-1H-1,2,3-triazol-4-yl)pyridin-3-aminium salt Tert-butyl (6-(5-(((1-(5-bromo-2-fluoropyridin-3-yl)ethoxy)carbonyl)amino)-1-methyl-1H-1,2,3-triazol-4-yl)pyridin-3-yl)carbamate (0.125 mmol) was taken up in 2 mL

218

DCM and 2 mL trifluoroacetic acid (TFA). Stirred for 5 minutes then concentrated. Taken up in 15 mL dichloroethane and concentrated again. This was repeated 2 times, and the resulting oil left under high vacuum overnight. The obtained 2,2,2-trifluoroacetic acid, 6-(5-(((1-(5-bromo-2-fluoropyridin-3-yl)ethoxy)carbonyl)amino)-1-methyl-1H-1,2,3-triazol-4-yl)pyridin-3-aminium salt used crude in the next step.

Step 3: 1-(5-bromo-2-fluoropyridin-3-yl)ethyl (1-methyl-4-(5-(2,2,2-trifluoroacetamido)pyridin-2-yl)-1H-1,2,3-triazol-5-yl)carbamate (Compound 12)

2,2,2-Trifluoroacetic acid, 6-(5-(((1-(5-bromo-2-fluoropyridin-3-yl)ethoxy)carbonyl)amino)-1-methyl-1H-1,2,3-triazol-4-yl)pyridin-3-aminium salt (0.125 mmol) taken up in 2 mL DCM and cooled to 0° C. This solution was treated with pyridine (0.36 mmol) and methanesulfonic anhydride (0.156 mmol). Allowed to warm to room temperature and stir for 30 minutes. The reaction was concentrated and the residue taken up in MeCN and water. Purification by RP HPLC provided 1-(5-bromo-2-fluoropyridin-3-yl)ethyl (1-methyl-4-(5-(2,2,2-trifluoroacetamido)pyridin-2-yl)-1H-1,2,3-triazol-5-yl)carbamate. (Compound 12) (MS (m/z) 532.04 [M+H]+). 1H NMR (400 MHz, DMSO-d6) δ 10.08 (s, 1H), 9.85 (m, 1H), 8.37-8.32 (m, 1H), 7.95 (d, J=8.6 Hz, 1H), 7.69 (dd, J=8.6, 2.7 Hz, 1H), 5.80 (s, 1H), 3.89 (s, 3H), 3.08 (s, 3H), 1.77-1.38 (m, 3H).

Example 36

Preparation of 1-(5-bromo-2-chloropyridin-3-yl) ethyl (1-methyl-4-(5-(2,2,2-trifluoroacetamido)pyridin-2-yl)-1H-1,2,3-triazol-5-yl)carbamate (Compound 13)

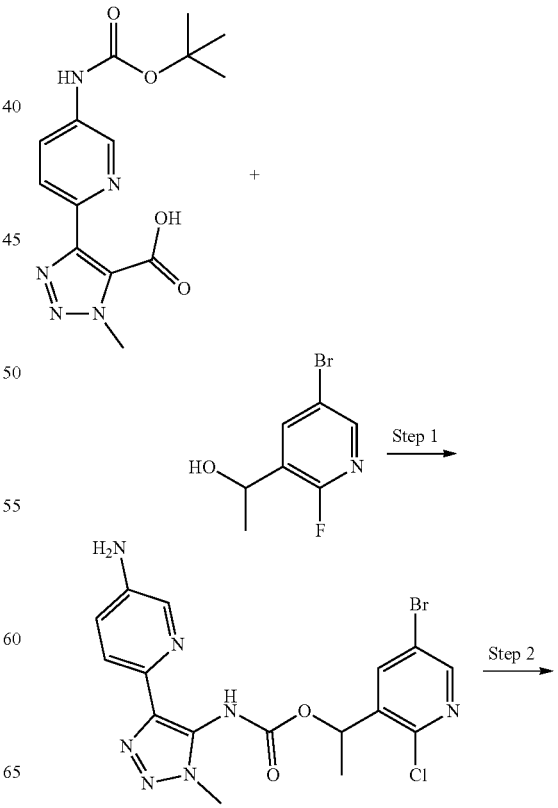

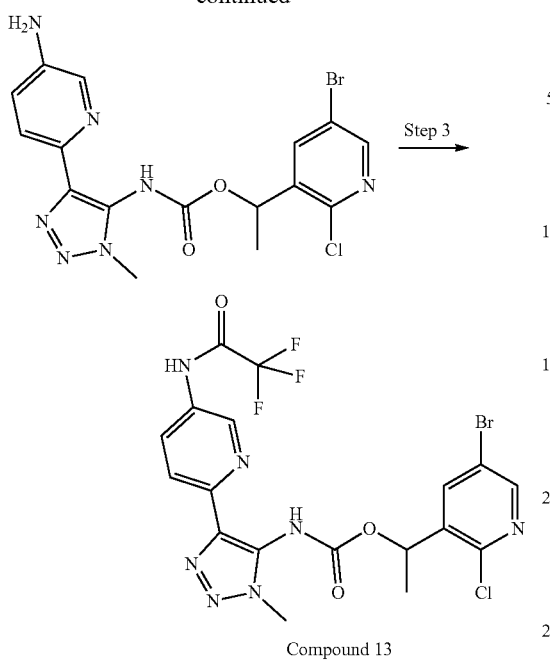

Compound 13

Following the procedure described in Example 35 for the synthesis of 1-(5-bromo-2-fluoropyridin-3-yl)ethyl (1-methyl-4-(5-(2,2,2-trifluoroacetamido)pyridin-2-yl)-1H-1,2,3-triazol-5-yl)carbamate, using 1-(5-bromo-2-chloropyridin-3-yl)ethan-1-ol (0.143 mmol) in place of 1-(5-bromo-2-fluoropyridin-3-yl)ethan-1-ol, 1-(5-bromo-2-chloropyridin-3-yl)ethyl (1-methyl-4-(5-(2,2,2-trifluoroacetamido)pyridin-2-yl)-1H-1,2,3-triazol-5-yl) carbamate was obtained (Compound 13). (MS (m/z) 548.03 [M+H]+). 1H NMR (400 MHz, DMSO-d6) δ 11.54 (s, 1H), 9.94 (s, 1H), 8.81 (s, 1H), 8.54 (s, 1H), 8.12 (dd, J=8.6, 2.6 Hz, 1H), 8.02 (d, J=8.6 Hz, 1H), 7.38 (s, 1H), 5.84 (s, 1H), 3.91 (s, 3H), 1.58 (s, 3H).

Example 37

Preparation of (R)-1-(5-chloro-2-fluoropyridin-3-yl) ethyl (4-(5-acetamidopyridin-2-yl)-1-methyl-1H-1,2, 3-triazol-5-yl)carbamate (Compound 14)

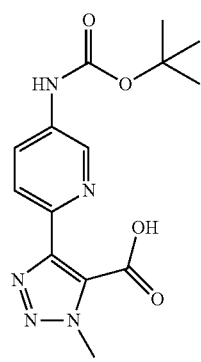

+

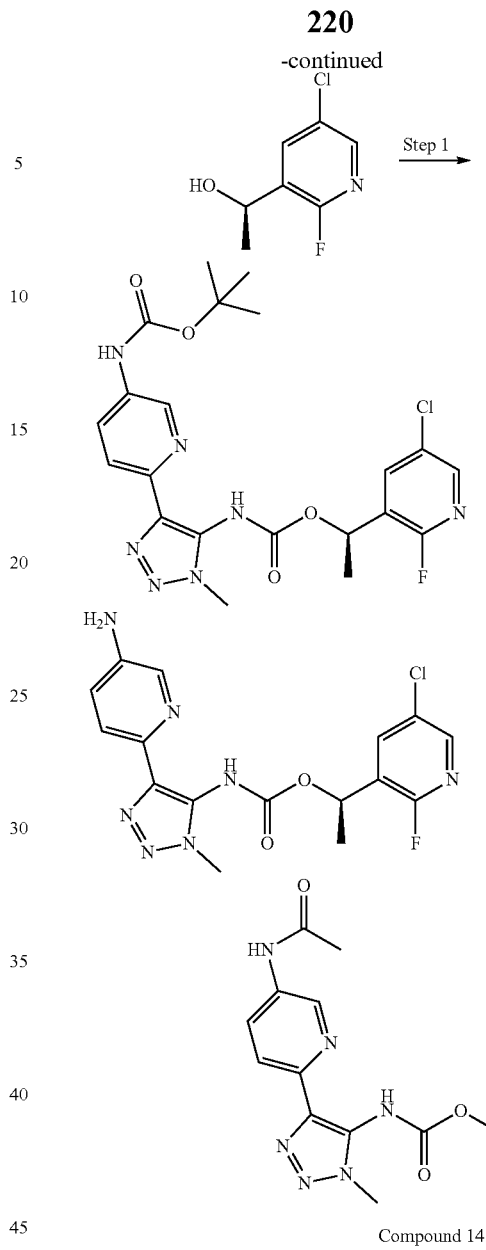

Compound 14

Step 1: (R)-1-(5-chloro-2-fluoropyridin-3-yl)ethyl (4-(5-((tert-butoxycarbonyl)amino)pyridin-2-yl)-1-methyl-1H-1,2,3-triazol-5-yl)carbamate Following the procedure described in Example 35, step 1 for the synthesis of 1-(5-bromo-2-fluoropyridin-3-yl)ethyl (1-methyl-4-(5-(2,2,2-trifluoroacetamido)pyridin-2-yl)-1H-1,2,3-triazol-5-yl)carbamate, using (R)-1-(5-chloro-2-fluoropyridin-3-yl)ethan-1-ol (0.43 mmol) in place of 1-(5-bromo-2-fluoropyridin-3-yl)ethan-1-ol, (R)-1-(5-chloro-2-fluoropyridin-3-yl)ethyl (4-(5-((tert-butoxycarbonyl)amino) pyridin-2-yl)-1-methyl-1H-1,2,3-triazol-5-yl)carbamate was obtained. (MS (m/z) 492.03 [M+H]+).

Step 2: (R)-1-(5-chloro-2-fluoropyridin-3-yl)ethyl (4-(5-aminopyridin-2-yl)-1-methyl-1H-1,2,3-triazol-5-yl)carbamate hydrochloride A solution of (R)-1-(5-chloro-2-fluoropyridin-3-yl)ethyl (4-(5-((tert-butoxycarbonyl)amino)pyridin-2-yl)-1-methyl- 1H-1,2,3-triazol-5-yl)carbamate (0.193 mmol) in 4N HCl in dioxane was stirred at room temperature for 1 hour. Reaction was concentrated and placed under vacuum overnight, providing (R)-1-(5-chloro-2-fluoropyridin-3-yl)ethyl (4-(5-aminopyridin-2-yl)-1-methyl-1H-1,2,3-triazol-5-yl)carbamate hydrochloride as an oil.

Step 3: (R)-1-(5-chloro-2-fluoropyridin-3-yl)ethyl (4-(5-acetamidopyridin-2-yl)-1-methyl-1H-1,2,3-triazol-5-yl)carbamate (Compound 14)

A solution of (R)-1-(5-chloro-2-fluoropyridin-3-yl)ethyl (4-(5-aminopyridin-2-yl)-1-methyl-1H-1,2,3-triazol-5-yl)carbamate hydrochloride (0.193 mmol) in 0.5 mL DCM was treated with pyridine (2.9 mmol) and cooled to 0° C. Acetyl chloride (0.212 mmol) was added and the mixture stirred at 0° C. for 45 minutes. Reaction was concentrated in vacuo and purified by RP HPLC to provide (R)-1-(5-chloro-2-fluoropyridin-3-yl)ethyl (4-(5-acetamidopyridin-2-yl)-1-methyl-1H-1,2,3-triazol-5-yl)carbamate. (Compound 14) (MS (m/z) 434.0 [M+H]+). H NMR (400 MHz, Acetonitrile-d3) δ 8.98-8.93 (m, 1H), 8.76 (s, 1H), 8.27 (d, J=3.0 Hz, 1H), 8.24-8.14 (m, 1H), 8.04 (d, J=8.7 Hz, 1H), 7.81 (ddd, J=9.0, 3.1, 0.7 Hz, 1H), 3.97 (s, 3H), 2.16 (s, 3H), 1.62-1.55 (m, 3H).

Example 38

Preparation of (R)-1-(2-chloro-5-fluoropyridin-3-yl)ethyl (4-(5-acetamidopyridin-2-yl)-1-methyl-1H-1,2,3-triazol-5-yl)carbamate (Compound 15)

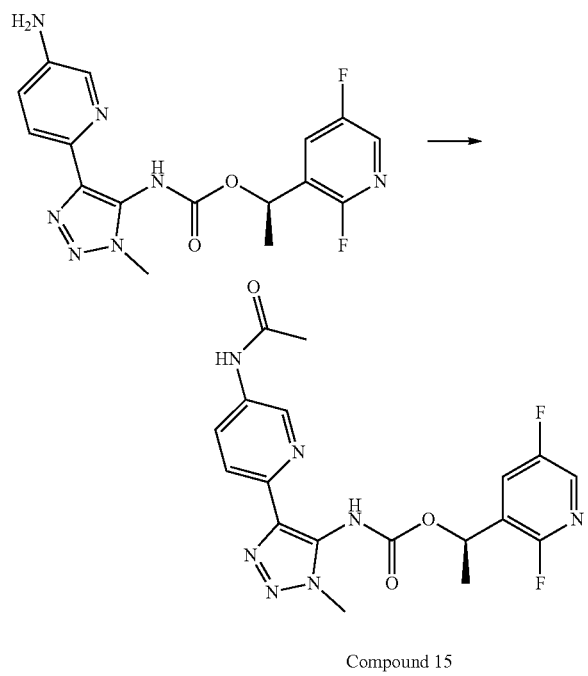

Compound 15

Following the procedure described in Example 39, step 3 for the synthesis of (R)-1-(5-chloro-2-fluoropyridin-3-yl)ethyl (4-(5-acetamidopyridin-2-yl)-1-methyl-1H-1,2,3-triazol-5-yl)carbamate, using (R)-1-(2-chloro-5-fluoropyridin-3-yl)ethyl (4-(5-aminopyridin-2-yl)-1-methyl-1H-1,2,3-triazol-5-yl)carbamate (0.23 mmol) in place of (R)-1-(5-chloro-2-fluoropyridin-3-yl)ethyl (4-(5-aminopyridin-2-yl)-1-methyl-1H-1,2,3-triazol-5-yl)carbamate, (R)-1-(2-chloro-5-fluoropyridin-3-yl)ethyl (4-(5-acetamidopyridin-2-yl)-1-methyl-1H-1,2,3-triazol-5-yl)carbamate (Compound 15) was obtained. (MS (m/z) 434.0 [M+H]+) H NMR (400 MHz, Acetonitrile-d3) δ 8.98-8.93 (m, 1H), 8.76 (s, 1H), 8.27 (d, J=3.0 Hz, 1H), 8.24-8.14 (m, 1H), 8.04 (d, J=8.7 Hz, 1H), 7.81 (ddd, J=9.0, 3.1, 0.7 Hz, 1H), 3.97 (s, 3H), 2.16 (s, 3H), 1.62-1.55 (m, 3H).

Example 39

Preparation of (R)-1-(2-chloropyridin-3-4)ethyl (4-(5-formamidopyridin-2-yl)-1-methyl-1H-1,2,3-triazol-5-yl)carbamate (Compound 16)

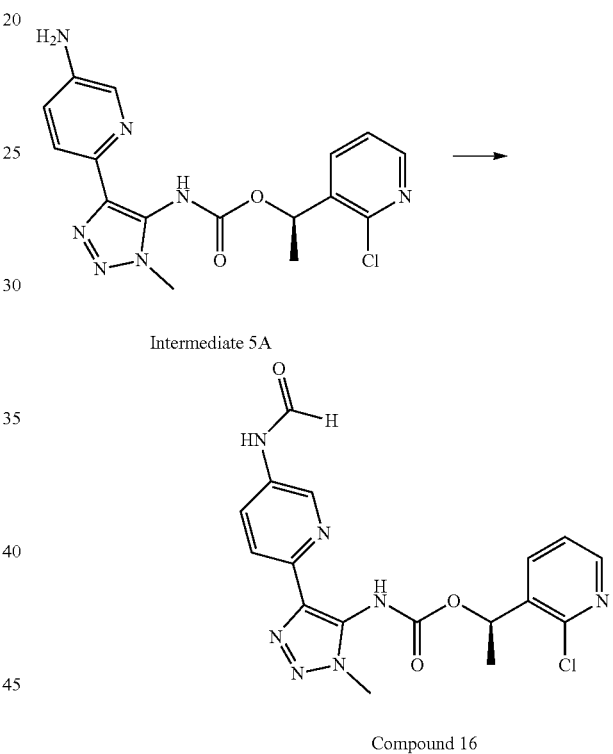

Compound 16

To the acetic anhydride (3 mmol) at room temperature under an argon atmosphere was added formic acid (5 mmol). The reaction mixture was stirred at room temperature for 30 minutes. Then (R)-1-(2-chloropyridin-3-yl) ethyl (4-(5-aminopyridin-2-yl)-1-methyl-1H-1,2,3-triazol-5-yl) carbamate hydrochloride (Intermediate 5A) (0.37 mmol) in THF (0.33 mL) at room temperature was added to the reaction mixture. The reaction mixture was stirred at 60° C. for 1 hour. The reaction mixture was concentrated to dryness and then co-evaporated with toluene. The residue was purified by reverse-phase HPLC to provide (R)-1-(2-chloropyridin-3-yl)ethyl (4-(5-formamidopyridin-2-yl)-1-methyl-1H-1,2,3-triazol-5-yl)carbamate. (Compound 41) (MS (m/z) 402.0 [M+H]⁺). ¹H NMR (400 MHz, Methanol-d₄) δ 8.89 (d, 1H), 8.37 (d, 2H), 8.19-8.03 (m, 1H), 8.02-7.89 (m, 1H), 7.80-7.59 (m, 1H), 7.49 (s, 1H), 6.09 (m, 1H), 4.00 (d, 3H), 1.63 (s, 3H).

Example 40

Preparation of (R)-1-(2-chloropyridin-3-yl)ethyl(4-(5-((methoxycarbonyl)amino)pyridin-2-yl)-1-methyl-1H-1,2,3-triazol-5-yl)carbamate (Compound 17)

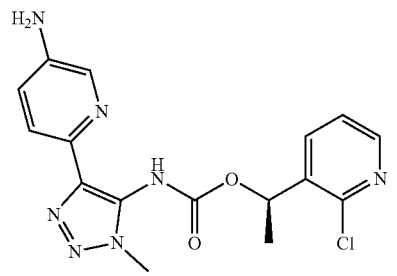

Intermediate 5A

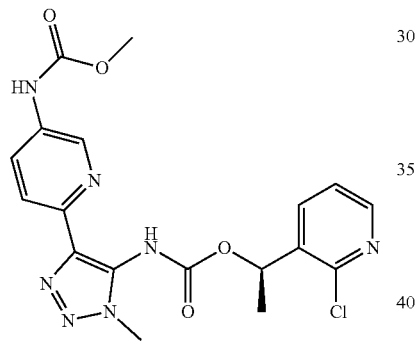

Compound 17

(R)-1-(2-chloropyridin-3-yl)ethyl (4-(5-aminopyridin-2-yl)-1-methyl-1H-1,2,3-triazol-5-yl)carbamate hydrochloride salt (Intermediate 5A) (0.78 mmol) was dissolved in dichloromethane (1 mL), pyridine (0.2 mL). Methyl chloroformate chloride (0.14 mmol) was added dropwise at room temperature. After 30 minutes, the reaction was concentrated and dissolved in tetrahydrofuran (2 mL), and 0.5 M aqueous sodium hydroxide solution (2 mL) and stirred vigorously for 10 minutes. The reaction was quenched with sat. ammonium chloride, and extracted with ethyl acetate (2×10 mL). The combined organics were dried over sodium sulfate, concentrated, and purified by reverse-phase HPLC to provide (R)-1-(2-chloropyridin-3-yl)ethyl (4-(5-((methoxycarbonyl)amino)pyridin-2-yl)-1-methyl-1H-1,2,3-triazol-5-yl)carbamate. (Compound 17) (MS (m/z) 432.1 [M+H]$^+$). $^1$H NMR (400 MHz, Methanol-d$_4$) δ 8.70 (s, 1H), 8.31 (s, 1H), 8.13-7.92 (m, 2H), 7.87 (d, J=8.4 Hz, 1H), 7.46 (s, 1H), 6.21-5.92 (m, 1H), 3.98 (s, 3H), 3.81 (s, 3H), 1.61 (s, 3H).

Example 41

Preparation of (S)-2-fluoro-1-phenylethyl (4-(4-((methoxycarbonyl)amino)phenyl)-1-methyl-1H-1,2,3-triazol-5-yl)carbamate (Compound 18)

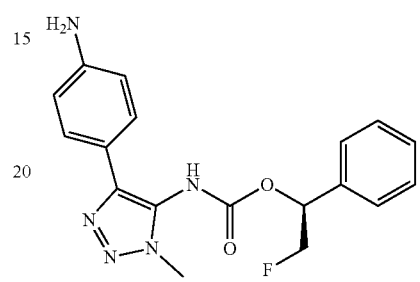

Intermediate 8D

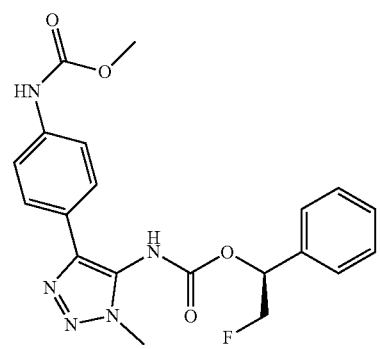

Compound 18

Following the procedure described in Example 40 for the synthesis of (R)-1-(2-chloropyridin-3-yl)ethyl (4-(5-((methoxycarbonyl)amino)pyridin-2-yl)-1-methyl-1H-1,2,3-triazol-5-yl)carbamate, using (S)-2-fluoro-1-phenylethyl (4-(4-aminophenyl)-1-methyl-1H-1,2,3-triazol-5-yl)carbamate (Intermediate 8D) (0.06 mmol) in place of (R)-1-(2-chloropyridin-3-yl)ethyl (4-(5-aminopyridin-2-yl)-1-methyl-1H-1,2,3-triazol-5-yl)carbamate, (S)-2-fluoro-1-phenylethyl (4-(4-((methoxycarbonyl)amino)phenyl)-1-methyl-1H-1,2,3-triazol-5-yl)carbamate was obtained. (Compound 18) (MS (m/z) 414.1 [M+H]$^+$). $^1$H NMR (400 MHz, Methanol-d$_4$) δ 7.87-6.82 (m, 9H), 6.03 (s, 1H), 4.81-4.56 (m, 2H), 3.92 (s, 3H), 3.78 (s, 3H).

Example 42

Preparation of (S)-2-fluoro-1-(3-fluorophenyl)ethyl (4-(5-((methoxycarbonyl)amino)pyridin-2-yl)-1-methyl-1H-1,2,3-triazol-5-yl)carbamate (Compound 19)

Example 43

Preparation of (R)-1-(2-chlorophenyl)ethyl(4-(5-((methoxycarbonyl)amino)pyridin-2-yl)-1-methyl-1H-1,2,3-triazol-5-yl)carbamate (Compound 20)

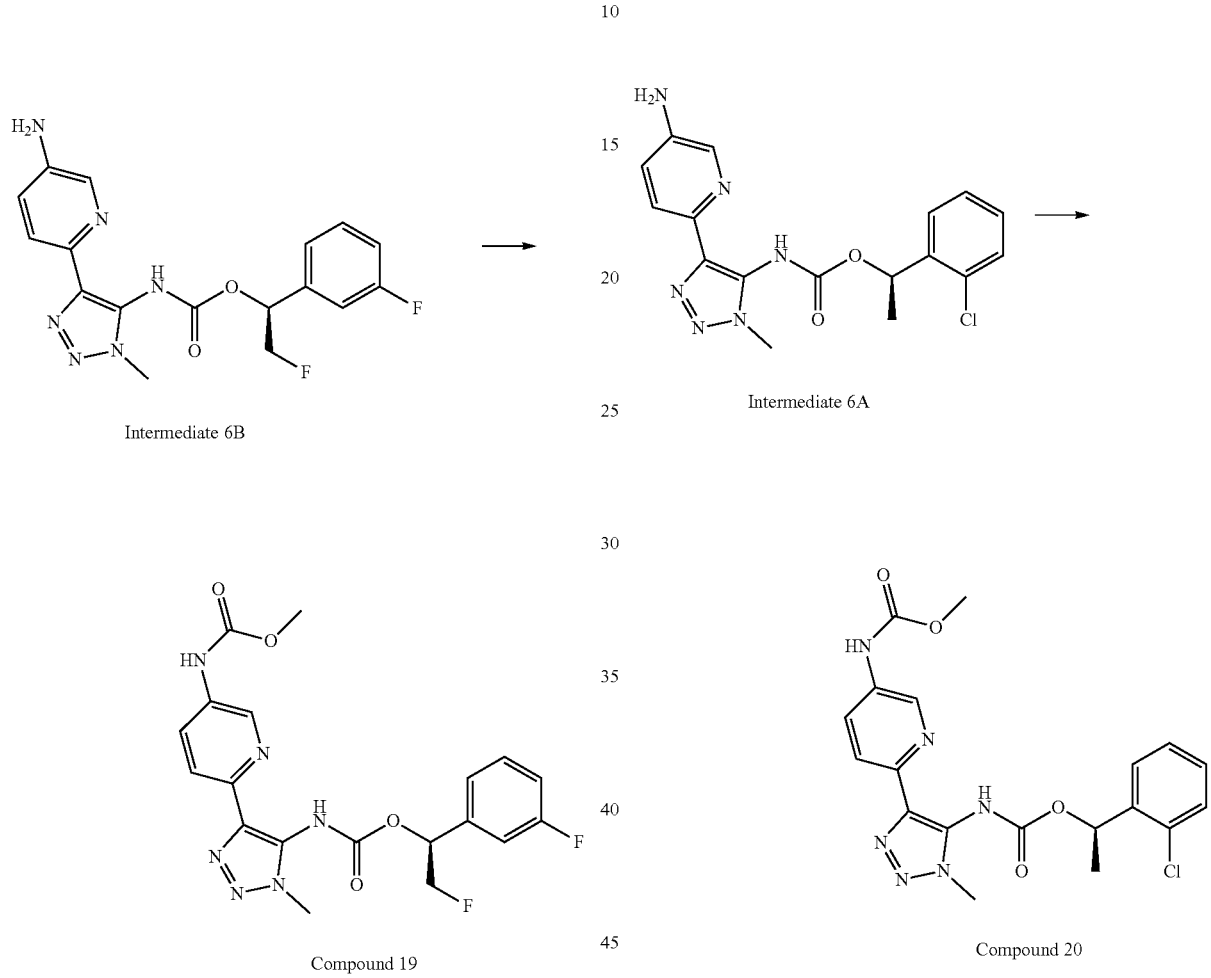

Following the procedure described in Example 40 for the synthesis of (R)-1-(2-chloropyridin-3-yl)ethyl (4-(5-((methoxycarbonyl)amino)pyridin-2-yl)-1-methyl-1H-1,2,3-triazol-5-yl)carbamate, using (S)-2-fluoro-1-(3-fluorophenyl)ethyl (4-(5-aminopyridin-2-yl)-1-methyl-1H-1,2,3-triazol-5-yl)carbamate (Intermediate 6B) (0.05 mmol) in place of (R)-1-(2-chloropyridin-3-yl)ethyl (4-(5-aminopyridin-2-yl)-1-methyl-1H-1,2,3-triazol-5-yl)carbamate, (S)-2-fluoro-1-(3-fluorophenyl)ethyl (4-(5-((methoxycarbonyl)amino)pyridin-2-yl)-1-methyl-1H-1,2,3-triazol-5-yl)carbamate was obtained. (Compound 19) (MS (m/z) 433.2 [M+H]$^+$). $^1$H NMR (400 MHz, Methanol-d$_4$) δ 8.69 (s, 1H), 8.01 (d, J=8.3 Hz, 1H), 7.84 (d, J=8.7 Hz, 1H), 7.57-6.62 (m, 4H), 6.09-5.77 (m, 1H), 4.80-4.47 (m, 2H), 3.97 (s, 3H), 3.79 (s, 3H).

Following the procedure described in Example 40 for the synthesis of (R)-1-(2-chloropyridin-3-yl)ethyl (4-(5-((methoxycarbonyl)amino)pyridin-2-yl)-1-methyl-1H-1,2,3-triazol-5-yl)carbamate, using (R)-1-(2-chlorophenyl)ethyl (4-(5-aminopyridin-2-yl)-1-methyl-1H-1,2,3-triazol-5-yl)carbamate (Intermediate 6A) (0.03 mmol) in place of (R)-1-(2-chloropyridin-3-yl)ethyl (4-(5-aminopyridin-2-yl)-1-methyl-1H-1,2,3-triazol-5-yl)carbamate, (R)-1-(2-chlorophenyl)ethyl (4-(5-((methoxycarbonyl)amino)pyridin-2-yl)-1-methyl-1H-1,2,3-triazol-5-yl)carbamate (Compound 20) was obtained. (MS (m/z) 431.2 [M+H]$^+$). $^1$H NMR (400 MHz, Methanol-d$_4$) δ 8.74 (s, 1H), 8.02 (d, J=7.6 Hz, 1H), 7.83 (d, J=8.7 Hz, 1H), 7.74-7.00 (m, 4H), 6.14 (d, J=6.7 Hz, 1H), 3.96 (s, 3H), 3.79 (s, 3H), 1.42 (s, 3H).

Example 44

Preparation of (R)-1-(2-chloropyridin-3-yl)ethyl(4-(5-((ethoxycarbonyl)amino)pyridin-2-yl)-1-methyl-1H-1,2,3-triazol-5-yl)carbamate (Compound 21)

Example 45

Preparation of (R)-1-(2-chloropyridin-3-yl)ethyl(4-(5-((isobutoxycarbonyl)amino)pyridin-2-yl)-1-methyl-1H-1,2,3-triazol-5-yl)carbamate (Compound 22)

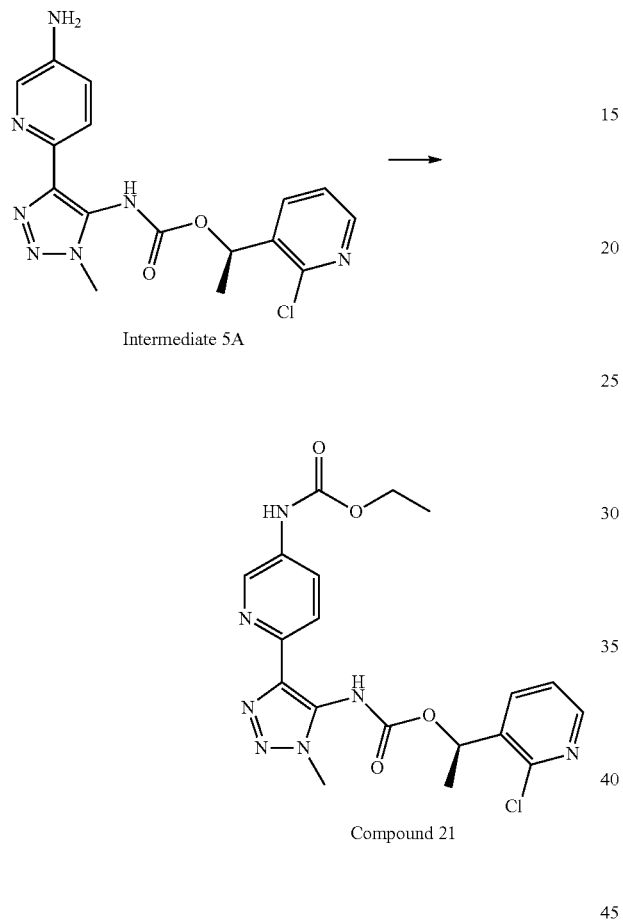

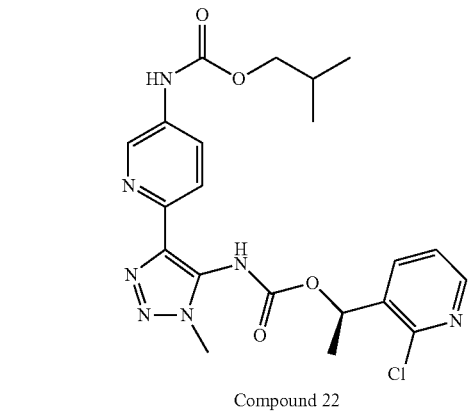

(R)-1-(2-chloropyridin-3-yl)ethyl (4-(5-aminopyridin-2-yl)-1-methyl-1H-1,2,3-triazol-5-yl)carbamate hydrochloride salt (Intermediate 5A) (0.10 mmol) suspended in dichloromethane (1 mL) was treated with N,N-diisopropylethylamine (30 μL, 0.17 mmol) followed by ethyl chloroformate (0.210 mmol). The reaction mixture was stirred at room temperature for 15 minutes. The reaction mixture was concentrated. The residue was purified on the HPLC and the fractions were dried by a lyophilizer. The lyophilized solid was dissolved in dissolved in methyl tetrahydrofuran (1 mL) and treated with 1N sodium hydroxide solution (400 μL). The reaction mixture was heated at 55° C. for 30 minutes. After cooling to room temperature, the reaction mixture was concentrated. The residue was purified on the HPLC to provide (R)-1-(2-chloropyridin-3-yl)ethyl (4-(5-((ethoxycarbonyl)amino)pyridin-2-yl)-1-methyl-1H-1,2,3-triazol-5-yl)carbamate (Compound 21). (MS (m/z) 446.0 [M+H]$^+$). $^1$H NMR (400 MHz, Methanol-d$_4$) δ 8.80 (s, 1H), 8.34 (s, 1H), 8.06 (d, J=8.7 Hz, 2H), 7.89 (d, J=8.7 Hz, 1H), 7.51 (s, 1H), 6.08 (d, J=6.9 Hz, 1H), 4.27 (q, J=7.1 Hz, 2H), 4.00 (s, 3H), 1.65 (s, 3H), 1.36 (t, J=7.1 Hz, 3H).

Following the procedure described in Example 44 for the synthesis of (R)-1-(2-chloropyridin-3-yl)ethyl (4-(5-((ethoxycarbonyl)amino)pyridin-2-yl)-1-methyl-1H-1,2,3-triazol-5-yl)carbamate, using isobutyl chloroformate (0.2 mmol) in place of methyl chloroformate, (R)-1-(2-chloropyridin-3-yl)ethyl (4-(5-((isobutoxycarbonyl)amino)pyridin-2-yl)-1-methyl-1H-1,2,3-triazol-5-yl)carbamate (Compound 22) was obtained. (MS (m/z) 474.1 [M+H]$^+$). $^1$H NMR (400 MHz, Methanol-d$_4$) δ 8.84 (s, 1H), 8.34 (s, 1H), 8.09 (d, J=8.9 Hz, 2H), 7.90 (d, J=8.6 Hz, 1H), 7.51 (s, 1H), 6.09 (d, J=7.1 Hz, 1H), 4.01 (d, J=6.7 Hz, 2H), 4.00 (s, 4H), 2.04 (dq, J=13.4, 6.7 Hz, 1H), 1.65 (s, 3H), 1.03 (d, J=6.7 Hz, 6H).

Example 46

Preparation of (R)-1-(2-chloropyridin-3-yl)ethyl (4-(5-acetamidopyridin-2-yl)-1-methyl-1H-1,2,3-triazol-5-yl)carbamate (Compound 23)

Example 47

Preparation of (R)-1-(2-chlorophenyl)ethyl (4-(5-acetamidopyridin-2-yl)-1-methyl-1H-1,2,3-triazol-5-yl)carbamate (Compound 24)

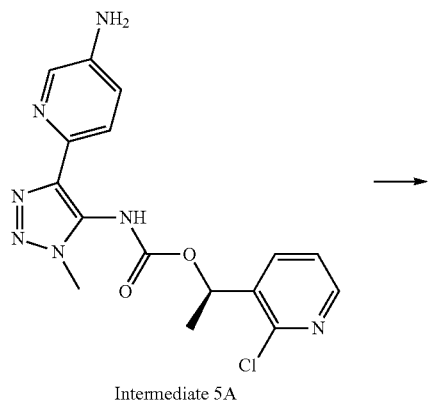

Intermediate 5A

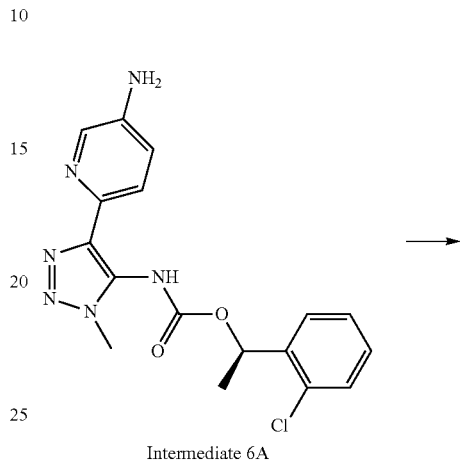

Intermediate 6A

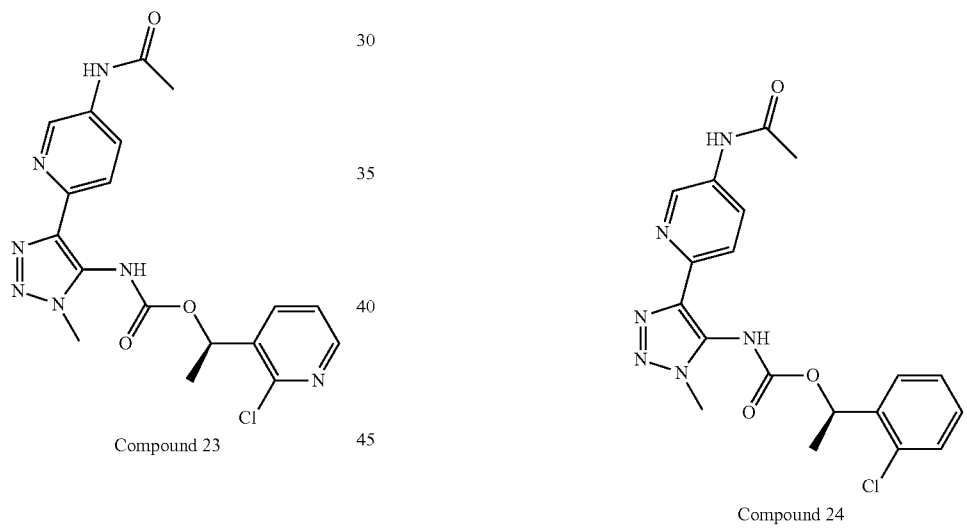

Compound 23

Compound 24

The hydrochloride salt of (R)-1-(2-chloropyridin-3-yl)ethyl (4-(5-aminopyridin-2-yl)-1-methyl-1H-1,2,3-triazol-5-yl)carbamate (Intermediate 5A) (0.07 mmol) was dissolved in dichloromethane (1 mL) and pyridine (0.2 mL). Acetyl chloride (0.14 mmol) was added dropwise at room temperature. After 30 min, the reaction was concentrated and dissolved in tetrahydrofuran (2 mL), and 1 M aqueous sodium hydroxide solution (2 mL) and stirred vigorously for 10 minutes. The reaction was quenched with sat. ammonium chloride, and extracted with ethyl acetate (2×10 mL). The combined organics were dried over sodium sulfate, concentrated, and purified by reverse-phase HPLC to provide (R)-1-(2-chloropyridin-3-yl)ethyl (4-(5-acetamidopyridin-2-yl)-1-methyl-1H-1,2,3-triazol-5-yl)carbamate. (Compound 23) (MS (m/z) 416.1 [M+H]$^+$). $^1$H NMR (400 MHz, Methanol-$d_4$) δ 8.83 (s, 1H), 8.31 (s, 1H), 8.21-7.95 (m, 2H), 7.89 (d, J=8.6 Hz, 1H), 7.46 (s, 1H), 6.08 (m, 1H), 3.98 (s, 3H), 2.20 (s, 3H), 1.61 (s, 3H).

Following the procedure described in Example 46 for the synthesis of (R)-1-(2-chloropyridin-3-yl)ethyl (4-(5-acetamidopyridin-2-yl)-1-methyl-1H-1,2,3-triazol-5-yl)carbamate, using (R)-1-(2-chlorophenyl)ethyl (4-(5-aminopyridin-2-yl)-1-methyl-1H-1,2,3-triazol-5-yl)carbamate (Intermediate 6A) (0.03 mmol) in place of (R)-1-(2-chloropyridin-3-yl)ethyl (4-(5-aminopyridin-2-yl)-1-methyl-1H-1,2,3-triazol-5-yl)carbamate, (R)-1-(2-chlorophenyl)ethyl (4-(5-acetamidopyridin-2-yl)-1-methyl-1H-1,2,3-triazol-5-yl)carbamate was obtained (Compound 24). (MS (m/z) 415.2 [M+H]$^+$). $^1$H NMR (400 MHz, Methanol-$d_4$) δ 8.88 (s, 1H), 8.10 (dd, J=8.6, 2.6 Hz, 1H), 7.86 (d, J=8.6 Hz, 1H), 7.71-7.05 (m, 4H), 6.29-5.90 (m, 1H), 3.96 (s, 3H), 2.18 (s, 3H), 1.55 (s, 3H).

Example 48

Preparation of (S)-2-fluoro-1-(3-fluorophenyl)ethyl (4-(5-acetamidopyridin-2-yl)-1-methyl-1H-1,2,3-triazol-5-yl)carbamate (Compound 25)

Example 49

Preparation of 1-(2-fluoro-5-methylpyridin-4-yl)ethyl (4-(5-(3,3-difluorocyclobutane-1-carboxamido)pyridin-2-yl)-1-methyl-1H-1,2,3-triazol-5-yl)carbamate (Compound 26)

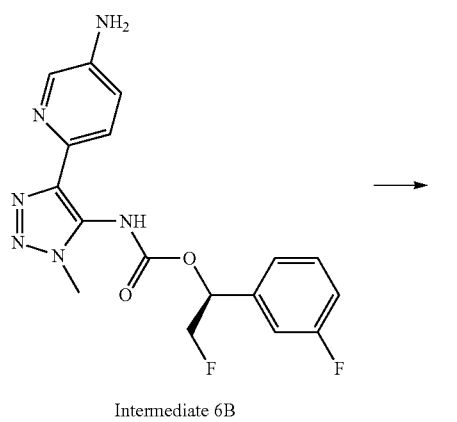

Intermediate 6B

Compound 25

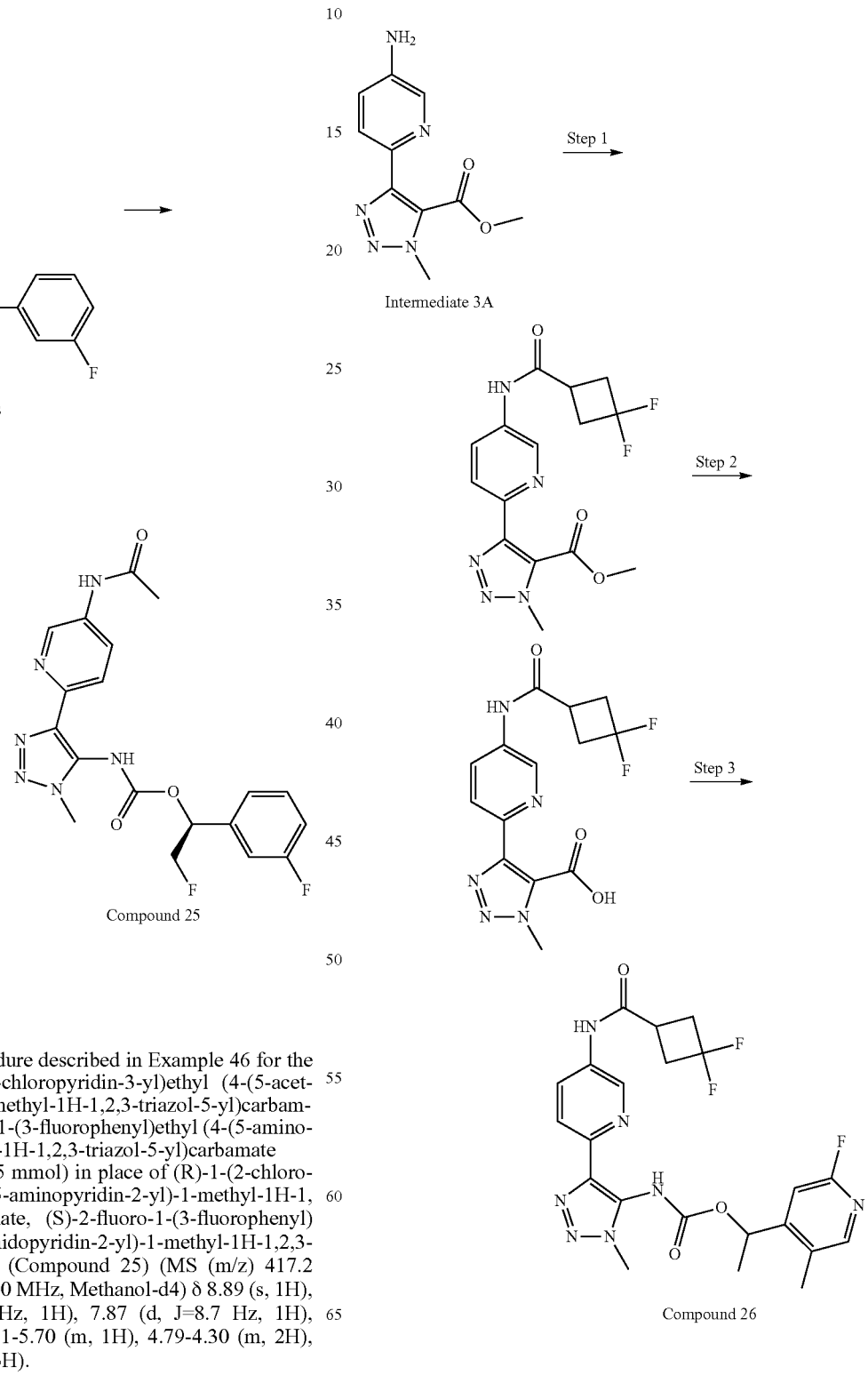

Following the procedure described in Example 46 for the synthesis of (R)-1-(2-chloropyridin-3-yl)ethyl (4-(5-acetamidopyridin-2-yl)-1-methyl-1H-1,2,3-triazol-5-yl)carbamate, using (S)-2-fluoro-1-(3-fluorophenyl)ethyl (4-(5-aminopyridin-2-yl)-1-methyl-1H-1,2,3-triazol-5-yl)carbamate (Intermediate 6B) (0.05 mmol) in place of (R)-1-(2-chloropyridin-3-yl)ethyl (4-(5-aminopyridin-2-yl)-1-methyl-1H-1,2,3-triazol-5-yl)carbamate, (S)-2-fluoro-1-(3-fluorophenyl)ethyl (4-(5-acetamidopyridin-2-yl)-1-methyl-1H-1,2,3-triazol-5-yl)carbamate. (Compound 25) (MS (m/z) 417.2 [M+H]$^+$). 1H NMR (400 MHz, Methanol-d4) δ 8.89 (s, 1H), 8.12 (dd, J=8.8, 2.4 Hz, 1H), 7.87 (d, J=8.7 Hz, 1H), 7.56-6.58 (m, 4H), 6.11-5.70 (m, 1H), 4.79-4.30 (m, 2H), 3.98 (s, 3H), 2.18 (s, 3H).

Step 1: methyl 4-(5-(3,3-difluorocyclobutane-1-carboxamido)pyridin-2-yl)-1-methyl-1H-1,2,3-triazole-5-carboxylate To a mixture of methyl 4-(5-aminopyridin-2-yl)-1-methyl-1H-1,2,3-triazole-5-carboxylate hydrochloride (Intermediate 3A) (4.3 mmol) in a 5:1 mixture of DCM: pyridine (25 mL) was added 3,3-difluorocyclobutane-1-carboxylic acid (5.1 mmol) and N-Ethyl-N'-(3-dimethylaminopropyl) carbodiimide hydrochloride (5.1 mmol). The reaction mixture was left with magnetic stirring for 2 hours at which point, the reaction was concentrated to provide the crude methyl 4-(5-(3,3-difluorocyclobutane-1-carboxamido)pyridin-2-yl)-1-methyl-1H-1,2,3-triazole-5-carboxylate which was used directly in the next step.

Step 2: 4-(5-(3,3-difluorocyclobutane-1-carboxamido)pyridin-2-yl)-1-methyl-1H-1,2,3-triazole-5-carboxylic acid Crude methyl 4-(5-(3,3-difluorocyclobutane-1-carboxamido)pyridin-2-yl)-1-methyl-1H-1,2,3-triazole-5-carboxylate (4.3 mmol) was treated with 2 M aqueous NaOH (50 mL), and THF (25 mL) and stirred vigorously for 30 minutes. Next, the reaction was treated with conc. HCl until pH=5. The precipitate was filtered and dried under vacuum to provide 4-(5-(3,3-difluorocyclobutane-1-carboxamido) pyridin-2-yl)-1-methyl-1H-1,2,3-triazole-5-carboxylic acid which was used in the next step without further purification.

Step 3: 1-(2-fluoro-5-methylpyridin-4-yl)ethyl (4-(5-(3,3-difluorocyclobutane-1-carboxamido)pyridin-2-yl)-1-methyl-1H-1,2,3-triazol-5-yl)carbamate (Compound 26)

A solution of 4-(5-(3,3-difluorocyclobutane-1-carboxamido)pyridin-2-yl)-1-methyl-1H-1,2,3-triazole-5-carboxylic acid (0.0889 mmol) in 100 □L DMF was treated with 50% T3P in DMF (0.178 mmol) TMS-N3 (0.156 mmol) and TEA (0.267 mmol) and the mixture stirred for 20 minutes. 1-(2-fluoro-5-methylpyridin-4-yl)ethan-1-ol (0.156 mmol) was added and the reaction heated at 65° C. for 2 hours. The reaction was cooled to rt and purified by RP HPLC to provide 1-(2-fluoro-5-methylpyridin-4-yl)ethyl (4-(5-(3,3-difluorocyclobutane-1-carboxamido)pyridin-2-yl)-1-methyl-1H-1,2,3-triazol-5-yl)carbamate (Compound 26). (MS (m/z) 490.04) [M+H]+) 1H NMR (400 MHz, Acetonitrile-d3) δ 9.00-8.89 (m, 1H), 8.88-8.75 (m, 1H), 8.55 (s, 1H), 8.20 (ddt, J=9.1, 5.8, 2.8 Hz, 1H), 8.07-7.97 (m, 2H), 7.06 (s, 1H), 5.90 (q, J=6.7 Hz, 1H), 3.96 (s, 3H), 3.18-3.06 (m, 1H), 3.02-2.79 (m, 3H), 2.31 (s, 3H), 2.10 (m, 1H), 1.53 (d, J=6.7 Hz, 3H).

Example 50

Preparation of 1-(2-fluoro-5-methylpyridin-4-yl) ethyl (4-(5-(1-cyanocyclopropane-1-carboxamido) pyridin-2-yl)-1-methyl-1H-1,2,3-triazol-5-yl)carbamate (Compound 27)

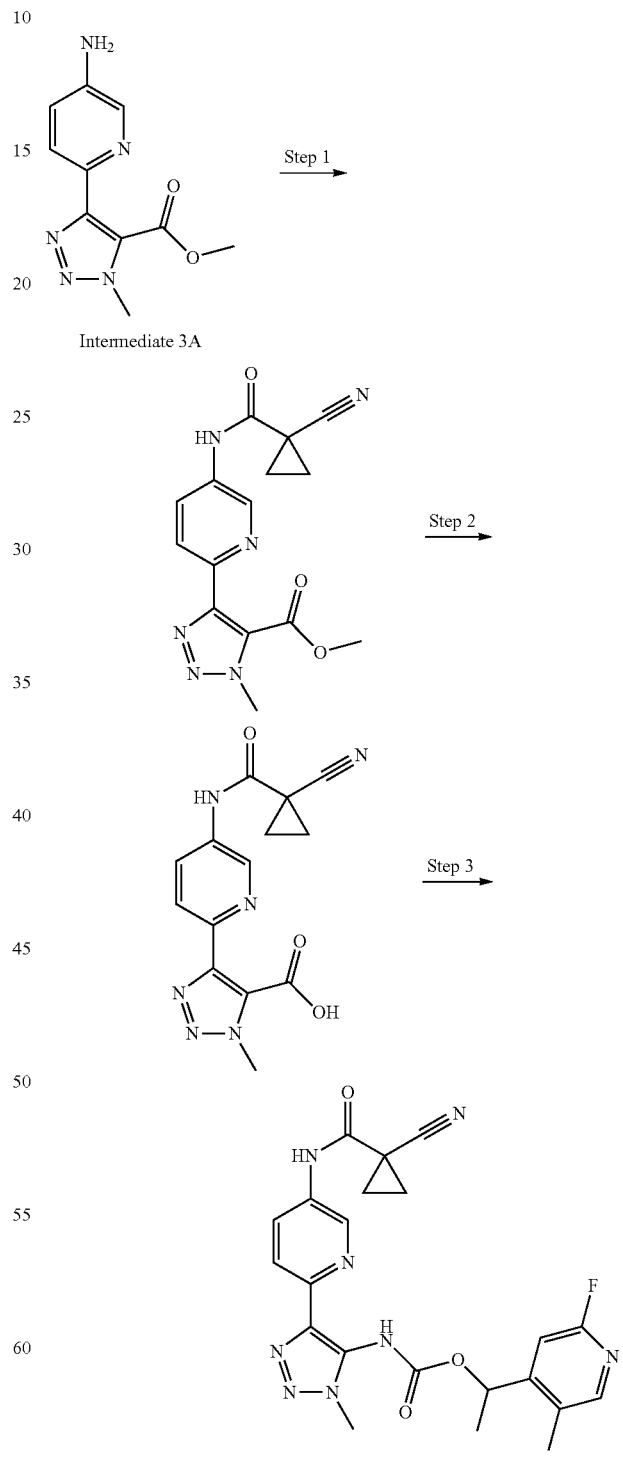

Compound 27

235

Step 1: methyl 4-(5-(1-cyanocyclopropane-1-carboxamido)pyridin-2-yl)-1-methyl-1H-1,2,3-triazole-5-carboxylate Following the procedure described in Example 49, step 1 for the synthesis methyl 4-(5-(3,3-difluorocyclobutane-1-carboxamido)pyridin-2-yl)-1-methyl-1H-1,2,3-triazole-5-carboxylate, using 1-cyanocyclopropane-1-carboxylic acid (5.1 mmol) in place of 3,3-difluorocyclobutane-1-carboxylic acid, methyl 4-(5-(1-cyanocyclopropane-1-carboxamido)pyridin-2-yl)-1-methyl-1H-1,2,3-triazole-5-carboxylate was obtained.

Step 2: 4-(5-(1-cyanocyclopropane-1-carboxamido)pyridin-2-yl)-1-methyl-1H-1,2,3-triazole-5-carboxylic acid Following the procedure described in Example 49, step 2 for the synthesis 4-(5-(3,3-difluorocyclobutane-1-carboxamido)pyridin-2-yl)-1-methyl-1H-1,2,3-triazole-5-carboxylic acid, using methyl 4-(5-(1-cyanocyclopropane-1-carboxamido)pyridin-2-yl)-1-methyl-1H-1,2,3-triazole-5-carboxylate (5.1 mmol) in place of methyl 4-(5-(3,3-difluorocyclobutane-1-carboxamido)pyridin-2-yl)-1-methyl-1H-1,2,3-triazole-5-carboxylate, 4-(5-(1-cyanocyclopropane-1-carboxamido)pyridin-2-yl)-1-methyl-1H-1,2,3-triazole-5-carboxylic acid was obtained.

Step 3: 1-(2-fluoro-5-methylpyridin-4-yl)ethyl(4-(5-(1-cyanocyclopropane-1-carboxamido)pyridin-2-yl)-1-methyl-1H-1,2,3-triazol-5-yl)carbamate (Compound 27)

Following the procedure described in Example 49, step 3 for the synthesis of 1-(2-fluoro-5-methylpyridin-4-yl)ethyl (4-(5-(3,3-difluorocyclobutane-1-carboxamido)pyridin-2-yl)-1-methyl-1H-1,2,3-triazol-5-yl)carbamate, using 4-(5-(1-cyanocyclopropane-1-carboxamido)pyridin-2-yl)-1-methyl-1H-1,2,3-triazole-5-carboxylic acid (0.0961 mmol) in place of 4-(5-(3,3-difluorocyclobutane-1-carboxamido)pyridin-2-yl)-1-methyl-1H-1,2,3-triazole-5-carboxylic acid, 4-(5-(3,3-difluorocyclobutane-1-carboxamido)pyridin-2-yl)-1-methyl-1H-1,2,3-triazole-5-carboxylic acid was obtained (Compound 27). (MS (m/z) 465.12 [M+H]+). 1H NMR (400 MHz, Acetonitrile-d3) δ 9.00-8.89 (m, 1H), 8.88-8.75 (m, 1H), 8.55 (s, 1H), 8.20 (ddt, J=9.1, 5.8, 2.8 Hz, 1H), 8.07-7.97 (m, 2H), 7.06 (s, 1H), 5.90 (q, J=6.7 Hz, 1H), 3.96 (s, 3H), 3.18-3.06 (m, 1H), 3.02-2.79 (m, 3H), 2.31 (s, 3H), 2.10 (m, 1H), 1.53 (d, J=6.7 Hz, 3H).

Example 51

Preparation of (R)-1-(2,5-difluoropyridin-3-yl)ethyl (4-(5-(3,3-difluorocyclobutane-1-carboxamido)pyridin-2-yl)-1-methyl-1H-1,2,3-triazol-5-yl)carbamate (Compound 28)

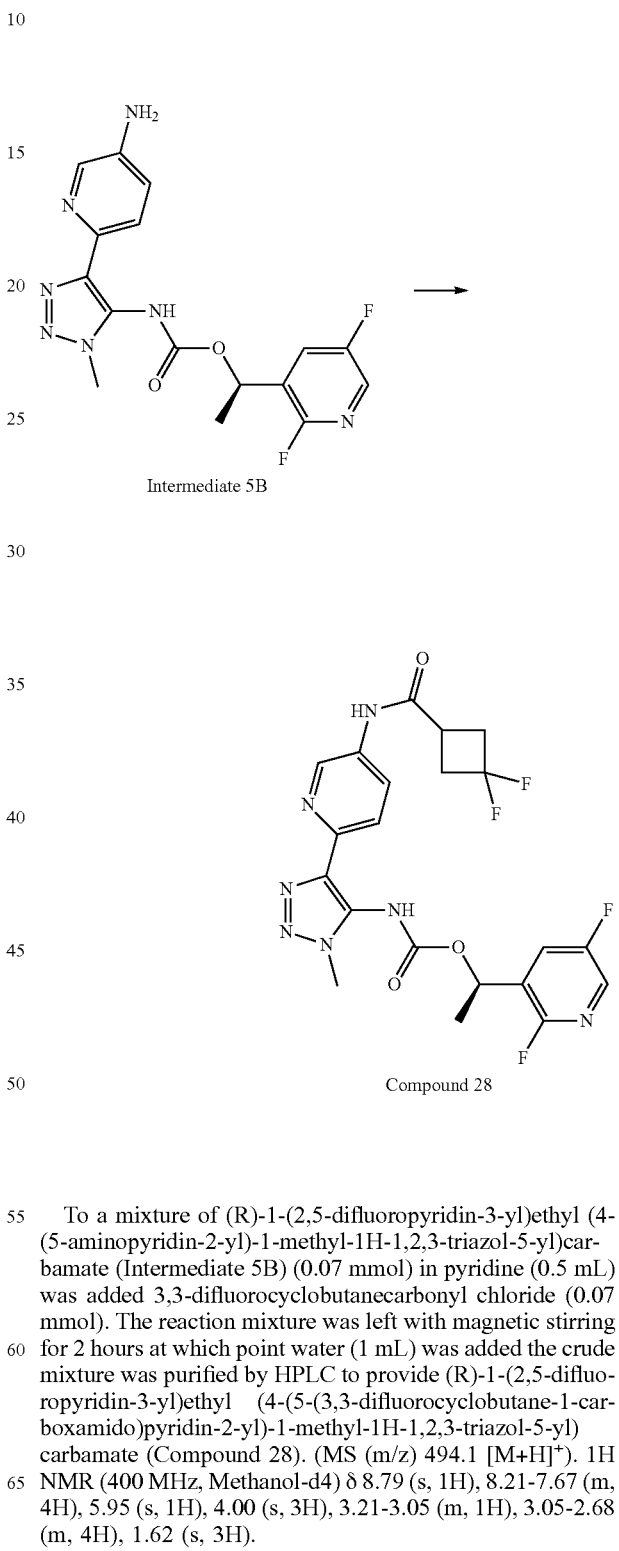

To a mixture of (R)-1-(2,5-difluoropyridin-3-yl)ethyl (4-(5-aminopyridin-2-yl)-1-methyl-1H-1,2,3-triazol-5-yl)carbamate (Intermediate 5B) (0.07 mmol) in pyridine (0.5 mL) was added 3,3-difluorocyclobutanecarbonyl chloride (0.07 mmol). The reaction mixture was left with magnetic stirring for 2 hours at which point water (1 mL) was added the crude mixture was purified by HPLC to provide (R)-1-(2,5-difluoropyridin-3-yl)ethyl (4-(5-(3,3-difluorocyclobutane-1-carboxamido)pyridin-2-yl)-1-methyl-1H-1,2,3-triazol-5-yl) carbamate (Compound 28). (MS (m/z) 494.1 [M+H]+). 1H NMR (400 MHz, Methanol-d4) δ 8.79 (s, 1H), 8.21-7.67 (m, 4H), 5.95 (s, 1H), 4.00 (s, 3H), 3.21-3.05 (m, 1H), 3.05-2.68 (m, 4H), 1.62 (s, 3H).

Example 52

Preparation of Compounds 29 to 37

Compounds 29 to 37 were generally synthesized according Scheme C, Step 4. For example, (R)-1-(2-chloropyridin-3-yl)ethyl (4-(5-benzamidopyridin-2-yl)-1-methyl-1H-1,2,3-triazol-5-yl)carbamate (Compound 29) was prepared as follows.

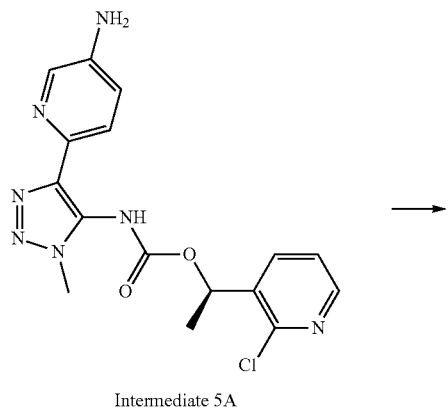

Intermediate 5A

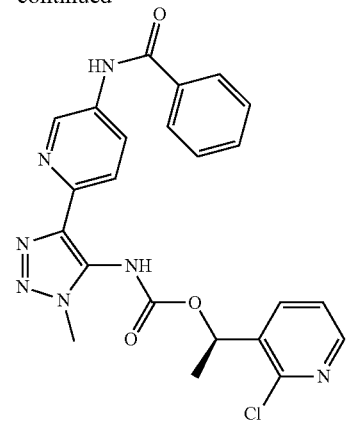

Compound 29

To a mixture of (R)-1-(2-chloropyridin-3-yl)ethyl (4-(5-aminopyridin-2-yl)-1-methyl-1H-1,2,3-triazol-5-yl)carbamate hydrochloride (Intermediate 5A) (0.07 mmol) in pyridine (0.5 mL) was added benzoyl chloride (0.07 mmol). The reaction mixture was left with magnetic stirring for 2 h at which point water (1 mL) was added the crude mixture was purified by HPLC to provide (R)-1-(2-chloropyridin-3-yl)ethyl (4-(5-benzamidopyridin-2-yl)-1-methyl-1H-1,2,3-triazol-5-yl)carbamate (Compound 29). (MS (m/z) 478.1 [M+H]$^+$). $^1$H NMR (400 MHz, Methanol-d$_4$) δ 9.02 (s, 1H), 8.46-7.88 (m, 6H), 7.88-7.01 (m, 4H), 6.09 (q, J=6.6 Hz, 1H), 3.99 (s, 3H), 1.62 (s, 3H).

Compounds 30-37 (Table 1) were similarly prepared according to Scheme C, Step 4 by reacting (R)-1-(2-chloropyridin-3-yl)ethyl (4-(5-aminopyridin-2-yl)-1-methyl-1H-1,2,3-triazol-5-yl)carbamate (Intermediate 5A) (Example 21) with a Reagent listed in Table 1 following the general process described for Compound 29.

TABLE 1

Compounds prepared according to Scheme C, Step 4.

| Compound No. | Structure | Reagent | LCMS m/z | 1H NMR |
|---|---|---|---|---|
| Compound 29 (R)-1-(2-chloropyridin-3-yl)ethyl (4-(5-benzamidopyridin-2-yl)-1-methyl-1H-1,2,3-triazol-5-yl)carbamate | 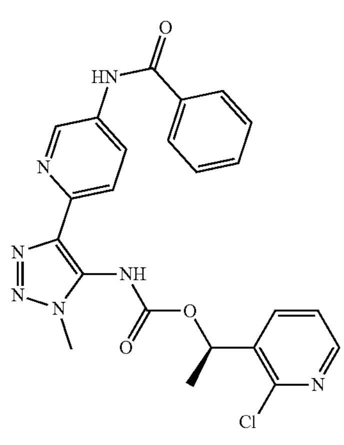 [SMILES: C[C@@H](OC(=O)Nc1c(-c2ccc(NC(=O)c3ccccc3)cn2)nnn1C)c1cccnc1Cl] | | 478.1 | 1H NMR (400 MHz, Methanol-d4) δ 9.02 (s, 1H), 8.46-7.88 (m, 6H), 7.88-7.01 (m, 4H), 6.09 (q, J = 6.6 Hz, 1H), 3.99 (s, 3H), 1.62 (s, 3H). |

TABLE 1-continued

Compounds prepared according to Scheme C, Step 4.

| Compound No. | Structure | Reagent | LCMS m/z | 1H NMR |
|---|---|---|---|---|
| Compound 30 (R)-1-(2-chloropyridin-3-yl)ethyl (4-(5-butyramidopyridin-2-yl)-1-methyl-1H-1,2,3-triazol-5-yl)carbamate | 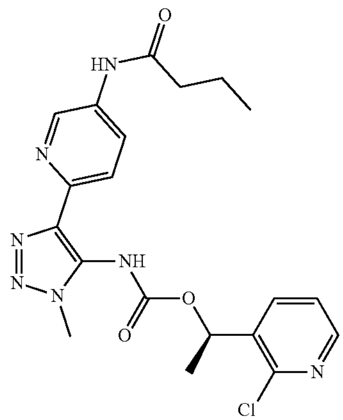 [SMILES: CCCC(=O)Nc1ccc(-c2nnn(C)c2NC(=O)O[C@H](C)c2cccnc2Cl)nc1] | | 444.1 | 1H NMR (400 MHz, Methanol-d4) δ 8.85 (s, 1H), 8.53-7.71 (m, 4H), 7.46 (s, 1H), 6.08 (d, J = 7.1 Hz, 1H), 3.99 (s, 3H), 2.43 (t, J = 7.4 Hz, 2H), 1.88-1.23 (m, 5H), 1.05 (t, J = 7.4 Hz, 3H). |
| Compound 31 (R)-1-(2-chloropyridin-3-yl)ethyl (4-(5-(2-methoxyacetamido)pyridin-2-yl)-1-methyl-1H-1,2,3-triazol-5-yl)carbamate | 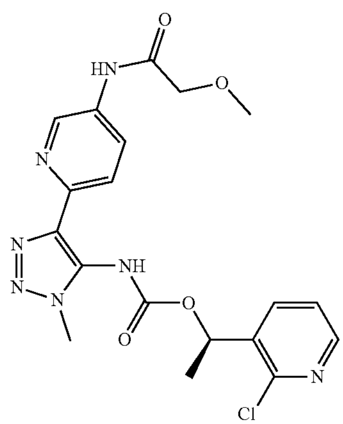 [SMILES: COCC(=O)Nc1ccc(-c2nnn(C)c2NC(=O)O[C@H](C)c2cccnc2Cl)nc1] | | 446.1 | 1H NMR (400 MHz, Methanol-d4) δ 8.92 (s, 1H), 8.51-7.79 (m, 4H), 7.47 (s, 1H), 6.08 (d, J = 6.5 Hz, 1H), 4.12 (d, J = 2.5 Hz, 2H), 3.99 (d, J = 2.6 Hz, 3H), 3.54 (d, J = 2.5 Hz, 3H), 1.90-1.23 (m, 3H). |
| Compound 32 (R)-1-(2-chloropyridin-3-yl)ethyl (1-methyl-4-(5-(1-methylcyclopropane-1-carboxamido)pyridin-2-yl)-1H-1,2,3-triazol-5-yl)carbamate | 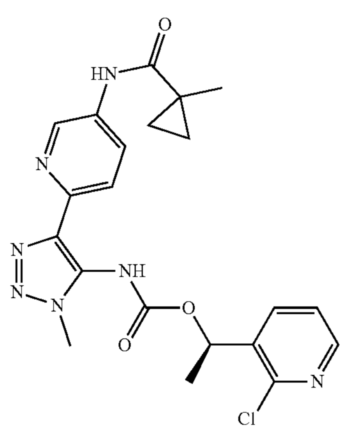 | | 456.2 | 1H NMR (400 MHz, Methanol-d4) δ 8.85 (s, 1H), 8.53-7.69 (m, 4H), 7.46 (s, 1H), 6.08 (d, J = 6.8 Hz, 1H), 3.98 (s, 3H), 1.51 (s, 6H), 1.27 (q, J = 3.8 Hz, 2H), 0.82-0.73 (m, 2H). |

TABLE 1-continued

Compounds prepared according to Scheme C, Step 4.

| Compound No. | Structure | Reagent | LCMS m/z | 1H NMR |
|---|---|---|---|---|
| Compound 33 (R)-1-(2-chloropyridin-3-yl)ethyl (1-methyl-4-(5-propionamidopyridin-2-yl)-1H-1,2,3-triazol-5-yl)carbamate | 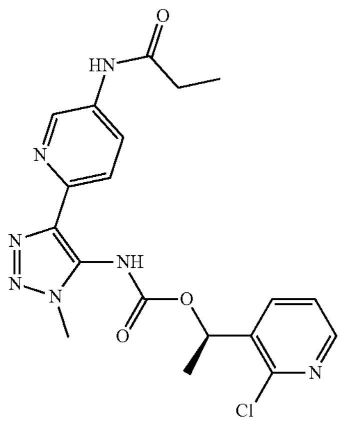 [SMILES: CCC(=O)Nc1ccc(-c2nnn(C)c2NC(=O)O[C@H](C)c2cccnc2Cl)nc1] | | 430.1 | 1H NMR (400 MHz, Methanol-d4) δ 8.84 (s, 1H), 8.49-7.71 (m, 4H), 7.44 (dd, J = 7.7, 4.7 Hz, 1H), 6.08 (d, J = 6.6 Hz, 1H), 3.99 (s, 3H), 2.47 (q, J = 7.6 Hz, 2H), 1.84-1.38 (m, 3H), 1.25 (t, J = 7.6 Hz, 3H). |
| Compound 34 (R)-1-(2-chloropyridin-3-yl)ethyl (4-(5-(cyclopropanecarboxamido)pyridin-2-yl)-1-methyl-1H-1,2,3-triazol-5-yl)carbamate | 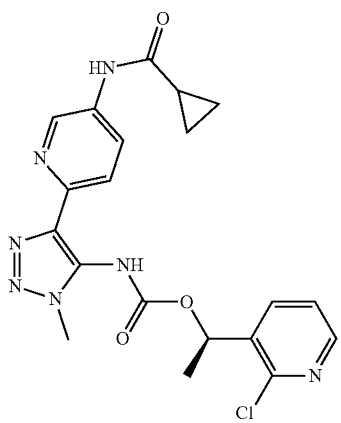 [SMILES: C[C@@H](OC(=O)Nc1c(-c2ccc(NC(=O)C3CC3)cn2)nnn1C)c1cccnc1Cl] | | 442.1 | 1H NMR (400 MHz, Methanol-d4) δ 8.84 (s, 1H), 8.53-7.73 (m, 4H), 7.44 (dd, J = 7.7, 4.7 Hz, 1H), 6.08 (d, J = 6.7 Hz, 1H), 3.98 (s, 3H), 1.83 (tt, J = 7.9, 4.6 Hz, 1H), 1.78-1.35 (m, 3H), 0.98 (ddt, J = 34.8, 8.0, 2.9 Hz, 4H). |
| Compound 35 (R)-1-(2-chloropyridin-3-yl)ethyl (4-(5-(cyclobutanecarboxamido)pyridin-2-yl)-1-methyl-1H-1,2,3-triazol-5-yl)carbamate | 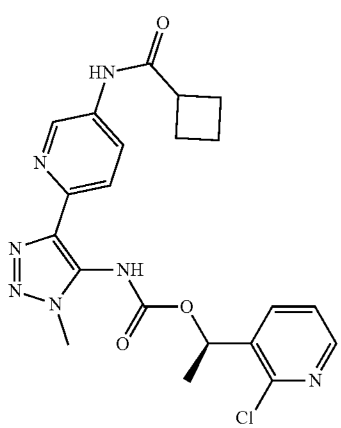 [SMILES: C[C@@H](OC(=O)Nc1c(-c2ccc(NC(=O)C3CCC3)cn2)nnn1C)c1cccnc1Cl] | | 456.2 | 1H NMR (400 MHz, Methanol-d4) δ 8.85 (s, 1H), 8.55-7.76 (m, 4H), 7.44 (dd, J = 7.7, 4.8 Hz, 1H), 6.08 (d, J = 6.9 Hz, 1H), 3.98 (s, 3H), 2.51-2.33 (m, 2H), 2.26 (dddd, J = 10.2, 8.6, 6.8, 3.3 Hz, 2H), 2.17-2.02 (m, 1H), 2.02-1.88 (m, 1H), 1.57 (d, J = 31.9 Hz, 3H). |

TABLE 1-continued

Compounds prepared according to Scheme C, Step 4.

| Compound No. | Structure | Reagent | LCMS m/z | 1H NMR |
|---|---|---|---|---|
| Compound 36 (R)-1-(2-chloropyridin-3-yl)ethyl (4-(5-(2,2-difluoroacetamido)pyridin-2-yl)-1-methyl-1H-1,2,3-triazol-5-yl)carbamate | 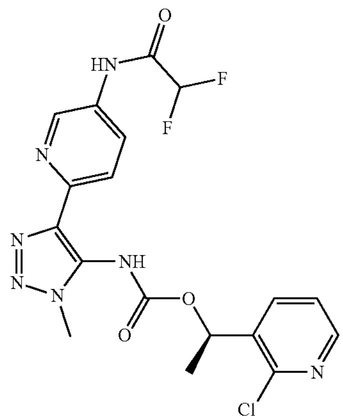 [SMILES: C[C@@H](OC(=O)Nc1c(-c2ccc(NC(=O)C(F)F)cn2)nnn1C)c1cccnc1Cl] | | 452.1 | 1H NMR (400 MHz, Methanol-d4) δ 8.93 (s, 1H), 8.43-7.72 (m, 4H), 7.47 (s, 1H), 6.52-5.83 (m, 2H), 3.99 (s, 3H), 1.58 (d, J = 26.9 Hz, 3H). |
| Compound 37 (R)-1-(2-chloropyridin-3-yl)ethyl (4-(5-(3,3-difluorocyclobutane-1-carboxamido)pyridin-2-yl)-1-methyl-1H-1,2,3-triazol-5-yl)carbamate | 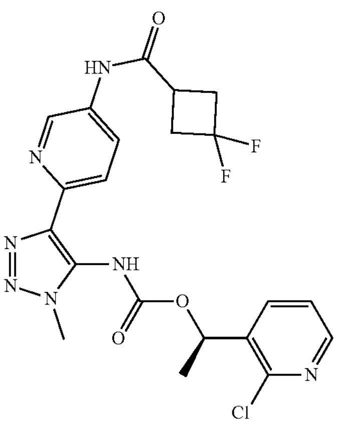 [SMILES: C[C@@H](OC(=O)Nc1c(-c2ccc(NC(=O)C3CC(F)(F)C3)cn2)nnn1C)c1cccnc1Cl] | | 492.2 | 1H NMR (400 MHz, Methanol-d4) δ 8.85 (s, 1H), 8.53-7.72 (m, 4H), 7.47 (s, 1H), 6.07 (d, J = 6.5 Hz, 1H), 3.99 (s, 3H), 3.15 (pd, J = 8.4, 3.2 Hz, 1H), 3.05-2.69 (m, 4H), 1.61 (s, 3H). |

Example 53

Preparation of (R)-1-(2-chloropyridin-3-yl)ethyl (4-(5-(azetidine-3-carboxamido)pyridin-2-yl)-1-methyl-1H-1,2,3-triazol-5-yl)carbamate (Compound 38)

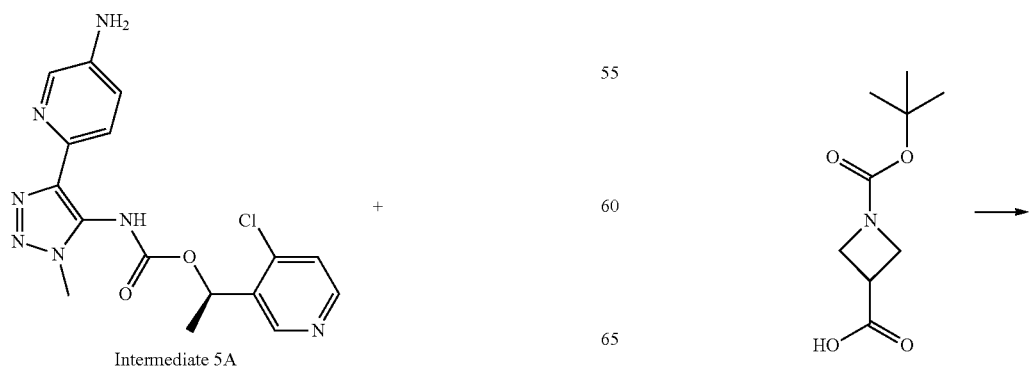

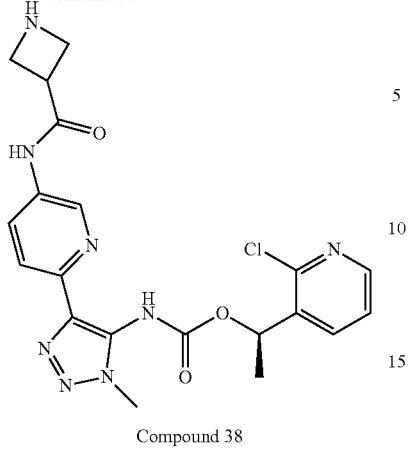

Compound 38

To a mixture of (R)-1-(2-chloropyridin-3-yl)ethyl (4-(5-aminopyridin-2-yl)-1-methyl-1H-1,2,3-triazol-5-yl)carbamate hydrochloride (Intermediate 5A) (0.06 mmol) in pyridine (0.5 mL) was added 1-Boc-azetidine-3-carboxylic acid (0.067 mmol) and N-Ethyl-N'-(3-dimethylaminopropyl) carbodiimide hydrochloride (0.064 mmol). The reaction mixture was left with magnetic stirring for 2 hours at which point it was concentrated in vacuo and trifluoroacetic acid (0.2 mL) was added. The reaction mixture was left with magnetic stirring for 0.5 h at which point water (1 mL) and pyridine (0.5 mL) was added the crude mixture was purified by HPLC to provide (R)-1-(2-chloropyridin-3-yl)ethyl (4-(5-(azetidine-3-carboxamido)pyridin-2-yl)-1-methyl-1H-1,2,3-triazol-5-yl)carbamate (Compound 38). (MS (m/z) 457.1 [M+H]+). ¹H NMR (400 MHz, Methanol-$d_4$) δ 8.86 (s, 1H), 8.61-7.76 (m, 4H), 7.59 (d, J=90.0 Hz, 1H), 6.07 (s, 1H), 4.53-4.18 (m, 4H), 4.00 (s, 3H), 3.87 (tt, J=8.9, 7.1 Hz, 1H), 1.66 (d, J=36.7 Hz, 3H).

Example 54

Preparation of Compounds 39 to 184 and 195 to 296

Compounds 39 to 184 and 195 to 296 were generally synthesized according Scheme C, Step 4. For example, (R)-1-(2,5-difluoropyridin-3-yl)ethyl(4-(5-(1-cyanocyclopropane-1-carboxamido) pyridin-2-yl)-1-methyl-1H-1,2,3-triazol-5-yl)carbamate (Compound 39) was prepared as follows.

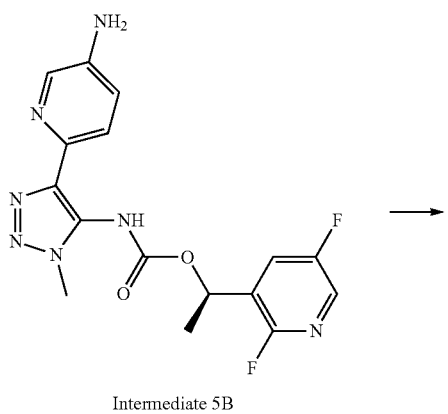

Intermediate 5B

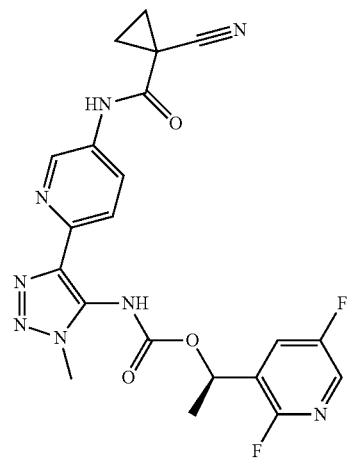

Compound 39

To a mixture of (R)-1-(2,5-difluoropyridin-3-yl)ethyl (4-(5-aminopyridin-2-yl)-1-methyl-1H-1,2,3-triazol-5-yl)carbamate hydrochloride (Intermediate 5B) (0.06 mmol) in pyridine (0.5 mL) was added 1-cyanocyclopropane-1-carboxylic acid (0.067 mmol) and N-Ethyl-N'-(3-dimethylaminopropyl) carbodiimide hydrochloride (0.067 mmol). The reaction mixture was left with magnetic stirring for 2 hours at which point water (1 mL) was added the crude mixture was purified by HPLC to provide (R)-1-(2,5-difluoropyridin-3-yl)ethyl (4-(5-(1-cyanocyclopropane-1-carboxamido) pyridin-2-yl)-1-methyl-1H-1,2,3-triazol-5-yl)carbamate (Compound 39). (MS (m/z) 469.1 [M+H]+). ¹H NMR (400 MHz, Methanol-$d_4$) δ 8.79 (s, 1H), 8.33-7.46 (m, 4H), 5.95 (d, J=6.9 Hz, 1H), 4.00 (s, 3H), 1.82-1.36 (m, 7H).

Compounds 40-160 and 195-206 (Table 2) were similarly prepared according to Scheme C, Step 4 by reacting (R)-1-(2-chloropyridin-3-yl)ethyl (4-(5-aminopyridin-2-yl)-1-methyl-1H-1,2,3-triazol-5-yl)carbamate, Intermediate 5A (Example 21) with the Reagent listed in Table 2 in place of 1-cyanocyclopropane-1-carboxylic acid following the general process described for Compound 39.

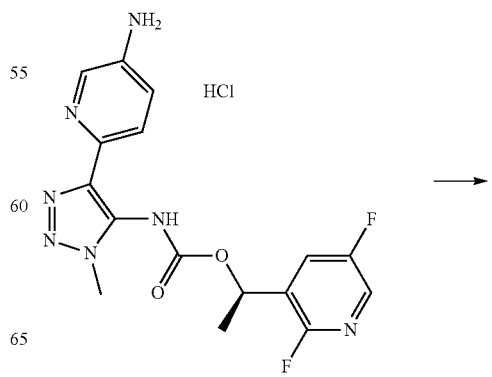

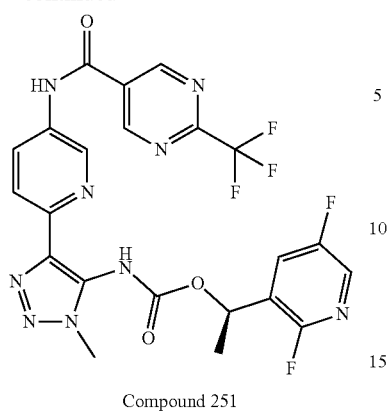

Compound 251

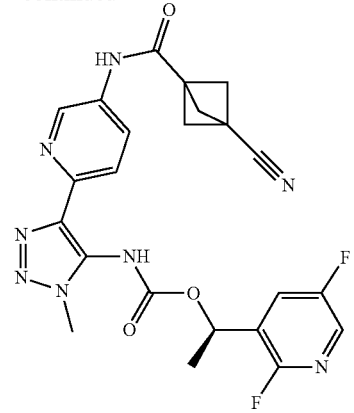

Compound 162

To a mixture of (R)-1-(2,5-difluoropyridin-3-yl)ethyl (4-(5-aminopyridin-2-yl)-1-methyl-1H-1,2,3-triazol-5-yl)carbamate hydrochloride (Intermediate 5B) (0.073 mmol) in pyridine (1.0 mL) was added 2-(trifluoromethyl)pyrimidine-5-carboxylic acid (0.082 mmol) and N-Ethyl-N'-(3-dimethylaminopropyl) carbodiimide hydrochloride (0.087 mmol). The reaction mixture was left with magnetic stirring for 2 hours at which point water (1 mL) was added and the crude mixture was purified by HPLC to provide (R)-1-(2,5-difluoropyridin-3-yl)ethyl (1-methyl-4-(5-(2-(trifluoromethyl)pyrimidine-5-carboxamido)pyridin-2-yl)-1H-1,2,3-triazol-5-yl)carbamate (Compound 251). (MS (m/z) 550.0 [M+H]$^+$). $^1$H NMR (400 MHz, Methanol-d$_4$) δ 9.47 (s, 2H), 8.95 (s, 1H), 8.25 (dd, J=8.6, 2.6 Hz, 1H), 8.03 (s, 1H), 7.98 (dd, J=8.7, 0.7 Hz, 1H), 7.87 (s, 1H), 5.95 (d, J=7.1 Hz, 1H), 3.99 (s, 3H), 1.61 (s, 3H).

Compounds 161-165 and 207-284 (Table 2) were similarly prepared according to Scheme C, Step 4 by reacting (R)-1-(2,5-difluoropyridin-3-yl)ethyl (4-(5-aminopyridin-2-yl)-1-methyl-1H-1,2,3-triazol-5-yl)carbamate, Intermediate 5B (Example 22) with the Reagent listed in Table 2 in place of 1-cyanocyclopropane-1-carboxylic acid following the general process described for Compound 39.

To a mixture of (R)-1-(2,5-difluoropyridin-3-yl)ethyl (4-(5-aminopyridin-2-yl)-1-methyl-1H-1,2,3-triazol-5-yl)carbamate hydrochloride (Intermediate 5B) (0.073 mmol) in pyridine (0.5 mL) was added 3-cyanobicyclo[1.1.1]pentane-1-carboxylic acid (0.080 mmol) and N-Ethyl-N'-(3-dimethylaminopropyl) carbodiimide hydrochloride (0.080 mmol). The reaction mixture was left with magnetic stirring for 2 hours at which point water (1 mL) was added the crude mixture was purified by HPLC to provide (R)-1-(2,5-difluoropyridin-3-yl)ethyl (4-(5-(3-cyanobicyclo[1.1.1]pentane-1-carboxamido)pyridin-2-yl)-1-methyl-1H-1,2,3-triazol-5-yl) carbamate (Compound 162). LCMS ((m/z) 495.175 [M+H]$^+$). $^1$H NMR (400 MHz, Methanol-d$_4$) δ 1H NMR (400 MHz, Methanol-d4) δ 8.83 (s, 1H), 8.22-7.58 (m, 4H), 5.94 (d, J=7.0 Hz, 1H), 3.99 (s, 3H), 2.64 (s, 6H), 1.61 (s, 3H).

Compounds 166-168, 285, and 288-290 (Table 2) were similarly prepared according to Scheme C, Step 4 by reacting (R)-1-(2-chloro-5-fluoropyridin-3-yl)ethyl (4-(5-aminopyridin-2-yl)-1-methyl-1H-1,2,3-triazol-5-yl)carbamate, Intermediate 5C (Example 23) with the Reagent listed in Table 2 in place of 1-cyanocyclopropane-1-carboxylic acid following the general process described for Compound 39.

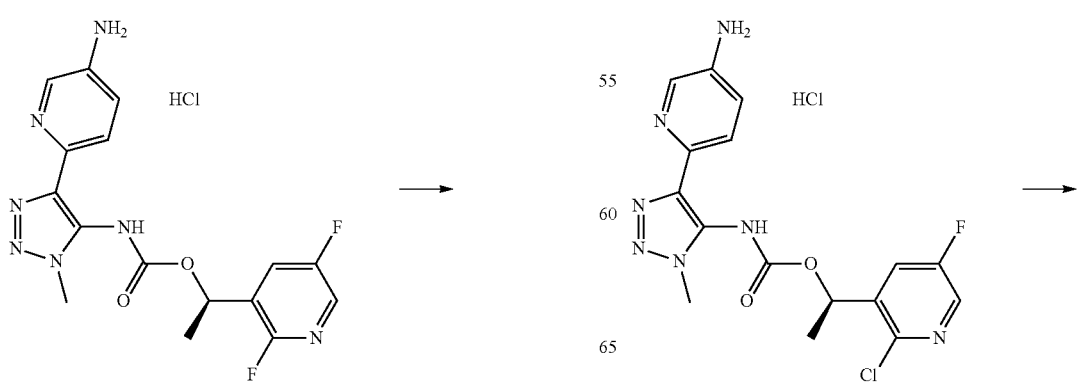

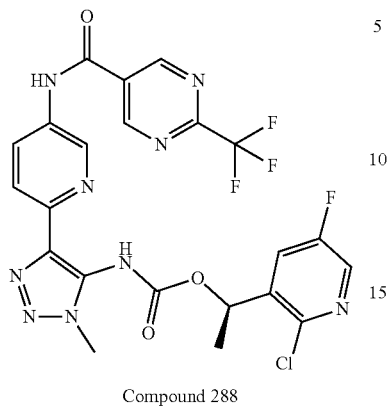

Compound 288

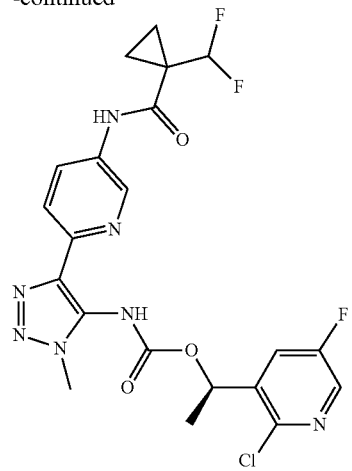

Compound 166

To a mixture of (R)-1-(2-chloro-5-fluoropyridin-3-yl) ethyl (4-(5-aminopyridin-2-yl)-1-methyl-1H-1,2,3-triazol-5-yl)carbamate hydrochloride (Intermediate 5C) (0.070 mmol) in pyridine (1.0 mL) was added 6-(trifluoromethyl) nicotinic acid (0.077 mmol) and N-Ethyl-N'-(3-dimethylaminopropyl) carbodiimide hydrochloride (0.084 mmol). The reaction mixture was left with magnetic stirring for 2 hours at which point water (1 mL) was added and the crude mixture was purified by HPLC to provide (R)-1-(2-chloro-5-fluoropyridin-3-yl)ethyl (1-methyl-4-(5-(6-(trifluoromethyl)nicotinamido)pyridin-2-yl)-1H-1,2,3-triazol-5-yl)carbamate (Compound 288). (MS (m/z) 565.0 [M+H]$^+$). $^1$H NMR (400 MHz, Methanol-d$_4$) δ 9.26 (d, J=2.1 Hz, 1H), 8.97 (s, 1H), 8.64-8.52 (m, 1H), 8.34-8.15 (m, 2H), 8.11-7.68 (m, 3H), 6.03 (d, J=7.2 Hz, 1H), 4.00 (s, 3H), 1.60 (s, 3H).

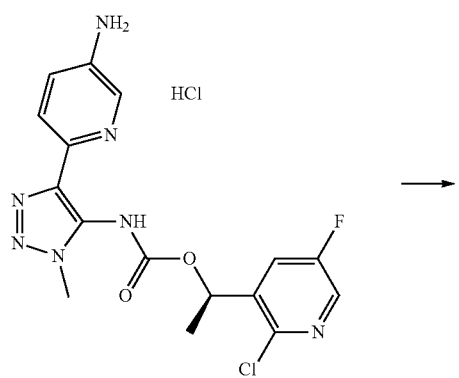

To a mixture of (R)-1-(2-chloro-5-fluoropyridin-3-yl) ethyl (4-(5-aminopyridin-2-yl)-1-methyl-1H-1,2,3-triazol-5-yl)carbamate hydrochloride (Intermediate 5C) (0.054 mmol) in pyridine (2.0 mL) was added 1-(difluoromethyl) cyclopropane-1-carboxylic acid (0.081 mmol) and N-Ethyl-N'-(3-dimethylaminopropyl) carbodiimide hydrochloride (0.107 mmol). The reaction mixture was left with magnetic stirring for 2 hours, concentrated and purified by HPLC to provide (R)-1-(2-chloro-5-fluoropyridin-3-yl)ethyl (4-(5-(1-(difluoromethyl)cyclopropane-1-carboxamido)pyridin-2-yl)-1-methyl-1H-1,2,3-triazol-5-yl)carbamate (Compound 166). (MS (m/z) 510.15 [M+H]$^+$). $^1$H NMR (400 MHz, DMSO-d$_6$) δ 9.86 (bs, 1H), 9.63 (s, 1H), 8.73 (s, 1H), 8.42 (bs, 1H), 8.10-7.82 (m, 3H), 6.58 (t, J=56.9 Hz, 1H), 5.83 (bs, 1H), 3.89 (s, 3H), 1.57 (bs, 3H), 1.43-1.27 (m, 2H), 1.24-1.03 (m, 2H).

Compounds 169-174 and 290-296 (Table 2) were similarly prepared according to Scheme C, Step 4 by reacting (R)-1-(2-fluoropyridin-3-yl)ethyl (4-(5-aminopyridin-2-yl)-1-methyl-1H-1,2,3-triazol-5-yl)carbamate, Intermediate 5D (Example 24) with the Reagent listed in Table 2 in place of 1-cyanocyclopropane-1-carboxylic acid following the general process described for Compound 39.

Compounds 175-180 (Table 2) were similarly prepared according to Scheme C, Step 4 by reacting (R)-1-(5-fluoro-2-methylpyridin-3-yl)ethyl (4-(5-aminopyridin-2-yl)-1-methyl-1H-1,2,3-triazol-5-yl)carbamate, Intermediate 5E (Example 25) with the Reagent listed in Table 2 in place of 1-cyanocyclopropane-1-carboxylic acid following the general process described for Compound 39.

Compounds 181-182 (Table 2) were similarly prepared according to Scheme C, Step 4 by reacting 1-(2-chloro-6-fluoropyridin-3-yl)ethyl (4-(5-aminopyridin-2-yl)-1-methyl-1H-1,2,3-triazol-5-yl)carbamate, Intermediate 5F (Example 34) with the Reagent listed in Table 2 in place of 1-cyanocyclopropane-1-carboxylic acid following the general process described for Compound 39.

Compounds 183-184 (Table 2) were similarly prepared according to Scheme C, Step 4 by reacting (R)-1-(2-chloropyridin-3-yl)ethyl (4-(5-amino-4-fluoropyridin-2-yl)-1-methyl-1H-1,2,3-triazol-5-yl)carbamate, Intermediate 7B (Example 18) with the Reagent listed in Table 2 in place of 1-cyanocyclopropane-1-carboxylic acid following the general process described for Compound 39.

Compounds 201-204, 245-246, and 265-270 (Table 2) were prepared using racemic mixtures of reagents listed in Table 2 and purified by chiral SFC purification to provide single stereoisomers.

TABLE 2

Compounds prepared according to Scheme C, Step 4.

| Compound No. | Structure | Reagent | LCMS m/z | 1H NMR |
|---|---|---|---|---|
| Compound 39 (R)-1-(2,5-difluoropyridin-3-yl)ethyl (4-(5-(1-cyanocyclopropane-1-carboxamido)pyridin-2-yl)-1-methyl-1H-1,2,3-triazol-5-yl)carbamate | 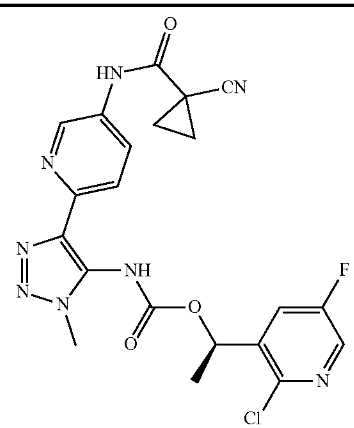 | | 469.1 | 1H NMR (400 MHz, Methanol-d4) δ 8.79 (s, 1H), 8.33-7.46 (m, 4H), 5.95 (d, J = 6.9 Hz, 1H), 4.00 (s, 3H), 1.82-1.36 (m, 7H). |
| Compound 40 (R)-1-(2-chloropyridin-3-yl)ethyl (4-(5-(1-chlorocyclopropane-1-carboxamido)pyridin-2-yl)-1-methyl-1H-1,2,3-triazol-5-yl)carbamate | 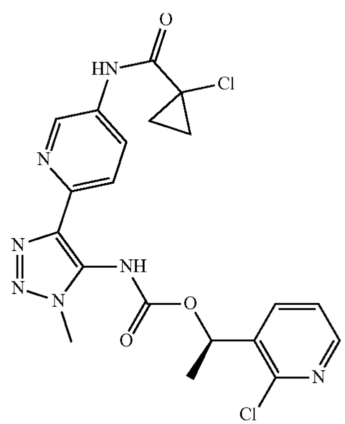 [SMILES: C[C@@H](OC(=O)Nc1c(-c2ccc(NC(=O)C3(Cl)CC3)cn2)nnn1C)c1cccnc1Cl] | | 476.3 | 1H NMR (400 MHz, Methanol-d4) δ 8.87 (s, 1H), 8.48-7.76 (m, 4H), 7.46 (s, 1H), 6.08 (q, J = 6.5 Hz, 1H), 3.99 (s, 3H), 1.76-1.70 (m, 2H), 1.64 (d, J = 28.0 Hz, 3H), 1.46-1.38 (m, 2H). |

TABLE 2-continued

Compounds prepared according to Scheme C, Step 4.

| Compound No. | Structure | Reagent | LCMS m/z | 1H NMR |
|---|---|---|---|---|
| Compound 41 (R)-1-(2-chloropyridin-3-yl)ethyl (4-(5-(6,6-difluorospiro[3.3]heptane-2-carboxamido)pyridin-2-yl)-1-methyl-1H-1,2,3-triazol-5-yl)carbamate | 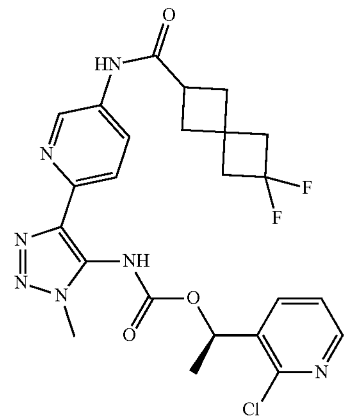 [SMILES: C[C@@H](OC(=O)Nc1c(-c2ccc(NC(=O)C3CC4(C3)CC(F)(F)C4)cn2)nnn1C)c1cccnc1Cl] | | 532.2 | 1H NMR (400 MHz, Methanol-d4) δ 8.84 (s, 1H), 8.54-7.71 (m, 4H), 7.46 (s, 1H), 6.07 (d, J = 7.1 Hz, 1H), 3.98 (s, 3H), 3.26 (p, J = 8.4 Hz, 1H), 2.69 (td, J = 12.2, 2.6 Hz, 2H), 2.64-2.45 (m, 4H), 2.45-2.31 (m, 2H), 1.61 (s, 3H). |
| Compound 42 (R)-1-(2-chloropyridin-3-yl)ethyl (4-(5-(2-oxaspiro[3.3]heptane-6-carboxamido)pyridin-2-yl)-1-methyl-1H-1,2,3-triazol-5-yl)carbamate | 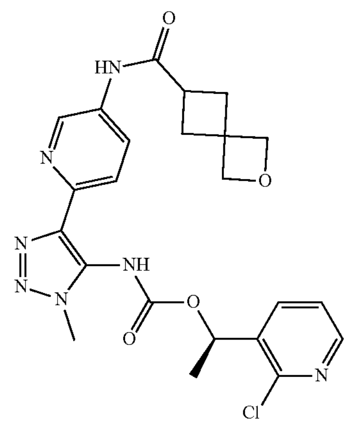 [SMILES: C[C@@H](OC(=O)Nc1c(-c2ccc(NC(=O)C3CC4(COC4)C3)cn2)nnn1C)c1cccnc1Cl] | | 498.2 | 1H NMR (400 MHz, Methanol-d4) δ 8.83 (s, 1H), 8.52-7.74 (m, 4H), 7.46 (s, 1H), 6.07 (d, J = 7.0 Hz, 1H), 4.76 (s, 2H), 4.70 (s, 2H), 3.98 (s, 3H), 3.11 (p, J = 7.9 Hz, 1H), 2.56 (d, J = 8.0 Hz, 4H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 43 (R)-1-(2-chloropyridin-3-yl)ethyl (4-(5-(1,1-dioxidothietane-3-carboxamido)pyridin-2-yl)-1-methyl-1H-1,2,3-triazol-5-yl)carbamate | 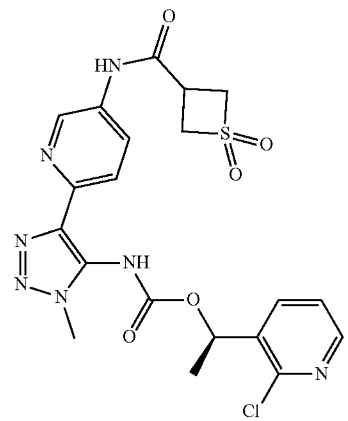 [SMILES: C[C@@H](OC(=O)Nc1c(-c2ccc(NC(=O)C3CS(=O)(=O)C3)cn2)nnn1C)c1cccnc1Cl] | | 506.2 | 1H NMR (400 MHz, Methanol-d4) δ 8.84 (s, 1H), 8.48-7.73 (m, 4H), 7.47 (s, 1H), 6.07 (d, J = 7.2 Hz, 1H), 4.63-4.45 (m, 2H), 4.45-4.25 (m, 2H), 3.55 (tt, J = 9.8, 7.6 Hz, 1H), 1.61 (s, 3H). |
| Compound 44 (R)-1-(2-chloropyridin-3-yl)ethyl (1-methyl-4-(5-(3-(oxetan-3-yl)bicyclo[1.1.1]pentane-1-carboxamido)pyridin-2-yl)-1H-1,2,3-triazol-5-yl)carbamate | 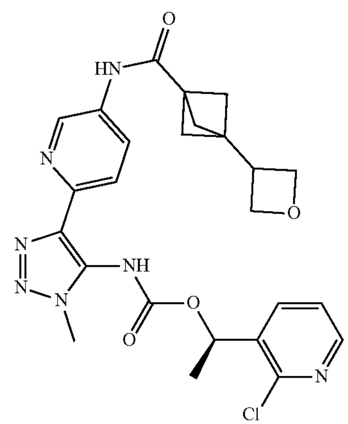 [SMILES: C[C@@H](OC(=O)Nc1c(-c2ccc(NC(=O)C34CC(C5COC5)(C3)C4)cn2)nnn1C)c1cccnc1Cl] | | 524.2 | 1H NMR (400 MHz, Methanol-d4) δ 8.92 (s, 1H), 8.46-7.70 (m, 4H), 7.47 (s, 1H), 6.08 (d, J = 7.1 Hz, 1H), 4.81 (dd, J = 7.9, 6.0 Hz, 2H), 4.52 (t, J = 6.0 Hz, 2H), 3.99 (s, 3H), 3.18 (tt, J = 8.0, 5.9 Hz, 1H), 2.15 (s, 6H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 45 (R)-1-(2-chloropyridin-3-yl)ethyl (4-(5-(3-(difluoromethyl)bicyclo[1.1.1]pentane-1-carboxamido)pyridin-2-yl)-1-methyl-1H-1,2,3-triazol-5-yl)carbamate | 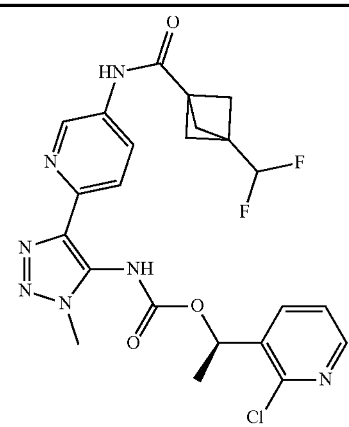 | | 518.2 | 1H NMR (400 MHz, Methanol-d4) δ 8.91 (s, 1H), 8.53-7.79 (m, 4H), 7.46 (s, 1H), 6.25-5.60 (m, 2H), 3.99 (s, 3H), 2.26 (s, 6H), 1.61 (s, 3H). |
| Compound 46 (R)-1-(2-chloropyridin-3-yl)ethyl (4-(5-(3-methoxybicyclo[1.1.1]pentane-1-carboxamido)pyridin-2-yl)-1-methyl-1H-1,2,3-triazol-5-yl)carbamate | 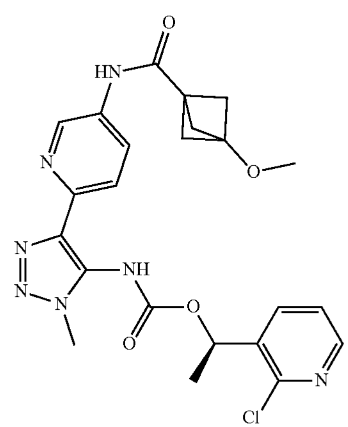 [SMILES: COC12CC(C(=O)Nc3ccc(-c4nnn(C)c4NC(=O)O[C@H](C)c4cccnc4Cl)nc3)(C1)C2] | | 498.1 | 1H NMR (400 MHz, Methanol-d4) δ 8.90 (s, 1H), 8.47-7.76 (m, 4H), 7.46 (s, 1H), 6.08 (d, J = 6.9 Hz, 1H), 3.99 (s, 3H), 3.36 (s, 3H), 2.28 (s, 6H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 47 (R)-1-(2-chloropyridin-3-yl)ethyl (1-methyl-4-(5-(3-methylbicyclo[1.1.1]pentane-1-carboxamido)pyridin-2-yl)-1H-1,2,3-triazol-5-yl)carbamate | 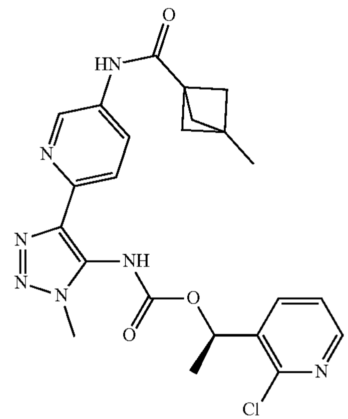 [SMILES: C[C@@H](OC(=O)Nc1c(-c2ccc(NC(=O)C34CC(C)(C3)C4)cn2)nnn1C)c1cccnc1Cl] | | 482.2 | 1H NMR (400 MHz, Methanol-d4) δ 8.90 (s, 1H), 8.48-7.71 (m, 4H), 7.46 (s, 1H), 6.08 (d, J = 7.0 Hz, 1H), 3.98 (s, 3H), 2.05 (s, 6H), 1.61 (s, 3H), 1.26 (s, 3H). |
| Compound 48 (R)-1-(2-chloropyridin-3-yl)ethyl (1-methyl-4-(5-(1-(trifluoromethyl)cyclobutane-1-carboxamido)pyridin-2-yl)-1H-1,2,3-triazol-5-yl)carbamate | 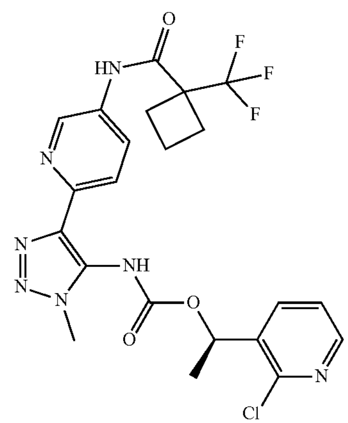 [SMILES: C[C@@H](OC(=O)Nc1c(-c2ccc(NC(=O)C3(C(F)(F)F)CCC3)cn2)nnn1C)c1cccnc1Cl] | | 524.2 | 1H NMR (400 MHz, Methanol-d4) δ 8.90 (s, 1H), 8.46-7.74 (m, 4H), 7.46 (s, 1H), 6.08 (d, J = 6.7 Hz, 1H), 3.99 (s, 3H), 2.90-2.69 (m, 2H), 2.60 (ddt, J = 9.5, 7.7, 5.7 Hz, 2H), 2.20-1.96 (m, 2H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 49 (R)-1-(2-chloropyridin-3-yl)ethyl (4-(5-(2,2-dimethylcyclopropane-1-carboxamido)pyridin-2-yl)-1-methyl-1H-1,2,3-triazol-5-yl)carbamate | 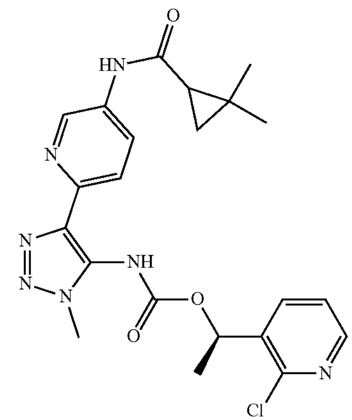 [SMILES: C[C@@H](OC(=O)Nc1c(-c2ccc(NC(=O)C3CC3(C)C)cn2)nnn1C)c1cccnc1Cl] | | 470.2 | 1H NMR (400 MHz, Methanol-d4) δ 8.85 (s, 1H), 8.43-7.68 (m, 4H), 7.46 (s, 1H), 6.08 (d, J = 6.5 Hz, 1H), 3.98 (s, 3H), 1.82-1.43 (m, 4H), 1.30-1.21 (m, 6H), 1.21-1.16 (m, 1H), 0.90 (dd, J = 7.9, 4.3 Hz, 1H). |
| Compound 50 (R)-1-(2-chloropyridin-3-yl)ethyl (4-(5-((1S,2S)-2-cyanocyclopropane-1-carboxamido)pyridin-2-yl)-1-methyl-1H-1,2,3-triazol-5-yl)carbamate | 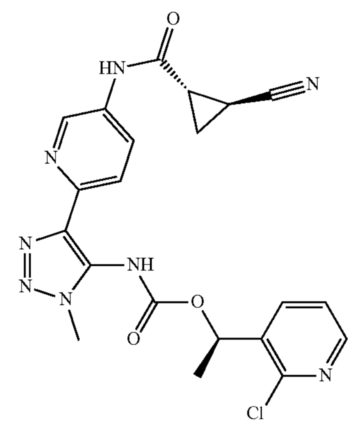 [SMILES: C[C@@H](OC(=O)Nc1c(-c2ccc(NC(=O)[C@H]3C[C@@H]3C#N)cn2)nnn1C)c1cccnc1Cl] | | 467.0 | 1H NMR (400 MHz, Methanol-d4) δ 8.84 (s, 1H), 8.55-7.00 (m, 5H), 6.08 (d, J = 7.1 Hz, 1H), 3.99 (s, 3H), 2.48 (ddd, J = 8.6, 5.9, 4.2 Hz, 1H), 2.23-2.03 (m, 1H), 1.58 (dddd, J = 14.8, 8.6, 6.0, 4.6 Hz, 5H). |

TABLE 2-continued

Compounds prepared according to Scheme C, Step 4.

| Compound No. | Structure | Reagent | LCMS m/z | 1H NMR |
|---|---|---|---|---|
| Compound 51 (R)-1-(2-chloropyridin-3-yl)ethyl (4-(5-(((1R,2R)-2-cyanocyclopropane-1-carboxamido)pyridin-2-yl)-1-methyl-1H-1,2,3-triazol-5-yl)carbamate | | | 467.0 | 1H NMR (400 MHz, Methanol-d4) δ 8.84 (s, 1H), 8.52-7.18 (m, 5H), 6.08 (d, J = 6.8 Hz, 1H), 3.99 (s, 3H), 2.48 (ddd, J = 8.6, 5.9, 4.3 Hz, 1H), 2.24-2.02 (m, 1H), 1.59 (dddd, J = 16.1, 8.5, 6.0, 4.6 Hz, 5H). |
| Compound 52 (R)-1-(2-chloropyridin-3-yl)ethyl (4-(5-(((1R,2S)-2-fluorocyclopropane-1-carboxamido)pyridin-2-yl)-1-methyl-1H-1,2,3-triazol-5-yl)carbamate | | | 460.1 | 1H NMR (400 MHz, Methanol-d4) δ 8.82 (s, 1H), 8.48-7.73 (m, 4H), 7.46 (s, 1H), 6.08 (d, J = 6.7 Hz, 1H), 4.96 (ddd, J = 6.2, 3.3, 1.6 Hz, 1H), 2.29 (dddd, J = 17.3, 10.5, 6.6, 1.6 Hz, 1H), 1.91-1.15 (m, 5H). |

TABLE 2-continued

Compounds prepared according to Scheme C, Step 4.

| Compound No. | Structure | Reagent | LCMS m/z | 1H NMR |
|---|---|---|---|---|
| Compound 53 (R)-1-(2-chloropyridin-3-yl)ethyl (4-(5-((1S,2S)-2-fluorocyclopropane-1-carboxamido)pyridin-2-yl)-1-methyl-1H-1,2,3-triazol-5-yl)carbamate | | | 460.2 | 1H NMR (400 MHz, Methanol-d4) δ 8.86 (s, 1H), 8.61-7.72 (m, 4H), 7.47 (s, 1H), 6.08 (d, J = 6.7 Hz, 1H), 4.97 (td, J = 6.2, 3.7 Hz, 1H), 3.99 (s, 3H), 2.09-2.01 (m, 1H), 1.82 (dtd, J = 23.0, 7.1, 3.7 Hz, 1H), 1.61 (s, 3H), 1.23 (dddd, J = 12.7, 9.2, 7.0, 6.0 Hz, 1H). |
| Compound 54 (R)-1-(2-chloropyridin-3-yl)ethyl (1-methyl-4-(5-(oxetane-2-carboxamido)pyridin-2-yl)-1H-1,2,3-triazol-5-yl)carbamate | | | 458.2 | 1H NMR (400 MHz, Methanol-d4) δ 8.96 (s, 1H), 8.48-7.77 (m, 4H), 7.47 (s, 1H), 6.08 (d, J = 6.5 Hz, 1H), 5.21 (ddd, J = 9.2, 6.7, 0.8 Hz, 1H), 4.86-4.73 (m, 2H), 3.99 (s, 3H), 3.14 (dtd, J = 11.5, 8.9, 6.5 Hz, 1H), 2.79 (ddtd, J = 11.4, 9.2, 6.9, 2.6 Hz, 1H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 55 (R)-1-(2-chloropyridin-3-yl)ethyl (1-methyl-4-(5-(1-(trifluoromethyl)cyclopropane-1-carboxamido)pyridin-2-yl)-1H-1,2,3-triazol-5-yl)carbamate | 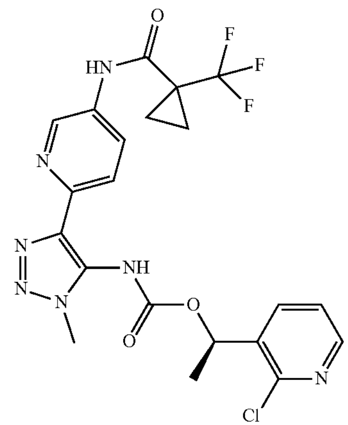 [SMILES: C[C@@H](OC(=O)Nc1c(-c2ccc(NC(=O)C3(C(F)(F)F)CC3)cn2)nnn1C)c1cccnc1Cl] | | 510.2 | 1H NMR (400 MHz, Methanol-d4) δ 8.84 (s, 1H), 8.58-7.72 (m, 4H), 7.46 (s, 1H), 6.08 (d, J = 6.8 Hz, 1H), 3.99 (s, 3H), 1.92-1.16 (m, 7H). |
| Compound 56 (R)-1-(2-chloropyridin-3-yl)ethyl (4-(5-((1R,2R)-2-fluorocyclopropane-1-carboxamido)pyridin-2-yl)-1-methyl-1H-1,2,3-triazol-5-yl)carbamate | 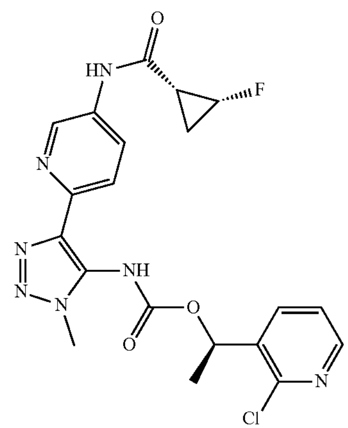 [SMILES: C[C@@H](OC(=O)Nc1c(-c2ccc(NC(=O)[C@H]3C[C@H]3F)cn2)nnn1C)c1cccnc1Cl] | | 460.1 | 1H NMR (400 MHz, Methanol-d4) δ 8.87 (s, 1H), 8.51-7.71 (m, 4H), 7.46 (s, 1H), 6.08 (q, J = 6.6 Hz, 1H), 4.98 (td, J = 6.2, 3.7 Hz, 1H), 3.99 (s, 3H), 2.11-2.01 (m, 1H), 1.82 (dtd, J = 23.0, 7.1, 3.7 Hz, 1H), 1.62 (s, 3H), 1.23 (dddd, J = 12.8, 9.3, 7.0, 6.0 Hz, 1H). |

TABLE 2-continued

Compounds prepared according to Scheme C, Step 4.

| Compound No. | Structure | Reagent | LCMS m/z | 1H NMR |
|---|---|---|---|---|
| Compound 57 (R)-1-(2-chloropyridin-3-yl)ethyl (1-methyl-4-(5-(oxetane-3-carboxamido)pyridin-2-yl)-1H-1,2,3-triazol-5-yl)carbamate | 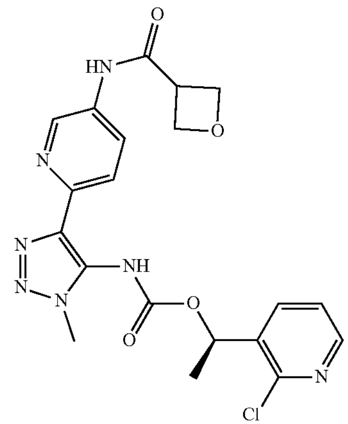 | | 458.2 | 1H NMR (400 MHz, Methanol-d4) δ 8.86 (s, 1H), 8.53-7.77 (m, 4H), 7.47 (s, 1H), 6.07 (s, 1H), 4.92 (q, J = 6.2, 4.3 Hz, 4H), 4.02 (d, J = 30.2 Hz, 4H), 1.58 (d, J = 28.0 Hz, 3H). |
| Compound 58 (R)-1-(2-chloropyridin-3-yl)ethyl (1-methyl-4-(5-(nicotinamido)pyridin-2-yl)-1H-1,2,3-triazol-5-yl)carbamate | 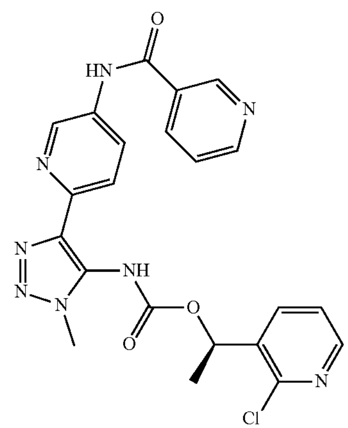 [SMILES: C[C@@H](OC(=O)Nc1c(-c2ccc(NC(=O)c3cccnc3)cn2)nnn1C)c1cccnc1Cl] | | 479.2 | 1H NMR (400 MHz, Methanol-d4) δ 9.16 (dd, J = 2.3, 0.9 Hz, 1H), 9.02 (s, 1H), 8.77 (dd, J = 4.9, 1.6 Hz, 1H), 8.42 (ddd, J = 8.0, 2.3, 1.6 Hz, 1H), 8.32 (s, 1H), 8.25-7.83 (m, 3H), 7.64 (ddd, J = 8.0, 4.9, 0.9 Hz, 1H), 7.49 (s, 1H), 6.09 (d, J = 6.8 Hz, 1H), 4.00 (s, 3H), 1.62 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 59 (R)-1-(2-chloropyridin-3-yl)ethyl (4-(5-(2-cyanoacetamido)pyridin-2-yl)-1-methyl-1H-1,2,3-triazol-5-yl)carbamate | 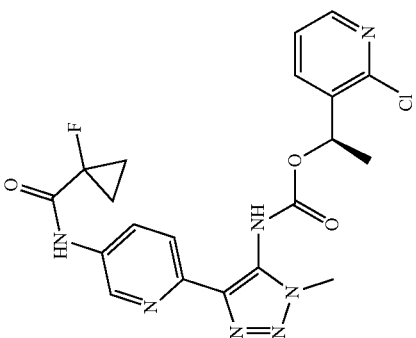 | 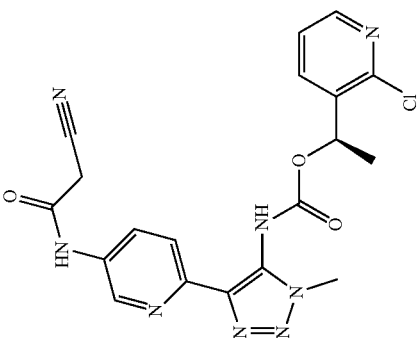 | 441.1 | 1H NMR (400 MHz, Methanol-d4) δ 8.82 (s, 1H), 8.52-7.74 (m, 4H), 7.44 (dd, J = 7.8, 4.8 Hz, 1H), 6.08 (d, J = 6.9 Hz, 1H), 3.99 (s, 3H), 3.84 (s, 2H), 1.95-1.09 (m, 3H). |
| Compound 60 (R)-1-(2-chloropyridin-3-yl)ethyl (4-(5-(1-fluorocyclopropane-1-carboxamido)pyridin-2-yl)-1-methyl-1H-1,2,3-triazol-5-yl)carbamate | 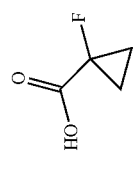 | 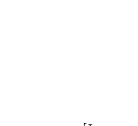 | 460.1 | 1H NMR (400 MHz, Methanol-d4) δ 8.93 (s, 1H), 8.57-7.74 (m, 4H), 7.47 (s, 1H), 6.08 (q, J = 6.6 Hz, 1H), 3.99 (s, 3H), 1.84-1.34 (m, 7H). |

TABLE 2-continued

Compounds prepared according to Scheme C, Step 4.

| Compound No. | Structure | Reagent | LCMS m/z | 1H NMR |
|---|---|---|---|---|
| Compound 61 (R)-1-(2-chloropyridin-3-yl)ethyl (4-(5-(isonicotinamido)pyridin-2-yl)-1-methyl-1H-1,2,3-triazol-5-yl)carbamate | | | 479.1 | 1H NMR (400 MHz, Methanol-d4) δ 9.02 (s, 1H), 8.87-8.70 (m, 2H), 8.48-7.77 (m, 6H), 7.49 (s, 1H), 6.09 (d, J = 6.7 Hz, 1H), 4.00 (s, 3H), 1.62 (s, 3H). |
| Compound 62 (R)-1-(2-chloropyridin-3-yl)ethyl (4-(5-((1r,3R)-3-fluorocyclobutane-1-carboxamido)pyridin-2-yl)-1-methyl-1H-1,2,3-triazol-5-yl)carbamate | | | 474.2 | 1H NMR (400 MHz, Methanol-d4) δ 8.84 (s, 1H), 8.50-7.77 (m, 4H), 6.08 (d, J = 6.2 Hz, 1H), 5.48-5.07 (m, 1H), 3.99 (s, 3H), 2.78-2.38 (m, 4H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 63 (R)-1-(2-chloropyridin-3-yl)ethyl (4-(5-(2,2-difluorocyclobutane-1-carboxamido)pyridin-2-yl)-1-methyl-1H-1,2,3-triazol-5-yl)carbamate | 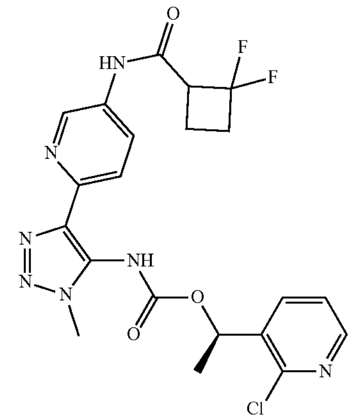 [SMILES: C[C@@H](OC(=O)Nc1c(-c2ccc(NC(=O)C3CCC3(F)F)cn2)nnn1C)c1cccnc1Cl] | | 492.1 | 1H NMR (400 MHz, Methanol-d4) δ 8.88 (s, 1H), 8.57-7.73 (m, 4H), 7.47 (s, 1H), 6.08 (q, J = 6.5 Hz, 1H), 3.99 (s, 3H), 3.93-3.77 (m, 1H), 2.64 (dddd, J = 13.4, 11.8, 9.3, 7.6 Hz, 2H), 2.33 (tt, J = 12.0, 7.6 Hz, 1H), 2.11-2.00 (m, 1H), 1.61 (s, 3H). |
| Compound 64 (R)-1-(2-chloropyridin-3-yl)ethyl (4-(5-(3-cyanobicyclo[1.1.1]pentane-1-carboxamido)pyridin-2-yl)-1-methyl-1H-1,2,3-triazol-5-yl)carbamate | 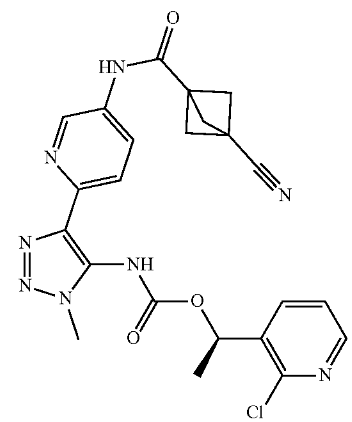 [SMILES: C[C@@H](OC(=O)Nc1c(-c2ccc(NC(=O)C34CC(C#N)(C3)C4)cn2)nnn1C)c1cccnc1Cl] | | 493.2 | 1H NMR (400 MHz, Methanol-d4) δ 8.88 (s, 1H), 8.51-7.74 (m, 4H), 7.46 (s, 1H), 6.07 (d, J = 6.4 Hz, 1H), 3.98 (s, 3H), 2.64 (s, 6H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 65 (R)-1-(2-chloropyridin-3-yl)ethyl (4-(5-((S)-2,2-difluorocyclopropane-1-carboxamido)pyridin-2-yl)-1-methyl-1H-1,2,3-triazol-5-yl)carbamate | 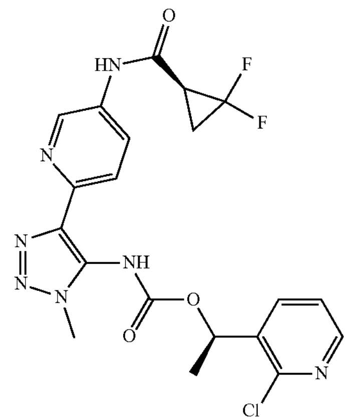 [SMILES: C[C@@H](OC(=O)Nc1c(-c2ccc(NC(=O)[C@@H]3CC3(F)F)cn2)nnn1C)c1cccnc1Cl] | | 478.1 | 1H NMR (400 MHz, Methanol-d4) δ 8.85 (s, 1H), 8.53-7.74 (m, 4H), 7.47 (s, 1H), 6.08 (d, J = 7.0 Hz, 1H), 2.76 (ddd, J = 13.1, 10.8, 7.7 Hz, 1H), 2.16 (dtd, J = 12.7, 7.7, 6.1 Hz, 1H), 1.90 (dddd, J = 12.6, 10.8, 7.8, 4.9 Hz, 1H), 1.61 (s, 3H). |
| Compound 66 (R)-1-(2-chloropyridin-3-yl)ethyl (4-(5-(1-cyanocyclobutane-1-carboxamido)pyridin-2-yl)-1-methyl-1H-1,2,3-triazol-5-yl)carbamate | 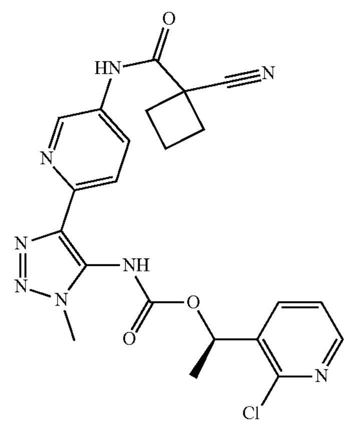 [SMILES: C[C@@H](OC(=O)Nc1c(-c2ccc(NC(=O)C3(C#N)CCC3)cn2)nnn1C)c1cccnc1Cl] | | 481.2 | 1H NMR (400 MHz, Methanol-d4) δ 8.88 (s, 1H), 8.46-7.75 (m, 4H), 7.47 (s, 1H), 6.08 (d, J = 6.9 Hz, 1H), 3.99 (s, 3H), 2.89 (dtd, J = 11.0, 7.4, 1.5 Hz, 2H), 2.76-2.64 (m, 2H), 2.30 (dtt, J = 11.6, 9.2, 7.4 Hz, 1H), 2.21-2.02 (m, 1H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 67 (R)-1-(2-chloropyridin-3-yl)ethyl (4-(5-(1-cyanocyclopropane-1-carboxamido)pyridin-2-yl)-1-methyl-1H-1,2,3-triazol-5-yl)carbamate | 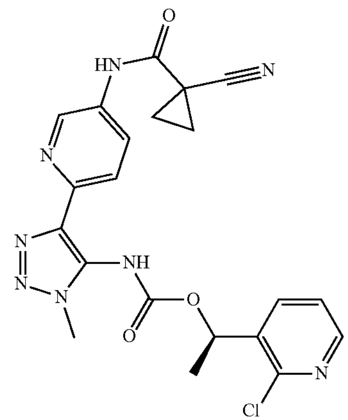 [SMILES: C[C@@H](OC(=O)Nc1c(-c2ccc(NC(=O)C3(C#N)CC3)cn2)nnn1C)c1cccnc1Cl] | | 467.1 | 1H NMR (400 MHz, Methanol-d4) δ 8.84 (s, 1H), 8.50-7.76 (m, 4H), 7.46 (s, 1H), 6.30-5.74 (m, 1H), 3.99 (s, 3H), 1.84-1.38 (m, 7H). |
| Compound 68 (R)-1-(2-chloropyridin-3-yl)ethyl (4-(5-(bicyclo[1.1.1]pentane-1-carboxamido)pyridin-2-yl)-1-methyl-1H-1,2,3-triazol-5-yl)carbamate | 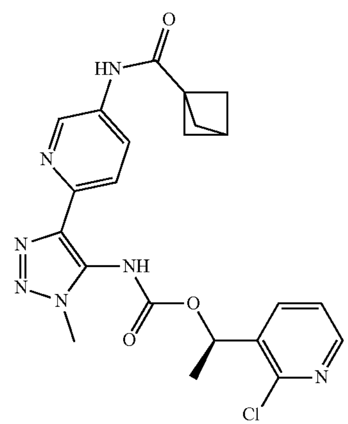 [SMILES: C[C@@H](OC(=O)Nc1c(-c2ccc(NC(=O)C34CC(C3)C4)cn2)nnn1C)c1cccnc1Cl] | | 468.2 | 1H NMR (400 MHz, Methanol-d4) δ 8.90 (s, 1H), 8.47-7.71 (m, 4H), 7.46 (s, 1H), 6.08 (d, J = 6.8 Hz, 1H), 3.98 (s, 3H), 2.53 (s, 1H), 2.22 (s, 6H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 69 (R)-1-(2-chloropyridin-3-yl)ethyl (4-(5-((1S,2R)-2-fluorocyclopropane-1-carboxamido)pyridin-2-yl)-1-methyl-1H-1,2,3-triazol-5-yl)carbamate | 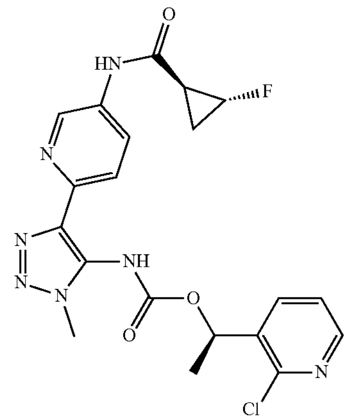 [SMILES: C[C@@H](OC(=O)Nc1c(-c2ccc(NC(=O)[C@@H]3C[C@H]3F)cn2)nnn1C)c1cccnc1Cl] | | 460.2 | 1H NMR (400 MHz, Methanol-d4) δ 8.82 (s, 1H), 8.48-7.71 (m, 4H), 7.46 (s, 1H), 6.08 (d, J = 6.7 Hz, 1H), 4.96 (ddd, J = 6.2, 3.4, 1.6 Hz, 1H), 3.98 (s, 3H), 2.29 (dddd, J = 17.3, 10.4, 6.6, 1.6 Hz, 1H), 1.89-1.16 (m, 5H). |
| Compound 70 (R)-1-(2-chloropyridin-3-yl)ethyl (4-(5-(3-fluorobicyclo[1.1.1]pentane-1-carboxamido)pyridin-2-yl)-1-methyl-1H-1,2,3-triazol-5-yl)carbamate | 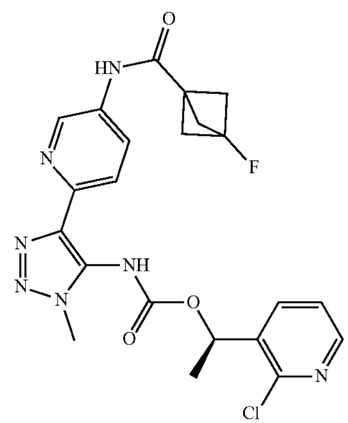 [SMILES: C[C@@H](OC(=O)Nc1c(-c2ccc(NC(=O)C34CC(F)(C3)C4)cn2)nnn1C)c1cccnc1Cl] | | 486.2 | 1H NMR (400 MHz, Methanol-d4) δ 8.89 (s, 1H), 8.47-7.71 (m, 4H), 7.46 (s, 1H), 6.08 (d, J = 6.9 Hz, 1H), 3.99 (s, 3H), 2.47 (d, J = 2.4 Hz, 6H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 71 (R)-1-(2-chloropyridin-3-yl)ethyl (4-(5-((1s,3S)-3-fluorocyclobutane-1-carboxamido)pyridin-2-yl)-1-methyl-1H-1,2,3-triazol-5-yl)carbamate | 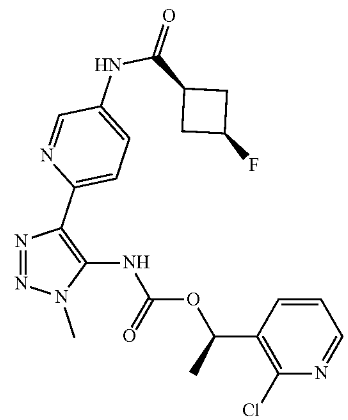 [SMILES: C[C@@H](OC(=O)Nc1c(-c2ccc(NC(=O)[C@H]3C[C@@H](F)C3)cn2)nnn1C)c1cccnc1Cl] | | 474.2 | 1H NMR (400 MHz, Methanol-d4) δ 8.86 (s, 1H), 8.54-7.79 (m, 4H), 7.47 (s, 1H), 6.08 (d, J = 7.0 Hz, 1H), 5.12-4.89 (m, 1H), 2.84-2.71 (m, 1H), 2.71-2.58 (m, 2H), 2.50 (ddddd, J = 19.4, 11.9, 9.6, 7.6, 2.0 Hz, 2H), 1.61 (s, 3H). |
| Compound 72 (R)-1-(2-chloropyridin-3-yl)ethyl (1-methyl-4-(5-(3-(trifluoromethyl)bicyclo[1.1.1]pentane-1-carboxamido)pyridin-2-yl)-1H-1,2,3-triazol-5-yl)carbamate | | | 536.2 | 1H NMR (400 MHz, Methanol-d4) δ 8.90 (s, 1H), 8.44-7.71 (m, 4H), 7.46 (s, 1H), 6.08 (d, J = 6.5 Hz, 1H), 3.99 (s, 3H), 2.39 (s, 6H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 73 (R)-1-(2-chloropyridin-3-yl)ethyl (1-methyl-4-(5-(spiro[3.3]heptane-2-carboxamido)pyridin-2-yl)-1H-1,2,3-triazol-5-yl)carbamate | | | 496.2 | 1H NMR (400 MHz, Methanol-d4) δ 8.84 (s, 1H), 8.46-7.69 (m, 4H), 7.47 (s, 1H), 6.07 (d, J = 6.9 Hz, 1H), 3.98 (s, 3H), 3.16 (p, J = 8.5 Hz, 1H), 2.39-2.20 (m, 4H), 2.14 (ddd, J = 7.3, 5.9, 1.2 Hz, 2H), 1.99 (dd, J = 8.5, 5.9 Hz, 2H), 1.92-1.79 (m, 2H), 1.61 (s, 3H). |
| Compound 74 (R)-1-(2-chloropyridin-3-yl)ethyl (4-(5-(1-cyanospiro[2.3]hexane-1-carboxamido)pyridin-2-yl)-1-methyl-1H-1,2,3-triazol-5-yl)carbamate | | | 507.2 | 1H NMR (400 MHz, Methanol-d4) δ 8.85 (s, 1H), 8.52-7.73 (m, 4H), 7.46 (s, 1H), 6.25-5.91 (m, 1H), 3.99 (s, 3H), 2.65 (ddd, J = 12.0, 9.3, 6.8 Hz, 1H), 2.40-2.06 (m, 6H), 1.90-1.36 (m, 4H). |

TABLE 2-continued

Compounds prepared according to Scheme C, Step 4.

| Compound No. | Structure | Reagent | LCMS m/z | 1H NMR |
|---|---|---|---|---|
| Compound 75 (R)-1-(2-chloropyridin-3-yl)ethyl (4-(5-(3-cyclopropylpropiolamido)pyridin-2-yl)-1-methyl-1H-1,2,3-triazol-5-yl)carbamate | 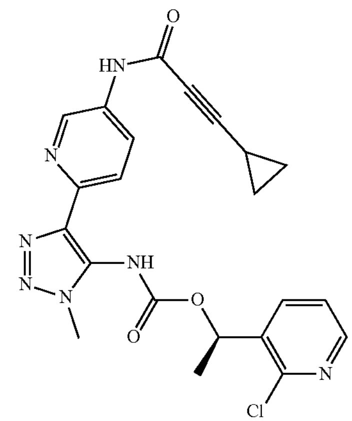 [SMILES: C[C@@H](OC(=O)Nc1c(-c2ccc(NC(=O)C#CC3CC3)cn2)nnn1C)c1cccnc1Cl] | | 466.2 | 1H NMR (400 MHz, Methanol-d4) δ 8.83 (s, 1H), 8.49-7.69 (m, 4H), 7.46 (s, 1H), 6.07 (d, J = 6.7 Hz, 1H), 3.98 (s, 3H), 1.91-1.33 (m, 4H), 1.07-1.00 (m, 2H), 0.95-0.86 (m, 2H). |
| Compound 76 (R)-1-(2-chloropyridin-3-yl)ethyl (4-(5-(but-2-ynamido)pyridin-2-yl)-1-methyl-1H-1,2,3-triazol-5-yl)carbamate | | | 440.0 | 1H NMR (400 MHz, Methanol-d4) δ 8.84 (s, 1H), 8.48-7.75 (m, 4H), 7.46 (s, 1H), 6.08 (d, J = 6.7 Hz, 1H), 3.98 (s, 3H), 2.08 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 77 (R)-1-(2-chloropyridin-3-yl)ethyl (4-(5-(dispiro[3.1.3⁶.1⁴]decane-2-carboxamido)pyridin-2-yl)-1-methyl-1H-1,2,3-triazol-5-yl)carbamate | | | 537.2 | 1H NMR (400 MHz, Methanol-d4) δ 8.83 (s, 1H), 8.52-7.70 (m, 4H), 7.46 (s, 1H), 6.07 (d, J = 7.0 Hz, 1H), 3.98 (s, 3H), 3.19 (q, J = 8.5 Hz, 1H), 2.34 (td, J = 10.0, 1.7 Hz, 2H), 2.21 (dd, J = 11.9, 8.6 Hz, 2H), 2.15 (s, 2H), 2.03-1.92 (m, 6H), 1.89-1.77 (m, 2H), 1.61 (s, 3H). |
| Compound 78 (R)-1-(2-chloropyridin-3-yl)ethyl (1-methyl-4-(5-(2-(trifluoromethyl)spiro[3.3]heptane-2-carboxamido)pyridin-2-yl)-1H-1,2,3-triazol-5-yl)carbamate | 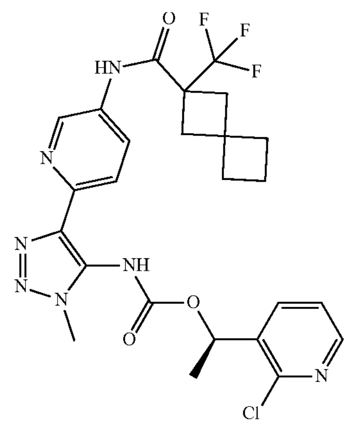 [SMILES: C[C@@H](OC(=O)Nc1c(-c2ccc(NC(=O)C3(C(F)(F)F)CC4(CCC4)C3)cn2)nnn1C)c1cccnc1Cl] | | 564.1 | 1H NMR (400 MHz, Methanol-d4) δ 8.88 (s, 1H), 8.53-7.74 (m, 4H), 7.46 (s, 1H), 6.08 (d, J = 6.8 Hz, 1H), 3.99 (s, 3H), 2.77 (d, J = 13.3 Hz, 2H), 2.62 (d, J = 13.8 Hz, 2H), 2.10 (dt, J = 21.0, 7.5 Hz, 4H), 1.92-1.81 (m, 2H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 79 (R)-1-(2-chloropyridin-3-yl)ethyl (4-(5-(2-cyanospiro[3.3]heptane-2-carboxamido)pyridin-2-yl)-1-methyl-1H-1,2,3-triazol-5-yl)carbamate | 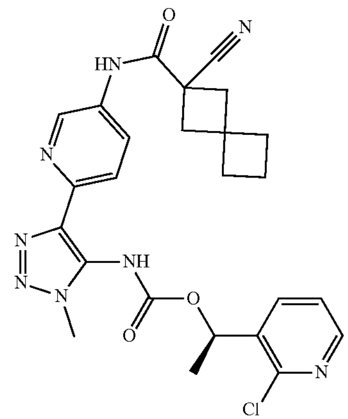 [SMILES: C[C@@H](OC(=O)Nc1c(-c2ccc(NC(=O)C3(C#N)CC4(CCC4)C3)cn2)nnn1C)c1cccnc1Cl] | | 521.2 | 1H NMR (400 MHz, Methanol-d4) δ 8.86 (s, 1H), 8.46-7.74 (m, 4H), 7.47 (s, 1H), 6.08 (d, J = 6.8 Hz, 1H), 3.99 (s, 3H), 2.96-2.80 (m, 2H), 2.80-2.58 (m, 2H), 2.28 (t, J = 7.5 Hz, 2H), 2.07 (dd, J = 8.7, 6.1 Hz, 2H), 1.97-1.85 (m, 2H), 1.61 (s, 3H). |
| Compound 80 (R)-1-(2-chloropyridin-3-yl)ethyl (4-(5-(6-cyanospiro[3.3]heptane-2-carboxamido)pyridin-2-yl)-1-methyl-1H-1,2,3-triazol-5-yl)carbamate | 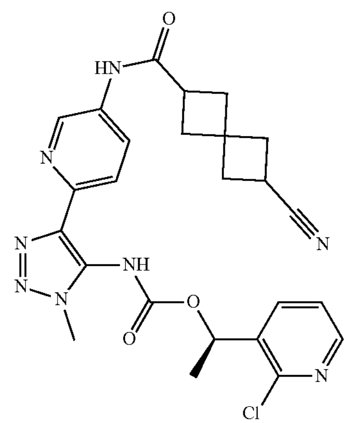 [SMILES: C[C@@H](OC(=O)Nc1c(-c2ccc(NC(=O)C3CC4(CC(C#N)C4)C3)cn2)nnn1C)c1cccnc1Cl] | | 521.3 | 1H NMR (400 MHz, Methanol-d4) δ 8.83 (s, 1H), 8.49-7.74 (m, 4H), 7.46 (s, 1H), 6.07 (d, J = 7.0 Hz, 1H), 3.98 (s, 3H), 3.18 (h, J = 8.2 Hz, 2H), 2.60 (ddd, J = 11.6, 8.4, 3.3 Hz, 1H), 2.42 (dddd, J = 29.1, 15.3, 11.7, 7.0 Hz, 7H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 81 (R)-1-(2-chloropyridin-3-yl)ethyl (4-(5-(6-fluorospiro[3.3]heptane-2-carboxamido)pyridin-2-yl)-1-methyl-1H-1,2,3-triazol-5-yl)carbamate | 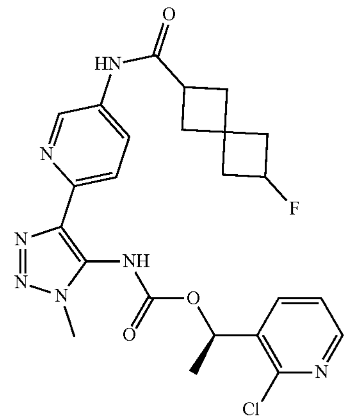 [SMILES: C[C@@H](OC(=O)Nc1c(-c2ccc(NC(=O)C3CC4(CC(F)C4)C3)cn2)nnn1C)c1cccnc1Cl] | | 514.3 | 1H NMR (400 MHz, Methanol-d4) δ 8.84 (s, 1H), 8.58-7.71 (m, 4H), 7.47 (s, 1H), 6.07 (d, J = 6.8 Hz, 1H), 5.00 (p, J = 6.7 Hz, 1H), 3.98 (s, 3H), 3.24 (p, J = 8.4 Hz, 1H), 2.60 (dq, J = 12.5, 6.4 Hz, 1H), 2.53-2.34 (m, 3H), 2.34-2.08 (m, 4H), 1.61 (s, 3H). |
| Compound 82 (R)-1-(2-chloropyridin-3-yl)ethyl (4-(5-(3-chlorobicyclo[1.1.1]pentane-1-carboxamido)pyridin-2-yl)-1-methyl-1H-1,2,3-triazol-5-yl)carbamate | 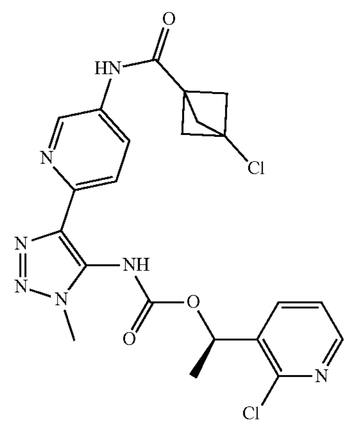 | | 502.2 | 1H NMR (400 MHz, Methanol-d4) δ 8.88 (s, 1H), 8.52-7.72 (m, 4H), 7.46 (s, 1H), 6.07 (d, J = 7.0 Hz, 1H), 3.98 (s, 3H), 2.54 (s, 6H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 83 (R)-1-(2-chloropyridin-3-yl)ethyl (1-methyl-4-(5-(3-oxocyclobutane-1-carboxamido)pyridin-2-yl)-1H-1,2,3-triazol-5-yl)carbamate | 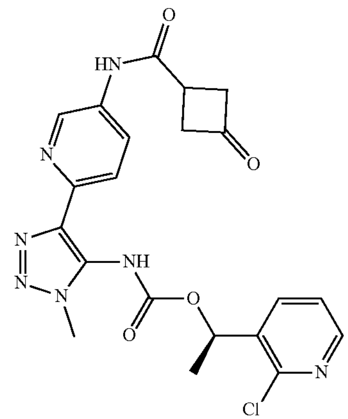 [SMILES: C[C@@H](OC(=O)Nc1c(-c2ccc(NC(=O)C3CC(=O)C3)cn2)nnn1C)c1cccnc1Cl] | | 470.2 | 1H NMR (400 MHz, Methanol-d4) δ 8.88 (s, 1H), 8.54-7.72 (m, 4H), 7.47 (s, 1H), 6.08 (d, J = 7.0 Hz, 1H), 3.99 (s, 3H), 3.57-3.34 (m, 5H), 1.61 (s, 3H). |
| Compound 84 (R)-1-(2-chloropyridin-3-yl)ethyl (4-(5-(3,3-dimethylcyclobutane-1-carboxamido)pyridin-2-yl)-1-methyl-1H-1,2,3-triazol-5-yl)carbamate | | | 484.2 | 1H NMR (400 MHz, Methanol-d4) δ 8.85 (s, 1H), 8.55-7.77 (m, 4H), 7.47 (s, 1H), 6.08 (d, J = 6.7 Hz, 1H), 3.98 (s, 3H), 3.25 (q, J = 8.7 Hz, 1H), 2.17 (ddd, J = 10.8, 9.2, 1.9 Hz, 2H), 2.09-1.96 (m, 2H), 1.61 (s, 3H), 1.26 (s, 3H), 1.16 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 85 (R)-1-(2-chloropyridin-3-yl)ethyl (4-(5-((3R,5r)-1,1-difluorospiro[2.3]hexane-5-carboxamido)pyridin-2-yl)-1-methyl-1H-1,2,3-triazol-5-yl)carbamate | 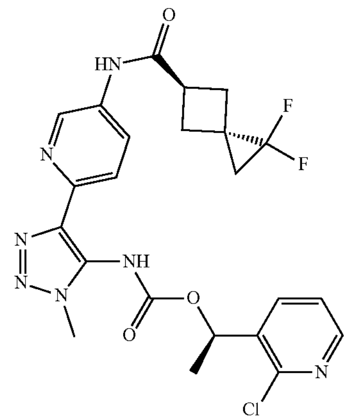 [SMILES: C[C@@H](OC(=O)Nc1c(-c2ccc(NC(=O)[C@H]3C[C@@]4(CC4(F)F)C3)cn2)nnn1C)c1cccnc1Cl] | | 518.1 | 1H NMR (400 MHz, Methanol-d4) δ 8.87 (s, 1H), 8.46-7.72 (m, 4H), 7.48 (s, 1H), 6.08 (d, J = 6.7 Hz, 1H), 3.99 (s, 3H), 3.55-3.41 (m, 1H), 2.71 (dd, J = 12.5, 6.6 Hz, 2H), 2.39 (t, J = 11.1 Hz, 2H), 1.61 (s, 3H), 1.36 (t, J = 8.5 Hz, 2H). |
| Compound 86 (R)-1-(2-chloropyridin-3-yl)ethyl (4-(5-((3S,5s)-1,1-difluorospiro[2.3]hexane-5-carboxamido)pyridin-2-yl)-1-methyl-1H-1,2,3-triazol-5-yl)carbamate | 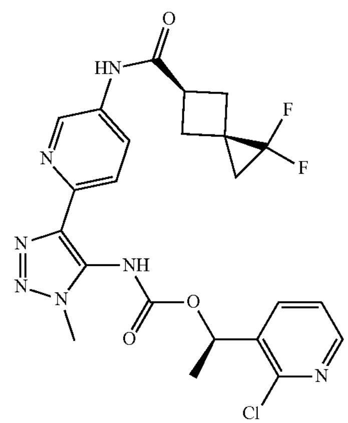 [SMILES: C[C@@H](OC(=O)Nc1c(-c2ccc(NC(=O)[C@H]3C[C@]4(CC4(F)F)C3)cn2)nnn1C)c1cccnc1Cl] | | 518.7 | 1H NMR (400 MHz, Methanol-d4) δ 8.86 (s, 1H), 8.53-7.73 (m, 4H), 7.47 (s, 1H), 6.08 (d, J = 7.5 Hz, 1H), 3.99 (s, 3H), 3.41 (t, J = 8.7 Hz, 1H), 2.66-2.46 (m, 4H), 1.61 (s, 3H), 1.30 (t, J = 8.5 Hz, 2H). |

TABLE 2-continued

Compounds prepared according to Scheme C, Step 4.

| Compound No. | Structure | Reagent | LCMS m/z | 1H NMR |
|---|---|---|---|---|
| Compound 87 (R)-1-(2-chloropyridin-3-yl)ethyl (4-(5-(5-cyanospiro[2.3]hexane-5-carboxamido)pyridin-2-yl)-1-methyl-1H-1,2,3-triazol-5-yl)carbamate | 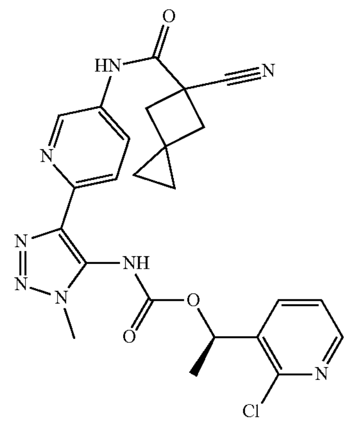 [SMILES: C[C@@H](OC(=O)Nc1c(-c2ccc(NC(=O)C3(C#N)CC4(CC4)C3)cn2)nnn1C)c1cccnc1Cl] | | 507.2 | 1H NMR (400 MHz, Methanol-d4) δ 8.89 (s, 1H), 8.55-7.72 (m, 4H), 7.47 (s, 1H), 6.31-5.75 (m, 1H), 3.99 (s, 3H), 3.05 (dd, J = 11.7, 1.7 Hz, 2H), 2.77 (dt, J = 11.1, 1.6 Hz, 2H), 1.62 (s, 3H), 0.78-0.64 (m, 2H), 0.64-0.47 (m, 2H). |
| Compound 88 (R)-1-(2-chloropyridin-3-yl)ethyl (1-methyl-4-(5-(spiro[2.3]hexane-5-carboxamido)pyridin-2-yl)-1H-1,2,3-triazol-5-yl)carbamate | 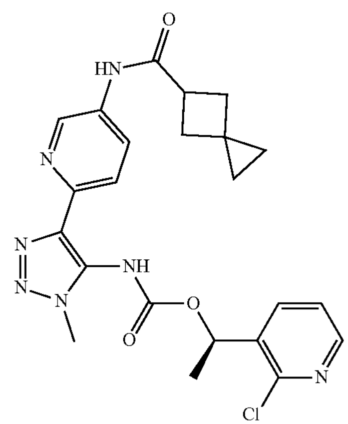 [SMILES: C[C@@H](OC(=O)Nc1c(-c2ccc(NC(=O)C3CC4(CC4)C3)cn2)nnn1C)c1cccnc1Cl] | | 482.3 | 1H NMR (400 MHz, Methanol-d4) δ 8.87 (s, 1H), 8.54-7.74 (m, 4H), 7.47 (s, 1H), 6.08 (d, J = 6.7 Hz, 1H), 3.99 (s, 3H), 3.48 (tt, J = 8.9, 7.6 Hz, 1H), 2.69-2.54 (m, 2H), 2.36-2.20 (m, 2H), 1.61 (s, 3H), 0.64-0.31 (m, 4H). |

TABLE 2-continued

Compounds prepared according to Scheme C, Step 4.

| Compound No. | Structure | Reagent | LCMS m/z | 1H NMR |
|---|---|---|---|---|
| Compound 89 (R)-1-(2-chloropyridin-3-yl)ethyl (4-(5-(1-cyanospiro[2.4]heptane-1-carboxamido)pyridin-2-yl)-1-methyl-1H-1,2,3-triazol-5-yl)carbamate | 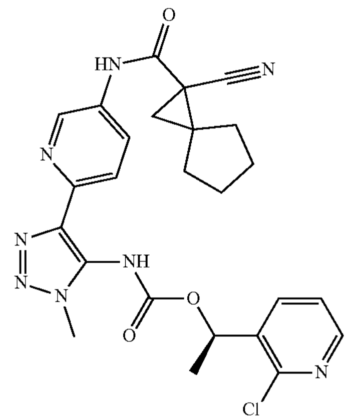 [SMILES: C[C@@H](OC(=O)Nc1c(-c2ccc(NC(=O)C3(C#N)CC34CCCC4)cn2)nnn1C)c1cccnc1Cl] | | 521.2 | 1H NMR (400 MHz, Methanol-d4) δ 8.85 (s, 1H), 8.47-7.70 (m, 4H), 7.47 (s, 1H), 6.08 (d, J = 6.9 Hz, 1H), 3.99 (s, 3H), 2.26-2.07 (m, 2H), 1.95-1.44 (m, 11H). |
| Compound 90 (R)-1-(2-chloropyridin-3-yl)ethyl (4-(5-((S)-2,2-difluorocyclobutane-1-carboxamido)pyridin-2-yl)-1-methyl-1H-1,2,3-triazol-5-yl)carbamate | 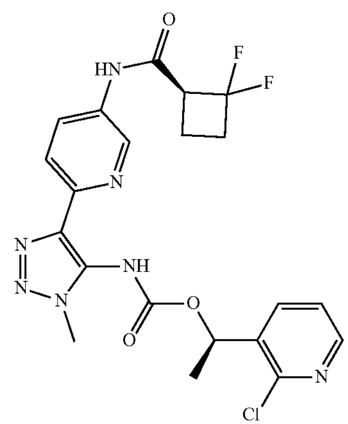 [SMILES: C[C@@H](OC(=O)Nc1c(-c2ccc(NC(=O)[C@@H]3CCC3(F)F)cn2)nnn1C)c1cccnc1Cl] | | 492.1 | 1H NMR (400 MHz, Acetonitrile-d3) δ 7.50 (s, 1H), 7.05-6.42 (m, 4H), 6.09 (s, 1H), 4.71 (d, J = 6.9 Hz, 1H), 2.56-2.37 (m, 1H), 1.36-1.15 (m, 2H), 0.95 (d, J = 11.4 Hz, 1H), 0.65 (s, 1H), 0.24 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 91 (R)-1-(2-chloropyridin-3-yl)ethyl (4-(5-((R)-2,2-difluorocyclobutane-1-carboxamido)pyridin-2-yl)-1-methyl-1H-1,2,3-triazol-5-yl)carbamate | 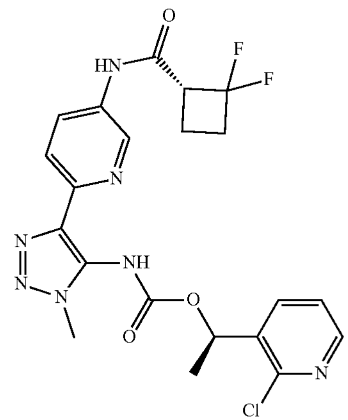 [SMILES: C[C@@H](OC(=O)Nc1c(-c2ccc(NC(=O)[C@H]3CCC3(F)F)cn2)nnn1C)c1cccnc1Cl] | | 492.0 | 1H NMR (400 MHz, Methanol-d4) δ 8.85 (s, 1H), 8.40-7.77 (m, 4H), 7.44 (s, 1H), 6.06 (d, J = 6.9 Hz, 1H), 3.97 (s, 3H), 3.92-3.72 (m, 1H), 2.71-2.50 (m, 2H), 2.30 (d, J = 11.4 Hz, 1H), 2.00 (s, 1H), 1.59 (s, 3H). |
| Compound 92 (R)-1-(2-chloropyridin-3-yl)ethyl (4-(5-(1-carbamoylcyclopropane-1-carboxamido)pyridin-2-yl)-1-methyl-1H-1,2,3-triazol-5-yl)carbamate | 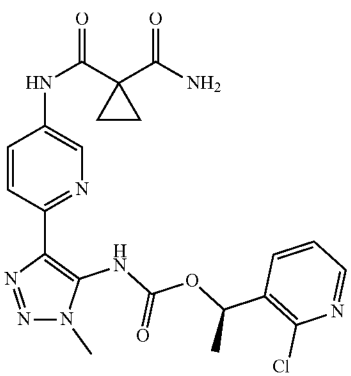 [SMILES: C[C@@H](OC(=O)Nc1c(-c2ccc(NC(=O)C3(C(N)=O)CC3)cn2)nnn1C)c1cccnc1Cl] | | 485.1 | 1H NMR (400 MHz, Acetonitrile-d3) δ 11.63 (s, 1H), 8.99 (d, J = 2.5 Hz, 1H), 8.57 (s, 1H), 8.34 (dd, J = 4.8, 1.9 Hz, 1H), 8.23 (dd, J = 8.8, 2.5 Hz, 1H), 8.03 (d, J = 8.8 Hz, 1H), 7.92 (s, 1H), 7.40 (d, J = 6.6 Hz, 1H), 6.33 (s, 1H), 6.04 (q, J = 6.6 Hz, 2H), 3.96 (s, 3H), 1.70 (q, J = 4.4 Hz, 2H), 1.58 (d, J = 6.5 Hz, 3H), 1.52 (q, J = 4.4 Hz, 2H). |

TABLE 2-continued

Compounds prepared according to Scheme C, Step 4.

| Compound No. | Structure | Reagent | LCMS m/z | 1H NMR |
|---|---|---|---|---|
| Compound 93 (R)-1-(2-chloropyridin-3-yl)ethyl (4-(5-(3-cyanooxetane-3-carboxamido)pyridin-2-yl)-1-methyl-1H-1,2,3-triazol-5-yl)carbamate | 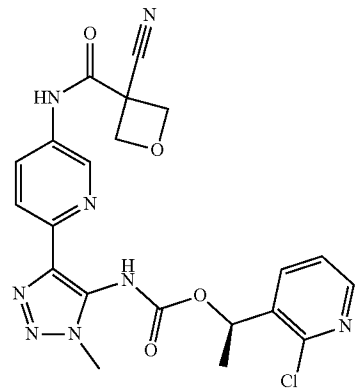 [SMILES: C[C@@H](OC(=O)Nc1c(-c2ccc(NC(=O)C3(C#N)COC3)cn2)nnn1C)c1cccnc1Cl] | | 483.1 | 1H NMR (400 MHz, DMSO-d6) δ 10.82 (s, 1H), 9.95 (s, 1H), 8.78 (s, 1H), 8.36 (s, 1H), 8.07 (dd, J = 8.6, 2.6 Hz, 1H), 8.02-7.90 (m, 2H), 7.61-7.45 (m, 1H), 5.89 (d, J = 7.1 Hz, 1H), 5.09-4.93 (m, 4H), 3.89 (s, 3H), 1.53 (s, 3H). |
| Compound 94 (R)-1-(2-chloropyridin-3-yl)ethyl (1-methyl-4-(5-(1-(pyridin-3-yl)cyclopropane-1-carboxamido)pyridin-2-yl)-1H-1,2,3-triazol-5-yl)carbamate | 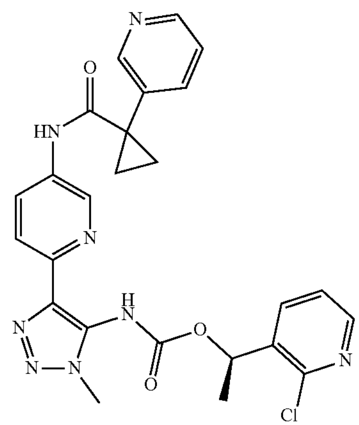 [SMILES: C[C@@H](OC(=O)Nc1c(-c2ccc(NC(=O)C3(c4cccnc4)CC3)cn2)nnn1C)c1cccnc1Cl] | | 519.1 | 1H NMR (400 MHz, DMSO-d6) δ 9.81 (brs, 1H), 9.43 (s, 1H), 8.72 (s, 1H), 8.65 (d, J = 2.3 Hz, 1H), 8.53 (dd, J = 4.8, 1.6 Hz, 1H), 8.35 (s, 1H), 7.99 (dd, J = 8.7, 2.6 Hz, 1H), 7.92-7.75 (m, 2H), 7.50-7.40 (m, 3H), 5.86 (m, 1H), 3.87 (s, 3H), 1.61-1.57 (m, 4H), 1.25-1.24 (m, 3H). |

TABLE 2-continued

Compounds prepared according to Scheme C, Step 4.

| Compound No. | Structure | Reagent | LCMS m/z | 1H NMR |
|---|---|---|---|---|
| Compound 95 (R)-1-(2-chloropyridin-3-yl)ethyl (4-(5-(4-cyanotetrahydro-2H-pyran-4-carboxamido)pyridin-2-yl)-1-methyl-1H-1,2,3-triazol-5-yl)carbamate | 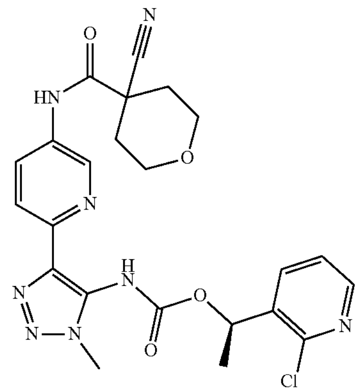 [SMILES: C[C@@H](OC(=O)Nc1c(-c2ccc(NC(=O)C3(C#N)CCOCC3)cn2)nnn1C)c1cccnc1Cl] | | 511.2 | 1H NMR (400 MHz, DMSO-d6) δ 10.42 (s, 1H), 9.85 (brs,1H), 8.80 (s, 1H), 8.36 (s, 1H), 8.08 (dd, J = 8.6, 2.5 Hz, 1H), 7.94 (d, J = 8.6 Hz, 2H), 7.60-7.45 (m, 1H), 5.95-5.83 (m, 1H), 4.00 (dt, J = 12.2, 3.4 Hz, 2H), 3.88 (s, 3H), 3.60 (ddd, J = 12.4, 9.9, 3.8 Hz, 2H), 2.26-2.09 (m, 4H), 1.65-1.40 (m, 3H) |
| Compound 96 (R)-1-(2-chloropyridin-3-yl)ethyl (4-(5-(3-ethyloxetane-3-carboxamido)pyridin-2-yl)-1-methyl-1H-1,2,3-triazol-5-yl)carbamate | 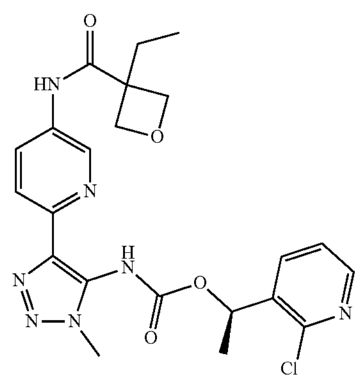 [SMILES: CCC1(C(=O)Nc2ccc(-c3nnn(C)c3NC(=O)O[C@H](C)c3cccnc3Cl)nc2)COC1] | | 486.2 | 1H NMR (400 MHz, DMSO-d6) δ 9.98 (s, 1H), 9.73 (s, 1H), 8.85-8.78 (m, 1H), 8.40-8.32 (m, 1H), 8.07 (dd, J = 8.6, 2.5 Hz, 1H), 7.91 (d, J = 8.6 Hz, 1H), 7.62-7.45 (m, 2H), 5.92-5.80 (m, 1H), 4.84 (d, J = 6.2 Hz, 2H), 4.42 (d, J = 6.2 Hz, 2H), 3.88 (s, 3H), 2.10 (q, J = 7.4 Hz, 2H), 1.75-1.45 (m, 3H), 0.87 (t, J = 7.4 Hz, 3H). |

TABLE 2-continued

Compounds prepared according to Scheme C, Step 4.

| Compound No. | Structure | Reagent | LCMS m/z | 1H NMR |
|---|---|---|---|---|
| Compound 97 (R)-1-(2-chloropyridin-3-yl)ethyl (1-methyl-4-(5-(3-methyloxetane-3-carboxamido)pyridin-2-yl)-1H-1,2,3-triazol-5-yl)carbamate | 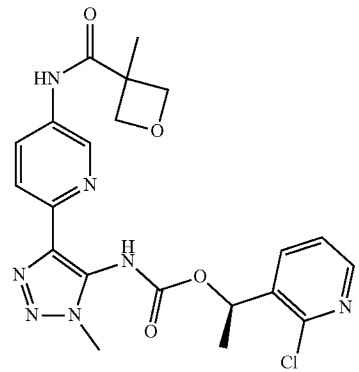 [SMILES: C[C@@H](OC(=O)Nc1c(-c2ccc(NC(=O)C3(C)COC3)cn2)nnn1C)c1cccnc1Cl] | | 472.2 | 1H NMR (400 MHz, DMSO-d6) δ 10.01 (s, 1H), 9.85 (s, 1H), 8.81 (s, 1H), 8.45-8.35 (m, 1H), 8.08 (dd, J = 8.6, 2.5 Hz, 1H), 7.92 (d, J = 8.6 Hz, 1H), 7.65-7.43 (m, 2H), 5.95-5.82 (m, 1H), 4.88 (d, J = 6.0 Hz, 2H), 4.39 (d, J = 6.1 Hz, 2H), 3.89 (s, 3H), 1.65 (s, 3H), 1.55 (s, 3H) |
| Compound 98 (R)-1-(2-chloropyridin-3-yl)ethyl (4-(5-(6-cyanopicolinamido)pyridin-2-yl)-1-methyl-1H-1,2,3-triazol-5-yl)carbamate | 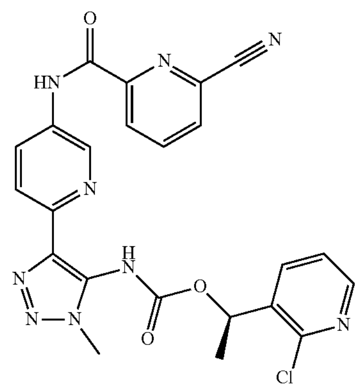 [SMILES: C[C@@H](OC(=O)Nc1c(-c2ccc(NC(=O)c3cccc(C#N)n3)cn2)nnn1C)c1cccnc1Cl] | | 504.1 | ¹H NMR (400 MHz, Methanol-d₄) δ 9.11 (s, 1H), 8.51 (d, J = 7.7 Hz, 1H), 8.38-8.22 (m, 4H), 8.16-8.08 (m, 2H), 7.98 (d, J = 8.7 Hz, 1H), 6.07 (s, 1H), 3.98 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 99 (R)-1-(2-chloropyridin-3-yl)ethyl (4-(5-(6-cyanonicotinamido)pyridin-2-yl)-1-methyl-1H-1,2,3-triazol-5-yl)carbamate | 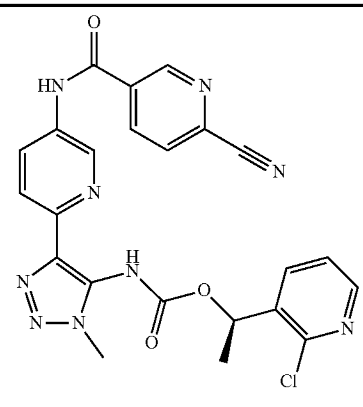 | | 504.2 | ¹H NMR (400 MHz, Methanol-d₄) δ 9.25 (dd, J = 2.2, 0.8 Hz, 1H), 9.00 (s, 1H), 8.52 (dd, J = 8.1, 2.2 Hz, 1H), 8.30 (s, 1H), 8.21 (dd, J = 8.6, 2.6 Hz, 1H), 8.06 (dd, J = 8.1, 0.9 Hz, 1H), 8.00-7.37 (m, 3H), 6.07 (d, J = 6.9 Hz, 1H), 3.98 (s, 3H), 1.60 (s, 3H). |
| Compound 100 (R)-1-(2-chloropyridin-3-yl)ethyl (4-(5-(2-cyanoisonicotinamido)pyridin-2-yl)-1-methyl-1H-1,2,3-triazol-5-yl)carbamate | 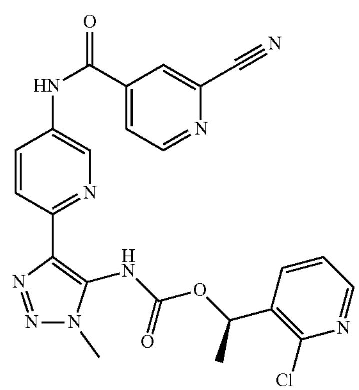 [SMILES: C[C@@H](OC(=O)Nc1c(-c2ccc(NC(=O)c3ccnc(C#N)c3)cn2)nnn1C)c1cccnc1Cl] | | 504.2 | ¹H NMR (400 MHz, Methanol-d₄) δ 9.00 (s, 1H), 8.93 (dd, J = 5.1, 0.9 Hz, 1H), 8.40 (dd, J = 1.7, 0.9 Hz, 1H), 8.30 (s, 1H), 8.21 (dd, J = 8.6, 2.6 Hz, 1H), 8.18-8.04 (m, 2H), 7.97 (d, J = 8.6 Hz, 1H), 7.56-7.39 (m, 1H), 6.07 (s, 1H), 3.98 (s, 3H), 1.60 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 101 (R)-1-(2-chloropyridin-3-yl)ethyl (1-methyl-4-(5-(3-methylisonicotinamido)pyridin-2-yl)-1H-1,2,3-triazol-5-yl)carbamate | 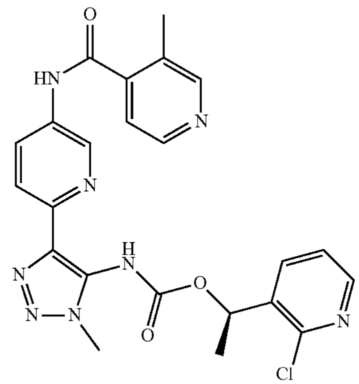 [SMILES: Cc1cnccc1C(=O)Nc1ccc(-c2nnn(C)c2NC(=O)O[C@H](C)c2cccnc2Cl)nc1] | | 493.0 | 1H NMR (400 MHz, Methanol-d4) δ 8.94 (s, 1H), 8.56 (s, 1H), 8.54 (d, J = 5.0 Hz, 1H), 8.30 (s, 1H), 8.16 (dd, J = 8.6, 2.6 Hz, 1H), 8.06 (s, 1H), 7.95 (d, J = 8.6 Hz, 1H), 7.56 (d, J = 5.0 Hz, 1H), 7.47 (s, 1H), 6.07 (d, J = 6.2 Hz, 1H), 3.98 (s, 3H), 2.50 (s, 3H), 1.60 (s, 3H). |
| Compound 102 (R)-1-(2-chloropyridin-3-yl)ethyl (1-methyl-4-(5-(2-methylisonicotinamido)pyridin-2-yl)-1H-1,2,3-triazol-5-yl)carbamate | 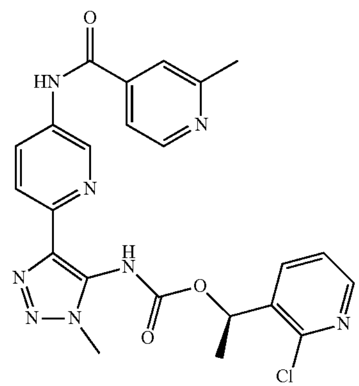 [SMILES: Cc1cc(C(=O)Nc2ccc(-c3nnn(C)c3NC(=O)O[C@H](C)c3cccnc3Cl)nc2)ccn1] | | 493.0 | 1H NMR (400 MHz, Methanol-d4) δ 9.00 (s, 1H), 8.62 (d, J = 5.2 Hz, 1H), 8.30 (s, 1H), 8.20 (dd, J = 8.7, 2.6 Hz, 1H), 8.07 (s, 1H), 7.96 (d, J = 8.7 Hz, 1H), 7.82 (s, 1H), 7.73 (dd, J = 5.3, 1.6 Hz, 1H), 7.47 (s, 1H), 6.07 (d, J = 6.8 Hz, 1H), 3.98 (s, 3H), 2.66 (s, 3H), 1.60 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 103 (R)-1-(2-chloropyridin-3-yl)ethyl (4-(5-(2-chloroisonicotinamido)pyridin-2-yl)-1-methyl-1H-1,2,3-triazol-5-yl)carbamate | 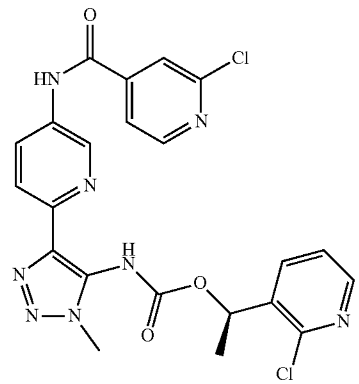 [SMILES: C[C@@H](OC(=O)Nc1c(-c2ccc(NC(=O)c3ccnc(Cl)c3)cn2)nnn1C)c1cccnc1Cl] | | 513.2 | 1H NMR (400 MHz, Methanol-d4) δ 9.00 (s, 1H), 8.59 (dd, J = 5.1, 0.7 Hz, 1H), 8.30 (s, 1H), 8.20 (dd, J = 8.7, 2.6 Hz, 1H), 8.07 (s, 1H), 8.03-7.90 (m, 2H), 7.87 (dd, J = 5.1, 1.5 Hz, 1H), 7.47 (s, 1H), 6.07 (d, J = 6.8 Hz, 1H), 3.98 (s, 3H), 1.60 (s, 3H). |
| Compound 104 (R)-1-(2-chloropyridin-3-yl)ethyl (4-(5-(2-oxabicyclo[2.1.1]hexane-4-carboxamido)pyridin-2-yl)-1-methyl-1H-1,2,3-triazol-5-yl)carbamate | 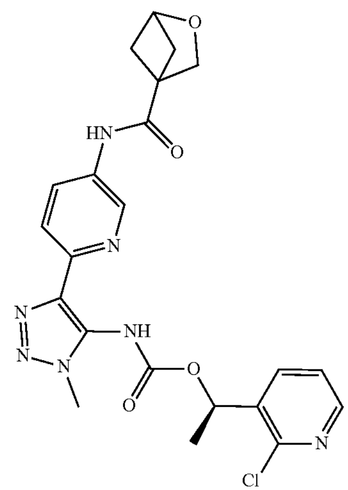 [SMILES: C[C@@H](OC(=O)Nc1c(-c2ccc(NC(=O)C34COC(C3)C4)cn2)nnn1C)c1cccnc1Cl] | | 484.1 | 1H NMR (400 MHz, DMSO-d6) δ 10.04-9.54 (m, 2H), 8.86 (bs, 1H), 8.36 (bs, 1H), 8.20-7.83 (m, 3H), 7.53 (bs, 1H), 5.88 (bs, 1H), 4.52 (s, 1H), 3.98-3.75 (m, 5H), 2.28-2.15 (m, 2H), 1.87-1.74 (m, 2H), 1.56 (bs, 3H). |

TABLE 2-continued

Compounds prepared according to Scheme C, Step 4.

| Compound No. | Structure | Reagent | LCMS m/z | 1H NMR |
|---|---|---|---|---|
| Compound 105 (R)-1-(2-chloropyridin-3-yl)ethyl (4-(5-(2-oxabicyclo[2.1.1]hexane-1-carboxamido)pyridin-2-yl)-1-methyl-1H-1,2,3-triazol-5-yl)carbamate | 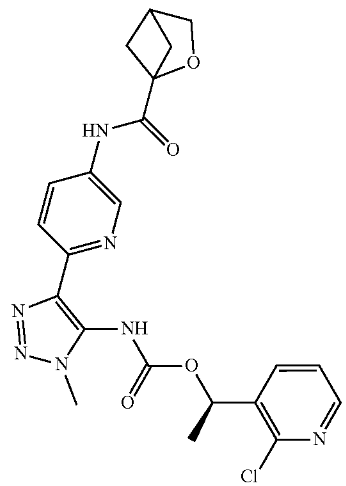 [SMILES: C[C@@H](OC(=O)Nc1c(-c2ccc(NC(=O)C34CC(CO3)C4)cn2)nnn1C)c1cccnc1Cl] | | 484.2 | 1H NMR (400 MHz, DMSO-d6) δ 10.09 (s, 1H), 9.85 (bs, 1H), 8.93 (bs, 1H), 8.36 (bs, 1H), 8.21 (dd, J = 8.6, 2.5 Hz, 1H), 8.04 (bs, 1H), 7.90 (d, J = 8.7 Hz, 1H), 7.55 (bs, 1H), 5.87 (bs, 1H), 3.99-3.75 (m, 5H), 3.00 (t, J = 3.3 Hz, 1H), 2.27-2.11 (m, 2H), 1.77-1.30 (m, 5H). |
| Compound 106 (R)-1-(2-chloropyridin-3-yl)ethyl (4-(5-(1H-imidazole-4-carboxamido)pyridin-2-yl)-1-methyl-1H-1,2,3-triazol-5-yl)carbamate | 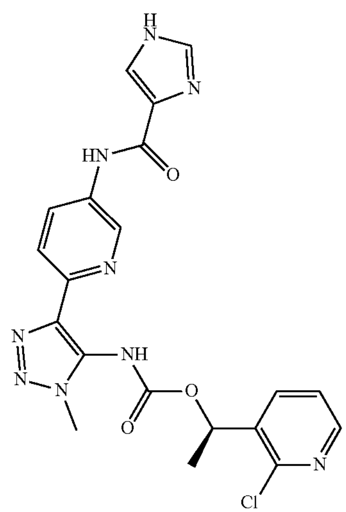 [SMILES: C[C@@H](OC(=O)Nc1c(-c2ccc(NC(=O)c3c[nH]cn3)cn2)nnn1C)c1cccnc1Cl] | | 482.1 | 1H NMR (400 MHz, DMSO-d6) δ 10.29 (s, 1H), 9.83 (bs, 1H), 8.88 (s, 1H), 8.36 (bs, 1H), 8.16 (dd, J = 8.6, 2.6 Hz, 1H), 8.09-7.73 (m, 4H), 7.52 (bs, 1H), 5.87 (bs, 1H), 3.97-3.80 (m, 6H), 1.51 (bs, 3H). |

TABLE 2-continued

Compounds prepared according to Scheme C, Step 4.

| Compound No. | Structure | Reagent | LCMS m/z | 1H NMR |
|---|---|---|---|---|
| Compound 107 (R)-1-(2-chloropyridin-3-yl)ethyl (4-(5-(3,3-difluoropropanamido)pyridin-2-yl)-1-methyl-1H-1,2,3-triazol-5-yl)carbamate | 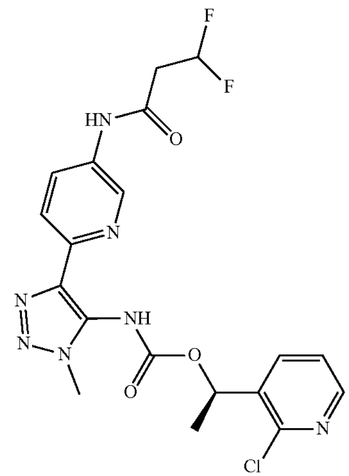 [SMILES: C[C@@H](OC(=O)Nc1c(-c2ccc(NC(=O)CC(F)F)cn2)nnn1C)c1cccnc1Cl] | | 468.2 | 1H NMR (400 MHz, DMSO-d6) δ 12.70 (s, 1H), 10.24 (s, 1H), 9.83 (bs, 1H), 9.06 (s, 1H), 8.48-8.25 (m, 2H), 8.06 (bs, 1H), 7.96-7.78 (m, 3H), 7.60 (bs, 1H), 5.88 (bs, 1H), 3.88 (s, 3H), 1.57 (bs, 3H). |
| Compound 108 (R)-1-(2-chloropyridin-3-yl)ethyl (4-(5-(3-hydroxy-3-methylcyclobutane-1-carboxamido)pyridin-2-yl)-1-methyl-1H-1,2,3-triazol-5-yl)carbamate | 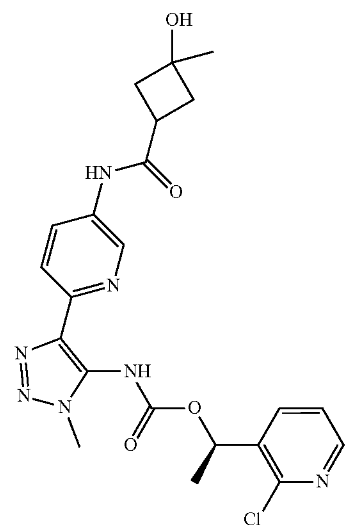 [SMILES: C[C@@H](OC(=O)Nc1c(-c2ccc(NC(=O)C3CC(C)(O)C3)cn2)nnn1C)c1cccnc1Cl] | | 466.1 | 1H NMR (400 MHz, DMSO-d6) δ 10.48 (s, 1H), 9.82 (bs, 1H), 8.75 (bs, 1H), 8.36 (bs, 1H), 8.04 (dd, J = 8.6, 2.5 Hz, 1H), 7.93 (d, J = 8.6 Hz, 1H), 7.53 (bs, 2H), 6.42 (tt, J = 55.8, 4.8 Hz, 1H), 5.87 (bs, 1H), 3.88 (s, 3H), 3.13 (td, J = 16.8, 4.8 Hz, 2H), 1.56 (bs, 3H). |

TABLE 2-continued

Compounds prepared according to Scheme C, Step 4.

| Compound No. | Structure | Reagent | LCMS m/z | 1H NMR |
|---|---|---|---|---|
| Compound 109 (R)-1-(2-chloropyridin-3-yl)ethyl (4-(5-(3-hydroxy-3-methylcyclobutane-1-carboxamido)pyridin-2-yl)-1-methyl-1H-1,2,3-triazol-5-yl)carbamate | 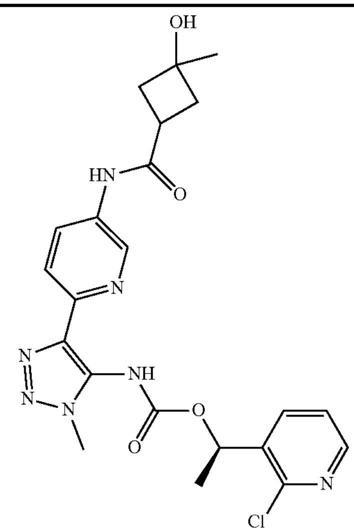 | | 486.1 | 1H NMR (400 MHz, DMSO-d6) δ 10.09 (s, 1H), 9.83 (bs, 1H), 8.77 (bs, 1H), 8.36 (bs, 1H), 8.10-7.99 (m, 2H), 7.88 (d, J = 8.6 Hz, 1H), 7.53 (bs, 1H), 5.87 (bs, 1H), 5.10 (s, 1H), 3.87 (s, 3H), 2.80-2.71 (m, 1H), 2.32-2.17 (m, 2H), 2.15-2.10 (m, 2H), 1.55 (bs, 3H), 1.29 (s, 3H). |
| Compound 110 (R)-1-(2-chloropyridin-3-yl)ethyl (4-(5-(1-(fluoromethyl)cyclopropane-1-carboxamido)pyridin-2-yl)-1-methyl-1H-1,2,3-triazol-5-yl)carbamate | 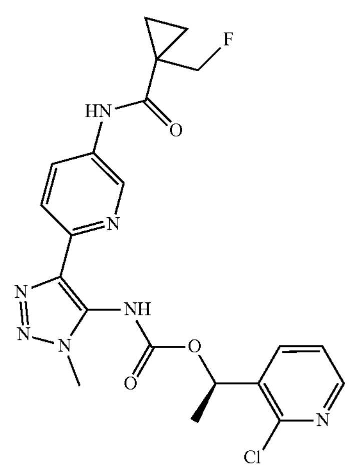 [SMILES: C[C@@H](OC(=O)Nc1c(-c2ccc(NC(=O)C3(CF)CC3)cn2)nnn1C)c1cccnc1Cl] | | 474.2 | 1H NMR (400 MHz, DMSO-d6) δ 9.83 (bs, 1H), 9.62 (s, 1H), 8.81 (bs, 1H), 8.36 (bs, 1H), 8.08 (dd, J = 8.6, 2.5 Hz, 2H), 7.90 (d, J = 8.6 Hz, 1H), 7.53 (bs, 1H), 5.87 (bs, 1H), 4.71 (d, J = 48.5 Hz, 2H), 3.87 (s, 3H), 1.56 (bs, 3H), 1.40-1.27 (m, 2H), 1.01 (qd, J = 4.3, 1.1 Hz, 2H). |

TABLE 2-continued
Compounds prepared according to Scheme C, Step 4.
| Compound No. | Structure | Reagent | LCMS m/z | 1H NMR |
|---|---|---|---|---|
| Compound 111 (R)-1-(2-chloropyridin-3-yl)ethyl (4-(5-(4-hydroxy-4-methylpent-2-ynamidopyridin-2-yl)-1-methyl-1H-1,2,3-triazol-5-yl)carbamate | 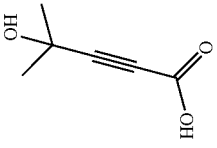 | 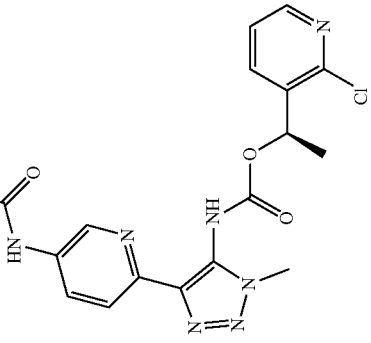 | 484.2 | 1H NMR (400 MHz, DMSO-d6) δ 10.92 (bs, 1H), 9.84 (bs, 1H), 8.76 (bs, 1H), 8.36 (bs, 1H), 8.20-7.85 (m, 3H), 7.54 (bs, 1H), 5.87 (bs, 1H), 5.75 (s, 1H), 3.88 (s, 3H), 1.67-1.37 (m, 9H). |

TABLE 2-continued

Compounds prepared according to Scheme C, Step 4.

| Compound No. | Structure | Reagent | LCMS m/z | 1H NMR |
|---|---|---|---|---|
| Compound 112 (R)-1-(2-chloropyridin-3-yl)ethyl (1-methyl-4-(5-(1-methyl-1H-pyrazole-4-carboxamido)pyridin-2-yl)-1H-1,2,3-triazol-5-yl)carbamate | 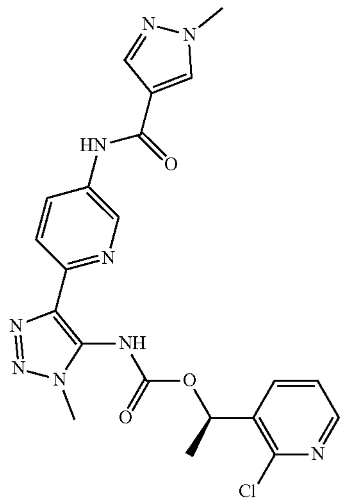 [SMILES: C[C@@H](OC(=O)Nc1c(-c2ccc(NC(=O)c3cnn(C)c3)cn2)nnn1C)c1cccnc1Cl] | | 482.1 | 1H NMR (400 MHz DMSO-d6) δ 10.07 (s, 1H), 9.85 (bs, 1H), 8.93 (bs, 1H), 8.36 (s, 2H), 8.22-7.98 (m, 3H), 7.94 (d, J = 8.6 Hz, 1H), 7.55 (bs, 1H), 5.88 (bs, 1H), 3.92 (s, 3H), 3.88 (s, 3H), 1.57 (bs, 3H). |
| Compound 113 (R)-1-(2-chloropyridin-3-yl)ethyl (4-(5-(1H-pyrazole-4-carboxamido)pyridin-2-yl)-1-methyl-1H-1,2,3-triazol-5-yl)carbamate | 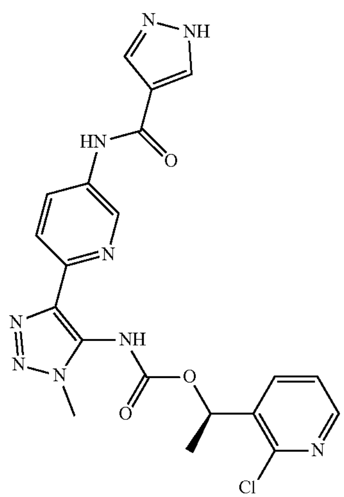 [SMILES: C[C@@H](OC(=O)Nc1c(-c2ccc(NC(=O)c3cn[nH]c3)cn2)nnn1C)c1cccnc1Cl] | | 468.2 | 1H NMR (400 MHz, DMSO-d6) δ 13.33 (s, 1H), 10.06 (s, 1H), 9.87 (bs, 1H), 8.94 (bs, 1H), 8.36 (bs, 2H), 8.23-7.96 (m, 2H), 7.94 (d, J = 8.6 Hz, 1H), 7.55 (bs, 1H), 5.88 (bs, 1H), 3.88 (s, 3H), 1.57 (bs, 3H). |

TABLE 2-continued
Compounds prepared according to Scheme C, Step 4.
| Compound No. | Structure | Reagent | LCMS m/z | 1H NMR |
|---|---|---|---|---|
| Compound 114 (R)-1-(2-chloropyridin-3-yl)ethyl (4-(5-(4-fluorobicyclo[2.2.2]octane-1-carboxamido)pyridin-2-yl)-1-methyl-1H-1,2,3-triazol-5-yl)carbamate | 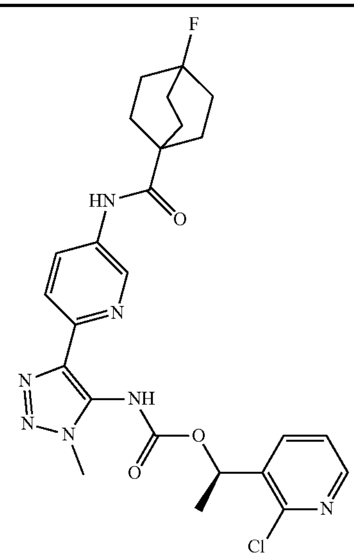 | 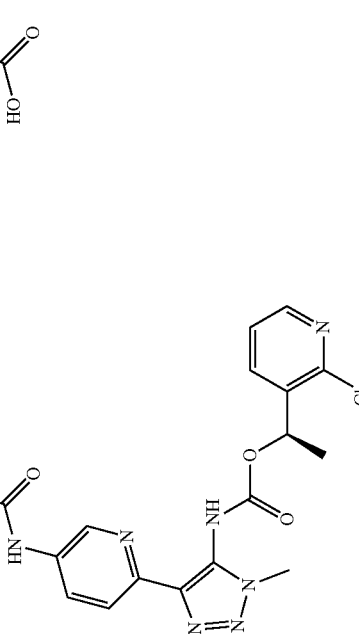 | 527.9 | 1H NMR (400 MHz, DMSO-d6) δ 9.84 (bs, 1H), 9.48 (s, 1H), 8.80 (bs, 1H), 8.35 (bs, 1H), 8.20-7.92 (m, 2H), 7.87 (d, J = 8.7 Hz, 1H), 7.53 (bs, 1H), 5.87 (bs, 1H), 3.87 (s, 3H), 2.10-1.97 (m, 6H), 1.89-1.75 (m, 6H), 1.56 (bs, 3H). |

TABLE 2-continued

Compounds prepared according to Scheme C, Step 4.

| Compound No. | Structure | Reagent | LCMS m/z | 1H NMR |
|---|---|---|---|---|
| Compound 115 (R)-1-(2-chloropyridin-3-yl)ethyl (4-(5-(4-hydroxybicyclo[2.2.2]octane-1-carboxamido)pyridin-2-yl)-1-methyl-1H-1,2,3-triazol-5-yl)carbamate | 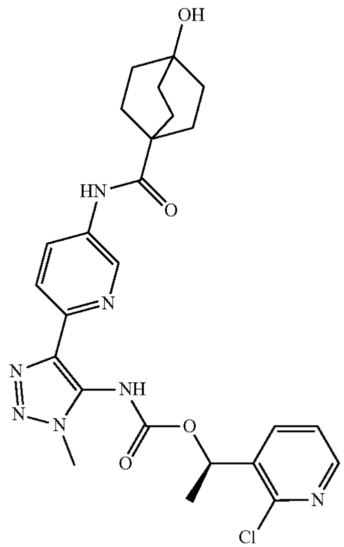 [SMILES: C[C@@H](OC(=O)Nc1c(-c2ccc(NC(=O)C34CCC(O)(CC3)CC4)cn2)nnn1C)c1cccnc1Cl] | | 525.9 | 1H NMR (400 MHz, DMSO-d6) δ 9.84 (bs, 1H), 9.40 (s, 1H), 8.80 (bs, 1H), 8.35 (bs, 1H), 8.15-7.92 (m, 2H), 7.86 (d, J = 8.7 Hz, 1H), 7.53 (bs, 1H), 5.87 (bs, 1H), 4.36 (s, 1H), 3.87 (s, 3H), 2.01-1.78 (m, 6H), 1.78-1.31 (m, 9H). |
| Compound 116 (R)-1-(2-chloropyridin-3-yl)ethyl (4-(5-(1-(difluoromethyl)cyclopropane-1-carboxamido)pyridin-2-yl)-1-methyl-1H-1,2,3-triazol-5-yl)carbamate | 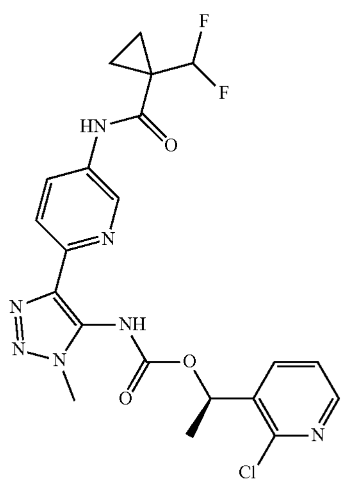 [SMILES: C[C@@H](OC(=O)Nc1c(-c2ccc(NC(=O)C3(C(F)F)CC3)cn2)nnn1C)c1cccnc1Cl] | | 491.9 | 1H NMR (400 MHz, DMSO-d6) δ 9.85 (bs, 1H), 9.64 (s, 1H), 8.77 (s, 1H), 8.36 (bs, 1H), 8.16-7.94 (m, 2H), 7.91 (d, J = 8.6 Hz, 1H), 7.53 (bs, 1H), 6.58 (t, J = 56.9 Hz, 1H), 5.87 (bs, 1H), 3.87 (s, 3H), 1.75-1.27 (m, 5H), 1.28-0.99 (m, 2H). |

TABLE 2-continued

Compounds prepared according to Scheme C, Step 4.

| Compound No. | Structure | Reagent | LCMS m/z | 1H NMR |
|---|---|---|---|---|
| Compound 117 (R)-1-(2-chloropyridin-3-yl)ethyl (4-(5-(3-hydroxybicyclo[1.1.1]pentane-1-carboxamido)pyridin-2-yl)-1-methyl-1H-1,2,3-triazol-5-yl)carbamate | 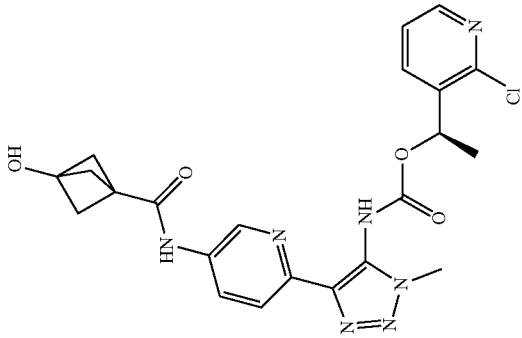 | 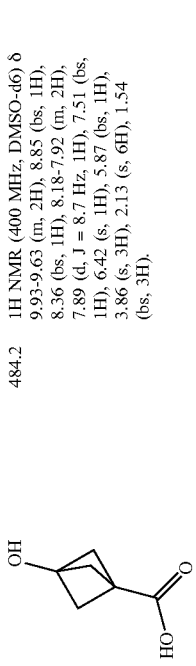 | 484.2 | 1H NMR (400 MHz, DMSO-d6) δ 9.93-9.63 (m, 2H), 8.85 (bs, 1H), 8.36 (bs, 1H), 8.18-7.92 (m, 2H), 7.89 (d, J = 8.7 Hz, 1H), 7.51 (bs, 1H), 6.42 (s, 1H), 5.87 (bs, 1H), 3.86 (s, 3H), 2.13 (s, 6H), 1.54 (bs, 3H). |
| Compound 118 (R)-1-(2-chloropyridin-3-yl)ethyl (4-(5-(3-hydroxy-3-methylbutanamido)pyridin-2-yl)-1-methyl-1H-1,2,3-triazol-5-yl)carbamate | 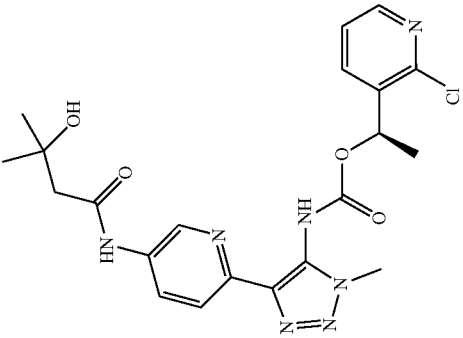 | 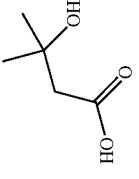 | 474.2 | 1H NMR (400 MHz, DMSO-d6) δ 10.10 (s, 1H), 9.83 (bs, 1H), 8.75 (bs, 1H), 8.35 (bs, 1H), 8.17-792 (m, 2H), 7.88 (d, J = 8.6 Hz, 1H), 7.53 (bs, 1H), 5.86 (bs, 1H), 4.74 (s, 1H), 3.87 (s, 3H), 2.47 (s, 2H), 1.46 (bs, 3H), 1.26 (s, 6H). |

TABLE 2-continued

Compounds prepared according to Scheme C, Step 4.

| Compound No. | Structure | Reagent | LCMS m/z | 1H NMR |
|---|---|---|---|---|
| Compound 119 (R)-1-(2-chloropyridin-3-yl)ethyl (4-(5-(1-(difluoromethyl)-3,3-difluorocyclobutane-1-carboxamido)pyridin-2-yl)-1-methyl-1H-1,2,3-triazol-5-yl)carbamate | 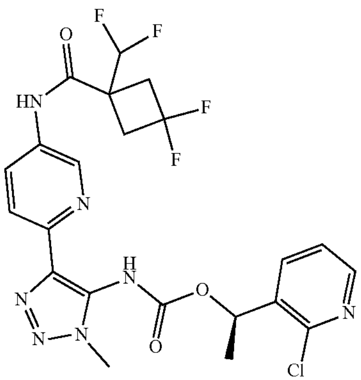 [SMILES: C[C@@H](OC(=O)Nc1c(-c2ccc(NC(=O)C3(C(F)F)CC(F)(F)C3)cn2)nnn1C)c1cccnc1Cl] | | 542.1 | 1H NMR (400 MHz, Methanol-d4) δ 8.95 (s, 1H), 8.32 (s, 1H), 8.15 (m, 2H), 7.95 (d, 1H), 7.50 (s, 1H), 6.33 (t, J = 55.9 Hz, 1H), 6.08 (d, 1H), 4.00 (s, 3H), 3.23 (m, 2H), 3.07 (m, 2H), 1.64 (s, 3H). |
| Compound 120 (R)-1-(2-chloropyridin-3-yl)ethyl (1-methyl-4-(5-(3-oxo-1-(trifluoromethyl)cyclobutane-1-carboxamido)pyridin-2-yl)-1H-1,2,3-triazol-5-yl)carbamate | 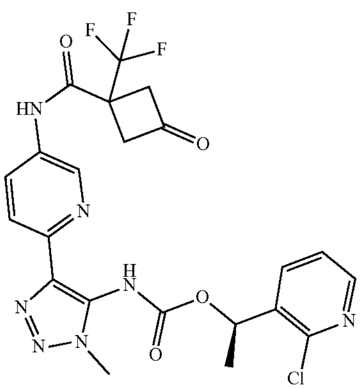 [SMILES: C[C@@H](OC(=O)Nc1c(-c2ccc(NC(=O)C3(C(F)(F)F)CC(=O)C3)cn2)nnn1C)c1cccnc1Cl] | | 538.1 | 1H NMR (400 MHz, Methanol-d4) δ 9.13-8.71 (m, 1H), 8.32 (s, 2H), 8.24-7.70 (m, 2H), 7.62-7.33 (m, 1H), 6.08 (d, 1H), 3.96 (m, 5H), 3.68-3.46 (m, 1H), 3.08-2.61 (m, 2H), 1.87-1.40 (m, 3H). |

TABLE 2-continued

Compounds prepared according to Scheme C, Step 4.

| Compound No. | Structure | Reagent | LCMS m/z | 1H NMR |
|---|---|---|---|---|
| Compound 121 (R)-1-(2-chloropyridin-3-yl)ethyl (4-(5-((1s,3S)-3-cyano-1-methylcyclobutane-1-carboxamido)pyridin-2-yl)-1-methyl-1H-1,2,3-triazol-5-yl)carbamate | 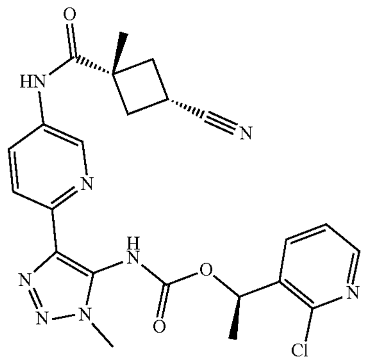 [SMILES: C[C@@H](OC(=O)Nc1c(-c2ccc(NC(=O)[C@]3(C)C[C@H](C#N)C3)cn2)nnn1C)c1cccnc1Cl] | | 495.1 | 1H NMR (400 MHz, Methanol-d4) δ 9.05 (s, 1H), 8.34 (s, 1H), 8.28-8.00 (m, 2H), 7.94 (d, 1H), 7.51 (s, 1H), 6.09 (d, 1H), 4.01 (s, 3H), 3.39 (m, 1H), 2.94-2.78 (m, 2H), 2.49-2.34 (m, 2H), 1.58 (m, 6H). |
| Compound 122 (R)-1-(2-chloropyridin-3-yl)ethyl (4-(5-((1r,3R)-3-cyano-1-methylcyclobutane-1-carboxamido)pyridin-2-yl)-1-methyl-1H-1,2,3-triazol-5-yl)carbamate | 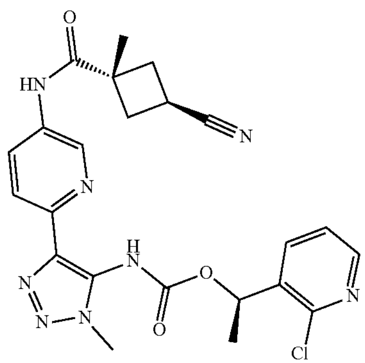 [SMILES: C[C@@H](OC(=O)Nc1c(-c2ccc(NC(=O)[C@]3(C)C[C@@H](C#N)C3)cn2)nnn1C)c1cccnc1Cl] | | 495.1 | 1H NMR (400 MHz, Methanol-d4) δ 8.97 (d, 1H), 8.34 (s, 1H), 8.27-7.99 (m, 2H), 7.93 (d, 1H), 7.51 (s, 1H), 6.08 (d, 1H), 4.01 (s, 3H), 3.28-3.16 (m, 1H), 3.13-2.96 (m, 2H), 2.49-2.21 (m, 2H), 1.67 (s, 6H). |

TABLE 2-continued

Compounds prepared according to Scheme C, Step 4.

| Compound No. | Structure | Reagent | LCMS m/z | 1H NMR |
|---|---|---|---|---|
| Compound 123 (R)-1-(2-chloropyridin-3-yl)ethyl (4-(5-(3-cyano-3-fluorocyclobutane-1-carboxamido)pyridin-2-yl)-1-methyl-1H-1,2,3-triazol-5-yl)carbamate | 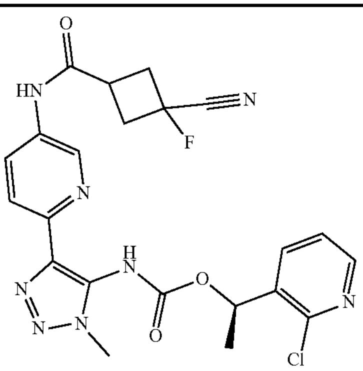 | | 499.0 | 1H NMR (400 MHz, Methanol-d4) δ 8.91 (s, 1H), 8.32 (s, 1H), 8.23-7.75 (m, 3H), 7.49 (s, 1H), 6.08 (d, 1H), 4.90-4.65 (m, 2H), 4.00 (s, 3H), 2.83-2.65 (m, 1H), 1.93-1.80 (m, 2H), 1.55 (d, 3H). |
| Compound 124 (R)-1-(2-chloropyridin-3-yl)ethyl (4-(5-((R)-2-hydroxypropanamido)pyridin-2-yl)-1-methyl-1H-1,2,3-triazol-5-yl)carbamate | 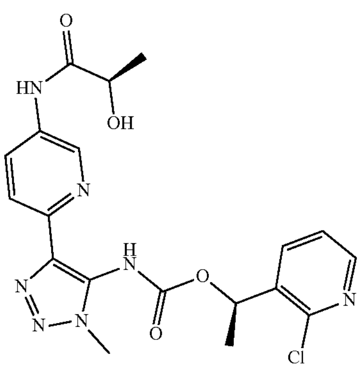 [SMILES: C[C@@H](O)C(=O)Nc1ccc(-c2nnn(C)c2NC(=O)O[C@H](C)c2cccnc2Cl)nc1] | | 446.0 | 1H NMR (400 MHz, Methanol-d4) δ 9.26-8.87 (m, 1H), 8.47-8.20 (m, 2H), 8.20-7.77 (m, 2H), 7.49 (s, 1H), 6.09 (m, 1H), 4.34 (m, 1H), 4.00 (s, 3H), 1.86-1.53 (m, 3H), 1.49 (d, 3H). |

TABLE 2-continued

Compounds prepared according to Scheme C, Step 4.

| Compound No. | Structure | Reagent | LCMS m/z | 1H NMR |
|---|---|---|---|---|
| Compound 125 (R)-1-(2-chloropyridin-3-yl)ethyl (4-(5-((S)-2-hydroxypropanamido)pyridin-2-yl)-1-methyl-1H-1,2,3-triazol-5-yl)carbamate | 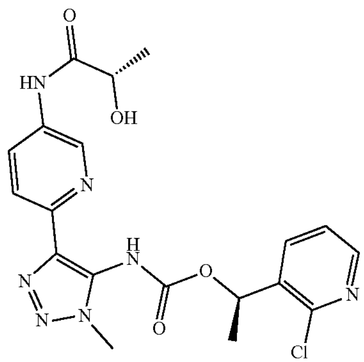 [SMILES: C[C@H](O)C(=O)Nc1ccc(-c2nnn(C)c2NC(=O)O[C@H](C)c2cccnc2Cl)nc1] | | 446.0 | 1H NMR (400 MHz, Methanol-d4) δ 9.26-8.86 (m, 1H), 8.44-8.19 (m, 2H), 8.19-7.77 (m, 2H), 7.49 (s, 1H), 6.09 (q, 1H), 4.34 (q, 1H), 4.00 (s, 3H), 1.63 (s, 3H), 1.48 (d, 3H). |
| Compound 126 (R)-1-(2-chloropyridin-3-yl)ethyl (4-(5-(2-hydroxyacetamido)pyridin-2-yl)-1-methyl-1H-1,2,3-triazol-5-yl)carbamate | 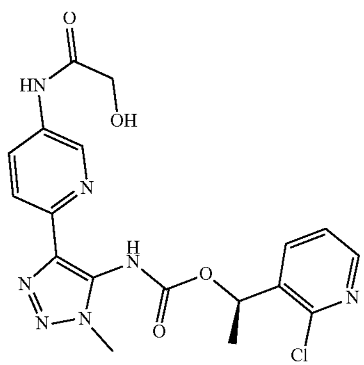 [SMILES: C[C@@H](OC(=O)Nc1c(-c2ccc(NC(=O)CO)cn2)nnn1C)c1cccnc1Cl] | | 432.0 | 1H NMR (400 MHz, Methanol-d4) δ 9.01 (s, 1H), 8.51-8.29 (m, 1H), 8.23 (dd, 1H), 8.18-7.80 (m, 2H), 7.48 (s, 1H), 6.09 (m, 1H), 4.20 (s, 2H), 4.00 (s, 3H), 1.62 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 127 (R)-1-(2-chloropyridin-3-yl)ethyl (4-(5-((1r,3R)-3-cyanocyclobutane-1-carboxamido)pyridin-2-yl)-1-methyl-1H-1,2,3-triazol-5-yl)carbamate | 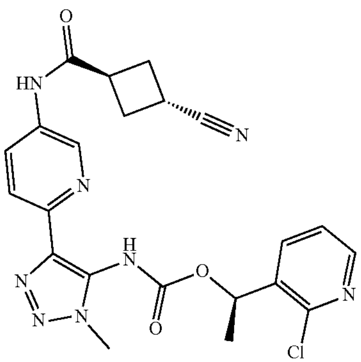 [SMILES: C[C@@H](OC(=O)Nc1c(-c2ccc(NC(=O)[C@H]3C[C@H](C#N)C3)cn2)nnn1C)c1cccnc1Cl] | | 481.1 | 1H NMR (400 MHz, Methanol-d4) δ 8.96 (d, 1H), 8.33 (s, 1H), 8.12 (m, 2H), 7.91 (d, 1H), 7.43 (d, 1H), 6.08 (d, 1H), 3.99 (s, 3H), 3.45 (m, 2H), 2.85-2.48 (m, 4H), 1.62 (s, 3H). |
| Compound 128 (R)-1-(2-chloropyridin-3-yl)ethyl (4-(5-((1s,3S)-3-cyanocyclobutane-1-carboxamido)pyridin-2-yl)-1-methyl-1H-1,2,3-triazol-5-yl)carbamate | 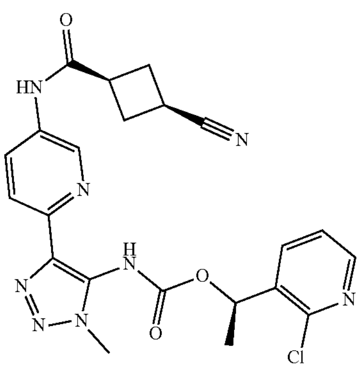 [SMILES: C[C@@H](OC(=O)Nc1c(-c2ccc(NC(=O)[C@H]3C[C@@H](C#N)C3)cn2)nnn1C)c1cccnc1Cl] | | 481.1 | 1H NMR (400 MHz, Methanol-d4) δ 8.91 (s, 1H), 8.32 (s, 1H), 7.91-8.12 (m, 3H), 6.08 (d, 1H), 3.99 (s, 3H), 3.32-3.54 (m, 2H), 2.80 (m, 2H), 2.64 (m, 2H), 1.62 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 129 (R)-1-(2-chloropyridin-3-yl)ethyl (4-(5-(2-cyano-2-methyl)propanamido)pyridin-2-yl)-1-methyl-1H-1,2,3-triazol-5-yl)carbamate | | | 469.1 | 1H NMR (400 MHz, Methanol-d4) δ 8.98 (s, 1H), 8.33 (s, 1H), 8.22 (m, 1H), 7.97 (m, 2H), 7.48 (s, 1H), 6.09 (m, 1H), 4.01 (s, 3H), 1.75 (s, 6H), 1.61 (s, 3H). |
| Compound 130 (R)-1-(2-chloropyridin-3-yl)ethyl (4-(5-(2-cyanocyclopropane-1-carboxamido)pyridin-2-yl)-1-methyl-1H-1,2,3-triazol-5-yl)carbamate | 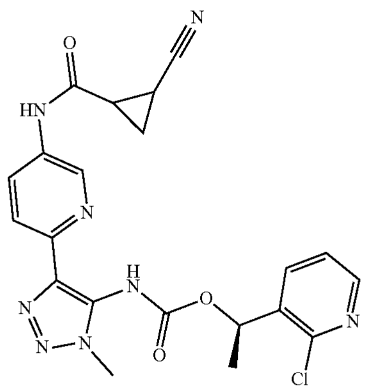 [SMILES: C[C@@H](OC(=O)Nc1c(-c2ccc(NC(=O)C3CC3C#N)cn2)nnn1C)c1cccnc1Cl] | | 467.1 | 1H NMR (400 MHz, Methanol-d4) δ 8.99 (s, 1H), 8.44-8.26(m, 1H), 8.23-7.85 (m, 3H), 7.47 (s, 1H), 6.08 (m, 1H), 4.00 (s, 3H), 2.49 (m, 1H), 2.14 (m, 1H), 1.79-1.44 (m, 5H). |

TABLE 2-continued

Compounds prepared according to Scheme C, Step 4.

| Compound No. | Structure | Reagent | LCMS m/z | 1H NMR |
|---|---|---|---|---|
| Compound 131 (R)-1-(2-chloropyridin-3-yl)ethyl (4-(5-(1,3-difluorocyclobutane-1-carboxamido)pyridin-2-yl)-1-methyl-1H-1,2,3-triazol-5-yl)carbamate | 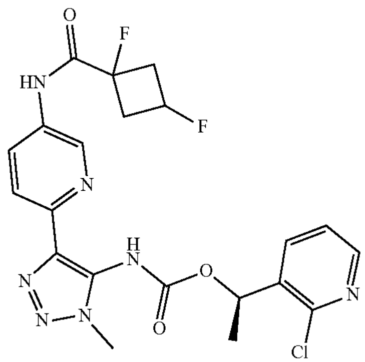 [SMILES: C[C@@H](OC(=O)Nc1c(-c2ccc(NC(=O)C3(F)CC(F)C3)cn2)nnn1C)c1cccnc1Cl] | | 492.1 | 1H NMR (400 MHz, Methanol-d4) δ 8.96 (d, 1H), 8.45-8.20 (m, 2H), 8.20-7.85 (m, 2H), 7.51 (s, 1H), 6.09 (d, 1H), 5.18-4.96 (m, 1H), 4.00 (s, 3H), 3.24-3.05 (m, 2H), 2.93-2.59 (m, 2H), 1.61 (d, 3H). |
| Compound 132 (R)-1-(2-chloropyridin-3-yl)ethyl (4-(5-(1-cyano-3-fluorocyclobutane-1-carboxamido)pyridin-2-yl)-1-methyl-1H-1,2,3-triazol-5-yl)carbamate | 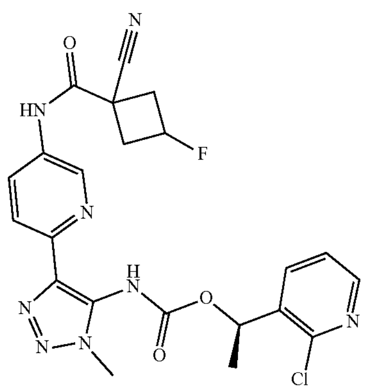 [SMILES: C[C@@H](OC(=O)Nc1c(-c2ccc(NC(=O)C3(C#N)CC(F)C3)cn2)nnn1C)c1cccnc1Cl] | | 499.1 | 1H NMR (400 MHz, Methanol-d4) δ 9.11-8.82 (m, 1H), 8.34 (s, 1H), 8.23-8.09 (m, 2H), 7.99 (m, 1H), 7.70-7.31 (m, 1H), 6.09 (d, 1H), 5.34 (m, 1H), 4.00 (s, 3H), 3.20-2.82 (m, 4H), 1.64 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 133 (R)-1-(2-chloropyridin-3-yl)ethyl (4-(5-((1r,3R)-1-fluoro-3-hydroxycyclobutane-1-carboxamido)pyridin-2-yl)-1-methyl-1H-1,2,3-triazol-5-yl)carbamate | 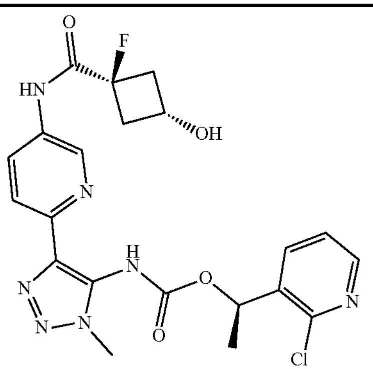 | | 490.0 | 1H NMR (400 MHz, Methanol-d4) δ 9.07 (s, 1H), 8.50-8.23 (m, 2H), 8.22-7.83 (m, 2H), 7.51 (s, 1H), 6.09 (d, 1H), 4.62 (m, 1H), 4.00 (s, 3H), 2.90-2.56 (m, 4H), 1.65 (s, 3H). |
| Compound 134 (R)-1-(2-chloropyridin-3-yl)ethyl (4-(5-((1s,3S)-1-fluoro-3-hydroxycyclobutane-1-carboxamido)pyridin-2-yl)-1-methyl-1H-1,2,3-triazol-5-yl)carbamate | 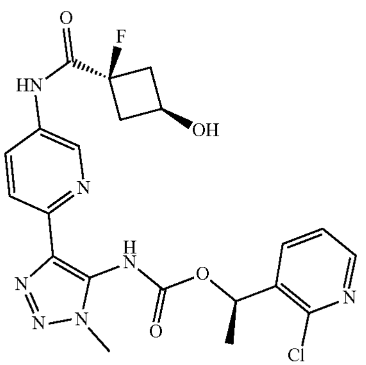 [SMILES: C[C@@H](OC(=O)Nc1c(-c2ccc(NC(=O)[C@]3(F)C[C@@H](O)C3)cn2)nnn1C)c1cccnc1Cl] | | 490.0 | 1H NMR (400 MHz, Methanol-d4) δ 9.03 (s, 1H), 8.46-8.20 (m, 2H), 8.20-7.85 (m, 2H), 7.51 (s, 1H), 6.09 (d, 1H), 4.23 (m, 1H), 4.00 (s, 3H), 3.04 (m, 2H), 2.59-2.34 (m, 2H), 1.64 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 135 (R)-1-(2-chloropyridin-3-yl)ethyl (4-(5-(1-cyano-3-hydroxycyclobutane-1-carboxamido)pyridin-2-yl)-1-methyl-1H-1,2,3-triazol-5-yl)carbamate | 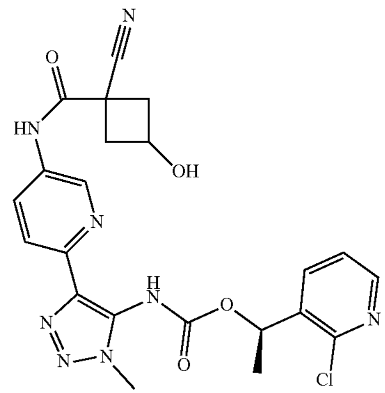 [SMILES: C[C@@H](OC(=O)Nc1c(-c2ccc(NC(=O)C3(C#N)CC(O)C3)cn2)nnn1C)c1cccnc1Cl] | | 497.1 | 1H NMR (400 MHz, Methanol-d4) δ 8.98 (s, 1H), 8.33 (s, 1H), 8.22 (m, 1H), 8.15-7.86 (m, 2H), 7.48 (s, 1H), 6.09 (m, 1H), 4.63-4.25 (m, 1H), 4.01 (s, 3H), 3.18 (m, 1H), 3.06-2.91 (m, 1H), 2.80-2.56 (m, 2H), 1.63 (s, 3H). |
| Compound 136 (R)-1-(2-chloropyridin-3-yl)ethyl (4-(5-(3-hydroxy-3-(trifluoromethyl)cyclobutane-1-carboxamido)pyridin-2-yl)-1-methyl-1H-1,2,3-triazol-5-yl)carbamate | 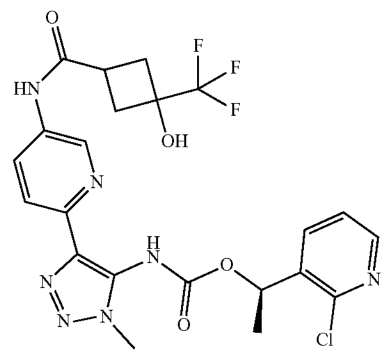 [SMILES: C[C@@H](OC(=O)Nc1c(-c2ccc(NC(=O)C3CC(O)(C(F)(F)F)C3)cn2)nnn1C)c1cccnc1Cl] | | 540.1 | 1H NMR (400 MHz, Methanol-d4) δ 9.03 (s, 1H), 8.33 (s, 1H), 8.19 (m, 1H), 8.13-7.85 (m, 2H), 7.49 (s, 1H), 6.09 (m, 1H), 4.01 (s, 3H), 3.09 (m, 1H), 2.84-2.68 (m, 2H), 2.65-2.47 (m, 2H), 1.63 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 137 (R)-1-(2-chloropyridin-3-yl)ethyl (4-(5-((1R,2S)-2-cyanocyclopropane-1-carboxamido)pyridin-2-yl)-1-methyl-1H-1,2,3-triazol-5-yl)carbamate | 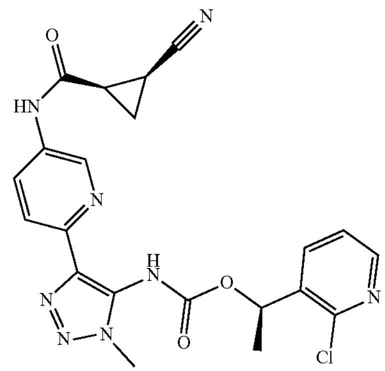 [SMILES: C[C@@H](OC(=O)Nc1c(-c2ccc(NC(=O)[C@@H]3C[C@@H]3C#N)cn2)nnn1C)c1cccnc1Cl] | | 467.1 | 1H NMR (400 MHz, Methanol-d4) δ 9.24-8.84 (m, 1H), 8.33 (d, 1H), 8.25-7.99 (m, 2H), 7.94 (d, 1H), 7.50 (s, 1H), 6.20-5.97 (m, 1H), 4.09-3.87 (m, 3H), 2.40 (m, 1H), 2.18 (m, 1H), 1.80-1.43 (m, 5H). |
| Compound 138 (R)-1-(2-chloropyridin-3-yl)ethyl (4-(5-((1s,3S)-3-cyano-3-methoxycyclobutane-1-carboxamido)pyridin-2-yl)-1-methyl-1H-1,2,3-triazol-5-yl)carbamate | 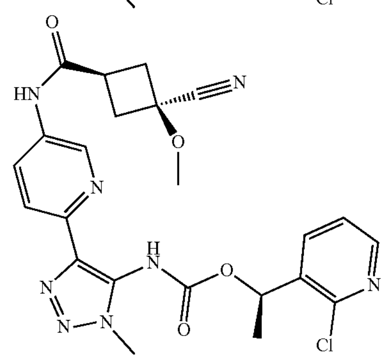 | | 511.1 | 1H NMR (400 MHz, Methanol-d4) δ 9.00 (s, 1H), 8.33 (s, 1H), 8.17 (m, 2H), 7.92 (d, 1H), 7.48 (s, 1H), 6.08 (m, 1H), 4.00 (s, 3H), 3.41 (s, 3H), 3.29-3.15 (m, 1H), 2.93-2.79 (m, 2H), 2.66 (m, 2H), 1.63 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 139 (R)-1-(2-chloropyridin-3-yl)ethyl (4-(5-((1r,3R)-3-cyano-3-methoxycyclobutane-1-carboxamido)pyridin-2-yl)-1-methyl-1H-1,2,3-triazol-5-yl)carbamate | 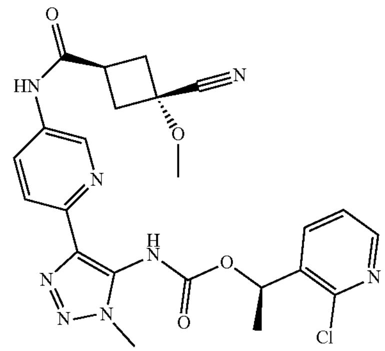 [SMILES: CO[C@]1(C#N)C[C@@H](C(=O)Nc2ccc(-c3nnn(C)c3NC(=O)O[C@H](C)c3cccnc3Cl)nc2)C1] | | 511.1 | 1H NMR (400 MHz, Methanol-d4) δ 9.02 (s, 1H), 8.34 (s, 1H), 8.17 (m, 2H), 7.92 (m, 1H), 7.49 (s, 1H), 6.08 (m, 1H), 4.01 (s, 3H), 3.52-3.38 (m, 4H), 3.00-2.84 (m, 2H), 2.70 (m, 2H), 1.63 (s, 3H). |
| Compound 140 (R)-1-(2-chloropyridin-3-yl)ethyl (4-(5-((1s,3S)-3-cyano-3-hydroxycyclobutane-1-carboxamido)pyridin-2-yl)-1-methyl-1H-1,2,3-triazol-5-yl)carbamate | 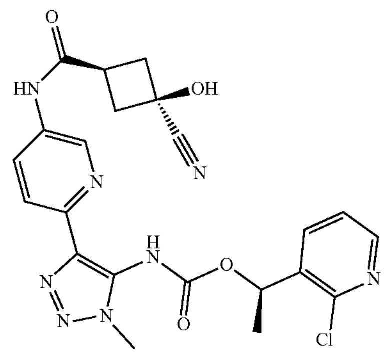 [SMILES: C[C@@H](OC(=O)Nc1c(-c2ccc(NC(=O)[C@H]3C[C@](O)(C#N)C3)cn2)nnn1C)c1cccnc1Cl] | | 497.1 | 1H NMR (400 MHz, Methanol-d4) δ 8.97 (d, 1H), 8.47-8.28 (m, 1H), 8.19 (m, 2H), 8.10 (d, 1H), 7.92 (d, 1H), 7.48 (s, 1H), 6.08 (m, 1H), 4.00 (s, 3H), 3.19 (m, 1H), 2.94-2.80 (m, 2H), 2.65 (m, 2H), 1.63 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 141 (R)-1-(2-chloropyridin-3-yl)ethyl (4-(5-(1-cyano-3-oxocyclobutane-1-carboxamido)pyridin-2-yl)-1-methyl-1H-1,2,3-triazol-5-yl)carbamate | 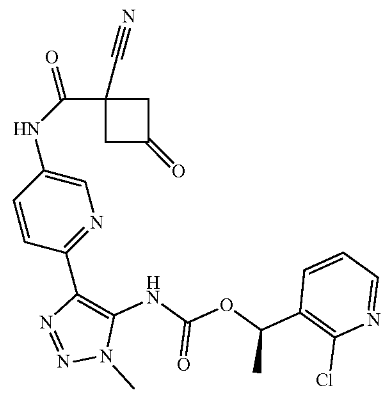 [SMILES: C[C@@H](OC(=O)Nc1c(-c2ccc(NC(=O)C3(C#N)CC(=O)C3)cn2)nnn1C)c1cccnc1Cl] | | 495.0 | 1H NMR (400 MHz, Methanol-d4) δ 8.92 (s, 1H), 8.32 (s, 1H), 8.22-8.08 (m, 2H), 7.96 (d, 1H), 7.48 (s, 1H), 6.09 (m, 1H), 4.00 (s, 3H), 3.15-2.74 (m, 4H), 1.62 (s, 3H). |
| Compound 142 (R)-1-(2-chloropyridin-3-yl)ethyl (4-(5-(2-cyanocyclobutane-1-carboxamido)pyridin-2-yl)-1-methyl-1H-1,2,3-triazol-5-yl)carbamate | 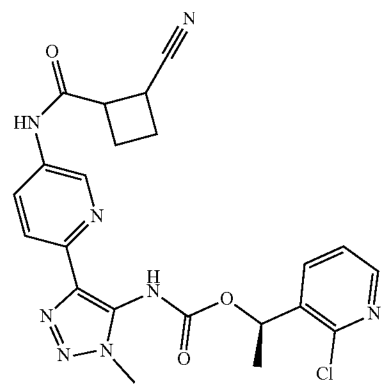 [SMILES: C[C@@H](OC(=O)Nc1c(-c2ccc(NC(=O)C3CCC3C#N)cn2)nnn1C)c1cccnc1Cl] | | 481.1 | 1H NMR (400 MHz, Methanol-d4) δ 9.17-8.85 (m, 1H), 8.45-8.28 (m, 1H), 8.20 (m, 1H), 8.13-7.84 (m, 2H), 7.48 (s, 1H), 6.08 (m, 1H), 4.00 (s, 3H), 3.65 (m, 2H), 2.50-2.23 (m, 4H), 1.59 (d, 3H). |

TABLE 2-continued

Compounds prepared according to Scheme C, Step 4.

| Compound No. | Structure | Reagent | LCMS m/z | 1H NMR |
|---|---|---|---|---|
| Compound 143 (R)-1-(2-chloropyridin-3-yl)ethyl (4-(5-(2-cyanopropanamido)pyridin-2-yl)-1-methyl-1H-1,2,3-triazol-5-yl)carbamate | 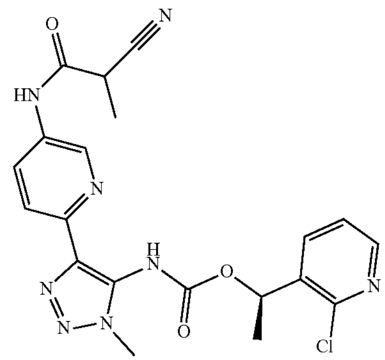 [SMILES: CC(C#N)C(=O)Nc1ccc(-c2nnn(C)c2NC(=O)O[C@H](C)c2cccnc2Cl)nc1] | | 455.0 | 1H NMR (400 MHz, Methanol-d4) δ 8.91 (d, 1H), 8.33 (s, 1H), 8.15 (m, 1H), 7.95 (d, 2H), 7.48 (s, 1H), 6.09 (m, 1H), 4.00 (s, 3H), 3.92 (m, 1H), 1.66 (m, 6H). |
| Compound 144 (R)-1-(2-chloropyridin-3-yl)ethyl (4-(5-(3,3-difluoro-1-methylcyclobutane-1-carboxamido)pyridin-2-yl)-1-methyl-1H-1,2,3-triazol-5-yl)carbamate | 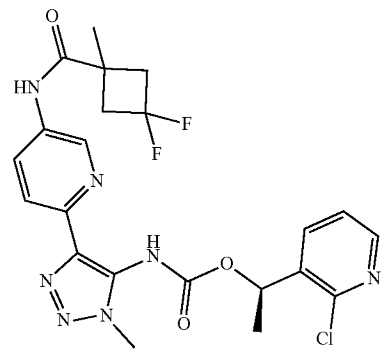 [SMILES: C[C@@H](OC(=O)Nc1c(-c2ccc(NC(=O)C3(C)CC(F)(F)C3)cn2)nnn1C)c1cccnc1Cl] | | 506.1 | 1H NMR (400 MHz, Methanol-d4) δ 9.07 (s, 1H), 8.46-8.20 (m, 2H), 7.95 (d, 2H), 7.48 (s, 1H), 6.09 (m, 1H), 4.01 (s, 3H), 3.25-3.05 (m, 2H), 2.68-2.46 (m, 2H), 1.64 (s, 6H). |

TABLE 2-continued

Compounds prepared according to Scheme C, Step 4.

| Compound No. | Structure | Reagent | LCMS m/z | 1H NMR |
|---|---|---|---|---|
| Compound 145 (R)-1-(2-chloropyridin-3-yl)ethyl (4-(5-(1,3-dicyano-2,2-dimethylcyclopropane-1-carboxamido)pyridin-2-yl)-1-methyl-1H-1,2,3-triazol-5-yl)carbamate | 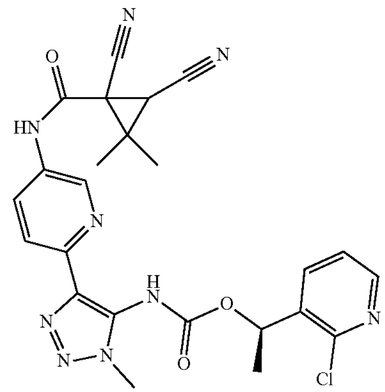 [SMILES: C[C@@H](OC(=O)Nc1c(-c2ccc(NC(=O)C3(C#N)C(C#N)C3(C)C)cn2)nnn1C)c1cccnc1Cl] | | 520.1 | 1H NMR (400 MHz, Methanol-d4) δ 8.91 (s, 1H), 8.32 (s, 1H), 8.16 (m, 2H), 7.95 (m, 1H), 7.46 (s, 1H), 6.08 (m, 1H), 4.00 (s, 3H), 3.04 (d, 1H), 1.66 (m, 6H), 1.32 (d, 3H). |
| Compound 146 (R)-1-(2-chloropyridin-3-yl)ethyl (4-(5-(1-cyano-2,2-dimethylcyclopropane-1-carboxamido)pyridin-2-yl)-1-methyl-1H-1,2,3-triazol-5-yl)carbamate | 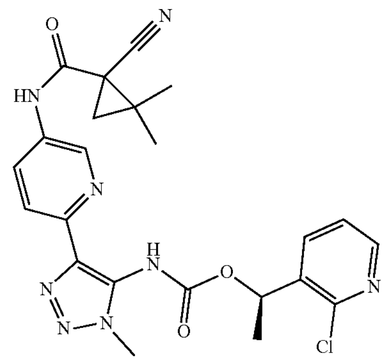 [SMILES: C[C@@H](OC(=O)Nc1c(-c2ccc(NC(=O)C3(C#N)CC3(C)C)cn2)nnn1C)c1cccnc1Cl] | | 495.1 | 1H NMR (400 MHz, Methanol-d4) δ 8.98 (s, 1H), 8.33 (s, 1H), 8.22 (m, 1H), 7.96 (m, 2H), 7.48 (s, 1H), 6.09 (m, 1H), 4.00 (s, 3H), 1.93 (d, 1H), 1.63 (s, 3H), 1.53 (s, 3H), 1.47 (d, 1H), 1.24 (d, 3H). |

TABLE 2-continued

Compounds prepared according to Scheme C, Step 4.

| Compound No. | Structure | Reagent | LCMS m/z | 1H NMR |
|---|---|---|---|---|
| Compound 147 (R)-1-(2-chloropyridin-3-yl)ethyl (4-(5-(1-cyano-2-(trifluoromethyl)cyclopropane-1-carboxamido)pyridin-2-yl)-1-methyl-1H-1,2,3-triazol-5-yl)carbamate | 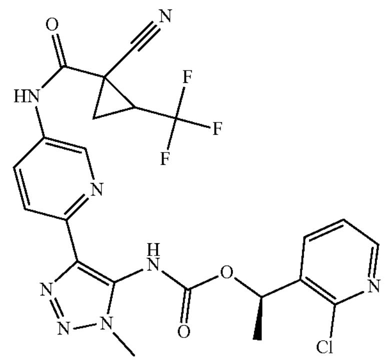 [SMILES: C[C@@H](OC(=O)Nc1c(-c2ccc(NC(=O)C3(C#N)CC3C(F)(F)F)cn2)nnn1C)c1cccnc1Cl] | | 535.1 | 1H NMR (400 MHz, Methanol-d4) δ 8.93 (s, 1H), 8.42-8.27 (m, 1H), 8.20 (m, 2H), 8.15-7.86 (m, 1H), 7.47 (s, 1H), 6.09 (m, 1H), 4.00 (s, 3H), 3.12-2.95 (m, 1H), 2.25-2.07 (m, 2H), 1.62 (s, 3H). |
| Compound 148 (R)-1-(2-chloropyridin-3-yl)ethyl (4-(5-(1-cyano-2-methylcyclopropane-1-carboxamido)pyridin-2-yl)-1-methyl-1H-1,2,3-triazol-5-yl)carbamate | 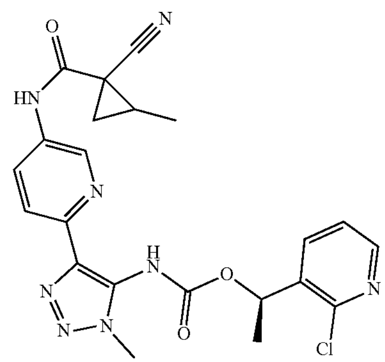 [SMILES: CC1CC1(C#N)C(=O)Nc1ccc(-c2nnn(C)c2NC(=O)O[C@H](C)c2cccnc2Cl)nc1] | | 481.1 | 1H NMR (400 MHz, Methanol-d4) δ 8.95 (s, 1H), 8.33 (d, 1H), 8.21 (dd, 1H), 7.94 (d, 2H), 7.48 (s, 1H), 6.09 (m, 1H), 4.00 (s, 3H), 2.16-2.02 (m, 1H), 1.98 (dd, J = 8.9, 4.6 Hz, 1H), 1.63 (s, 3H), 1.44 (m, 4H). |

TABLE 2-continued

Compounds prepared according to Scheme C, Step 4.

| Compound No. | Structure | Reagent | LCMS m/z | 1H NMR |
|---|---|---|---|---|
| Compound 149 (R)-1-(2-chloropyridin-3-yl)ethyl (1-methyl-4-(5-(spiro[2.2]pentane-1-carboxamido)pyridin-2-yl)-1H-1,2,3-triazol-5-yl)carbamate | 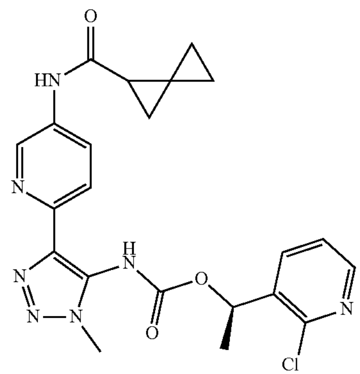 [SMILES: C[C@@H](OC(=O)Nc1c(-c2ccc(NC(=O)C3CC34CC4)cn2)nnn1C)c1cccnc1Cl] | | 468.1 | 1H NMR (400 MHz, Methanol-d4) δ 9.10 (s, 1H), 8.34 (s, 1H), 8.30-8.00 (m, 2H), 7.93 (d, J = 8.8 Hz, 1H), 7.51 (s, 1H), 6.09 (q, J = 6.6 Hz, 1H), 4.01 (s, 3H), 2.20 (dd, J = 7.4, 4.2 Hz, 1H), 1.83-1.40 (m, 5H), 1.10-0.86 (m, 4H). |
| Compound 150 (R)-1-(2-chloropyridin-3-yl)ethyl (1-methyl-4-(5-((S)-5-oxopyrrolidine-3-carboxamido)pyridin-2-yl)-1H-1,2,3-triazol-5-yl)carbamate | 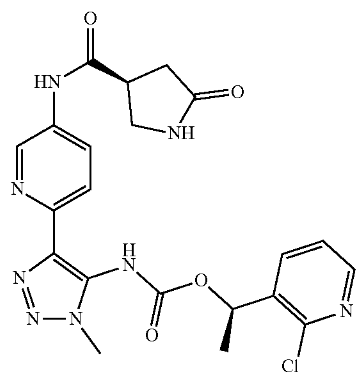 [SMILES: C[C@@H](OC(=O)Nc1c(-c2ccc(NC(=O)[C@@H]3CNC(=O)C3)cn2)nnn1C)c1cccnc1Cl] | | 485.1 | 1H NMR (400 MHz, Methanol-d4) δ 9.05 (s, 1H), 8.43-8.26 (m, 1H), 8.25-8.01 (m, 2H), 7.94 (d, J = 8.7 Hz, 1H), 7.47 (d, J = 30.4 Hz, 1H), 6.08 (d, J = 7.1 Hz, 1H), 4.01 (s, 3H), 3.79-3.61 (m, 2H), 3.55 (tt, J = 8.9, 6.5 Hz, 1H), 2.78-2.60 (m, 2H), 1.84-1.39 (m, 3H). |

TABLE 2-continued

Compounds prepared according to Scheme C, Step 4.

| Compound No. | Structure | Reagent | LCMS m/z | 1H NMR |
|---|---|---|---|---|
| Compound 151 (R)-1-(2-chloropyridin-3-yl)ethyl (1-methyl-4-(5-((S)-5-oxopyrrolidine-2-carboxamido)pyridin-2-yl)-1H-1,2,3-triazol-5-yl)carbamate | 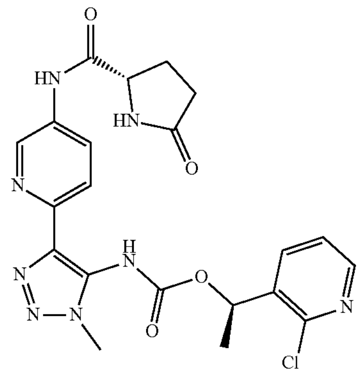 [SMILES: C[C@@H](OC(=O)Nc1c(-c2ccc(NC(=O)[C@@H]3CCC(=O)N3)cn2)nnn1C)c1cccnc1Cl] | | 485.1 | 1H NMR (400 MHz, Methanol-d4) δ 9.01 (s, 1H), 8.31 (d, J = 20.5 Hz, 1H), 8.26-8.01 (m, 2H), 7.94 (d, J = 8.7 Hz, 1H), 7.64-7.38 (m, 1H), 6.08 (d, J = 6.5 Hz, 1H), 4.41 (dd, J = 8.7, 4.6 Hz, 1H), 4.01 (s, 3H), 2.67-2.35 (m, 3H), 2.27 (d, J = 10.5 Hz, 1H), 1.55 (d, J = 73.8 Hz, 3H). |
| Compound 152 (R)-1-(2-chloropyridin-3-yl)ethyl (1-methyl-4-(5-((R)-5-oxopyrrolidine-2-carboxamido)pyridin-2-yl)-1H-1,2,3-triazol-5-yl)carbamate | 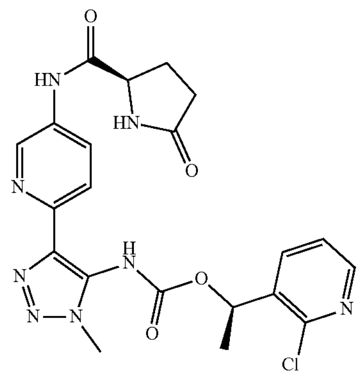 [SMILES: C[C@@H](OC(=O)Nc1c(-c2ccc(NC(=O)[C@H]3CCC(=O)N3)cn2)nnn1C)c1cccnc1Cl] | | 485.1 | 1H NMR (400 MHz, Methanol-d4) δ 8.98 (s, 1H), 8.40-8.25 (m, 1H), 8.23-8.01 (m, 2H), 7.93 (d, J = 8.8 Hz, 1H), 7.62-7.40 (m, 1H), 6.08 (d, J = 7.5 Hz, 1H), 4.41 (dd, J = 8.7, 4.6 Hz, 1H), 4.00 (s, 3H), 2.67-2.45 (m, 2H), 2.39 (ddd, J = 16.9, 9.7, 5.5 Hz, 1H), 2.31-2.19 (m, 1H), 1.82-1.43 (m, 3H). |

TABLE 2-continued

Compounds prepared according to Scheme C, Step 4.

| Compound No. | Structure | Reagent | LCMS m/z | 1H NMR |
|---|---|---|---|---|
| Compound 153 (R)-1-(2-chloropyridin-3-yl)ethyl (4-(5-(1,3-dioxolane-2-carboxamido)pyridin-2-yl)-1-methyl-1H-1,2,3-triazol-5-yl)carbamate | 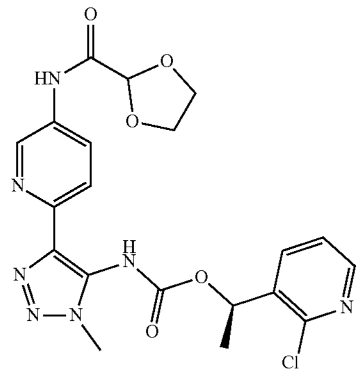 [SMILES: C[C@@H](OC(=O)Nc1c(-c2ccc(NC(=O)C3OCCO3)cn2)nnn1C)c1cccnc1Cl] | | 474.1 | 1H NMR (400 MHz, Methanol-d4) δ 9.04 (s, 1H), 8.43-8.18 (m, 2H), 8.07 (s, 1H), 7.95 (d, J = 8.7 Hz, 1H), 7.48 (s, 1H), 6.09 (q, J = 6.6 Hz, 1H), 4.25-4.12 (m, 2H), 4.12-4.03 (m, 2H), 4.00 (s, 3H), 1.63 (s, 3H). |
| Compound 154 (R)-1-(2-chloropyridin-3-yl)ethyl (4-(5-((1r,3R)-3-hydroxycyclobutane-1-carboxamido)pyridin-2-yl)-1-methyl-1H-1,2,3-triazol-5-yl)carbamate | 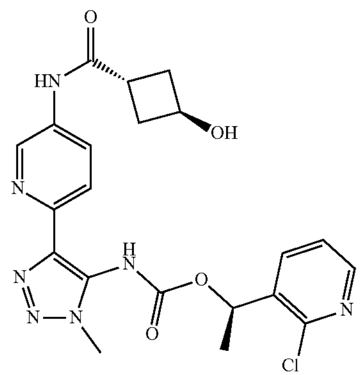 [SMILES: C[C@@H](OC(=O)Nc1c(-c2ccc(NC(=O)[C@H]3C[C@H](O)C3)cn2)nnn1C)c1cccnc1Cl] | | 472.1 | 1H NMR (400 MHz, Methanol-d4) δ 9.02 (s, 1H), 8.33 (s, 1H), 8.18 (dd, J = 8.7, 2.5 Hz, 2H), 7.92 (d, J = 8.7 Hz, 1H), 7.48 (s, 1H), 6.09 (q, J = 6.6 Hz, 1H), 4.58-4.46 (m, 1H), 4.00 (s, 3H), 3.21 (ttd, J = 9.9, 3.8, 1.1 Hz, 1H), 2.70-2.52 (m, 2H), 2.28 (dtd, J = 12.9, 6.7, 3.0 Hz, 2H), 1.63 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 155 (R)-1-(2-chloropyridin-3-yl)ethyl (4-(5-((1s,3S)-3-hydroxycyclobutane-1-carboxamido)pyridin-2-yl)-1-methyl-1H-1,2,3-triazol-5-yl)carbamate | 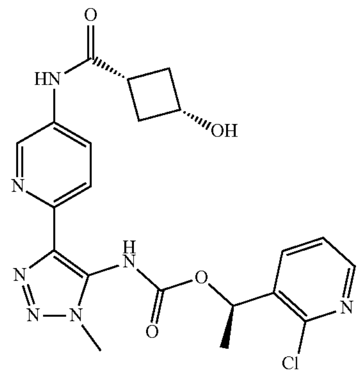 [SMILES: C[C@@H](OC(=O)Nc1c(-c2ccc(NC(=O)[C@H]3C[C@@H](O)C3)cn2)nnn1C)c1cccnc1Cl] | | 472.1 | 1H NMR (400 MHz, Methanol-d4) δ 9.02 (s, 1H), 8.44-8.28 (m, 1H), 8.25-8.06 (m, 2H), 7.99-7.87 (m, 1H), 7.48 (s, 1H), 6.09 (q, J = 6.6 Hz, 1H), 4.19 (tt, J = 8.3, 6.9 Hz, 1H), 4.00 (s, 3H), 2.77 (tt, J = 9.7, 7.4 Hz, 1H), 2.57 (dddd, J = 9.4, 7.2, 5.5, 2.8 Hz, 2H), 2.24 (dtt, J = 11.5, 8.2, 1.4 Hz, 2H), 1.63 (s, 3H). |
| Compound 156 (R)-1-(2-chloropyridin-3-yl)ethyl (4-(5-((1r,3R)-3-methoxycyclobutane-1-carboxamido)pyridin-2-yl)-1-methyl-1H-1,2,3-triazol-5-yl)carbamate | 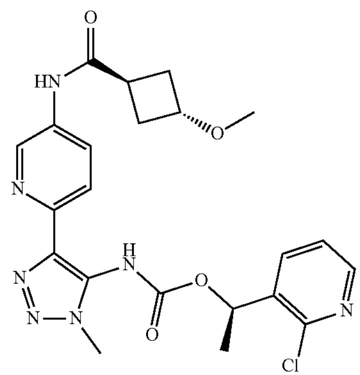 [SMILES: CO[C@H]1C[C@H](C(=O)Nc2ccc(-c3nnn(C)c3NC(=O)O[C@H](C)c3cccnc3Cl)nc2)C1] | | 486.1 | 1H NMR (400 MHz, Methanol-d4) δ 9.04 (s, 1H), 8.34 (s, 1H), 8.18 (dd, J = 8.7, 2.4 Hz, 2H), 7.92 (d, J = 8.8 Hz, 1H), 7.51 (s, 1H), 6.09 (d, J = 7.4 Hz, 1H), 4.26-4.10 (m, 1H), 4.01 (s, 3H), 3.29 (s, 3H), 3.24 (dddd, J = 9.7, 8.5, 4.3, 1.0 Hz, 1H), 2.65-2.53 (m, 2H), 2.30 (dtd, J = 13.0, 6.1, 4.2 Hz, 2H), 1.65 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 157 (R)-1-(2-chloropyridin-3-yl)ethyl (4-(5-((1s,3S)-3-methoxycyclobutane-1-carboxamido)pyridin-2-yl)-1-methyl-1H-1,2,3-triazol-5-yl)carbamate | 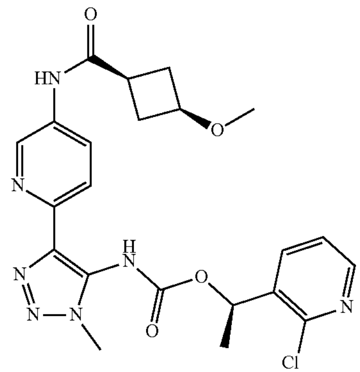 [SMILES: CO[C@H]1C[C@@H](C(=O)Nc2ccc(-c3nnn(C)c3NC(=O)O[C@H](C)c3cccnc3Cl)nc2)C1] | | 486.1 | 1H NMR (400 MHz, Methanol-d4) δ 9.01 (s, 1H), 8.33 (s, 1H), 8.16 (dd, J = 8.7, 2.5 Hz, 2H), 7.92 (d, J = 8.7 Hz, 1H), 7.51 (s, 1H), 6.09 (d, J = 6.8 Hz, 1H), 4.00 (s, 3H), 3.91 (tt, J = 8.1, 6.7 Hz, 1H), 3.28 (s, 3H), 2.85 (tt, J = 9.7, 7.7 Hz, 1H), 2.56 (dddd, J = 12.3, 7.5, 4.0, 1.3 Hz, 2H), 2.23 (dddq, J = 11.1, 9.4, 7.9, 1.6 Hz, 2H), 1.65 (s, 3H). |
| Compound 158 (R)-1-(2-chloropyridin-3-yl)ethyl (4-(5-(((1R,5R)-3-oxabicyclo[3.1.0]hexane-6-carboxamido)pyridin-2-yl)-1-methyl-1H-1,2,3-triazol-5-yl)carbamate | | | 484.1 | 1H NMR (400 MHz, Methanol-d4) δ 8.99 (s, 1H), 8.34 (s, 1H), 8.15 (dd, J = 8.7, 2.5 Hz, 2H), 7.92 (d, J = 8.7 Hz, 1H), 7.50 (s, 1H), 6.09 (d, J = 7.4 Hz, 1H), 4.03-3.93 (m, 4H), 3.82 (dd, J = 8.6, 1.8 Hz, 2H), 2.31-2.23 (m, 2H), 1.76 (t, J = 3.2 Hz, 1H), 1.65 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 159 (R)-1-(2-chloropyridin-3-yl)ethyl (4-(5-(2-oxabicyclo[3.1.0]hexane-6-carboxamido)pyridin-2-yl)-1-methyl-1H-1,2,3-triazol-5-yl)carbamate | 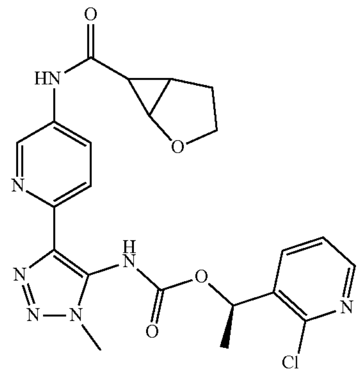 [SMILES: C[C@@H](OC(=O)Nc1c(-c2ccc(NC(=O)C3C4CCOC43)cn2)nnn1C)c1cccnc1Cl] | | 484.1 | 1H NMR (400 MHz, Methanol-d4) δ 8.94 (s, 1H), 8.34 (s, 1H), 8.11 (dd, J = 8.7, 2.5 Hz, 1H), 7.91 (d, J = 8.7 Hz, 1H), 7.50 (s, 1H), 6.09 (d, J = 6.9 Hz, 1H), 4.24 (dd, J = 5.0, 2.7 Hz, 1H), 4.12 (td, J = 9.5, 3.0 Hz, 1H), 4.00 (s, 3H), 3.58 (td, J = 9.5, 7.7 Hz, 1H), 2.35-2.20 (m, 2H), 2.20-2.06 (m, 2H), 1.64 (s, 3H). |
| Compound 160 (R)-1-(2-chloropyridin-3-yl)ethyl (1-methyl-4-(5-(1-(3-methylisoxazol-5-yl)cyclopropane-1-carboxamido)pyridin-2-yl)-1H-1,2,3-triazol-5-yl)carbamate | 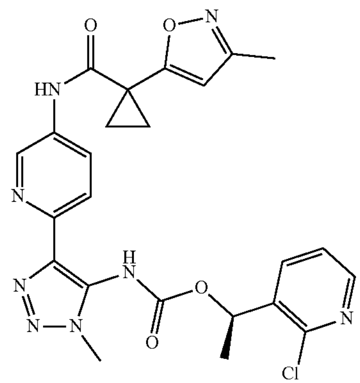 [SMILES: Cc1cc(C2(C(=O)Nc3ccc(-c4nnn(C)c4NC(=O)O[C@H](C)c4cccnc4Cl)nc3)CC2)on1] | | 523.1 | 1H NMR (400 MHz, Methanol-d4) δ 8.90 (s, 1H), 8.33 (s, 1H), 8.22-8.00 (m, 2H), 7.92 (d, J = 8.7 Hz, 1H), 7.50 (s, 1H), 6.37 (s, 1H), 6.08 (d, J = 7.0 Hz, 1H), 4.00 (s, 3H), 2.32 (s, 3H), 1.76 (q, J = 4.3 Hz, 2H), 1.58 (d, J = 48.4 Hz, 3H), 1.46 (q, J = 4.3 Hz, 2H). |

TABLE 2-continued

Compounds prepared according to Scheme C, Step 4.

| Compound No. | Structure | Reagent | LCMS m/z | 1H NMR |
|---|---|---|---|---|
| Compound 161 (R)-1-(2,5-difluoropyridin-3-yl)ethyl (4-(5-((1S,2R)-2-fluorocyclopropane-1-carboxamido)pyridin-2-yl)-1-methyl-1H-1,2,3-triazol-5-yl)carbamate | 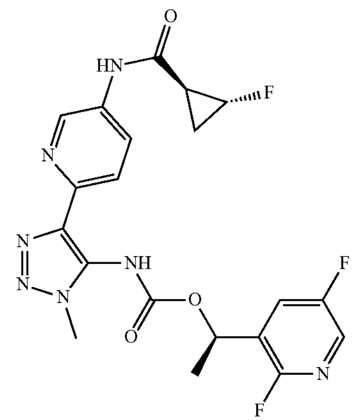 [SMILES: C[C@@H](OC(=O)Nc1c(-c2ccc(NC(=O)[C@@H]3C[C@H]3F)cn2)nnn1C)c1cc(F)cnc1F] | | 462.1 | 1H NMR (400 MHz, Methanol-d4) δ 8.77 (s, 1H), 8.24-7.50 (m, 4H), 5.95 (d, J = 7.6 Hz, 1H), 3.99 (s, 3H), 2.29 (dddd, J = 17.3, 10.4, 6.6, 1.6 Hz, 1H), 1.90-1.24 (m, 5H). |
| Compound 162 (R)-1-(2,5-difluoropyridin-3-yl)ethyl (4-(5-(3-cyanobicyclo[1.1.1]pentane-1-carboxamido)pyridin-2-yl)-1-methyl-1H-1,2,3-triazol-5-yl)carbamate | 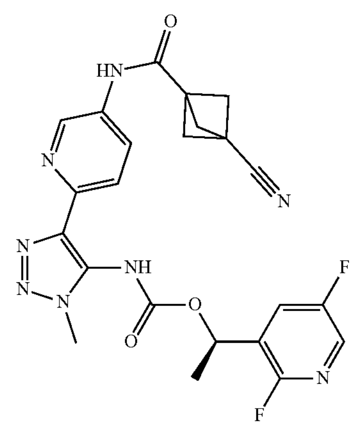 [SMILES: C[C@@H](OC(=O)Nc1c(-c2ccc(NC(=O)C34CC(C#N)(C3)C4)cn2)nnn1C)c1cc(F)cnc1F] | | 495.2 | 1H NMR (400 MHz, Methanol-d4) δ 8.83 (s, 1H), 8.22-7.58 (m, 4H), 5.94 (d, J = 7.0 Hz, 1H), 3.99 (s, 3H), 2.64 (s, 6H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 163 (R)-1-(2,5-difluoropyridin-3-yl)ethyl (4-(5-(3-fluorobicyclo[1.1.1]pentane-1-carboxamido)pyridin-2-yl)-1-methyl-1H-1,2,3-triazol-5-yl)carbamate | 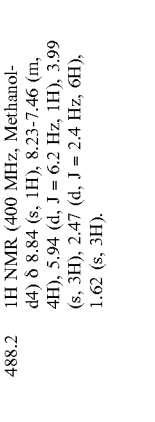 | 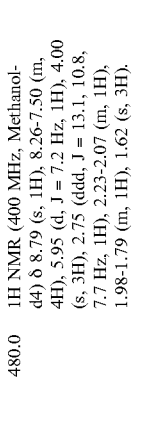 | 488.2 | 1H NMR (400 MHz, Methanol-d4) δ 8.84 (s, 1H), 8.23-7.46 (m, 4H), 5.94 (d, J = 6.2 Hz, 1H), 3.99 (s, 3H), 2.47 (d, J = 2.4 Hz, 6H), 1.62 (s, 3H). |
| Compound 164 (R)-1-(2,5-difluoropyridin-3-yl)ethyl (4-(5-((S)-2,2-difluorocyclopropane-1-carboxamido)pyridin-2-yl)-1-methyl-1H-1,2,3-triazol-5-yl)carbamate | 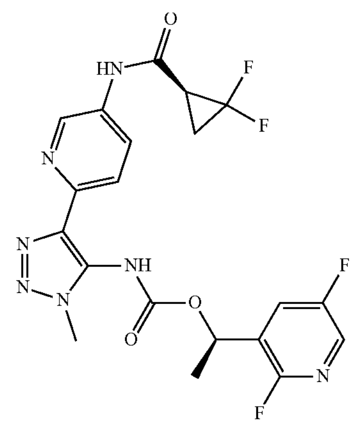 [SMILES: C[C@@H](OC(=O)Nc1c(-c2ccc(NC(=O)[C@@H]3CC3(F)F)cn2)nnn1C)c1cc(F)cnc1F] |  | 480.0 | 1H NMR (400 MHz, Methanol-d4) δ 8.79 (s, 1H), 8.26-7.50 (m, 4H), 5.95 (d, J = 7.2 Hz, 1H), 4.00 (s, 3H), 2.75 (ddd, J = 13.1, 10.8, 7.7 Hz, 1H), 2.23-2.07 (m, 1H), 1.98-1.79 (m, 1H), 1.62 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 165 (R)-1-(2,5-difluoropyridin-3-yl)ethyl (4-(5-(1-(difluoromethyl)cyclopropane-1-carboxamido)pyridin-2-yl)-1-methyl-1H-1,2,3-triazol-5-yl)carbamate | 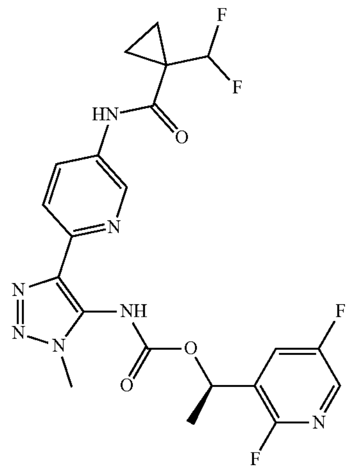 [SMILES: C[C@@H](OC(=O)Nc1c(-c2ccc(NC(=O)C3(C(F)F)CC3)cn2)nnn1C)c1cc(F)cnc1F] | | 494.1 | 1H NMR (400 MHz, DMSO-d$_6$) δ 9.81 (bs, 1H), 9.63 (s, 1H), 8.70 (s, 1H), 8.19 (bs, 1H), 8.08-7.94 (m, 2H), 7.91 (d, J = 8.6 Hz, 1H), 6.58 (t, J = 56.9 Hz, 1H), 5.79 (bs, 1H), 3.88 (s, 3H), 1.57 (bs, 3H), 1.42-1.30 (m, 2H), 1.25-1.08 (m, 2H). |
| Compound 166 (R)-1-(2-chloro-5-fluoropyridin-3-yl)ethyl (4-(5-(1-(difluoromethyl)cyclopropane-1-carboxamido)pyridin-2-yl)-1-methyl-1H-1,2,3-triazol-5-yl)carbamate | 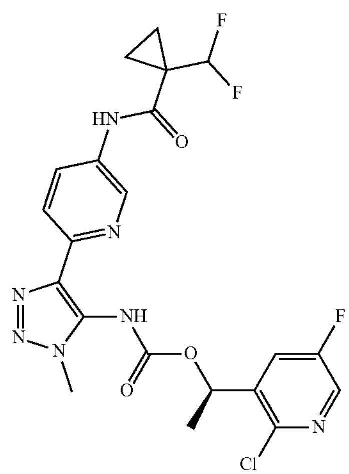 [SMILES: C[C@@H](OC(=O)Nc1c(-c2ccc(NC(=O)C3(C(F)F)CC3)cn2)nnn1C)c1cc(F)cnc1Cl] | | 510.2 | 1H NMR (400 MHz, DMSO-d6) δ 9.86 (bs, 1H), 9.63 (s, 1H), 8.73 (bs, 1H), 8.42 (bs, 1H), 8.10-7.82 (m, 3H), 6.58 (t, J = 56.9 Hz, 1H), 5.83 (bs, 1H), 3.89 (s, 3H), 1.57 (bs, 3H), 1.43-1.35 (m, 2H), 1.27-1.03 (m, 2H). |

TABLE 2-continued

Compounds prepared according to Scheme C, Step 4.

| Compound No. | Structure | Reagent | LCMS m/z | 1H NMR |
|---|---|---|---|---|
| Compound 167 (R)-1-(2-chloro-5-fluoropyridin-3-yl)ethyl (4-(5-(3-cyanobicyclo[1.1.1]pentane-1-carboxamido)pyridin-2-yl)-1-methyl-1H-1,2,3-triazol-5-yl)carbamate | 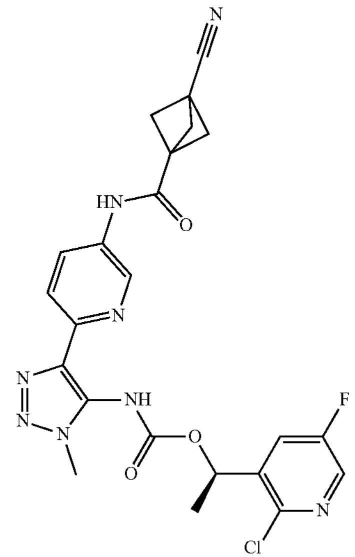 [SMILES: C[C@@H](OC(=O)Nc1c(-c2ccc(NC(=O)C34CC(C#N)(C3)C4)cn2)nnn1C)c1cc(F)cnc1Cl] | | 511.2 | 1H NMR (400 MHz, DMSO-d6) δ 10.01 (s, 1H), 9.86 (bs, 1H), 8.78 (s, 1H), 8.42 (bs, 1H), 8.12-7.80 (m, 3H), 5.83 (bs, 1H), 3.89 (s, 3H), 2.58 (s, 6H), 1.56 (bs, 3H). |
| Compound 168 (R)-1-(2-chloro-5-fluoropyridin-3-yl)ethyl (4-(5-(1-cyanocyclopropane-1-carboxamido)pyridin-2-yl)-1-methyl-1H-1,2,3-triazol-5-yl)carbamate | 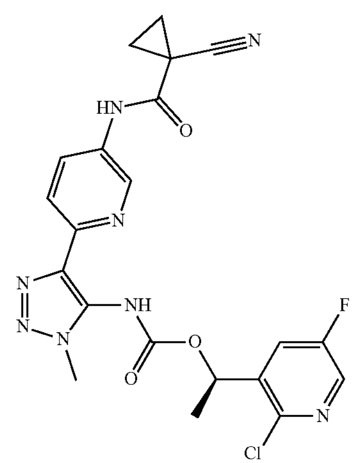 [SMILES: C[C@@H](OC(=O)Nc1c(-c2ccc(NC(=O)C3(C#N)CC3)cn2)nnn1C)c1cc(F)cnc1Cl] | | 485.2 | 1H NMR (400 MHz, DMSO-d6) δ 10.28 (s, 1H), 9.89 (bs, 1H), 8.73 (s, 1H), 8.43 (bs, 1H), 8.07-7.83 (m, 3H), 5.83 (bs, 1H), 3.89 (s, 3H), 1.76-1.67 (m, 4H), 1.57 (bs, 3H). |

TABLE 2-continued

Compounds prepared according to Scheme C, Step 4.

| Compound No. | Structure | Reagent | LCMS m/z | 1H NMR |
|---|---|---|---|---|
| Compound 169 (R)-1-(2-fluoropyridin-3-yl)ethyl (4-(5-((1S,2R)-2-fluorocyclopropane-1-carboxamido)pyridin-2-yl)-1-methyl-1H-1,2,3-triazol-5-yl)carbamate | 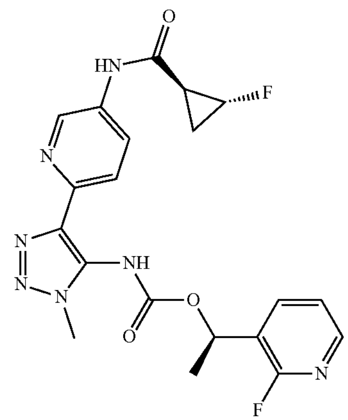 [SMILES: C[C@@H](OC(=O)Nc1c(-c2ccc(NC(=O)[C@@H]3C[C@H]3F)cn2)nnn1C)c1cccnc1F] | | 444.1 | 1H NMR (400 MHz, Methanol-d4) δ 8.79 (s, 1H), 8.43-7.72 (m, 4H), 7.35 (s, 1H), 5.99 (q, J = 6.3 Hz, 1H), 3.98 (s, 3H), 2.29 (dddd, J = 17.3, 10.5, 6.6, 1.6 Hz, 1H), 1.80-1.46 (m, 4H), 1.40 (dq, J = 13.0, 6.5 Hz, 1H). |
| Compound 170 (R)-1-(2-fluoropyridin-3-yl)ethyl (1-methyl-4-(5-(3-(trifluoromethyl)bicyclo[1.1.1]pentane-1-carboxamido)pyridin-2-yl)-1H-1,2,3-triazol-5-yl)carbamate | 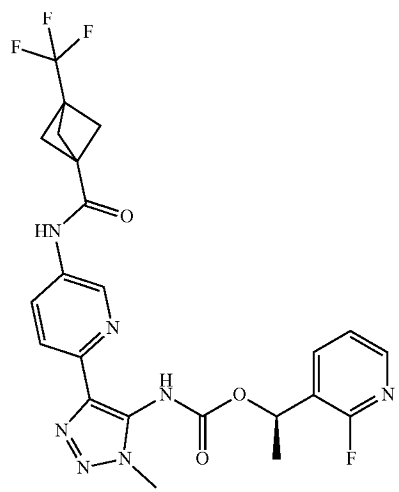 [SMILES: C[C@@H](OC(=O)Nc1c(-c2ccc(NC(=O)C34CC(C(F)(F)F)(C3)C4)cn2)nnn1C)c1cccnc1F] | | 520.1 | 1H NMR (400 MHz, Methanol-d4) δ 8.87 (s, 1H), 8.25-7.96 (m, 3H), 7.92 (dd, J = 8.6, 0.8 Hz, 1H), 7.36 (s, 1H), 6.10-5.66 (m, 1H), 3.98 (s, 3H), 2.39 (s, 6H), 1.62 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 171 (R)-1-(2-fluoropyridin-3-yl)ethyl (4-(5-(3,3-difluorocyclobutane-1-carboxamido)pyridin-2-yl)-1-methyl-1H-1,2,3-triazol-5-yl)carbamate | 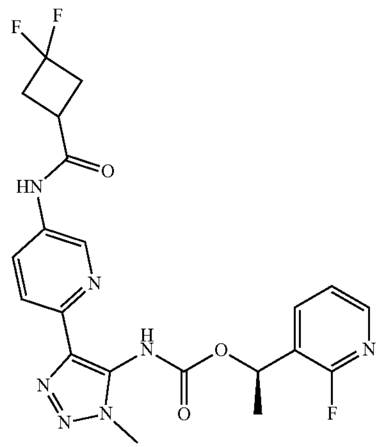 [SMILES: C[C@@H](OC(=O)Nc1c(-c2ccc(NC(=O)C3CC(F)(F)C3)cn2)nnn1C)c1cccnc1F] | | 476.1 | 1H NMR (400 MHz, Methanol-$d_4$) δ 8.82 (s, 1H), 8.28-8.00 (m, 3H), 7.90 (d, J = 8.4 Hz, 1H), 7.54-7.10 (m, 1H), 6.14-5.79 (m, 1H), 3.98 (s, 3H), 3.17-3.13 (m, 1H), 3.03-2.72 (m, 4H), 1.62 (s, 3H). |
| Compound 172 (R)-1-(2-fluoropyridin-3-yl)ethyl (4-(5-(1-cyanocyclopropane-1-carboxamido)pyridin-2-yl)-1-methyl-1H-1,2,3-triazol-5-yl)carbamate | 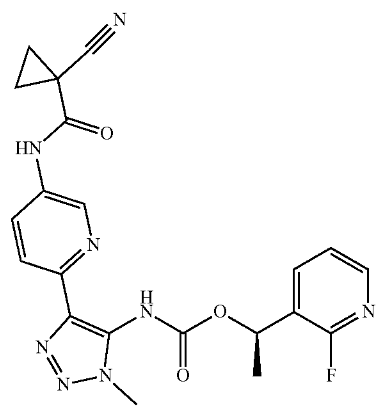 [SMILES: C[C@@H](OC(=O)Nc1c(-c2ccc(NC(=O)C3(C#N)CC3)cn2)nnn1C)c1cccnc1F] | | 451.1 | 1H NMR (400 MHz, Methanol-d4) δ 8.81 (s, 1H), 8.15 (s, 1H), 8.07 (dd, J = 8.6, 2.6 Hz, 1H), 7.93 (dd, J = 8.6, 0.8 Hz, 1H), 7.36 (s, 1H), 5.99 (d, J = 7.1 Hz, 1H), 3.99 (s, 3H), 1.88-1.42 (m, 8H). |

TABLE 2-continued

Compounds prepared according to Scheme C, Step 4.

| Compound No. | Structure | Reagent | LCMS m/z | 1H NMR |
|---|---|---|---|---|
| Compound 173 (R)-1-(2-fluoropyridin-3-yl)ethyl (4-(5-(3-fluorobicyclo[1.1.1]pentane-1-carboxamido)pyridin-2-yl)-1-methyl-1H-1,2,3-triazol-5-yl)carbamate | 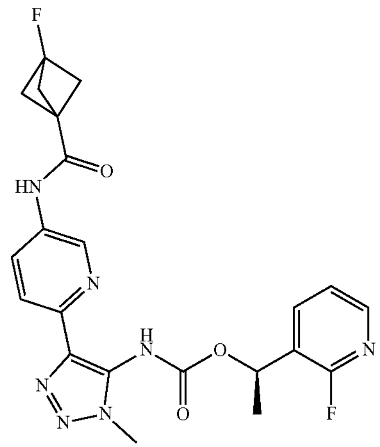 [SMILES: C[C@@H](OC(=O)Nc1c(-c2ccc(NC(=O)C34CC(F)(C3)C4)cn2)nnn1C)c1cccnc1F] | | 470.1 | ¹H NMR (400 MHz, Methanol-d₄) δ 8.86(s, 1H), 8.24-8.02 (m, 3H), 7.91 (dd, J = 8.7, 0.8 Hz, 1H), 7.51-7.21 (m, 1H), 6.19-5.83 (m, 1H), 3.98 (s, 3H), 2.47 (d, J = 2.4 Hz, 6H), 1.80-1.44 (m, 3H). |
| Compound 174 (R)-1-(2-fluoropyridin-3-yl)ethyl (4-(5-(3-cyanobicyclo[1.1.1]pentane-1-carboxamido)pyridin-2-yl)-1-methyl-1H-1,2,3-triazol-5-yl)carbamate | 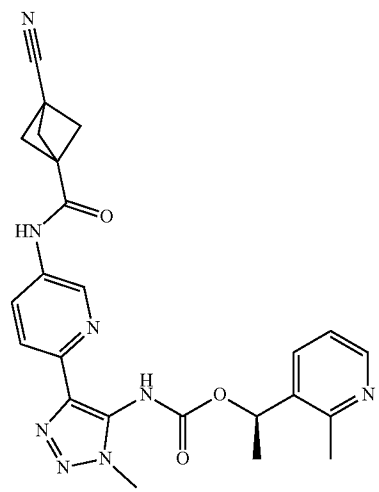 [SMILES: Cc1ncccc1[C@@H](C)OC(=O)Nc1c(-c2ccc(NC(=O)C34CC(C#N)(C3)C4)cn2)nnn1C] | | 477.1 | ¹H NMR (400 MHz, Methanol-d₄) δ 8.85 (s, 1H), 8.28-7.96 (m, 3H), 7.91 (dd, J = 8.7, 0.8 Hz, 1H), 7.35 (s, 1H), 6.14-5.82 (m, 1H), 3.98 (s, 3H), 2.64 (s, 6H), 1.62 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 175 (R)-1-(5-fluoro-2-methylpyridin-3-yl)ethyl (4-(5-(3,3-difluorocyclobutane-1-carboxamido)pyridin-2-yl)-1-methyl-1H-1,2,3-triazol-5-yl)carbamate | 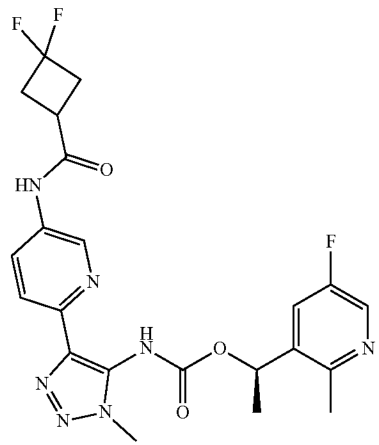 [SMILES: Cc1ncc(F)cc1[C@@H](C)OC(=O)Nc1c(-c2ccc(NC(=O)C3CC(F)(F)C3)cn2)nnn1C] | | 490.1 | ¹H NMR (400 MHz, Methanol-d₄) δ 8.78 (s, 1H), 8.25 (s, 1H), 8.10 (dd, J = 8.6, 2.6 Hz, 1H), 7.89 (dd, J = 8.7, 0.8 Hz, 1H), 7.84-7.40 (m, 1H), 6.14-5.72 (m, 1H), 3.98 (s, 3H), 3.22-3.08 (m, 1H), 3.07-2.71 (m, 4H), 2.56 (s, 3H), 1.80-1.39 (m, 3H). |
| Compound 176 (R)-1-(5-fluoro-2-methylpyridin-3-yl)ethyl (4-(5-((1S,2R)-2-fluorocyclopropane-1-carboxamido)pyridin-2-yl)-1-methyl-1H-1,2,3-triazol-5-yl)carbamate | 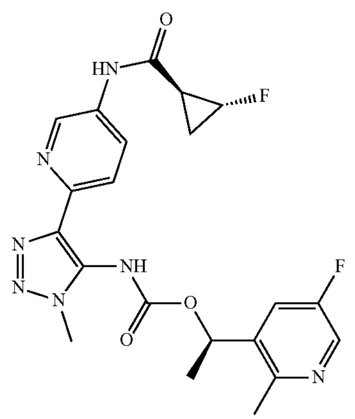 [SMILES: Cc1ncc(F)cc1[C@@H](C)OC(=O)Nc1c(-c2ccc(NC(=O)[C@@H]3C[C@H]3F)cn2)nnn1C] | | 458.2 | 1H NMR (400 MHz, Methanol-d4) δ 8.75 (s, 1H), 8.36-7.24 (m, 4H), 5.98 (d, J = 6.7 Hz, 1H), 3.97 (s, 3H), 2.56 (s, 3H), 2.29 (dddd, J = 17.3, 10.5, 6.6, 1.6 Hz, 1H), 1.81-1.34 (m, 5H). |

TABLE 2-continued

Compounds prepared according to Scheme C, Step 4.

| Compound No. | Structure | Reagent | LCMS m/z | 1H NMR |
|---|---|---|---|---|
| Compound 177 (R)-1-(5-fluoro-2-methylpyridin-3-yl)ethyl (4-(5-(1-cyanocyclopropane-1-carboxamido)pyridin-2-yl)-1-methyl-1H-1,2,3-triazol-5-yl)carbamate | 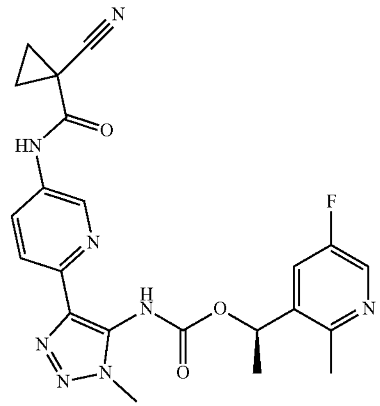 [SMILES: Cc1ncc(F)cc1[C@@H](C)OC(=O)Nc1c(-c2ccc(NC(=O)C3(C#N)CC3)cn2)nnn1C] | | 465.1 | 1H NMR (400 MHz, Methanol-d4) δ 8.77 (s, 1H), 8.27 (s, 1H), 8.07 (dd, J = 8.6, 2.6 Hz, 1H), 7.92 (dd, J = 8.6, 0.8 Hz, 1H), 7.71 (s, 1H), 6.18-5.80 (m, 1H), 3.98 (s, 3H), 2.56 (s, 3H), 1.81-1.67 (m, 4H), 1.59 (s, 3H). |
| Compound 178 (R)-1-(5-fluoro-2-methylpyridin-3-yl)ethyl (4-(5-(3-cyanobicyclo[1.1.1]pentane-1-carboxamido)pyridin-2-yl)-1-methyl-1H-1,2,3-triazol-5-yl)carbamate | 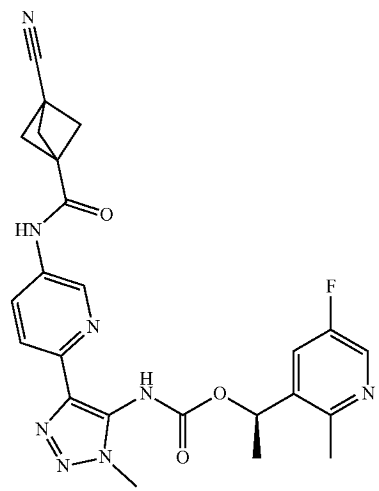 [SMILES: Cc1ncc(F)cc1[C@@H](C)OC(=O)Nc1c(-c2ccc(NC(=O)C34CC(C#N)(C3)C4)cn2)nnn1C] | | 491.1 | 1H NMR (400 MHz, Methanol-d4) δ 8.81 (s, 1H), 8.26 (s, 1H), 8.09 (dd, J = 8.7, 2.6 Hz, 1H), 7.90 (dd, J = 8.6, 0.8 Hz, 1H), 7.86-7.51 (m, 1H), 6.10-5.87 (m, 1H), 3.98 (s, 3H), 2.64 (s, 6H), 2.56 (s, 3H), 1.59 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 179 (R)-1-(5-fluoro-2-methylpyridin-3-yl)ethyl (4-(5-(3-fluorobicyclo[1.1.1]pentane-1-carboxamido)pyridin-2-yl)-1-methyl-1H-1,2,3-triazol-5-yl)carbamate | 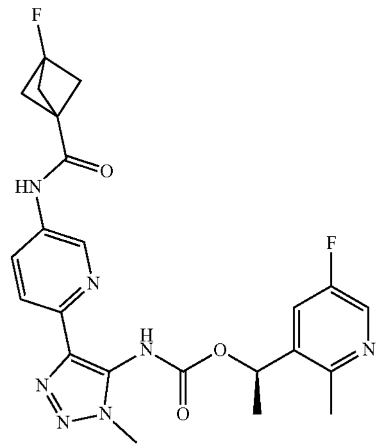 [SMILES: Cc1ncc(F)cc1[C@@H](C)OC(=O)Nc1c(-c2ccc(NC(=O)C34CC(F)(C3)C4)cn2)nnn1C] | | 484.1 | $^1$H NMR (400 MHz, Methanol-$d_4$) δ 8.82 (s, 1H), 8.26 (s, 1H), 8.10 (dd, J = 8.7, 2.6 Hz, 1H), 7.90 (dd, J = 8.6, 0.8 Hz, 1H), 7.86-7.53 (m, 1H), 6.11-5.81 (m, 1H), 3.98 (s, 3H), 2.56 (s, 3H), 2.47 (d, J = 2.4 Hz, 6H), 1.59 (s, 3H). |
| Compound 180 (R)-1-(5-fluoro-2-methylpyridin-3-yl)ethyl (4-(5-((S)-2,2-difluorocyclopropane-1-carboxamido)pyridin-2-yl)-1-methyl-1H-1,2,3-triazol-5-yl)carbamate | 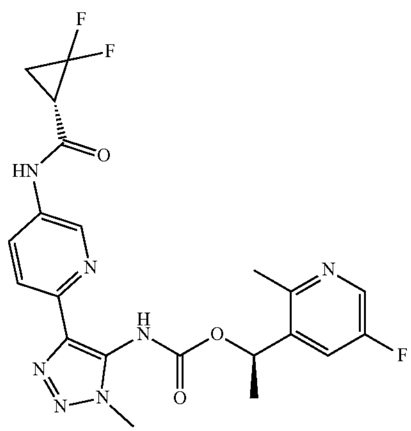 [SMILES: Cc1ncc(F)cc1[C@@H](C)OC(=O)Nc1c(-c2ccc(NC(=O)[C@@H]3CC3(F)F)cn2)nnn1C] | | 476.1 | 1H NMR (400 MHz, Methanol-d4) δ 8.77 (s, 1H), 8.26 (s, 1H), 8.10 (dd, J = 8.7, 2.6 Hz, 1H), 7.91 (dd, J = 8.6, 0.8 Hz, 1H), 7.86-7.49 (m, 1H), 6.09-5.82 (m, 1H), 3.98 (s, 3H), 2.75 (ddd, J = 13.2, 10.8, 7.8 Hz, 1H), 2.56 (s, 3H), 2.23-2.07 (m, 1H), 1.95-1.80 (m, 1H), 1.59 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 181 1-(2-chloro-6-fluoropyridin-3-yl)ethyl (4-(5-(1-cyanocyclopropane-1-carboxamido)pyridin-2-yl)-1-methyl-1H-1,2,3-triazol-5-yl)carbamate | 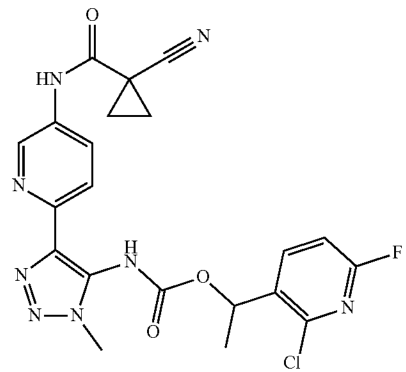 [SMILES: CC(OC(=O)Nc1c(-c2ccc(NC(=O)C3(C#N)CC3)cn2)nnn1C)c1ccc(F)nc1Cl] | | 485.0 | 1H NMR (400 MHz, Methanol-d4) δ 8.93 (s, 1H), 8.19 (dd, J = 8.7, 2.5 Hz, 2H), 7.97 (d, J = 8.7 Hz, 1H), 7.17 (s, 1H), 6.08 (d, J = 6.8 Hz, 1H), 4.00 (s, 3H), 1.86-1.75 (m, 2H), 1.75-1.67 (m, 2H), 1.63 (s, 3H). |
| Compound 182 1-(2-chloro-6-fluoropyridin-3-yl)ethyl (4-(5-acetamidopyridin-2-yl)-1-methyl-1H-1,2,3-triazol-5-yl)carbamate | 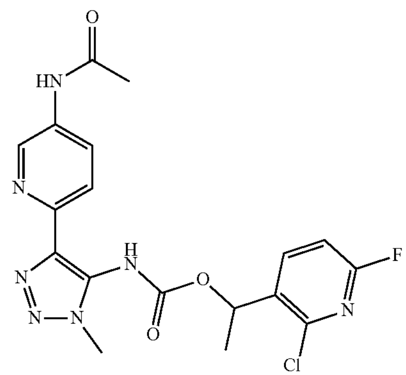 [SMILES: CC(=O)Nc1ccc(-c2nnn(C)c2NC(=O)OC(C)c2ccc(F)nc2Cl)nc1] | | 434.0 | 1H NMR (400 MHz, Methanol-d4) δ 9.00 (s, 1H), 8.15 (dd, J = 8.7, 2.5 Hz, 2H), 7.94 (d, J = 8.7 Hz, 1H), 7.17 (s, 1H), 6.08 (q, J = 6.6 Hz, 1H), 4.00 (s, 3H), 2.22 (s, 3H), 1.63 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 183 (R)-1-(2-chloropyridin-3-yl)ethyl (4-(5-(1-cyanocyclopropane-1-carboxamido)-4-fluoropyridin-2-yl)-1-methyl-1H-1,2,3-triazol-5-yl)carbamate | 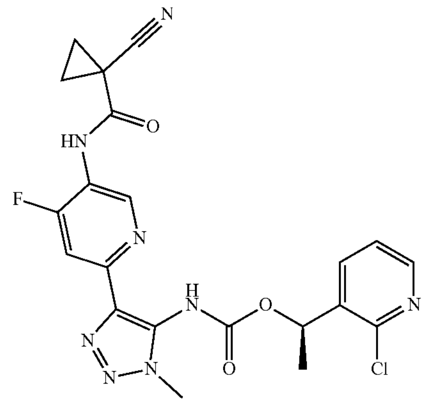 [SMILES: C[C@@H](OC(=O)Nc1c(-c2cc(F)c(NC(=O)C3(C#N)CC3)cn2)nnn1C)c1cccnc1Cl] | | 485.1 | 1H NMR (400 MHz, Methanol-d4) δ 8.83 (d, J = 9.7 Hz, 1H), 8.32 (d, J = 4.7 Hz, 1H), 8.04 (s, 1H), 7.84 (d, J = 11.1 Hz, 1H), 7.47 (s, 1H), 6.16-5.98 (m, 1H), 3.99 (s, 3H), 1.86-1.69 (m, 4H), 1.61 (s, 3H). |
| Compound 184 (R)-1-(2-chloropyridin-3-yl)ethyl (4-(5-(3-cyanobicyclo[1.1.1]pentane-1-carboxamido)-4-fluoropyridin-2-yl)-1-methyl-1H-1,2,3-triazol-5-yl)carbamate | 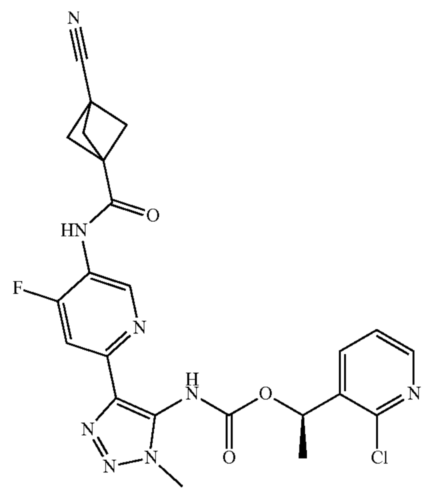 [SMILES: C[C@@H](OC(=O)Nc1c(-c2cc(F)c(NC(=O)C34CC(C#N)(C3)C4)cn2)nnn1C)c1cccnc1Cl] | | 511.1 | 1H NMR (400 MHz, Methanol-d4) δ 8.84 (d, J = 9.7 Hz, 1H), 8.32 (d, J = 4.9 Hz, 1H), 8.06 (s, 1H), 7.82 (d, J = 11.3 Hz, 1H), 7.47 (s, 1H), 6.21-5.89 (m, 1H), 3.99 (s, 3H), 2.66 (s, 6H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 195 (R)-1-(2-chloropyridin-3-yl)ethyl (1-methyl-4-(5-((R)-5-oxopyrrolidine-3-carboxamido)pyridin-2-yl)-1H-1,2,3-triazol-5-yl)carbamate | 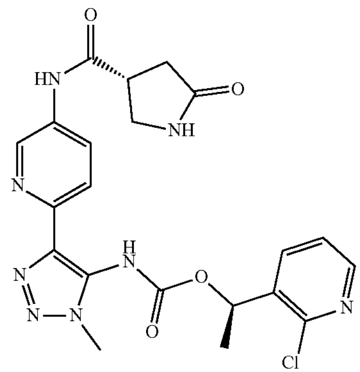 [SMILES: C[C@@H](OC(=O)Nc1c(-c2ccc(NC(=O)[C@H]3CNC(=O)C3)cn2)nnn1C)c1cccnc1Cl] | | 485.1 | 1H NMR (400 MHz, Methanol-d4) δ 9.02 (s, 1H), 8.34 (s, 1H), 8.25-8.01 (m, 2H), 7.93 (d, J = 8.8 Hz, 1H), 7.51 (s, 1H), 6.08 (d, J = 6.8 Hz, 1H), 4.01 (s, 3H), 3.78-3.62 (m, 2H), 3.54 (tt, J = 8.9, 6.6 Hz, 1H), 2.79-2.60 (m, 2H), 1.65 (s, 3H). |
| Compound 196 (R)-1-(2-chloropyridin-3-yl)ethyl (4-(5-(2-(1,3-dioxolan-2-yl)acetamido)pyridin-2-yl)-1-methyl-1H-1,2,3-triazol-5-yl)carbamate | | | 488.1 | 1H NMR (400 MHz, Methanol-d4) δ 9.02 (s, 1H), 8.34 (s, 1H), 8.18 (dd, J = 8.8, 2.5 Hz, 1H), 8.10 (s, 1H), 7.93 (d, J = 8.7 Hz, 1H), 7.51 (s, 1H), 6.09 (q, J = 6.6 Hz, 1H), 5.32 (t, J = 5.0 Hz, 1H), 4.07-4.02 (m, 2H), 4.01 (s, 3H), 3.95-3.89 (m, 2H), 2.80 (d, J = 5.0 Hz, 2H), 1.65 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 197 (R)-1-(2-chloropyridin-3-yl)ethyl (1-methyl-4-(5-((1R,2R)-2-phenylcyclopropane-1-carboxamido)pyridin-2-yl)-1H-1,2,3-triazol-5-yl)carbamate | 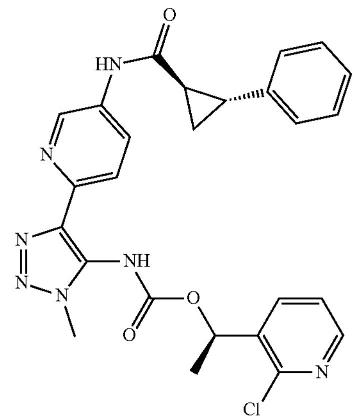 [SMILES: C[C@@H](OC(=O)Nc1c(-c2ccc(NC(=O)[C@@H]3C[C@H]3c3ccccc3)cn2)nnn1C)c1cccnc1Cl] | | 518.2 | 1H NMR (400 MHz, Methanol-d4) δ 8.85 (s, 1H), 8.43-7.77 (m, 4H), 7.65-7.05 (m, 6H), 6.08 (d, J = 6.8 Hz, 1H), 3.98 (s, 3H), 2.54 (dddd, J = 8.8, 6.3, 4.1, 2.0 Hz, 1H), 2.10 (ddd, J = 8.2, 5.3, 4.1 Hz, 1H), 1.80-1.33 (m, 5H). |
| Compound 198 (R)-1-(2-chloropyridin-3-yl)ethyl (4-(5-(3,3-difluoro-1-(pyridin-3-yl)cyclobutane-1-carboxamido)pyridin-2-yl)-1-methyl-1H-1,2,3-triazol-5-yl)carbamate | 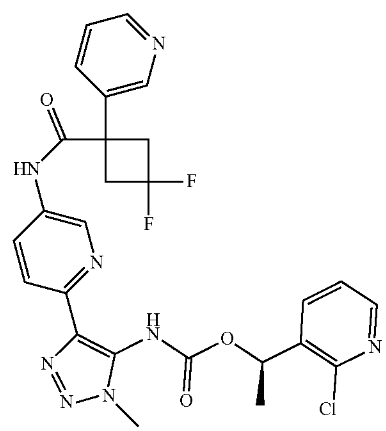 [SMILES: C[C@@H](OC(=O)Nc1c(-c2ccc(NC(=O)C3(c4cccnc4)CC(F)(F)C3)cn2)nnn1C)c1cccnc1Cl] | | 569.2 | 1H NMR (400 MHz, Methanol-d4) δ 9.00 (s, 1H), 8.95-8.49 (m, 2H), 8.45-7.71 (m, 5H), 7.50 (s, 1H), 6.05 (s, 1H), 3.99 (s, 3H), 3.71 (m, 2H), 3.44-3.35 (m, 2H), 1.63 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 199 (R)-1-(2-chloropyridin-3-yl)ethyl (4-(5-(2,2-difluorospiro[2.2]pentane-1-carboxamido)pyridin-2-yl)-1-methyl-1H-1,2,3-triazol-5-yl)carbamate | 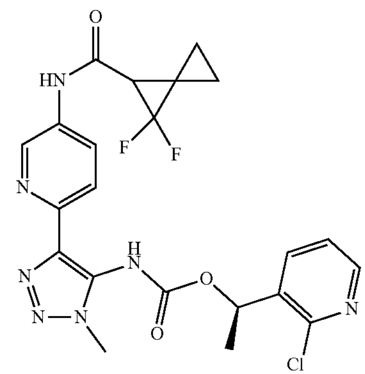 [SMILES: C[C@@H](OC(=O)Nc1c(-c2ccc(NC(=O)C3C(F)(F)C34CC4)cn2)nnn1C)c1cccnc1Cl] | | 504.1 | 1H NMR (400 MHz, Methanol-d4) δ 9.01 (s, 1H), 8.33 (s, 1H), 8.17 (ddd, J = 8.8, 4.3, 2.4 Hz, 2H), 7.94 (d, J = 8.7 Hz, 1H), 7.51 (s, 1H), 6.09 (d, J = 6.8 Hz, 1H), 4.01 (s, 3H), 2.98-2.90 (m, 1H), 1.65 (s, 3H), 1.51 (d, J = 6.4 Hz, 1H), 1.48-1.39 (m, 1H), 1.33 (dq, J = 23.5, 7.6, 6.2 Hz, 2H). |
| Compound 200 (R)-1-(2-chloropyridin-3-yl)ethyl (4-(5-(3,3-difluoro-1-(hydroxymethyl)cyclobutane-1-carboxamido)pyridin-2-yl)-1-methyl-1H-1,2,3-triazol-5-yl)carbamate | 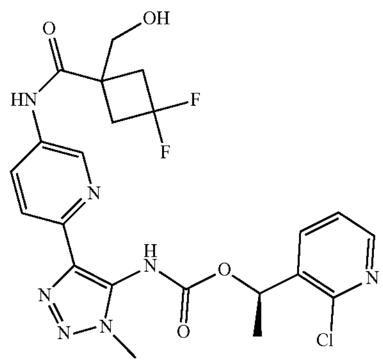 [SMILES: C[C@@H](OC(=O)Nc1c(-c2ccc(NC(=O)C3(CO)CC(F)(F)C3)cn2)nnn1C)c1cccnc1Cl] | | 522.2 | 1H NMR (400 MHz, Methanol-d4) δ 9.08 (s, 1H), 8.49-8.21 (m, 2H), 8.01 (m, 2H), 7.50 (s, 1H), 6.16-5.97 (m, 1H), 3.97 (m, 5H), 3.08 (m, 2H), 2.70 (m, 2H), 1.63 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 201 (R)-1-(2-chloropyridin-3-yl)ethyl (4-(5-(((1R,2R)-1-cyano-2-(trifluoromethyl)cyclopropane-1-carboxamido)pyridin-2-yl)-1-methyl-1H-1,2,3-triazol-5-yl)carbamate | | (Rac) | 535.1 | 1H NMR (400 MHz, Methanol-d4) δ 8.88-8.76 (m, 1H), 8.40-8.26 (m, 1H), 8.05 (m, 2H), 7.91 (m, 1H), 7.48 (s, 1H), 6.07 (m, 1H), 3.98 (s, 3H), 3.10-2.91 (m, 1H), 2.27-2.08 (m, 2H), 1.62 (s, 3H). |
| Compound 202 (R)-1-(2-chloropyridin-3-yl)ethyl (4-(5-(((1S,2S)-1-cyano-2-(trifluoromethyl)cyclopropane-1-carboxamido)pyridin-2-yl)-1-methyl-1H-1,2,3-triazol-5-yl)carbamate | | (Rac) | 535.1 | 1H NMR (400 MHz, Methanol-d4) δ 8.84 (s, 1H), 8.39-8.22 (m, 1H), 8.05 (m, 2H), 7.92 (m, 1H), 7.46 (m, 1H), 6.07 (m, 1H), 3.98 (s, 3H), 3.12-2.95 (m, 1H), 2.24-2.07 (m, 2H), 1.63 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 203 (R)-1-(2-chloropyridin-3-yl)ethyl (4-(5-((R)-2-cyanopropanamido)pyridin-2-yl)-1-methyl-1H-1,2,3-triazol-5-yl)carbamate | 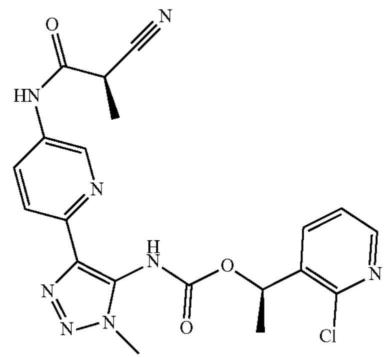 [SMILES: C[C@H](C#N)C(=O)Nc1ccc(-c2nnn(C)c2NC(=O)O[C@H](C)c2cccnc2Cl)nc1] | | 455.1 | 1H NMR (400 MHz, Methanol-d4) δ 9.05-8.72 (m, 1H), 8.44-8.23 (m, 1H), 8.19-7.79 (m, 3H), 7.44 (m, 1H), 6.07 (m, 1H), 3.99 (s, 3H), 3.92 (m, 1H), m 1.81-1.48 (m, 6H). |
| Compound 204 (R)-1-(2-chloropyridin-3-yl)ethyl (4-(5-((S)-2-cyanopropanamido)pyridin-2-yl)-1-methyl-1H-1,2,3-triazol-5-yl)carbamate | 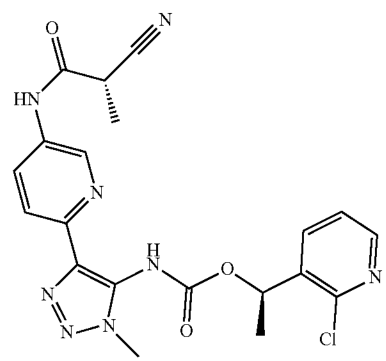 [SMILES: C[C@@H](C#N)C(=O)Nc1ccc(-c2nnn(C)c2NC(=O)O[C@H](C)c2cccnc2Cl)nc1] | | 455.1 | 1H NMR (400 MHz, Methanol-d4) δ 8.83 (s, 1H), 8.39-8.22 (m, 1H), 8.04 (m, 2H), 7.92 (m, 1H), 7.43 (m, 1H), 6.07 (m, 1H), 3.98 (s, 3H), 3.95-3.82 (m, 1H), 1.73-1.48 (m, 6H), |

TABLE 2-continued

Compounds prepared according to Scheme C, Step 4.

| Compound No. | Structure | Reagent | LCMS m/z | 1H NMR |
|---|---|---|---|---|
| Compound 205 (R)-1-(2-chloropyridin-3-yl)ethyl (1-methyl-4-(5-(2-(trifluoromethyl)pyrimidine-5-carboxamido)pyridin-2-yl)-1H-1,2,3-triazol-5-yl)carbamate | 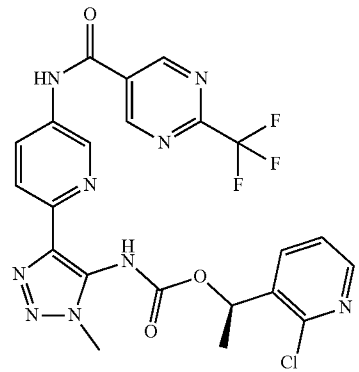 [SMILES: C[C@@H](OC(=O)Nc1c(-c2ccc(NC(=O)c3cnc(C(F)(F)F)nc3)cn2)nnn1C)c1cccnc1Cl] | | 547.9 | 1H NMR (400 MHz, Methanol-d4) δ 9.48 (s, 2H), 9.00 (s, 1H), 8.30 (s, 1H), 8.21 (dd, J = 8.7, 2.6 Hz, 1H), 8.15-7.88 (m, 2H), 7.47 (s, 1H), 6.07 (d, J = 6.7 Hz, 1H), 3.98 (s, 3H), 1.60 (s, 3H). |
| Compound 206 (R)-1-(2-chloropyridin-3-yl)ethyl (4-(5-(2-(difluoromethyl)pyrimidine-5-carboxamido)pyridin-2-yl)-1-methyl-1H-1,2,3-triazol-5-yl)carbamate | 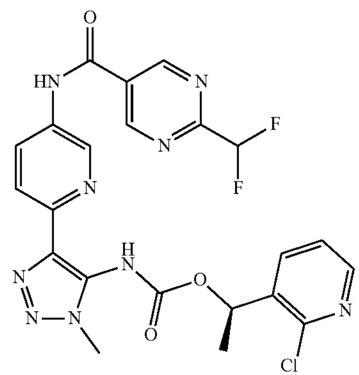 [SMILES: C[C@@H](OC(=O)Nc1c(-c2ccc(NC(=O)c3cnc(C(F)F)nc3)cn2)nnn1C)c1cccnc1Cl] | | 530.0 | 1H NMR (400 MHz, Methanol-d4) δ 9.43 (s, 2H), 9.00 (s, 1H), 8.30 (s, 1H), 8.21 (dd, J = 8.6, 2.6 Hz, 1H), 8.15-7.84 (m, 2H), 7.47 (s, 1H), 6.84 (t, J = 54.2 Hz, 1H), 6.07 (d, J = 6.8 Hz, 1H), 3.98 (s, 3H), 1.60 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 207 (R)-1-(2,5-difluoropyridin-3-yl)ethyl (1-methyl-4-(5-((1RS,2RS)-2-methylcyclopropane-1-carboxamido)pyridin-2-yl)-1H-1,2,3-triazol-5-yl)carbamate | 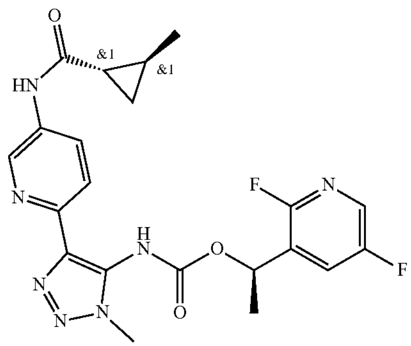 [SMILES: C[C@@H](OC(=O)Nc1c(-c2ccc(NC(=O)[C@H]3C[C@@H]3C)cn2)nnn1C)c1cc(F)cnc1F] | (Rac) | 458.1 | 1H NMR (400 MHz, Methanol-d4) δ 8.78 (s, 1H), 8.27-7.50 (m, 4H), 5.95 (d, J = 7.6 Hz, 1H), 3.99 (s, 3H), 1.82-1.31 (m, 5H), 1.26-1.15 (m, 4H), 0.76 (ddd, J = 8.0, 6.3, 3.9 Hz, 1H). |
| Compound 208 (R)-1-(2,5-difluoropyridin-3-yl)ethyl (4-(5-((1RS,2RS)-2-(fluoromethyl)cyclopropane-1-carboxamido)pyridin-2-yl)-1-methyl-1H-1,2,3-triazol-5-yl)carbamate | 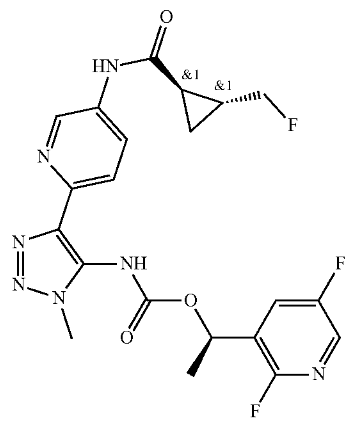 [SMILES: C[C@@H](OC(=O)Nc1c(-c2ccc(NC(=O)[C@@H]3C[C@H]3CF)cn2)nnn1C)c1cc(F)cnc1F] | | 476.1 | 1H NMR (400 MHz, Methanol-d4) δ 8.79 (s, 1H), 8.23-7.52 (m, 4H), 5.95 (d, J = 7.3 Hz, 1H), 4.53 (ddd, J = 48.7, 10.0, 5.8 Hz, 1H), 4.38-4.09 (m, 1H), 3.99 (s, 3H), 1.92-1.79 (m, 2H), 1.62 (s, 3H), 1.31 (dq, J = 8.3, 3.8 Hz, 1H), 1.01 (dt, J = 10.8, 5.5 Hz, 1H). |

TABLE 2-continued

Compounds prepared according to Scheme C, Step 4.

| Compound No. | Structure | Reagent | LCMS m/z | 1H NMR |
|---|---|---|---|---|
| Compound 209 (R)-1-(2,5-difluoropyridin-3-yl)ethyl (1-methyl-4-(5-((1RS,2RS)-2-(trifluoromethyl)cyclopropane-1-carboxamido)pyridin-2-yl)-1H-1,2,3-triazol-5-yl)carbamate | 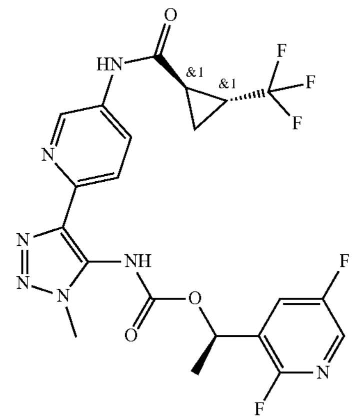 [SMILES: C[C@@H](OC(=O)Nc1c(-c2ccc(NC(=O)[C@@H]3C[C@H]3C(F)(F)F)cn2)nnn1C)c1cc(F)cnc1F] | | 512.1 | 1H NMR (400 MHz, Methanol-d4) δ 8.79 (s, 1H), 8.34-7.48 (m, 4H), 5.95 (d, J = 5.6 Hz, 1H), 3.99 (s, 3H), 2.38-2.13 (m, 2H), 1.85-1.18 (m, 5H). |
| Compound 210 (R)-1-(2,5-difluoropyridin-3-yl)ethyl (4-(5-((1RS,2RS)-2-methoxycyclopropane-1-carboxamido)pyridin-2-yl)-1-methyl-1H-1,2,3-triazol-5-yl)carbamate | 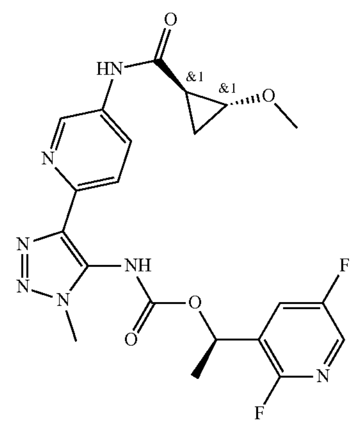 | | 474.2 | 1H NMR (400 MHz, Methanol-d4) δ 8.77 (s, 1H), 8.32-7.55 (m, 4H), 5.95 (d, J = 7.1 Hz, 1H), 3.99 (s, 3H), 3.61 (ddt, J = 6.1, 3.9, 1.8 Hz, 1H), 3.44 (d, J = 1.2 Hz, 3H), 1.96 (ddd, J = 9.5, 5.8, 2.0 Hz, 1H), 1.62 (s, 3H), 1.38-1.19 (m, 2H). |

TABLE 2-continued

Compounds prepared according to Scheme C, Step 4.

| Compound No. | Structure | Reagent | LCMS m/z | 1H NMR |
|---|---|---|---|---|
| Compound 211 (R)-1-(2,5-difluoropyridin-3-yl)ethyl (1-methyl-4-(5-((1RS,2RS)-2-nitrocyclopropane-1-carboxamido)pyridin-2-yl)-1H-1,2,3-triazol-5-yl)carbamate | 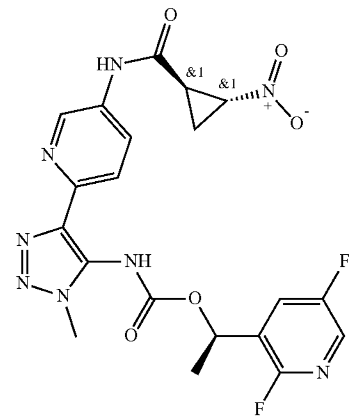 | | 489.1 | 1H NMR (400 MHz, Methanol-d4) δ 8.78 (s, 1H), 8.34-7.55 (m, 4H), 5.94 (d, J = 6.7 Hz, 1H), 4.77-4.63 (m, 1H), 3.99 (s, 3H), 2.96 (ddd, J = 10.0, 7.1, 2.7 Hz, 1H), 2.17-2.02 (m, 1H), 1.84 (tdd, J = 7.1, 5.7, 1.1 Hz, 1H), 1.61 (s, 3H). |
| Compound 212 (R)-1-(2,5-difluoropyridin-3-yl)ethyl (4-(5-(6-chloronicotinamido)pyridin-2-yl)-1-methyl-1H-1,2,3-triazol-5-yl)carbamate | 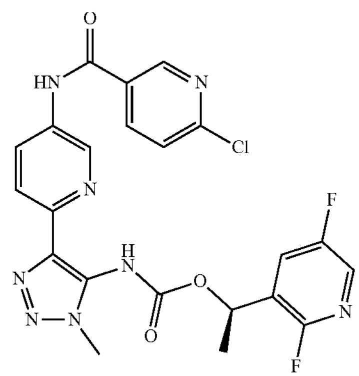 [SMILES: C[C@@H](OC(=O)Nc1c(-c2ccc(NC(=O)c3ccc(Cl)nc3)cn2)nnn1C)c1cc(F)cnc1F] | | 515.0 | 1H NMR (400 MHz, Methanol-d4) δ 9.03-8.85 (m, 2H), 8.35 (dd, J = 8.3, 2.5 Hz, 1H), 8.23 (dd, J = 8.6, 2.6 Hz, 1H), 8.02 (s, 1H), 7.99-7.72 (m, 2H), 7.64 (dd, J = 8.3, 0.7 Hz, 1H), 5.94 (d, J = 7.0 Hz, 1H), 3.99 (s, 3H), 1.60 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 213 (R)-1-(2,5-difluoropyridin-3-yl)ethyl (4-(5-(2-fluoroisonicotinamido)pyridin-2-yl)-1-methyl-1H-1,2,3-triazol-5-yl)carbamate | 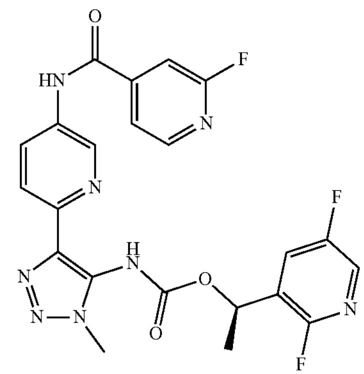 [SMILES: C[C@@H](OC(=O)Nc1c(-c2ccc(NC(=O)c3ccnc(F)c3)cn2)nnn1C)c1cc(F)cnc1F] | | 499.1 | 1H NMR (400 MHz, Methanol-d4) δ 8.95 (s, 1H), 8.42 (d, J = 5.2 Hz, 1H), 8.24 (dd, J = 8.7, 2.6 Hz, 1H), 8.02 (s, 1H), 7.97 (dd, J = 8.6, 0.7 Hz, 1H), 7.94-7.68 (m, 2H), 7.59 (d, J = 1.8 Hz, 1H), 5.94 (d, J = 6.7 Hz, 1H), 3.99 (s, 3H), 1.60 (s, 3H). |
| Compound 214 (R)-1-(2,5-difluoropyridin-3-yl)ethyl (4-(5-(3-(difluoromethyl)oxetane-3-carboxamido)pyridin-2-yl)-1-methyl-1H-1,2,3-triazol-5-yl)carbamate | 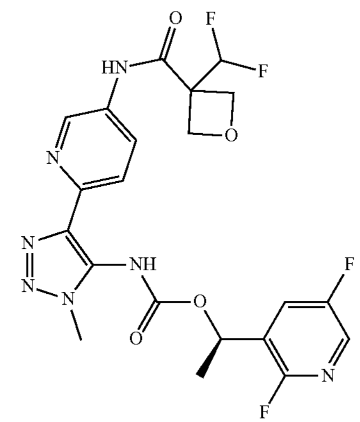 [SMILES: C[C@@H](OC(=O)Nc1c(-c2ccc(NC(=O)C3(C(F)F)COC3)cn2)nnn1C)c1cc(F)cnc1F] | | 510.2 | 1H NMR (400 MHz, Methanol-d4) δ 8.83 (s, 1H), 8.28-7.35 (m, 4H), 6.43 (t, J = 55.6 Hz, 1H), 5.95 (d, J = 6.8 Hz, 1H), 5.03 (dt, J = 7.0, 1.8 Hz, 2H), 4.85 (d, J = 7.0 Hz, 2H), 4.00 (s, 3H), 1.62 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 215 (R)-1-(2,5-difluoropyridin-3-yl)ethyl (1-methyl-4-(5-(3-(methylsulfonyl)bicyclo[1.1.1]pentane-1-carboxamido)pyridin-2-yl)-1H-1,2,3-triazol-5-yl)carbamate | 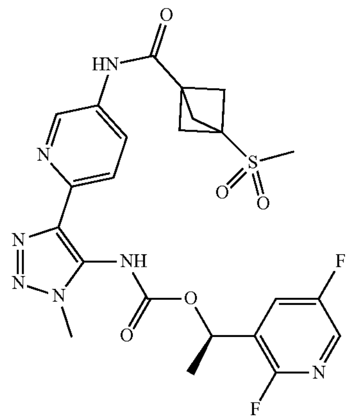 [SMILES: C[C@@H](OC(=O)Nc1c(-c2ccc(NC(=O)C34CC(S(C)(=O)=O)(C3)C4)cn2)nnn1C)c1cc(F)cnc1F] | | 548.1 | 1H NMR (400 MHz, Methanol-d4) δ 8.85 (s, 1H), 8.22-7.49 (m, 4H), 5.95 (d, J = 7.2 Hz, 1H), 4.00 (s, 3H), 2.99 (s, 3H), 2.58 (s, 6H), 1.62 (s, 3H). |
| Compound 216 (R)-1-(2,5-difluoropyridin-3-yl)ethyl (4-(5-((1RS,2RS)-2-(difluoromethyl)cyclopropane-1-carboxamido)pyridin-2-yl)-1-methyl-1H-1,2,3-triazol-5-yl)carbamate | 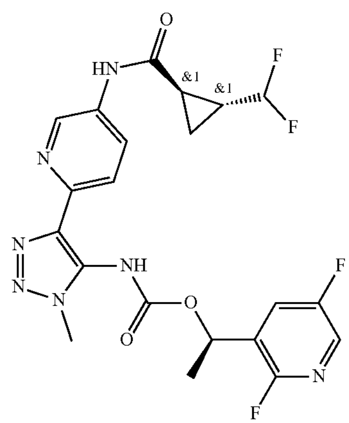 | | 519.1 | 1H NMR (400 MHz, Methanol-d4) δ 8.86 (s, 1H), 8.16 (m, 1H), 8.12-7.72 (m, H), 6.20-5.96 (m, 2H), 4.01 (s, 3H), 2.61 (m, 1H), 2.13-1.96 (m, 2H), 1.65 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 217 (R)-1-(2,5-difluoropyridin-3-yl)ethyl (1-methyl-4-(5-((1RS,2RS)-2-(pyridin-4-yl)cyclopropane-1-carboxamido)pyridin-2-yl)-1H-1,2,3-triazol-5-yl)carbamate | | | 521.1 | 1H NMR (400 MHz, Methanol-d4) δ 8.79 (s, 1H), 8.47-8.36 (m, 2H), 8.16-7.77 (m, 4H), 7.31-7.23 (m, 2H), 5.95 (d, J = 7.3 Hz, 1H), 3.99 (s, 3H), 2.56 (ddd, J = 9.1, 6.3, 4.0 Hz, 1H), 2.25 (ddd, J = 8.5, 5.5, 4.0 Hz, 1H), 1.83-1.35 (m, 5H). |
| Compound 218 (R)-1-(2,5-difluoropyridin-3-yl)ethyl (4-(5-((1S,2R)-2-chlorocyclopropane-1-carboxamido)pyridin-2-yl)-1-methyl-1H-1,2,3-triazol-5-yl)carbamate | | | 478.2 | 1H NMR (400 MHz, Methanol-d4) δ 8.79 (s, 1H), 8.24-7.51 (m, 4H), 5.95 (d, J = 7.4 Hz, 1H), 3.99 (s, 3H), 2.36 (ddd, J = 8.6, 5.7, 3.7 Hz, 1H), 2.18-2.07 (m, 1H), 1.89-1.33 (m, 5H). |

TABLE 2-continued

Compounds prepared according to Scheme C, Step 4.

| Compound No. | Structure | Reagent | LCMS m/z | 1H NMR |
|---|---|---|---|---|
| Compound 219 (R)-1-(2,5-difluoropyridin-3-yl)ethyl (4-(5-(difluoromethyl)nicotinamido)pyridin-2-yl)-1-methyl-1H-1,2,3-triazol-5-yl)carbamate | | | 531.1 | 1H NMR (400 MHz, Methanol-d4) δ 9.34-9.18 (m, 1H), 9.01-8.90 (m, 2H), 8.58 (s, 1H), 8.26 (dd, J = 8.6, 2.6 Hz, 1H), 8.02 (s, 1H), 8.00-7.75 (m, 2H), 7.05 (t, J = 55.3 Hz, 1H), 5.95 (d, J = 7.3 Hz, 1H), 3.99 (s, 3H), 1.60 (s, 3H). |
| Compound 220 (R)-1-(2,5-difluoropyridin-3-yl)ethyl (4-(5-(6-fluoronicotinamido)pyridin-2-yl)-1-methyl-1H-1,2,3-triazol-5-yl)carbamate | 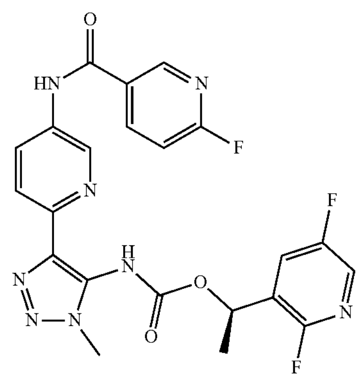 [SMILES: C[C@@H](OC(=O)Nc1c(-c2ccc(NC(=O)c3ccc(F)nc3)cn2)nnn1C)c1cc(F)cnc1F] | | 499.1 | 1H NMR (400 MHz, Methanol-d4) δ 8.94 (s, 1H), 8.83 (d, J = 2.5 Hz, 1H), 8.50 (ddd, J = 8.6, 7.5, 2.6 Hz, 1H), 8.23 (dd, J = 8.6, 2.6 Hz, 1H), 8.02 (s, 1H), 7.98-7.67 (m, 2H), 7.24 (dd, J = 8.6, 2.5 Hz, 1H), 5.94 (d, J = 7.0 Hz, 1H), 3.99 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 221 (R)-1-(2,5-difluoropyridin-3-yl)ethyl (1-methyl-4-(5-(6-methylnicotinamido)pyridin-2-yl)-1H-1,2,3-triazol-5-yl)carbamate | 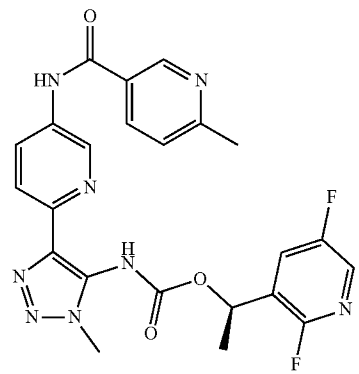 [SMILES: Cc1ccc(C(=O)Nc2ccc(-c3nnn(C)c3NC(=O)O[C@H](C)c3cc(F)cnc3F)nc2)cn1] | | 495.1 | 1H NMR (400 MHz, Methanol-d4) δ 9.01 (d, J = 2.4 Hz, 1H), 8.94 (s, 1H), 8.29 (dd, J = 8.2, 2.4 Hz, 1H), 8.23 (dd, J = 8.6, 2.6 Hz, 1H), 8.02 (s, 1H), 7.99-7.66 (m, 2H), 7.48 (d, J = 8.2 Hz, 1H), 5.94 (d, J = 6.5 Hz, 1H), 3.99 (s, 3H), 2.64 (s, 3H), 1.61 (s, 3H). |
| Compound 222 (R)-1-(2,5-difluoropyridin-3-yl)ethyl (4-(5-(6-(difluoromethyl)nicotinamido)pyridin-2-yl)-1-methyl-1H-1,2,3-triazol-5-yl)carbamate | 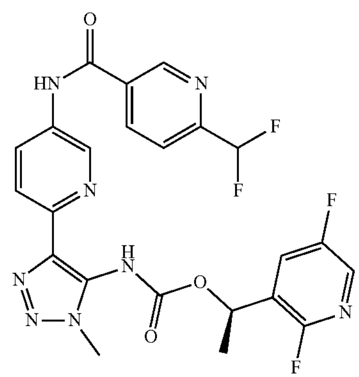 [SMILES: C[C@@H](OC(=O)Nc1c(-c2ccc(NC(=O)c3ccc(C(F)F)nc3)cn2)nnn1C)c1cc(F)cnc1F] | | 531.1 | 1H NMR (400 MHz, Methanol-d4) δ 9.19 (s, 1H), 8.96 (s, 1H), 8.52 (dd, J = 8.1, 2.2 Hz, 1H), 8.25 (dd, J = 8.6, 2.6 Hz, 1H), 8.02 (s, 1H), 7.97 (d, J = 8.7 Hz, 1H), 7.90-7.61 (m, 2H), 6.82 (t, J = 55.0 Hz, 1H), 5.94 (d, J = 7.3 Hz, 1H), 3.99 (s, 3H), 1.60 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 223 (R)-1-(2,5-difluoropyridin-3-yl)ethyl (4-(5-(2-methoxyisonicotinamido)pyridin-2-yl)-1-methyl-1H-1,2,3-triazol-5-yl)carbamate | 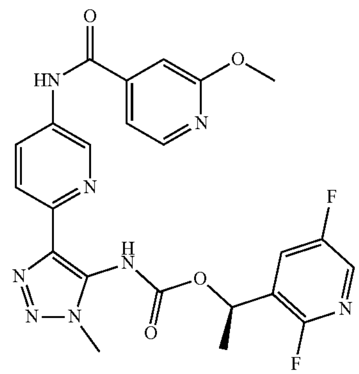 [SMILES: COc1cc(C(=O)Nc2ccc(-c3nnn(C)c3NC(=O)O[C@H](C)c3cc(F)cnc3F)nc2)ccn1] | | 511.1 | 1H NMR (400 MHz, Methanol-d4) δ 8.94 (s, 1H), 8.32 (dd, J = 5.3, 0.8 Hz, 1H), 8.22 (dd, J = 8.6, 2.6 Hz, 1H), 8.02 (s, 1H), 8.00-7.71 (m, 2H), 7.43 (dd, J = 5.3, 1.5 Hz, 1H), 7.31 (dd, J = 1.5, 0.8 Hz, 1H), 5.94 (d, J = 7.0 Hz, 1H), 4.06-3.92 (m, 6H), 1.60 (s, 3H). |
| Compound 224 (R)-1-(2,5-difluoropyridin-3-yl)ethyl (4-(5-(2-(difluoromethyl)isonicotinamido)pyridin-2-yl)-1-methyl-1H-1,2,3-triazol-5-yl)carbamate | 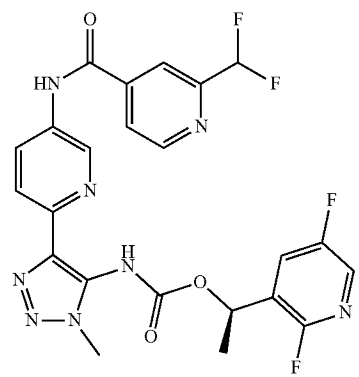 [SMILES: C[C@@H](OC(=O)Nc1c(-c2ccc(NC(=O)c3ccnc(C(F)F)c3)cn2)nnn1C)c1cc(F)cnc1F] | | 531.1 | 1H NMR (400 MHz, Methanol-d4) δ 8.97 (s, 1H), 8.86 (d, J = 5.1 Hz, 1H), 8.32-8.19 (m, 2H), 8.10-8.01 (m, 2H), 8.00-7.75 (m, 2H), 6.85 (t, J = 55.1 Hz, 1H), 5.94 (d, J = 6.4 Hz, 1H), 3.99 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 225 (R)-1-(2,5-difluoropyridin-3-yl)ethyl (1-methyl-4-(5-(2-(trifluoromethyl)isonicotinamido)pyridin-2-yl)-1H-1,2,3-triazol-5-yl)carbamate | 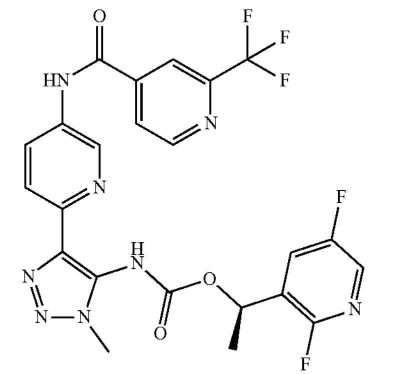 | | 549.1 | 1H NMR (400 MHz, Methanol-d4) δ 9.10-8.85 (m, 2H), 8.35 (t, J = 1.2 Hz, 1H), 8.26 (dd, J = 8.6, 2.6 Hz, 1H), 8.16 (dd, J = 5.0, 1.6 Hz, 1H), 8.02 (s, 1H), 8.01-7.66 (m, 2H), 5.94 (d, J = 6.4 Hz, 1H), 3.99 (s, 3H), 1.61 (s, 3H). |
| Compound 226 (R)-1-(2,5-difluoropyridin-3-yl)ethyl (4-(5-(3,3-difluoro-1-methylcyclobutane-1-carboxamido)pyridin-2-yl)-1-methyl-1H-1,2,3-triazol-5-yl)carbamate | 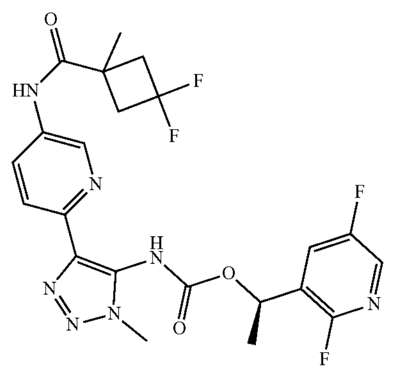 [SMILES: C[C@@H](OC(=O)Nc1c(-c2ccc(NC(=O)C3(C)CC(F)(F)C3)cn2)nnn1C)c1cc(F)cnc1F] | | 508.0 | 1H NMR (400 MHz, Methanol-d4) δ 9.04 (s, 1H), 8.42-8.18 (m, 1H), 8.06 (s, 1H), 7.96 (m, 2H), 5.96 (m, 1H), 4.02 (s, 3H), 3.27-2.96 (m, 2H), 2.70-2.41 (m, 2H), 1.64 (s, 6H). |

TABLE 2-continued

Compounds prepared according to Scheme C, Step 4.

| Compound No. | Structure | Reagent | LCMS m/z | 1H NMR |
|---|---|---|---|---|
| Compound 227 (R)-1-(2,5-difluoropyridin-3-yl)ethyl (1-methyl-4-(5-(4-methylisoxazole-5-carboxamido)pyridin-2-yl)-1H-1,2,3-triazol-5-yl)carbamate | 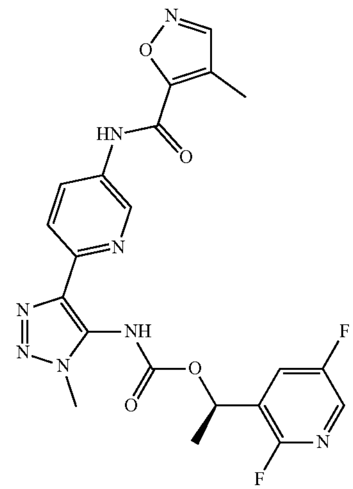 [SMILES: Cc1cnoc1C(=O)Nc1ccc(-c2nnn(C)c2NC(=O)O[C@H](C)c2cc(F)cnc2F)nc1] | | 485.1 | 1H NMR (400 MHz, DMSO-d6) δ 10.98 (bs, 1H), 9.82 (bs, 1H), 8.89 (bs, 1H), 8.75 (s, 1H), 8.29-7.25 (m, 4H), 5.80 (bs, 1H), 3.89 (s, 3H), 2.32 (s, 3H), 1.40 (bs, 3H). |
| Compound 228 (R)-1-(2,5-difluoropyridin-3-yl)ethyl (1-methyl-4-(5-(3-methyl-1,1-dioxidothietane-3-carboxamido)pyridin-2-yl)-1H-1,2,3-triazol-5-yl)carbamate | 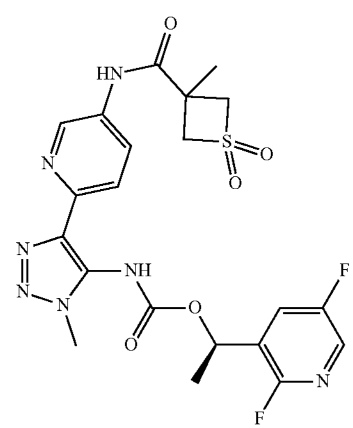 [SMILES: C[C@@H](OC(=O)Nc1c(-c2ccc(NC(=O)C3(C)CS(=O)(=O)C3)cn2)nnn1C)c1cc(F)cnc1F] | | 522.1 | 1H NMR (400 MHz, Methanol-d4) δ 8.81 (s, 1H), 8.23-7.60 (m, 4H), 5.95 (d, J = 7.0 Hz, 1H), 4.80-4.68 (m, 2H), 4.14-3.91 (m, 5H), 1.86 (s, 3H), 1.62 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 229 (R)-1-(2,5-difluoropyridin-3-yl)ethyl (4-(5-((1RS,5SR,6SR)-3,3-dioxido-3-thiabicyclo[3.1.0]hexane-6-carboxamido)pyridin-2-yl)-1-methyl-1H-1,2,3-triazol-5-yl)carbamate | 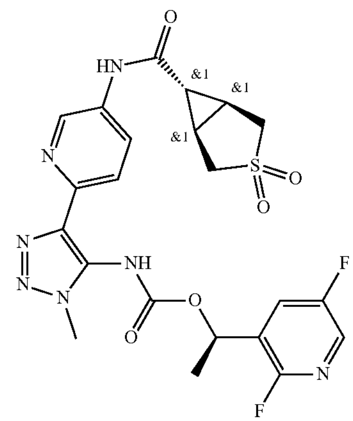 [SMILES: C[C@@H](OC(=O)Nc1c(-c2ccc(NC(=O)[C@H]3[C@@H]4CS(=O)(=O)C[C@@H]43)cn2)nnn1C)c1cc(F)cnc1F] | | 534.1 | 1H NMR (400 MHz, Methanol-d4) δ 8.77 (s, 1H), 8.27-7.62 (m, 4H), 5.95 (d, J = 6.4 Hz, 1H), 4.00 (s, 3H), 3.61-3.44 (m, 2H), 2.46-2.31 (m, 2H), 2.29-2.18 (m, 1H), 1.62 (s, 3H). |
| Compound 230 (R)-1-(2,5-difluoropyridin-3-yl)ethyl (4-(5-((1RS,5SR,6SR)-3,3-difluorobicyclo[3.1.0]hexane-6-carboxamido)pyridin-2-yl)-1-methyl-1H-1,2,3-triazol-5-yl)carbamate | 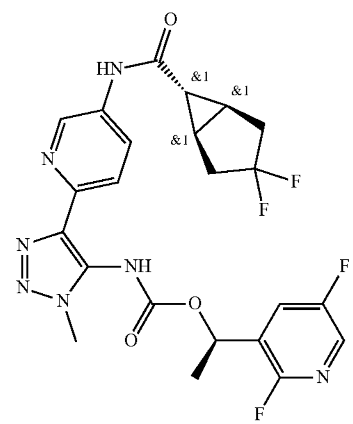 [SMILES: C[C@@H](OC(=O)Nc1c(-c2ccc(NC(=O)[C@H]3[C@@H]4CC(F)(F)C[C@@H]43)cn2)nnn1C)c1cc(F)cnc1F] | | 520.2 | 1H NMR (400 MHz, Methanol-d4) δ 8.77 (s, 1H), 8.18-7.59 (m, 4H), 6.09-5.77 (m, 1H), 3.99 (s, 3H), 2.55 (dtd, J = 23.8, 14.4, 3.1 Hz, 2H), 2.31 (dd, J = 19.4, 14.9 Hz, 2H), 2.13-1.99 (m, 2H), 1.85 (q, J = 3.0 Hz, 1H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 231 (R)-1-(2,5-difluoropyridin-3-yl)ethyl (1-methyl-4-(5-(6-methylpyridazine-4-carboxamido)pyridin-2-yl)-1H-1,2,3-triazol-5-yl)carbamate | | | 496.1 | 1H NMR (400 MHz, Methanol-d4) δ 9.49 (d, J = 2.1 Hz, 1H), 8.96 (s, 1H), 8.25 (dd, J = 8.6, 2.6 Hz, 1H), 8.09 (d, J = 2.1 Hz, 1H), 8.03 (s, 1H), 8.02-7.70 (m, 2H), 5.94 (d, J = 6.7 Hz, 1H), 3.99 (s, 3H), 2.83 (s, 3H), 1.61 (s, 3H). |
| Compound 232 (R)-1-(2,5-difluoropyridin-3-yl)ethyl (4-(5-(2-aminoisonicotinamido)pyridin-2-yl)-1-methyl-1H-1,2,3-triazol-5-yl)carbamate | | | 496.1 | 1H NMR (400 MHz, Methanol-d4) δ 8.93 (s, 1H), 8.21 (dd, J = 8.6, 2.6 Hz, 1H), 8.09-8.05 (m, 1H), 8.03 (s, 1H), 7.99-7.76 (m, 2H), 7.10-6.96 (m, 2H), 5.94 (d, J = 7.1 Hz, 1H), 3.99 (s, 2H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 233 (R)-1-(2,5-difluoropyridin-3-yl)ethyl (1-methyl-4-(5-(pyrimidine-5-carboxamido)pyridin-2-yl)-1H-1,2,3-triazol-5-yl)carbamate | 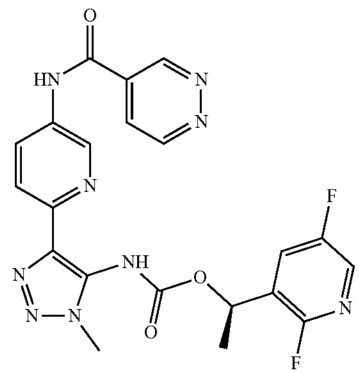 [SMILES: C[C@@H](OC(=O)Nc1c(-c2ccc(NC(=O)c3ccnnc3)cn2)nnn1C)c1cc(F)cnc1F] | | 482.1 | 1H NMR (400 MHz, Methanol-d4) δ 9.39-9.23 (m, 3H), 8.95 (s, 1H), 8.25 (dd, J = 8.7, 2.6 Hz, 1H), 8.03 (s, 1H), 8.00-7.91 (m, 2H), 5.95 (d, J = 7.1 Hz, 1H), 3.99 (s, 3H), 1.61 (s, 3H). |
| Compound 234 (R)-1-(2,5-difluoropyridin-3-yl)ethyl (1-methyl-4-(5-(2-methylpyrimidine-5-carboxamido)pyridin-2-yl)-1H-1,2,3-triazol-5-yl)carbamate | 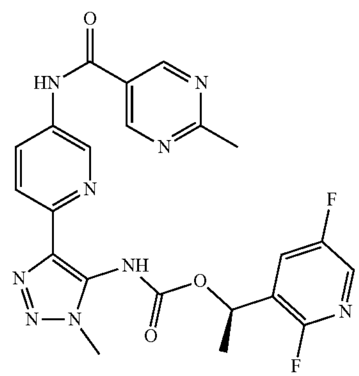 [SMILES: Cc1ncc(C(=O)Nc2ccc(-c3nnn(C)c3NC(=O)O[C@H](C)c3cc(F)cnc3F)nc2)cn1] | | 496.1 | 1H NMR (400 MHz, Methanol-d4) δ 9.21 (s, 2H), 8.94 (s, 1H), 8.23 (dd, J = 8.7, 2.6 Hz, 1H), 8.03 (s, 1H), 8.00-7.91 (m, 2H), 5.94 (d, J = 7.5 Hz, 1H), 3.99 (s, 3H), 2.79 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 235 (R)-1-(2,5-difluoropyridin-3-yl)ethyl (4-(5-(2-cyanopyrimidine-5-carboxamido)pyridin-2-yl)-1-methyl-1H-1,2,3-triazol-5-yl)carbamate | 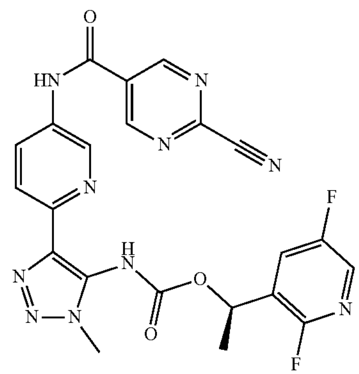 [SMILES: C[C@@H](OC(=O)Nc1c(-c2ccc(NC(=O)c3cnc(C#N)nc3)cn2)nnn1C)c1cc(F)cnc1F] | | 507.1 | 1H NMR (400 MHz, DMSO-d6) δ 11.01 (s, 1H), 9.87 (s, 1H), 9.48 (s, 2H), 8.88 (s, 1H), 8.21 (dd, J = 8.6, 2.6 Hz, 2H), 8.07-7.86 (m, 2H), 5.81 (s, 1H), 3.90 (s, 3H), 1.55 (s, 3H). |
| Compound 236 (R)-1-(2,5-difluoropyridin-3-yl)ethyl (1-methyl-4-(5-(1-methyl-6-oxo-1,6-dihydropyridine-3-carboxamido)pyridin-2-yl)-1H-1,2,3-triazol-5-yl)carbamate | 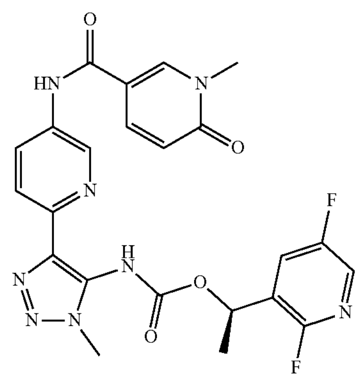 [SMILES: C[C@@H](OC(=O)Nc1c(-c2ccc(NC(=O)c3ccc(=O)n(C)c3)cn2)nnn1C)c1cc(F)cnc1F] | | 511.1 | 1H NMR (400 MHz, Methanol-d4) δ 8.89 (s, 1H), 8.50 (d, J = 2.6 Hz, 1H), 8.17 (dd, J = 8.6, 2.6 Hz, 1H), 8.07 (dd, J = 9.5, 2.7 Hz, 1H), 8.02 (s, 1H), 7.97-7.73 (m, 2H), 6.61 (d, J = 9.5 Hz, 1H), 5.94 (d, J = 7.1 Hz, 1H), 3.99 (s, 3H), 3.66 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 237 (R)-1-(2,5-difluoropyridin-3-yl)ethyl (4-(5-(((1RS,2RS)-2-(6-fluoropyridin-3-yl)cyclopropane-1-carboxamido)pyridin-2-yl)-1-methyl-1H-1,2,3-triazol-5-yl)carbamate | | | 539.0 | 1H NMR (400 MHz, Methanol-d4) δ 8.79 (s, 1H), 8.21-7.66 (m, 6H), 7.04 (dd, J = 8.5, 2.6 Hz, 1H), 5.94 (d, J = 6.9 Hz, 1H), 3.99 (s, 3H), 2.60 (dt, J = 10.1, 5.4 Hz, 1H), 2.14 (ddd, J = 8.3, 5.2, 4.1 Hz, 1H), 1.84-1.34 (m, 5H). |
| Compound 238 (R)-1-(2,5-difluoropyridin-3-yl)ethyl (4-(5-(((1RS,2RS)-2-(3-chloropyridin-4-yl)cyclopropane-1-carboxamido)pyridin-2-yl)-1-methyl-1H-1,2,3-triazol-5-yl)carbamate | | | 555.0 | 1H NMR (400 MHz, Methanol-d4) δ 8.80 (s, 1H), 8.55 (s, 1H), 8.42 (d, J = 5.1 Hz, 1H), 8.25-7.51 (m, 4H), 7.20 (d, J = 5.2 Hz, 1H), 5.95 (d, J = 6.3 Hz, 1H), 4.00 (s, 3H), 2.84 (dddd, J = 8.6, 6.3, 4.4, 1.5 Hz, 1H), 2.24-2.10 (m, 1H), 1.90-1.31 (m, 5H). |

TABLE 2-continued

Compounds prepared according to Scheme C, Step 4.

| Compound No. | Structure | Reagent | LCMS m/z | 1H NMR |
|---|---|---|---|---|
| Compound 239 (R)-1-(2,5-difluoropyridin-3-yl)ethyl (1-methyl-4-(5-(4-methyl-1,2,5-oxadiazole-3-carboxamido)pyridin-2-yl)-1H-1,2,3-triazol-5-yl)carbamate | 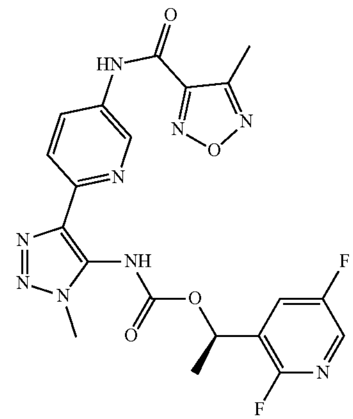 [SMILES: Cc1nonc1C(=O)Nc1ccc(-c2nnn(C)c2NC(=O)O[C@H](C)c2cc(F)cnc2F)nc1] | | 486.0 | 1H NMR (400 MHz, DMSO-d6) δ 11.33 (bs, 1H), 9.82 (bs, 1H), 8.88 (s, 1H), 8.29-8.10 (m, 2H), 8.10-7.74 (m, 2H), 5.80 (bs, 1H), 3.90 (s, 3H), 2.58 (s, 3H), 1.56 (bs, 3H). |
| Compound 240 (R)-1-(2,5-difluoropyridin-3-yl)ethyl (4-(5-((1r,3R)-3-cyano-1-methylcyclobutane-1-carboxamido)pyridin-2-yl)-1-methyl-1H-1,2,3-triazol-5-yl)carbamate | 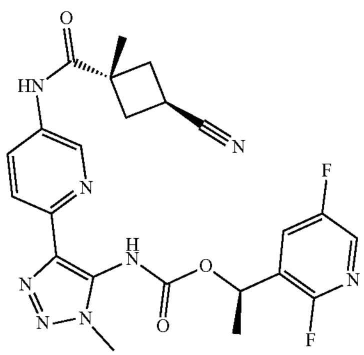 [SMILES: C[C@@H](OC(=O)Nc1c(-c2ccc(NC(=O)[C@]3(C)C[C@@H](C#N)C3)cn2)nnn1C)c1cc(F)cnc1F] | | 497.1 | 1H NMR (400 MHz, Methanol-d4) δ 9.03 (s, 1H), 8.27 (m, 1H), 8.13-7.74 (m, 3H), 5.95 (m, 1H), 4.01 (s, 3H), 3.28-3.13 (m, 1H), 3.11-2.98 (m, 2H), 2.35 (m, 2H), 1.66 (s, 6H). |

TABLE 2-continued

Compounds prepared according to Scheme C, Step 4.

| Compound No. | Structure | Reagent | LCMS m/z | 1H NMR |
|---|---|---|---|---|
| Compound 241 (R)-1-(2,5-difluoropyridin-3-yl)ethyl (4-(5-(2,5-difluoronicotinamido)pyridin-2-yl)-1-methyl-1H-1,2,3-triazol-5-yl)carbamate | 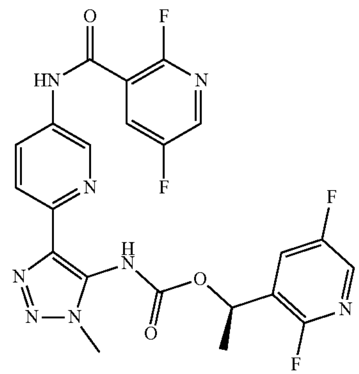 [SMILES: C[C@@H](OC(=O)Nc1c(-c2ccc(NC(=O)c3cc(F)cnc3F)cn2)nnn1C)c1cc(F)cnc1F] | | 517.0 | 1H NMR (400 MHz, Methanol-d4) δ 8.89 (s, 1H), 8.31 (dd, J = 3.1, 1.7 Hz, 1H), 8.25-8.10 (m, 2H), 8.03 (s, 1H), 8.01-7.93 (m, 2H), 5.94 (d, J = 6.7 Hz, 1H), 3.99 (s, 3H), 1.60 (s, 3H). |
| Compound 242 (R)-1-(2,5-difluoropyridin-3-yl)ethyl (1-methyl-4-(5-(6-(trifluoromethyl)nicotinamido)pyridin-2-yl)-1H-1,2,3-triazol-5-yl)carbamate | 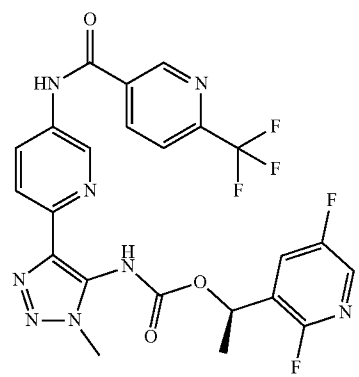 [SMILES: C[C@@H](OC(=O)Nc1c(-c2ccc(NC(=O)c3ccc(C(F)(F)F)nc3)cn2)nnn1C)c1cc(F)cnc1F] | | 549.0 | 1H NMR (400 MHz, Methanol-d4) δ 9.25 (d, J = 2.1 Hz, 1H), 9.06-8.84 (m, 1H), 8.56 (dd, J = 8.2, 2.1 Hz, 1H), 8.23 (dd, J = 8.6, 2.6 Hz, 1H), 8.02 (s, 1H), 7.99 (d, J = 8.1 Hz, 1H), 7.98-7.72 (m, 2H), 5.95 (d, J = 7.3 Hz, 1H), 3.99 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 243 (R)-1-(2,5-difluoropyridin-3-yl)ethyl (4-(5-(2,3-difluoroisonicotinamido)pyridin-2-yl)-1-methyl-1H-1,2,3-triazol-5-yl)carbamate | 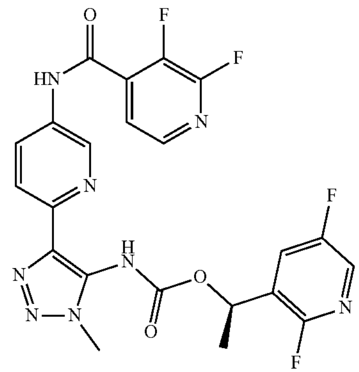 [SMILES: C[C@@H](OC(=O)Nc1c(-c2ccc(NC(=O)c3ccnc(F)c3F)cn2)nnn1C)c1cc(F)cnc1F] | | 516.9 | 1H NMR (400 MHz, Methanol-d4) δ 8.88 (s, 1H), 8.21 (dd, J = 8.6, 2.6 Hz, 1H), 8.14 (dd, J = 5.0, 1.4 Hz, 1H), 8.08-7.69 (m, 3H), 7.61 (dd, J = 5.0, 4.1 Hz, 1H), 5.94 (d, J = 6.9 Hz, 1H), 3.99 (s, 3H), 1.60 (s, 3H). |
| Compound 244 (R)-1-(2,5-difluoropyridin-3-yl)ethyl (4-(5-(2,6-difluoroisonicotinamido)pyridin-2-yl)-1-methyl-1H-1,2,3-triazol-5-yl)carbamate | 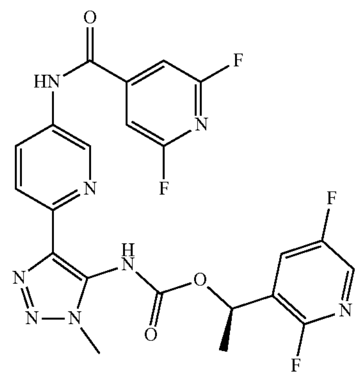 [SMILES: C[C@@H](OC(=O)Nc1c(-c2ccc(NC(=O)c3cc(F)nc(F)c3)cn2)nnn1C)c1cc(F)cnc1F] | | 516.9 | 1H NMR (400 MHz, Methanol-d4) δ 8.94 (s, 1H), 8.23 (dd, J = 8.7, 2.6 Hz, 1H), 8.12-7.67 (m, 3H), 7.52 (s, 2H), 5.94 (d, J = 7.0 Hz, 1H), 3.99 (s, 3H), 1.60 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 245 (R)-1-(2,5-difluoropyridin-3-yl)ethyl (4-(5-((1R,2R)-1-cyano-2-(difluoromethyl)cyclopropane-1-carboxamido)pyridin-2-yl)-1-methyl-1H-1,2,3-triazol-5-yl)carbamate | 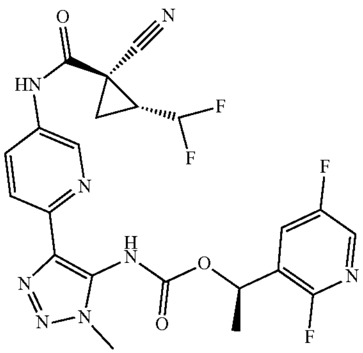 [SMILES: C[C@@H](OC(=O)Nc1c(-c2ccc(NC(=O)[C@]3(C#N)C[C@H]3C(F)F)cn2)nnn1C)c1cc(F)cnc1F] | | 519.1 | 1H NMR (400 MHz, Methanol-d4) δ 8.79 (s, 1H), 8.16-7.99 (m, 2H), 7.93 (m, 2H), 6.20-5.93 (m, 2H), 3.99 (s, 3H), 2.66-2.48 (m, 1H), 2.10-1.90 (m, 2H), 1.61 (s, 3H). |
| Compound 246 (R)-1-(2,5-difluoropyridin-3-yl)ethyl (4-(5-((1S,2S)-1-cyano-2-(difluoromethyl)cyclopropane-1-carboxamido)pyridin-2-yl)-1-methyl-1H-1,2,3-triazol-5-yl)carbamate | 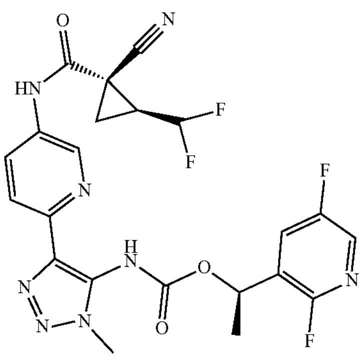 [SMILES: C[C@@H](OC(=O)Nc1c(-c2ccc(NC(=O)[C@@]3(C#N)C[C@@H]3C(F)F)cn2)nnn1C)c1cc(F)cnc1F] | | 519.1 | 1H NMR (400 MHz, Methanol-d4) δ 8.80 (s, 1H), 8.15-7.99 (m, 2H), 7.98-7.83 (m, 2H), 6.20-5.94 (m, 2H), 3.99 (s, 3H), 2.59 (m, 1H), 2.10-1.92 (m, 2H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 247 (R)-1-(2,5-difluoropyridin-3-yl)ethyl (4-(5-(((1RS,3RS)-2,2-difluoro-3-phenylcyclopropane-1-carboxamido)pyridin-2-yl)-1-methyl-1H-1,2,3-triazol-5-yl)carbamate | | | 556.0 | 1H NMR (400 MHz, Methanol-d4) δ 8.82 (s, 1H), 8.31-8.26 (m, 4H), 7.49-7.24 (m, 5H), 5.95 (d, J = 7.5 Hz, 1H), 4.00 (s, 3H), 3.65 (ddd, J = 11.7, 7.8, 5.1 Hz, 1H), 3.09 (ddd, J = 11.2, 7.9, 3.0 Hz, 1H), 1.62 (s, 3H). |
| Compound 248 (R)-1-(2,5-difluoropyridin-3-yl)ethyl (4-(5-(((1RS,2SR)-3,3-difluoro-[1,1'-bi(cyclopropane)]-2-carboxamido)pyridin-2-yl)-1-methyl-1H-1,2,3-triazol-5-yl)carbamate | | | 520.0 | 1H NMR (400 MHz, Methanol-d4) δ 8.76 (s, 1H), 8.26-7.59 (m, 4H), 5.94 (d, J = 7.0 Hz, 1H), 3.99 (s, 3H), 2.44 (dd, J = 13.2, 7.4 Hz, 1H), 2.26 (dtd, J = 13.6, 7.0, 3.6 Hz, 1H), 1.61 (s, 3H), 1.07-0.82 (m, 1H), 0.81-0.53 (m, 2H), 0.53-0.24 (m, 2H). |

TABLE 2-continued

Compounds prepared according to Scheme C, Step 4.

| Compound No. | Structure | Reagent | LCMS m/z | 1H NMR |
|---|---|---|---|---|
| Compound 249 (R)-1-(2,5-difluoropyridin-3-yl)ethyl (1-methyl-4-(5-(2-methylpyrimidine-4-carboxamido)pyridin-2-yl)-1H-1,2,3-triazol-5-yl)carbamate | 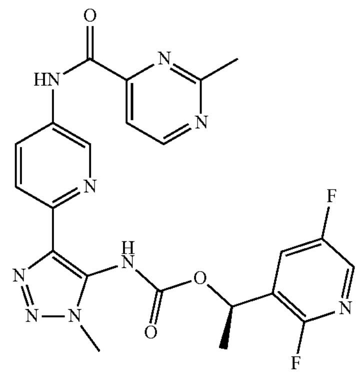 [SMILES: Cc1nccc(C(=O)Nc2ccc(-c3nnn(C)c3NC(=O)O[C@H](C)c3cc(F)cnc3F)nc2)n1] | | 496.0 | 1H NMR (400 MHz, Methanol-d4) δ 9.05 (s, 1H), 8.97 (d, J = 5.1 Hz, 1H), 8.35 (dd, J = 8.6, 2.6 Hz, 1H), 8.10-7.70 (m, 4H), 5.95 (d, J = 6.5 Hz, 1H), 3.99 (s, 3H), 2.86 (s, 3H), 1.61 (s, 3H). |
| Compound 250 (R)-1-(2,5-difluoropyridin-3-yl)ethyl (4-(5-(6-chloropyridazine-3-carboxamido)pyridin-2-yl)-1-methyl-1H-1,2,3-triazol-5-yl)carbamate | 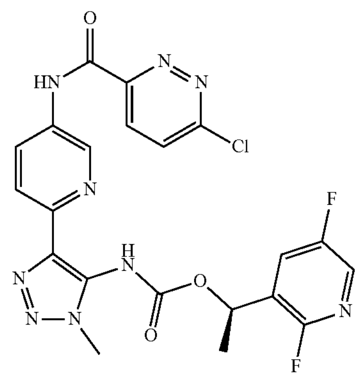 [SMILES: C[C@@H](OC(=O)Nc1c(-c2ccc(NC(=O)c3ccc(Cl)nn3)cn2)nnn1C)c1cc(F)cnc1F] | | 516.0 | 1H NMR (400 MHz, Methanol-d4) δ 9.06 (s, 1H), 8.41 (d, J = 8.8 Hz, 1H), 8.35 (dd, J = 8.7, 2.6 Hz, 1H), 8.04 (t, J = 6.6 Hz, 2H), 8.01-7.95 (m, 2H), 5.95 (d, J = 7.0 Hz, 1H), 3.99 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 251 (R)-1-(2,5-difluoropyridin-3-yl)ethyl (1-methyl-4-(5-(2-(trifluoromethyl)pyrimidine-5-carboxamido)pyridin-2-yl)-1H-1,2,3-triazol-5-yl)carbamate | 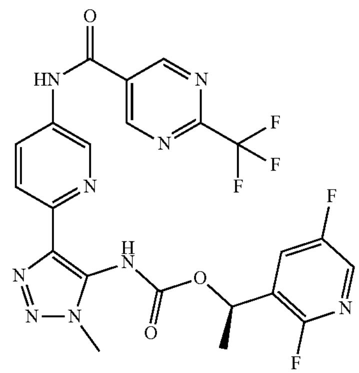 | | 550.0 | 1H NMR (400 MHz, Methanol-d4) δ 9.47 (s, 2H), 8.95 (s, 1H), 8.25 (dd, J = 8.6, 2.6 Hz, 1H), 8.03 (s, 1H), 7.98 (dd, J = 8.7, 0.7 Hz, 1H), 7.87 (s, 1H), 5.95 (d, J = 7.1 Hz, 1H), 3.99 (s, 3H), 1.61 (s, 3H). |
| Compound 252 (R)-1-(2,5-difluoropyridin-3-yl)ethyl (4-(5-(2-(difluoromethyl)pyrimidine-5-carboxamido)pyridin-2-yl)-1-methyl-1H-1,2,3-triazol-5-yl)carbamate | 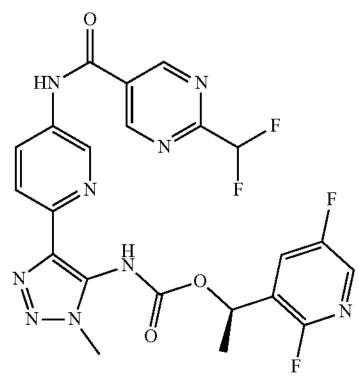 [SMILES: C[C@@H](OC(=O)Nc1c(-c2ccc(NC(=O)c3cnc(C(F)F)nc3)cn2)nnn1C)c1cc(F)cnc1F] | | 532.0 | 1H NMR (400 MHz, Methanol-d4) δ 9.42 (s, 2H), 9.01-8.87 (m, 1H), 8.25 (dd, J = 8.7, 2.6 Hz, 1H), 8.03 (s, 1H), 7.98 (dd, J = 8.7, 0.8 Hz, 1H), 7.83 (d, J = 45.1 Hz, 1H), 6.84 (t, J = 54.1 Hz, 1H), 5.95 (d, J = 6.8 Hz, 1H), 3.99 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 253 (R)-1-(2,5-difluoropyridin-3-yl)ethyl (4-(5-(4-chloronicotinamido)pyridin-2-yl)-1-methyl-1H-1,2,3-triazol-5-yl)carbamate | 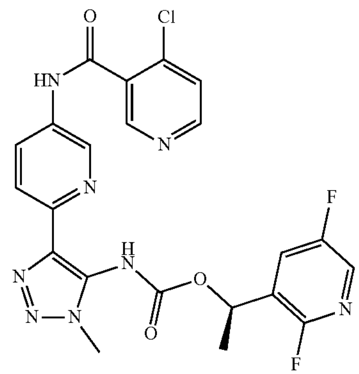 [SMILES: C[C@@H](OC(=O)Nc1c(-c2ccc(NC(=O)c3cnccc3Cl)cn2)nnn1C)c1cc(F)cnc1F] | | 515.0 | 1H NMR (400 MHz, Methanol-d4) δ 8.88 (s, 1H), 8.78 (s, 1H), 8.62 (d, J = 5.5 Hz, 1H), 8.21 (dd, J = 8.7, 2.6 Hz, 1H), 8.02 (s, 1H), 8.00–7.94 (m, 2H), 7.66 (d, J = 5.5 Hz, 1H), 5.94 (d, J = 6.6 Hz, 1H), 3.99 (s, 3H), 1.60 (s, 3H). |
| Compound 254 (R)-1-(2,5-difluoropyridin-3-yl)ethyl (4-(5-(2-fluoro-6-(trifluoromethyl)nicotinamido)pyridin-2-yl)-1-methyl-1H-1,2,3-triazol-5-yl)carbamate | 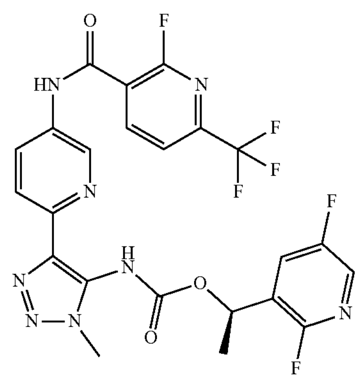 [SMILES: C[C@@H](OC(=O)Nc1c(-c2ccc(NC(=O)c3ccc(C(F)(F)F)nc3F)cn2)nnn1C)c1cc(F)cnc1F] | | 566.9 | 1H NMR (400 MHz, Methanol-d4) δ 8.89 (s, 1H), 8.54 (t, J = 8.1 Hz, 1H), 8.22 (dd, J = 8.7, 2.6 Hz, 1H), 8.03 (s, 1H), 7.98 (dd, J = 8.7, 0.8 Hz, 1H), 7.95–7.87 (m, 2H), 5.94 (d, J = 6.7 Hz, 1H), 3.99 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 255 (R)-1-(2,5-difluoropyridin-3-yl)ethyl (4-(5-(4,6-difluoronicotinamido)pyridin-2-yl)-1-methyl-1H-1,2,3-triazol-5-yl)carbamate | 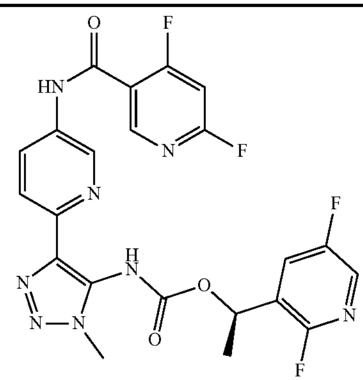 | | 517.0 | 1H NMR (400 MHz, Methanol-d4) δ 8.88 (s, 1H), 8.65 (d, J = 9.7 Hz, 1H), 8.21 (dd, J = 8.7, 2.6 Hz, 1H), 8.02 (s, 1H), 8.00-7.73 (m, 2H), 7.16 (dd, J = 9.8, 1.7 Hz, 1H), 5.94 (d, J = 7.1 Hz, 1H), 3.99 (s, 3H), 1.61 (s, 3H). |
| Compound 256 (R)-1-(2,5-difluoropyridin-3-yl)ethyl (1-methyl-4-(5-(2-methyloxazole-5-carboxamido)pyridin-2-yl)-1H-1,2,3-triazol-5-yl)carbamate | 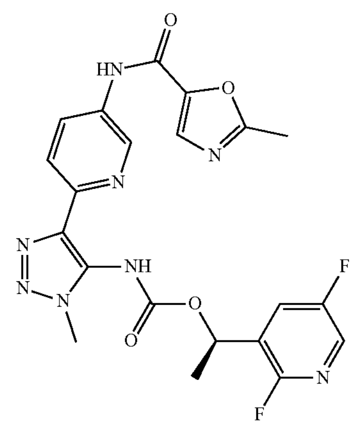 [SMILES: Cc1nnc(C(=O)Nc2ccc(-c3nnn(C)c3NC(=O)O[C@H](C)c3cc(F)cnc3F)nc2)o1] | | 485.0 | 1H NMR (400 MHz, DMSO-d6) δ 10.59 (bs, 1H), 9.82 (bs, 1H), 8.85 (bs, 1H), 8.36-8.12 (m, 2H), 8.11-7.83 (m, 3H), 5.80 (bs, 1H), 3.89 (s, 3H), 2.56 (s, 3H), 1.57 (bs, 3H). |

TABLE 2-continued

Compounds prepared according to Scheme C, Step 4.

| Compound No. | Structure | Reagent | LCMS m/z | 1H NMR |
|---|---|---|---|---|
| Compound 257 (R)-1-(2,5-difluoropyridin-3-yl)ethyl (1-methyl-4-(5-(5-methyl-1,3,4-oxadiazole-2-carboxamido)pyridin-2-yl)-1H-1,2,3-triazol-5-yl)carbamate | 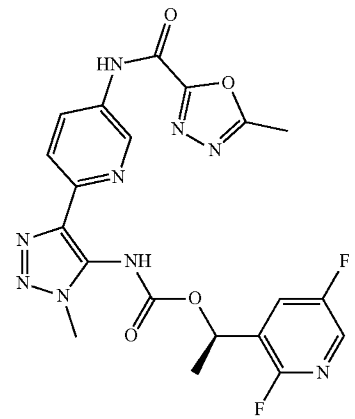 | 5-methyl-1,3,4-oxadiazole-2-carboxylic acid | 486.0 | 1H NMR (400 MHz, DMSO-d6) δ 11.47 (bs, 1H), 9.80 (bs, 1H), 8.91 (s, 1H), 8.39-8.11 (m, 2H), 8.11-7.64 (m, 2H), 5.80 (bs, 1H), 3.89 (s, 3H), 2.65 (s, 3H), 1.38 (d, J = 118.8 Hz, 3H). |
| Compound 258 (R)-1-(2,5-difluoropyridin-3-yl)ethyl (4-(5-(3-cyanoisoxazole-5-carboxamido)pyridin-2-yl)-1-methyl-1H-1,2,3-triazol-5-yl)carbamate | 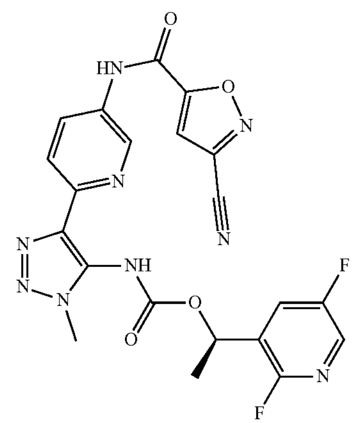 [SMILES: C[C@@H](OC(=O)Nc1c(-c2ccc(NC(=O)c3cc(C#N)no3)cn2)nnn1C)c1cc(F)cnc1F] | 3-cyanoisoxazole-5-carboxylic acid | 495.9 | 1H NMR (400 MHz, DMSO-d6) δ 11.29 (bs, 1H), 9.83 (bs, 1H), 8.87 (s, 1H), 8.38-7.56 (m, 5H), 5.80 (bs, 1H), 3.90 (s, 3H), 1.56 (bs, 3H). |

TABLE 2-continued

Compounds prepared according to Scheme C, Step 4.

| Compound No. | Structure | Reagent | LCMS m/z | 1H NMR |
|---|---|---|---|---|
| Compound 259 (R)-1-(2,5-difluoropyridin-3-yl)ethyl (1-methyl-4-(5-(6-(trifluoromethyl)pyridazine-4-carboxamido)pyridin-2-yl)-1H-1,2,3-triazol-5-yl)carbamate | 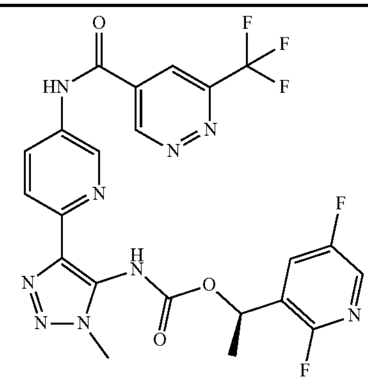 | | 550.0 | 1H NMR (400 MHz, Methanol-d4) δ 9.91 (d, J = 2.0 Hz, 1H), 8.97 (s, 1H), 8.63 (d, J = 2.1 Hz, 1H), 8.27 (dd, J = 8.7, 2.6 Hz, 1H), 8.03 (s, 1H), 8.01-7.64 (m, 2H), 5.95 (d, J = 7.0 Hz, 1H), 3.99 (s, 3H), 1.61 (s, 3H). |
| Compound 260 (R)-1-(2,5-difluoropyridin-3-yl)ethyl (1-methyl-4-(5-(3-methylisoxazole-5-carboxamido)pyridin-2-yl)-1H-1,2,3-triazol-5-yl)carbamate | 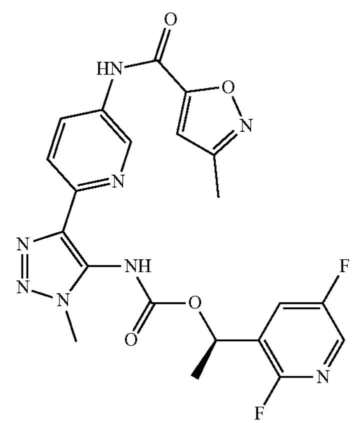 [SMILES: Cc1cc(C(=O)Nc2ccc(-c3nnn(C)c3NC(=O)O[C@H](C)c3cc(F)cnc3F)nc2)on1] | | 485.0 | 1H NMR (400 MHz, DMSO-d6) δ 10.99 (bs, 1H), 9.82 (bs, 1H), 8.89 (s, 1H), 8.38-7.69 (m, 4H), 7.16 (s, 1H), 5.78 (bs, 1H), 3.89 (s, 3H), 2.36 (s, 3H), 1.56 (bs, 3H). |

TABLE 2-continued

Compounds prepared according to Scheme C, Step 4.

| Compound No. | Structure | Reagent | LCMS m/z | 1H NMR |
|---|---|---|---|---|
| Compound 261 (R)-1-(2,5-difluoropyridin-3-yl)ethyl (4-(5-(3-fluoro-2-(trifluoromethyl)isonicotinamido)pyridin-2-yl)-1-methyl-1H-1,2,3-triazol-5-yl)carbamate | 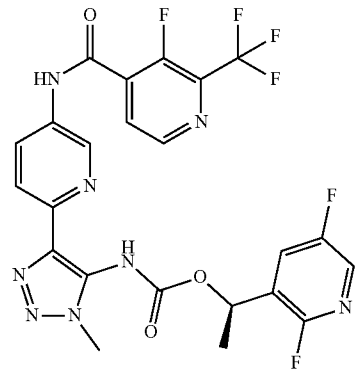 [SMILES: C[C@@H](OC(=O)Nc1c(-c2ccc(NC(=O)c3ccnc(C(F)(F)F)c3F)cn2)nnn1C)c1cc(F)cnc1F] | | 567.0 | 1H NMR (400 MHz, Methanol-d4) δ 8.89 (s, 1H), 8.69 (d, J = 4.8 Hz, 1H), 8.21 (dd, J = 8.6, 2.6 Hz, 1H), 8.07-7.76 (m, 4H), 5.94 (d, J = 6.8 Hz, 1H), 3.99 (s, 3H), 1.60 (s, 3H). |
| Compound 262 (R)-1-(2,5-difluoropyridin-3-yl)ethyl (4-(5-(6-chloro-2-fluoronicotinamido)pyridin-2-yl)-1-methyl-1H-1,2,3-triazol-5-yl)carbamate | 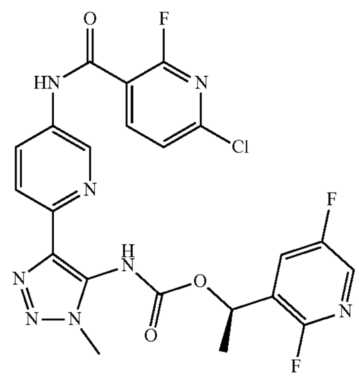 [SMILES: C[C@@H](OC(=O)Nc1c(-c2ccc(NC(=O)c3ccc(Cl)nc3F)cn2)nnn1C)c1cc(F)cnc1F] | | 533.0 | 1H NMR (400 MHz, Methanol-d4) δ 8.88 (s, 1H), 8.32 (dd, J = 9.1, 7.9 Hz, 1H), 8.20 (dd, J = 8.7, 2.6 Hz, 1H), 8.02 (s, 1H), 8.00-7.75 (m, 2H), 7.56 (dd, J = 7.9, 1.1 Hz, 1H), 5.94 (d, J = 7.1 Hz, 1H), 3.99 (s, 3H), 1.60 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 263 (R)-1-(2,5-difluoropyridin-3-yl)ethyl (4-(5-(4-chloro-5-fluoronicotinamido)pyridin-2-yl)-1-methyl-1H-1,2,3-triazol-5-yl)carbamate | 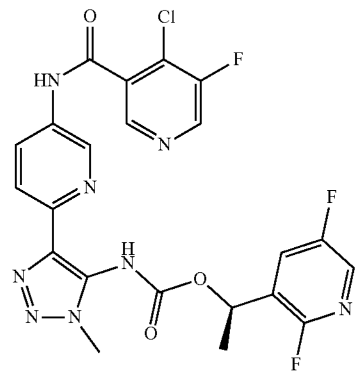 [SMILES: C[C@@H](OC(=O)Nc1c(-c2ccc(NC(=O)c3cncc(F)c3Cl)cn2)nnn1C)c1cc(F)cnc1F] | | 533.0 | 1H NMR (400 MHz, Methanol-d4) δ 8.88 (s, 1H), 8.71 (d, J = 1.1 Hz, 1H), 8.65 (s, 1H), 8.21 (dd, J = 8.6, 2.6 Hz, 1H), 8.02 (s, 1H), 8.00-7.76 (m, 2H), 5.94 (d, J = 7.1 Hz, 1H), 3.99 (s, 3H), 1.61 (s, 3H). |
| Compound 264 (R)-1-(2,5-difluoropyridin-3-yl)ethyl (1-methyl-4-(5-(2,3,6-trifluoroisonicotinamido)pyridin-2-yl)-1H-1,2,3-triazol-5-yl)carbamate | 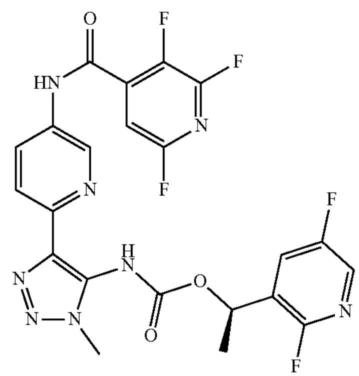 [SMILES: C[C@@H](OC(=O)Nc1c(-c2ccc(NC(=O)c3cc(F)nc(F)c3F)cn2)nnn1C)c1cc(F)cnc1F] | | 535.0 | 1H NMR (400 MHz, Methanol-d4) δ 8.87 (s, 1H), 8.20 (dd, J = 8.6, 2.6 Hz, 1H), 8.07-7.71 (m, 3H), 7.36 (t, J = 2.9 Hz, 1H), 5.94 (d, J = 6.3 Hz, 1H), 3.99 (s, 3H), 1.60 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 265 (R)-1-(2,5-difluoropyridin-3-yl)ethyl (1-methyl-4-(5-((1R,2R)-2-(pyridin-2-yl)cyclopropane-1-carboxamido)pyridin-2-yl)-1H-1,2,3-triazol-5-yl)carbamate | 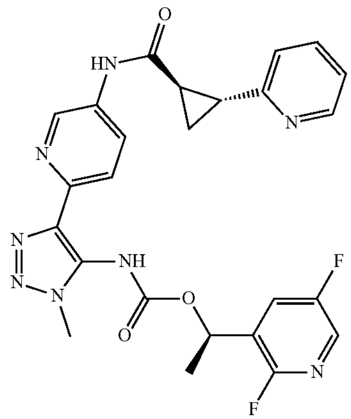 [SMILES: C[C@@H](OC(=O)Nc1c(-c2ccc(NC(=O)[C@@H]3C[C@H]3c3ccccn3)cn2)nnn1C)c1cc(F)cnc1F] | | 521.0 | 1H NMR (400 MHz, Methanol-d4) δ 8.80 (s, 1H), 8.58-8.32 (m, 1H), 8.27-7.60 (m, 5H), 7.40 (dd, J = 7.9, 1.0 Hz, 1H), 7.24 (ddd, J = 7.5, 4.9, 1.1 Hz, 1H), 5.95 (s, 1H), 3.99 (s, 3H), 2.68 (ddd, J = 9.5, 6.2, 3.9 Hz, 1H), 2.51-2.28 (m, 1H), 1.85-1.51 (m, 5H). |
| Compound 266 (R)-1-(2,5-difluoropyridin-3-yl)ethyl (1-methyl-4-(5-((1S,2S)-2-(pyridin-2-yl)cyclopropane-1-carboxamido)pyridin-2-yl)-1H-1,2,3-triazol-5-yl)carbamate | 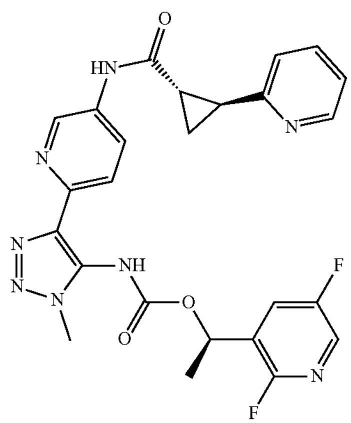 [SMILES: C[C@@H](OC(=O)Nc1c(-c2ccc(NC(=O)[C@H]3C[C@@H]3c3ccccn3)cn2)nnn1C)c1cc(F)cnc1F] | | 521.0 | 1H NMR (400 MHz, Methanol-d4) δ 8.80 (s, 1H), 8.52-8.38 (m, 1H), 8.22-7.60 (m, 5H), 7.48-7.32 (m, 1H), 7.24 (ddd, J = 7.6, 5.0, 1.2 Hz, 1H), 5.95 (s, 1H), 3.99 (s, 3H), 2.68 (ddd, J = 9.3, 6.1, 3.8 Hz, 1H), 2.39 (ddd, J = 9.1, 5.5, 3.9 Hz, 1H), 1.82-1.50 (m, 5H). |

TABLE 2-continued

Compounds prepared according to Scheme C, Step 4.

| Compound No. | Structure | Reagent | LCMS m/z | 1H NMR |
|---|---|---|---|---|
| Compound 267 (R)-1-(2,5-difluoropyridin-3-yl)ethyl (4-(5-((1S,2R)-[1,1'-bi(cyclopropane)]-2-carboxamido)pyridin-2-yl)-1-methyl-1H-1,2,3-triazol-5-yl)carbamate | | | 484.0 | 1H NMR (400 MHz, Methanol-d4) δ 8.77 (s, 1H), 8.39-7.53 (m, 4H), 5.94 (s, 1H), 3.99 (s, 3H), 1.56 (ddt, J = 72.3, 9.9, 4.5 Hz, 5H), 1.13 (dt, J = 9.0, 4.5 Hz, 1H), 0.94 (td, J = 8.2, 4.8 Hz, 1H), 0.84-0.71 (m, 1H), 0.57-0.36 (m, 2H), 0.22 (d, J =4.9 Hz, 2H). |
| Compound 268 (R)-1-(2,5-difluoropyridin-3-yl)ethyl (4-(5-((1R,2S)-[1,1'-bi(cyclopropane)]-2-carboxamido)pyridin-2-yl)-1-methyl-1H-1,2,3-triazol-5-yl)carbamate | 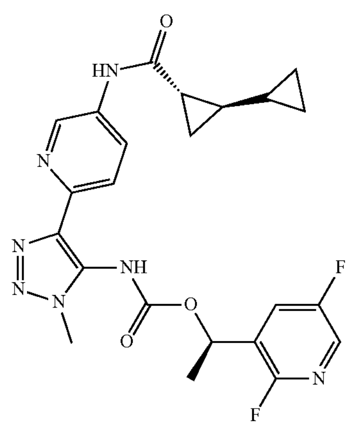 [SMILES: C[C@@H](OC(=O)Nc1c(-c2ccc(NC(=O)[C@H]3C[C@@H]3C3CC3)cn2)nnn1C)c1cc(F)cnc1F] | | 484.0 | 1H NMR (400 MHz, Methanol-d4) δ 8.78 (s, 1H), 8.26-7.62 (m, 4H), 5.94 (d, J = 6.1 Hz, 1H), 3.99 (s, 3H), 1.86-1.41 (m, 5H), 1.14 (dt, J = 9.0, 4.5 Hz, 1H), 0.94 (td, J = 8.2, 4.9 Hz, 1H), 0.85-0.72 (m, 1H), 0.63-0.37 (m, 2H), 0.21 (d, J = 5.0 Hz, 2H). |

TABLE 2-continued

Compounds prepared according to Scheme C, Step 4.

| Compound No. | Structure | Reagent | LCMS m/z | 1H NMR |
|---|---|---|---|---|
| Compound 269 (R)-1-(2,5-difluoropyridin-3-yl)ethyl (4-(5-((1R,2R)-1-cyano-2-fluorocyclopropane-1-carboxamido)pyridin-2-yl)-1-methyl-1H-1,2,3-triazol-5-yl)carbamate | 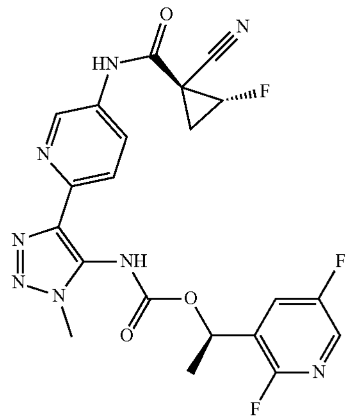 [SMILES: C[C@@H](OC(=O)Nc1c(-c2ccc(NC(=O)[C@]3(C#N)C[C@H]3F)cn2)nnn1C)c1cc(F)cnc1F] | | 487.0 | 1H NMR (400 MHz, Methanol-d4) δ 8.68 (d, J = 89.1 Hz, 1H), 8.23-7.57 (m, 4H), 5.95 (d, J = 6.7 Hz, 1H), 5.26 (ddd, J = 62.8, 5.8, 4.4 Hz, 1H), 4.00 (d, J = 3.9 Hz, 3H), 2.32-2.12 (m, 2H), 1.62 (s, 4H). |
| Compound 270 (R)-1-(2,5-difluoropyridin-3-yl)ethyl (4-(5-((1S,2S)-1-cyano-2-fluorocyclopropane-1-carboxamido)pyridin-2-yl)-1-methyl-1H-1,2,3-triazol-5-yl)carbamate | 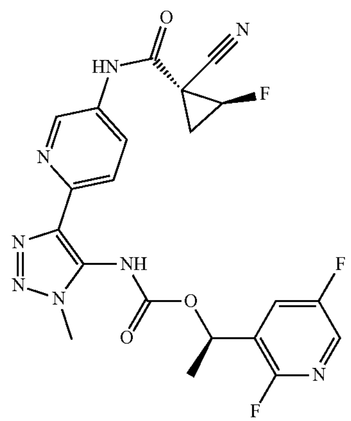 [SMILES: C[C@@H](OC(=O)Nc1c(-c2ccc(NC(=O)[C@@]3(C#N)C[C@@H]3F)cn2)nnn1C)c1cc(F)cnc1F] | | 487.0 | 1H NMR (400 MHz, Methanol-d4) δ 8.79 (s, 1H), 8.22-7.61 (m, 3H), 5.95 (s, 1H), 5.26 (ddd, J = 62.8, 5.9, 4.3 Hz, 1H), 4.00 (s, 3H), 2.32-2.07 (m, 2H), 1.62 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 271 (R)-1-(2,5-difluoropyridin-3-yl)ethyl (4-(5-(6-(1-cyanocyclopropyl)nicotinamido)pyridin-2-yl)-1-methyl-1H-1,2,3-triazol-5-yl)carbamate | 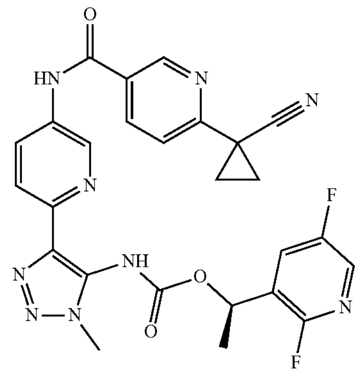 [SMILES: C[C@@H](OC(=O)Nc1c(-c2ccc(NC(=O)c3ccc(C4(C#N)CC4)nc3)cn2)nnn1C)c1cc(F)cnc1F] | | 546.0 | 1H NMR (400 MHz, Methanol-d4) δ 9.04 (dd, J = 2.4, 0.9 Hz, 1H), 8.94 (s, 1H), 8.35 (dd, J = 8.3, 2.3 Hz, 1H), 8.23 (dd, J = 8.7, 2.6 Hz, 1H), 8.02 (s, 1H), 7.98-7.90 (m, 1H), 7.92-7.75 (m, 2H), 5.94 (d, J = 6.9 Hz, 1H), 3.99 (s, 3H), 1.97-1.88 (m, 2H), 1.85 (p, J = 6.4, 5.9 Hz, 2H), 1.60 (s, 3H). |
| Compound 272 (R)-1-(2,5-difluoropyridin-3-yl)ethyl (4-(5-(6-(1,1-difluoroethyl)nicotinamido)pyridin-2-yl)-1-methyl-1H-1,2,3-triazol-5-yl)carbamate | 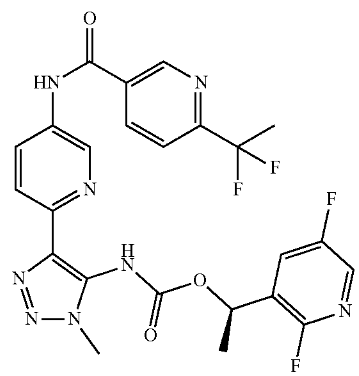 [SMILES: C[C@@H](OC(=O)Nc1c(-c2ccc(NC(=O)c3ccc(C(C)(F)F)nc3)cn2)nnn1C)c1cc(F)cnc1F] | | 545.0 | 1H NMR (400 MHz, Methanol-d4) δ 9.18 (dd, J = 2.2, 0.9 Hz, 1H), 8.96 (s, 1H), 8.48 (dd, J = 8.2, 2.3 Hz, 1H), 8.25 (dd, J = 8.7, 2.6 Hz, 1H), 8.03 (s, 1H), 7.97 (dd, J = 8.6, 0.8 Hz, 1H), 7.93-7.69 (m, 2H), 5.94 (d, J = 7.1 Hz, 1H), 3.99 (s, 3H), 2.04 (t, J = 18.7 Hz, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 273 (R)-1-(2,5-difluoropyridin-3-yl)ethyl (1-methyl-4-(5-(2-(methylsulfonyl)isonicotinamido)pyridin-2-yl)-1H-1,2,3-triazol-5-yl)carbamate | 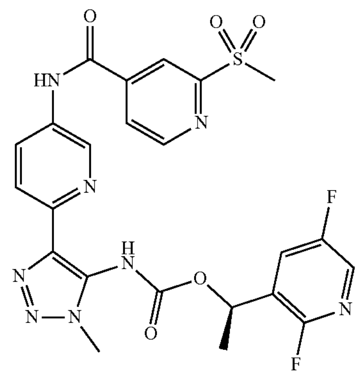 [SMILES: C[C@@H](OC(=O)Nc1c(-c2ccc(NC(=O)c3ccnc(S(C)(=O)=O)c3)cn2)nnn1C)c1cc(F)cnc1F] | | 559.0 | 1H NMR (400 MHz, Methanol-d4) δ 8.97 (dd, J = 5.0, 0.8 Hz, 1H), 8.60 (dd, J = 1.7, 0.8 Hz, 1H), 8.27 (dd, J = 8.7, 2.6 Hz, 1H), 8.20 (dd, J = 5.0, 1.7 Hz, 1H), 8.03 (s, 1H), 8.00-7.75 (m, 2H), 5.94 (d, J = 7.0 Hz, 1H), 3.99 (s, 3H), 3.30 (s, 3H), 1.61 (s, 3H). |
| Compound 274 (R)-1-(2,5-difluoropyridin-3-yl)ethyl (1-methyl-4-(5-(1-methyl-1H-benzo[d]imidazole-6-carboxamido)pyridin-2-yl)-1H-1,2,3-triazol-5-yl)carbamate | 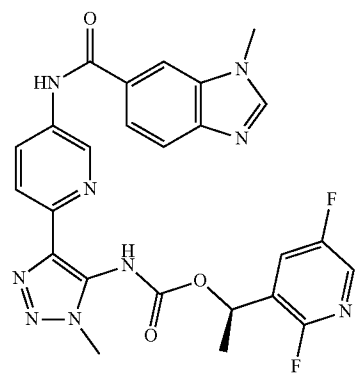 [SMILES: C[C@@H](OC(=O)Nc1c(-c2ccc(NC(=O)c3ccc4ncn(C)c4c3)cn2)nnn1C)c1cc(F)cnc1F] | | 534.0 | 1H NMR (400 MHz, Methanol-d4) δ 8.99 (s, 1H), 8.32 (s, 1H), 8.27 (dd, J = 8.8, 2.3 Hz, 2H), 8.02 (s, 1H), 7.99-7.83 (m, 3H), 7.80 (d, J = 8.5 Hz, 1H), 5.95 (d, J = 7.1 Hz, 1H), 4.01 (s, 3H), 3.99 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 275 (R)-1-(2,5-difluoropyridin-3-yl)ethyl (4-(5-(2-fluoro-5-(trifluoromethyl)nicotinamido)pyridin-2-yl)-1-methyl-1H-1,2,3-triazol-5-yl)carbamate | 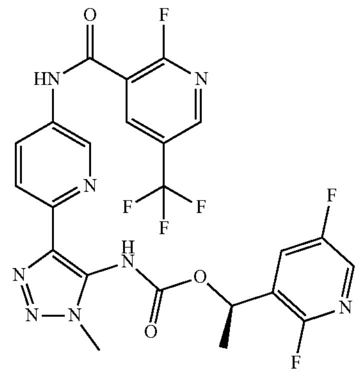 [SMILES: C[C@@H](OC(=O)Nc1c(-c2ccc(NC(=O)c3cc(C(F)(F)F)cnc3F)cn2)nnn1C)c1cc(F)cnc1F] | | 567.0 | 1H NMR (400 MHz, Methanol-d4) δ 8.89 (s, 1H), 8.78 (d, J = 2.3 Hz, 1H), 8.66 (dd, J = 8.1, 2.5 Hz, 1H), 8.23 (dd, J = 8.6, 2.6 Hz, 1H), 8.03 (s, 1H), 8.00-7.68 (m, 2H), 5.94 (d, J = 7.1 Hz, 1H), 3.99 (s, 3H), 1.61 (s, 3H). |
| Compound 276 (R)-1-(2,5-difluoropyridin-3-yl)ethyl (4-(5-(3,4-dimethylisoxazole-5-carboxamido)pyridin-2-yl)-1-methyl-1H-1,2,3-triazol-5-yl)carbamate | 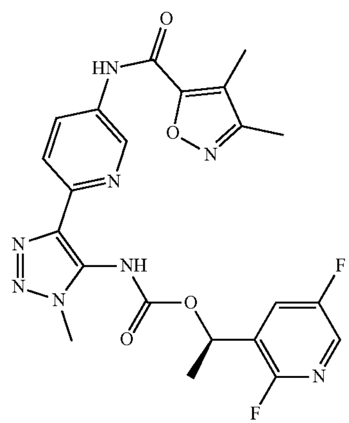 [SMILES: Cc1noc(C(=O)Nc2ccc(-c3nnn(C)c3NC(=O)O[C@H](C)c3cc(F)cnc3F)nc2)c1C] | | 499.0 | 1H NMR (400 MHz, DMSO-d6) δ 10.93 (s, 1H), 9.82 (bs, 1H), 8.90 (s, 1H), 8.33-7.80 (m, 4H), 5.80 (bs, 1H), 3.89 (s, 3H), 2.29 (s, 3H), 2.25 (s, 3H), 1.58 (bs, 3H). |

TABLE 2-continued

Compounds prepared according to Scheme C, Step 4.

| Compound No. | Structure | Reagent | LCMS m/z | 1H NMR |
|---|---|---|---|---|
| Compound 277 (R)-1-(2,5-difluoropyridin-3-yl)ethyl (1-methyl-4-(5-(2-methyl-3H-imidazo[4,5-b]pyridine-6-carboxamido)pyridin-2-yl)-1H-1,2,3-triazol-5-yl)carbamate | 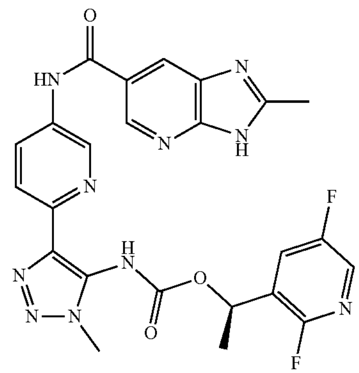 [SMILES: Cc1nc2cc(C(=O)Nc3ccc(-c4nnn(C)c4NC(=O)O[C@H](C)c4cc(F)cnc4F)nc3)cnc2[nH]1] | | 535.0 | 1H NMR (400 MHz, Methanol-d4) δ 8.97 (s, 1H), 8.95 (d, J = 2.0 Hz, 1H), 8.49 (d, J = 2.0 Hz, 1H), 8.26 (dd, J = 8.6, 2.6 Hz, 1H), 8.03 (s, 1H), 8.00-7.77 (m, 2H), 5.95 (s, 1H), 3.99 (s, 3H), 2.68 (s, 3H), 1.61 (s, 3H). |
| Compound 278 (R)-1-(2,5-difluoropyridin-3-yl)ethyl (1-methyl-4-(5-(1-methyl-1H-pyrazolo[4,3-b]pyridine-6-carboxamido)pyridin-2-yl)-1H-1,2,3-triazol-5-yl)carbamate | 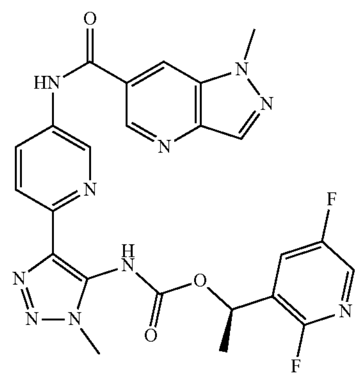 [SMILES: C[C@@H](OC(=O)Nc1c(-c2ccc(NC(=O)c3cnc4cnn(C)c4c3)cn2)nnn1C)c1cc(F)cnc1F] | | 535.0 | 1H NMR (400 MHz, DMSO-d6) δ 10.80 (s, 1H), 9.81 (s, 1H), 9.08 (d, J = 1.9 Hz, 1H), 8.93 (s, 1H), 8.77 (t, J = 1.4 Hz, 1H), 8.42 (d, J = 1.0 Hz, 1H), 8.33-8.12 (m, 2H), 8.08-7.87 (m, 2H), 5.81 (s, 1H), 4.20 (s, 3H), 3.88 (s, 3H), 1.54 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 279 (R)-1-(2,5-difluoropyridin-3-yl)ethyl (1-methyl-4-(5-(3-methylbenzo[d]isoxazole-6-carboxamido)pyridin-2-yl)-1H-1,2,3-triazol-5-yl)carbamate | | | 535.0 | 1H NMR (400 MHz, Methanol-d4) δ 8.98 (s, 1H), 8.26 (dd, J = 8.6, 2.6 Hz, 1H), 8.21 (t, J = 1.0 Hz, 1H), 8.02 (s, 1H), 8.00-7.80 (m, 4H), 5.95 (d, J = 6.9 Hz, 1H), 3.99 (s, 3H), 2.64 (s, 3H), 1.61 (s, 3H). |
| Compound 280 (R)-1-(2,5-difluoropyridin-3-yl)ethyl (4-(5-(2-cyclopropyloxazole-5-carboxamido)pyridin-2-yl)-1-methyl-1H-1,2,3-triazol-5-yl)carbamate | | | 511.0 | 1H NMR (400 MHz, DMSO-d6) δ 10.47 (bs, 1H), 9.80 (bs, 1H), 8.84 (s, 1H), 8.34-8.09 (m, 2H), 8.09-7.65 (m, 3H), 5.79 (bs, 1H), 3.88 (s, 3H), 2.30-2.18 (m, 1H), 1.53 (bs, 3H), 1.21-1.00 (m, 4H). |

TABLE 2-continued

Compounds prepared according to Scheme C, Step 4.

| Compound No. | Structure | Reagent | LCMS m/z | 1H NMR |
|---|---|---|---|---|
| Compound 281 (R)-1-(2,5-difluoropyridin-3-yl)ethyl (4-(5-(3-methoxyisoxazole-5-carboxamido)pyridin-2-yl)-1-methyl-1H-1,2,3-triazol-5-yl)carbamate | 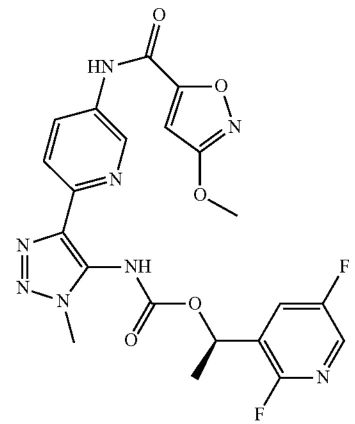 [SMILES: COc1cc(C(=O)Nc2ccc(-c3nnn(C)c3NC(=O)O[C@H](C)c3cc(F)cnc3F)nc2)on1] | | 501.0 | 1H NMR (400 MHz, DMSO-d6) δ 10.97 (bs, 1H), 9.82 (bs, 1H), 8.87 (s, 1H), 8.36-7.65 (m, 4H), 7.06 (s, 1H), 5.80 (bs, 1H), 3.99 (s, 3H), 3.89 (s, 3H), 1.54 (bs, 3H). |
| Compound 282 (R)-1-(2,5-difluoropyridin-3-yl)ethyl (4-(5-(2-(dimethylamino)pyrimidine-5-carboxamido)pyridin-2-yl)-1-methyl-1H-1,2,3-triazol-5-yl)carbamate | 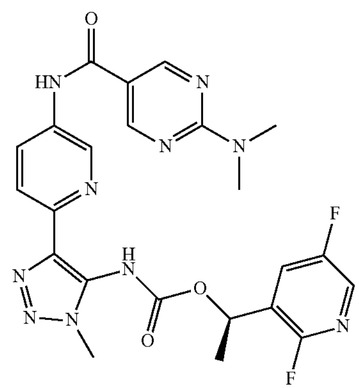 [SMILES: C[C@@H](OC(=O)Nc1c(-c2ccc(NC(=O)c3cnc(N(C)C)nc3)cn2)nnn1C)c1cc(F)cnc1F] | | 524.9 | 1H NMR (400 MHz, Methanol-d4) δ 8.90 (s, 2H), 8.19 (dd, J = 8.6, 2.6 Hz, 1H), 8.10-7.99 (m, 2H), 7.97-7.69 (m, 2H), 5.94 (d, J = 7.1 Hz, 1H), 3.98 (s, 3H), 3.28 (s, 6H), 1.60 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 283 (R)-1-(2,5-difluoropyridin-3-yl)ethyl (4-(5-(2-cyclopropylpyrimidine-5-carboxamido)pyridin-2-yl)-1-methyl-1H-1,2,3-triazol-5-yl)carbamate | 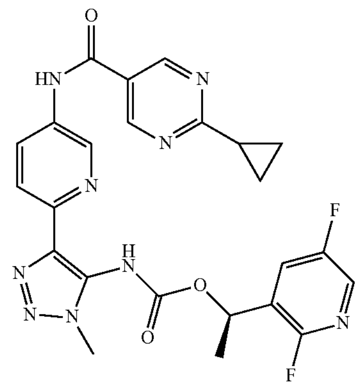 [SMILES: C[C@@H](OC(=O)Nc1c(-c2ccc(NC(=O)c3cnc(C4CC4)nc3)cn2)nnn1C)c1cc(F)cnc1F] | | 522.0 | 1H NMR (400 MHz, Methanol-d4) δ 9.12 (s, 2H), 8.93 (s, 1H), 8.23 (dd, J = 8.6, 2.6 Hz, 1H), 8.02 (s, 1H), 7.99-7.76 (m, 2H), 5.94 (d, J = 7.1 Hz, 1H), 3.99 (s, 3H), 2.42-2.26 (m, 1H), 1.61 (s, 3H), 1.22 (tt, J = 8.1, 2.9 Hz, 4H). |
| Compound 284 (R)-1-(2,5-difluoropyridin-3-yl)ethyl (1-methyl-4-(5-(2-morpholinopyrimidine-5-carboxamido)pyridin-2-yl)-1H-1,2,3-triazol-5-yl)carbamate | 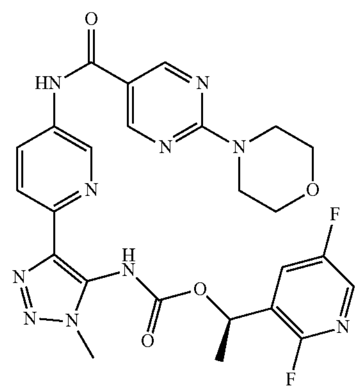 [SMILES: C[C@@H](OC(=O)Nc1c(-c2ccc(NC(=O)c3cnc(N4CCOCC4)nc3)cn2)nnn1C)c1cc(F)cnc1F] | | 567.0 | 1H NMR (400 MHz, Methanol-d4) δ 8.92 (s, 2H), 8.19 (dd, J = 8.7, 2.6 Hz, 1H), 8.09-7.99 (m, 2H), 7.98-7.76 (m, 2H), 5.94 (d, J = 6.8 Hz, 1H), 3.99 (s, 3H), 3.94 (dd, J = 5.6, 4.2 Hz, 4H), 3.80-3.71 (m, 4H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 285 (R)-1-(2-chloro-5-fluoropyridin-3-yl)ethyl (4-(5-((1RS,2RS)-2-cyanocyclopropane-1-carboxamido)pyridin-2-yl)-1-methyl-1H-1,2,3-triazol-5-yl)carbamate | 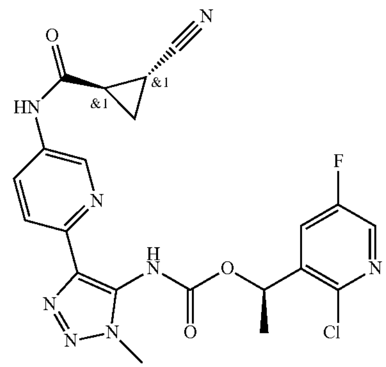 [SMILES: C[C@@H](OC(=O)Nc1c(-c2ccc(NC(=O)[C@@H]3C[C@H]3C#N)cn2)nnn1C)c1cc(F)cnc1Cl] | | 485.1 | 1H NMR (400 MHz, Methanol-d4) δ 9.13-8.76 (m, 1H), 8.43-8.07 (m, 2H), 7.93 (m, 2H), 6.03 (m, 1H), 4.01 (s, 3H), 2.48 (m, 1H), 2.12 (m, 1H), 1.84-1.32 (m, 5H). |
| Compound 288 (R)-1-(2-chloro-5-fluoropyridin-3-yl)ethyl 4-(5-(6-(trifluoromethyl)nicotinamido)pyridin-2-yl)-1H-1,2,3-triazol-5-yl)carbamate | | | 565.0 | 1H NMR (400 MHz, Methanol-d4) δ 9.26 (d, J = 2.1 Hz, 1H), 8.97 (s, 1H), 8.64-8.52 (m, 1H), 8.34-8.15 (m, 2H), 8.11-7.68 (m, 3H), 6.03 (d, J = 7.2 Hz, 1H), 4.00 (s, 3H), 1.60 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 289 (R)-1-(2-chloro-5-fluoropyridin-3-yl)ethyl (4-(5-(2-(difluoromethyl)pyrimidine-5-carboxamido)pyridin-2-yl)-1-methyl-1H-1,2,3-triazol-5-yl)carbamate | 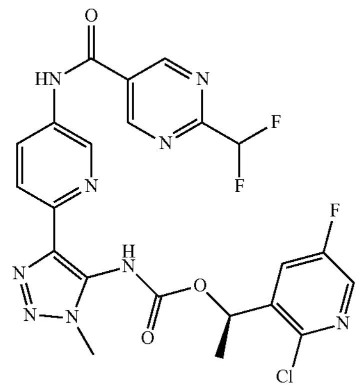 [SMILES: C[C@@H](OC(=O)Nc1c(-c2ccc(NC(=O)c3cnc(C(F)F)nc3)cn2)nnn1C)c1cc(F)cnc1Cl] | | 548.0 | 1H NMR (400 MHz, Methanol-d4) δ 9.42 (s, 2H), 8.97 (s, 1H), 8.24 (dd, J = 8.7, 2.6 Hz, 2H), 8.03-7.71 (m, 2H), 6.84 (t, J = 54.2 Hz, 1H), 6.03 (s, 1H), 3.99 (s, 3H), 1.60 (s, 3H). |
| Compound 290 (R)-1-(2-chloro-5-fluoropyridin-3-yl)ethyl-4-(5-(2-(trifluoromethyl)pyrimidine-5-carboxamido)pyridin-2-yl)-1H-1,2,3-triazol-5-yl)carbamate | | | 566.0 | 1H NMR (400 MHz, Methanol-d4) δ 9.47 (s, 2H), 8.97 (s, 1H), 8.37-8.14 (m, 2H), 8.05-7.66 (m, 2H), 6.03 (d, J = 7.0 Hz, 1H), 4.00 (s, 3H), 1.60 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 291 (R)-1-(2-fluoropyridin-3-yl)ethyl (4-(5-(3,3-difluoro-1-methylcyclobutane-1-carboxamido)pyridin-2-yl)-1-methyl-1H-1,2,3-triazol-5-yl)carbamate | 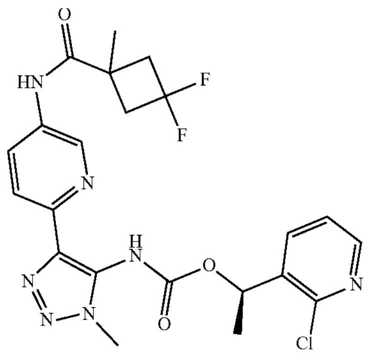 [SMILES: C[C@@H](OC(=O)Nc1c(-c2ccc(NC(=O)C3(C)CC(F)(F)C3)cn2)nnn1C)c1cccnc1Cl] | | 490.1 | 1H NMR (400 MHz, Methanol-d4) δ 8.96 (m, 1H), 8.34-7.99 (m, 3H), 7.93 (m, 1H), 7.39 (s, 1H), 6.00 (m, 1H), 4.00 (s, 3H), 3.25-3.05 (m, 2H), 2.68-2.45 (m, 2H), 1.65 (s, 6H). |
| Compound 292 (R)-1-(2-fluoropyridin-3-yl)ethyl (4-(5-(6-chloronicotinamido)pyridin-2-yl)-1-methyl-1H-1,2,3-triazol-5-yl)carbamate | 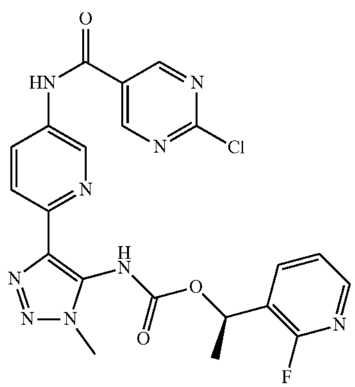 [SMILES: C[C@@H](OC(=O)Nc1c(-c2ccc(NC(=O)c3cnc(Cl)nc3)cn2)nnn1C)c1cccnc1F] | | 496.9 | 1H NMR (400 MHz, Methanol-d4) δ 8.96 (dd, J = 2.6, 0.7 Hz, 2H), 8.36 (dd, J = 8.4, 2.6 Hz, 1H), 8.21 (dd, J = 8.6, 2.6 Hz, 1H), 8.16-8.06 (m, 2H), 7.99-7.90 (m, 1H), 7.64 (dd, J = 8.3, 0.7 Hz, 1H), 7.36 (s, 1H), 5.99 (d, J = 6.8 Hz, 1H), 3.98 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 293 (R)-1-(2-fluoropyridin-3-yl)ethyl (4-(5-(2-chloroisonicotinamido)pyridin-2-yl)-1-methyl-1H-1,2,3-triazol-5-yl)carbamate | 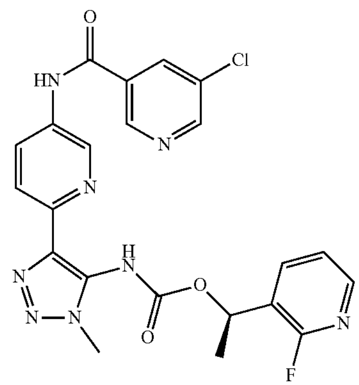 [SMILES: C[C@@H](OC(=O)Nc1c(-c2ccc(NC(=O)c3cncc(Cl)c3)cn2)nnn1C)c1cccnc1F] | | 497.0 | 1H NMR (400 MHz, Methanol-d4) δ 8.99 (s, 1H), 8.61 (dd, J = 5.1, 0.8 Hz, 1H), 8.24 (dd, J = 8.6, 2.6 Hz, 1H), 8.18-8.11 (m, 2H), 8.05-7.95 (m, 2H), 7.89 (dd, J = 5.1, 1.5 Hz, 1H), 7.38 (s, 1H), 6.01 (d, J = 7.1 Hz, 1H), 4.00 (s, 3H), 1.63 (s, 3H). |
| Compound 294 (R)-1-(2-fluoropyridin-3-yl)ethyl (4-(5-(2,3-difluoroisonicotinamido)pyridin-2-yl)-1-methyl-1H-1,2,3-triazol-5-yl)carbamate | 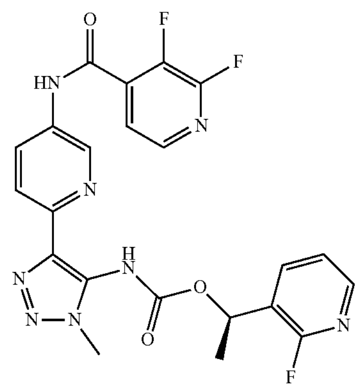 [SMILES: C[C@@H](OC(=O)Nc1c(-c2ccc(NC(=O)c3ccnc(F)c3F)cn2)nnn1C)c1cccnc1F] | | 499.0 | 1H NMR (400 MHz, Methanol-d4) δ 8.91 (s, 1H), 8.27-8.10 (m, 4H), 7.97 (dd, J = 8.7, 0.7 Hz, 1H), 7.62 (dd, J = 5.0, 4.1 Hz, 1H), 7.36 (s, 1H), 5.99 (d, J = 6.7 Hz, 1H), 3.98 (s, 3H), 1.61 (s, 3H). |

TABLE 2-continued

Compounds prepared according to Scheme C, Step 4.

| Compound No. | Structure | Reagent | LCMS m/z | 1H NMR |
|---|---|---|---|---|
| Compound 295 (R)-1-(2-fluoropyridin-3-yl)ethyl (4-(5-(6-(difluoromethyl)nicotinamido)pyridin-2-yl)-1-methyl-1H-1,2,3-triazol-5-yl)carbamate | 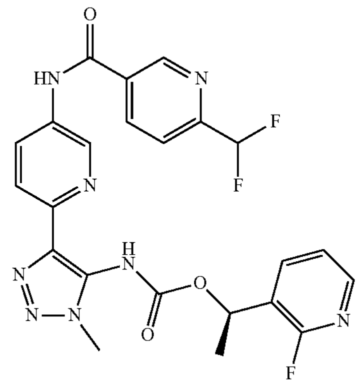 [SMILES: C[C@@H](OC(=O)Nc1c(-c2ccc(NC(=O)c3ccc(C(F)F)nc3)cn2)nnn1C)c1cccnc1F] | | 513.0 | 1H NMR (400 MHz, Methanol-d4) δ 9.21 (d, J = 2.0 Hz, 1H), 8.98 (s, 1H), 8.53 (dd, J = 8.1, 2.2 Hz, 1H), 8.23 (dd, J = 8.7, 2.6 Hz, 1H), 8.16-8.08 (m, 2H), 7.96 (d, J = 8.6 Hz, 1H), 7.88 (d, J = 8.1 Hz, 1H), 7.36 (s, 1H), 6.83 (t, J = 55.0 Hz, 1H), 5.99 (d, J = 6.9 Hz, 1H), 3.98 (s, 3H), 1.61 (s, 3H). |
| Compound 296 (R)-1-(2-fluoropyridin-3-yl)ethyl (1-methyl-4-(5-(6-(trifluoromethyl)nicotinamido)pyridin-2-yl)-1H-1,2,3-triazol-5-yl)carbamate | 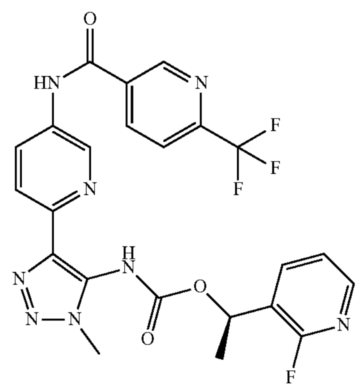 [SMILES: C[C@@H](OC(=O)Nc1c(-c2ccc(NC(=O)c3ccc(C(F)(F)F)nc3)cn2)nnn1C)c1cccnc1F] | | 531.0 | 1H NMR (400 MHz, Methanol-d4) δ 9.27 (d, J = 2.1 Hz, 1H), 8.98 (s, 1H), 8.58 (dd, J = 8.2, 2.2 Hz, 1H), 8.27-8.19 (m, 1H), 8.17-8.07 (m, 2H), 7.99 (dd, J = 16.5, 8.4 Hz, 2H), 7.36 (s, 1H), 5.99 (d, J = 6.6 Hz, 1H), 3.98 (s, 3H), 1.61 (s, 3H). |

Example 55

Preparation of (R)-1-(2-chloropyridin-3-yl) ethyl (4-(5-((1r,3R)-3-cyano-3-fluorocyclobutane-1-carboxamido) pyridin-2-yl)-1-methyl-1H-1,2,3-triazol-5-yl)carbamate (Compound 185)

Example 56

Preparation of (R)-1-(2-chloropyridin-3-yl)ethyl (4-(5-(1-cyano-3,3-difluorocyclobutane-1-carboxamido)pyridin-2-yl)-1-methyl-1H-1,2,3-triazol-5-yl) carbamate (Compound 186)

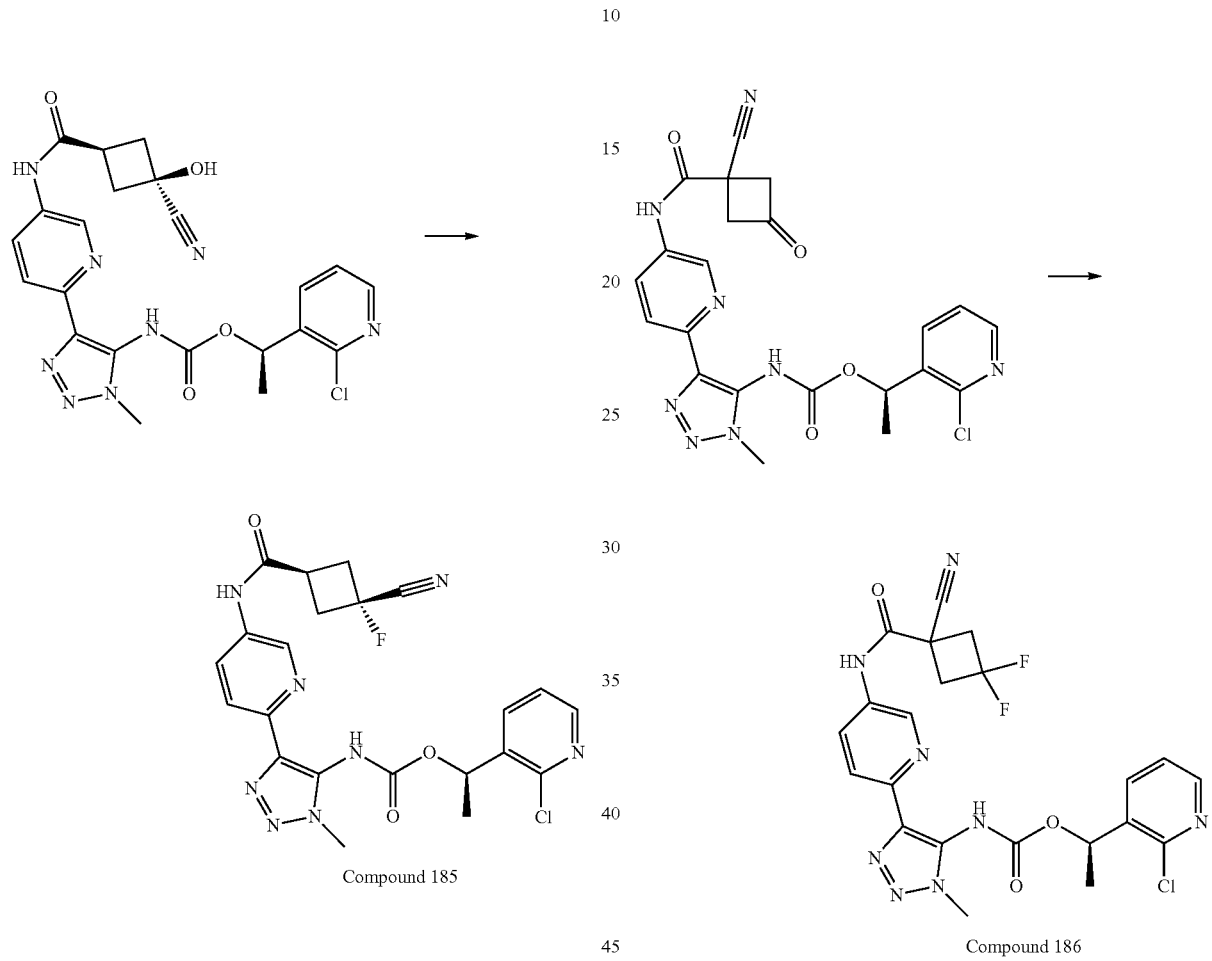

Compound 185

Compound 186

To a stirring dichloromethane (1 mL) solution of (R)-1-(2-chloropyridin-3-yl)ethyl (4-(5-((1s,3S)-3-cyano-3-hydroxycyclobutane-1-carboxamido)pyridin-2-yl)-1-methyl-1H-1,2,3-triazol-5-yl)carbamate (Compound 139) (0.04 mmol) at 0° C. was added (diethylamino)sulfur trifluoride (0.04 mmol). It was slowly warmed up to room temperature and stirred for 12 hours. The mixture was diluted with dichloromethane and washed with saturated aqueous sodium carbonate solution and brine. The aqueous layer was extracted with dichloromethane, and the combined organic extracts were dried (sodium sulfate), filtered, and concentrated in vacuo to afford the title Compound as yellowish oil. The residue was purified by reverse-phase HPLC to provide (R)-1-(2-chloropyridin-3-yl) ethyl (4-(5-((1r,3R)-3-cyano-3-fluorocyclobutane-1-carboxamido) pyridin-2-yl)-1-methyl-1H-1,2,3-triazol-5-yl)carbamate (Compound 185). (MS (m/z) 499.1 [M+H]$^+$). 1H NMR (400 MHz, Methanol-d4) δ 8.92 (s, 1H), 8.32 (s, 1H), 8.21-7.78 (m, 3H), 7.39 (d, 1H), 6.21-5.92 (m, 1H), 5.01-4.65 (m, 2H), 4.00 (s, 3H), 2.76 (m, 1H), 1.94-1.79 (m, 2H), 1.55 (d, 3H).

To a stirring dichloromethane (1 mL) solution of (R)-1-(2-chloropyridin-3-yl)ethyl (4-(5-(1-cyano-3-oxocyclobutane-1-carboxamido)pyridin-2-yl)-1-methyl-1H-1,2,3-triazol-5-yl)carbamate (20 mg, 0.04 mmol) at 0° C. was added (diethylamino)sulfur trifluoride (30 mg, 0.19 mmol). It was slowly warmed up to room temperature and stirred for 12 hours. The mixture was diluted with dichloromethane and washed with saturated aqueous sodium carbonate solution. The mixture was concentrated in vacuo. The residue was purified by reverse-phase HPLC to provide (R)-1-(2-chloropyridin-3-yl)ethyl (4-(5-(1-cyano-3,3-difluorocyclobutane-1-carboxamido) pyridin-2-yl)-1-methyl-1H-1,2,3-triazol-5-yl)carbamate (Compound 186). (MS (m/z) 517.0 [M+H]$^+$). $^1$H NMR (400 MHz, Methanol-d$_4$) δ 9.10-8.82 (m, 1H), 8.33 (s, 1H), 8.29-8.02 (m, 2H), 7.97 (d, 1H), 7.51 (s, 1H), 6.09 (d, 1H), 4.02 (d, 3H), 3.57 (m, 2H), 3.33 (m, 2H), 1.65 (s, 3H).

Example 57

Preparation of (S)-2-fluoro-1-(3-fluorophenyl)ethyl (1-methyl-4-(5-(3-methylureido)pyridin-2-yl)-1H-1,2,3-triazol-5-yl)carbamate (Compound 187)

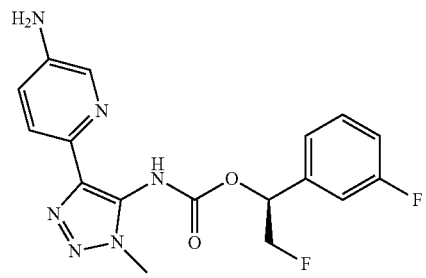

Intermediate 6B

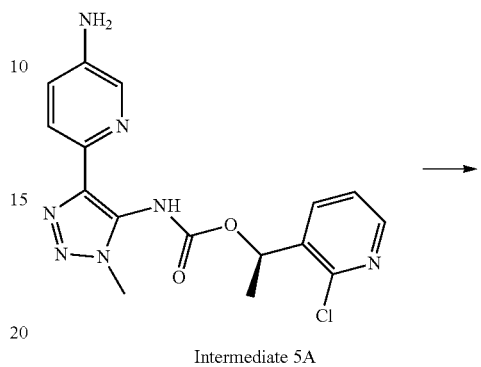

Intermediate 5A

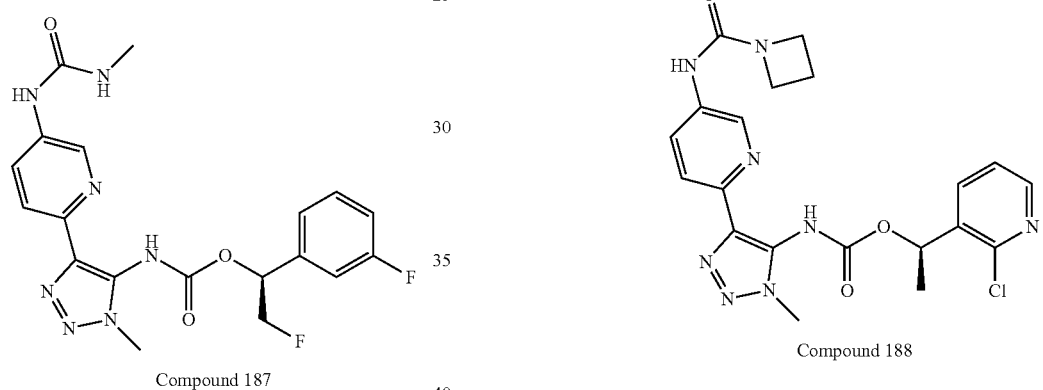

Compound 187

Compound 188

The hydrochloride salt of (S)-2-fluoro-1-(3-fluorophenyl)ethyl (4-(5-aminopyridin-2-yl)-1-methyl-1H-1,2,3-triazol-5-yl)carbamate (Intermediate 6B) (0.05 mmol) was dissolved in dichloromethane (1 mL), pyridine (0.2 mL). Triphosgene (0.1 mmol) was added and after 10 minutes a 2M solution of methylamine (0.5 mmol) in THF was added. After 30 min, the reaction was concentrated and dissolved in tetrahydrofuran (2 mL), and 1 M aqueous sodium hydroxide solution (2 mL) and stirred vigorously for 10 minutes. The reaction was quenched with sat. ammonium chloride, and extracted with ethyl acetate (2×10 mL). The combined organics were dried over sodium sulfate, concentrated, and purified by reverse-phase HPLC to provide (S)-2-fluoro-1-(3-fluorophenyl)ethyl (1-methyl-4-(5-(3-methylureido)pyridin-2-yl)-1H-1,2,3-triazol-5-yl)carbamate (Compound 187). (MS (m/z) 432.2 [M+H]+). $^1$H NMR (400 MHz, Methanol-$d_4$) δ 8.81 (s, 1H), 8.02 (dd, J=8.7, 2.4 Hz, 1H), 7.81 (d, J=8.8 Hz, 1H), 7.61-6.59 (m, 4H), 6.14-5.62 (m, 1H), 4.78-4.39 (m, 2H), 3.98 (s, 3H), 2.80 (s, 3H).

Example 58

Preparation of Compounds 188 to 194

Compounds 188 to 194 were generally synthesized according Scheme C, Step 4. For example, (R)-1-(2-chloropyridin-3-yl)ethyl (4-(5-(azetidine-1-carboxamido)pyridin-2-yl)-1-methyl-1H-1,2,3-triazol-5-yl)carbamate (Compound 188) was prepared as follows.

(R)-1-(2-chloropyridin-3-yl)ethyl (4-(5-aminopyridin-2-yl)-1-methyl-1H-1,2,3-triazol-5-yl)carbamate (Intermediate 5A) (Example 21) (0.07 mmol) was taken up in 0.2 mL DCM and 0.1 mL DMF and treated with triethyl-amine (0.183 mmol)) and phenylchloroformate (0.08 mmol). The reaction was stirred for 15 min and azetidine (0.112 mmol) was added as a solution in THF. After 15 min the reaction was concentrated, then taken up in aqueous MeCN and acidified with TFA. Purified by RP-HPLC to provide (R)-1-(2-chloropyridin-3-yl)ethyl (4-(5-(azetidine-1-carboxamido)pyridin-2-yl)-1-methyl-1H-1,2,3-triazol-5-yl)carbamate as the TFA salt (Compound 188). (MS (m/z) 457.1 [M+H]+). 1H NMR (400 MHz, Acetonitrile-d3) δ 8.93 (s, 1H), 8.59 (bs, 1H), 8.34 (dd, J=4.8, 1.9 Hz, 1H), 8.14 (ddd, J=8.8, 2.6, 1.2 Hz, 1H), 7.97 (d, J=8.8 Hz, 1H), 7.39 (d, J=15.7 Hz, 2H), 6.04 (q, J=6.6 Hz, 1H), 4.14-4.05 (m, 4H), 3.96 (s, 3H), 2.31 (dq, J=8.2, 7.4 Hz, 2H), 1.59 (d, J=6.6 Hz, 3H).

Compounds 188-194 (Table 3) were similarly prepared according to Scheme C, step 4 by reacting (R)-1-(2-chloropyridin-3-yl)ethyl (4-(5-aminopyridin-2-yl)-1-methyl-1H-1,2,3-triazol-5-yl)carbamate, Intermediate 5A (Example 21) with the Reagent listed in Table 3 in place of azetidine following the general process described for Compound 188.

TABLE 3

Compounds prepared according to Scheme C, Step 4.

| Compound No. | Structure | Reagent | LCMS m/z | 1H NMR |
|---|---|---|---|---|
| Compound 188 (R)-1-(2-chloropyridin-3-yl)ethyl (4-(5-(azetidine-1-carboxamido)pyridin-2-yl)-1-methyl-1H-1,2,3-triazol-5-yl)carbamate | 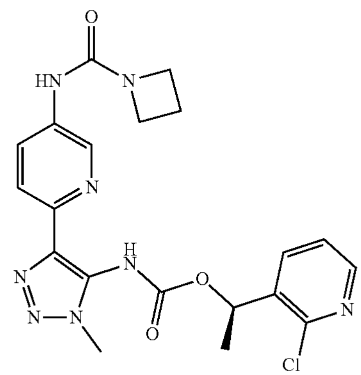 [SMILES: C[C@@H](OC(=O)Nc1c(-c2ccc(NC(=O)N3CCC3)cn2)nnn1C)c1cccnc1Cl] | | 457.1 | 1H NMR (400 MHz, Acetonitrile-d3) δ 8.93 (s, 1H), 8.59 (bs, 1H), 8.34 (dd, J = 4.8, 1.9 Hz, 1H), 8.14 (ddd, J = 8.8, 2.6, 1.2 Hz, 1H), 7.97 (d, J = 8.8 Hz, 1H), 7.39 (d, J = 15.7 Hz, 2H), 6.04 (q, J = 6.6 Hz, 1H), 4.14-4.05 (m, 4H), 3.96 (s, 3H), 2.31 (dq, J = 8.2, 7.4 Hz, 2H), 1.59 (d, J = 6.6 Hz, 3H). |
| Compound 189 (R)-1-(2-chloropyridin-3-yl)ethyl (4-(5-(3-cyanobicyclo[1.1.1]pentane-1-carboxamido)-4-fluoropyridin-2-yl)-1-methyl-1H-1,2,3-triazol-5-yl)carbamate | 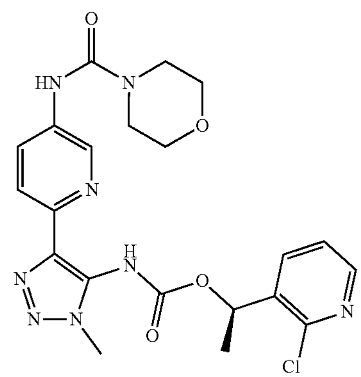 [SMILES: C[C@@H](OC(=O)Nc1c(-c2ccc(NC(=O)N3CCOCC3)cn2)nnn1C)c1cccnc1Cl] | | 487.1 | 1H NMR (400 MHz, Acetonitrile-d3) δ 8.90 (d, J = 22.7 Hz, 1H), 8.62 (s, 1H), 8.35 (dd, J = 4.8, 1.9 Hz, 1H), 8.19-8.07 (m, 1H), 7.99 (dd, J = 8.8, 2.2 Hz, 1H), 7.92 (s, 1H), 7.68 (d, J = 34.5 Hz, 1H), 7.41 (s, 1H), 6.04 (q, J = 6.6 Hz, 1H), 3.96 (s, 3H), 3.71 (dd, J = 5.6, 4.1 Hz, 3H), 3.51 (t, J = 4.9 Hz, 4H), 1.95 (s, 0H), 1.59 (d, J = 6.6 Hz, 3H). |
| Compound 190 (R)-1-(2-chloropyridin-3-yl)ethyl (1-methyl-4-(5-((R)-3-methylpyrrolidine-1-carboxamido)pyridin-2-yl)-1H-1,2,3-triazol-5-yl)carbamate | 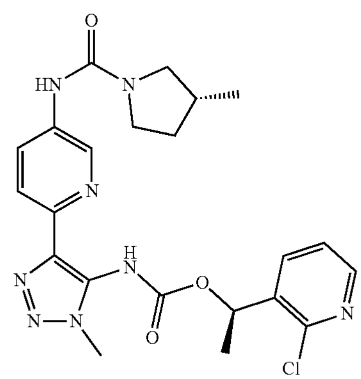 [SMILES: C[C@@H]1CCN(C(=O)Nc2ccc(-c3nnn(C)c3NC(=O)O[C@H](C)c3cccnc3Cl)nc2)C1] | | 485.1 | 1H NMR (400 MHz, Acetonitrile-d3) d 9.08 (s, 1H), 8.34 (dd, J = 4.8, 1.9 Hz, 1H), 8.24 (dd, J = 8.9, 2.4 Hz, 1H), 7.98 (d, J = 8.9 Hz, 1H), 7.54 (s, 1H), 7.42 (s, 2H), 6.03 (q, J = 6.6 Hz, 1H), 3.96 (s, 3H), 3.70-3.54 (m, 2H), 2.99 (dd, J = 9.9, 8.1 Hz, 1H), 2.35 (t, J = 7.4 Hz, 1H), 2.14-2.05 (m, 1H), 2.09 (s, 1H), 1.68-1.55 (m, 4H), 1.11 (d, J = 6.6 Hz, 3H). |
| Compound 191 (R)-1-(2-chloropyridin-3-yl)ethyl (4-(5-(3-cyanoazetidine-1-carboxamido)pyridin-2-yl)-1-methyl-1H-1,2,3-triazol-5-yl)carbamate | 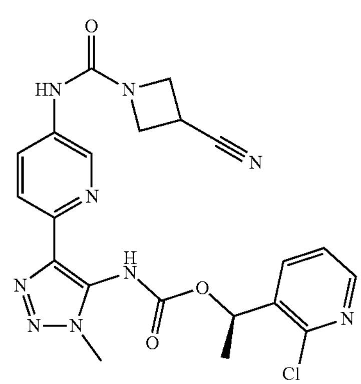 [SMILES: C[C@@H](OC(=O)Nc1c(-c2ccc(NC(=O)N3CC(C#N)C3)cn2)nnn1C)c1cccnc1Cl] | | 482.1 | 1H NMR (400 MHz, Acetonitrile-d3) δ 8.79 (m, 2H), 8.47 (s, 1H), 8.15 (d, J = 20.4 Hz, 1H), 8.05 (dd, J = 8.7, 2.4 Hz, 1H), 8.00 (s, 1H), 7.06 (s, 1H), 5.90 (q, J = 6.6 Hz, 1H), 3.96 (t, J = 1.0 Hz, 3H), 2.31 (s, 3H), 1.78-1.68 (m, 5H), 1.54 (d, J = 6.1 Hz, 3H). |

US 11,912,686 B2

TABLE 3-continued

Compounds prepared according to Scheme C, Step 4.

| Compound No. | Structure | Reagent | LCMS m/z | 1H NMR |
|---|---|---|---|---|
| Compound 192 (R)-1-(2-chloropyridin-3-yl)ethyl (1-methyl-4-(5-((R)-2-methylpyrrolidine-1-carboxamido)pyridin-2-yl)-1H-1,2,3-triazol-5-yl)carbamate | 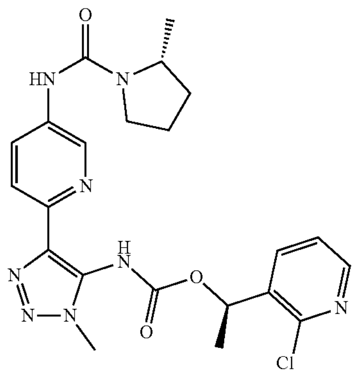 [SMILES: C[C@@H]1CCCN1C(=O)Nc1ccc(-c2nnn(C)c2NC(=O)O[C@H](C)c2cccnc2Cl)nc1] | | 485.1 | 1H NMR (400 MHz, Acetonitrile-d3) δ 9.01 (d, J = 2.4 Hz, 1H), 8.78 (s, 1H), 8.34 (dd, J = 4.8, 1.9 Hz, 1H), 8.21 (dd, J = 8.8, 2.5 Hz, 1H), 7.98 (d, J = 8.8 Hz, 1H), 7.40 (s, 1H), 6.04 (q, J = 6.6 Hz, 1H), 4.13 (pd, J = 6.4, 2.8 Hz, 1H), 3.96 (s, 3H), 3.55 (ddd, J = 9.9, 7.5, 3.6 Hz, 1H), 3.50-3.39 (m, 1H), 2.07 (dddd, J = 13.6, 10.9, 5.7, 4.0 Hz, 2H), 1.95 (d, J = 1.7 Hz, OH), 1.73-1.61 (m, 1H), 1.59 (d, J = 5.9 Hz, 3H), 1.24 (d, J = 6.3 Hz, 3H). |
| Compound 193 (R)-1-(2-chloropyridin-3-yl)ethyl (4-(5-(3,3-difluoropyrrolidine-1-carboxamido)pyridin-2-yl)-1-methyl-1H-1,2,3-triazol-5-yl)carbamate | 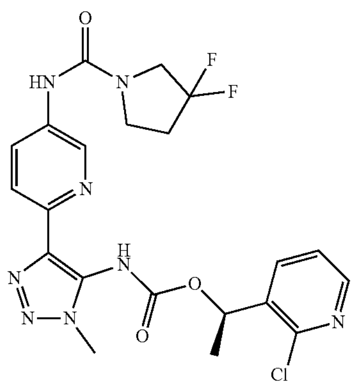 [SMILES: C[C@@H](OC(=O)Nc1c(-c2ccc(NC(=O)N3CCC(F)(F)C3)cn2)nnn1C)c1cccnc1Cl] | | 507.1 | 1H NMR (400 MHz, Acetonitrile-d3) d 8.91 (s, 1H), 8.58 (s, 0H), 8.35 (dd, J = 4.7, 1.8 Hz, 1H), 8.15 (dd, J = 8.8, 2.4 Hz, 1H), 7.99 (d, J = 8.8 Hz, 1H), 7.47 (s, 1H), 7.42 (s, 1H), 6.04 (q, J = 6.6 Hz, 1H),, 3.96 (s, 3H), 3.86 (t, J = 13.1 Hz, 2H), 3.73 (t, J = 7.4 Hz, 2H), 2.51 (tt, J = 14.3, 7.4 Hz, 2H), 1.58 (s, 3H). |
| Compound 194 (R)-1-(2-chloropyridin-3-yl)ethyl (1-methyl-4-(5-(pyrrolidine-1-carboxamido)pyridin-2-yl)-1H-1,2,3-triazol-5-yl)carbamate | 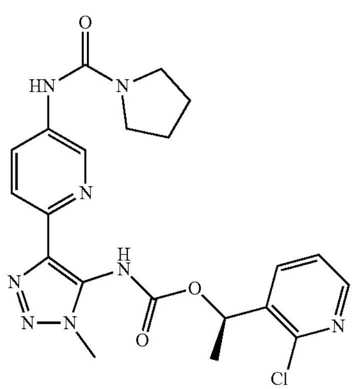 [SMILES: C[C@@H](OC(=O)Nc1c(-c2ccc(NC(=O)N3CCCC3)cn2)nnn1C)c1cccnc1Cl] | | 471.1 | 1H NMR (400 MHz, Acetonitrile-d3) d 9.08 (s, 1H), 8.34 (dd, J = 4.8, 1.9 Hz, 1H), 8.24 (dd, J = 8.9, 2.4 Hz, 1H), 7.98 (d, J = 8.9 Hz, 1H), 7.54 (s, 1H), 7.42 (s, 2H), 6.03 (q, J = 6.6 Hz, 1H), 3.96 (s, 3H), 3.70-3.54 (m, 2H), 2.99 (dd, J = 9.9, 8.1 Hz, 1H), 2.35 (t, J = 7.4 Hz, 1H), 2.14-2.05 (m, 1H), 2.09 (s, 1H), 1.68-1.55 (m, 4H), 1.11 (d, J = 6.6 Hz, 3H). |

Example 59

Preparation of Compounds 297 to 303

Compounds 297 to 304 were generally synthesized according Scheme C, Step 4, followed by protecting group removal. For example, (R)-1-(2,5-difluoropyridin-3-yl)ethyl (4-(5-(3-cyanoazetidine-3-carboxamido)pyridin-2-yl)-1-methyl-1H-1,2,3-triazol-5-yl)carbamate (Compound 297) was prepared as follows.

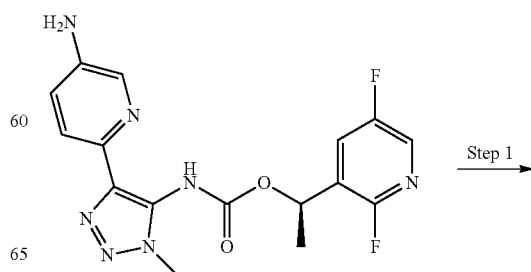

Step 1

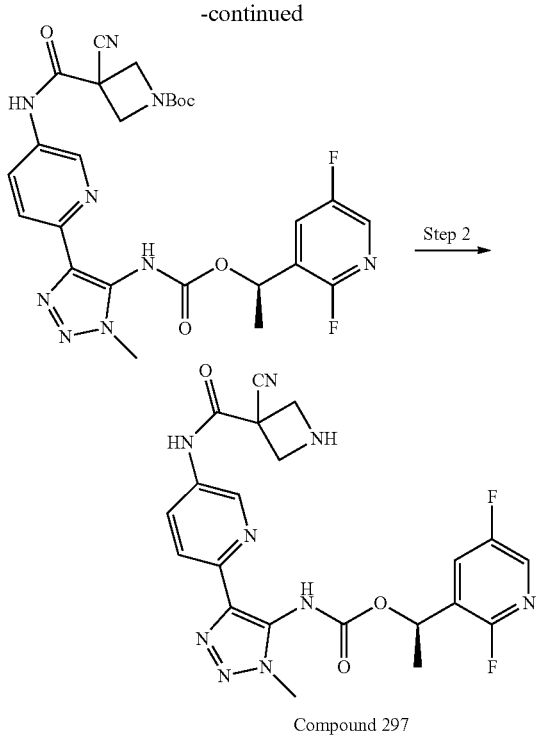

Compound 297

Step 1: tert-butyl (R)-3-cyano-3-((6-(5-(((1-(2,5-difluoropyridin-3yl)ethoxy)carbonyl)amino)-1-methyl-1H-1,2,3-triazol-4-yl)pyridin-3-yl)carbamoyl)azetidine-1-carboxylate A vial was charged with (R)-1-(2,5-difluoropyridin-3-yl)ethyl (4-(5-aminopyridin-2-yl)-1-methyl-1H-1,2,3-triazol-5-yl)carbamate hydrochloride (Intermediate 5B) (0.12 mmol), 1-(tert-butoxycarbonyl)-3-cyanoazetidine-3-carboxylic acid (0.15 mmol), N-ethyl-N'-(3-dimethylaminopropyl) carbodiimide hydrochloride (0.24 mmol) and pyridine (2 mL). The reaction mixture was stirred for 2 hours at room temperature, concentrated, diluted with water and extracted with EtOAc (3×). The combined organic layers were washed with brine, dried over MgSO₄, filtered and concentrated to provide tert-butyl (R)-3-cyano-3-((6-(5-(((1-(2,5-difluoropyridin-3-yl)ethoxy)carbonyl)amino)-1-methyl-1H-1,2,3-triazol-4-yl)pyridin-3-yl)carbamoyl)azetidine-1-carboxylate, which was used without further purification. (MS (m/z) 584.3 [M+H]⁺).

Step 2: (R)-1-(2,5-difluoropyridin-3-yl)ethyl (4-(5-(3-cyanoazetidine-3-carboxamido)pyridin-2-yl)-1-methyl-1H-1,2,3-triazol-5-yl)carbamate A solution of tert-butyl (R)-3-cyano-3-((6-(5-(((1-(2,5-difluoropyridin-3-yl)ethoxy)carbonyl)amino)-1-methyl-1H-1,2,3-triazol-4-yl)pyridin-3-yl)carbamoyl)azetidine-1-carboxylate (0.12 mmol) in DCM (3 mL) and TFA (1 mL) was stirred at room temperature for 1 hour. The reaction was concentrated and purified by reverse phase HPLC to provide (R)-1-(2,5-difluoropyridin-3-yl)ethyl (4-(5-(3-cyanoazetidine-3-carboxamido)pyridin-2-yl)-1-methyl-1H-1,2,3-triazol-5-yl)carbamate as the trifluoroacetic acid salt. (MS (m/z) 484.0 [M+H]⁺). 1H NMR (400 MHz, DMSO-d6) δ 10.94 (s, 1H), 9.85 (bs, 1H), 9.31 (bs, 2H), 8.69 (bs, 1H), 8.20 (bs, 1H), 8.11-7.83 (m, 3H), 5.80 (bs, 1H), 4.53 (q, J=11.4 Hz, 4H), 3.90 (s, 3H), 1.41 (bs, 3H).

Compounds 298-303 (Table 4) were similarly prepared according to Scheme C, Step 4 by reacting (R)-1-(2,5-difluoropyridin-3-yl)ethyl (4-(5-aminopyridin-2-yl)-1-methyl-1H-1,2,3-triazol-5-yl)carbamate hydrochloride, (Intermediate 5B) (Example 22) with the Reagent listed in Table 4 in place of 1-(tert-butoxycarbonyl)-3-cyanoazetidine-3-carboxylic acid.

TABLE 4

Compounds prepared according to Scheme C, Step 4.

| Compound No. | Structure | Reagent | LCMS m/z | 1H NMR |
|---|---|---|---|---|
| Compound 297 (R)-1-(2,5-difluoropyridin-3-yl)ethyl (4-(5-(3-cyanoazetidine-3-carboxamido)pyridin-2-yl)-1-methyl-1H-1,2,3-triazol-5-yl)carbamate | 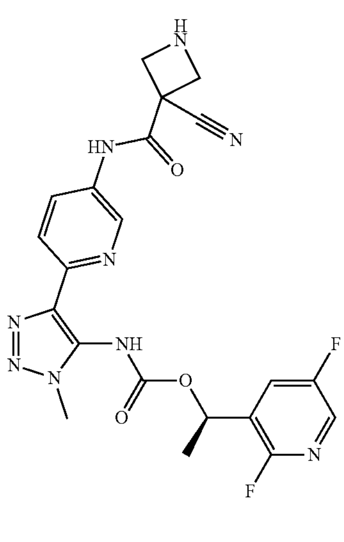 [SMILES: C[C@@H](OC(=O)Nc1c(-c2ccc(NC(=O)C3(C#N)CNC3)cn2)nnn1C)c1cc(F)cnc1F] | Boc | 484.0 | 1H NMR (400 MHz, DMSO-d6) δ 10.94 (s, 1H), 9.85 (bs, 1H), 9.31 (bs, 2H), 8.69 (bs, 1H), 8.20 (bs, 1H), 8.11-7.83 (m, 3H), 5.80 (bs, 1H), 4.53 (q, J = 11.4 Hz, 4H), 3.90 (s, 3H), 1.41 (bs, 3H). |

TABLE 4-continued

Compounds prepared according to Scheme C, Step 4.

| Compound No. | Structure | Reagent | LCMS m/z | 1H NMR |
|---|---|---|---|---|
| Compound 298 (R)-1-(2,5-difluoropyridin-3-yl)ethyl (4-(5-(3-(difluoromethyl)azetidine-3-carboxamido)pyridin-2-yl)-1-methyl-1H-1,2,3-triazol-5-yl)carbamate | 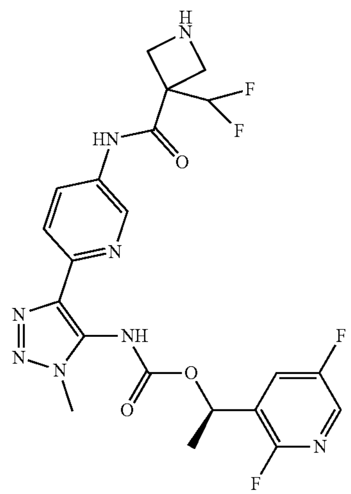 [SMILES: C[C@@H](OC(=O)Nc1c(-c2ccc(NC(=O)C3(C(F)F)CNC3)cn2)nnn1C)c1cc(F)cnc1F] | | 509.2 | 1H NMR (400 MHz, DMSO-d6) δ 10.61 (s, 1H), 9.84 (bs, 1H), 9.20 (bs, 1H), 8.87 (bs, 1H), 8.71 (bs, 1H), 8.35-7.75 (m, 4H), 6.63 (t, J = 55.1 Hz, 1H), 5.79 (bs, 1H), 4.51-4.30 (m, 2H), 4.29-4.10 (m, 2H), 3.89 (s, 3H), 1.81-1.07 (bs, 3H). |
| Compound 299 (R)-1-(2,5-difluoropyridin-3-yl)ethyl (4-(5-(4-cyanopiperidine-4-carboxamido)pyridin-2-yl)-1-methyl-1H-1,2,3-triazol-5-yl)carbamate | 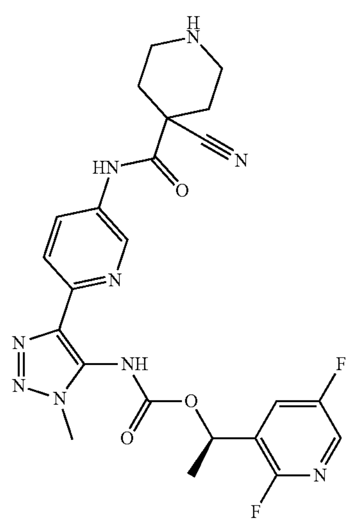 [SMILES: C[C@@H](OC(=O)Nc1c(-c2ccc(NC(=O)C3(C#N)CCNCC3)cn2)nnn1C)c1cc(F)cnc1F] | | 512.1 | 1H NMR (400 MHz, DMSO-d6) δ 11.95 (bs, 1H), 10.66 (s, 1H), 9.84 (bs, 1H), 8.97-8.40 (m, 3H), 8.34-7.89 (m, 3H), 5.79 (bs, 1H), 3.90 (s, 3H), 3.56-3.37 (m, 2H), 3.22-3.01 (m, 2H), 2.49-2.39 (m, 2H), 2.37-2.19 (m, 2H), 1.58 (bs, 3H). |
| Compound 300 (R)-1-(2,5-difluoropyridin-3-yl)ethyl (4-(5-(1-(aminomethyl)-2,2-difluorocyclopropane-1-carboxamido)pyridin-2-yl)-1-methyl-1H-1,2,3-triazol-5-yl)carbamate | 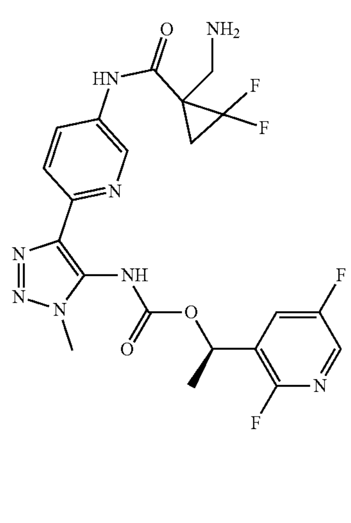 [SMILES: C[C@@H](OC(=O)Nc1c(-c2ccc(NC(=O)C3(CN)CC3(F)F)cn2)nnn1C)c1cc(F)cnc1F] | | 509.0 | 1H NMR (400 MHz, DMSO-d6) δ 10.43 (d, J = 4.4 Hz, 1H), 9.83 (bs, 1H), 8.77-8.65 (m, 1H), 8.42-7.80 (m, 5H), 5.80 (bs, 1H), 3.89 (s, 3H), 3.79 (dd, J = 14.1, 5.3 Hz, 1H), 3.08 (dd, J = 13.7, 6.1 Hz, 1H), 2.47 (m, 1H), 2.24-2.06 (m, 1H), 1.57 (bs, 3H). |

TABLE 4-continued

Compounds prepared according to Scheme C, Step 4.

| Compound No. | Structure | Reagent | LCMS m/z | 1H NMR |
|---|---|---|---|---|
| Compound 301 (R)-1-(2,5-difluoropyridin-3-yl)ethyl (4-(5-(1-(aminomethyl)-3,3-difluorocyclobutane-1-carboxamido)pyridin-2-yl)-1-methyl-1H-1,2,3-triazol-5-yl)carbamate | 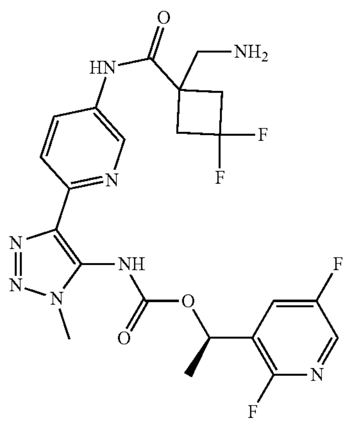 [SMILES: C[C@@H](OC(=O)Nc1c(-c2ccc(NC(=O)C3(CN)CC(F)(F)C3)cn2)nnn1C)c1cc(F)cnc1F] | | 523.0 | 1H NMR (400 MHz, DMSO-d6) δ 10.26 (s, 1H), 9.82 (bs, 1H), 8.74 (s, 1H), 8.32-7.74 (m, 7H), 5.80 (bs, 1H), 3.89 (s, 3H), 3.53-3.34 (m, 2H), 3.20 (q, J = 13.3 Hz, 2H), 2.90 (q, J = 12.6 Hz, 2H), 1.56 (bs, 3H). |
| Compound 302 (R)-1-(2,5-difluoropyridin-3-yl)ethyl (4-(5-(3-cyanopyrrolidine-3-carboxamido)pyridin-2-yl)-1-methyl-1H-1,2,3-triazol-5-yl)carbamate | 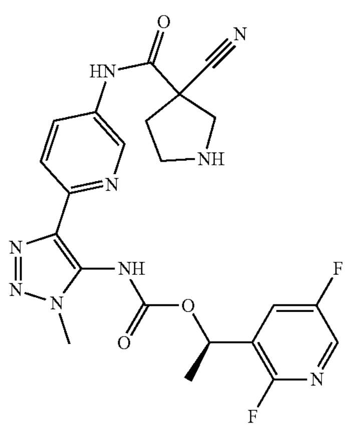 [SMILES: C[C@@H](OC(=O)Nc1c(-c2ccc(NC(=O)C3(C#N)CCNC3)cn2)nnn1C)c1cc(F)cnc1F] | | 498.0 | 1H NMR (400 MHz, DMSO-d6) δ 10.90 (s, 1H), 9.84 (bs, 1H), 9.37 (bs, 2H), 8.71 (s, 1H), 8.37-7.79 (m, 4H), 5.79 (bs, 1H), 4.00 (d, J = 12.6 Hz, 1H), 3.92-3.82 (m, 4H), 3.52-3.41 (m, 1H), 3.42-3.30 (m, 1H), 2.75 (t, J = 7.2 Hz, 2H), 1.58 (bs, 3H). |
| Compound 303 (R)-1-(2,5-difluoropyridin-3-yl)ethyl (4-(5-(1-(aminomethyl)cyclobutane-1-carboxamido)pyridin-2-yl)-1-methyl-1H-1,2,3-triazol-5-yl)carbamate | 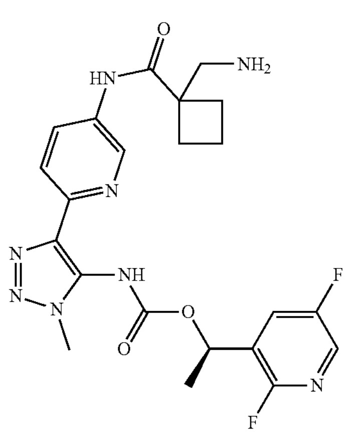 [SMILES: C[C@@H](OC(=O)Nc1c(-c2ccc(NC(=O)C3(CN)CCC3)cn2)nnn1C)c1cc(F)cnc1F] | | 487.1 | 1H NMR (400 MHz, DMSO-d6) δ 9.98 (s, 1H), 9.82 (bs, 1H), 8.77 (d, J = 2.4 Hz, 1H), 8.21 (bs, 1H), 8.13 (dd, J = 8.7, 2.5 Hz, 1H), 8.03 (bs, 1H), 7.94 (d, J = 8.7 Hz, 1H), 7.85 (bs, 3H), 5.80 (bs, 1H), 3.89 (s, 3H), 3.40-3.28 (m, 2H), 2.59-2.52 (m, 2H), 2.18-1.93 (m, 3H), 1.93-1.78 (m, 1H), 1.55 (bs, 3H). |

Example 60

Preparation of (R)-1-(2-chloro-5-fluoropyridin-3-yl) ethyl (4-(5-(1-(aminomethyl)-3,3-difluorocyclobutane-1-carboxamido)pyridin-2-yl)-1-methyl-1H-1,2,3-triazol-5-yl)carbamate (Compound 304)

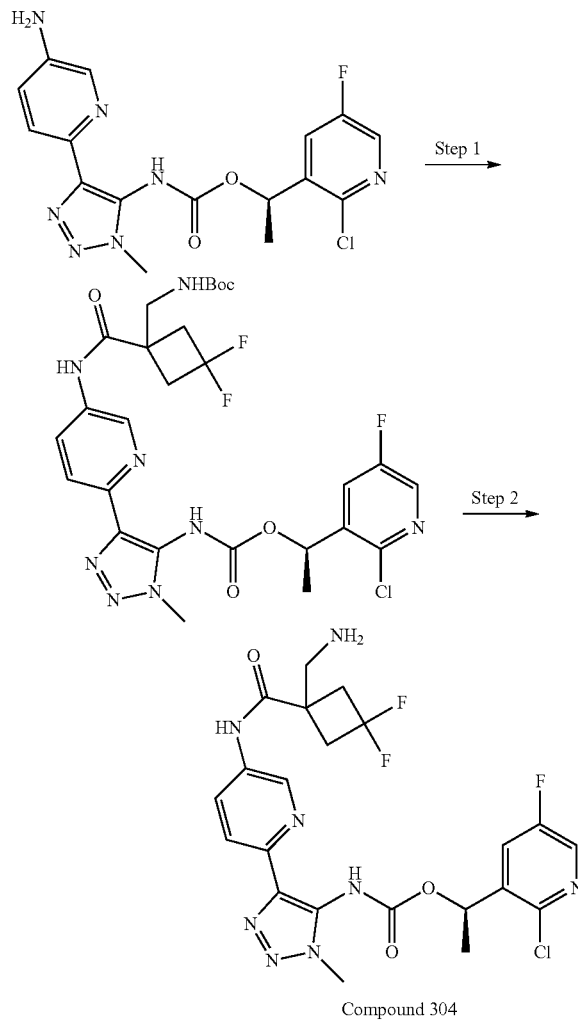

Compound 304

Step 1: (R)-1-(2-chloro-5-fluoropyridin-3-yl)ethyl (4-(5-(1-(((tert-butoxycarbonyl)amino)methyl)-3,3-difluorocyclobutane-1-carboxamido)pyridin-2-yl)-1-methyl-1H-1,2,3-triazol-5-yl)carbamate A vial was charged with (R)-1-(2-chloro-5-fluoropyridin-3-yl)ethyl (4-(5-aminopyridin-2-yl)-1-methyl-1H-1,2,3-triazol-5-yl)carbamate hydrochloride (Intermediate 5C) (0.19 mmol), 1-(((tert-butoxycarbonyl)amino)methyl)-3,3-difluorocyclobutane-1-carboxylic acid (0.25 mmol), N-ethyl-N'-(3-dimethylaminopropyl) carbodiimide hydrochloride (0.38 mmol) and pyridine (2 mL). The reaction mixture was stirred for 2 hours at RT, concentrated, diluted with water and extracted with EtOAc (3×). The combined organic layers were washed with brine, dried over MgSO₄, filtered and concentrated to provide (R)-1-(2-chloro-5-fluoropyridin-3-yl)ethyl (4-(5-(1-(((tert-butoxycarbonyl)amino) methyl)-3,3-difluorocyclobutane-1-carboxamido)pyridin-2-yl)-1-methyl-1H-1,2,3-triazol-5-yl)carbamate which was used without further purification. (MS (m/z) 639.1. [M+H]⁺).

Step 2: (R)-1-(2-chloro-5-fluoropyridin-3-yl)ethyl (4-(5-(1-(aminomethyl)-3,3-difluorocyclobutane-1-carboxamido)pyridin-2-yl)-1-methyl-1H-1,2,3-triazol-5-yl)carbamate A solution of (R)-1-(2-chloro-5-fluoropyridin-3-yl)ethyl (4-(5-(1-(((tert-butoxycarbonyl)amino)methyl)-3,3-difluorocyclobutane-1-carboxamido)pyridin-2-yl)-1-methyl-1H-1,2,3-triazol-5-yl)carbamate (0.12 mmol) in DCM (3 mL) and TFA (1 mL) was stirred at RT for 18 hours. The reaction was concentrated and purified by reverse phase HPLC to provide (R)-1-(2-chloro-5-fluoropyridin-3-yl)ethyl (4-(5-(1-(aminomethyl)-3,3-difluorocyclobutane-1-carboxamido) pyridin-2-yl)-1-methyl-1H-1,2,3-triazol-5-yl)carbamate as the trifluoroacetic acid salt. (MS (m/z) 539.0 [M+H]⁺). 1H NMR (400 MHz, DMSO-d6) δ 10.24 (s, 1H), 9.87 (bs, 1H), 8.76 (s, 1H), 8.44 (bs, 1H), 8.15-7.68 (m, 5H), 5.84 (bs, 1H), 3.90 (s, 3H), 3.51-3.22 (m, 2H), 3.21 (q, J=13.3 Hz, 2H), 2.90 (q, J=13.0 Hz, 2H), 1.57 (bs, 3H).

Example 61

Preparation of (R)-1-(2,5-difluoropyridin-3-yl)ethyl (4-(5-(3-cyano-1-(2,2,2-trifluoroethyl)azetidine-3-carboxamido)pyridin-2-yl)-1-methyl-1H-1,2,3-triazol-5-yl)carbamate (Compound 305)

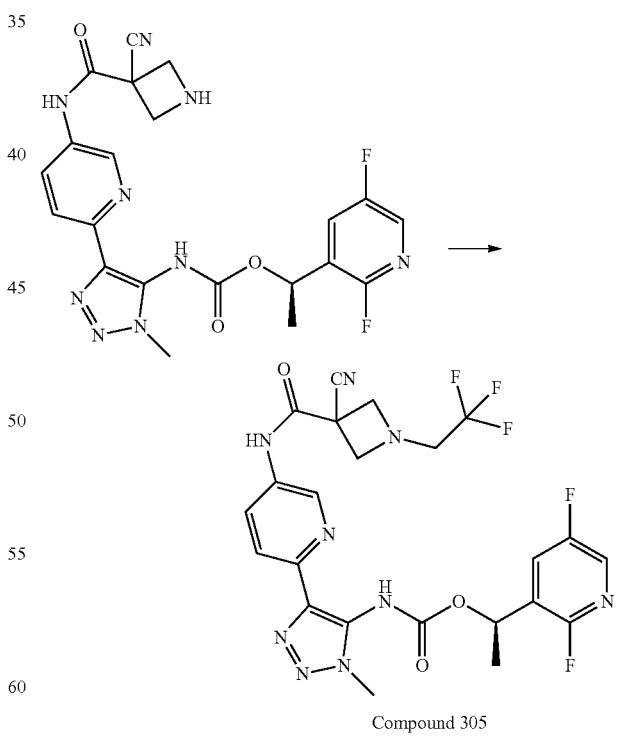

Compound 305

A vial was charged with (R)-1-(2,5-difluoropyridin-3-yl) ethyl (4-(5-(3-cyanoazetidine-3-carboxamido)pyridin-2-yl)-1-methyl-1H-1,2,3-triazol-5-yl)carbamate as the trifluoroacetic acid salt (0.03 mmol), triethylamine (0.15 mmol) and ACN (2 mL). 2,2,2-Trifluoroethyl trifluoromethanesulfonate (0.09 mmol) was added and the solution was heated at 60° C. for 2 hours. The reaction was concentrated and purified by reverse phase HPLC to provide (R)-1-(2,5-difluoropyridin-3-yl)ethyl (4-(5-(3-cyano-1-(2,2,2-trifluoroethyl)azetidine-3-carboxamido)pyridin-2-yl)-1-methyl-1H-1,2,3-triazol-5-yl)carbamate. (MS (m/z) 565.9 [M+H]⁺). 1H NMR (400 MHz, DMSO-d6) δ 10.77 (bs, 1H), 9.84 (bs, 1H), 8.70 (bs, 1H), 8.19 (bs, 1H), 8.13-7.91 (m, 3H), 5.80 (bs, 1H), 3.96 (d, J=7.6 Hz, 2H), 3.93-3.86 (m, 5H), 3.37 (q, J=10.1 Hz, 2H), 1.58 (bs, 3H).

Example 62

Preparation of (R)-1-(2-chloropyridin-3-yl)ethyl (1-methyl-4-(5-((1r,3R)-3-((2,2,2-trifluoroethyl)amino)cyclobutane-1-carboxamido)pyridin-2-yl)-1H-1,2,3-triazol-5-yl)carbamate (Compound 306)

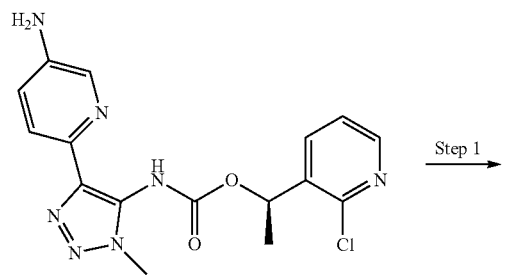

Step 1

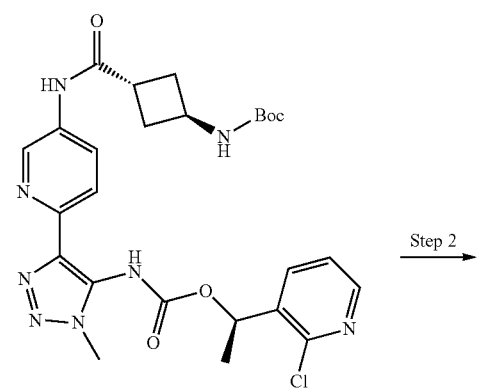

Step 2

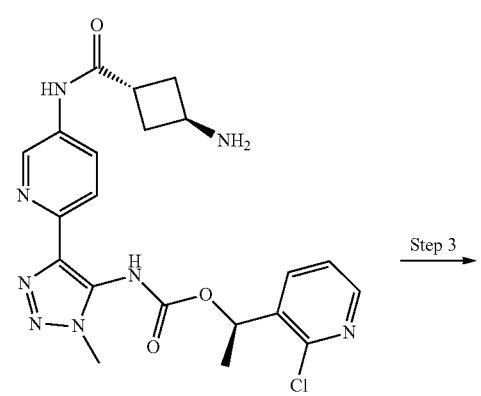

Step 3

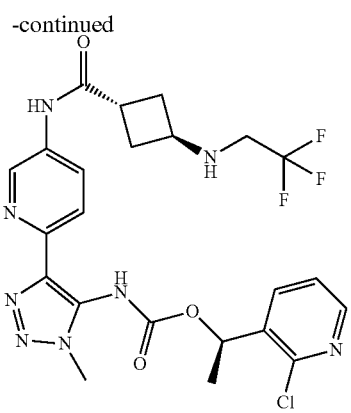

Compound 306

Step 1: (R)-1-(2-chloropyridin-3-yl)ethyl (4-(5-((1r,3R)-3-((tert-butoxycarbonyl)amino)cyclobutane-1-carboxamido)pyridin-2-yl)-1-methyl-1H-1,2,3-triazol-5-yl)carbamate (R)-1-(2-chloropyridin-3-yl)ethyl (4-(5-aminopyridin-2-yl)-1-methyl-1H-1,2,3-triazol-5-yl)carbamate hydrochloride (0.146 mmol) suspended in dimethylformamide (2 mL) was treated with (1r,3r)-3-((tert-butoxycarbonyl)amino)cyclobutane-1-carboxylic acid (0.186 mmol), 1-ethyl-3-(3-dimethylaminopropyl)carbodiimide hydrochloride (0.438 mmol), and pyridine (0.869 mmol). The reaction mixture was stirred at room temperature for 30 minutes. The reaction mixture was concentrated to give the crude product.

Step 2: (R)-1-(2-chloropyridin-3-yl)ethyl (4-(5-((1r,3R)-3-aminocyclobutane-1-carboxamido)pyridin-2-yl)-1-methyl-1H-1,2,3-triazol-5-yl)carbamate (R)-1-(2-chloropyridin-3-yl)ethyl(4-(5-((1r,3R)-3-((tert-butoxycarbonyl)amino)cyclobutane-1-carboxamido)pyridin-2-yl)-1-methyl-1H-1,2,3-triazol-5-yl)carbamate (0.105 mmol) dissolved in dichloromethane (2 mL) was treated with trifluoroacetic acid (10.5 mmol). The reaction mixture was stirred at room temperature overnight. The reaction mixture was concentrated. The residue was re-dissolved in ethyl acetate and washed with saturated sodium bicarbonate solution. The layers were separated. The organic layer was concentrated to give the crude product.

Step 3: (R)-1-(2-chloropyridin-3-yl)ethyl (1-methyl-4-(5-((1r,3R)-3-((2,2,2-trifluoroethyl)amino)cyclobutane-1-carboxamido)pyridin-2-yl)-1H-1,2,3-triazol-5-yl)carbamate (R)-1-(2-chloropyridin-3-yl)ethyl(4-(5-((1r,3R)-3-aminocyclobutane-1-carboxamido)pyridin-2-yl)-1-methyl-1H-1,2,3-triazol-5-yl)carbamate (0.0425 mmol) dissolved in acetonitrile (4 mL) was treated with triethylamine (0.215 mmol) followed by 2,2,2-trifluoroethyl trifluoromethanesulfonate (0.144 mmol). The reaction mixture was stirred at room temperature overnight and then concentrated. The residue was purified by HPLC to give (R)-1-(2-chloropyridin-3-yl)ethyl (1-methyl-4-(5-((1r,3R)-3-((2,2,2-trifluoroethyl)amino)cyclobutane-1-carboxamido)pyridin-2-yl)-1H-1,2,3-triazol-5-yl)carbamate. (MS (m/z) 553.1 [M+H]+). 1H NMR (400 MHz, Methanol-d4) δ 8.86 (s, 1H), 8.39-8.24 (m, 2H), 8.09 (dd, J=8.5, 2.8 Hz, 1H), 7.90 (d, J=8.8 Hz, 1H), 7.45 (dd, J=7.7, 4.8 Hz, 1H), 6.07 (s, 1H), 4.16 (p, J=8.0 Hz, 1H), 3.99 (s, 3H), 3.94 (t, J=9.1 Hz, 1H), 2.74 (td, J=8.6, 8.1, 4.1 Hz, 2H), 2.57 (dt, J=13.6, 9.3 Hz, 2H), 1.55 (d, J=46.0 Hz, 3H).

Example 63

Preparation of (R)-1-(2-chloropyridin-3-yl)ethyl (1-methyl-4-(5-((1s,3S)-3-((2,2,2-trifluoroethyl)amino)cyclobutane-1-carboxamido)pyridin-2-yl)-1H-1,2,3-triazol-5-yl)carbamate (Compound 307)

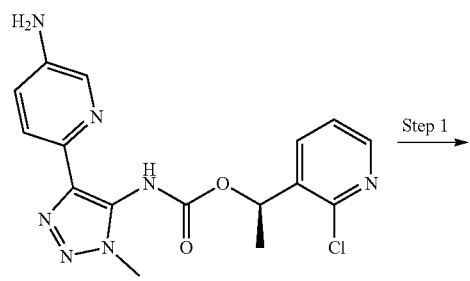

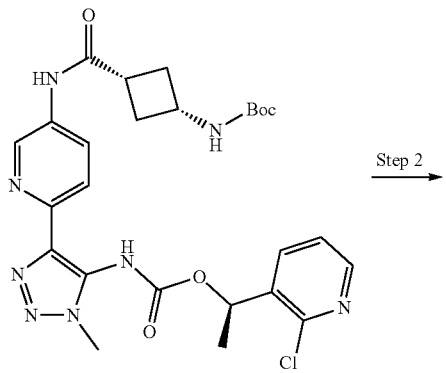

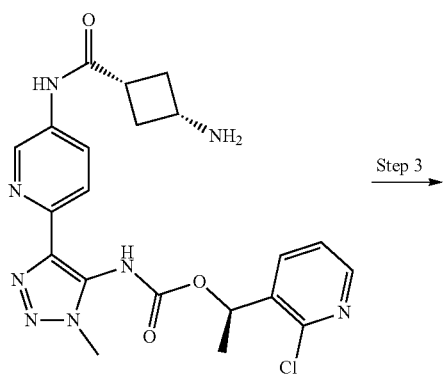

-continued

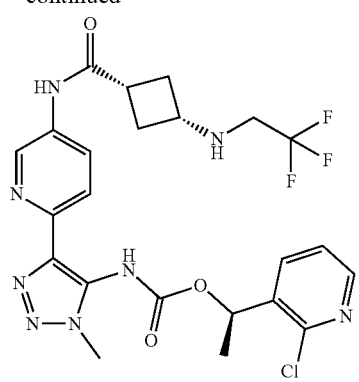

Compound 307

The title compound was prepared similarly to Example 62 using (1s,3s)-3-((tert-butoxycarbonyl)amino)cyclobutane-1-carboxylic acid (0.186 mmol) in place of (1r,3r)-3-((tert-butoxycarbonyl)amino)cyclobutane-1-carboxylic acid. (MS (m/z) 553 [M+H]+). 1H NMR (400 MHz, Methanol-d4) δ 8.84 (s, 1H), 8.31 (s, 1H), 8.09 (dd, J=8.7, 2.6 Hz, 1H), 7.90 (d, J=8.6 Hz, 1H), 7.46 (s, 2H), 6.07 (s, 1H), 3.99 (s, 3H), 3.82-3.69 (m, 2H), 3.11 (d, J=8.5 Hz, 2H), 2.74-2.60 (m, 2H), 2.43 (d, J=10.6 Hz, 2H), 1.61 (s, 3H).

Example 64

Preparation of (R)-1-(2-chloropyridin-3-yl)ethyl (1-methyl-4-(5-((1R,5S,6r)-3-(2,2,2-trifluoroethyl)-3-azabicyclo[3.1.0]hexane-6-carboxamido)pyridin-2-yl)-1H-1,2,3-triazol-5-yl)carbamate (Compound 308)

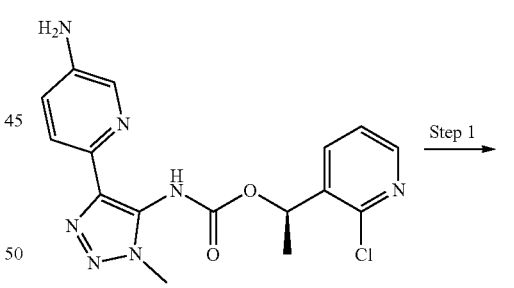

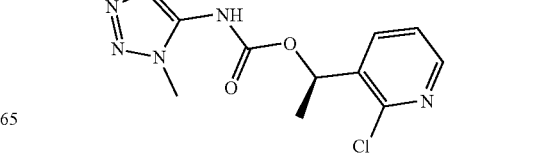

521
-continued

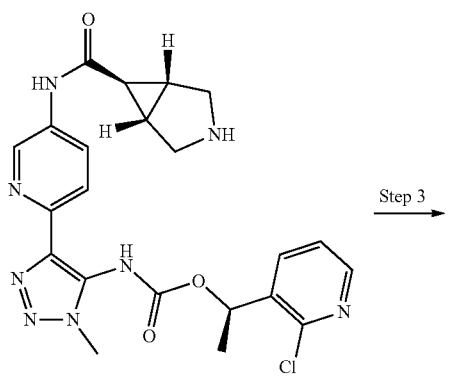

522
-continued

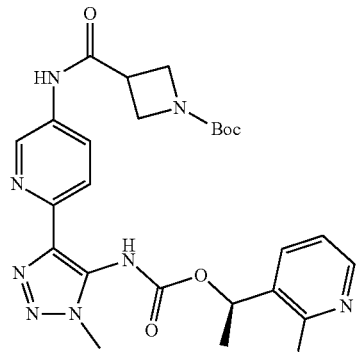

Step 3 →

Step 2 →

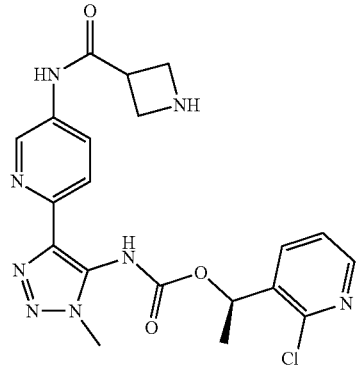

Compound 308

The title compound was prepared similarly to Example 62 using exo-3-[(tert-butoxy)carbonyl]-3-azabicyclo[3.1.0]hexane-6-carboxylic acid (0.186 mmol) in place of (1r,3r)-3-((tert-butoxycarbonyl)amino)cyclobutane-1-carboxylic acid. (MS (m/z) 565.1 [M+H]+). 1H NMR (400 MHz, Methanol-d4) δ 8.95 (s, 1H), 8.33 (s, 1H), 8.13 (d, J=7.8 Hz, 2H), 7.90 (d, J=8.8 Hz, 1H), 7.48 (s, 1H), 6.09 (d, J=6.9 Hz, 1H), 4.00 (s, 2H), 3.24 (dt, J=19.5, 9.5 Hz, 4H), 2.87-2.76 (m, 2H), 2.21 (t, J=2.9 Hz, 1H), 2.10 (t, J=2.7 Hz, 2H), 1.63 (s, 3H).

Example 65

Preparation of (R)-1-(2-chloropyridin-3-yl)ethyl (1-methyl-4-(5-(1-(2,2,2-trifluoroethyl)azetidine-3-carboxamido)pyridin-2-yl)-1H-1,2,3-triazol-5-yl) carbamate (Compound 309)

Step 3 →

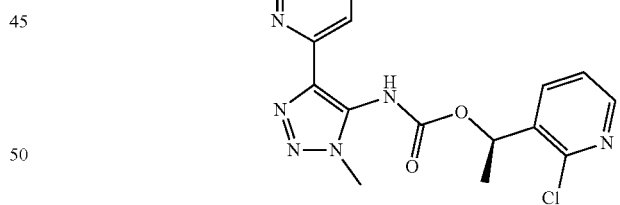

Compound 309

The title compound was prepared similarly to Example 62 using 1-(tert butoxycarbonyl)azetidine-3-carboxylic acid (0.186 mmol) in place of (1r,3r)-3-((tert-butoxycarbonyl)amino)cyclobutane-1-carboxylic acid. (MS (m/z) 539.1 [M+H]+). 1H NMR (400 MHz, Methanol-d4) δ 8.90 (s, 1H), 8.33 (s, 1H), 8.14 (d, J=9.2 Hz, 1H), 7.92 (d, J=8.4 Hz, 1H), 4.43 (d, J=7.8 Hz, 2H), 4.13 (d, J=9.1 Hz, 2H), 4.00 (s, 2H), 3.86 (q, J=8.0 Hz, 1H), 1.62 (s, 3H).

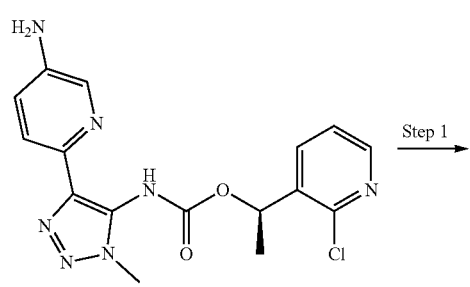

Step 1 →

Example 66

Preparation of (R)-1-(2-chloropyridin-3-yl)ethyl (4-(5-(1-amino-3,3-difluorocyclobutane-1-carboxamido)pyridin-2-yl)-1-methyl-1H-1,2,3-triazol-5-yl) carbamate (Compound 310)

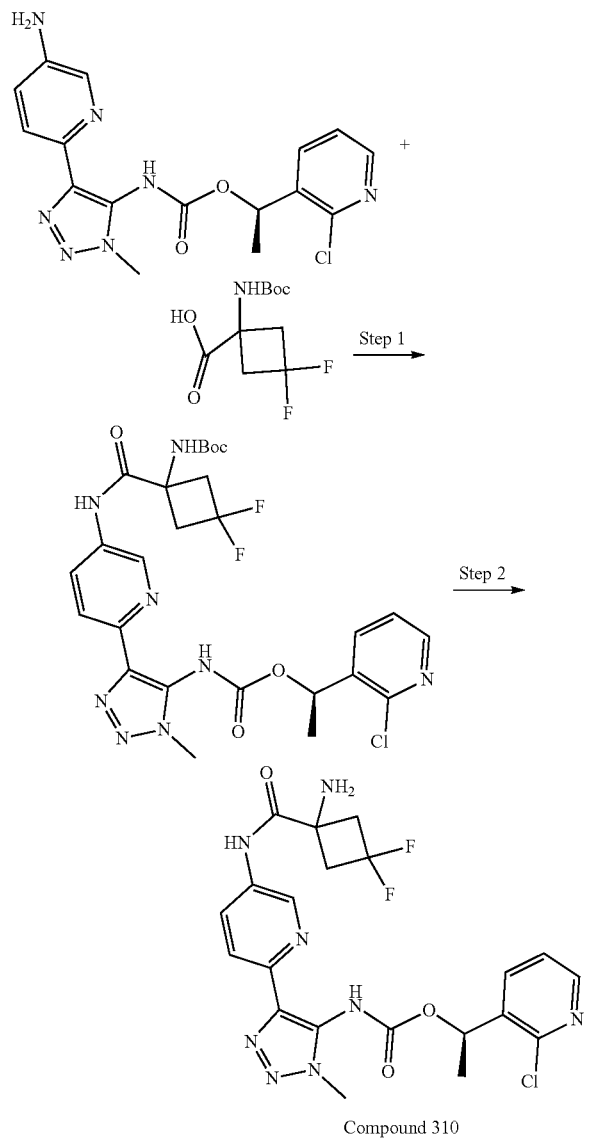

Compound 310

Step 1: (R)-1-(2-chloropyridin-3-yl)ethyl (4-(5-(1-((tert-butoxycarbonyl)amino)-3,3-difluorocyclobutane-1-carboxamido)pyridin-2-yl)-1-methyl-1H-1,2,3-triazol-5-yl) carbamate A mixture of (R)-1-(2-chloropyridin-3-yl)ethyl (4-(5-aminopyridin-2-yl)-1-methyl-1H-1,2,3-triazol-5-yl)carbamate hydrochloride (25 mg, 0.061 mmol), 1-((tert-butoxycarbonyl)amino)-3,3-difluorocyclobutane-1-carboxylic acid (31 mg, 0.122 mmol), EDCI (20 mg, 0.1 mmol) in pyridine (1 ml) was stirred 1 h at room temperature. The residue was purified by prep-HPLC with Gilson prep HPLC (Gemini column, 30-85% CH$_3$CN in H$_2$O with 0.1% TFA) to give an intermediate. MS: 607.15 (M+1).

Step 2: (R)-1-(2-chloropyridin-3-yl)ethyl (4-(5-(1-amino-3,3-difluorocyclobutane-1-carboxamido)pyridin-2-yl)-1-methyl-1H-1,2,3-triazol-5-yl)carbamate Above intermediate (20 mg) was treated with 2 mL of 4 N HCl in dioxane and the mixture was stirred at room temperature overnight. The mixture was concentrated. The residue was purified by prep-HPLC with Gilson prep HPLC (Gemini column, 30-85% CH$_3$CN in H$_2$O with 0.1% TFA) to give the product. (MS (m/z) 507 [M+H]+). 1H NMR (400 MHz, Methanol-d4) δ 8.89 (s, 1H), 8.32 (s, 1H), 8.15 (m, 1H), 7.95 (m, 1H), 7.68-7.25 (m, 2H), 6.08 (s, 1H), 4.00 (s, 3H), 3.72 (m, 2H), 3.19 (m, 2H), 1.86-1.40 (m, 3H).

Example 67

Synthesis of (R)-1-(2-chloropyridin-3-yl)ethyl(4-(5-(3-(cyclopropylamino)cyclobutane-1-carboxamido)pyridin-2-yl)-1-methyl-1H-1,2,3-triazol-5-yl)carbamate (Compound 311)

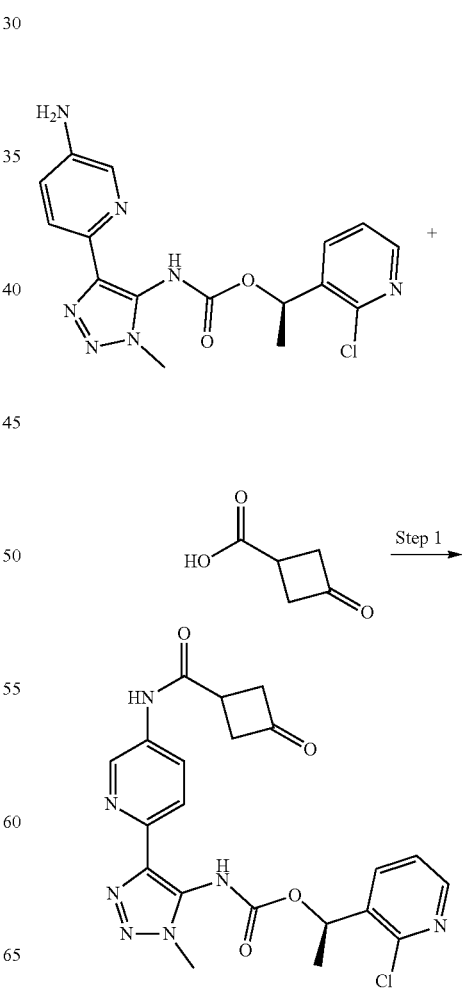

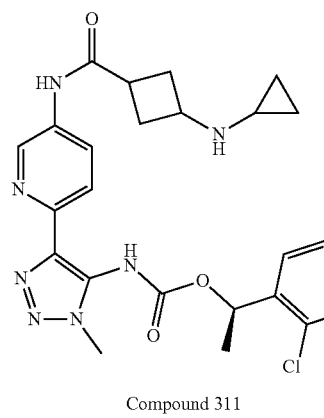

Compound 311

Step 1. (R)-1-(2-chloropyridin-3-yl)ethyl (1-methyl-4-(5-(3-oxocyclobutane-1-carboxamido)pyridin-2-yl)-1H-1,2,3-triazol-5-yl)carbamate (R)-1-(2-chloropyridin-3-yl)ethyl (4-(5-aminopyridin-2-yl)-1-methyl-1H-1,2,3-triazol-5-yl)carbamate hydrochloride (0.0975 mmol) suspended in dimethylformamide (2 mL) was treated with 3-oxocyclobutane-1-carboxylic acid (0.131 mmol), 1-ethyl-3-(3-dimethylaminopropyl)carbodiimide hydrochloride (0.292 mmol), and pyridine (0.621 mmol). The reaction mixture was stirred at room temperature for 30 min. The reaction mixture was diluted with ethyl acetate and washed with water. The layers were separated. The organic layer was concentrated to give crude (R)-1-(2-chloropyridin-3-yl)ethyl (1-methyl-4-(5-(3-oxocyclobutane-1-carboxamido)pyridin-2-yl)-1H-1,2,3-triazol-5-yl) carbamate.

Step 2. (R)-1-(2-chloropyridin-3-yl)ethyl (1-methyl-4-(5-(3-oxocyclobutane-1-carboxamido)pyridin-2-yl)-1H-1,2,3-triazol-5-yl)carbamate (R)-1-(2-chloropyridin-3-yl)ethyl(1-methyl-4-(5-(3-oxocyclobutane-1-carboxamido)pyridin-2-yl)-1H-1,2,3-triazol-5-yl)carbamate (0.0638 mmol) suspended in dichloromethane (1 mL) was treated with cyclopropanamine (0.144 mmol) and triethylamine (0.215 mmol). After stirring at room temperature for 10 min, sodium triacetoxyborohydride (0.330 mmol) was added. The reaction mixture was stirred at room temperature for 30 minutes. Trifluoroacetic acid (6.53 mmol) was added to quench the reaction. The reaction mixture was then concentrated and purified by HPLC to give (R)-1-(2-chloropyridin-3-yl)ethyl (1-methyl-4-(5-(3-oxocyclobutane-1-carboxamido)pyridin-2-yl)-1H-1,2,3-triazol-5-yl)carbamate. (MS (m/z) 511.2 [M+H]+). 1H NMR (400 MHz, Methanol-d4) δ 8.88 (s, 1H), 8.32 (s, 1H), 8.20-8.00 (m, 2H), 7.91 (d, J=8.6 Hz, 1H), 7.48 (s, 1H), 6.08 (d, J=7.1 Hz, 1H), 4.00 (s, 3H), 3.98-3.91 (m, 1H), 3.29-3.17 (m, 1H), 2.75 (ddt, J=15.7, 12.1, 8.4 Hz, 3H), 2.65-2.48 (m, 2H), 1.78-1.37 (m, 3H), 0.95 (dtt, J=7.4, 5.2, 2.8 Hz, 2H), 0.92-0.84 (m, 2H).

Example 68

Synthesis of (R)-1-(2-chloropyridin-3-yl)ethyl(4-(5-(3-acetamidobicyclo[1.1.1]pentane-1-carboxamido)pyridin-2-yl)-1-methyl-1H-1,2,3-triazol-5-yl)carbamate (Compound 312)

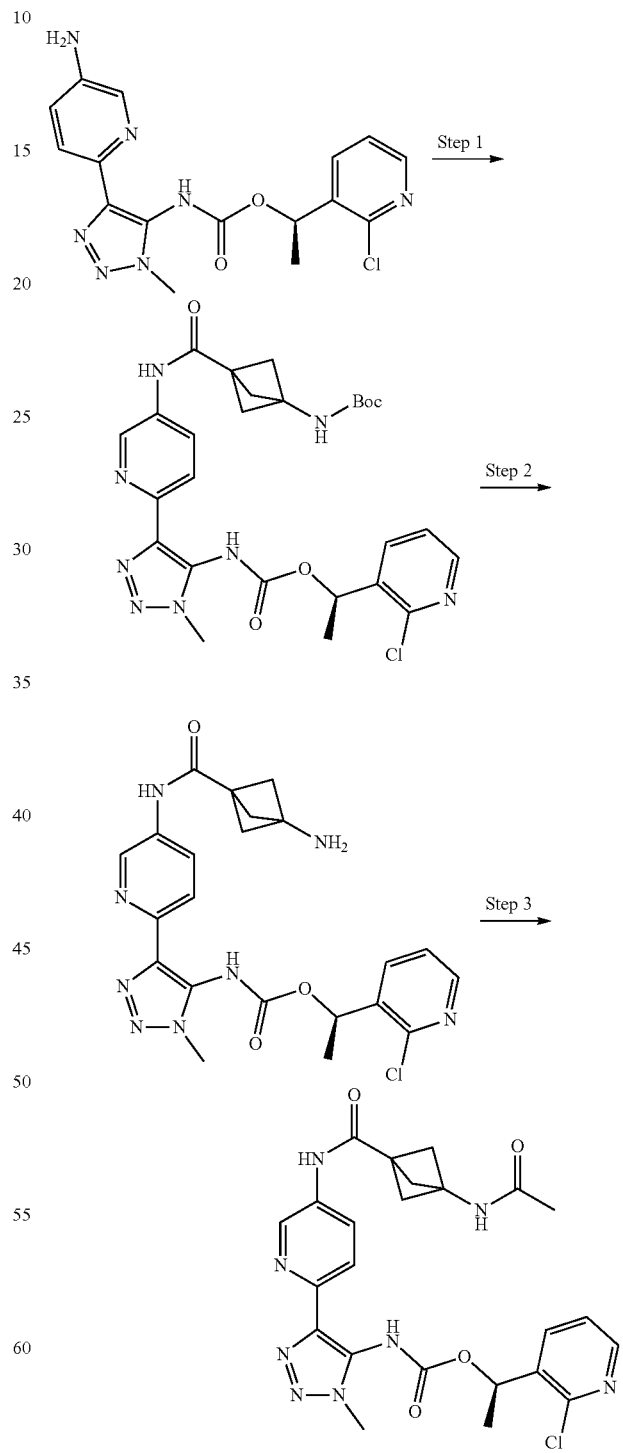

Compound 312

Step 1. (R)-1-(2-chloropyridin-3-yl)ethyl (4-(5-(3-((tert-butoxycarbonyl)amino)bicyclo[1.1.1]pentane-1-carboxamido)pyridin-2-yl)-1-methyl-1H-1,2,3-triazol-5-yl)carbamate Prepared according to procedures described in Step 1 of Example 62 using 3-((tert-butoxycarbonyl)amino)bicyclo[1.1.1]pentane-1-carboxylic acid (0.186 mmol) in place of (1r,3r)-3-((tert-butoxycarbonyl)amino)cyclobutane-1-carboxylic acid.

Step 2. (R)-1-(2-chloropyridin-3-yl)ethyl (4-(5-(3-aminobicyclo[1.1.1]pentane-1-carboxamido)pyridin-2-yl)-1-methyl-1H-1,2,3-triazol-5-yl)carbamate Prepared according to procedures described in Step 2 of Example 62.

Step 3. (R)-1-(2-chloropyridin-3-yl)ethyl (4-(5-(3-acetamidobicyclo[1.1.1]pentane-1-carboxamido)pyridin-2-yl)-1-methyl-1H-1,2,3-triazol-5-yl)carbamate (R)-1-(2-chloropyridin-3-yl)ethyl (4-(5-(3-aminobicyclo[1.1.1]pentane-1-carboxamido)pyridin-2-yl)-1-methyl-1H-1,2,3-triazol-5-yl)carbamate (0.0425 mmol) dissolved in acetonitrile was treated with triethylamine (0.287 mmol) followed by acetic anhydride (0.212 mmol). The reaction mixture was stirred at room temperature for 20 minutes. The reaction mixture was concentrated and purified by HPLC to provide the bis-acylated product. The bis-acylated product was dissolved in tetrahydrofuran (2 mL) and treated with 1N sodium hydroxide solution (800 µL). The reaction mixture was stirred at room temperature for 100 min. The reaction mixture was concentrated and purified by HPLC to give (R)-1-(2-chloropyridin-3-yl)ethyl (4-(5-(3-acetamidobicyclo[1.1.1]pentane-1-carboxamido)pyridin-2-yl)-1-methyl-1H-1,2,3-triazol-5-yl)carbamate. (MS (m/z) 525.1 [M+H]+). 1H NMR (400 MHz, Methanol-d4) δ 8.93 (s, 1H), 8.32 (s, 1H), 8.13 (dd, J=8.6, 2.6 Hz, 1H), 7.92 (d, J=8.8 Hz, 1H), 7.55 (s, 2H), 6.08 (d, J=6.4 Hz, 1H), 3.99 (s, 3H), 2.44 (s, 6H), 1.94 (d, J=8.8 Hz, 3H), 1.62 (s, 3H).

Example 69

Preparation of (R)-1-(2,5-difluoropyridin-3-yl)ethyl (4-(5-(1-cyanocyclopropane-1-carboxamido)-6-methylpyridin-2-yl)-1-methyl-1H-1,2,3-triazol-5-yl)carbamate (Compound 313)

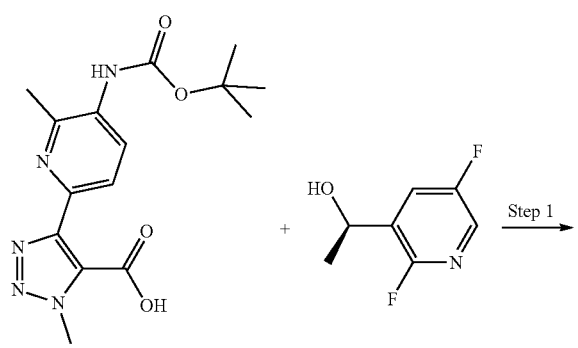

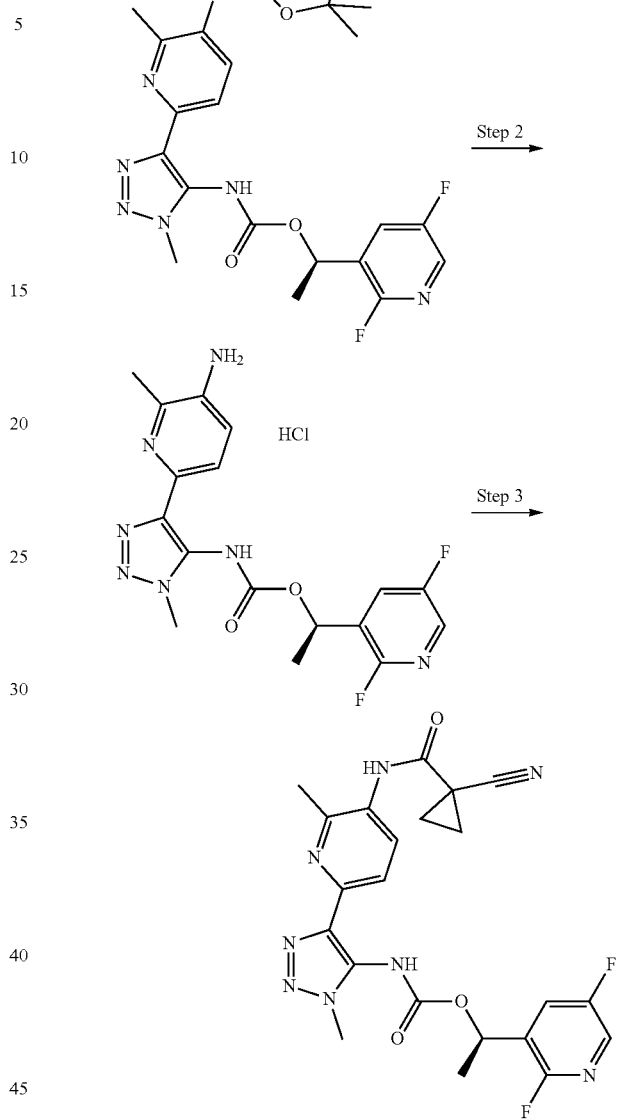

Compound 313

Step 1: tert-butyl (R)-(6-(5-(((1-(2,5-difluoropyridin-3-yl)ethoxy)carbonyl)amino)-1-methyl-1H-1,2,3-triazol-4-yl)-2-methylpyridin-3-yl)carbamate 4-(5-((tert-butoxycarbonyl)amino)-6-methylpyridin-2-yl)-1-methyl-1H-1,2,3-triazole-5-carboxylic acid (3 mmol), Azidotrimethylsilane (3 mmol), and T3P (50% in THF) (4.5 mmol) was dissolved in THF (20 mL). Triethyl amine (6 mmol) was added dropwise at RT resulting in a clear solution after 5-30 minutes. (R)-1-(2,5-difluoropyridin-3-yl)ethan-1-ol (4.5 mmol) was added and the reaction was heated at 80 C for 2 h. Silica gel was then added and the crude mixture was concentrated in vacuo and then purified by column chromatography to afford tert-butyl (R)-(6-(5-(((1-(2,5-difluoropyridin-3-yl)ethoxy)carbonyl)amino)-1-methyl-1H-1,2,3-triazol-4-yl)-2-methylpyridin-3-yl)carbamate (2.95 mmol).

Step 2: (R)-1-(2,5-difluoropyridin-3-yl)ethyl (4-(5-amino-6-methylpyridin-2-yl)-1-methyl-1H-1,2,3-triazol-5-yl)carbamate hydrogen chloride (R)-(6-(5-(((1-(2,5-difluoropyridin-3-yl)ethoxy)carbonyl)amino)-1-methyl-1H-1,2,3-triazol-4-yl)-2-methylpyridin-3-yl)carbamate (2.95 mmol) was suspended in 10 mL 4 M hydrochloric acid in dioxanes for 1 h. The mixture was then concentrated in vacuo to afford (R)-1-(2,5-difluoropyridin-3-yl)ethyl(4-(5-amino-6-methylpyridin-2-yl)-1-methyl-1H-1,2,3-triazol-5-yl)carbamate hydrogen chloride and was used without further purification.

Step 3: (R)-1-(2,5-difluoropyridin-3-yl)ethyl (4-(5-(1-cyanocyclopropane-1-carboxamido)-6-methylpyridin-2-yl)-1-methyl-1H-1,2,3-triazol-5-yl)carbamate To a mixture of (R)-1-(2,5-difluoropyridin-3-yl)ethyl (4-(5-amino-6-methylpyridin-2-yl)-1-methyl-1H-1,2,3-triazol-5-yl)carbamate hydrogen chloride (0.127 mmol) in pyridine (1 mL) was added 1-cyanocyclopropane-1-carboxylic acid (0.254 mmol) and N-Ethyl-N'-(3-dimethylaminopropyl) carbodiimide hydrochloride (0.139 mmol). The reaction mixture was left with magnetic stirring for 2 hours at which point water (1 mL) was added the crude mixture was purified by HPLC to provide (R)-1-(2,5-difluoropyridin-3-yl)ethyl (4-(5-(1-cyanocyclopropane-1-carboxamido)-6-methylpyridin-2-yl)-1-methyl-1H-1,2,3-triazol-5-yl)carbamate. (MS (m/z) 483 [M+H]+). 1H NMR (400 MHz, Methanol-d4) δ 8.17-7.66 (m, 4H), 5.95 (s, 1H), 3.99 (s, 3H), 2.46 (s, 3H), 1.82-1.39 (m, 7H).

Example 70

Preparation of (R)-1-(2,5-difluoropyridin-3-yl)ethyl (1-methyl-4-(6-methyl-5-(2-(trifluoromethyl)pyrimidine-5-carboxamido)pyridin-2-yl)-1H-1,2,3-triazol-5-yl)carbamate (Compound 314)

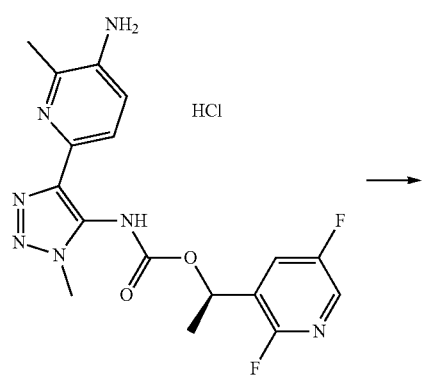

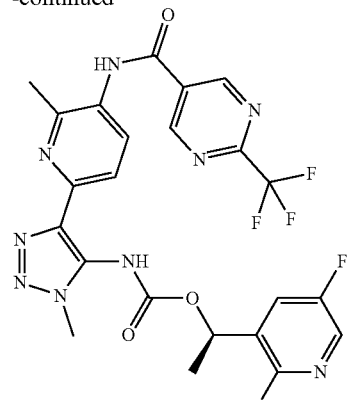

Compound 314

Step 1: (R)-1-(2,5-difluoropyridin-3-yl)ethyl (1-methyl-4-(6-methyl-5-(2-(trifluoromethyl)pyrimidine-5-carboxamido)pyridin-2-yl)-1H-1,2,3-triazol-5-yl)carbamate To a mixture of (R)-1-(2,5-difluoropyridin-3-yl)ethyl (4-(5-amino-6-methylpyridin-2-yl)-1-methyl-1H-1,2,3-triazol-5-yl)carbamate hydrochloride (0.127 mmol) in pyridine (0.5 mL) was added 2-(trifluoromethyl)pyrimidine-5-carboxylic acid (0.254 mmol) and N-Ethyl-N'-(3-dimethylaminopropyl) carbodiimide hydrochloride (0.139 mmol). The reaction mixture was left with magnetic stirring for 2 hours at which point water (1 mL) was added the crude mixture was purified by HPLC to provide (R)-1-(2,5-difluoropyridin-3-yl)ethyl (1-methyl-4-(6-methyl-5-(2-(trifluoromethyl)pyrimidine-5-carboxamido)pyridin-2-yl)-1H-1,2,3-triazol-5-yl)carbamate. LCMS (MS (m/z) 564 [M+H]+). 1H NMR (400 MHz, Methanol-d4) δ 9.47 (s, 2H), 8.22-7.60 (m, 4H), 5.97 (s, 1H), 4.01 (s, 3H), 2.53 (s, 3H), 1.58 (d, J=27.1 Hz, 3H).

Example 71

Preparation of (R)-1-(2-chloropyridin-3-yl)ethyl (4-(6-fluoro-5-(6-(trifluoromethyl)nicotinamido)pyridin-2-yl)-1-methyl-1H-1,2,3-triazol-5-yl)carbamate (Compound 315)

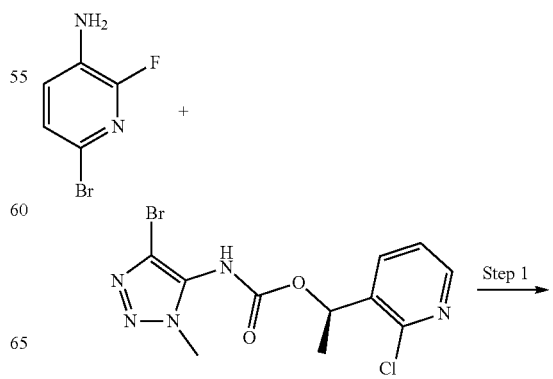

-continued

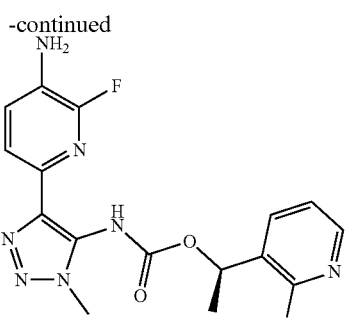

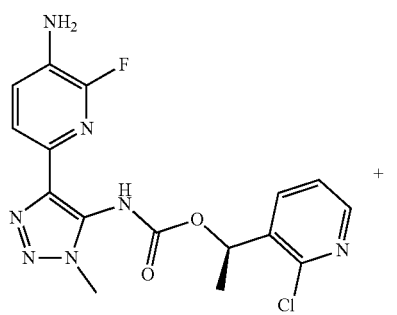

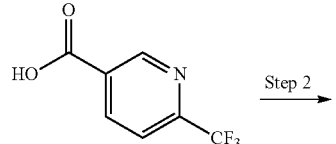

Step 2 →

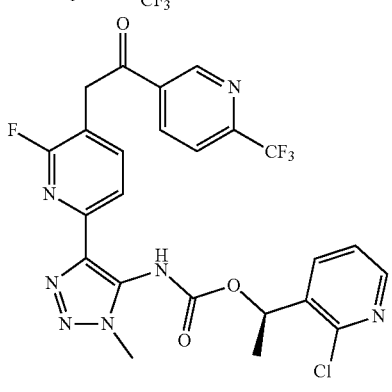

Compound 315

Step 1: (R)-1-(2-chloropyridin-3-yl)ethyl (4-(5-amino-6-fluoropyridin-2-yl)-1-methyl-1H-1,2,3-triazol-5-yl)carbamate To a solution of (R)-1-(2-chloropyridin-3-yl)ethyl (4-bromo-1-methyl-1H-1,2,3-triazol-5-yl)carbamate (1.4 mmol) in tetrahydrofuran (15 mL) at −78° C. was added a 1M solution of lithium bis(trimethylsilyl)amide (1.4 mmol). After 15 minutes, a 2.5 M solution of n-butyllithium (3.5 mmol) was added. After 1 hour, a 2 M solution of zinc chloride (3.5 mmol) was added, and the reaction was stirred at 15° C. for 30 minutes. At this point 6-bromo-2-fluoropyridin-3-amine (1.7 mmol) and [1,1′-bis(diphenylphosphino)ferrocene]dichloropalladium(II) (0.14 mmol) were added to the reaction and the reaction mixture was heated to 80° C. for 3 hours. After completion of the reaction, the mixture was cooled and quenched with sat. NaHCO$_3$, and extracted with ethyl acetate (30 mL, ×2). The organics were separated, dried over sodium sulfate, and filtered through a plug of silica and used in the next step without further purification.

Step 2: (R)-1-(2-chloropyridin-3-yl)ethyl (4-(6-fluoro-5-(6-(trifluoromethyl)nicotinamido)pyridin-2-yl)-1-methyl-1H-1,2,3-triazol-5-yl)carbamate To a mixture of (R)-1-(2-chloropyridin-3-yl)ethyl (4-(5-amino-6-fluoropyridin-2-yl)-1-methyl-1H-1,2,3-triazol-5-yl)carbamate (0.15 mmol) in pyridine (1 mL) was added 6-(trifluoromethyl)nicotinic acid (0.3 mmol) and N-ethyl-N′-(3-dimethylaminopropyl) carbodiimide hydrochloride (0.3 mmol). The reaction mixture was left with magnetic stirring for 2 hours at which point water (1 mL) was added the crude mixture was purified by HPLC to provide (R)-1-(2-chloropyridin-3-yl)ethyl (4-(6-fluoro-5-(6-(trifluoromethyl)nicotinamido)pyridin-2-yl)-1-methyl-1H-1,2,3-triazol-5-yl)carbamate (Compound 315). (MS (m/z) 565 [M+H]+). 1H NMR (400 MHz, Methanol-d4) δ 9.31-9.13 (m, 1H), 8.67-8.43 (m, 2H), 8.43-8.06 (m, 2H), 8.07-7.80 (m, 2H), 7.49 (s, 1H), 6.12 (q, J=6.6 Hz, 1H), 4.00 (s, 3H), 1.55 (s, 3H).

Example 72

Preparation of (R)-1-(2-chloropyridin-3-yl)ethyl (4-(5-(1-cyanocyclopropane-1-carboxamido)-6-fluoropyridin-2-yl)-1-methyl-1H-1,2,3-triazol-5-yl)carbamate (Compound 316)

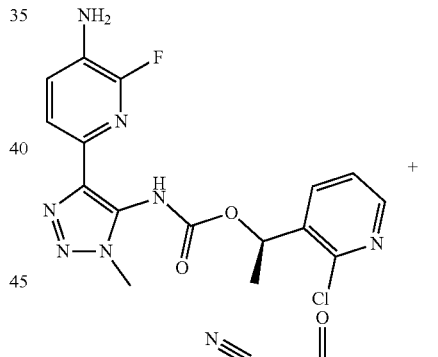

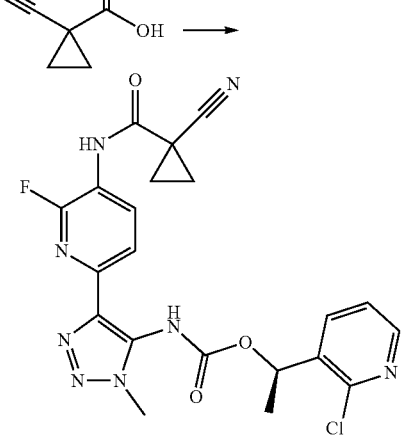

Compound 316

To a mixture of (R)-1-(2-chloropyridin-3-yl)ethyl (4-(5-amino-6-fluoropyridin-2-yl)-1-methyl-1H-1,2,3-triazol-5-yl)carbamate (0.15 mmol) in pyridine (1 mL) was added 1-cyanocyclopropane-1-carboxylic acid (0.3 mmol) and N-ethyl-N'-(3-dimethylaminopropyl) carbodiimide hydrochloride (0.3 mmol). The reaction mixture was left with magnetic stirring for 2 hours at which point water (1 mL) was added the crude mixture was purified by HPLC to provide (R)-1-(2-chloropyridin-3-yl)ethyl (4-(5-(1-cyanocyclopropane-1-carboxamido)-6-fluoropyridin-2-yl)-1-methyl-1H-1,2,3-triazol-5-yl)carbamate. (MS (m/z) 485 [M+H]+). 1H NMR (400 MHz, Methanol-d4) δ 8.49-8.24 (m, 2H), 8.24-8.04 (m, 1H), 7.93 (d, J=8.5 Hz, 1H), 7.68-7.26 (m, 1H), 6.11 (q, J=6.7 Hz, 1H), 3.98 (s, 3H), 1.92-1.50 (m, 7H).

Example 73

Preparation of (R)-1-(2-chloropyridin-3-yl)ethyl (4-(4-fluoro-5-(6-(trifluoromethyl)nicotinamido)pyridin-2-yl)-1-methyl-1H-1,2,3-triazol-5-yl)carbamate (Compound 317)

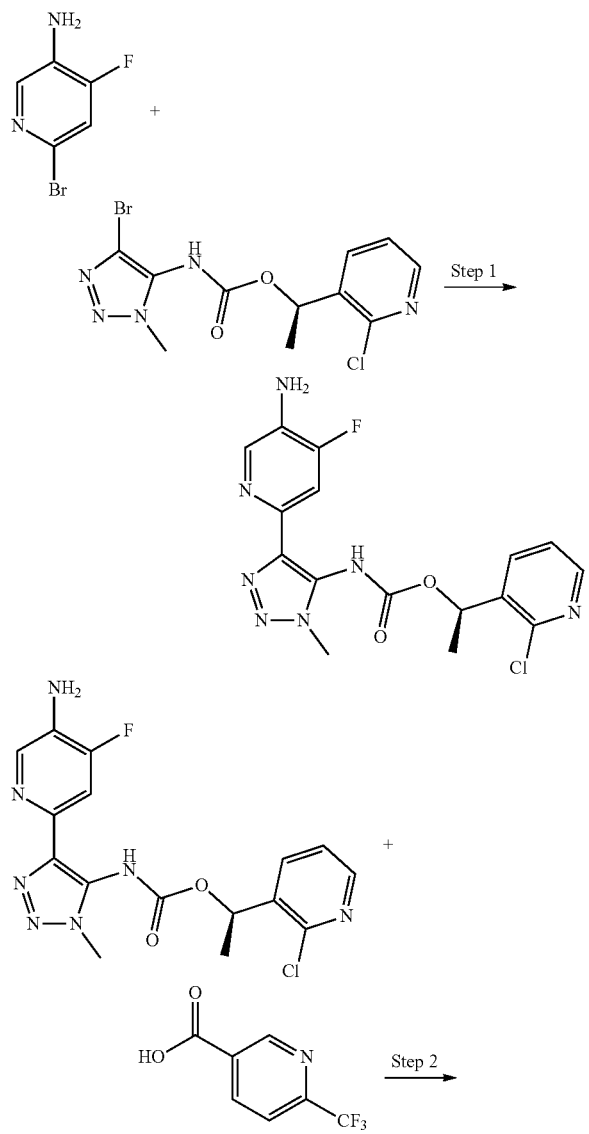

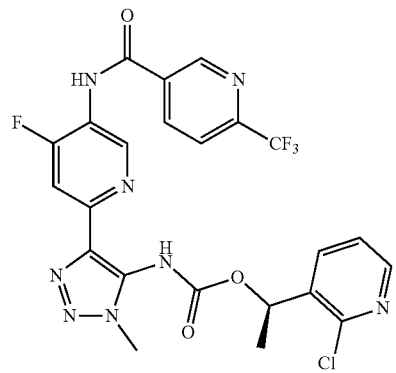

Compound 317

Step 1: (R)-1-(2-chloropyridin-3-yl)ethyl (4-(5-amino-4-fluoropyridin-2-yl)-1-methyl-1H-1,2,3-triazol-5-yl)carbamate To a solution of (R)-1-(2-chloropyridin-3-yl)ethyl (4-bromo-1-methyl-1H-1,2,3-triazol-5-yl)carbamate (1.4 mmol) in tetrahydrofuran (15 mL) at −78° C. was added a 1M solution of lithium bis(trimethylsilyl)amide (1.4 mmol). After 15 minutes, a 2.5 M solution of n-butyllithium (3.5 mmol) was added. After 1 hour, a 2 M solution of zinc chloride (3.5 mmol) was added, and the reaction was stirred at 15° C. for 30 minutes. At this point 6-bromo-4-fluoropyridin-3-amine (1.7 mmol) and [1,1'-bis(diphenylphosphino)ferrocene]dichloropalladium(II) (0.14 mmol) were added to the reaction and the reaction mixture was heated to 80° C. for 3 hours. After completion of the reaction, the mixture was cooled and quenched with sat. NaHCO₃, and extracted with ethyl acetate (30 mL, ×2). The organics were separated, dried over sodium sulfate, and filtered through a plug of silica and used in the next step without further purification.

Step 2: (R)-1-(2-chloropyridin-3-yl)ethyl (4-(4-fluoro-5-(6-(trifluoromethyl)nicotinamido)pyridin-2-yl)-1-methyl-1H-1,2,3-triazol-5-yl)carbamate To a mixture of (R)-1-(2-chloropyridin-3-yl)ethyl (4-(5-amino-6-fluoropyridin-2-yl)-1-methyl-1H-1,2,3-triazol-5-yl)carbamate (0.15 mmol) in pyridine (1 mL) was added 6-(trifluoromethyl)nicotinic acid (0.3 mmol) and N-Ethyl-N'-(3-dimethylaminopropyl) carbodiimide hydrochloride (0.3 mmol). The reaction mixture was left with magnetic stirring for 2 hours at which point water (1 mL) was added the crude mixture was purified by HPLC to provide (R)-1-(2-chloropyridin-3-yl)ethyl (4-(4-fluoro-5-(6-(trifluoromethyl)nicotinamido)pyridin-2-yl)-1-methyl-1H-1,2,3-triazol-5-yl)carbamate. (MS (m/z) 564.9 [M+H]+). 1H NMR (400 MHz, Methanol-d4) δ 9.38-9.20 (m, 1H), 8.60 (d, J=8.1 Hz, 1H), 8.35-8.26 (m, 1H), 8.07-7.93 (m, 2H), 7.88 (d, J=11.3 Hz, 1H), 7.63-7.34 (m, 2H), 6.16-6.03 (m, 1H), 4.01 (s, 3H), 1.55 (s, 3H).

Example 74

Preparation of (R)-1-(2-chloropyridin-3-yl)ethyl (4-(6-fluoro-5-(2-(trifluoromethyl)pyrimidine-5-carboxamido)pyridin-2-yl)-1-methyl-1H-1,2,3-triazol-5-yl)carbamate (Compound 318)

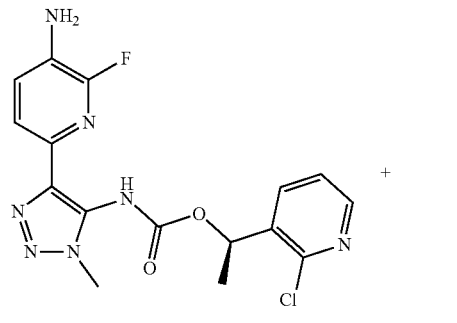

+

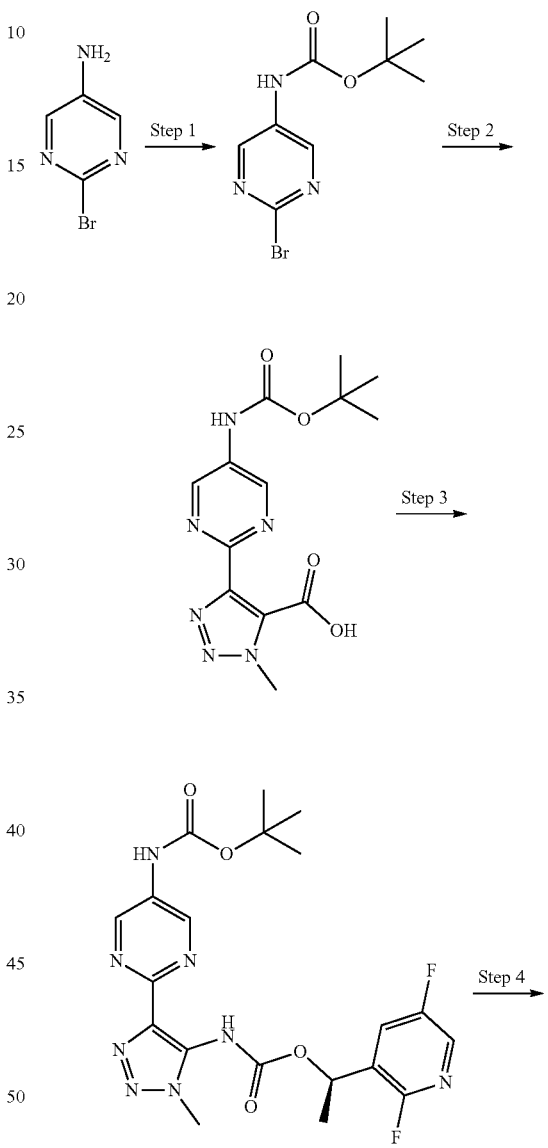

Compound 318

To a mixture of (R)-1-(2-chloropyridin-3-yl)ethyl (4-(5-amino-6-fluoropyridin-2-yl)-1-methyl-1H-1,2,3-triazol-5-yl)carbamate (0.15 mmol) in pyridine (1 mL) was added 2-(trifluoromethyl)pyrimidine-5-carboxylic acid (0.3 mmol) and N-Ethyl-N'-(3-dimethylaminopropyl) carbodiimide hydrochloride (0.3 mmol). The reaction mixture was left with magnetic stirring for 2 hours at which point water (1 mL) was added the crude mixture was purified by HPLC to provide (R)-1-(2-chloropyridin-3-yl)ethyl (4-(6-fluoro-5-(2-(trifluoromethyl)pyrimidine-5-carboxamido)pyridin-2-yl)-1-methyl-1H-1,2,3-triazol-5-yl)carbamate (MS (m/z) 566 [M+H]+). 1H NMR (400 MHz, Methanol-d4) δ 9.46 (s, 2H), 8.57 (dd, J=9.8, 8.2 Hz, 1H), 8.45-8.02 (m, 2H), 7.98 (d, J=8.2 Hz, 1H), 7.49 (s, 1H), 6.12 (q, J=6.5 Hz, 1H), 4.00 (s, 3H), 1.66 (s, 3H).

Example 75

Preparation of (R)-1-(2,5-difluoropyridin-3-yl)ethyl (4-(5-(6-chloronicotinamido)pyrimidin-2-yl)-1-methyl-1H-1,2,3-triazol-5-yl)carbamate (Compound 319)

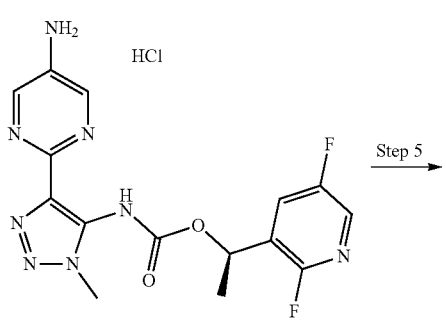

-continued

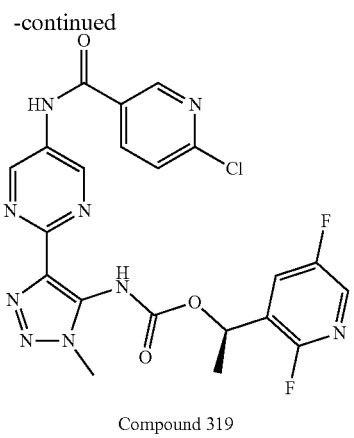

Compound 319

Step 1: tert-butyl (2-bromopyrimidin-5-yl)carbamate

To a solution of 2-bromopyrimidin-5-amine (23 mmol) in THF (28 mL) was added di-tert-butyl dicarbonate (34.4 mmol). The reaction was heated to 70° C. for 16 h, followed by addition of di-tert-butyl dicarbonate (18.3 mmol). The reaction was then stirred at 70° C. for 2 h. The reaction mixture was concentrated to provide tert-butyl (2-bromopyrimidin-5-yl)carbamate.

Step 2: 4-(5-((tert-butoxycarbonyl)amino)pyrimidin-2-yl)-1-methyl-1H-1,2,3-triazole-5-carboxylic acid (Intermediate 9)

To a solution of 4-bromo-1-methyl-1H-1,2,3-triazole-5-carboxylic acid (48.5 mmol) in tetrahydrofuran (500 mL) at −70° C. was added a 1M solution of lithium bis(trimethylsilyl)amide (53.4 mmol). After 15 minutes, a 2.5 M solution of n-butyllithium (101.8 mmol) was added. After 1 hour, a 2 M solution of zinc chloride (101.9 mmol) was added, and the reaction was stirred at 15° C. for 30 minutes. At this point tert-butyl (2-bromopyrimidin-5-yl)carbamate (29.1 mmol) and [1,1'-bis(diphenylphosphino)ferrocene]dichloropalladium(II) (4.85 mmol) were added to the reaction and the reaction mixture was heated to 90° C. for 16 h. After completion of the reaction, the mixture was cooled and aqueous 2M sodium hydroxide (800 mL) was added. The organics were separated, and aqueous layer was extracted with methyl tert-butyl ether (500 mL×2). The organics were discarded, and the aqueous layer was treated with 12M HCl (140 mL) and petroleum ether (160 mL). The product crashed out and was filtered and washed with 30:1 methyl tert-butyl ether/dichloromethane (70 mL), then purified by column chromatography, providing 4-(5-((tert-butoxycarbonyl)amino)pyrimidin-2-yl)-1-methyl-1H-1,2,3-triazole-5-carboxylic acid (Intermediate 9).

Step 3: tert-butyl (R)-(2-(5-(((1-(2,5-difluoropyridin-3-yl)ethoxy)carbonyl)amino)-1-methyl-1H-1,2,3-triazol-4-yl)pyrimidin-5-yl)carbamate 4-(5-((tert-butoxycarbonyl)amino)pyrimidin-2-yl)-1-methyl-1H-1,2,3-triazole-5-carboxylic acid (Intermediate 9) (0.97 mmol), Azidotrimethylsilane (1.46 mmol), and T3P (50% in DMF) (1.46 mmol) was dissolved in THF (5 mL). Triethylamine (1.95 mmol) was added dropwise at room temperature. The reaction was heated to 70° C. for 50 minutes before (R)-1-(2,5-difluoropyridin-3-yl)ethan-1-ol (1.45 mmol) was added and the reaction was heated at 70° C. for another 6 hours. The reaction was concentrated and then purified by column chromatography to provide tert-butyl (R)-(2-(5-(((1-(2,5-difluoropyridin-3-yl)ethoxy)carbonyl)amino)-1-methyl-1H-1,2,3-triazol-4-yl)pyrimidin-5-yl)carbamate.

Step 4: (R)-1-(2,5-difluoropyridin-3-yl)ethyl (4-(5-aminopyrimidin-2-yl)-1-methyl-1H-1,2,3-triazol-5-yl)carbamate To a solution of tert-butyl (R)-(2-(5-(((1-(2,5-difluoropyridin-3-yl)ethoxy)carbonyl)amino)-1-methyl-1H-1,2,3-triazol-4-yl)pyrimidin-5-yl)carbamate (0.52 mmol) in dichloromethane (3.4 mL) was added a 4M solution of HCl in 1,4-dioxane (3.8 mL). The reaction was stirred for 2 h at room temperature. The reaction was concentrated to provide (R)-1-(2,5-difluoropyridin-3-yl)ethyl (4-(5-aminopyrimidin-2-yl)-1-methyl-1H-1,2,3-triazol-5-yl)carbamate as the hydrochloride salt.

Step 5: (R)-1-(2,5-difluoropyridin-3-yl)ethyl (4-(5-(6-chloronicotinamido)pyrimidin-2-yl)-1-methyl-1H-1,2,3-triazol-5-yl)carbamate To a mixture of (R)-1-(2,5-difluoropyridin-3-yl)ethyl (4-(5-aminopyrimidin-2-yl)-1-methyl-1H-1,2,3-triazol-5-yl)carbamate hydrochloride (0.073 mmol) in pyridine (1 mL) was added 6-chloronicotinic acid (0.082 mmol) and N-Ethyl-N'-(3-dimethylaminopropyl) carbodiimide hydrochloride (0.087 mmol). The reaction mixture was stirred for 1 hour then concentrated. The residue was taken up in acetonitrile and water (2 mL) and purified by HPLC to provide (R)-1-(2,5-difluoropyridin-3-yl)ethyl (4-(5-(6-chloronicotinamido)pyrimidin-2-yl)-1-methyl-1H-1,2,3-triazol-5-yl)carbamate (Compound 319). (MS (m/z) 516.0 [M+H]+). 1H NMR (400 MHz, Methanol-d4) δ 9.19 (s, 2H), 8.98 (d, J=2.5 Hz, 1H), 8.37 (dd, J=8.3, 2.5 Hz, 1H), 8.04 (s, 1H), 7.71-7.59 (m, 2H), 5.96 (d, J=6.2 Hz, 1H), 4.01 (s, 3H), 1.61 (s, 3H).

Example 76

Preparation of (R)-1-(2,5-difluoropyridin-3-yl)ethyl (4-(5-(6-chloronicotinamido)pyrazin-2-yl)-1-methyl-1H-1,2,3-triazol-5-yl)carbamate (Compound 320)

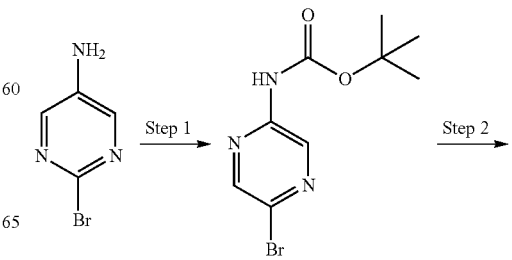

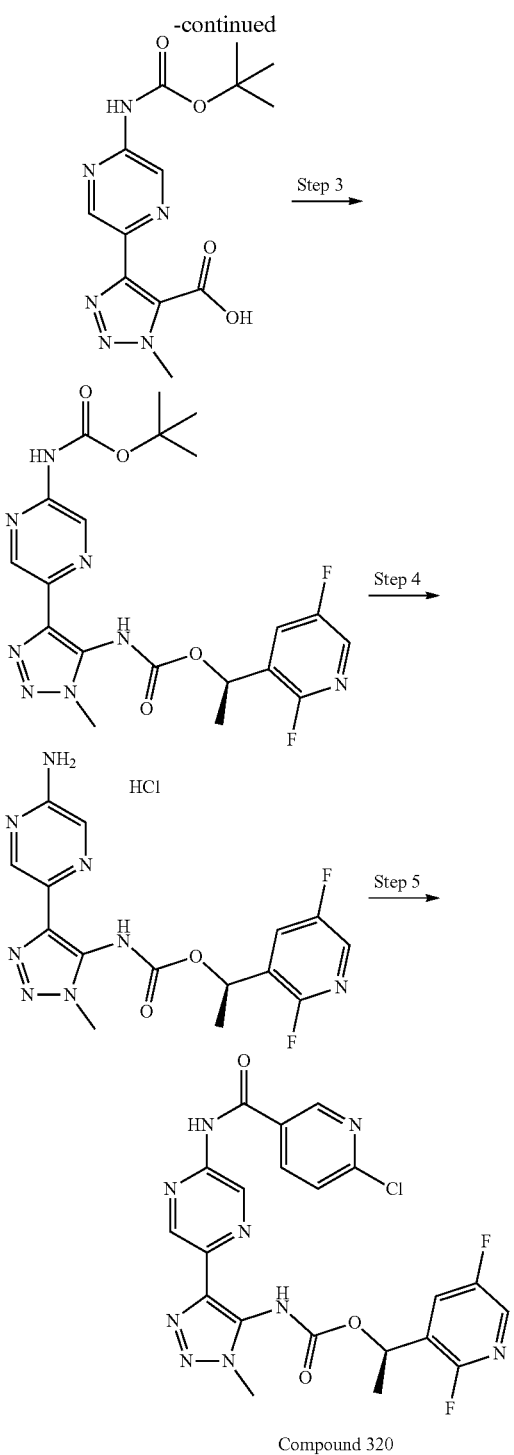

Compound 320

Step 1: tert-butyl (5-bromopyrazin-2-yl)carbamate

To a solution of 5-bromopyrazin-2-amine (689 mmol) in DCM (840 mL) was added diisopropylethylamine (2.07 mol), DMAP (689 mmol), and di-tert-butyl dicarbonate (34.4 mmol) at 0° C. The reaction was stirred at room temperature for 16 hours. The reaction mixture was concentrated, then purified by column chromatography to provide tert-butyl (5-bromopyrazin-2-yl)carbamate.

Step 2: 4-(5-((tert-butoxycarbonyl)amino)pyrazin-2-yl)-1-methyl-1H-1,2,3-triazole-5-carboxylic acid To a solution of 4-bromo-1-methyl-1H-1,2,3-triazole-5-carboxylic acid (242 mmol) in tetrahydrofuran (2.5 L) at −70° C. was added a 1M solution of lithium bis(trimethylsilyl)amide (266 mmol). After 15 minutes, a 2.5 M solution of n-butyllithium (507.5 mmol) was added. After 1 hour, a 2 M solution of zinc chloride (509.7 mmol) was added, and the reaction was stirred at 15° C. for 30 minutes. At this point tert-butyl (5-bromopyrazin-2-yl)carbamate (218 mmol) and [1,1'-bis(diphenylphosphino)ferrocene]dichloropalladium(II) (24.2 mmol) were added to the reaction and the reaction mixture was heated to 90° C. for 16 h. After completion of the reaction, the mixture was cooled and aqueous 2M sodium hydroxide (1.5 L) was added. The organics were separated, and aqueous layer was extracted with methyl tert-butyl ether (2.0 L×2). The organics were discarded, and the aqueous layer was treated with 12M HCl (250 mL) and methyl tert-butyl ether (900 mL). The product crashed out and was filtered and washed with methyl tert-butyl ether (300 mL), providing 4-(5-((tert-butoxycarbonyl)amino)pyrazin-2-yl)-1-methyl-1H-1,2,3-triazole-5-carboxylic acid.

Step 3: tert-butyl (R)-(5-(5-(((1-(2,5-difluoropyridin-3-yl)ethoxy)carbonyl)amino)-1-methyl-1H-1,2,3-triazol-4-yl)pyrazin-2-yl)carbamate 4-(5-((tert-butoxycarbonyl)amino)pyrazin-2-yl)-1-methyl-1H-1,2,3-triazole-5-carboxylic acid (0.62 mmol), Azidotrimethylsilane (0.94 mmol), and T3P (50% in DMF) (0.94 mmol) was dissolved in THF (5 mL). Triethylamine (1.25 mmol) was added dropwise at room temperature, followed by (R)-1-(2,5-difluoropyridin-3-yl)ethan-1-ol (0.93 mmol). The reaction was heated at 70° C. for 6 hours. The reaction was concentrated and then purified by column chromatography to provide tert-butyl (R)-(5-(5-(((1-(2,5-difluoropyridin-3-yl)ethoxy)carbonyl)amino)-1-methyl-1H-1,2,3-triazol-4-yl)pyrazin-2-yl)carbamate.

Step 4: (R)-1-(2,5-difluoropyridin-3-yl)ethyl (4-(5-aminopyrazin-2-yl)-1-methyl-1H-1,2,3-triazol-5-yl)carbamate (Intermediate 10)

To a solution of tert-butyl (R)-(5-(5-(((1-(2,5-difluoropyridin-3-yl)ethoxy)carbonyl)amino)-1-methyl-1H-1,2,3-triazol-4-yl)pyrazin-2-yl)carbamate (0.52 mmol) in dichloromethane (3.4 mL) was added a 4M solution of HCl in 1,4-dioxane (3.8 mL). The reaction was stirred for 2 h at room temperature. The reaction was concentrated to provide (R)-1-(2,5-difluoropyridin-3-yl)ethyl (4-(5-aminopyrazin-2-yl)-1-methyl-1H-1,2,3-triazol-5-yl)carbamate as the hydrochloride salt (Intermediate 10).

Step 5: (R)-1-(2,5-difluoropyridin-3-yl)ethyl (4-(5-(6-chloronicotinamido)pyrazin-2-yl)-1-methyl-1H-1,2,3-triazol-5-yl)carbamate To a mixture of (R)-1-(2,5-difluoropyridin-3-yl)ethyl (4-(5-aminopyrazin-2-yl)-1-methyl-1H-1,2,3-triazol-5-yl)carbamate hydrochloride (Intermediate 10) (0.073 mmol) in pyridine (1 mL) was added 6-chloronicotinic acid (0.082 mmol) and N-Ethyl-N'-(3-dimethylaminopropyl) carbodiimide hydrochloride (0.087 mmol). The reaction mixture was stirred for 1 h then concentrated. The residue was taken up in acetonitrile and water (2 mL) and purified by HPLC to provide (R)-1-(2,5-difluoropyridin-3-yl)ethyl (4-(5-(6-chloronicotinamido)pyrazin-2-yl)-1-methyl-1H-1,2,3-triazol-5-yl)carbamate (Compound 320). (MS (m/z) 515.9 [M+H]+). 1H NMR (400 MHz, Methanol-d4) δ 9.44 (s, 1H), 9.01-8.90 (m, 2H), 8.38 (dd, J=8.4, 2.5 Hz, 1H), 8.09-7.98 (m, 2H), 7.64 (dd, J=8.3, 0.7 Hz, 1H), 5.95 (d, J=7.0 Hz, 1H), 4.00 (s, 3H), 1.62 (s, 3H).

Example 77

Preparation of (R)-1-(2,5-difluoropyridin-3-yl)ethyl (4-(5-(6-(difluoromethyl)nicotinamido)pyrazin-2-yl)-1-methyl-1H-1,2,3-triazol-5-yl)carbamate (Compound 321)

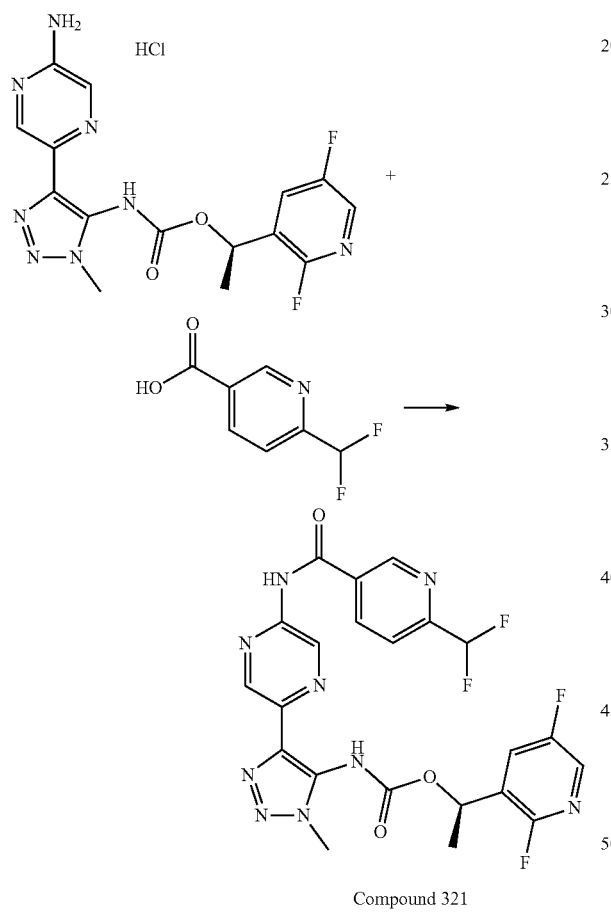

Compound 321

Following the procedure described in Example 76 for the preparation of (R)-1-(2,5-difluoropyridin-3-yl)ethyl (4-(5-(6-chloronicotinamido)pyrazin-2-yl)-1-methyl-1H-1,2,3-triazol-5-yl)carbamate, using 6-(difluoromethyl)nicotinic acid (0.08 mmol) in place of 6-chloronicotinic acid, (R)-1-(2,5-difluoropyridin-3-yl)ethyl (4-(5-(6-(difluoromethyl)nicotinamido)pyrazin-2-yl)-1-methyl-1H-1,2,3-triazol-5-yl)carbamate was obtained (Compound 321). (MS (m/z) 532.0 [M+H]+). 1H NMR (400 MHz, Methanol-d4) δ 9.46 (d, J=1.5 Hz, 1H), 9.29-9.16 (m, 1H), 8.97 (d, J=1.6 Hz, 1H), 8.55 (dd, J=8.2, 2.2 Hz, 1H), 8.05 (s, 1H), 7.93-7.78 (m, 2H), 6.83 (t, J=55.0 Hz, 1H), 5.95 (d, J=6.8 Hz, 1H), 4.00 (s, 3H), 1.62 (s, 3H).

Example 78

Preparation of (R)-1-(2,5-difluoropyridin-3-yl)ethyl (1-methyl-4-(5-(6-(trifluoromethyl)nicotinamido)pyrazin-2-yl)-1H-1,2,3-triazol-5-yl)carbamate (Compound 322)

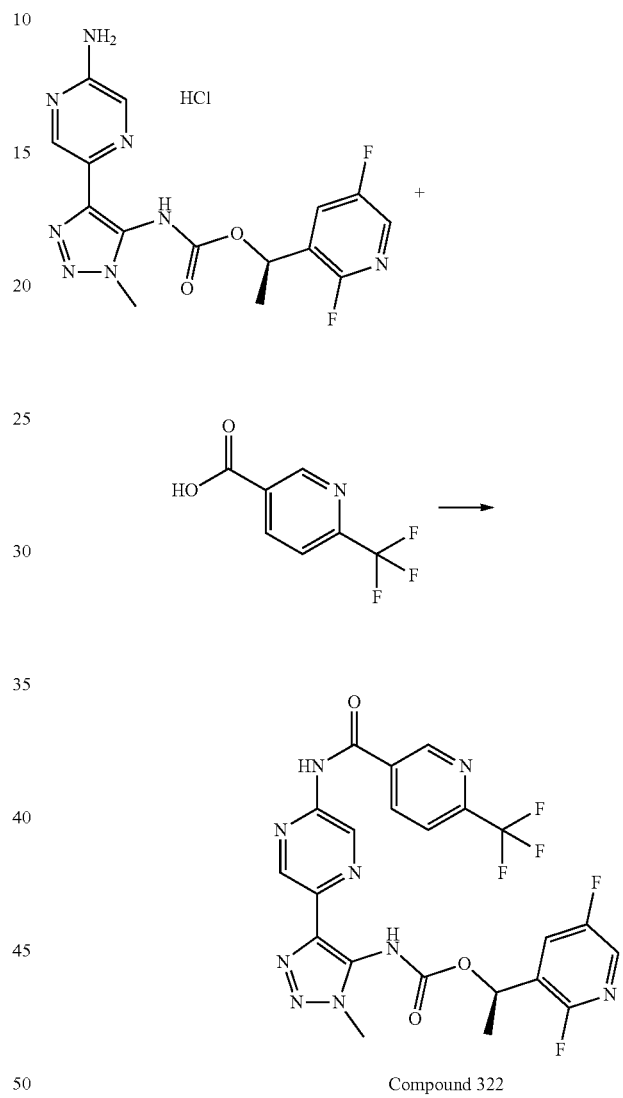

Compound 322

Following the procedure described in Example 76 for the preparation of (R)-1-(2,5-difluoropyridin-3-yl)ethyl (4-(5-(6-chloronicotinamido)pyrazin-2-yl)-1-methyl-1H-1,2,3-triazol-5-yl)carbamate, using 6-(trifluoromethyl)nicotinic acid (0.08 mmol) in place of 6-chloronicotinic acid, (R)-1-(2,5-difluoropyridin-3-yl)ethyl (1-methyl-4-(5-(6-(trifluoromethyl)nicotinamido)pyrazin-2-yl)-1H-1,2,3-triazol-5-yl)carbamate was obtained (Compound 322). (MS (m/z) 549.9 [M+H]+). 1H NMR (400 MHz, Methanol-d4) δ 9.49 (d, J=20.4 Hz, 1H), 9.27 (d, J=2.1 Hz, 1H), 8.98 (d, J=1.5 Hz, 1H), 8.70-8.50 (m, 1H), 8.11-7.70 (m, 3H), 5.95 (d, J=6.9 Hz, 1H), 4.00 (s, 3H), 1.63 (s, 3H).

Example 79

Preparation of (R)-1-(2,5-difluoropyridin-3-yl)ethyl (4-(5-(2,3-difluoroisonicotinamido)pyrazin-2-yl)-1-methyl-1H-1,2,3-triazol-5-yl)carbamate (Compound 323)

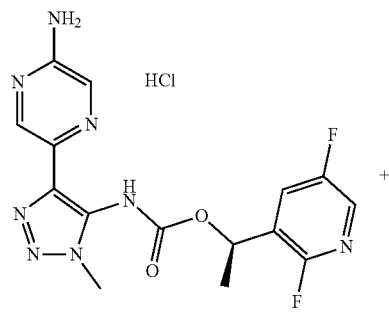

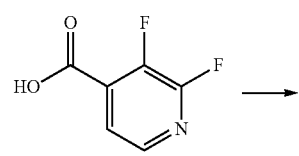

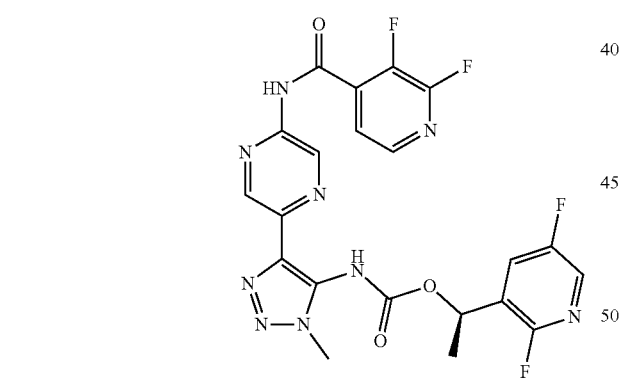

Compound 323

Following the procedure described in Example 76 for the preparation of (R)-1-(2,5-difluoropyridin-3-yl)ethyl (4-(5-(6-chloronicotinamido)pyrazin-2-yl)-1-methyl-1H-1,2,3-triazol-5-yl)carbamate, using 2,3-difluoroisonicotinic acid (0.08 mmol) in place of 6-chloronicotinic acid, (R)-1-(2,5-difluoropyridin-3-yl)ethyl (4-(5-(2,3-difluoroisonicotinamido)pyrazin-2-yl)-1-methyl-1H-1,2,3-triazol-5-yl)carbamate was obtained (Compound 323). (MS (m/z) 518.0 [M+H]+). 1H NMR (400 MHz, Methanol-d4) δ 9.41 (s, 1H), 8.96 (d, J=1.5 Hz, 1H), 8.14 (dd, J=5.1, 1.4 Hz, 1H), 8.05 (s, 1H), 8.00-7.72 (m, 1H), 7.62 (dd, J=5.0, 4.0 Hz, 1H), 5.95 (q, J=6.6 Hz, 1H), 4.00 (s, 3H), 1.62 (s, 3H).

Example 80

Preparation of (R)-1-(2-chloropyridin-3-yl)ethyl (4-(5-(2-(difluoromethyl)pyrimidine-5-carboxamido)pyrazin-2-yl)-1-methyl-1H-1,2,3-triazol-5-yl)carbamate (Compound 324)

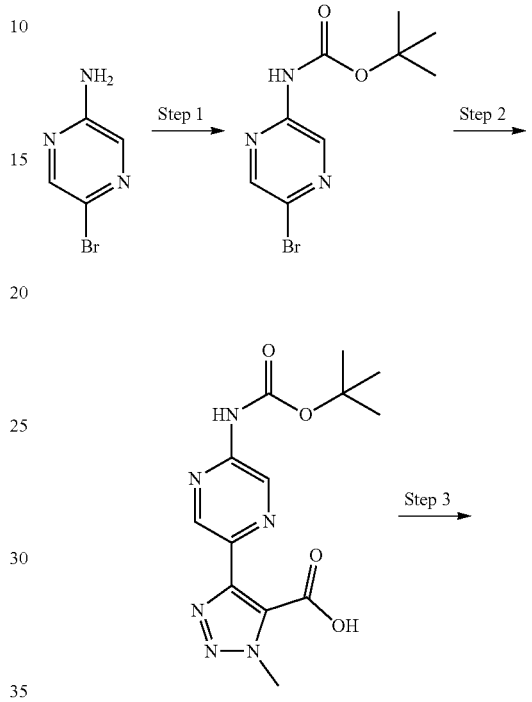

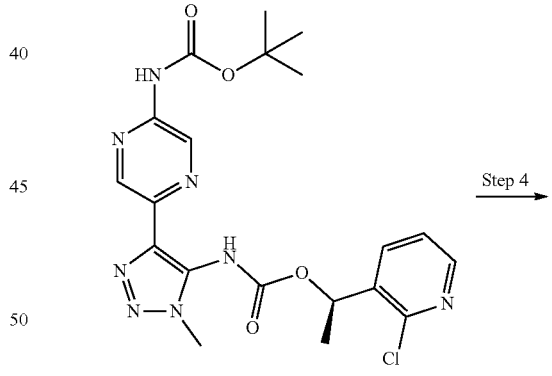

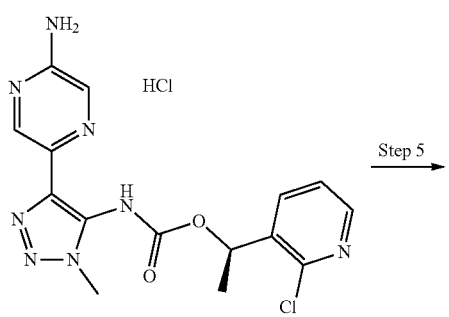

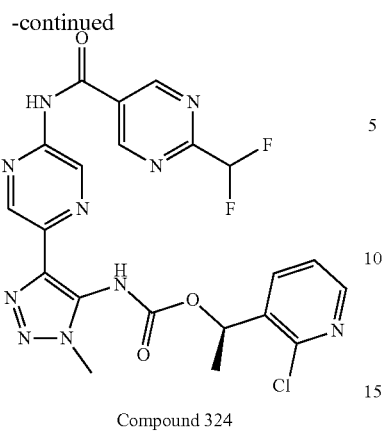

Compound 324

Following the procedure described in Example 76 for the preparation of (R)-1-(2,5-difluoropyridin-3-yl)ethyl (4-(5-(6-chloronicotinamido)pyrazin-2-yl)-1-methyl-1H-1,2,3-triazol-5-yl)carbamate, using (R)-1-(2-chloropyridin-3-yl)ethan-1-ol (4.64 mmol) in place of (R)-1-(2,5-difluoropyridin-3-yl)ethan-1-ol in step 3, and 2-(difluoromethyl)pyrimidine-5-carboxylic acid (0.08 mmol) in place of 6-chloronicotinic acid in step 5, (R)-1-(2-chloropyridin-3-yl)ethyl (4-(5-(2-(difluoromethyl)pyrimidine-5-carboxamido)pyrazin-2-yl)-1-methyl-1H-1,2,3-triazol-5-yl)carbamate was obtained (Compound 324). (MS (m/z) 531.0 [M+H]+). 1H NMR (400 MHz, Methanol-d4) δ 9.56-9.27 (m, 3H), 8.96 (s, 1H), 8.43-7.85 (m, 2H), 7.52 (s, 1H), 6.84 (t, J=54.2 Hz, 1H), 6.07 (t, J=6.5 Hz, 1H), 4.00 (s, 3H), 1.61 (s, 3H).

Example 81

Preparation of (R)-1-(2-fluoropyridin-3-yl)ethyl (1-methyl-4-(5-(2-(trifluoromethyl)pyrimidine-5-carboxamido)pyrazin-2-yl)-1H-1,2,3-triazol-5-yl)carbamate (Compound 325)

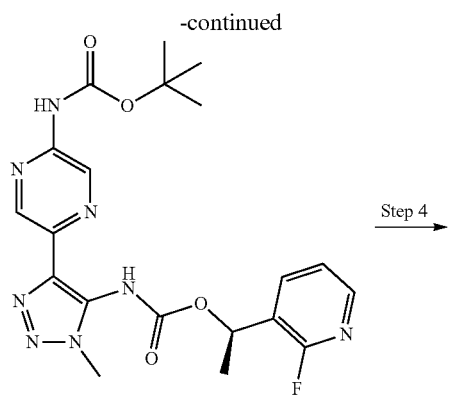

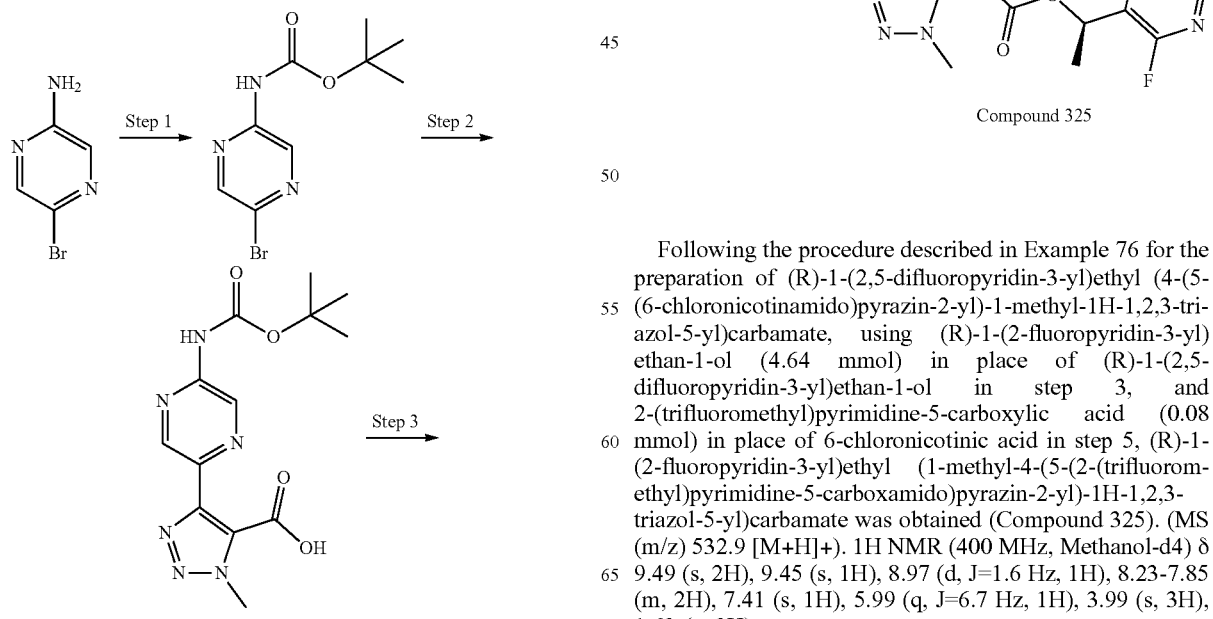

Compound 325

Following the procedure described in Example 76 for the preparation of (R)-1-(2,5-difluoropyridin-3-yl)ethyl (4-(5-(6-chloronicotinamido)pyrazin-2-yl)-1-methyl-1H-1,2,3-triazol-5-yl)carbamate, using (R)-1-(2-fluoropyridin-3-yl)ethan-1-ol (4.64 mmol) in place of (R)-1-(2,5-difluoropyridin-3-yl)ethan-1-ol in step 3, and 2-(trifluoromethyl)pyrimidine-5-carboxylic acid (0.08 mmol) in place of 6-chloronicotinic acid in step 5, (R)-1-(2-fluoropyridin-3-yl)ethyl (1-methyl-4-(5-(2-(trifluoromethyl)pyrimidine-5-carboxamido)pyrazin-2-yl)-1H-1,2,3-triazol-5-yl)carbamate was obtained (Compound 325). (MS (m/z) 532.9 [M+H]+). 1H NMR (400 MHz, Methanol-d4) δ 9.49 (s, 2H), 9.45 (s, 1H), 8.97 (d, J=1.6 Hz, 1H), 8.23-7.85 (m, 2H), 7.41 (s, 1H), 5.99 (q, J=6.7 Hz, 1H), 3.99 (s, 3H), 1.63 (s, 3H).

Example 82

Preparation of (R)-1-(2-fluoropyridin-3-yl)ethyl (1-methyl-4-(5-(6-(trifluoromethyl)nicotinamido)pyrazin-2-yl)-1H-1,2,3-triazol-5-yl)carbamate (Compound 326)

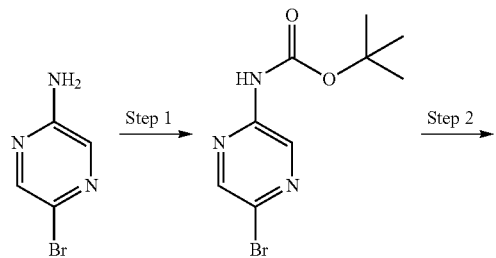

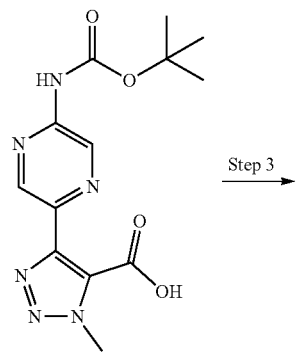

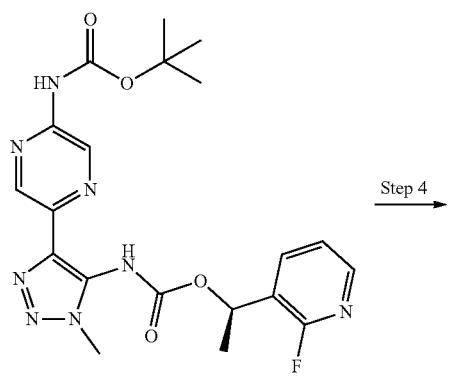

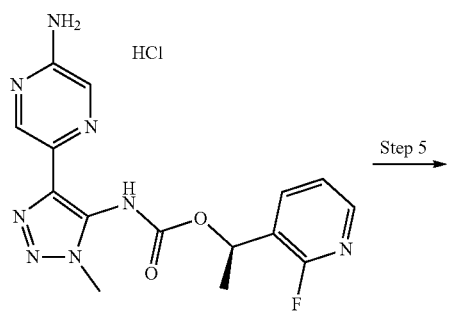

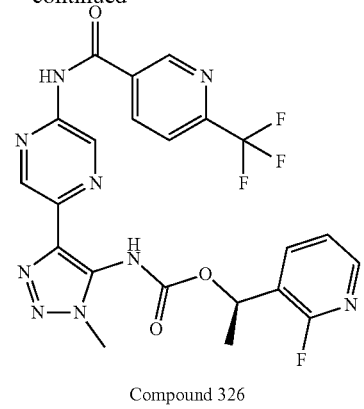

Compound 326

Following the procedure described in Example 76 for the preparation of (R)-1-(2,5-difluoropyridin-3-yl)ethyl (4-(5-(6-chloronicotinamido)pyrazin-2-yl)-1-methyl-1H-1,2,3-triazol-5-yl)carbamate, using (R)-1-(2-fluoropyridin-3-yl)ethan-1-ol (4.64 mmol) in place of (R)-1-(2,5-difluoropyridin-3-yl)ethan-1-ol in step 3, and 6-(trifluoromethyl)nicotinic acid (0.08 mmol) in place of 6-chloronicotinic acid in step 5, (R)-1-(2-fluoropyridin-3-yl)ethyl (1-methyl-4-(5-(6-(trifluoromethyl)nicotinamido)pyrazin-2-yl)-1H-1,2,3-triazol-5-yl)carbamate was obtained (Compound 326). (MS (m/z) 532.0 [M+H]+). 1H NMR (400 MHz, Methanol-d4) δ 9.47 (s, 1H), 9.28 (d, J=2.1 Hz, 1H), 8.97 (d, J=1.5 Hz, 1H), 8.60 (dd, J=8.3, 2.1 Hz, 1H), 8.25-8.06 (m, 2H), 8.01 (dd, J=8.2, 0.8 Hz, 1H), 7.41 (s, 1H), 5.99 (q, J=6.6 Hz, 1H), 3.99 (s, 3H), 1.63 (s, 3H).

Example 83

Preparation of (R)-1-(2-fluoropyridin-3-yl)ethyl (4-(5-(2-(difluoromethyl)pyrimidine-5-carboxamido)pyrazin-2-yl)-1-methyl-1H-1,2,3-triazol-5-yl)carbamate (Compound 327)

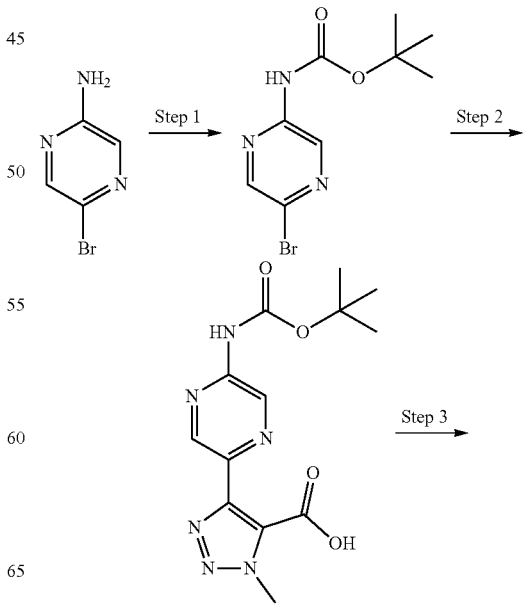

549
-continued

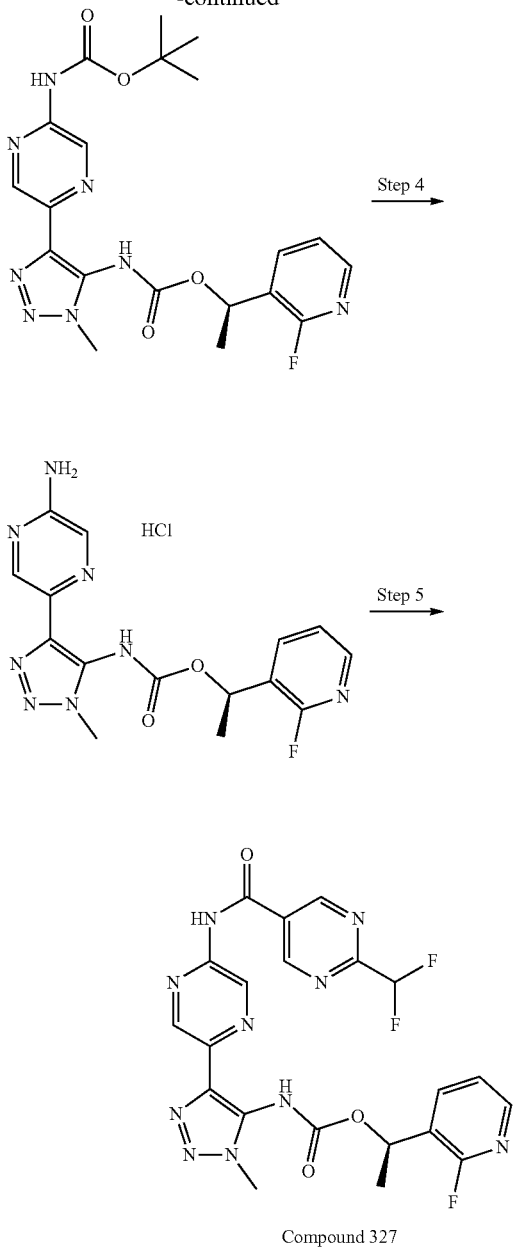

Compound 327

Following the procedure described in Example 76 for the preparation of (R)-1-(2,5-difluoropyridin-3-yl)ethyl (4-(5-(6-chloronicotinamido)pyrazin-2-yl)-1-methyl-1H-1,2,3-triazol-5-yl)carbamate, using (R)-1-(2-fluoropyridin-3-yl)ethan-1-ol (4.64 mmol) in place of (R)-1-(2,5-difluoropyridin-3-yl)ethan-1-ol in step 3, and 2-(difluoromethyl)pyrimidine-5-carboxylic acid (0.08 mmol) in place of 6-chloronicotinic acid in step 5, (R)-1-(2-fluoropyridin-3-yl)ethyl (4-(5-(2-(difluoromethyl)pyrimidine-5-carboxamido)pyrazin-2-yl)-1-methyl-1H-1,2,3-triazol-5-yl)carbamate was obtained (Compound 327). (MS (m/z) 514.9 [M+H]+). 1H NMR (400 MHz, Methanol-d4) δ 9.62-9.34 (m, 3H), 8.97 (s, 1H), 8.30-7.93 (m, 2H), 7.41 (s, 1H), 6.84 (t, J=54.1 Hz, 1H), 5.99 (d, J=7.2 Hz, 1H), 3.99 (s, 3H), 1.63 (s, 3H).

550

Example 84

Preparation of (R)-1-(2,5-difluoropyridin-3-yl)ethyl (4-(5-(1-cyanocyclopropane-1-carboxamido)pyrazin-2-yl)-1-methyl-1H-1,2,3-triazol-5-yl)carbamate (Compound 328)

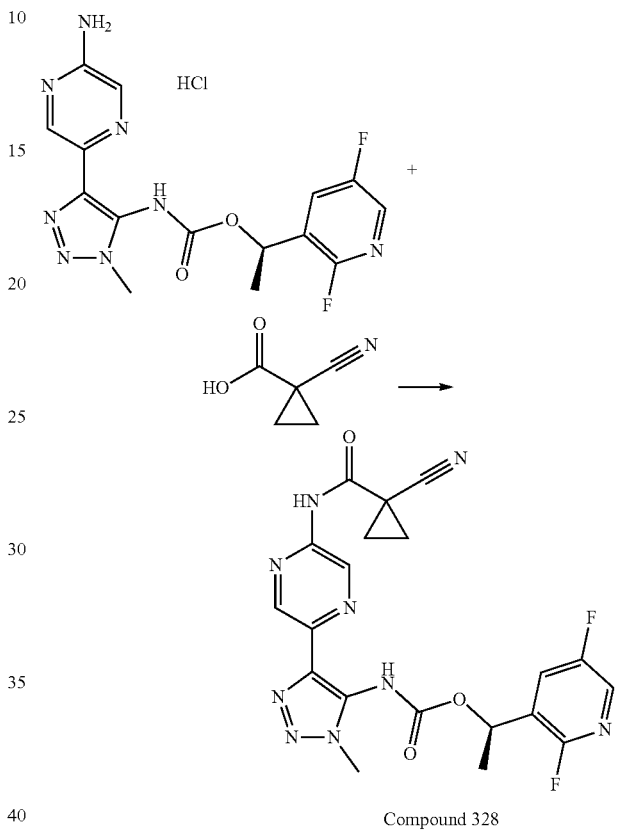

Compound 328

To a mixture of (R)-1-(2,5-difluoropyridin-3-yl)ethyl (4-(5-aminopyrazin-2-yl)-1-methyl-1H-1,2,3-triazol-5-yl)carbamate hydrochloride (Intermediate 10) (0.049 mmol), 1-cyanocyclopropanecarboxylic acid (0.058 mmol), and (1-Cyano-2-ethoxy-2-oxoethylidenaminooxy)dimethyl-amino-morpholino-carbenium hexafluorophosphate (0.058 mmol) in dichloromethane (0.5 mL) was added N,N-diisopropylethylamine (0.097 mmol). The reaction was stirred for 48 hours, then concentrated and purified by reverse-phase HPLC to provide (R)-1-(2,5-difluoropyridin-3-yl)ethyl (4-(5-(1-cyanocyclopropane-1 carboxamido)pyrazin-2-yl)-1-methyl-1H-1,2,3-triazol-5-yl)carbamate (Compound 328) (MS (m/z) 470.0 [M+H]+). 1H NMR (400 MHz, Methanol-d4) δ 9.22 (s, 1H), 8.96 (d, J=1.5 Hz, 1H), 8.11-7.67 (m, 2H), 5.95 (d, J=6.8 Hz, 1H), 4.01 (s, 3H), 1.88-1.80 (m, 2H), 1.80-1.72 (m, 2H), 1.62 (s, 3H).

Example 85

Preparation of Compounds 286-287 and 329-332

Compounds 286-287 and 329-332 were generally synthesized according Scheme C. For example, (R)-1-(2-chloro-5-fluoropyridin-3-yl)ethyl (4-(5-(1-cyanocyclopropane-1- carboxamido)pyrimidin-2-yl)-1-methyl-1H-1,2,3-triazol-5-yl)carbamate (Compound 329) was prepared as follows.

Preparation of (R)-1-(2-chloro-5-fluoropyridin-3-yl) ethyl (4-(5-(1-cyanocyclopropane-1-carboxamido) pyrimidin-2-yl)-1-methyl-1H-1,2,3-triazol-5-yl)carbamate (Compound 329)

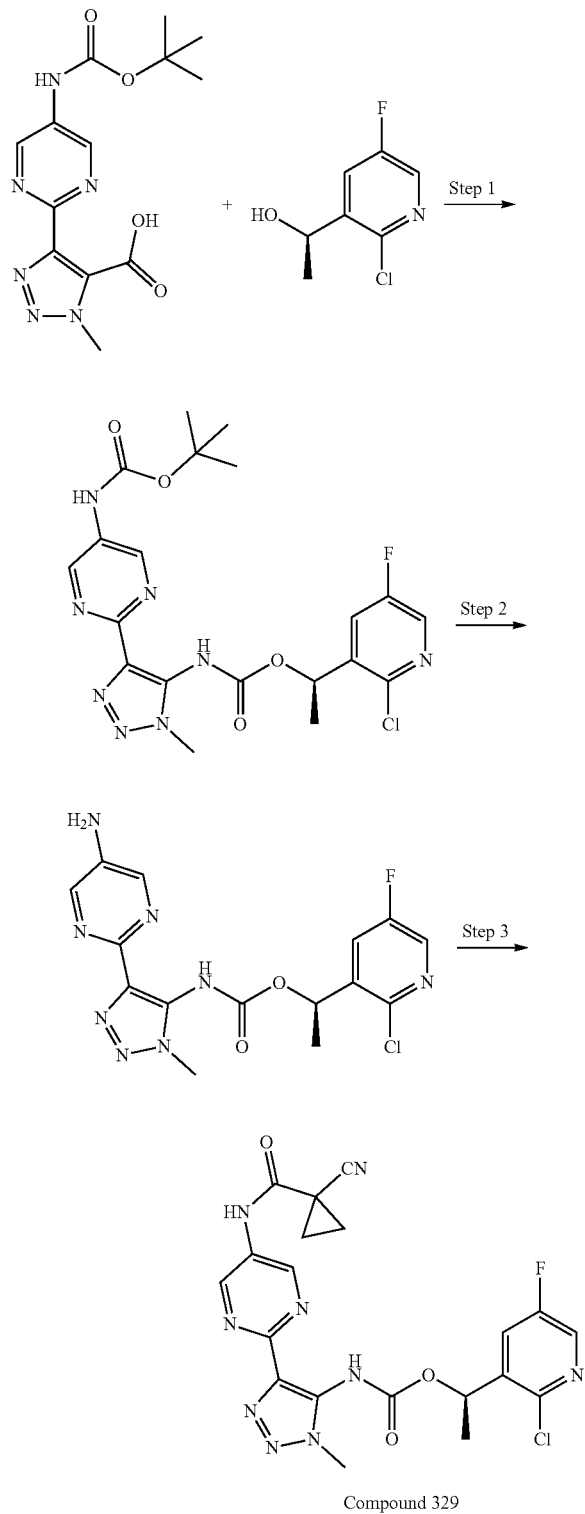

Compound 329

Step 1: (R)-1-(2-chloro-5-fluoropyridin-3-yl)ethyl (4-(5-((tert-butoxycarbonyl)amino)pyrimidin-2-yl)-1-methyl-1H-1,2,3-triazol-5-yl)carbamate To a mixture of 4-(5-((tert-butoxycarbonyl)amino)pyrimidin-2-yl)-1-methyl-1H-1,2,3-triazole-5-carboxylic acid (Intermediate 9) (0.62 mmol) in THF (5 mL) was added T3P (50% in DMF, 0.94 mmol), TMS-N3 (0.67 mmol) and triethylamine (1.2 mmol). The mixture was heated at 70° C. for 30 minutes. (R)-1-(2-chloro-5-fluoropyridin-3-yl)ethan-1-ol (0.94 mmol) was added and the solution was heated at 70° C. for 90 minutes. The reaction was cooled to room temperature, concentrated and purified by silica gel chromatography to provide (R)-1-(2-chloro-5-fluoropyridin-3-yl)ethyl (4-(5-((tert-butoxycarbonyl)amino)pyrimidin-2-yl)-1-methyl-1H-1,2,3-triazol-5-yl)carbamate. (MS (m/z) 493.2 [M+H]$^+$).

Step 2: (R)-1-(2-chloro-5-fluoropyridin-3-yl)ethyl (4-(5-aminopyrimidin-2-yl)-1-methyl-1H-1,2,3-triazol-5-yl)carbamate (Intermediate 11)

4 M HCl in 1,4-dioxane (20 mmol) was added to (R)-1-(2-chloro-5-fluoropyridin-3-yl)ethyl (4-(5-((tert-butoxycarbonyl)amino)pyrimidin-2-yl)-1-methyl-1H-1,2,3-triazol-5-yl)carbamate (0.49 mmol). The resulting suspension was stirred at RT for 18 hours. The reaction was concentrated to afford (R)-1-(2-chloro-5-fluoropyridin-3-yl)ethyl (4-(5-aminopyrimidin-2-yl)-1-methyl-1H-1,2,3-triazol-5-yl)carbamate as the hydrochoride salt (Intermediate 11). (MS (m/z) 393.1 [M+H]$^+$).

Step 3: (R)-1-(2-chloro-5-fluoropyridin-3-yl)ethyl (4-(5-(1-cyanocyclopropane-1-carboxamido)pyrimidin-2-yl)-1-methyl-1H-1,2,3-triazol-5-yl)carbamate A vial was charged with (R)-1-(2-chloro-5-fluoropyridin-3-yl)ethyl (4-(5-aminopyrimidin-2-yl)-1-methyl-1H-1,2,3-triazol-5-yl)carbamate hydrochloride (0.05 mmol) (Intermediate 11), 1-cyanocyclopropane-1-carboxylic acid (0.06 mmol), N-ethyl-N'-(3-dimethylaminopropyl) carbodiimide hydrochloride (0.07 mmol) and pyridine (2 mL). The reaction mixture was stirred at RT for 18 hours, concentrated and purified by reverse phase HPLC to provide (R)-1-(2-chloro-5-fluoropyridin-3-yl)ethyl (4-(5-(1-cyanocyclopropane-1-carboxamido)pyrimidin-2-yl)-1-methyl-1H-1,2,3-triazol-5-yl)carbamate. (MS (m/z) 486.2 [M+H]$^+$). 1H NMR (400 MHz, DMSO-d6) δ 10.45 (s, 1H), 9.98 (bs, 1H), 8.99 (s, 2H), 8.43 (bs, 1H), 7.94 (bs, 1H), 5.82 (bs, 1H), 3.91 (s, 3H), 1.84-1.68 (m, 4H), 1.55 (bs, 3H).

Compounds 286-287 and 329-332 (Table 5) were similarly prepared according to Scheme C, Step 4 by reacting (R)-1-(2-chloro-5-fluoropyridin-3-yl)ethyl (4-(5-aminopyrimidin-2-yl)-1-methyl-1H-1,2,3-triazol-5-yl)carbamate hydrochloride (Intermediate 11) with the Reagent listed in Table 4 in place of 1-cyanocyclopropane-1-carboxylic acid.

Compounds 286-287 were prepared using a mixture of (1S,2S)-1-cyano-2-(difluoromethyl)cyclopropane-1-carboxylic acid and (1R,2R)-1-cyano-2-(difluoromethyl)cyclopropane-1-carboxylic acid, followed by chiral SFC purification.

TABLE 5

Compounds prepared according to Scheme C.

| Compound No. | Structure | Reagent | LCMS m/z | 1H NMR |
|---|---|---|---|---|
| Compound 286 (R)-1-(2-chloro-5-fluoropyridin-3-yl)ethyl (4-(5-((1R,2R)-1-cyano-2-(difluoromethyl)cyclopropane-1-carboxamido)pyrimidin-2-yl)-1-methyl-1H-1,2,3-triazol-5-yl)carbamate | 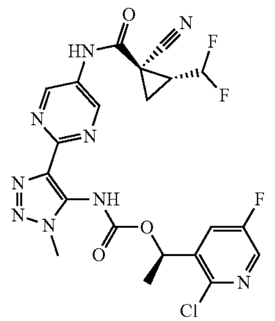 [SMILES: C[C@@H](OC(=O)Nc1c(-c2ncc(NC(=O)[C@]3(C#N)C[C@H]3C(F)F)cn2)nnn1C)c1cc(F)cnc1Cl] | | 536.0 | 1H NMR (400 MHz, DMSO-d6) δ 10.67 (bs, 1H), 9.99 (bs, 1H), 8.98 (s, 2H), 8.44 (bs, 1H), 7.94 (bs, 1H), 6.23 (ddd, J = 55.6, 54.3, 5.3 Hz, 1H), 5.83 (bs, 1H), 3.91 (s, 3H), 2.82-2.58 (m, 1H), 2.20-2.11 (m, 1H), 2.11-2.00 (m, 1H), 1.54 (bs, 3H). |
| Compound 287 (R)-1-(2-chloro-5-fluoropyridin-3-yl)ethyl (4-(5-((1S,2S)-1-cyano-2-(difluoromethyl)cyclopropane-1-carboxamido)pyrimidin-2-yl)-1-methyl-1H-1,2,3-triazol-5-yl)carbamate | 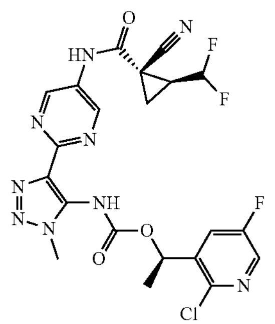 [SMILES: C[C@@H](OC(=O)Nc1c(-c2ncc(NC(=O)[C@@]3(C#N)C[C@@H]3C(F)F)cn2)nnn1C)c1cc(F)cnc1Cl] | | 536.0 | 1H NMR (400 MHz, DMSO-d6) δ 10.66 (s, 1H), 9.98 (bs, 1H), 8.99 (s, 2H), 8.44 (s, 1H), 7.94 (bs, 1H), 6.23 (ddd, J = 55.6, 54.3, 5.3 Hz, 1H), 5.83 (bs, 1H), 3.92 (s, 3H), 2.81-2.59 (m, 1H), 2.19-2.11 (m, 1H), 2.11-2.02 (m, 1H), 1.54 (m, 3H). |
| Compound 329 (R)-1-(2-chloro-5-fluoropyridin-3-yl)ethyl (4-(5-(1-cyanocyclopropane-1-carboxamido)pyrimidin-2-yl)-1-methyl-1H-1,2,3-triazol-5-yl)carbamate | 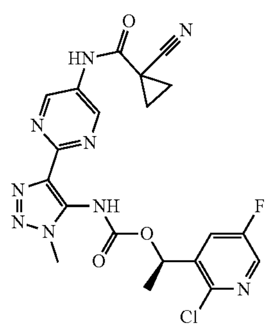 [SMILES: C[C@@H](OC(=O)Nc1c(-c2ncc(NC(=O)C3(C#N)CC3)cn2)nnn1C)c1cc(F)cnc1Cl] | | 486.2 | 1H NMR (400 MHz, DMSO-d6) δ 10.45 (s, 1H), 9.98 (bs, 1H), 8.99 (s, 2H), 8.43 (bs, 1H), 7.94 (bs, 1H), 5.82 (bs, 1H), 3.91 (s, 3H), 1.84-1.68 (m, 4H), 1.55 (bs, 3H). |
| Compound 330 (R)-1-(2-chloro-5-fluoropyridin-3-yl)ethyl (4-(5-(3-fluorobicyclo[1.1.1]pentane-1-carboxamido)pyrimidin-2-yl)-1-methyl-1H-1,2,3-triazol-5-yl)carbamate | 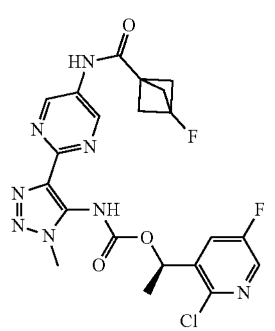 [SMILES: C[C@@H](OC(=O)Nc1c(-c2ncc(NC(=O)C34CC(F)(C3)C4)cn2)nnn1C)c1cc(F)cnc1Cl] | | 505.2 | 1H NMR (400 MHz, DMSO-d6) δ 10.18 (s, 1H), 9.91 (bs, 1H), 9.02 (s, 2H), 8.43 (bs, 1H), 7.94 (bs, 1H), 5.82 (bs, 1H), 3.91 (s, 3H), 2.45 (d, J = 2.5 Hz, 6H), 1.54 (bs, 3H). |

TABLE 5-continued

Compounds prepared according to Scheme C.

| Compound No. | Structure | Reagent | LCMS m/z | 1H NMR |
|---|---|---|---|---|
| Compound 331 (R)-1-(2-chloro-5-fluoropyridin-3-yl)ethyl (1-methyl-4-(5-((1R,2R)-2-(trifluoromethyl)cyclopropane-1-carboxamido)pyrimidin-2-yl)-1H-1,2,3-triazol-5-yl)carbamate | 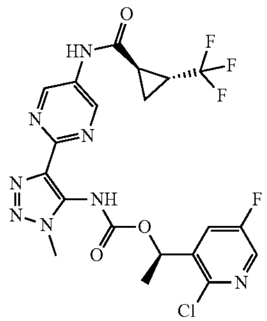 [SMILES: C[C@@H](OC(=O)Nc1c(-c2ncc(NC(=O)[C@@H]3C[C@H]3C(F)(F)F)cn2)nnn1C)c1cc(F)cnc1Cl] | | 529.0 | 1H NMR (400 MHz, DMSO-d6) δ 10.93 (s, 1H), 9.86 (bs, 1H), 8.97 (s, 2H), 8.42 (bs, 1H), 7.93 (bs, 1H), 5.79 (bs, 1H), 3.91 (s, 3H), 2.45-2.23 (m, 2H), 1.85-0.97 (m, 5H). |
| Compound 332 (R)-1-(2-chloro-5-fluoropyridin-3-yl)ethyl (1-methyl-4-(5-(6-(trifluoromethyl)nicotinamido)pyrimidin-2-yl)-1H-1,2,3-triazol-5-yl)carbamate | 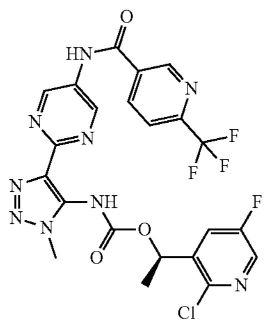 [SMILES: C[C@@H](OC(=O)Nc1c(-c2ncc(NC(=O)c3ccc(C(F)(F)F)nc3)cn2)nnn1C)c1cc(F)cnc1Cl] | | 566.0 | 1H NMR (400 MHz, DMSO-d6) δ 11.05 (bs, 1H), 10.01 (bs, 1H), 9.31 (d, J = 2.2 Hz, 1H), 9.16 (s, 2H), 8.63 (dd, J = 8.1, 2.2 Hz, 1H), 8.44 (bs, 1H), 8.18 (d, J = 8.2 Hz, 1H), 7.94 (bs, 1H), 5.85 (d, J = 7.5 Hz, 1H), 3.93 (s, 3H), 1.54 (bs, 3H). |

Example 86

Preparation of (R)-1-(2-chloro-5-fluoropyridin-3-yl)ethyl (4-(5-(3-fluorobicyclo[1.1.1]pentane-1-carboxamido)pyrazin-2-yl)-1-methyl-1H-1,2,3-triazol-5-yl)carbamate (Compound 333)

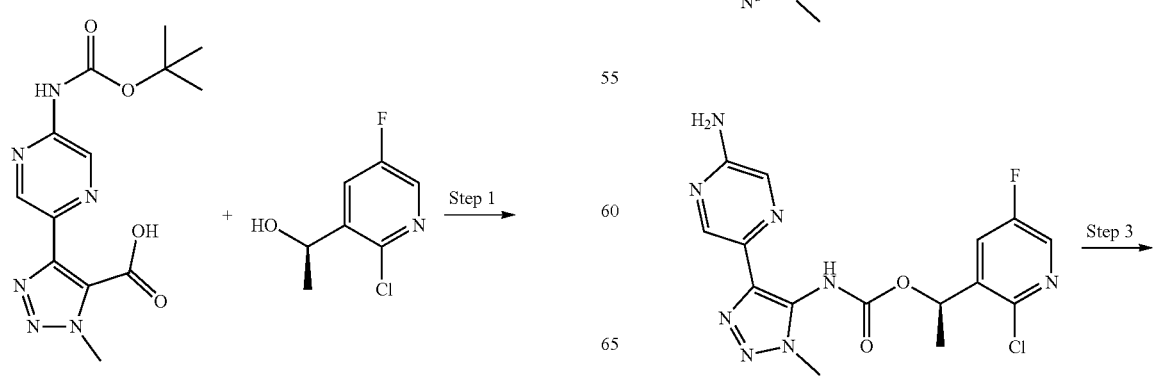

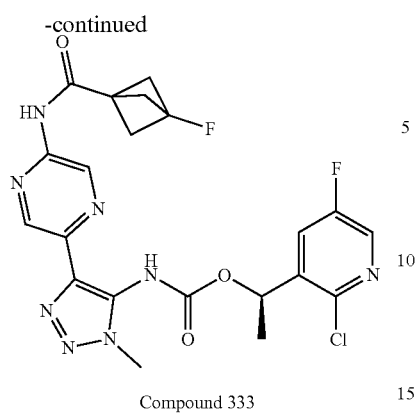

Compound 333

Step 1: (R)-1-(2-chloro-5-fluoropyridin-3-yl)ethyl (4-(5-((tert-butoxycarbonyl)amino)pyrazin-2-yl)-1-methyl-1H-1,2,3-triazol-5-yl)carbamate To a mixture of 4-(5-((tert-butoxycarbonyl)amino)pyrazin-2-yl)-1-methyl-1H-1,2,3-triazole-5-carboxylic acid (0.62 mmol) in THF (5 mL) was added T3P (50% in DMF, 0.94 mmol), TMS-N3 (0.69 mmol) and triethylamine (1.2 mmol). The mixture was heated at 70° C. for 30 minutes. (R)-1-(2-chloro-5-fluoropyridin-3-yl)ethan-1-ol (0.94 mmol) was added and the solution was heated at 70° C. for 90 minutes. The reaction was cooled to RT, concentrated and purified by silica gel chromatography to provide (R)-1-(2-chloro-5-fluoropyridin-3-yl)ethyl (4-(5-((tert-butoxycarbonyl)amino)pyrazin-2-yl)-1-methyl-1H-1,2,3-triazol-5-yl)carbamate. (MS (m/z) 492.9. [M+H]$^+$).

Step 2: (R)-1-(2-chloro-5-fluoropyridin-3-yl)ethyl (4-(5-aminopyrazin-2-yl)-1-methyl-1H-1,2,3-triazol-5-yl)carbamate 4 M HCl in 1,4-dioxane (14 mmol) was added to (R)-1-(2-chloro-5-fluoropyridin-3-yl)ethyl (4-(5-((tert-butoxycarbonyl)amino)pyrazin-2-yl)-1-methyl-1H-1,2,3-triazol-5-yl)carbamate (0.34 mmol). The resulting suspension was stirred at RT for 18 hours. The reaction was concentrated to afford (R)-1-(2-chloro-5-fluoropyridin-3-yl)ethyl (4-(5-aminopyrazin-2-yl)-1-methyl-1H-1,2,3-triazol-5-yl)carbamate as the hydrochoride salt.

Step 3: (R)-1-(2-chloro-5-fluoropyridin-3-yl)ethyl (4-(5-(3-fluorobicyclo[1.1.1]pentane-1-carboxamido)pyrazin-2-yl)-1-methyl-1H-1,2,3-triazol-5-yl)carbamate A vial was charged with (R)-1-(2-chloro-5-fluoropyridin-3-yl)ethyl (4-(5-aminopyrazin-2-yl)-1-methyl-1H-1,2,3-triazol-5-yl)carbamate hydrochloride (0.06 mmol), 3-fluorobicyclo[1.1.1]pentane-1-carboxylic acid (0.08 mmol), N-ethyl-N'-(3-dimethylaminopropyl) carbodiimide hydrochloride (0.12 mmol) and pyridine (2 mL). The reaction mixture was stirred at RT for 18 hours, concentrated and purified by reverse phase HPLC to provide (R)-1-(2-chloro-5-fluoropyridin-3-yl)ethyl (4-(5-(3-fluorobicyclo[1.1.1]pentane-1-carboxamido)pyrazin-2-yl)-1-methyl-1H-1,2,3-triazol-5-yl)carbamate. (MS (m/z) 505.2 [M+H]$^+$). 1H NMR (400 MHz, DMSO-d6) δ 10.92 (s, 1H), 10.03 (bs, 1H), 9.20 (d, J=1.6 Hz, 1H), 8.92 (d, J=1.5 Hz, 1H), 8.43 (bs, 1H), 7.94 (bs, 1H), 5.83 (bs, 1H), 3.92 (s, 3H), 2.47 (d, J=2.5 Hz, 6H), 1.55 (bs, 3H).

Example 87

Preparation of (R)-1-(2,5-difluoropyridin-3-yl)ethyl (4-(5-((1r,3R)-3-cyano-3-methoxycyclobutane-1-carboxamido)pyrimidin-2-yl)-1-methyl-1H-1,2,3-triazol-5-yl)carbamate (Compound 334) and (R)-1-(2,5-difluoropyridin-3-yl)ethyl (4-(5-((1s,3S)-3-cyano-3-methoxycyclobutane-1-carboxamido)pyrimidin-2-yl)-1-methyl-1H-1,2,3-triazol-5-yl)carbamate (Compound 335)

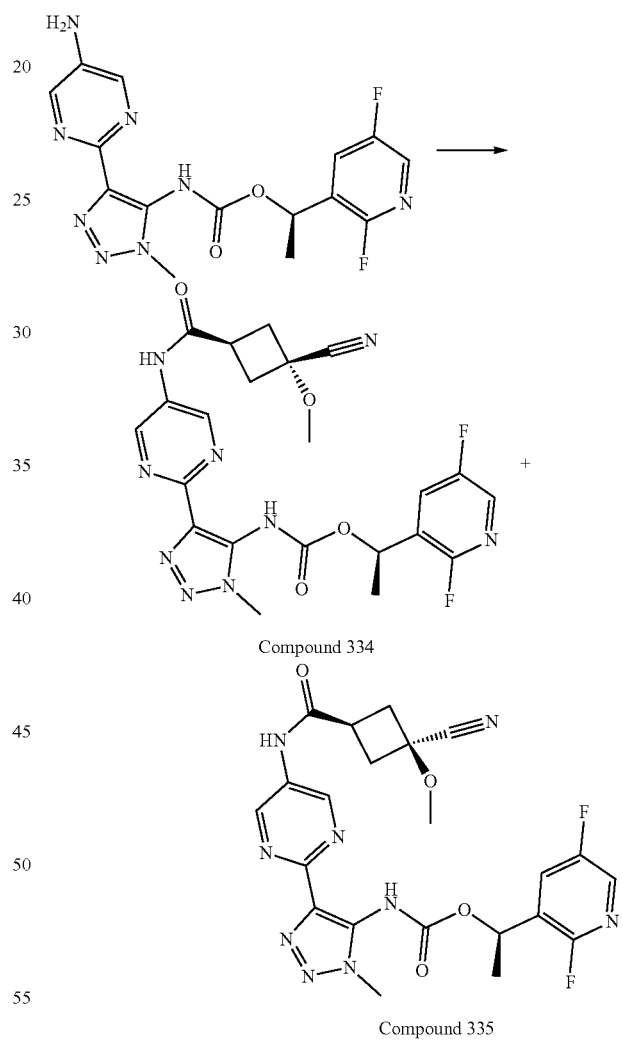

Compound 334

Compound 335

A mixture of the (R)-1-(2,5-difluoropyridin-3-yl)ethyl (4-(5-aminopyrimidin-2-yl)-1-methyl-1H-1,2,3-triazol-5-yl)carbamate hydrochloride (0.048 mmol), 3-cyano-3-methoxycyclobutane-1-carboxylic acid (2eq), EDCI (2 eq) in pyridine (1 mL) was stirred 1 h at room temperature. After completion of the reaction, the residue was purified by prep-HPLC with Gilson prep HPLC (Gemini column, 30-95% CH$_3$CN in H$_2$O with 0.1% TFA). Two peaks were isolated; the stereo structures are arbitrary assigned. Compound 334: (R)-1-(2,5-difluoropyridin-3-yl)ethyl (4-(5-((1r,3R)-3-cyano-3-methoxycyclobutane-1-carboxamido)pyrimidin-2-yl)-1-methyl-1H-1,2,3-triazol-5-yl)carbamate. (MS (m/z) 514.1 [M+H]+). 1H NMR (400 MHz, Methanol-d4) δ 9.06 (s, 2H), 8.07 (m, 1H), 7.98-7.69 (m, 1H), 5.96 (m, 1H), 4.02 (s, 3H), 3.46 (s, 2H) 2.99-2.79 (m, 2H), 2.76-2.48 (m, 2H), 1.63 (s, 3H). Compound 335: (R)-1-(2,5-difluoropyridin-3-yl)ethyl (4-(5-((1s,3S)-3-cyano-3-methoxycyclobutane-1-carboxamido)pyrimidin-2-yl)-1-methyl-1H-1,2,3-triazol-5-yl)carbamate. (MS (m/z) 514.1 [M+H]+). 1H NMR (400 MHz, Methanol-d4) δ 9.05 (s, 2H), 8.05 (s, 1H), 7.97-7.75 (m, 1H), 5.96 (m, 1H), 4.01 (s, 3H), 3.55-3.49 (m, 1H), 2.85 (m, 2H), 2.66 (m, 2H), 1.63 (s, 3H).

Example 88

Preparation of (R)-1-(2,5-difluoropyridin-3-yl)ethyl (4-(5-(1-cyanocyclopropane-1-carboxamido)-3-fluoropyridin-2-yl)-1-methyl-1H-1,2,3-triazol-5-yl)carbamate (Compound 336)

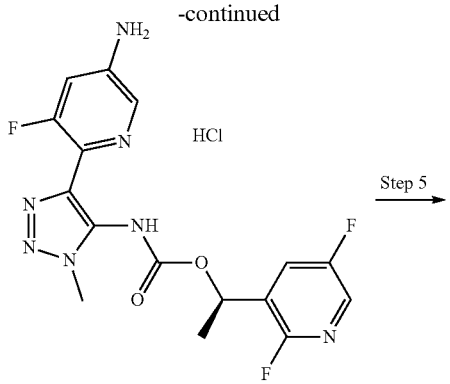

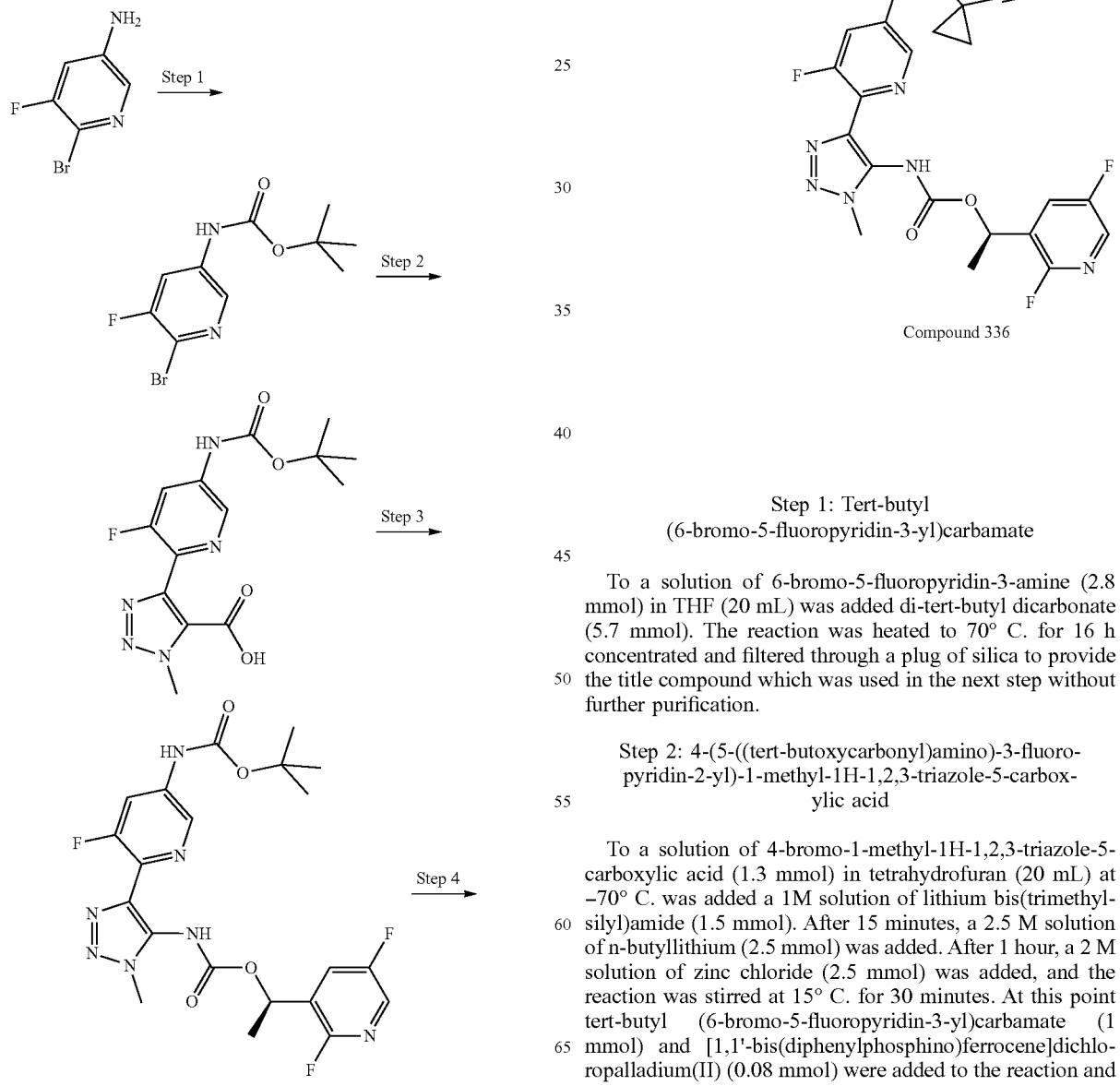

Compound 336

Step 1: Tert-butyl (6-bromo-5-fluoropyridin-3-yl)carbamate

To a solution of 6-bromo-5-fluoropyridin-3-amine (2.8 mmol) in THF (20 mL) was added di-tert-butyl dicarbonate (5.7 mmol). The reaction was heated to 70° C. for 16 h concentrated and filtered through a plug of silica to provide the title compound which was used in the next step without further purification.

Step 2: 4-(5-((tert-butoxycarbonyl)amino)-3-fluoropyridin-2-yl)-1-methyl-1H-1,2,3-triazole-5-carboxylic acid To a solution of 4-bromo-1-methyl-1H-1,2,3-triazole-5-carboxylic acid (1.3 mmol) in tetrahydrofuran (20 mL) at −70° C. was added a 1M solution of lithium bis(trimethylsilyl)amide (1.5 mmol). After 15 minutes, a 2.5 M solution of n-butyllithium (2.5 mmol) was added. After 1 hour, a 2 M solution of zinc chloride (2.5 mmol) was added, and the reaction was stirred at 15° C. for 30 minutes. At this point tert-butyl (6-bromo-5-fluoropyridin-3-yl)carbamate (1 mmol) and [1,1'-bis(diphenylphosphino)ferrocene]dichloropalladium(II) (0.08 mmol) were added to the reaction and the reaction mixture was heated to 90° C. for 3 hours. After completion of the reaction, the reaction was cooled and diluted with 1M aqueous hydrogen chloride solution (20 mL). The reaction mixture was extracted with ethyl acetate (30 mL×3). The combined organic layer was dried over sodium sulfate, concentrated, purified by column chromatography to provide 4-(5-((tert-butoxycarbonyl)amino)-3-fluoropyridin-2-yl)-1-methyl-1H-1,2,3-triazole-5-carboxylic acid.

Step 3: tert-butyl (R)-(6-(5-(((1-(2,5-difluoropyridin-3-yl)ethoxy)carbonyl)amino)-1-methyl-1H-1,2,3-triazol-4-yl)-5-fluoropyridin-3-yl)carbamate 4-(5-((tert-butoxycarbonyl)amino)-3-fluoropyridin-2-yl)-1-methyl-1H-1,2,3-triazole-5-carboxylic acid (3.1 mmol), Azidotrimethylsilane (4.7 mmol), and T3P (50% in DMF) (4.7 mmol) was dissolved in THF (5 mL). Triethyl amine (9.4 mmol) was added dropwise at RT resulting in a clear solution after 5-30 minutes. ((R)-1-(2,5-difluoropyridin-3-yl)ethan-1-ol (9.4 mmol) was added and the reaction was heated at 80° C. for 2 hours. Silica gel was then added and the crude mixture was concentrated in vacuo and then purified by column chromatography to afford tert-butyl (R)-(6-(5-(((1-(2,5-difluoropyridin-3-yl)ethoxy)carbonyl)amino)-1-methyl-1H-1,2,3-triazol-4-yl)-5-fluoropyridin-3-yl)carbamate (0.6 mmol).

Step 4: (R)-1-(2,5-difluoropyridin-3-yl)ethyl (4-(5-amino-3-fluoropyridin-2-yl)-1-methyl-1H-1,2,3-triazol-5-yl)carbamate hydrogen chloride salt (Intermediate 12)

Tert-butyl (R)-(6-(5-(((1-(2,5-difluoropyridin-3-yl)ethoxy)carbonyl)amino)-1-methyl-1H-1,2,3-triazol-4-yl)-5-fluoropyridin-3-yl)carbamate (0.6 mmol) was suspended in 1.6 mL 4 M hydrochloric acid in dioxanes for 1 hour. The mixture was then concentrated in vacuo to afford (R)-1-(2,5-difluoropyridin-3-yl)ethyl (4-(5-amino-3-fluoropyridin-2-yl)-1-methyl-1H-1,2,3-triazol-5-yl)carbamate hydrogen chloride salt (Intermediate 12) and was used without further purification.

Step 5: (R)-1-(2,5-difluoropyridin-3-yl)ethyl (4-(5-(1-cyanocyclopropane-1-carboxamido)-3-fluoropyridin-2-yl)-1-methyl-1H-1,2,3-triazol-5-yl)carbamate To a mixture of (R)-1-(2,5-difluoropyridin-3-yl)ethyl (4-(5-amino-3-fluoropyridin-2-yl)-1-methyl-1H-1,2,3-triazol-5-yl)carbamate hydrogen chloride salt (0.07 mmol) in pyridine (1 mL) was added 1-cyanocyclopropane-1-carboxylic acid (0.07 mmol) and N-ethyl-N'-(3-dimethylaminopropyl)carbodiimide hydrochloride (0.08 mmol). The reaction mixture was left with magnetic stirring for 2 hours at which point water (1 mL) was added the crude mixture was purified by HPLC to provide (R)-1-(2,5-difluoropyridin-3-yl)ethyl (4-(5-(1-cyanocyclopropane-1-carboxamido)-3-fluoropyridin-2-yl)-1-methyl-1H-1,2,3-triazol-5-yl)carbamate. (MS (m/z) 486.986 [M+H]+). 1H NMR (400 MHz, Methanol-d4) δ 8.78-8.52 (m, 1H), 8.19-7.53 (m, 3H), 5.90 (d, J=6.8 Hz, 1H), 4.02 (s, 3H), 1.91-1.35 (m, 7H).

Example 89

Preparation of ((R)-1-(2,5-difluoropyridin-3-yl)ethyl (4-(5-(3-cyanobicyclo[1.1.1]pentane-1-carboxamido)-3-fluoropyridin-2-yl)-1-methyl-1H-1,2,3-triazol-5-yl)carbamate (Compound 337)

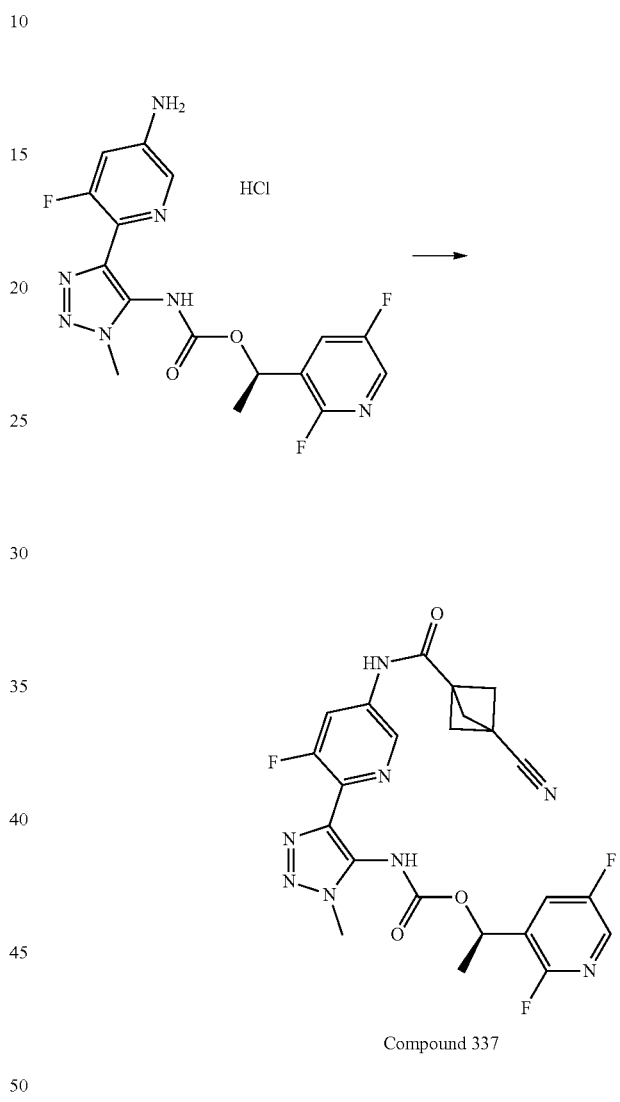

Compound 337

(R)-1-(2,5-difluoropyridin-3-yl)ethyl (4-(5-(3-cyanobicyclo[1.1.1]pentane-1-carboxamido)-3-fluoropyridin-2-yl)-1-methyl-1H-1,2,3-triazol-5-yl)carbamate Prepared following Example 88 using 3-cyanobicyclo[1.1.1]pentane-1-carboxylic acid (0.07 mmol) instead of 1-cyanocyclopropane-1-carboxylic acid, (R)-1-(2,5-difluoropyridin-3-yl)ethyl (4-(5-(3-cyanobicyclo[1.1.1]pentane-1-carboxamido)-3-fluoropyridin-2-yl)-1-methyl-1H-1,2,3-triazol-5-yl)carbamate was prepared. (MS (m/z) 513.010 [M+H]+). 1H NMR (400 MHz, Methanol-d4) δ 8.61 (s, 1H), 8.25-7.51 (m, 3H), 5.89 (d, J=7.0 Hz, 1H), 4.01 (s, 3H), 2.64 (s, 6H), 1.61 (s, 3H).

Example 90

Preparation of (R)-1-(2,5-difluoropyridin-3-yl)ethyl (4-(5-(6-chloronicotinamido)-3-fluoropyridin-2-yl)-1-methyl-1H-1,2,3-triazol-5-yl)carbamate (Compound 338)

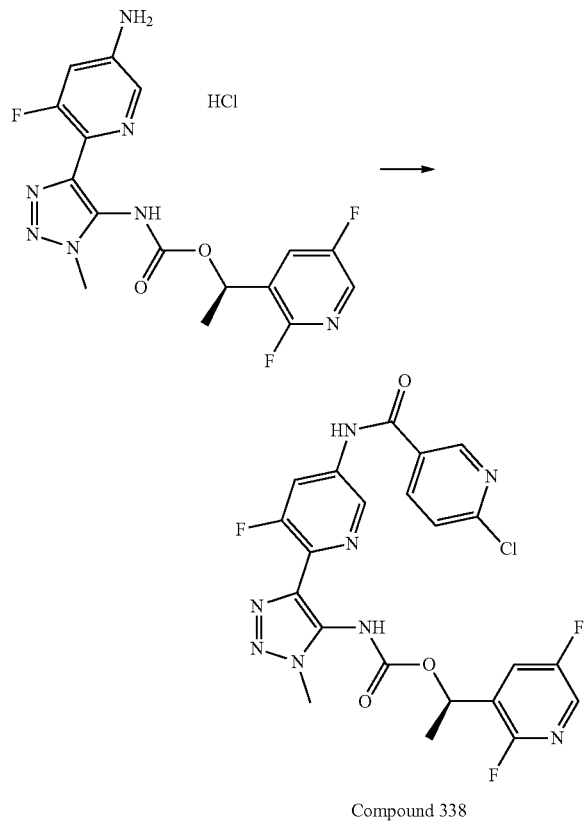

Compound 338

(R)-1-(2,5-difluoropyridin-3-yl)ethyl (4-(5-(6-chloronicotinamido)-3-fluoropyridin-2-yl)-1-methyl-1H-1,2,3-triazol-5-yl)carbamate Prepared following Example 88 using 6-chloronicotinic acid (0.07 mmol) instead of 1-cyanocyclopropane-1-carboxylic acid, (R)-1-(2,5-difluoropyridin-3-yl)ethyl(4-(5-(6-chloronicotinamido)-3-fluoropyridin-2-yl)-1-methyl-1H-1, 2,3-triazol-5-yl)carbamate was prepared. (MS (m/z) 532.975 [M+H]+). 1H NMR (400 MHz, Methanol-d4) δ 8.98 (dd, J=2.5, 0.7 Hz, 1H), 8.73 (s, 1H), 8.38 (dd, J=8.4, 2.5 Hz, 1H), 8.27 (dd, J=12.4, 2.1 Hz, 1H), 7.96 (d, J=78.6 Hz, 2H), 7.66 (dd, J=8.3, 0.8 Hz, 1H), 5.91 (d, J=6.8 Hz, 1H), 4.03 (s, 3H), 1.62 (s, 3H).

Example 91

Preparation of rac-(1R,2R)-1-cyano-2-(difluoromethyl)cyclopropane-1-carboxylic acid

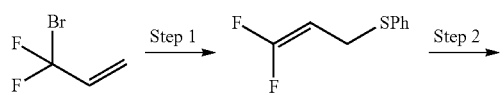

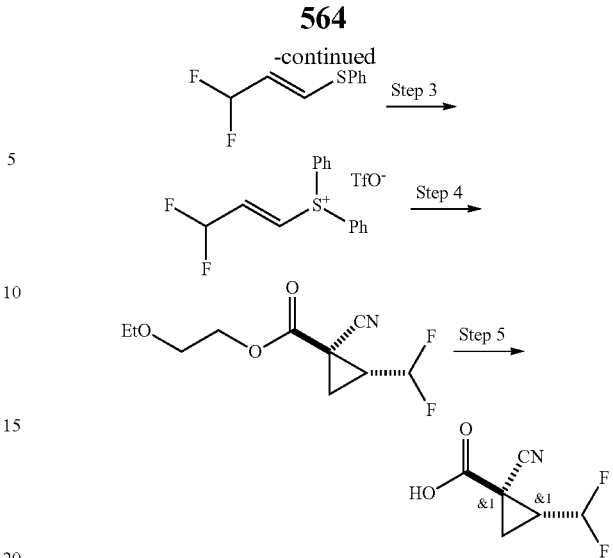

Step 1: (3,3-difluoroallyl)(phenyl)sulfane

NaH (153 mmol) was added to a 250 mL bottle under $N_2$. n-Hexane (50.0 mL), was added and stirred at 25° C. for 5 minutes. n-hexane was removed by syringe. Dioxane (120 mL) was added to the reaction at 0° C. PhSH (118 mmol) was added to the mixture at 0° C., and stirred at 0° C. for 0.5 hr. 3-bromo-3,3-difluoroprop-1-ene (177 mmol) was added to the mixture at 0° C. The reaction as warmed to 25° C., and stirred at 25° C. for 1 hour. The reaction was quenched with sat. $NH_4Cl$ (50.0 mL) at 0° C., and Extracted with ethyl acetate (100 mL*4). The organic phase was washed with brine (100 mL), and dried over anhydrous $Na_2SO_4$. The solution was filtered and concentrated under vacuum. The residue was purified by column chromatography to provide (3,3-difluoroallyl)(phenyl)sulfane.

Step 2: (E)-(3,3-difluoroprop-1-en-1-yl)(phenyl)sulfane (3,3-difluoroallyl)(phenyl)sulfane (53.7 mmol) was dissolved in DMSO (20.0 mL) in a 100 mL bottle. t-BuOK (2.68 mmol) was added to the mixture at 10° C. The mixture was warmed to 25° C., and stirred at 25° C. for 1 hr. The reaction was quenched with addition of $H_2O$ (200 mL) at 0-10° C. n-Hexane (100 mL) was added to the mixture, and the reaction was extracted with n-hexane (200 mL*5). Wash the combined organic phase with brine (100 mL), and dry over anhydrous $Na_2SO_4$. Filter and concentrate under vacuum to obtain (E)-(3,3-difluoroprop-1-en-1-yl)(phenyl) sulfane.

Step 3: (E)-(3,3-difluoroprop-1-en-1-yl)diphenylsulfonium trifluoromethanesulfonate Diphenyliodonium trifluoromethanesulfonate was added (48.8 mmol) to a 250 mL bottle, and DCE (60.0 mL) was added. (E)-(3,3-difluoroprop-1-en-1-yl)(phenyl)sulfane (51.3 mmol) was added, followed by Cu powder (244 mmol) to the bottle at 10° C. The reaction was stirred at 10-25° C. at 0.5 hr before immersing in a pre-heated oil bath (80° C.), and stirred for 2 hrs. The reaction was cooled to 20° C. and then filtered through a celite pad and washed with DCM (80 mL*4). The filtrate was concentrated and purified by column chromatography (SiO2, DCM/Acetone=100/1 to 20/1, Rf=0.50) to obtain (E)-(3,3-difluoroprop-1-en-1-yl)diphenylsulfonium trifluoromethanesulfonate.

Step 4: rac-2-ethoxyethyl (1R,2R)-1-cyano-2-(difluoromethyl)cyclopropane-1-carboxylate 2-Ethoxyethyl 2-cyanoacetate (63.6 mmol) in actone (100 mL) was added to a 250 mL bottle at 25° C. $K_2CO_3$ (191 mmol) was added followed by (E)-(3,3-difluoroprop-1-en-1-yl)diphenylsulfonium trifluoromethanesulfonate (70.0 mmol) to the bottle at 25° C. and stirred for 1 hour. The reaction was filtered through a celite pad and washed with DCM (100 ml*3). Concentrated the organic phase under vacuum, and purified by HPLC (column: Phenomenex luna C18 (250*70 mm, 15 μm); mobile phase: [water (0.1% TFA)-ACN]; B %: 25ACN %-55ACN %, 25 min). The product fraction was adjusted to pH=6-7 with sat. $NaHCO_3$. The fraction was concentrate under reduced pressure to remove ACN, then extracted with ethyl acetate (200 mL*3), and dried over anhydrous $Na_2SO_4$. Filtered and concentrated under vacuum to afford crude product, which was further Purified by prep HPLC (column: Welch Ultimate XB-CN 250*70*10 μm; mobile phase: [Hexane-EtOH (0.1% $NH_3 \cdot H_2O$)]; B %: 1%-40%, 15 min) and concentrated to obtain rac-2-ethoxyethyl (1R,2R)-1-cyano-2-(difluoromethyl)cyclopropane-1-carboxylate.

Step 5: rac-(1R,2R)-1-cyano-2-(difluoromethyl) cyclopropane-1-carboxylic acid rac-2-ethoxyethyl (1R,2R)-1-cyano-2-(difluoromethyl)cyclopropane-1-carboxylate (34.3 mmol) was added to a 100 mL bottle and suspended in THF (70.0 mL). $LiOH \cdot H_2O$ (2 M, 34.30 mL) was added to the mixture at 10° C., and stirred at 10-25° C. for 3 hours. The pH was adjusted to 2 with HCl (1N). The reaction was extracted with ethyl acetate (50.0 mL*6), and washed with brine (50.0 mL). The organics were dried over $Na_2SO_4$, filtered and concentrated under vacuum. The product was triturated with DCM (20.0 mL) and the precipitate was collected with by vacuum filtration to provide rac-(1R,2R)-1-cyano-2-(difluoromethyl)cyclopropane-1-carboxylic acid.

Example 92

Preparation of rac-(1S,2S)-1-cyano-2-fluorocyclopropane-1-carboxylic acid

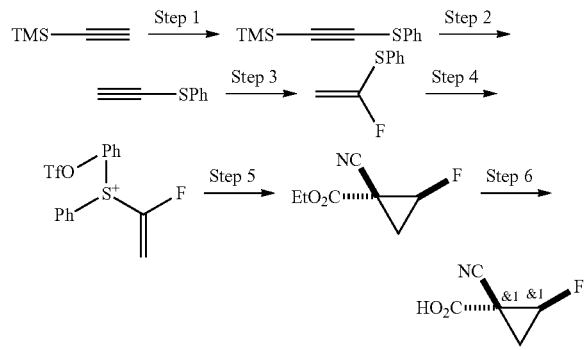

Step 1: trimethyl((phenylthio)ethynyl)silane

Ethynyltrimethylsilane (1.43 mol) in THF (1000 mL), was added n-BuLi (2.5 M, 570 mL, 1.43 mol) dropwise at -78° C. The reaction was stirred at -78° C. for 30 mins and then a solution of 1,2-diphenyldisulfane (1.43 mol) in THF (400 mL) was added at -78° C. dropwise. After stirring for 30 minutes at -78° C., the reaction was warmed up to 15° C. and stir for 5 hours. The reaction was cooled to 0° C. and $H_2O$ was added (500 mL) dropwise at 0° C. The reaction was extracted with EtOAc (500 mL*2), and the aqueous layer is poured into NaClO. The combined organic layers were washed with 0.1M NaOH (500 mL*3), $H_2O$ (500 mL), dried over $Na_2SO_4$, filtered and concentrated in vacuo. The residue was used in the next step directly without purification to obtain trimethyl((phenylthio)ethynyl)silane.

Step 2: ethynyl(phenyl)sulfane

Trimethyl((phenylthio)ethynyl)silane (1.28 mol) was added into MeOH (2000 mL). A mixture of $K_2CO_3$ (2.56 mol) in $H_2O$ (600 mL) was added dropwise at 15° C., and stirred for 16 hour. After concentration to remove MeOH, EtOAc (400 mL) and $H_2O$ (200 mL) was added. Separated and the aqueous layer extracted with EtOAc (200 mL*2). The combined organic layers were dried over $Na_2SO_4$, filtered and concentrated in vacuo. The residue was purified by column chromatography to obtain ethynyl(phenyl)sulfane.

Step 3: (1-fluorovinyl)(phenyl)sulfane

Ethynyl(phenyl)sulfane (1.16 mol), Pyr. (3.31 mol) was added into DCM (1000 mL). HF/Pyr. (4.62 mol) was added at 0° C., and then the reaction was warmed to 15° C. and stirred for 10 mins. Sat. $NaHCO_3$ and $NaHCO_3$ solid were added slowly to adjust pH=8. The organic layer was separated, washed with brine (1000 mL), dried over $Na_2SO_4$, filtered, and concentrated in vacuo. The residue was purified by column chromatography to obtain (1-fluorovinyl)(phenyl)sulfane.

Step 4: (1-fluorovinyl)diphenylsulfonium trifluoromethanesulfonate (1-Fluorovinyl)(phenyl)sulfane (272 mmol) was suspended into DCE (400 mL). Diphenyliodonium trifluoromethanesulfonate (258 mmol) and Cu (1.36 mol) were added at 15° C. The reaction was heated to 100° C. and stirred for 30 mins. The reaction was cooled to 15° C., filtered and the filter cake washed with DCM (100 mL). The filtrate was concentrated in vacuo, and the residue purified by column chromatography to obtain (1-fluorovinyl)diphenylsulfonium trifluoromethanesulfonate.

Step 5: rac-ethyl (1S,2S)-1-cyano-2-fluorocyclopropane-1-carboxylate

Ethyl 2-cyanoacetate (78.8 mmol) was added into MeCN (180 mL). DBU (94.6 mmol) was added at 15° C. and stirred for 10 min followed by the addition of (1-fluorovinyl) diphenylsulfonium trifluoromethanesulfonate (78.8 mmol) at 15° C. portion wise. After stirring at 15° C. for 30 minutes the reaction was quenched with addition of sat. $NH_4Cl$ (50 mL). The mixture was extracted with Ethyl Acetate (100 mL) two times and the combined organic layers dried over $Na_2SO_4$, filtered and concentrated in vacuo. The residue was purified by column chromatography to obtain rac-ethyl (1S,2S)-1-cyano-2-fluorocyclopropane-1-carboxylate.

Step 6: rac-(1S,2S)-1-cyano-2-fluorocyclopropane-1-carboxylic acid rac-Ethyl (1S,2S)-1-cyano-2-fluorocyclopropane-1-carboxylate (14.0 mmol) was suspended into MeCN (11.0 mL) and H$_2$O (2.00 mL). Triazabicyclodecene (29.4 mmol) was added at 15° C. and stirred for 1 hr. The reaction was extract with DCM (20 mL), and the aqueous layer was adjusted pH to 1-3 by HCl (4M). The aqueous layer was extract with EtOAc (20 mL*3). The combined organic layers were dried over Na$_2$SO$_4$, filtered and concentrated in vacuo. The residue was purified by column chromatography to obtain rac-(1S,2S)-1-cyano-2-fluorocyclopropane-1-carboxylic acid.

Example 93

Calcium Assay

In vitro LPAR1 activity was measured in an intracellular calcium mobilization assay.

CHO-K1 EDG2 cells (DiscoverX cat #93-0644C2) expressing human LPAR1 (NM_001401.3) were seeded in a total volume of 25 µL of Dulbecco's Modification of Eagle's Medium (DMEM) with 10% Fetal Bovine Serum, 1× PenStrepGlutamine, 300 µg/ml Hygromycin, and 800 µg/ml G418 into 384-well tissue culture plate (Grenier #781091) at 15,000 cells/well and incubated at 37° C. overnight. Prior to testing, 25 µL Calcium Loading Dye Component A (FLIPR Calcium 6 Assay Kit Molecular Device #R8190) and 2.5 mM Probenecid (Invitrogen #P36400, prepared fresh) in Hank's Balanced Salt Solution (Corning #21-023-CV), 20 mM HEPES (Corning #25-060-CI), 0.1% Bovine Serum Albumin (Sigma-Aldrich #A7906-500G) was add to the cells for 60 minutes at 37° C.

Agonist dose curves of LPA 18:2 (Avanti Polar Lipids cat #857138, 0.5 nM to 10 µM) were recorded to determine the LPA 18:2 EC$_{80}$ for subsequent antagonist assays. For agonist dose curves, cells were removed from the incubator 2 hours after dye loading and transferred to the FLIPR Tetra instrument (Molecular Devices, San Jose, CA). Calcium mobilization was monitored for 5 min and 10 µL 6×LPA in HBSS/20 mM Hepes/0.1% bovine serum albumin (BSA) was added to the cells 5 seconds into the assay.

To determine the LPAR1 antagonist activity of test compounds, cells were pre-incubated with test compound at a dose range of 0.5 nM to 10 µM, followed by LPA at EC$_{80}$ concentration (100 nM). After dye loading, cells were removed from the incubator and 0.3 µL of 200× antagonist was added. Cells were incubated for 60 minutes at 37° C. Antagonist activity was measured on a FLIPR Tetra. Calcium mobilization was monitored for 3.5 minutes and 10 µL 6× EC$_{80}$ LPA in HBSS, 20 mM HEPES, and 0.1% BSA was added to the cells 5 seconds into the assay. Signal amplitude (Maximum minus minimum) values were plotted against log$_{10}$ of antagonist concentration using Dose Response Tool (Gilead Sciences Inc.) to determine EC$_{50}$.

To assess the antagonistic potential of exemplified compounds EC$_{50}$ values were determined for Compounds 1 to 338 in the LPAR1 calcium mobilization assay. Results are shown in Table 6 (LPAR1 EC$_{50}$). The compound numbers correspond to the compound numbers in Examples 1 to 92. N/A=not available.

TABLE 6

| Compound | LPAR1 (EC$_{50}$; nM) |
|---|---|
| Compound 1 | 6519.3 |
| Compound 2 | 953.0 |
| Compound 3 | 10000 |
| Compound 4 | 10000 |
| Compound 5 | 1505.8 |
| Compound 6 | 1859.6 |
| Compound 7 | 315.1 |
| Compound 8 | 154.3 |
| Compound 9 | 2696.7 |
| Compound 10 | 1024.1 |
| Compound 11 | 731.2 |
| Compound 12 | 540.8 |
| Compound 13 | 148.1 |
| Compound 14 | 1202.9 |
| Compound 15 | 452.1 |
| Compound 16 | 2185.0 |
| Compound 17 | 29.3 |
| Compound 18 | 1129.3 |
| Compound 19 | 275.5 |
| Compound 20 | N/A |
| Compound 21 | 39.6 |
| Compound 22 | 43.4 |
| Compound 23 | 1105.0 |
| Compound 24 | N/A |
| Compound 25 | 2268.3 |
| Compound 26 | 587.4 |
| Compound 27 | 1277.1 |
| Compound 28 | 29.1 |
| Compound 29 | 261.4 |
| Compound 30 | 516.2 |
| Compound 31 | 2334.4 |
| Compound 32 | 798.9 |
| Compound 33 | 1018.3 |
| Compound 34 | 428.9 |
| Compound 35 | 103.1 |
| Compound 36 | 112.4 |
| Compound 37 | 54.6 |
| Compound 38 | 10000 |
| Compound 39 | 50.8 |
| Compound 40 | 75.2 |
| Compound 41 | 38.1 |
| Compound 42 | 201.1 |
| Compound 43 | 497.2 |
| Compound 44 | 165.0 |
| Compound 45 | 40.8 |
| Compound 46 | 29.7 |
| Compound 47 | 19.1 |
| Compound 48 | 22.8 |
| Compound 49 | 353.2 |
| Compound 50 | 1761.4 |
| Compound 51 | 88.7 |
| Compound 52 | 621.9 |
| Compound 53 | 1456.0 |
| Compound 54 | 7863.3 |
| Compound 55 | 477.7 |
| Compound 56 | 1135.1 |
| Compound 57 | 339.2 |
| Compound 58 | 205.2 |
| Compound 59 | 263.7 |
| Compound 60 | 140.4 |
| Compound 61 | 134.4 |
| Compound 62 | 109.8 |
| Compound 63 | 120.4 |
| Compound 64 | 76.4 |
| Compound 65 | 81.9 |
| Compound 66 | 66.6 |
| Compound 67 | 30.8 |
| Compound 68 | 40.8 |
| Compound 69 | 53.0 |
| Compound 70 | 47.8 |
| Compound 71 | 89.7 |
| Compound 72 | 17.0 |
| Compound 73 | 17.3 |
| Compound 74 | 1344.4 |
| Compound 75 | 23.4 |
| Compound 76 | 274.7 |
| Compound 77 | 25.5 |

TABLE 6-continued

| Compound | LPAR1 (EC$_{50}$; nM) |
|---|---|
| Compound 78 | 83.6 |
| Compound 79 | 16.0 |
| Compound 80 | 109.1 |
| Compound 81 | 22.8 |
| Compound 82 | 20.4 |
| Compound 83 | 343.7 |
| Compound 84 | 14.5 |
| Compound 85 | 11.2 |
| Compound 86 | 16.6 |
| Compound 87 | 16.1 |
| Compound 88 | 8.6 |
| Compound 89 | 312.3 |
| Compound 90 | 73.5 |
| Compound 91 | 187.0 |
| Compound 92 | 601.4 |
| Compound 93 | 133.0 |
| Compound 94 | 4817.8 |
| Compound 95 | 308.6 |
| Compound 96 | 2328.6 |
| Compound 97 | 395.4 |
| Compound 98 | 720.5 |
| Compound 99 | 53.9 |
| Compound 100 | 90.8 |
| Compound 101 | 1041.5 |
| Compound 102 | 85.6 |
| Compound 103 | 16.6 |
| Compound 104 | 559.9 |
| Compound 105 | 1582.1 |
| Compound 106 | 1758.3 |
| Compound 107 | 10000 |
| Compound 108 | 419.6 |
| Compound 109 | 1711.0 |
| Compound 110 | 68.2 |
| Compound 111 | 190.9 |
| Compound 112 | 1405.0 |
| Compound 113 | 775.1 |
| Compound 114 | 504.4 |
| Compound 115 | 654.2 |
| Compound 116 | 322.5 |
| Compound 117 | 1143.9 |
| Compound 118 | 1336.6 |
| Compound 119 | 49.9 |
| Compound 120 | 2466.1 |
| Compound 121 | 264.1 |
| Compound 122 | 122.9 |
| Compound 123 | 625.6 |
| Compound 124 | 3629.6 |
| Compound 125 | 2711.3 |
| Compound 126 | 1826.3 |
| Compound 127 | 415.7 |
| Compound 128 | 309.4 |
| Compound 129 | 492.5 |
| Compound 130 | 271.3 |
| Compound 131 | 260.4 |
| Compound 132 | 196.9 |
| Compound 133 | 343.9 |
| Compound 134 | 448.9 |
| Compound 135 | 725.7 |
| Compound 136 | 602.5 |
| Compound 137 | 1092.3 |
| Compound 138 | 84.9 |
| Compound 139 | 123.2 |
| Compound 140 | 349.3 |
| Compound 141 | 459.3 |
| Compound 142 | 217.4 |
| Compound 143 | 188.7 |
| Compound 144 | 36.1 |
| Compound 145 | 184.0 |
| Compound 146 | 271.0 |
| Compound 147 | 33.9 |
| Compound 148 | 30.4 |
| Compound 149 | 328.7 |
| Compound 150 | 879.5 |
| Compound 151 | 3151.9 |
| Compound 152 | 3987.9 |
| Compound 153 | 932.6 |
| Compound 154 | 667.8 |
| Compound 155 | 748.4 |
| Compound 156 | 50.7 |
| Compound 157 | 74.5 |
| Compound 158 | 117.1 |
| Compound 159 | 393.6 |
| Compound 160 | 1454.9 |
| Compound 161 | 66.8 |
| Compound 162 | 84.7 |
| Compound 163 | 32.6 |
| Compound 164 | 245.0 |
| Compound 165 | 487.1 |
| Compound 166 | 238.5 |
| Compound 167 | 99.4 |
| Compound 168 | 16.2 |
| Compound 169 | 190.6 |
| Compound 170 | 31.8 |
| Compound 171 | 140.5 |
| Compound 172 | 236.1 |
| Compound 173 | 181.0 |
| Compound 174 | 106.6 |
| Compound 175 | 35.4 |
| Compound 176 | 253.3 |
| Compound 177 | 48.3 |
| Compound 178 | 140.1 |
| Compound 179 | 46.5 |
| Compound 180 | 122.7 |
| Compound 181 | 428.4 |
| Compound 182 | 2046.8 |
| Compound 183 | 1059.1 |
| Compound 184 | 81.8 |
| Compound 185 | 1704.2 |
| Compound 186 | 100.5 |
| Compound 187 | 1236.1 |
| Compound 188 | 451.9 |
| Compound 189 | 989.3 |
| Compound 190 | 359.3 |
| Compound 191 | 620.2 |
| Compound 192 | 10000 |
| Compound 193 | 287.1 |
| Compound 194 | 832.3 |
| Compound 195 | 1538.5 |
| Compound 196 | 1029.5 |
| Compound 197 | 5.2 |
| Compound 198 | 613.1 |
| Compound 199 | 65.7 |
| Compound 200 | 94.0 |
| Compound 201 | 145.8 |
| Compound 202 | 5.0 |
| Compound 203 | 94.8 |
| Compound 204 | 132.2 |
| Compound 205 | 8.3 |
| Compound 206 | 71.8 |
| Compound 207 | 41.2 |
| Compound 208 | 21.1 |
| Compound 209 | 17.7 |
| Compound 210 | 243.2 |
| Compound 211 | 37.4 |
| Compound 212 | 56.4 |
| Compound 213 | 175.3 |
| Compound 214 | 356.8 |
| Compound 215 | 1995.6 |
| Compound 216 | 22.4 |
| Compound 217 | 58.1 |
| Compound 218 | 24.0 |
| Compound 219 | 37.7 |
| Compound 220 | 157.5 |
| Compound 221 | 374.3 |
| Compound 222 | 41.7 |
| Compound 223 | 118.5 |
| Compound 224 | 40.2 |
| Compound 225 | 16.3 |
| Compound 226 | 183.8 |
| Compound 227 | 205.5 |
| Compound 228 | 403.3 |
| Compound 229 | 863.9 |
| Compound 230 | 26.7 |
| Compound 231 | 411.7 |

TABLE 6-continued

| Compound | LPAR1 (EC$_{50}$; nM) |
|---|---|
| Compound 232 | 1106.2 |
| Compound 233 | 190.1 |
| Compound 234 | 136.4 |
| Compound 235 | 26.5 |
| Compound 236 | 1657.6 |
| Compound 237 | 19.3 |
| Compound 238 | 52.5 |
| Compound 239 | 62.3 |
| Compound 240 | N/A |
| Compound 241 | 110.7 |
| Compound 242 | 63.3 |
| Compound 243 | 71.9 |
| Compound 244 | 130.8 |
| Compound 245 | 11.7 |
| Compound 246 | 103.4 |
| Compound 247 | 13.0 |
| Compound 248 | 29.8 |
| Compound 249 | 536.9 |
| Compound 250 | 276.2 |
| Compound 251 | 38.5 |
| Compound 252 | 73.5 |
| Compound 253 | 550.7 |
| Compound 254 | 18.1 |
| Compound 255 | 346.3 |
| Compound 256 | 209.4 |
| Compound 257 | 442.7 |
| Compound 258 | 19.3 |
| Compound 259 | 101.0 |
| Compound 260 | 160.7 |
| Compound 261 | 11.9 |
| Compound 262 | 23.7 |
| Compound 263 | 691.3 |
| Compound 264 | 202.6 |
| Compound 265 | 19.5 |
| Compound 266 | 748.6 |
| Compound 267 | 588.2 |
| Compound 268 | 7.3 |
| Compound 269 | 126.9 |
| Compound 270 | 167.7 |
| Compound 271 | 228.6 |
| Compound 272 | 162.2 |
| Compound 273 | 248.2 |
| Compound 274 | 403.2 |
| Compound 275 | 241.0 |
| Compound 276 | 139.9 |
| Compound 277 | 954.8 |
| Compound 278 | 809.5 |
| Compound 279 | 97.4 |
| Compound 280 | 98.7 |
| Compound 281 | 86.6 |
| Compound 282 | 1186.8 |
| Compound 283 | 82.4 |
| Compound 284 | 907.9 |
| Compound 285 | 71.8 |
| Compound 286 | 104.3 |
| Compound 287 | 1426.5 |
| Compound 288 | 33.5 |
| Compound 289 | 21.5 |
| Compound 290 | 10.9 |
| Compound 291 | 157.2 |
| Compound 292 | 143.1 |
| Compound 293 | 27.3 |
| Compound 294 | 238.3 |
| Compound 295 | 391.0 |
| Compound 296 | 46.9 |
| Compound 297 | 354.1 |
| Compound 298 | 1254.5 |
| Compound 299 | 4991.0 |
| Compound 300 | 960.8 |
| Compound 301 | 66.9 |
| Compound 302 | 669.3 |
| Compound 303 | 565.4 |
| Compound 304 | 46.4 |
| Compound 305 | 1004.0 |
| Compound 306 | 99.7 |
| Compound 307 | N/A |
| Compound 308 | 336.5 |
| Compound 309 | 132.8 |
| Compound 310 | 453.9 |
| Compound 311 | 1533.2 |
| Compound 312 | 1528.3 |
| Compound 313 | 51.8 |
| Compound 314 | 2.9 |
| Compound 315 | 12.7 |
| Compound 316 | 41.6 |
| Compound 317 | 90.5 |
| Compound 318 | 9.5 |
| Compound 319 | 1496.6 |
| Compound 320 | 130.9 |
| Compound 321 | 309.1 |
| Compound 322 | 169.5 |
| Compound 323 | 177.5 |
| Compound 324 | 53.7 |
| Compound 325 | 185.1 |
| Compound 326 | 304.9 |
| Compound 327 | 255.2 |
| Compound 328 | 1132.7 |
| Compound 329 | 749.2 |
| Compound 330 | 599.6 |
| Compound 331 | 22.8 |
| Compound 332 | 354.1 |
| Compound 333 | 219.3 |
| Compound 334 | 3418.0 |
| Compound 335 | 778.4 |
| Compound 336 | 257.5 |
| Compound 337 | 163.2 |
| Compound 338 | 132.0 |

Unless otherwise defined, all technical and scientific terms used herein have the same meaning as commonly understood by one of ordinary skill in the art to which this disclosure belongs.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:
1. A compound that is of the formula:
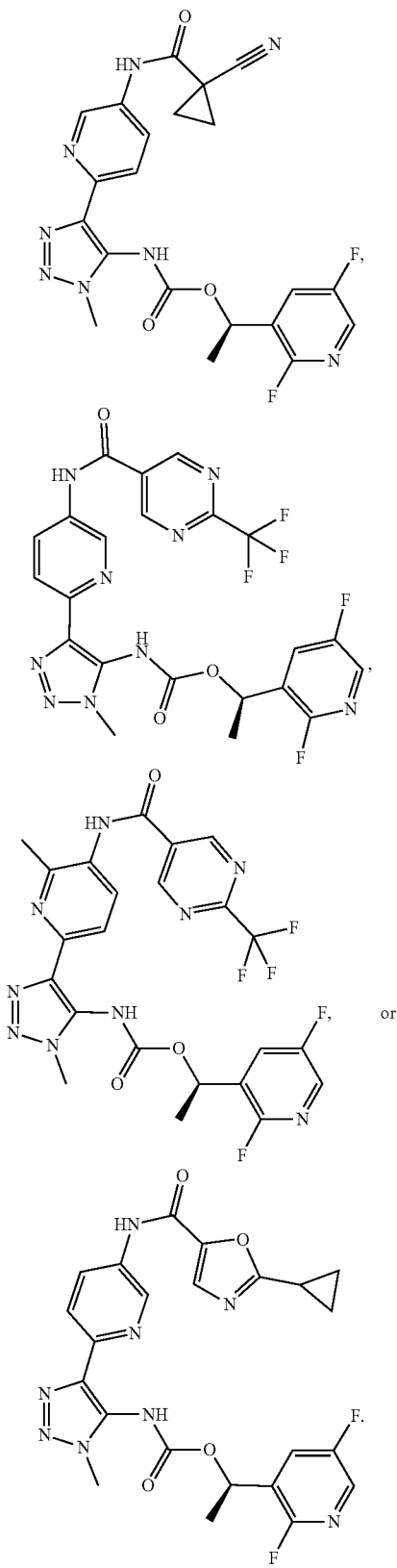
or a pharmaceutically acceptable salt thereof.
2. A compound of the formula:
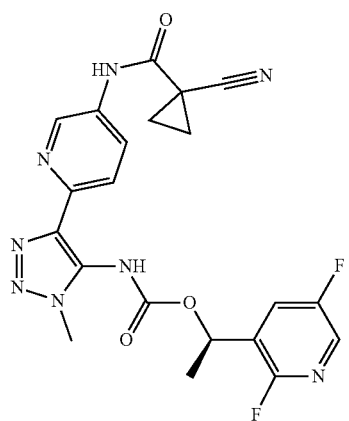 [SMILES: C[C@@H](OC(=O)Nc1c(-c2ccc(NC(=O)C3(C#N)CC3)cn2)nnn1C)c1cc(F)cnc1F]
or a pharmaceutically acceptable salt thereof.
3. A compound of the formula:
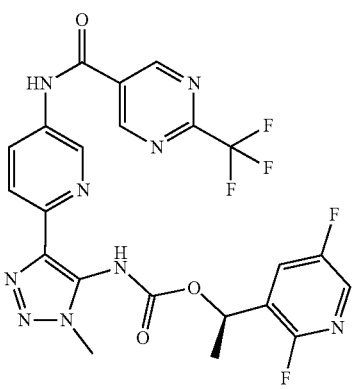 [SMILES: C[C@@H](OC(=O)Nc1c(-c2ccc(NC(=O)c3cnc(C(F)(F)F)nc3)cn2)nnn1C)c1cc(F)cnc1F]
or a pharmaceutically acceptable salt thereof.
4. A compound of the formula:
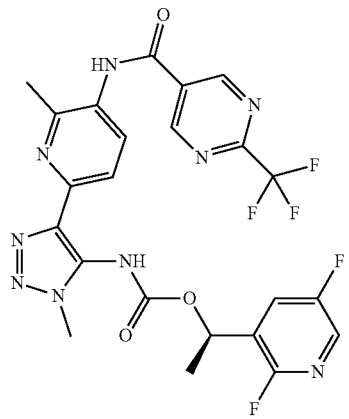 [SMILES: Cc1nc(-c2nnn(C)c2NC(=O)O[C@H](C)c2cc(F)cnc2F)ccc1NC(=O)c1cnc(C(F)(F)F)nc1]
or a pharmaceutically acceptable salt thereof.

5. A compound of the formula:
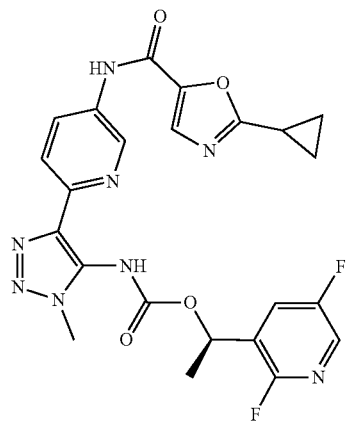 [SMILES: C[C@@H](OC(=O)Nc1c(-c2ccc(NC(=O)c3cnc(C4CC4)o3)cn2)nnn1C)c1cc(F)cnc1F]
or a pharmaceutically acceptable salt thereof.
* * * * *